(12) United States Patent
Jorand-Lebrun et al.

(10) Patent No.: US 9,073,892 B2
(45) Date of Patent: Jul. 7, 2015

(54) INDAZOLYL TRIAZOL DERIVATIVES

(75) Inventors: Catherine Jorand-Lebrun, Contamine-Sarzin (FR); Stefano Crosignani, St Genis-Pouilly (FR); Jerome Dorbais, Annecy (FR); Tania Grippi-Vallotton, Puplinge (CH); Adeline Pretre, Viry (FR)

(73) Assignee: Merck Serono S.A., Coinsins (CH)

( * ) Notice: Subject to any disclaimer, the term of this patent is extended or adjusted under 35 U.S.C. 154(b) by 0 days.

(21) Appl. No.: 13/995,803

(22) PCT Filed: Dec. 16, 2011

(86) PCT No.: PCT/EP2011/073015
§ 371 (c)(1),
(2), (4) Date: Jun. 19, 2013

(87) PCT Pub. No.: WO2012/084704
PCT Pub. Date: Jun. 28, 2012

(65) Prior Publication Data
US 2013/0274241 A1 Oct. 17, 2013

Related U.S. Application Data

(60) Provisional application No. 61/424,890, filed on Dec. 20, 2010.

(30) Foreign Application Priority Data

Dec. 20, 2010 (EP) .................................. 10195867

(51) Int. Cl.
| | |
|---|---|
| C07D 403/04 | (2006.01) |
| A61K 31/454 | (2006.01) |
| A61K 31/4192 | (2006.01) |
| A61K 45/06 | (2006.01) |
| C07D 401/14 | (2006.01) |
| C07D 403/14 | (2006.01) |
| A61K 31/537 | (2006.01) |
| A61K 31/551 | (2006.01) |

(52) U.S. Cl.
CPC .......... *C07D 403/04* (2013.01); *A61K 31/4192* (2013.01); *A61K 45/06* (2013.01); *C07D 401/14* (2013.01); *C07D 403/14* (2013.01); *A61K 31/454* (2013.01); *A61K 31/537* (2013.01); *A61K 31/551* (2013.01)

(58) Field of Classification Search
CPC ........................................................ C07D 403/04
USPC ........................................... 548/255; 514/406
See application file for complete search history.

(56) References Cited

U.S. PATENT DOCUMENTS

| | | |
|---|---|---|
| 2004/0087642 A1 | 5/2004 | Zeldis et al. |
| 2005/0090529 A1 | 4/2005 | McAlpine et al. |
| 2006/0258706 A1 | 11/2006 | Saindane et al. |

FOREIGN PATENT DOCUMENTS

| | | |
|---|---|---|
| WO | WO-2004 039325 | 5/2004 |
| WO | WO-2008 154241 | 12/2008 |

OTHER PUBLICATIONS

Vippagunta, et al. Advanced Drug Delivery Reviews 48 (2001) 3-26.*
Cancer and Metastasis Reviews (1998), 17 (1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online}, [retrieved on Jul. 6, 2007], Retrieved form the internet, URL; http://en.wikipedia.org/wiki/Cancer.*
International Search Report for PCT/EP2011/073015, Date of the actual completion of the international search: Jan. 20, 2012, Date of mailing of the international search report: Jan. 27, 2012.
Ex Parte Cai et al. Decision on Appeal before the Board of Patent Appeals and Interferences in the United States Patent and Trademark Office Board in U.S. Appl. No. 11/852,433. Notification Date: Dec. 9, 2011.
Ex Parte Liu et al. Decision on Appeal before the Board of Patent Appeals and Interferences in the United States Patent and Trademark Office Board in U.S. Appl. No. 10/820,647. Notification Date: Sep. 17, 2010.
Klampfer, Lidija, "Cytokines, Inflammation and Colon Cancer", Curr Cancer Drug Targets. Author Manuscript. pp. 1-25. Published in final edited form as Curr Cancer Drug Targets, 11(4):451-464. May 2011.
Srivastava, Ratika, et al. "Augmentation of therapeutic responses in melanoma by inhibition of IRAK-1,-4", Cancer Res. Author Manuscript. pp. 1-13. Published in final edited form as Cancer Res, 72(23):6209-6216, Dec. 1, 2012.
Wang, Zhulun, et al. "IRAK-4 Inhibitors for Inflammation", Current Topics in Medicinal Chemistry, 9(8):724-737. 2009.

* cited by examiner

*Primary Examiner* — Shawquia Jackson
(74) *Attorney, Agent, or Firm* — Millen, White, Zelano & Branigan, P.C.

(57) ABSTRACT

Compounds of Formula (I)

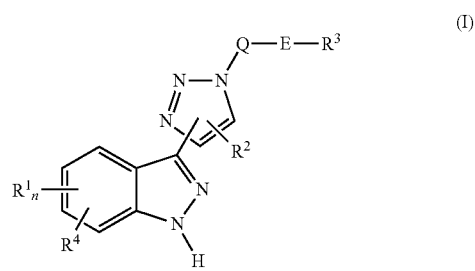

are used for the treatment of inflammation and autoimmune disorders.

28 Claims, No Drawings

INDAZOLYL TRIAZOL DERIVATIVES

This application claims benefit of U.S. Provisional Application No. 61/424,890, filed Dec. 20, 2010.

The present invention provides Indazolyl triazol derivatives of Formula (I) as IRAK inhibitors and their use in the treatment of cancer, and other diseases related to IRAK overexpression, like rheumatoid arthritis, systemic lupus erythematosus or lupus nephritis.

BACKGROUND

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278(5343): 1612-5). IRAK3 (also called IRAKM) was identified using a murine EST sequence encoding a polypeptide with significant homology to IRAK1 to screen a human phytohaemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem. Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

According to one aspect of the invention, are provided compounds of Formula (I).

According to another aspect of the invention, are provided compounds of Formula (I) which are suitable for the treatment and/or prevention of disorders related to IRAK.

According to another aspect of the invention, are provided compounds, which are able to modulate, especially inhibit the activity or function of IRAK in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective of IRAK-4 and/or IRAK-1 over the other isoforms.

According to another aspect of the invention is provided a kit or a set comprising at least one compound of Formula (I), preferably in combination with immunomodulating agents. Preferably, the kit consists of separate packs of:
(a) an effective amount of a compound of the formula (I) and/or pharmaceutically usable derivatives, solvates, salts, hydrates and stereoisomers thereof, including mixtures thereof in all ratios, and
(b) an effective amount of a further medicament active ingredient.

According to another aspect of the invention, is provided a process for the synthesis of compounds of Formulae (I) and related Formulae.

DETAILED DESCRIPTION OF THE INVENTION

In one embodiment, the present invention provides a compound of Formula (I)

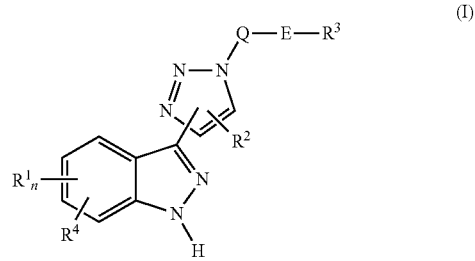

Wherein
Q denotes Ar or Het,

E denotes —$(CH_2)_mCO$—, —$(CH_2)_mSO_2$—, —$(CH_2)_q$—, —$(CH_2)_mNHCO$—, or a single bond, $R^1$ denotes H, OH, NH—$C_1$-$C_6$-alkyl, $OC_1$-$C_6$-alkyl, $C_1$-$C_6$-alkyl, $C_2$-$C_6$-alkenyl, $C_2$-$C_6$-alkynyl, Cyc, Hal, $Het^1$, O-$Het^1$, CO-$Het^1$, NH-$Het^1$, CO—$Ar^1$, O—$Ar^1$, $Ar^1$, NH—$Ar^1$, —$(CH_2)_qHet^1$, —CONH—$(CH_2)_qHet^1$, —CONH-$Het^1$, —$(CH_2)_qO$-$Het^1$, —$(CH_2)_qO$—$Ar^1$, —$(CH_2)_qAr^1$, —CONH—$(CH_2)_qAr^1$, —CONH—$Ar^1$, —CONH$C_3$-$C_6$-cycloalkyl, —$(CH_2)_q$Hal, —$(CH_2)_q$Cyc, $CF_3$, —$(CH_2)_sNH$—$(CH_2)_q$-$Het^1$, —$(CH_2)_sNH$—$(CH_2)_q$—$Ar^1$, wherein NH—$C_1$-$C_6$-alkyl, $OC_1$-$C_6$-alkyl, $C_1$-$C_6$-alkyl, $C_2$-$C_6$-alkenyl, $C_2$-$C_6$-alkynyl, $C_3$-$C_6$-cycloalkyl may be substituted by 1 to 3 groups independently selected from $OC_1$-$C_3$-alkyl, OH, $CONH_2$, $NH_2$, $R^2$ denotes H, $C_1$-$C_6$-alkyl, $C_2$-$C_6$-alkenyl, $C_2$-$C_6$-alkynyl, Hal, $CF_3$, preferably H, $R^3$ denotes $Het^1$, $Ar^1$, $NR^aR^b$, COOH, —$(CH_2)_qHet^1$, —$(CH_2)_qAr^1$, —$(CH_2)_qNR^aR^b$, —$(CH_2)_qCOOH$, or $C_1$-$C_6$-alkyl wherein 1 to 3 hydrogen atoms may be independently replaced by OH or $CF_3$.

$R^4$ denotes H, $C_1$-$C_6$-alkyl, $C_2$-$C_6$-alkenyl, Hal;

$R^a$ denotes H, linear, branched or cyclic $C_1$-$C_6$-alkyl, $R^b$ denotes H, $Het^b$, $Ar^b$, —CO-$Het^b$, —CO—$Ar^b$, a $C_3$-$C_8$-cycloalkyl or a linear or branched alkyl having 1 to 6 carbon atoms, wherein 1 to 3 hydrogen atoms may be replaced by $Het^b$, $Ar^b$, $NH_2$, N($C_1$-$C_6$-alkyl)$_2$, NH($C_1$-$C_6$-alkyl), N($C_1$-$C_6$-alkyl)($C_3$-$C_8$-cycloalkyl), NH($C_3$-$C_8$-cycloalkyl), O($C_1$-$C_6$-alkyl), CN, OH, $CF_3$, Hal, n is 0, 1, 2, 3 or 4, m is 0, 1, 2, 3 or 4, q is 1, 2, or 3, s is 0, 1, 2 or 3, Hal denotes Cl, Br, I, F, preferably Cl or F.

Ar denotes a divalent monocyclic or fused bicyclic arylene group having 6 to 14 carbon atoms, which may be further substituted with 1 to 4 substitutents selected from Hal, $C_1$-$C_6$-alkyl, —$(CH_2)_mOC_1$-$C_6$-alkyl, CN, OH, $NO_2$, $CF_3$, —$(CH_2)_mCOOH$, —$(CH_2)_mCOOC_1$-$C_6$-alkyl;

Het denotes a divalent monocyclic or fused bicyclic unsaturated, saturated or aromatic heterocyclic group having 1 to 5 heteroatom independently selected from N, O, S and/or a group —C=O, which may be further substituted with 1 to 4 substituent selected from Hal, $C_1$-$C_6$-alkyl, —$(CH_2)_mOC_1$-$C_6$-alkyl, CN, OH, $NO_2$, $CF_3$, —$(CH_2)_mCOOH$, —$(CH_2)_mCOOC_1$-$C_6$-alkyl;

$Ar^1$ denotes a monocyclic or bicyclic, aromatic carbocyclic ring having 6 to 14 carbon atoms, which is unsubstituted or monosubstituted, disubstituted or trisubstituted by Hal, —$CF_3$, —$OCF_3$, —$NO_2$, —CN, perfluoroalkyl, Hal, —$CF_3$, —$OCF_3$, —$NO_2$, —CN, perfluoroalkyl, linear or branched $C_1$-$C_6$-alkyl, cycloalkyl, —OH, —$OC_1$-$C_6$-alkyl, —$COC_1$-$C_6$-alkyl, —$NH_2$, —COH, —COOH, —$CONH_2$, a group $R^b$ such as —$CH_2O(C_1$-$C_6$-alkyl), —$SO_2NR^aR^b$ or $SO_2(C_1$-$C_6$alkyl).

$Het^1$ denotes a monocyclic or bicyclic (fused, bridged or spiro) saturated, unsaturated or aromatic heterocyclic ring having 1 to 4 heteroatom independently selected from N, O, S and/or a CO group, which is unsubstituted or monosubstituted, disubstituted or trisubstituted by Hal, —$CF_3$, —$OCF_3$, —$NO_2$, —CN, perfluoroalkyl, linear or branched $C_1$-$C_6$-alkyl, $C_3$-$C_8$-cycloalkyl, —OH, —$OC_1$-$C_6$-alkyl, —$NH_2$, —N($C_1$-$C_6$-alkyl)$_2$, —COH, —COOH, —$CONH_2$, —$COC_1$-$C_6$-alkyl, —NHCO($C_3$-$C_6$cycloalkyl), a group $R^b$ such as —$CH_2O(C_1$-$C_6$-alkyl), —$SO_2NR^aR^b$ or $SO_2(C_1$-$C_6$alkyl).

$Het^b$ denotes a monocyclic or bicyclic (fused or spiro) saturated, unsaturated or aromatic heterocyclic ring having 1 to 4 heteroatom independently selected from N, O, S and/or a CO group, which is unsubstituted or monosubstituted, disubstituted or trisubstituted by Hal, —$CF_3$, —$OCF_3$, —$NO_2$, —CN, perfluoroalkyl, —OH, —$OC_1$-$C_6$-alkyl, —$NH_2$, —COH, —COOH, —$CONH_2$, or by a linear or branched $C_1$-$C_6$-alkyl wherein 1 to 3 hydrogen atoms may be replaced by $NH_2$, N($C_1$-$C_6$-alkyl)$_2$, NH($C_1$-$C_6$-alkyl), N($C_1$-$C_6$-alkyl)($C_3$-$C_8$-cycloalkyl), NH($C_3$-$C_8$-cycloalkyl), O($C_1$-$C_6$-alkyl), CN, OH, $CF_3$, Hal, $C_3$-$C_8$-cycloalkyl, or by a 4 to 8-membered heterocyclic ring containing an heteroatom selected from O, S and N, $Ar^b$ denotes a monocyclic or bicyclic, aromatic carbocyclic ring having 6 to 14 carbon atoms, which is unsubstituted or monosubstituted, disubstituted or trisubstituted by Hal, —$CF_3$, —$OCF_3$, —$NO_2$, —CN, perfluoroalkyl, Hal, —$CF_3$, —$OCF_3$, —$NO_2$, —CN, perfluoroalkyl, —OH, —$OC_1$-$C_6$-alkyl, —$NH_2$, —COH, —COOH, —$CONH_2$, or by a linear or branched $C_1$-$C_6$-alkyl wherein 1 to 3 hydrogen atoms may be replaced by $NH_2$, N($C_1$-$C_6$-alkyl)$_2$, NH($C_1$-$C_6$-alkyl), N($C_1$-$C_6$-alkyl)($C_3$-$C_8$-cycloalkyl), NH($C_3$-$C_8$-cycloalkyl), O($C_1$-$C_6$-alkyl), CN, OH, $CF_3$, Hal, $C_3$-$C_8$-cycloalkyl, or by a 4 to 8-membered heterocyclic ring containing an heteroatom selected from O, S and N, Cyc denotes a saturated or unsaturated carbocyclic ring having 3 to 8 carbon atoms, preferably 5 or 6 carbon atoms, wherein 1 to 5 H atoms are replaced by Hal, —$CF_3$, —$OCF_3$, —$NO_2$, —CN, perfluoroalkyl, Hal, —$CF_3$, —$OCF_3$, —$NO_2$, —CN, perfluoroalkyl, linear or branched $C_1$-$C_6$-alkyl, cycloalkyl, —OH, —$OC_1$-$C_6$-alkyl, —$COC_1$-$C_6$-alkyl, —$NH_2$, —COH, —COOH, —$CONH_2$, a group $R^b$ such as —$CH_2O(C_1$-$C_6$-alkyl), —$SO_2NR^aR^b$ or $SO_2(C_1$-$C_6$alkyl).

and pharmaceutically acceptable derivatives, solvates, tautomers, salts, hydrates and stereoisomers thereof, including mixtures thereof in all ratios.

In another embodiment, Formula (I) embraces compounds of sub-Formulae (Ia) and (Ib)

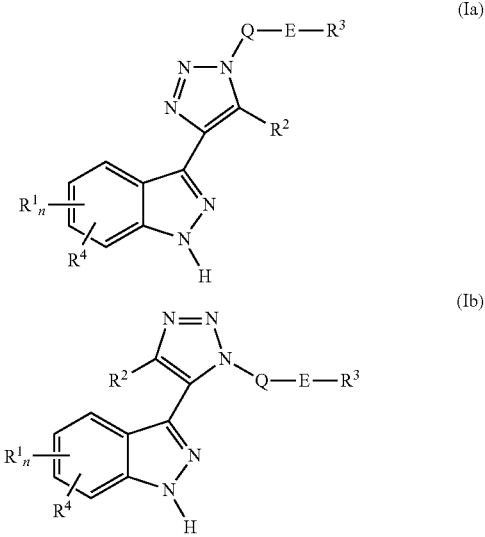

In another embodiment, the present invention provides compounds of Formula (I) and related Formulae (Ia) and (Ib) wherein Q denotes Ar, preferably phenylene.

E denotes —$(CH_2)_mCO$—, $R^1$ denotes H, $C_1$-$C_6$-alkyl, $C_2$-$C_6$-alkenyl, $C_2$-$C_6$-alkynyl, Cyc, Hal, Het$^1$, O-Het$^1$, O—Ar$^1$, Ar$^1$, —(CH$_2$)$_q$Het$^1$, —(CH$_2$)$_q$O-Het$^1$, —(CH$_2$)$_q$O—Ar$^1$, —(CH$_2$)$_q$Ar$^1$, —(CH$_2$)$_q$Hal, —(CH$_2$)$_q$Cyc, CF$_3$, $R^2$ denotes H, $C_1$-$C_6$-alkyl, $C_2$-$C_6$-alkenyl, $C_2$-$C_6$-alkynyl, Hal, CF$_3$, preferably H, $R^3$ denotes Het$^1$ or NR$^a$R$^b$, preferrably Het$^1$, $R^4$ denotes H, Wherein R$^a$, R$^b$, Het$^1$, Ar, Ar$^1$, m are as above defined.

In another embodiment, the present invention provides compounds of Formula (I) and related Formulae (Ia) and (Ib) wherein Q denotes Ar, preferably phenylene.

E denotes —(CH$_2$)$_m$CO—, $R^1$, $R^2$ are both H, $R^3$ denotes Het$^1$ or NR$^a$R$^b$, preferrably Het$^1$, $R^4$ denotes H, Wherein R$^a$, R$^b$, Het$^1$, Ar, m are as above defined.

In another embodiment, the present invention provides a compound Formulae (Ic), (Id) or (Ie)

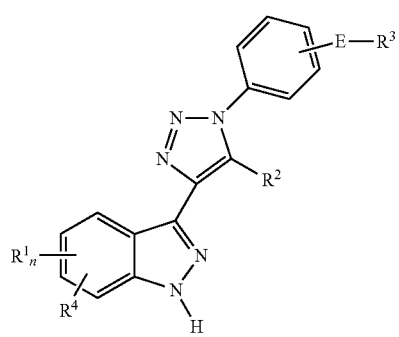

(Ic)

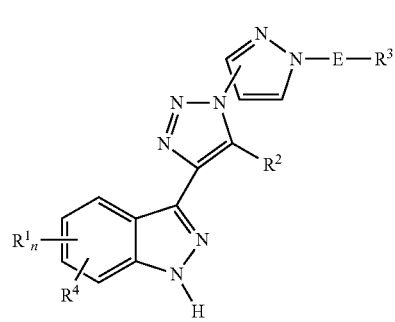

(Id)

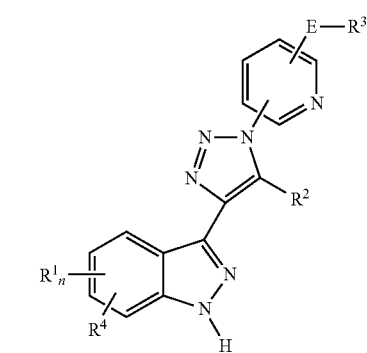

(Ie)

Wherein $R^1$, $R^3$, $R^2$, E, n are as above defined.

In another embodiment, the present invention provides compounds of Formula (If):

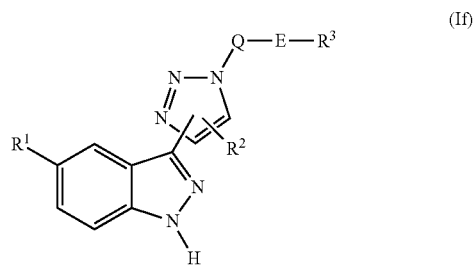

(If)

In another embodiment, the group E in Formulae (I), (Ia), (Ib), (Ic), (Id), (Ie) or (If) denotes —(CH$_2$)$_m$CO— or —(CH$_2$)$_m$NHCO—, wherein m is as defined above. Preferrably, m is 0, 1 or 2, more preferably m is 0 or 1.

In another embodiment, the group E in Formula (I), (Ia), (Ib), (Ic), (Id), (Ie) or (If) is —(CH$_2$)$_q$— or a single bond, wherein q is as defined above. Preferably, q is 1.

In another embodiment, in case Q is Ar, it is disubstituted in para or meta positions.

In another embodiment, the present invention provides compounds of Formula (If) wherein $R^2$ is as defined above, preferably H, Q is Ar, E is —CO—, —(CH$_2$)— or a bond, $R^3$ is Het$^1$, $R^1$ is selected from H, F, —CH$_3$, Het$^1$, —(CH$_2$)$_q$-Het$^1$, —NH-Het$^1$, —CONH—(CH$_2$)$_q$Het$^1$, —CONH-Het$^1$, —CONH—Ar$^1$, or a $C_2$-$C_6$-alkenyl which may be substituted by 1 to 3 groups independently selected from OC$_1$-C$_3$-alkyl, OH, CONH$_2$, and NH$_2$, wherein q is as defined above.

In another embodiments Het$^1$ denotes a monocyclic or bicyclic (fused or spiro) saturated, unsaturated or aromatic 5-12-membered heterocyclic ring having 1 to 3 heteroatoms independently selected from N, and a CO group, which is unsubstituted or monosubstituted, or disubstituted by C$_3$-C$_8$-cycloalkyl, —OH, —OC$_1$-C$_6$-alkyl, —NH$_2$, —N(C$_1$-C$_6$-alkyl)$_2$, —COHet$^b$, Het$^b$, Ar$^b$ or a linear or branched alkyl having 1 to 6 carbon atoms wherein 1 to 3 hydrogen atoms may be independently replaced by Het$^b$, Ar$^b$, OH, CF$_3$, In another embodiment, Het$^b$ denotes a saturated or aromatic 5- or 6-membered ring having 1 nitrogen atom, optionally substituted with 1 to 3 substituent selected from C$_1$-C$_6$-alkyl, OH, Hal. Preferably, Het$^b$ denotes a pyridine ring or a pyrrolidine ring.

In another embodiment, Ar$^b$ denotes a phenyl ring optionally substituted by 1 to 3 substitutents selected from Hal, preferably F, OH.

In another embodiment, in case Q is Ar, it denotes a phenylene wherein 1H atom may be replaced by a group selected from C$_1$-C$_6$-alkyl, O—C$_1$-C$_6$-alkyl or CF$_3$.

In another embodiment, in case Q is Het, it denotes a divalent monocyclic unsaturated or aromatic 5- or 6-membered heterocyclic group having 1 or 2 nitrogen atoms.

In another embodiment, only one of R$^a$ and R$^b$ in Formulae (I), (Ia), (Ib), (Ic), (Id), (Ie) or (If) denotes H and the remaining group as the meaning defined under Formula (I).

"C$_1$-C$_6$-alkyl" or "C$_1$-C$_6$-alkyl group" denotes a linear or branched alkyl chain having 1 to 6 carbon atoms.

"C$_1$-C$_3$-alkyl" or "C$_1$-C$_3$-alkyl group" denotes a linear or branched alkyl chain having 1 to 3 carbon atoms.

"C$_1$-C$_6$-alkyl" or "C$_1$-C$_3$-alkyl" may also include haloalkyl. Halo-alkyl contains 1 to 10 halogen atoms, preferably 1 to 3 halogen atoms. Halo-alkyl contains for example a group —CF$_3$, —CHF$_2$ or —CH$_2$F.

"C$_2$-C$_6$-alkenyl" or "C$_2$-C$_6$-alkenyl group" denotes a linear or branched carbon chain having 2 to 6 carbon atoms and 1 to 3 double bonds.

"C$_2$-C$_6$-alkynyl" or "C$_2$-C$_6$-alkynyl group" denotes a linear or branched carbon chain having 2 to 6 carbon atoms and 1 to 3 triple bonds.

A "leaving group" denotes a chemical moiety which can be removed or replaced by another chemical group.

Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

The following abbreviations refer to the abbreviations used below:

AcNH$_2$ (Acetamide), AcOH (Acetic acid), 9-BBN (9-Borabicyclo 3.3.1 nonane), BINAP (2,2'-bis(disphenylphosphino)-1,1'-binaphthalene), BOP (Benzotriazole-1-yl-oxy-tris-(dimethylamino)-phosphonium hexafluorophosphate) dba (dibenzylidene acetone), tBu (tert-Butyl), tBuOK (Potassium tert-butoxide), CDI (1,1'-Carbonyldiimidazole), COMU (1-Cyano-2-ethoxy-2-oxoethylidenaminooxy)dimethylamino-morpholino-carbenium hexafluorophosphate), DBU (1,8-Dizabicyclo[5.4.0]undec-7-ene), DCM (Dichloromethane), DIAD (Diisobutylazodicarboxylate), DIEA (diisopropyl ethylamine), DMA (dimethyl acetamide), DMAP (4-Dimethylaminopyridine), DMSO (Dimethyl Sulfoxide), DMF (N,N-Dimethylformamide), EDC (1-Ethyl-3-(3-dimethylaminopropyl)carbodiimide hydrochloride), EtOAc (Ethyl acetate), EtOH (Ethanol), g (gram), cHex (Cyclohexane), HPLC (High Performance Liquid Chromatography), hr (hour), MHz (Megahertz), MeOH (Methanol), min (minute), mL (milliliter), mmol (millimole), mM (millimolar), mp (melting point), MS (Mass Spectrometry), MW (microwave), NMM (N-Methyl Morpholine), NMR (Nuclear Magnetic Resonance), NBS (N-BromoSuccinimide), PBS (Phosphate Buffered Saline), PMB (para-methoxybenzyl), RT (room temperature), SPA (Scintillation Proximity Assay), TBAF (Tetra-ButylAmmoniumFluoride), TBTU (N,N,N',N'-Tetramethyl-O-(benzotriazol-1-yl)uronium tetrafluoroborate), TEA (Triethyl amine), TFA (Trifluoroacetic acid), THF (Tetrahydrofuran), PetEther (Petroleum ether), TBME (tert-Butyl Methyl Ether), TLC (Thin Layer Chromatography), TMS (Trimethylsilyl), TMSI (Trimethylsilyl iodide), UV (Ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Depending on the nature of Q, E, R$^1$, R$^2$, R$^3$, R$^a$, R$^b$, n, m, q, different synthetic strategies may be selected for the synthesis of compounds of Formula (I). In the process illustrated in the following schemes, Q, E, R$^1$, R$^2$, R$^3$, R$^a$, R$^b$, n, m, q, are as above defined in the description unless otherwise mentioned.

Generally, triazolo-indazole compounds of formula (I) and related Formulae (Ia) and (Ib), wherein Q, E, R$^1$, R$^2$, R$^3$, R$^a$, R$^b$, n, m, q are defined as above can be prepared by 1,3-dipolar cycloaddition between an alkyne of general formula (II) wherein R$^1$, R$^2$, n are as above defined and PG$_1$ is H or a nitrogen protecting group such as, but not limited to tert-butyloxycarbonyl, acetyl, tetrahydropyrane, PMB and an azide of general formula (III), as outlined in scheme 1 and wherein Q, E and R$^3$ are as above defined. General protocols for such cycloaddition are given below in the examples, using conditions and methods well known to those skilled in the art. This reaction is preferably performed with Cu(II) salts such as copper sulphate pentahydrate or copper acetate in the presence of reducing agent such as sodium ascorbate or metallic copper as catalytic system in a mixture of tert-butanol, THF, dioxane or acetonitrile, with water. Organic solvent such as THF, toluene, DCM, acetonitrile in the presence of stoechiometric amount of Cu(I) salt such as CuI, Cu(CH$_3$CN)$_4$PF$_6$, CuBr(PPh$_3$)$_4$ or CuIP(OEt)$_3$ or Cu(II) salts and an excess of a base such as TEA, DIEA, 2,6-lutidine, pyridine can also be used. The cycloaddition can be carried out at temperature rising from RT to 150° C. in thermic or MW conditions in 15 min to 72 h. In case PG$_1$ is a nitrogen protective group, the cycloaddition is followed by a suitable deprotection step. The suitable conditions of the deprotection step may be for example an hydrolysis under acidic conditions using e.g. hydrochloric acid in dioxan, at room temperature or at a temperature from 20° C. to 100° C.

Scheme 1

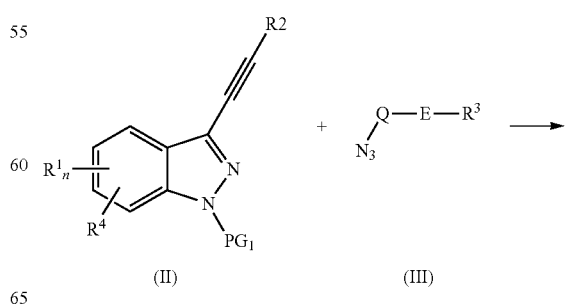

-continued

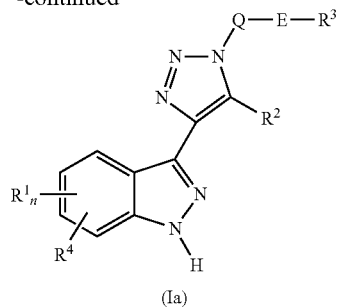

(Ia)

+

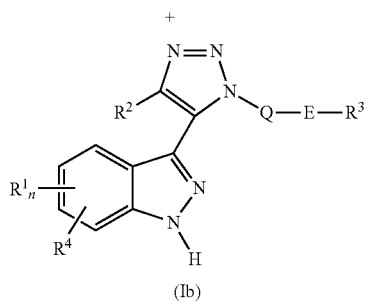

(Ib)

These conditions are applicable to any compound of general Formula (I).

Alkyne compounds of general formula (II) wherein $R^1$, $R^2$, n, $PG_1$ are as above defined can be obtained by coupling of a compound of Formula (IV) wherein $R^1$, n and $PG_1$ are as above defined and X denotes triflate or halide, preferably bromide or iodide with a compound of Formula (V) wherein $R^{2'}$ is a protective group such as but not limited to $Me_3Si$, or $R^2$ when $R^2$ is defined as above but preferrably not H, as outlined in Scheme 2. General protocols for such coupling are given below in the examples, using conditions and methods well known to those skilled in the art to perform such coupling. This reaction is preferably performed with an appropriate catalyst such as but not limited to dichlorobis(triphenylphosphine)palladium(II) or 1,1'-bis(diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. The reaction can also be performed in the presence of a suitable copper salt such as but not limited to copper (I) iodide, copper (I) bromide or copper (I) chloride. The reaction can be performed in the presence or absence of bases such as TEA, DIEA, NMM, piperidine, $Cs_2CO_3$, sodium phosphate, in the presence or absence of a suitable solvent such as THF, ACN, DMF or acetone. This coupling reaction can be carried out at a temperature between about 20° C. to about 100° C., preferably at about 70° C., for a few hours, such as one hour to 24 h. For a list of conditions described for the coupling of an aryl alkyne with an aryl or heteroaryl triflate or halide, see also *Chem. Rev.* 2007, 107, 874-892.

Scheme 2

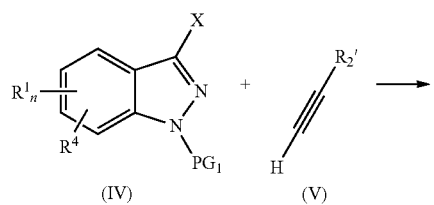

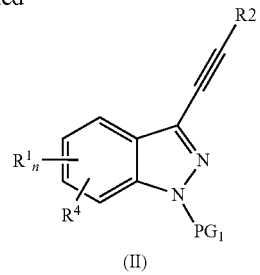

(II)

The method for preparing alkyne compounds of Formula (II) selected below:
3-ethynyl-1H-indazole
3-ethynyl-5-methyl-1H-indazole
tert-butyl 4-(3-ethynyl-1H-indazol-5-yl)piperidine-1-carboxylate
tert-butyl 3-ethynyl-5-(hydroxymethyl)-1H-indazole-1-carboxylate
tert-butyl 3-ethynyl-5-methyl-1H-indazole-1-carboxylate
5-bromo-3-ethynyl-1H-indazole
is more particularly described in the examples.

Compounds of general formula (IV) can be obtained by standard halogenation conditions when X is I, Cl, Br by treatment of indazole (VI) wherein $R^1$, n and $PG_1$ are as above defined with $X_2$ or NBX in a solvent such as DCM, DMF, Acetonitrile, THF or AcOH at temperatures rising from 0° C. to 100° C. for 1 h to 48 h as outlined in scheme 3.

Scheme 3

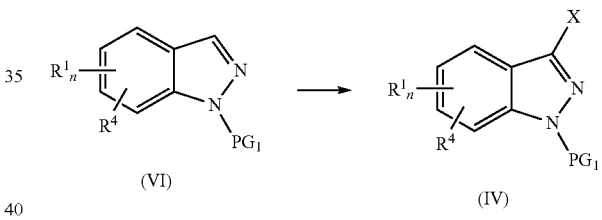

Compounds of general formula (VI) wherein $R^1$, n and $PG_1$ are as above defined are commercially available or can be obtained following standard indazole formation procedures described in literature (e.g. *Synthesis*, 1972, 375; *Bioorg. Med. Chem. Lett.*, 2001, 11, 1153-1156; *Bioorg. Med. Chem.*, 2008, 16, 1966-1982).

Indazoles formula (VI) and related formulae, wherein $R^1$, n and $PG_1$ are as above defined, can be converted to alternative indazoles of Formula (VI) and related formulae wherein $R^1$, n and $PG_1$ are as above defined, employing suitable interconversion techniques well known by those skilled in the art.

Indazole compounds of general formula (VIa) wherein $R^1$ is selected from $C_1$-$C_6$-alkyl, $C_2$-$C_6$-alkenyl, $C_2$-$C_6$-alkynyl, Cyc, $Het^1$, $Ar^1$, —$(CH_2)_q Het^1$, —$(CH_2)_q$O-$Het^1$, —$(CH_2)_q$O—$Ar^1$, —$(CH_2)_q Ar^1$, —$(CH_2)_q$Cyc, —$(CH_2)_q$NH—$(CH_2)_q$-$Het^1$, —$(CH_2)_q$NH—$(CH_2)_q$—$Ar^1$, wherein NH—$C_1$-$C_6$-alkyl, $OC_1$-$C_6$-alkyl, $C_1$-$C_6$-alkyl, $C_2$-$C_6$-alkenyl, $C_2$-$C_6$-alkynyl, may be substituted by 1 to 3 groups independently selected from $OC_1$-$C_3$-alkyl, OH, $CONH_2$, $NH_2$, $R^4$ is as above defined and PG1 is as above defined can be prepared by coupling reaction between indazole compounds of general formula (VIb) wherein $LG_1$ is a leaving group such as Cl, Br, I or a sulfonate ester such as triflate, and boronic acid or ester derivatives of Formula (VII) wherein R is H or an alkyl group and $R^1$ is as above defined, to give indazole compounds of general formula (VIc) wherein $R^1$ and $PG_1$ are as above defined, followed, or not followed, by a reduction of the resulting double bond as outlined in scheme 4. General protocols for such coupling are given below in the Examples, using conditions and methods well known to those skilled in the art to perform such coupling. In a typical procedure, indazole (VIb) and boronic acid or ester (VII) are heated in a suitable solvent, such as THF, toluene or dioxane, in the presence or absence of water as a co-solvent, in the presence of a base, such as as $Cs_2CO_3$, $K_2CO_3$, CsF, and with an appropriate catalyst such as but not limited to dichlorobis (triphenylphosphine)palladium(II), $Pd(PPh_3)_4$ or 1,1'-bis (diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. This coupling reaction can be carried out at a temperature between about 20° C. to about 150° C., preferably at about 120° C., for a few minutes to a few hours, possibly under microwave irradiation. The reduction step is usually performed under hydrogen pressure, between 1 and 60 bars, at a temperature ranging from RT to 80° C. in presence of a suitable catalyst such as Pd/C, $Pt_2O$ or Ra—Ni. Other sources of hydrogen such as ammonium formate can be used. R1 in Formula (VII) and (VIc) may be synthetic precursors of $R^1$ in Formula (VIa).

Scheme 4

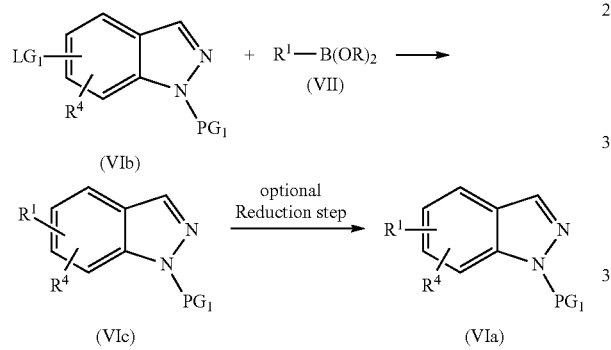

The conditions above-mentioned are applicable for instance in the reaction of scheme 4a wherein indazole compounds of general formula (VIa') wherein $R^c$ is H, $C_1$-$C_6$-alkyl, —$CONR^aR^b$, $SO_2NR^aR^b$ and PG1 is as above defined can be prepared by coupling reaction between indazole compounds of general formula (VIb') wherein $LG_1$ is a leaving group such as Cl, Br, I or a sulfonate ester such as triflate, and boronic acid or ester derivatives of Formula (VII') wherein R is H or an alkyl group and $R^c$ is as above defined.

Scheme 4a

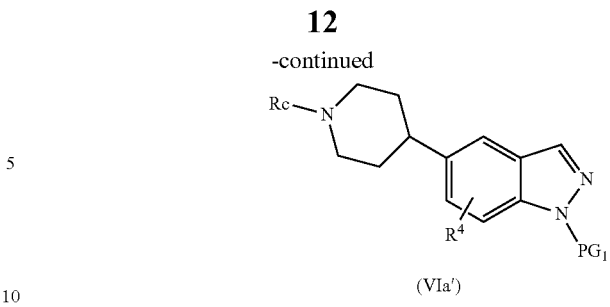

The method for preparing indazoles derivatives of Formula (VIa) selected below:

tert-butyl 4-(1H-indazol-5-yl)piperidine-1-carboxylate is more particularly described in the examples.

Alternatively, indazole compounds of general formula (VIa) wherein $R^1$, $R^4$, and $PG_1$ are as above defined can be prepared by coupling reaction between an indazole compound of general formula (VId) wherein R is H or an alkyl group and $PG_1$ is as above defined and compound of general formula (VIIa) wherein $R^1$ is as above defined and $LG_2$ is sulfonate ester such as triflate, followed, or not followed by a reduction of the resulting double bond as outlined in scheme 5. General protocols which can be used for such transformation are the same as above described.

Scheme 5

The conditions above-mentioned are applicable for instance in the reaction of scheme 5a wherein indazole compounds of general formula (VIa') wherein Rc is H, alkyl, amide, sulfonamide and $PG_1$ is as above defined can be prepared by coupling reaction between an indazole compound of general formula (VId') wherein R is H or an alkyl group and $PG_1$ is as above defined and compound of general formula (VIIa') wherein Rc is as above defined and $LG_2$ is sulfonate ester such as triflate.

Scheme 5a

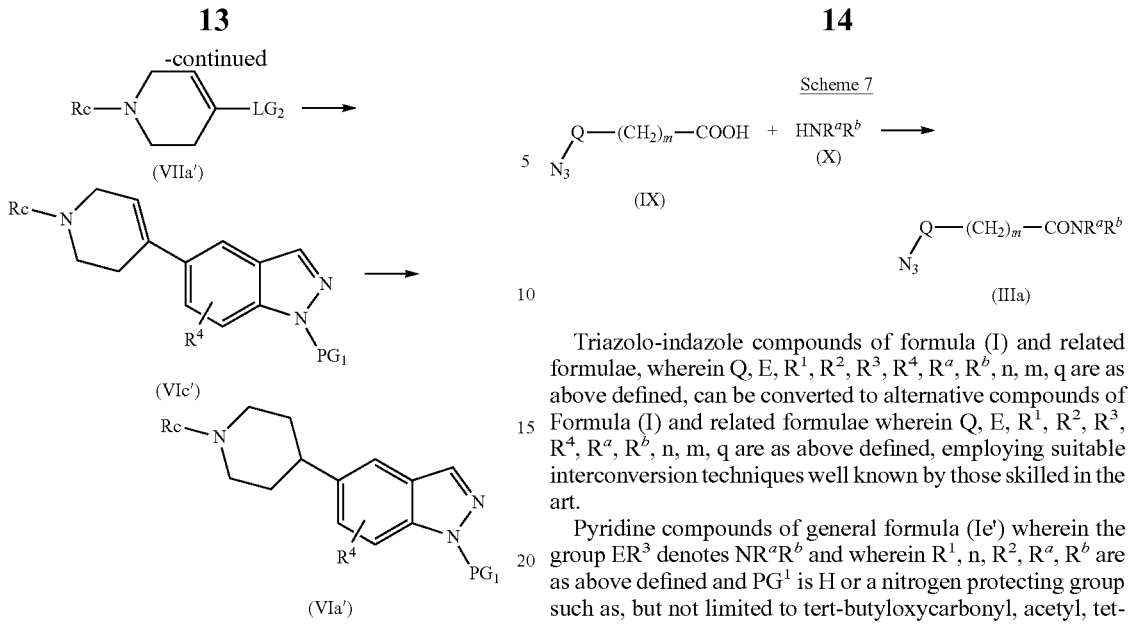

Azide compounds of general formula (III) wherein Q, E and R³ are as above defined can be prepared from amines of general formula (VIII) wherein Q, E and R³ are as above defined as outlined in scheme 6. General protocols for such reactions are given below in the examples, using conditions and methods well known to those skilled in the art. As an example, a two steps process can be used where amines (VIII) are first treated with sodium nitrite in a strong acid such as but not limited to AcOH, TFA or H₂SO₄ followed by NaN₃ in water at temperature rising from 0° C. to RT. A one pot procedure using tert-butylnitrile and TMS-azide in a solvent such as EtOAc at RT for 1 h to 12 h can also be used for such transformation. For a list of conditions described for azides formation see also *Angew. Chem. Int. Ed.*, 2005, 44, 5188-5244.

Scheme 6

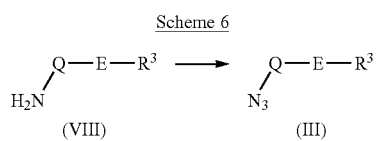

Alternatively, compounds of general formula (IIIa) wherein Q, m, $R^a$, $R^b$ are as above defined can be prepared by coupling of a carboxylic acid of Formula (IX) wherein Q and m are as above defined with an amine of general formula (X) wherein $R^a$, $R^b$ are as above defined as outlined in scheme 7. General protocols for such coupling are given below in the examples, using conditions and methods well known to those skilled in the art. Standard coupling agents, such as TBTU, COMU, EDC or isobutyl chloroformate can be used in the presence or not of a base such as DIEA, TEA or NMM in a suitable solvent such as DMF, Acetonitrile, THF or DCM at a temperature rising from about 0° C. to 50° C., preferably at 0° C. for a time of 30 minutes to a few hours. Alternatively, a carboxylic acid derivative (such as acyl chloride) can be coupled with the amine (X), using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours.

Scheme 7

$$\underset{N_3}{Q}-(CH_2)_m-COOH + HNR^aR^b \longrightarrow$$

(IX)                    (X)

$$\underset{N_3}{Q}-(CH_2)_m-CONR^aR^b$$

(IIIa)

Triazolo-indazole compounds of formula (I) and related formulae, wherein Q, E, R¹, R², R³, R⁴, $R^a$, $R^b$, n, m, q are as above defined, can be converted to alternative compounds of Formula (I) and related formulae wherein Q, E, R¹, R², R³, R⁴, $R^a$, $R^b$, n, m, q are as above defined, employing suitable interconversion techniques well known by those skilled in the art.

Pyridine compounds of general formula (Ie') wherein the group ER³ denotes $NR^aR^b$ and wherein R¹, n, R², $R^a$, $R^b$ are as above defined and PG¹ is H or a nitrogen protecting group such as, but not limited to tert-butyloxycarbonyl, acetyl, tetrahydropyrane, PMB can be prepared by reaction of a chloropyridine compound of general formula (Ie') wherein R¹, n, R² and PG₁ are as above defined, and wherein the group ER³ denotes Cl, and an amine of general formula (X) wherein $R^a$ and $R^b$ are as above defined as outlined in scheme 8. General protocols for such reaction are given below in the examples, using conditions and methods well known to those skilled in the art. This reaction is preferably performed at temperature rising from RT to 250° C. in the presence or not of a base such as Cs₂CO₃, K₂CO₃, TEA or DIEA and in a solvent such as DMF, DMSO, THF or the amine $HNR^aR^b$.

Scheme 8

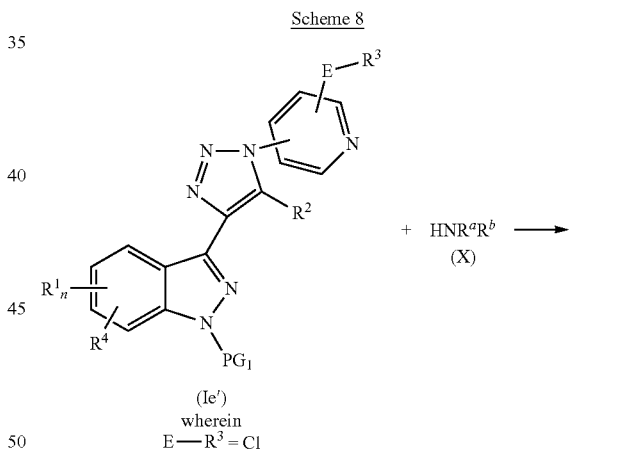

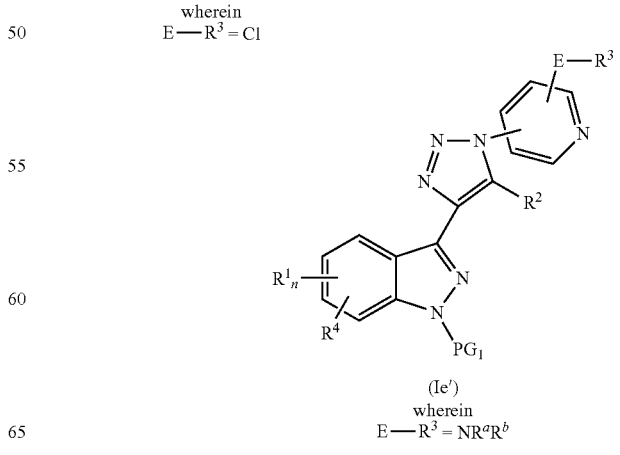

The method for preparing pyridine derivatives of Formula (e') selected below:
3-[1-(6-morpholin-4-ylpyridin-3-yl)-1H-1,2,3-triazol-4-yl]-1H-indazole
is more particularly described in the examples.

Amide compounds of general formula (I') wherein $R^3$ denotes $NR^aR^b$ and E denotes —$(CH_2)_mCO$, and $R^1$, $R^2$, $R^4$, Q, $R^a$, $R^b$, m, n are as above defined, and $PG_1$ is H or a nitrogen protecting group such as, but not limited to tert-butyloxycarbonyl, acetyl, tetrahydropyrane, PMB can be prepared by coupling of a carboxylic acid compound of general formula (I') wherein $R^3$ denotes —$(CH_2)_mCOOH$ and E denotes —$(CH_2)_q$ or a single bond, and $R^1$, $R^2$, $R^4$, Q, m, n, q and $PG_1$ are as above defined and an amine of general formula (X) wherein $R^a$ and $R^b$ are as above defined as outlined in scheme 9. General protocols for such reaction are given below in the examples, using conditions and methods well known to those skilled in the art. Standard coupling agent, such as TBTU, COMU, EDC or isobutyl chloroformate can be used in the presence or not of a base such as DIEA, TEA or NMM in a suitable solvent such as DMF, Acetonitrile, THF or DCM at a temperature rising from about 0° C. to 50° C., preferably at 0° C. for a time of 30 minutes to a few hours. Alternatively, a carboxylic acid derivative (such as acyl chloride) can be coupled with the amine $HNR^aR^b$, using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours.

Scheme 9

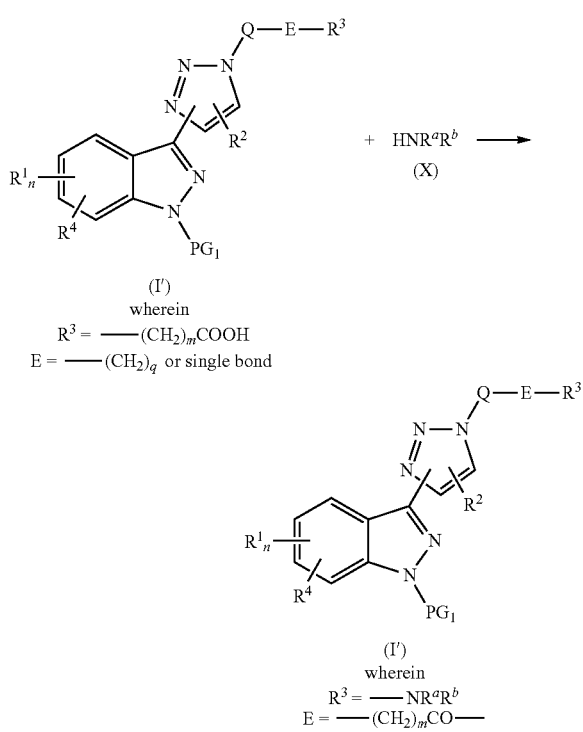

The method for preparing amide derivatives of Formula (I') selected below:
3-{1-[4-(2-morpholin-4-yl-2-oxoethyl)phenyl]-1H-1,2,3-triazol-4-yl}-1H-indazole
3-{1-[4-(2-oxo-2-pyrrolidin-1-ylethyl)phenyl]-1H-1,2,3-triazol-4-yl}-1H-indazole
3-{4-[4-(1H-indazol-3-yl)-1H-1,2,3-triazol-1-yl]phenyl}-N,N-dimethylpropanamide
3-{1-[4-(3-morpholin-4-yl-3-oxopropyl)phenyl]-1H-1,2,3-triazol-4-yl}-1H-indazole
3-{1-[4-(3-oxo-3-pyrrolidin-1-ylpropyl)phenyl]-1H-1,2,3-triazol-4-yl}-1H-indazole
3-(1-{4-[3-(4-methylpiperazin-1-yl)-3-oxopropyl]phenyl}-1H-1,2,3-triazol-4-yl)-1H-indazole
4-[4-(1H-indazol-3-yl)-1H-1,2,3-triazol-1-yl]-2-methoxy-N,N-dimethylbenzamide
1-{4-[4-(1H-indazol-3-yl)-1H-1,2,3-triazol-1-yl]benzoyl}pyrrolidin-3-ol
1-{4-[4-(1H-indazol-3-yl)-1H-1,2,3-triazol-1-yl]benzoyl}-N,N-dimethylpyrrolidin-3-amine
(1-{4-[4-(1H-indazol-3-yl)-1H-1,2,3-triazol-1-yl]benzoyl}piperidin-4-yl)methanol
1-(1-{4-[4-(1H-indazol-3-yl)-1H-1,2,3-triazol-1-yl]benzoyl}piperidin-3-yl)-N,N-dimethylmethanamine
1-{4-[4-(1H-indazol-3-yl)-1H-1,2,3-triazol-1-yl]benzoyl}piperidin-3-ol
4-[4-(1H-indazol-3-yl)-1H-1,2,3-triazol-1-yl]-N-(1-methyl-2-oxopyrrolidin-3-yl)benzamide
3-{1-[3-methoxy-4-(morpholin-4-ylcarbonyl)phenyl]-1H-1,2,3-triazol-4-yl}-1H-indazole
3-(1-{4-[2-(4-methylpiperazin-1-yl)-2-oxoethyl]phenyl}-1H-1,2,3-triazol-4-yl)-1H-indazole
1-{4-[4-(1H-indazol-3-yl)-1H-1,2,3-triazol-1-yl]benzoyl}piperidin-4-ol
1-{4-[4-(1H-indazol-3-yl)-1H-1,2,3-triazol-1-yl]benzoyl}-N,N-dimethylpiperidin-4-amine
3-[1-(4-{[3-(pyrrolidin-1-ylcarbonyl)piperidin-1-yl]carbonyl}phenyl)-1H-1,2,3-triazol-4-yl]-1H-indazole
3-[1-(4-{[3-(morpholin-4-ylmethyl)piperidin-1-yl]carbonyl}phenyl)-1H-1,2,3-triazol-4-yl]-1H-indazole
1-[(1-{4-[4-(1H-indazol-3-yl)-1H-1,2,3-triazol-1-yl]benzoyl}piperidin-3-yl)methyl]pyrrolidin-2-one
2-{4-[4-(1H-indazol-3-yl)-1H-1,2,3-triazol-1-yl]benzoyl}-8-methyl-2,8-diazaspiro[5.5]undecane
4-[4-(1H-indazol-3-yl)-1H-1,2,3-triazol-1-yl]-N-[(1-methylpiperidin-3-yl)methyl]benzamide
3-{1-[3-(2-morpholin-4-yl-2-oxoethyl)phenyl]-1H-1,2,3-triazol-4-yl}-1H-indazole
3-(1-{3-[2-(4-methylpiperazin-1-yl)-2-oxoethyl]phenyl}-1H-1,2,3-triazol-4-yl)-1H-indazole
3-{1-[3-(2-oxo-2-pyrrolidin-1-ylethyl)phenyl]-1H-1,2,3-triazol-4-yl}-1H-indazole
3-{1-[3-(3-morpholin-4-yl-3-oxopropyl)phenyl]-1H-1,2,3-triazol-4-yl}-1H-indazole
3-{1-[3-(3-oxo-3-pyrrolidin-1-ylpropyl)phenyl]-1H-1,2,3-triazol-4-yl}-1H-indazole
4-[4-(1H-indazol-3-yl)-1H-1,2,3-triazol-1-yl]-N-[2-(1-methylpyrrolidin-2-yl)ethyl]benzamide
1-(1-{4-[4-(1H-indazol-3-yl)-1H-1,2,3-triazol-1-yl]benzoyl}piperidin-4-yl)-N,N-dimethylmethanamine
2-(1-{4-[4-(1H-indazol-3-yl)-1H-1,2,3-triazol-1-yl]benzoyl}piperidin-2-yl)-N,N-dimethylethanamine
(3R)-1-{4-[4-(1H-indazol-3-yl)-1H-1,2,3-triazol-1-yl]benzoyl}piperidin-3-ol
(3S)-1-{4-[4-(1H-indazol-3-yl)-1H-1,2,3-triazol-1-yl]benzoyl}piperidin-3-ol
4-[4-(1H-indazol-3-yl)-1H-1,2,3-triazol-1-yl]-N-[1-(1-methylpiperidin-4-yl)-1H-pyrazol-4-yl]benzamide
((2S)-1-{4-[4-(1H-indazol-3-yl)-1H-1,2,3-triazol-1-yl]benzoyl}pyrrolidin-2-yl)methanol
(1-{4-[4-(1H-indazol-3-yl)-1H-1,2,3-triazol-1-yl]benzoyl}piperidin-2-yl)methanol
N-cyclohexyl-N-(2-hydroxyethyl)-4-[4-(1H-indazol-3-yl)-1H-1,2,3-triazol-1-yl]benzamide
3-[1-(4-{[(2S)-2-(methoxymethyl)pyrrolidin-1-yl]carbonyl}phenyl)-1H-1,2,3-triazol-4-yl]-1H-indazole 3-(1-{4-[(4-methoxypiperidin-1-yl)carbonyl]phenyl}-1H-1,2,3-triazol-4-yl)-1H-indazole
6-methyl-2-[(3-{1-[4-(morpholin-4-ylcarbonyl)phenyl]-1H-1,2,3-triazol-4-yl}-1H-indazol-5-yl)methyl]pyridazin-3(2H)-one
4-[4-(1H-indazol-3-yl)-1H-1,2,3-triazol-1-yl]-N-[1-(2-morpholin-4-ylethyl)-1H-pyrazol-4-yl]benzamide
4-[4-(1H-indazol-3-yl)-1H-1,2,3-triazol-1-yl]-N-[1-(1-methylpyrrolidin-3-yl)-1H-pyrazol-4-yl]benzamide
3-[1-(4-{[3-(2-methoxyethyl)piperidin-1-yl]carbonyl}phenyl)-1H-1,2,3-triazol-4-yl]-1H-indazole
1-{4-[4-(1H-indazol-3-yl)-1H-1,2,3-triazol-1-yl]benzoyl}azetidin-3-ol
3-{1-[4-({3-[(2-methyl-1H-imidazol-1-yl)methyl]piperidin-1-yl}carbonyl)phenyl]-1H-1,2,3-triazol-4-yl}-1H-indazole
4-[4-(1H-indazol-3-yl)-1H-1,2,3-triazol-1-yl]-N-(1-methylpiperidin-4-yl)benzamide
2-(1-{4-[4-(1H-indazol-3-yl)-1H-1,2,3-triazol-1-yl]benzoyl}piperidin-2-yl)ethanol
3-[1-(4-{[3-(methoxymethyl)piperidin-1-yl]carbonyl}phenyl)-1H-1,2,3-triazol-4-yl]-1H-indazole
N-(2-hydroxybutyl)-4-[4-(1H-indazol-3-yl)-1H-1,2,3-triazol-1-yl]benzamide
3-(1-{4-[(4-pyrrolidin-1-ylpiperidin-1-yl)carbonyl]phenyl}-1H-1,2,3-triazol-4-yl)-1H-indazole
4-[4-(1H-indazol-3-yl)-1H-1,2,3-triazol-1-yl]-N-[1-(8-methyl-8-azabicyclo[3.2.1]oct-3-yl)-1H-pyrazol-4-yl]benzamide
3-[1-(4-{[3-(1H-imidazol-1-ylmethyl)piperidin-1-yl]carbonyl}phenyl)-1H-1,2,3-triazol-4-yl]-1H-indazole
3-(1-{4-[(3-methoxypiperidin-1-yl)carbonyl]phenyl}-1H-1,2,3-triazol-4-yl)-1H-indazole is more particularly described in the examples.

Compounds of general formula (I') wherein E denotes —(CH$_2$)$_q$, R$^3$ is NR$^a$R$^b$, and R$^1$, R$^2$, R$^4$, Q, q, R$^a$, R$^b$, n are as above defined and PG$_1$ is H or a nitrogen protecting group such as, but not limited to tert-butyloxycarbonyl, acetyl, tetrahydropyrane, PMB can be prepared by reductive amination between an aldehyde compound of general formula (X$_1$) wherein R$^1$, R$^2$, R$^4$, Q, q, m and PG$_1$ are as above defined and an amine of general formula (X) wherein R$^a$ and R$^b$ are as above defined as outlined in scheme 10. General protocols for such reaction are given below in the examples, using conditions and methods well known to those skilled in the art. Standard reducing agents such as sodium triacetoxyborohydride or sodium cyanoborohydride can be used in suitable solvents such as DCM, 1,2-dichloroethane at temperature rising from RT to 70° C. for a few hours, such as one hour to 24 hours.

Scheme 10

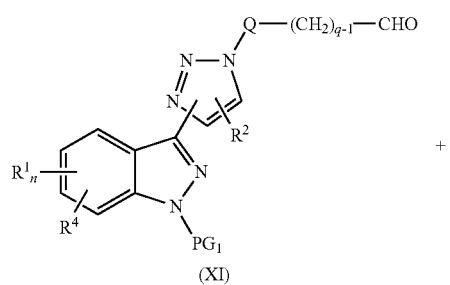

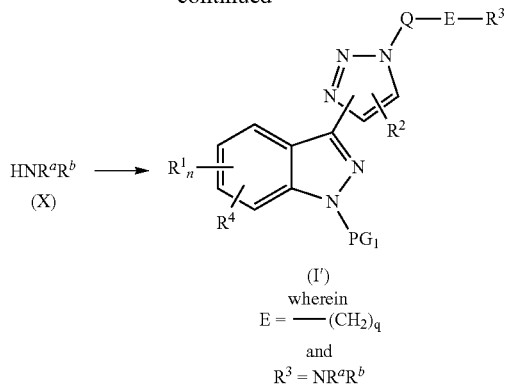

wherein
E = —(CH$_2$)$_q$
and
R$^3$ = NR$^a$R$^b$

The method for preparing amine derivatives of Formula (I') selected below:

5-methyl-3-{1-[4-(pyrrolidin-1-ylmethyl)phenyl]-1H-1,2,3-triazol-4-yl}-1H-indazole
5-methyl-3-{1-[4-(pyrrolidin-1-ylmethyl)phenyl]-1H-1,2,3-triazol-4-yl}-1H-indazole
5-methyl-3-{1-[4-(morpholin-4-ylmethyl)phenyl]-1H-1,2,3-triazol-4-yl}-1H-indazole
N-methyl-1-{4-[4-(5-methyl-1H-indazol-3-yl)-1H-1,2,3-triazol-1-yl]phenyl}methanamine
5-methyl-3-(1-{4-[(4-methylpiperazin-1-yl)methyl]phenyl}-1H-1,2,3-triazol-4-yl)-1H-indazole
N,N-dimethyl-1-{4-[4-(5-methyl-1H-indazol-3-yl)-1H-1,2,3-triazol-1-yl]phenyl}methanamine
5-methyl-3-{1-[4-(piperazin-1-ylmethyl)phenyl]-1H-1,2,3-triazol-4-yl}-1H-indazole is more particularly described in the examples.

Amide compounds of general formula (I') wherein E denotes —(CH$_2$)$_m$CO—, and R$^1$, R$^2$, R$^3$, R$^4$, m, n are as above defined and PG$_1$ is H or a nitrogen protecting group such as, but not limited to tert-butyloxycarbonyl, acetyl, tetrahydropyrane, PMB can be prepared by coupling of a amine compound of general formula (XIII) wherein R$^1$, R$^2$, R$^4$, Q, m, n and PG$_1$ are as above defined and an acid of general formula (XII) wherein R$^3$ is as above defined as outlined in scheme 11. General protocols for such reaction are given below in the examples, using conditions and methods well known to those skilled in the art. Standard coupling agent, such as TBTU, COMU, EDC or isobutyl chloroformate can be used in the presence or not of a base such as DIEA, TEA or NMM in a suitable solvent such as DMF, Acetonitrile or THF or DCM at a temperature rising from about 0° C. to 50° C., preferably at 0° C. for a time of 30 minutes to a few hours. Alternatively, a carboxylic acid derivative (such as acyl chloride, R$^3$COCl) can be coupled with the amine (XIII), using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours.

Scheme 11

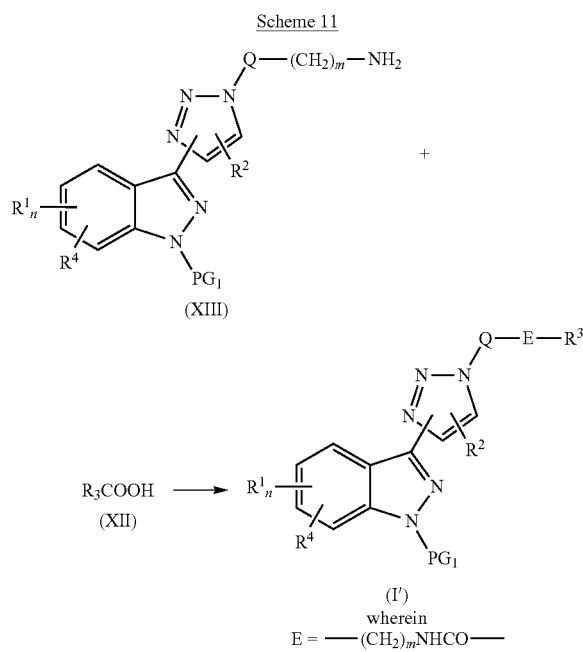

The method for preparing amide derivatives of Formula (I') selected below:
N-{4-[4-(1H-indazol-3-yl)-1H-1,2,3-triazol-1-yl]benzyl}cyclopentanecarboxamide
N-{4-[4-(1H-indazol-3-yl)-1H-1,2,3-triazol-1-yl]benzyl}acetamide
N-{4-[4-(1H-indazol-3-yl)-1H-1,2,3-triazol-1-yl]benzyl}isonicotinamide
N-{4-[4-(1H-indazol-3-yl)-1H-1,2,3-triazol-1-yl]benzyl}-2-morpholin-4-ylacetamide
N-{4-[4-(1H-indazol-3-yl)-1H-1,2,3-triazol-1-yl]benzyl}tetrahydro-2H-pyran-4-carboxamide
is more particularly described in the examples.

Pyridazinone compounds of general formula (If$^b$) wherein Q, E, R$^2$, R$^3$ are as above defined, PG$_1$ is H or a nitrogen protecting group such as, but not limited to tert-butyloxycarbonyl, acetyl, tetrahydropyrane, PMB and R$^d$ is H, C$_1$-C$_6$-alkyl, Ar$^1$, or Het$^1$ can be prepared following synthetic path outline in scheme 12. One preferred synthetic path involves the reaction of an alcohol compound of general formula (If') wherein R$^1$ denotes CH$_2$OH and Q, E, R$^2$, R$^3$, PG$_1$ are as above defined with a pyridazinone compound of general formula (XIV) wherein R$^d$ is as above defined under Mitsunobu reaction conditions. General protocols for such reaction are given below in the examples, using conditions and methods well known to those skilled in the art. This reaction is preferably performed in a solvent such as DCM, THF, DMF at a temperature rising from 0° C. to 50° C., preferably at RT in the presence of a phosphine, such as but not limited to triphenylphosphine, and an azadicarboxylate, such as but not limited to diisopropylazadicarboxylate. A second preferred synthetic path involves the reaction of compound of general formula (If') wherein R$^1$ denotes CH$_2$Hal, preferrably CH$_2$Br, and Q, E, R$^2$, R$^3$ and PG$_1$ are as above define or (If') wherein R$^1$ denotes CH$_2$LG$_3$ and Q, E, R$^2$, R$^3$, PG$_1$ are as above defined and LG$_3$ is a leaving group such Cl, Br, I, or a sulfonate ester such as mesylate with a pyridazinone (XIV) wherein R$^d$ is as above defined. General protocols for such reaction are given below in the examples, using conditions and methods well known to those skilled in the art. This reaction is preferably conducted in the presence of a base such as but not limited to NaH, tert-BuOK, NaOEt, K$_2$CO$_3$, Cs$_2$CO$_3$ in a solvent such as THF, ACN, DMF, EtOH at a temperature rising from RT to 80° C. Intermediate of general formula (If') wherein R$^1$ denotes CH$_2$Br can be obtained by bromation of methyl compound of general formula (If') wherein R$^1$ is CH$_3$ and wherein Q, E, R$^2$, R$^3$, PG$_1$ are as above defined, using conditions and methods well known to those skilled in the art, in the presence of a suitable source of bromine such as NBS or Br$_2$, a radical initiator such as AIBN, benzoylperoxide, or light in a suitable solvent such as CCl$_4$, HCCl$_3$, ACN at a temperature rising from about RT to 120° C. for a few hours. A preferred condition for this transformation is described in Synlett, (2005), 18, 2837-2842 and uses NBS in presence of ZrCl$_4$ in DCM. Intermediate of general formula (If') wherein R$^1$ is CH$_2$LG$_3$ can be obtained by sulfonylation or halogenation using conditions and methods well known to those skilled in the art. Standard conditions for the sulfonylation use appropriate sulfonyl chloride in presence of a base such as TEA, DIEA or pyridine in a solvent such as DCM or THF at a temperature rising from 0° C. to 50° C., preferably at RT. Standard condition for the halogenation use SOCl$_2$, POCl$_3$, PCl$_5$ in a solvent such as DCM at a temperature rising from 0° C. to 60° C., preferably at RT for a few hours.

Scheme 12

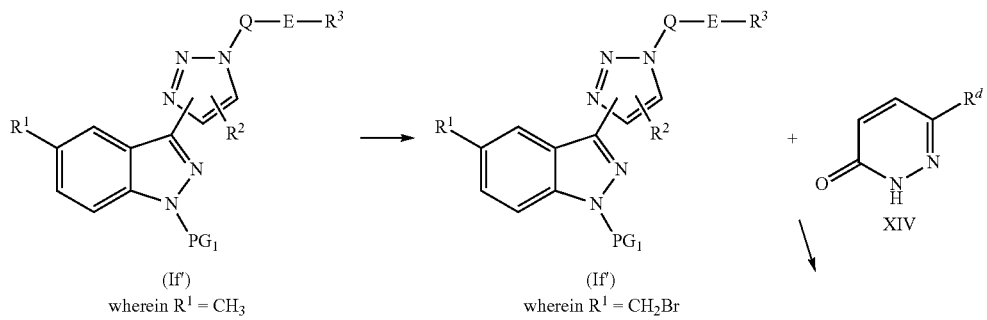

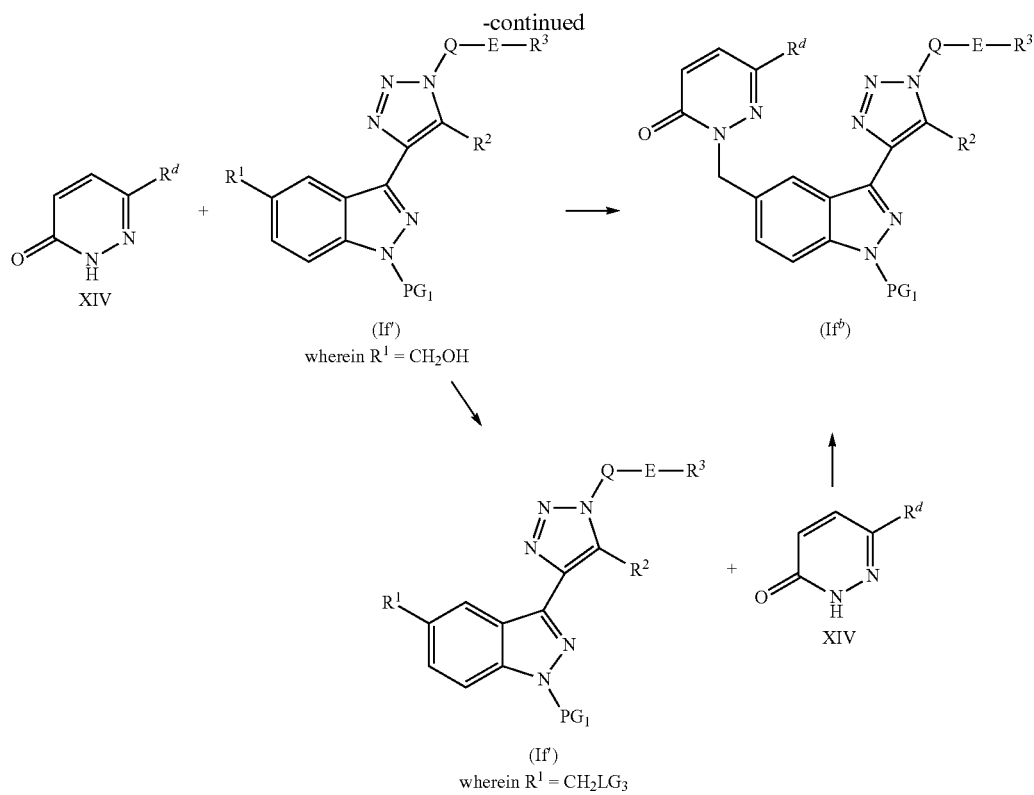

The above method is also suitable for the preparation of compounds of Formula (I) and related Formulae wherein $R^1$ is linked at another position of the indazol ring, e.g. positions 4, 6 or 7.

The method for preparing amide derivatives of Formula (If$^b$) selected below:
6-(3,5-difluorophenyl)-2-[(3-{1-[4-(morpholin-4-ylcarbonyl)phenyl]-1H-1,2,3-triazol-4-yl}-1H-indazol-5-yl)methyl]pyridazin-3(2H)-one
2-[(3-{1-[4-(morpholin-4-ylcarbonyl)phenyl]-1H-1,2,3-triazol-4-yl}-1H-indazol-5-yl)methyl]pyridazin-3(2H)-one
2-[(3-{1-[4-(morpholin-4-ylcarbonyl)phenyl]-1H-1,2,3-triazol-4-yl}-1H-indazol-5-yl)methyl]-6-pyridin-4-ylpyridazin-3(2H)-one
6-methyl-2-[(3-{1-[4-(morpholin-4-ylcarbonyl)phenyl]-1H-1,2,3-triazol-4-yl}-1H-indazol-5-yl)methyl]pyridazin-3(2H)-one
is more particularly described in the examples.

Indazoles of formula (If)) wherein $R^1$ is an $Ar^1$, $Het^1$, $C_2$-$C_6$-alkenyl, $C_2$-$C_6$-alkynyl, or Cyc and $PG_1$ is as above defined can be prepared by Suzuki-Miyura coupling reaction between an indazole of formula (If'), wherein $LG_1$ is Cl, Br, I or a sulfonate ester such as triflate, and a boronic acid or ester of Formula (XV) wherein $R^1$ is as above defined and R is H or an alkyl group (Miyaura, N.; Suzuki, A. Chem. Rev. 1995, 95, 2457; Takahiro I. and Toshiaki M., Tetrahedron Lett. 2005, 46, 3573-3577) as outlined in scheme 13. General protocols for such coupling are given below in the Examples, using conditions and methods well known to those skilled in the art to perform such coupling. In a typical procedure, indazole (If') wherein $R^1$ is $LG_1$ and boronic acid or ester (XV) are heated in a suitable solvent, such as THF, toluene or dioxane, in the presence or absence of water as a co-solvent, in the presence of a base, such as $Cs_2CO_3$, $K_2CO_3$, CsF, and with an appropriate catalyst such as but not limited to dichlorobis (triphenylphosphine)palladium(II), $Pd(PPh_3)_4$ or 1,1'-bis (diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. This coupling reaction can be carried out at a temperature between about 20° C. to about 150° C., preferably at about 120° C., for a few minutes to a few hours, possibly under microwave irradiation.

Scheme 13

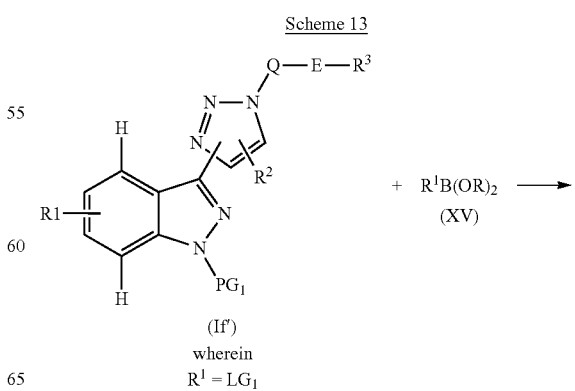

-continued

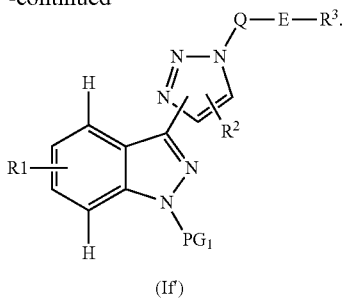

(If')

wherein R$^1$ = Ar$^1$, Het$^1$, Cyc or C$_2$-C$_6$-alkenyl or C$_2$-C$_6$-alkynyl Conditions above described are applicable to the reaction of scheme 13a wherein R$^1$, PG$_1$, R$^2$, Q, E, R$^3$ are as above defined.

Scheme 13a

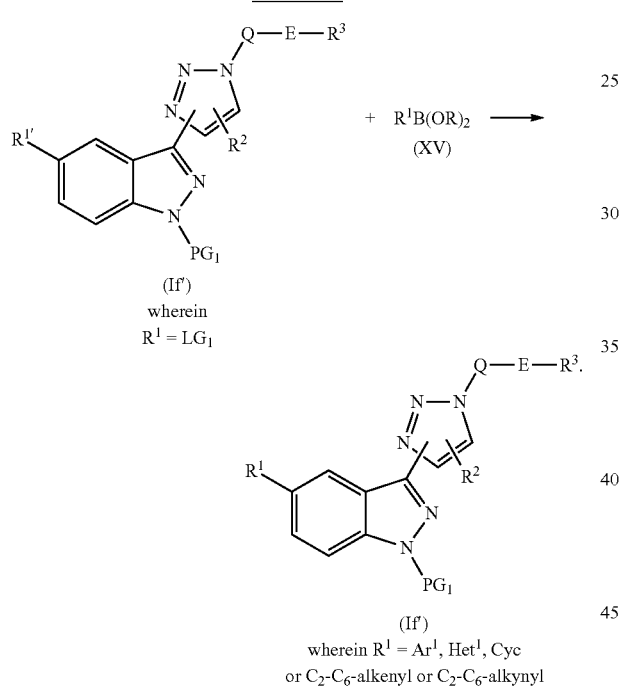

wherein R$^1$ = Ar$^1$, Het$^1$, Cyc or C$_2$-C$_6$-alkenyl or C$_2$-C$_6$-alkynyl The above method is also suitable for the preparation of compounds of Formula (I) and related Formulae wherein R$^1$ is linked at another position of the indazol ring, e.g. positions 4, 6 or 7.

The method for preparing amide derivatives of Formula (If') selected below:
5-(1-benzyl-1,2,3,6-tetrahydropyridin-4-yl)-3-{1-[4-(morpholin-4-ylcarbonyl)phenyl]-1H-1,2,3-triazol-4-yl}-1H-indazole
5-(1-methyl-1H-pyrazol-4-yl)-3-{1-[4-(morpholin-4-ylcarbonyl)phenyl]-1H-1,2,3-triazol-4-yl}-1H-indazole
5-(1-methyl-1,2,3,6-tetrahydropyridin-4-yl)-3-{1-[4-(morpholin-4-ylcarbonyl)phenyl]-1H-1,2,3-triazol-4-yl}-1H-indazole
is more particularly described in the examples.

Indazoles of formula (If$^c$) wherein Q, E, R$^2$, R$^3$ and PG$_1$ are as above defined and R$^c$ is H, C$_1$-C$_6$-alkyl, —CONR$^a$R$^b$, SO$_2$NR$^a$R$^b$ can be prepared by reaction of a compound of general formula (XVII) wherein Q, E, R$^2$, R$^3$ and PG1 are as above defined with a compound of general formula (XVI) wherein R$^c$ is as above described and LG$_3$ is a leaving group such Cl, Br, I, or a sulfonate ester such as mesylate as outlined in scheme 14. General protocols for such reaction are given below in the examples, using conditions and methods well known to those skilled in the art. This reaction is preferably performed in a solvent such as DCM, THF, DMF, ACN in the presence of a base such as K$_2$CO$_3$, NaHCO$_3$, Cs$_2$CO$_3$ in the presence or not of KI or NaI at a temperature rising from 0° C. to 100° C., possibly under microwave irradiation.

Scheme 14

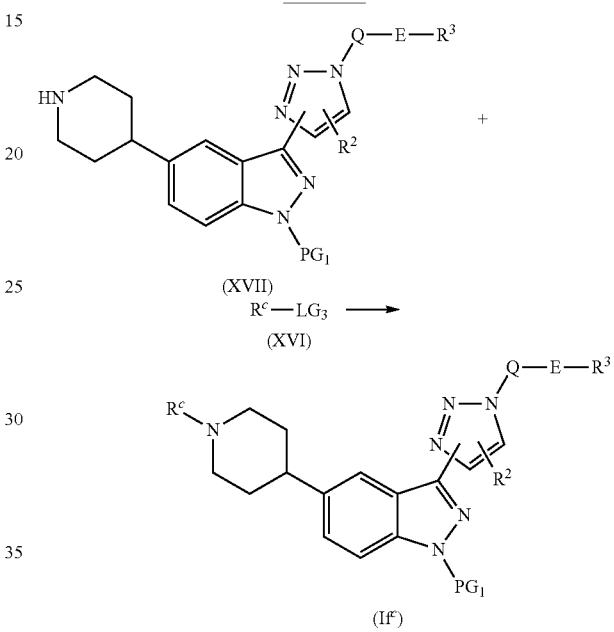

The above method is also suitable for the preparation of compounds of Formula (I) and related Formulae wherein R$^1$ is linked at another position of the indazol ring, e.g. positions 4, 6 or 7.

The method for preparing indazoles derivatives of Formula (If$^c$) selected below:
5-[1-(2-fluoroethyl)piperidin-4-yl]-3-{1-[4-(morpholin-4-ylcarbonyl)phenyl]-1H-1,2,3-triazol-4-yl}-1H-indazole
5-(1-acetylpiperidin-4-yl)-3-{1-[4-(morpholin-4-ylcarbonyl)phenyl]-1H-1,2,3-triazol-4-yl}-1H-indazole According to a further general process, compounds of Formula I can be converted to alternative compounds of Formula I, employing suitable interconversion techniques such as hereinafter described in the Examples.

If the above set out general synthetic methods are not applicable for obtaining compounds according to Formula I and/or necessary intermediates for the synthesis of compounds of formula I, suitable methods of preparation known by a person skilled on the art should be used. In general, the synthesis pathways for any individual compound of Formula I will depend on the specific substitutents of each molecule and upon the ready availability of intermediates necessary; again such factors being appreciated by those of ordinary skill in the art. For all the protection, de-protection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley-Interscience, 1991.

The group Q-E-R³ in Formula (I) and related Formulae (Ia), (Ib), (Ic), (Id), (Ie) and (If) preferably denotes one of the following groups:
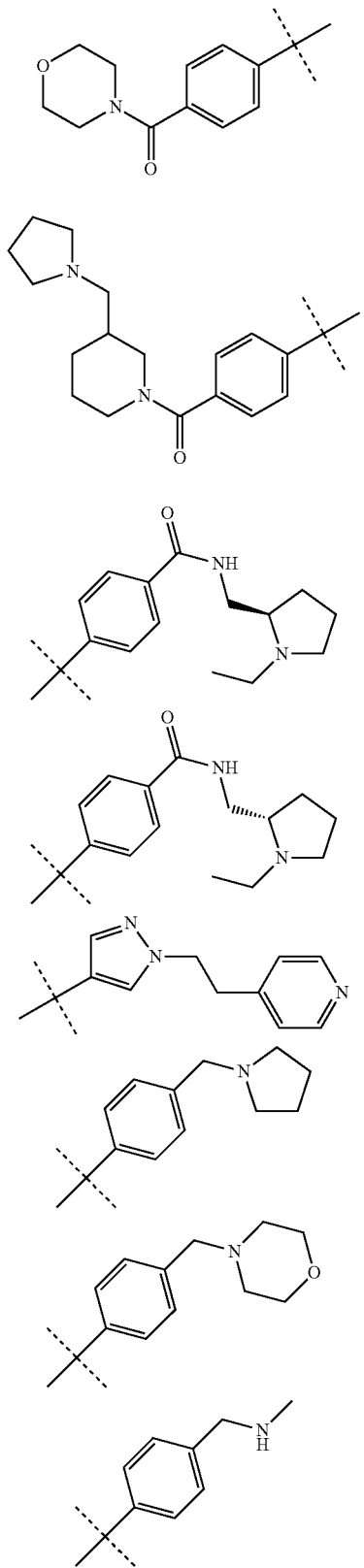
-continued
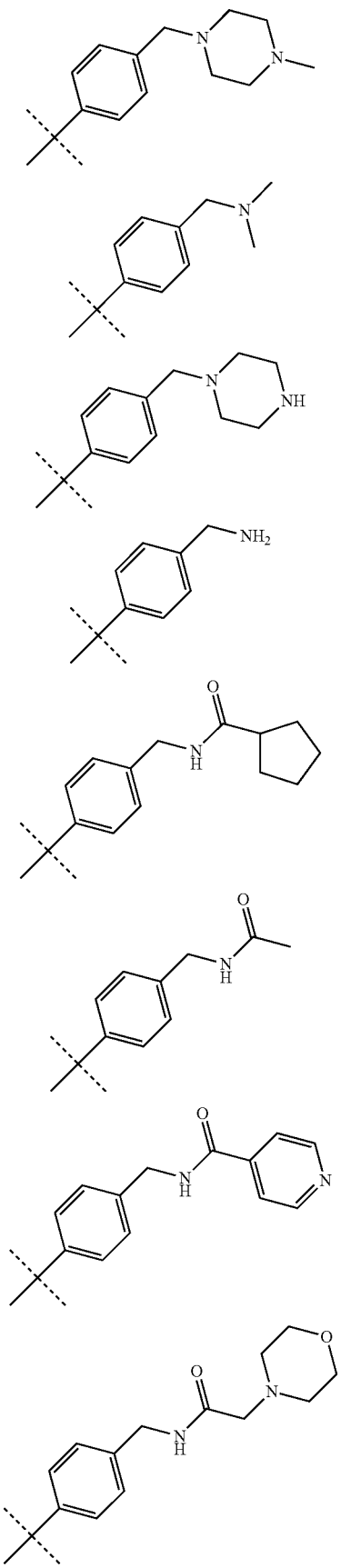

27
-continued
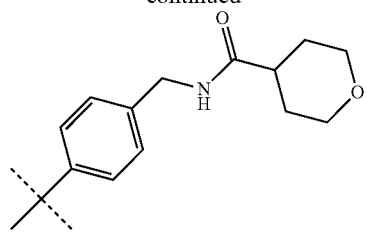
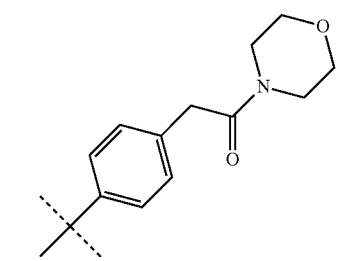
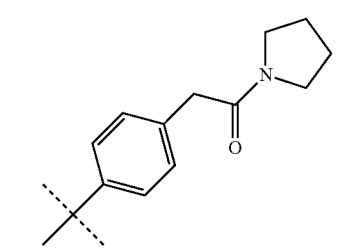
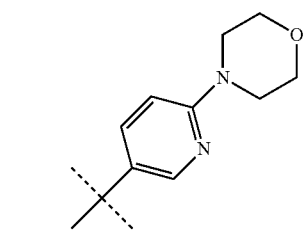
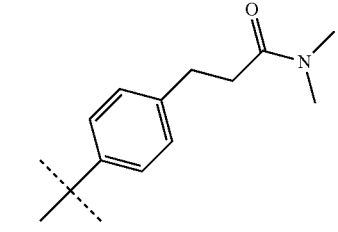
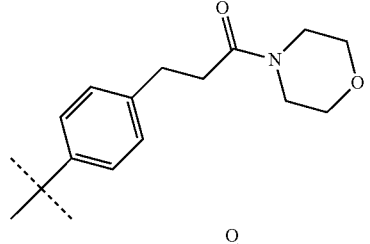
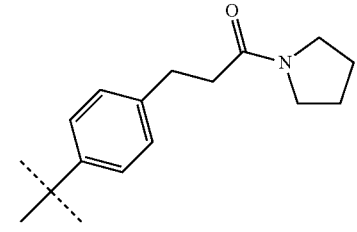
28
-continued
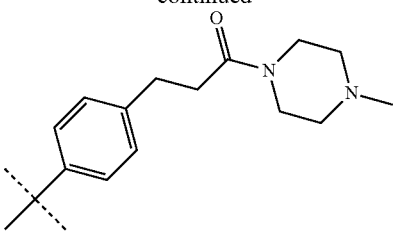
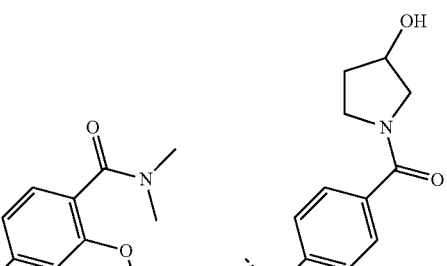
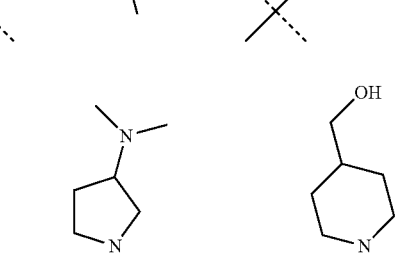
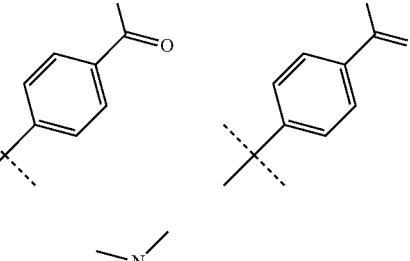
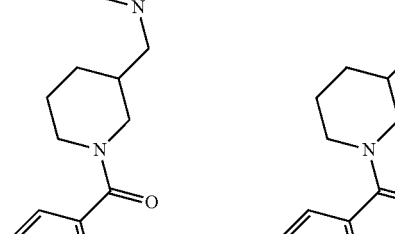
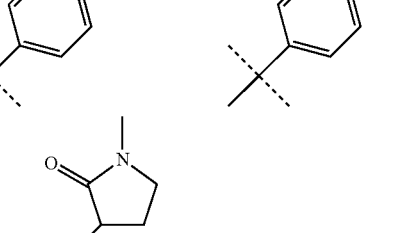
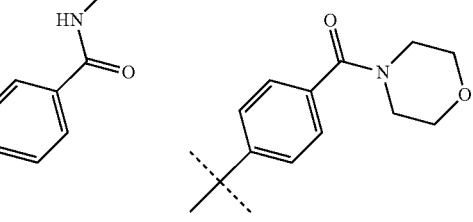

-continued
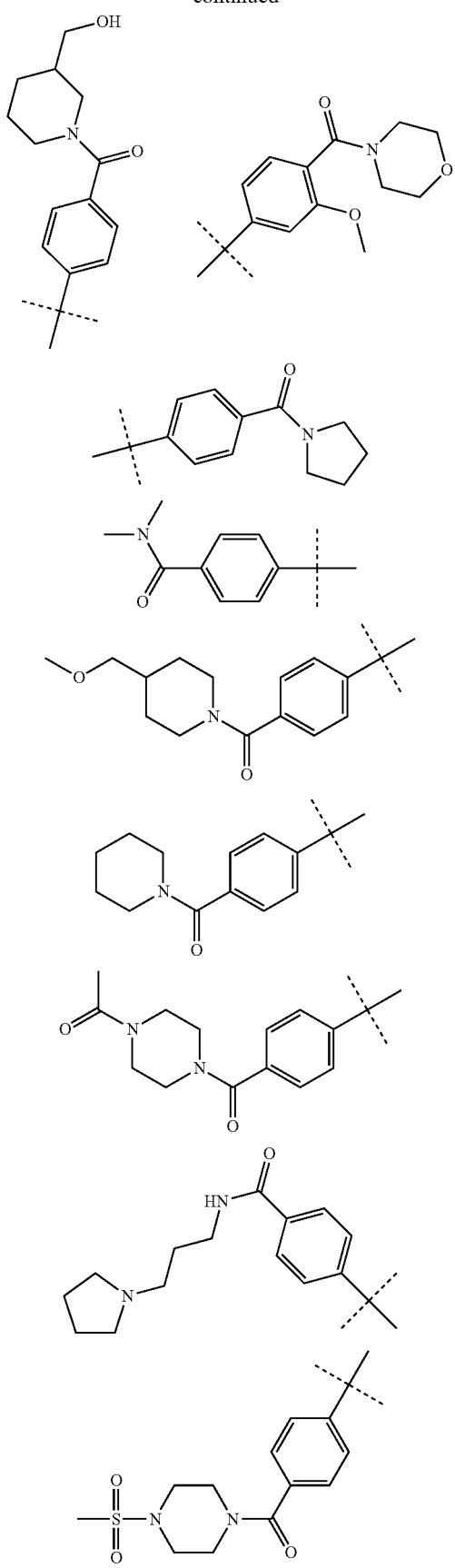
-continued
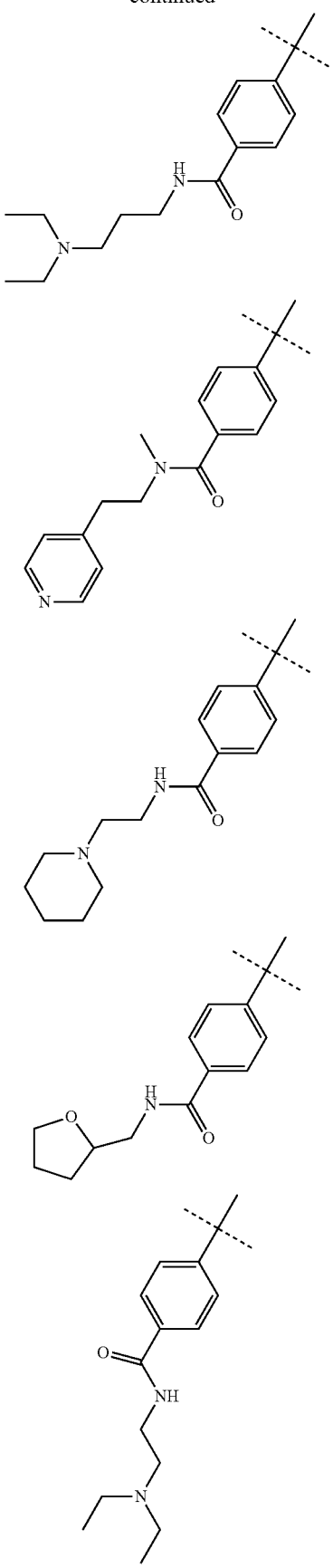

-continued
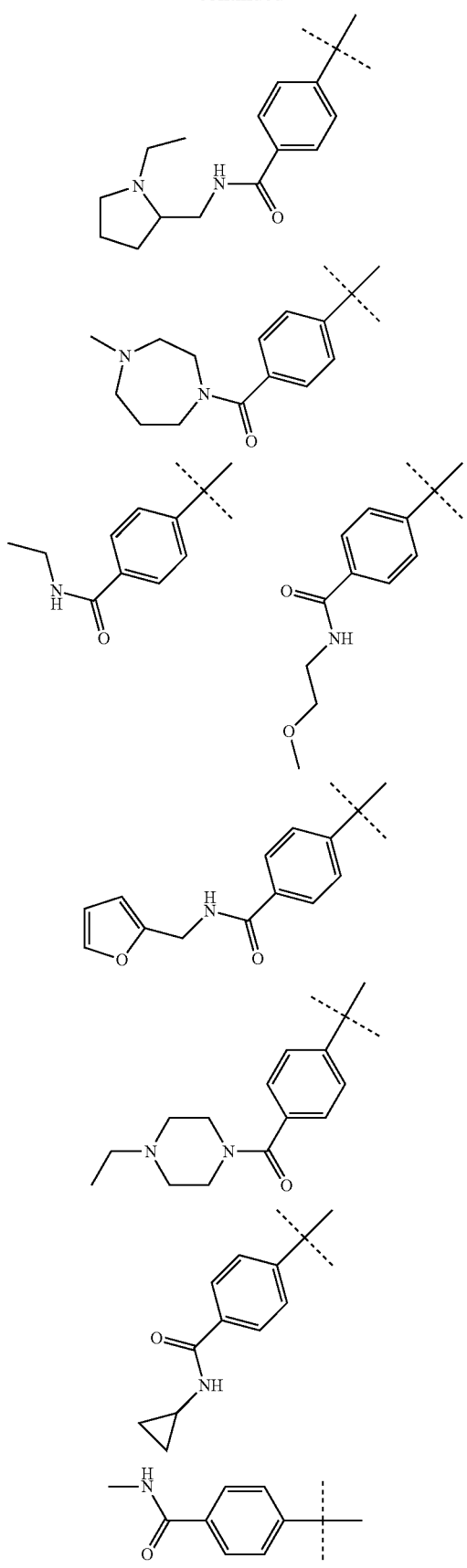
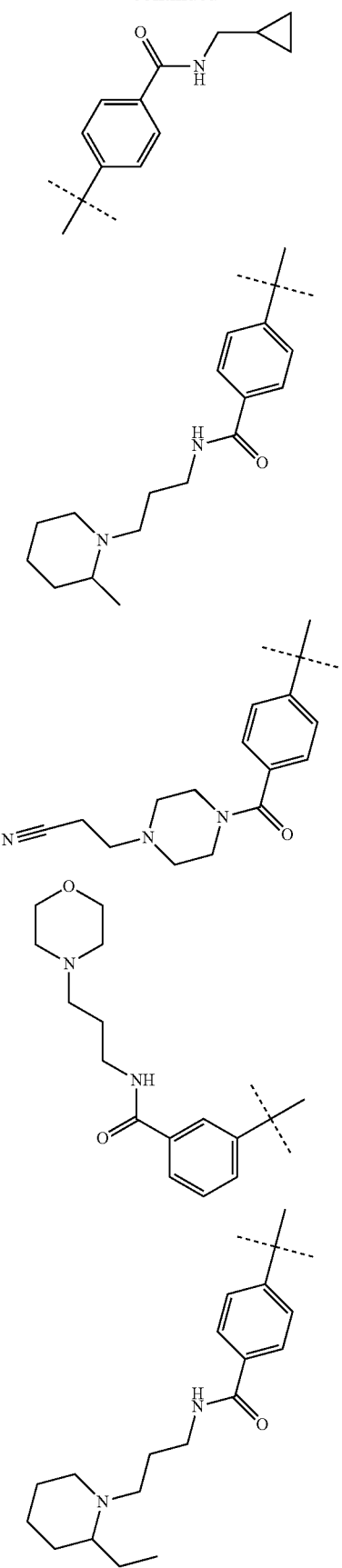

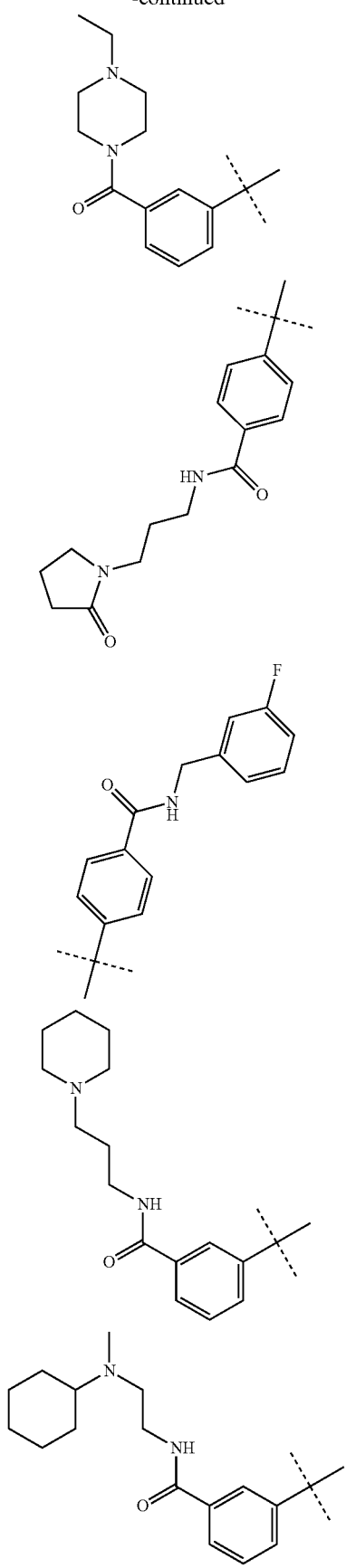
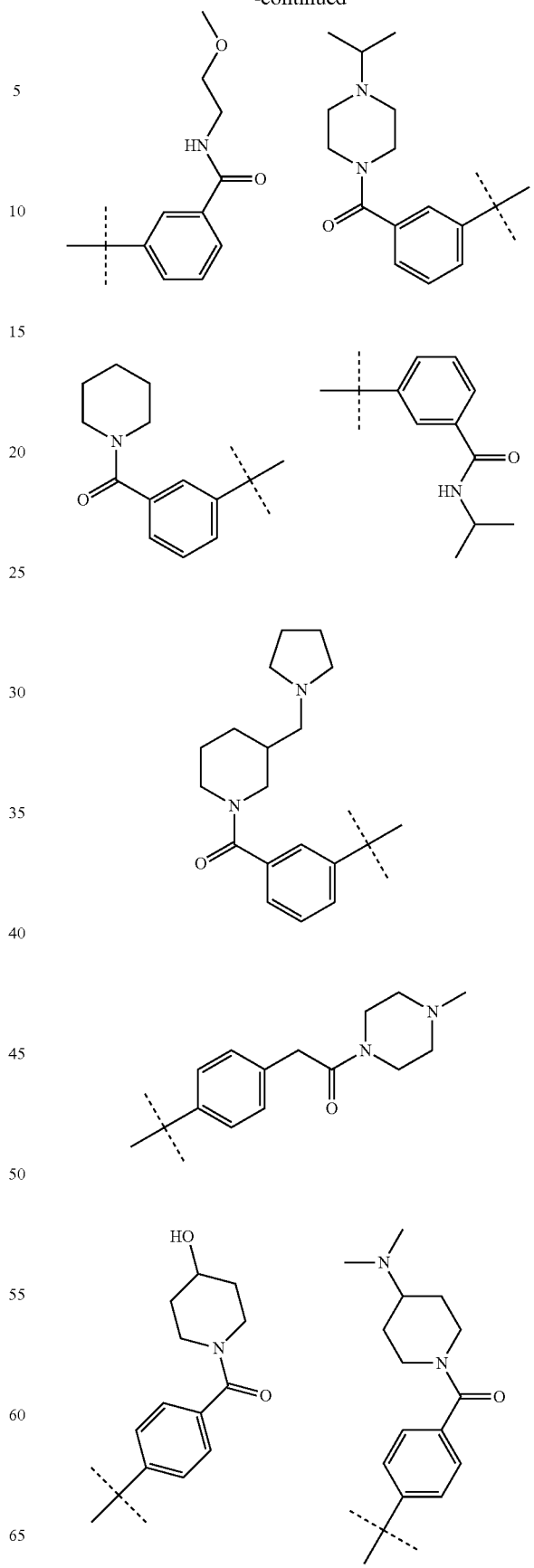

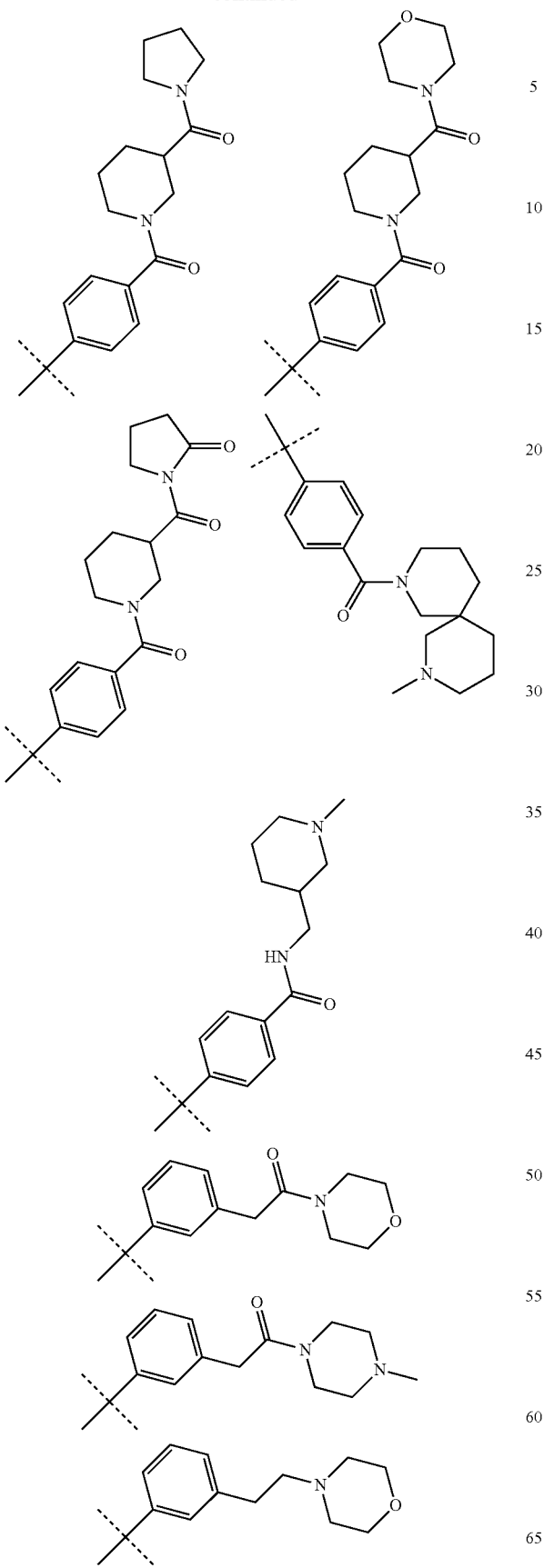
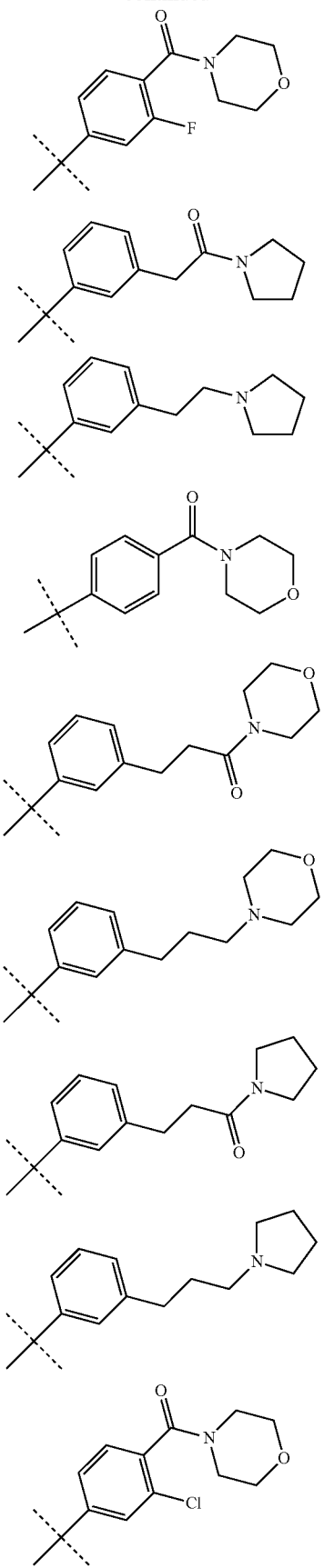

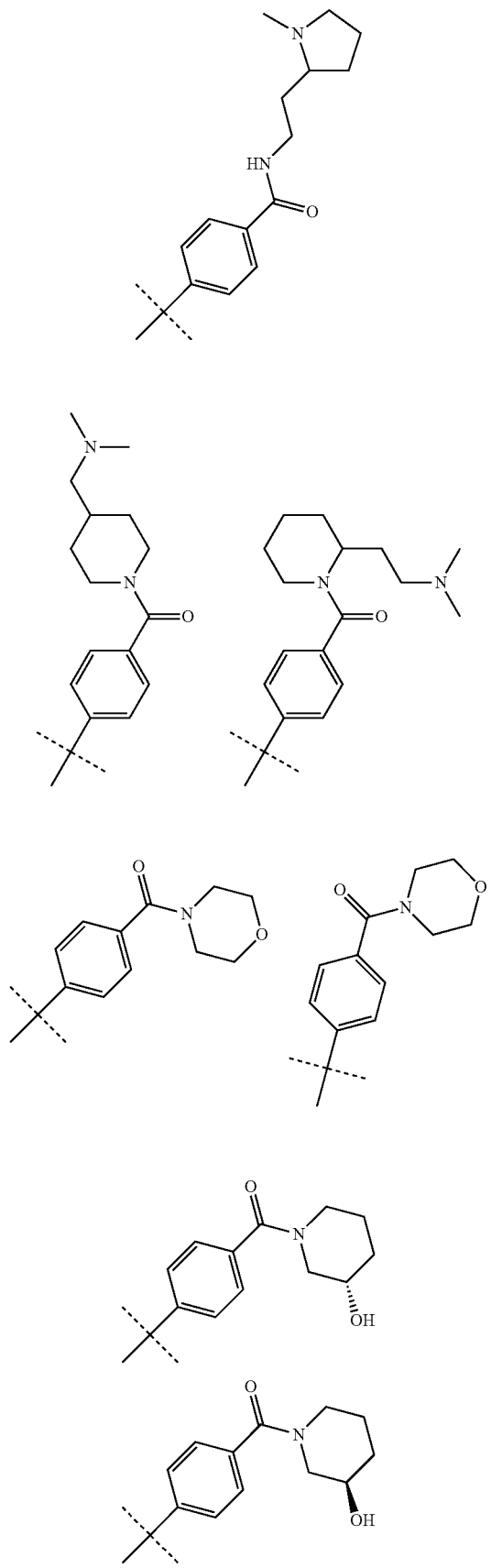
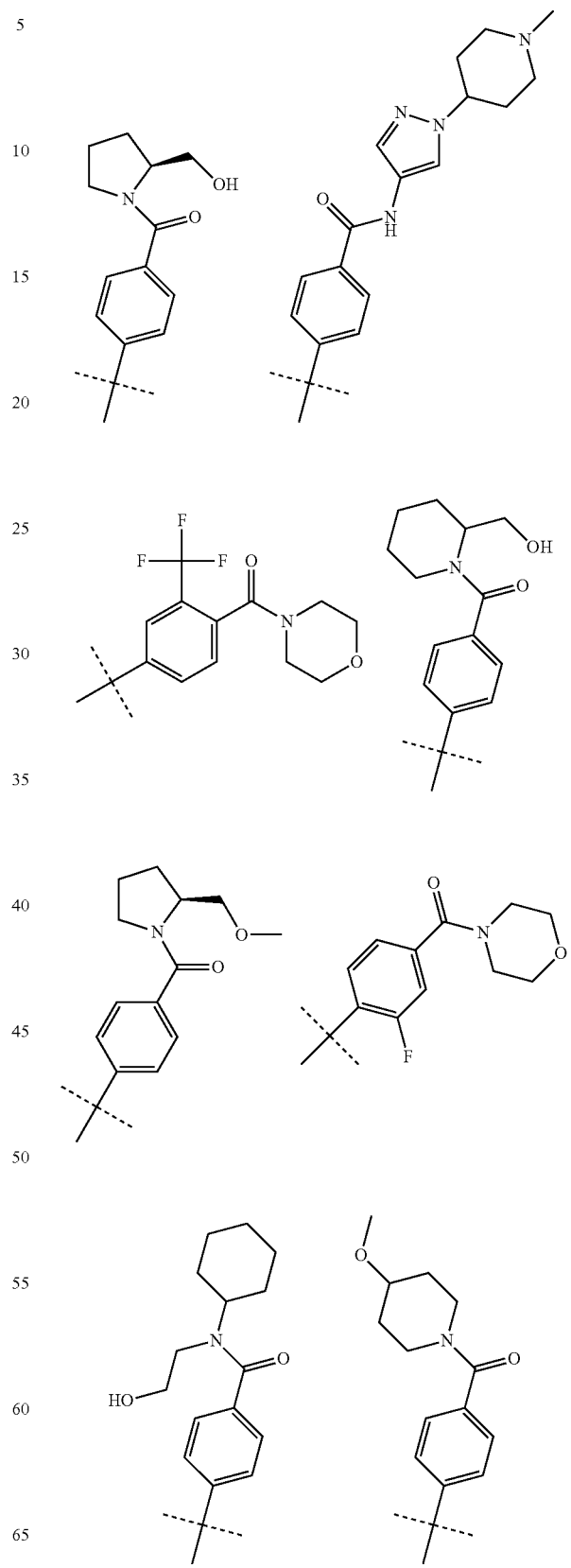

-continued
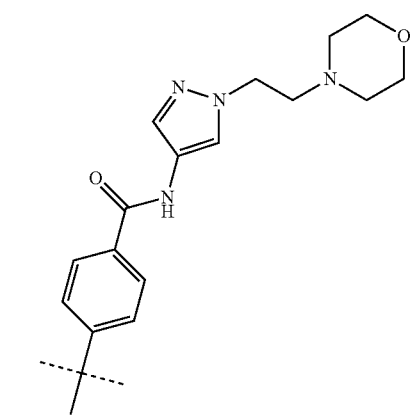
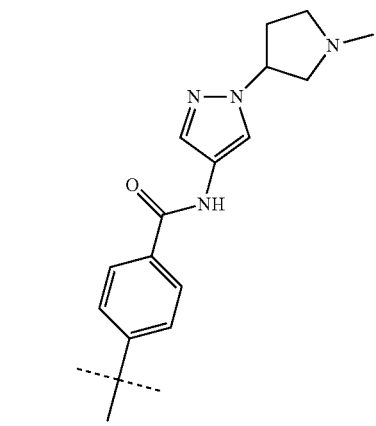
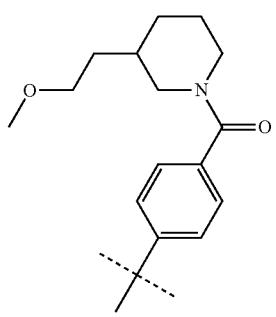
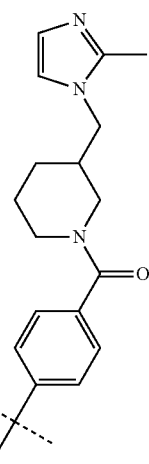
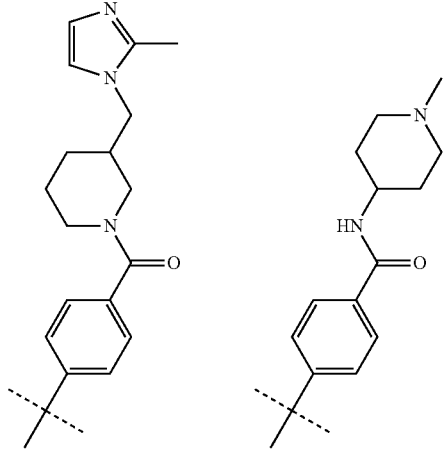
-continued
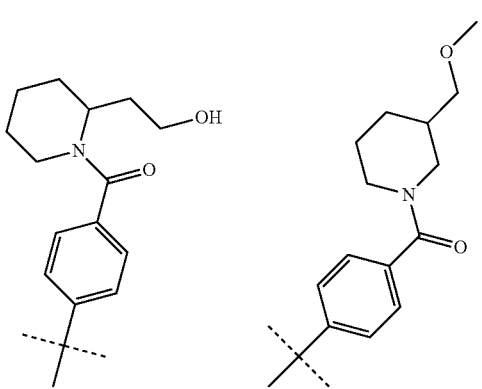
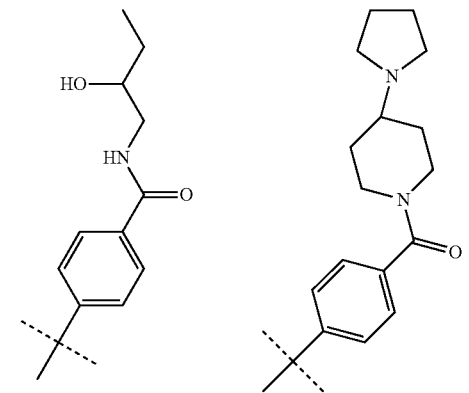
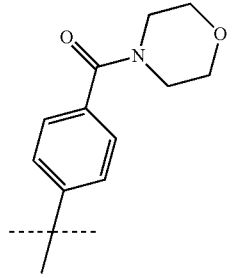
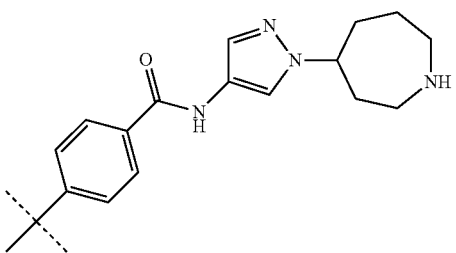
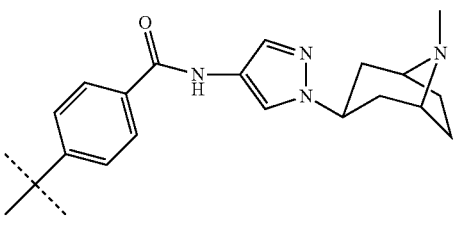

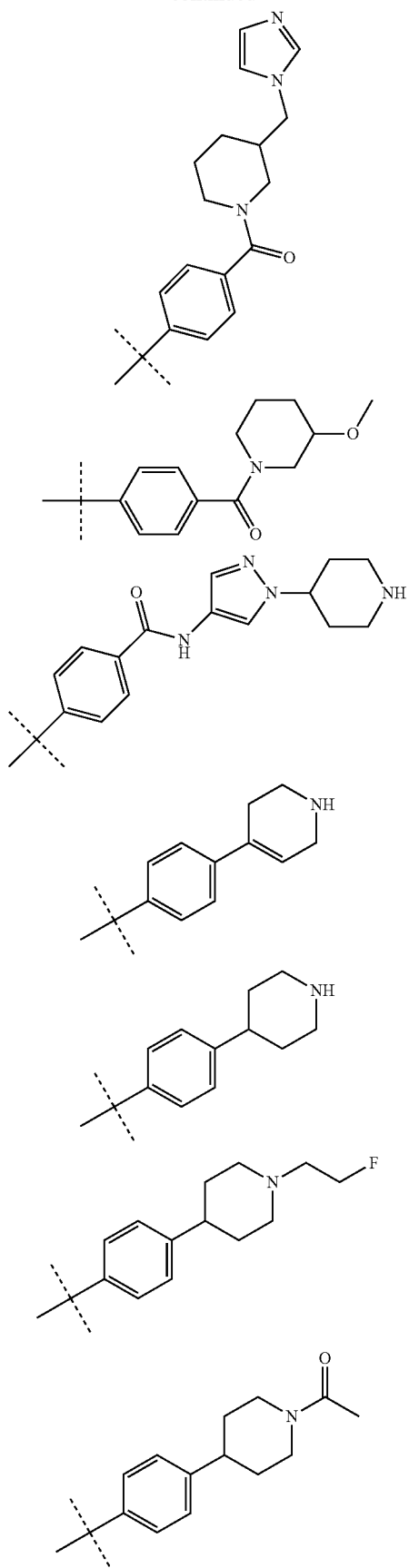
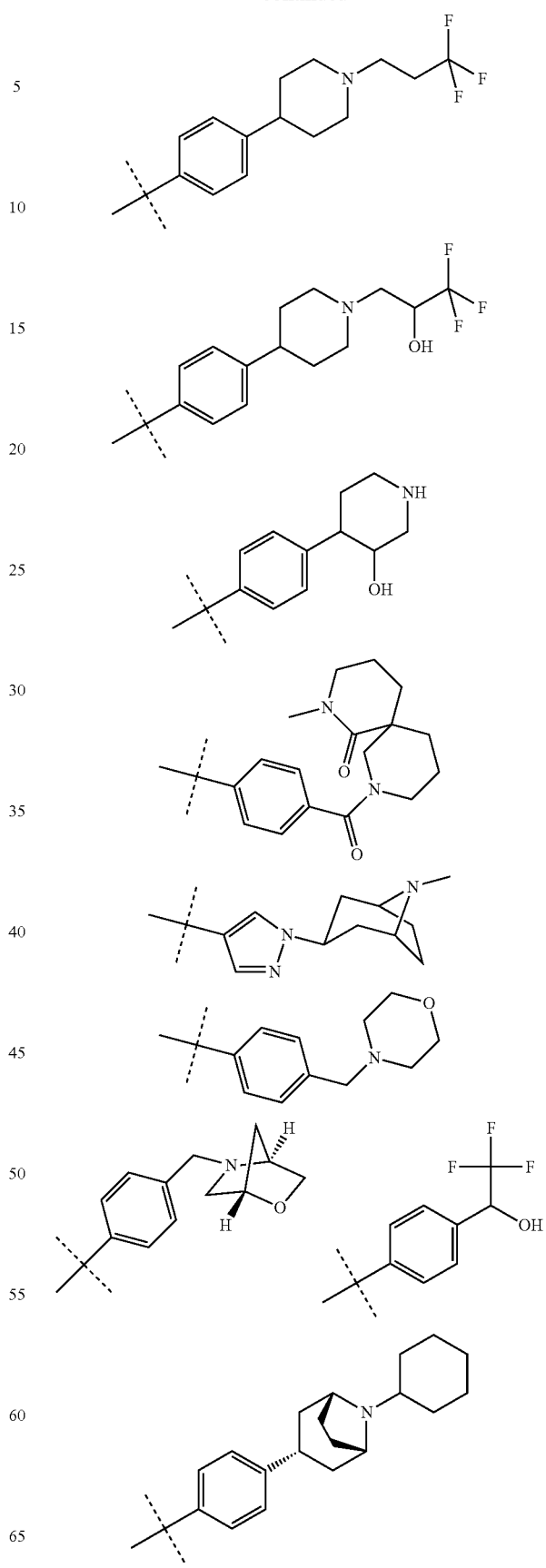

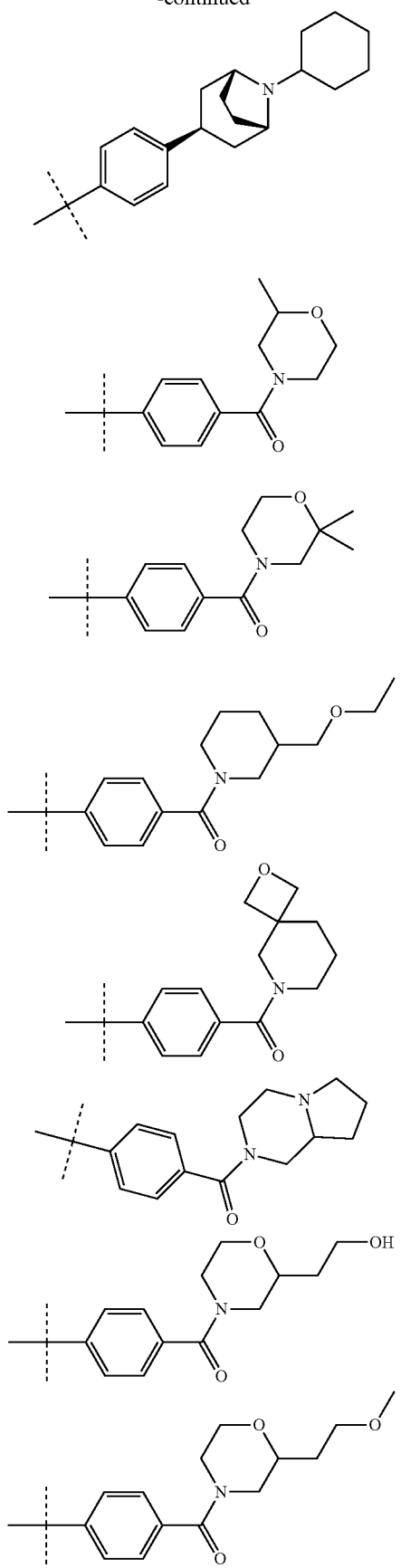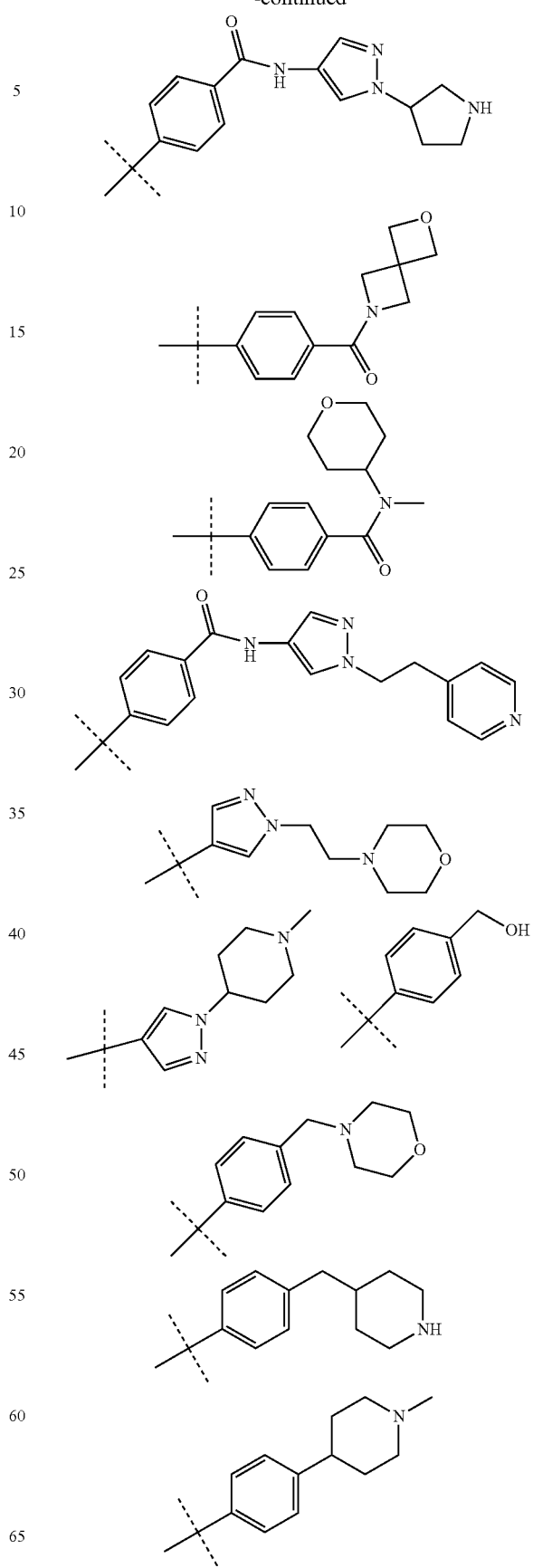

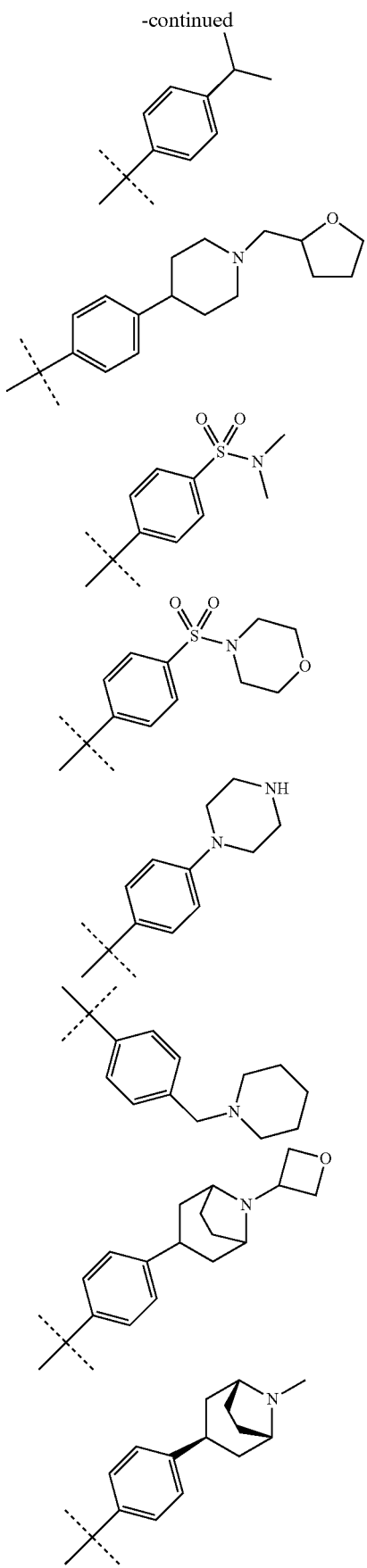
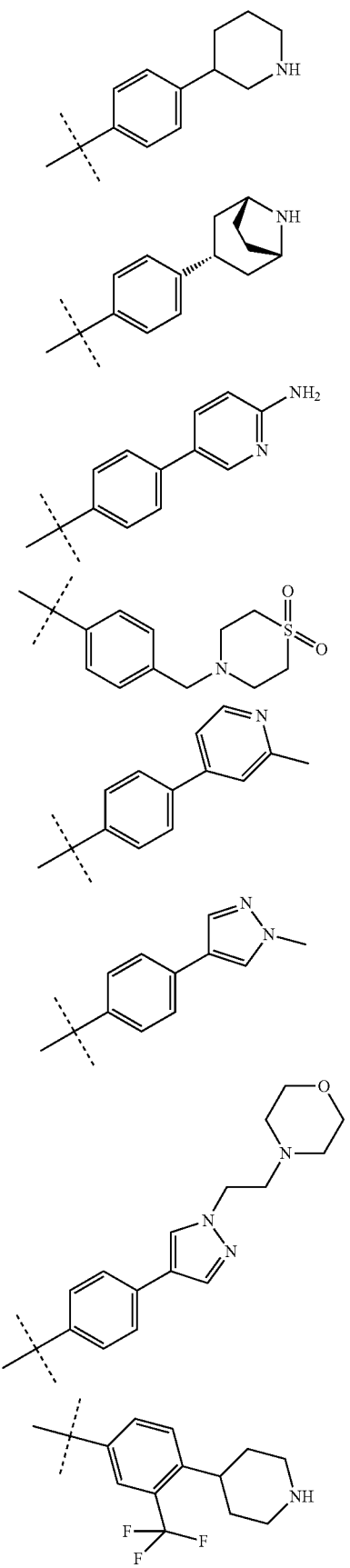

47
-continued
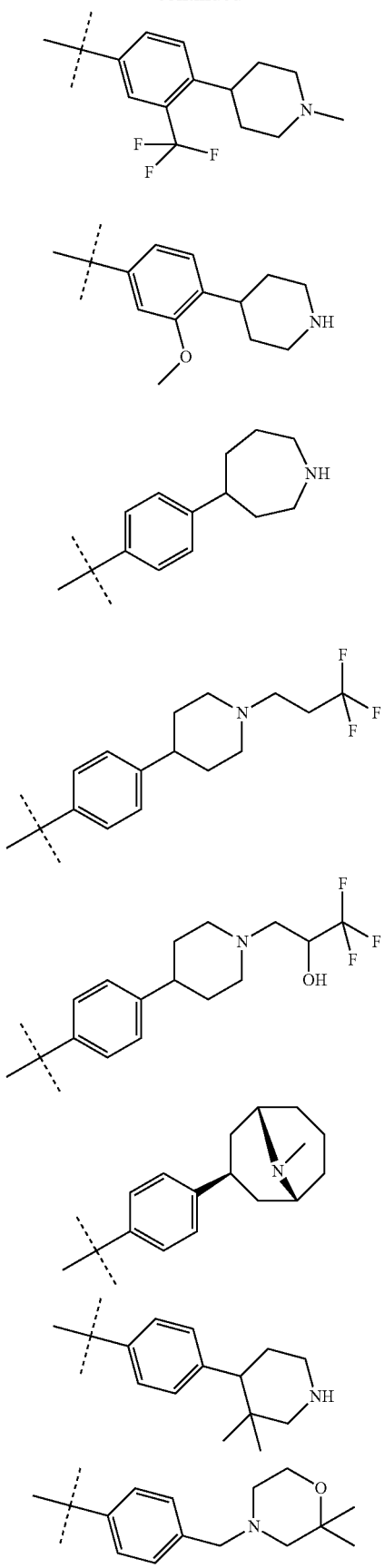
48
-continued
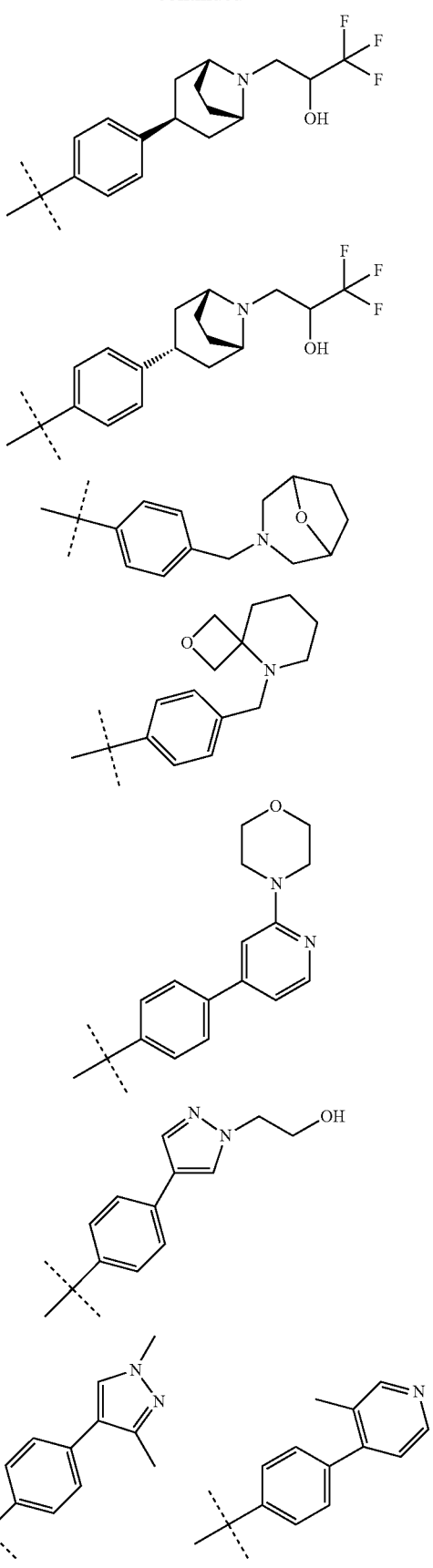

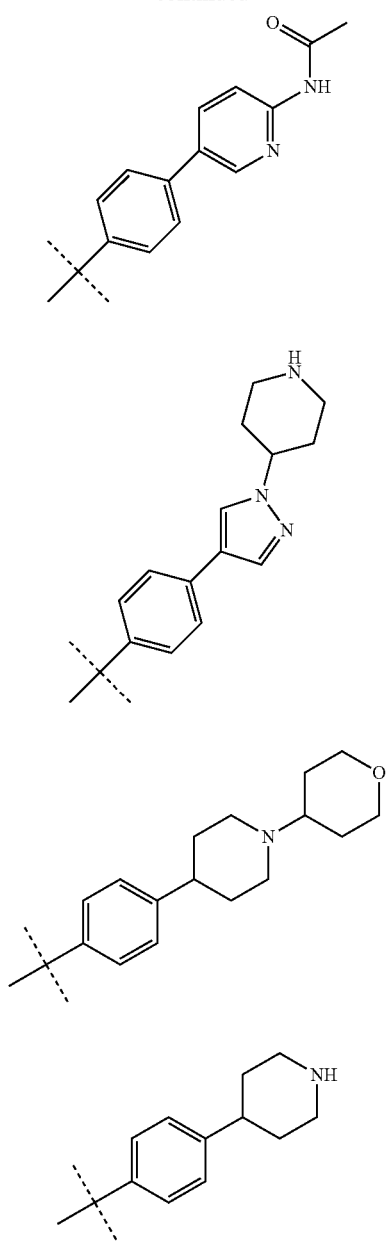
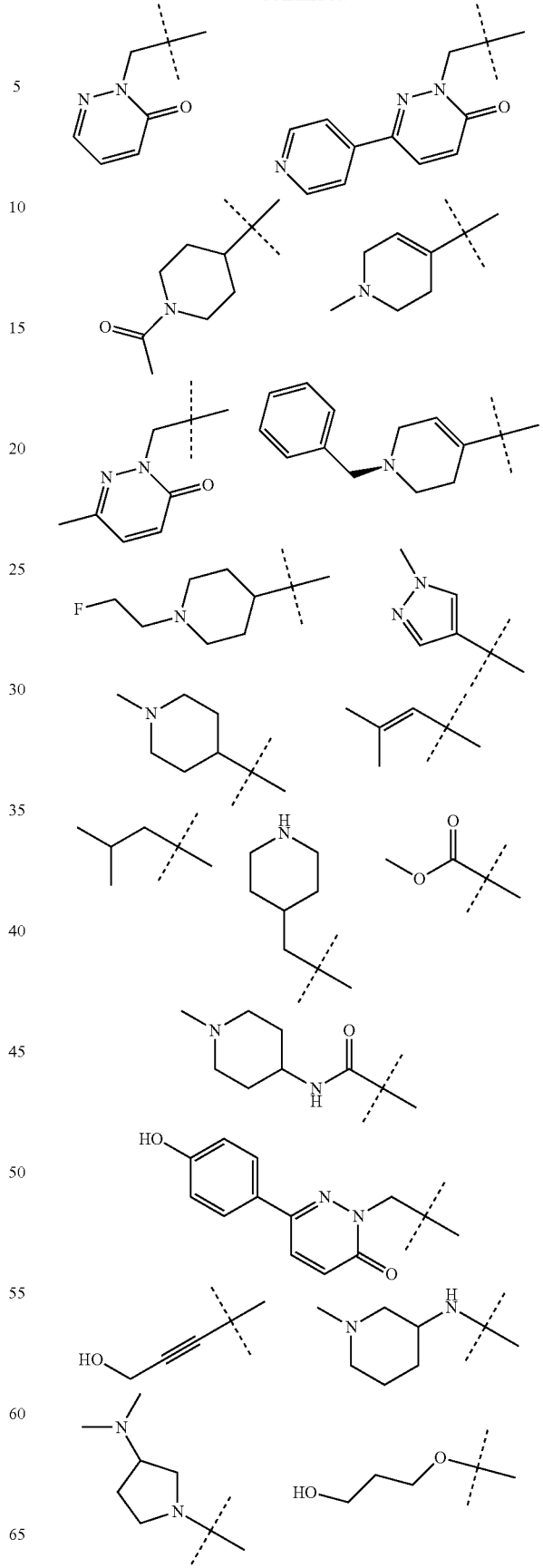
The group R[1] in Formula (I) and related Formulae (Ia), (Ib), (Ic), (Id), (Ie) and (If) preferably denotes H, Halogen such as F, Cl or Br, Methyl, trifluoromethyl, methoxy, hydroxy or one of the following groups:

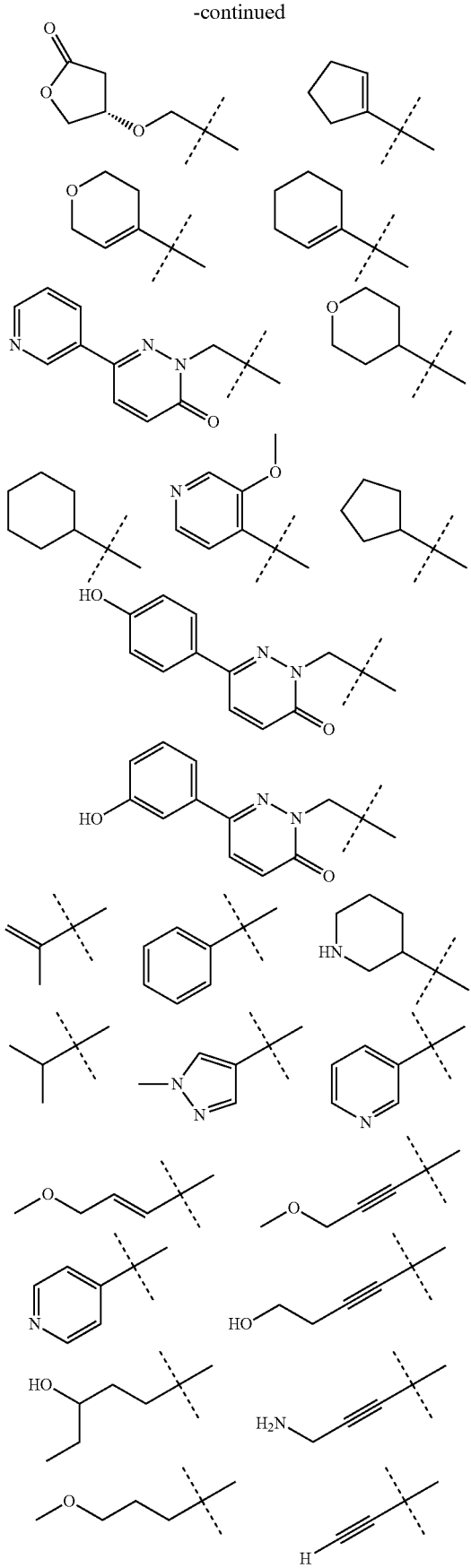
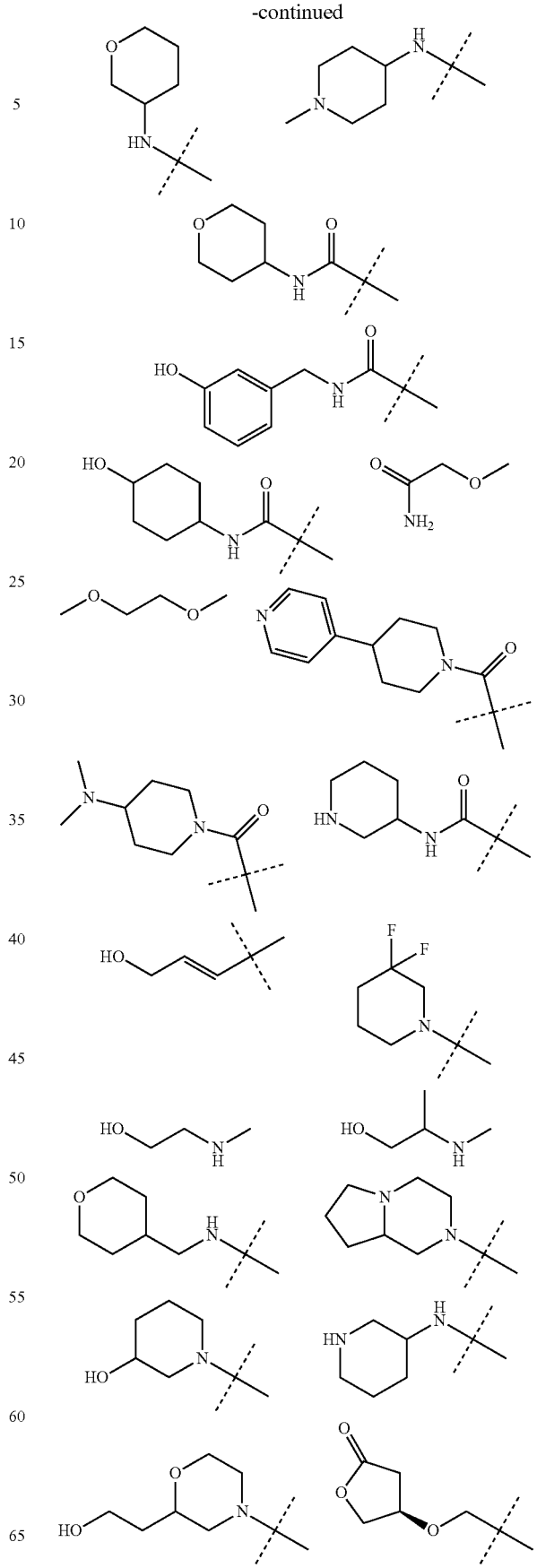

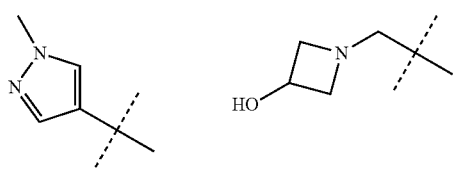
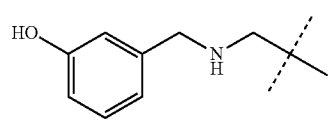
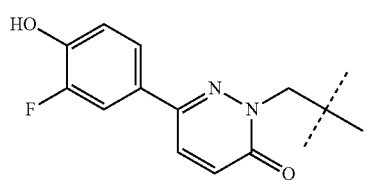
In a preferred embodiment, the present invention provides compounds of Formula (I) and related Formulae wherein the group Q-E-R³ is selected from
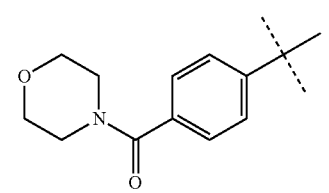
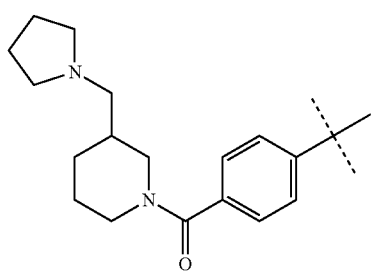

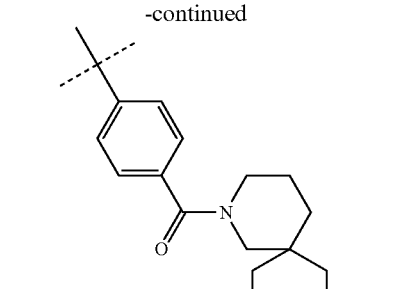
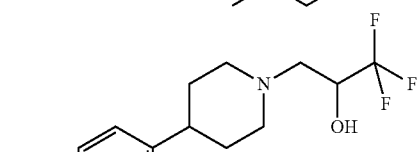
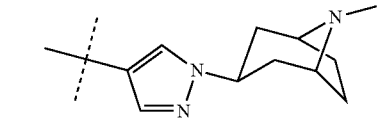
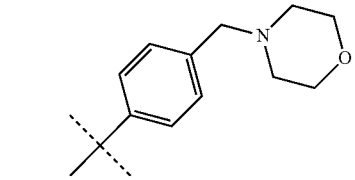
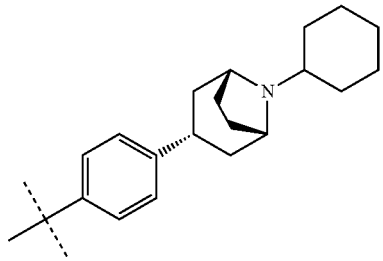
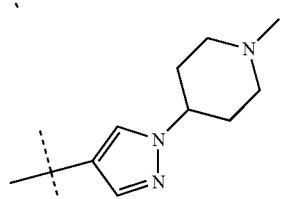
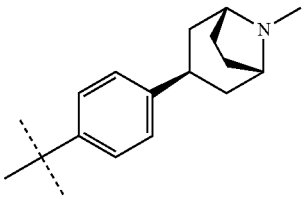
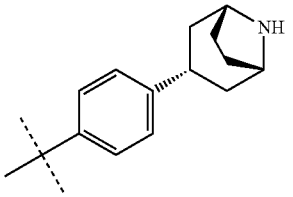

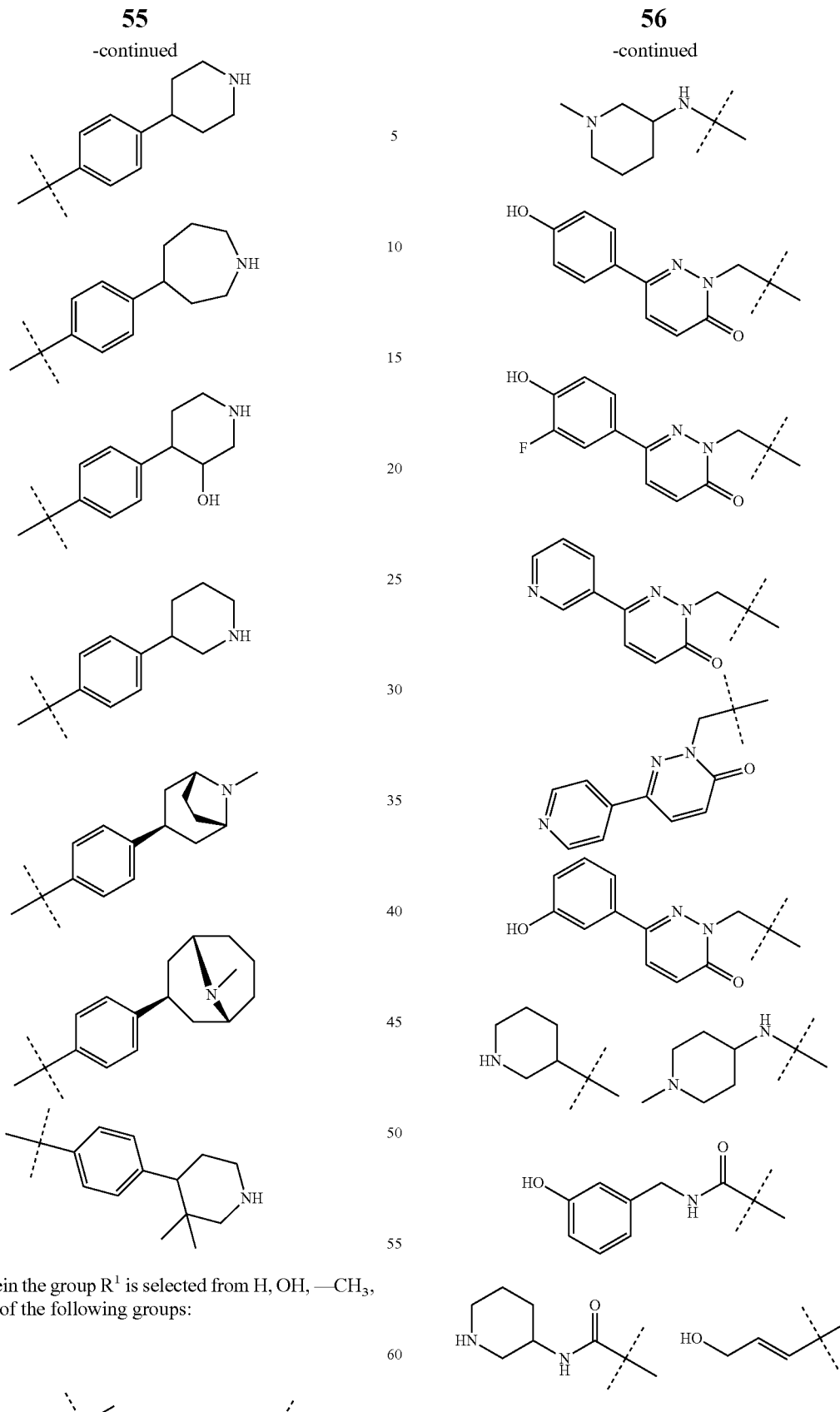
And wherein the group $R^1$ is selected from H, OH, —CH₃, F, Cl, or one of the following groups:
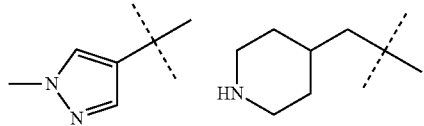
Preferred compounds of the present invention are selected from the following group:

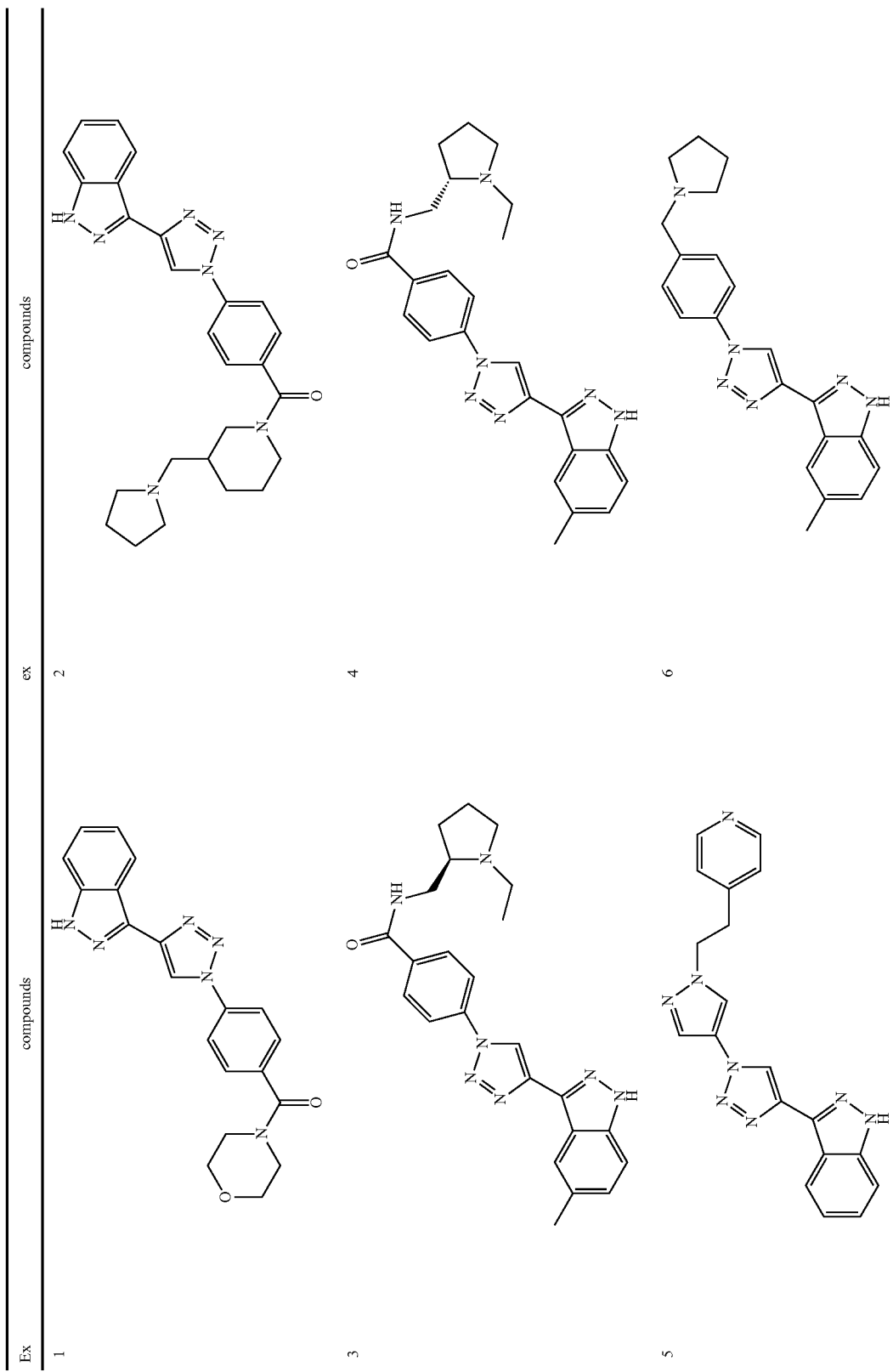

-continued

| Ex | compounds | ex | compounds |
|---|---|---|---|
| 7 | (5-methyl-1H-indazol-3-yl triazole with 4-(morpholinomethyl)phenyl) | 8 | (5-methyl-1H-indazol-3-yl triazole with 4-((methylamino)methyl)phenyl) |
| 9 | (5-methyl-1H-indazol-3-yl triazole with 4-((4-methylpiperazin-1-yl)methyl)phenyl) | 10 | (5-methyl-1H-indazol-3-yl triazole with 4-((dimethylamino)methyl)phenyl) |
| 11 | (5-methyl-1H-indazol-3-yl triazole with 4-(piperazin-1-ylmethyl)phenyl) | 12 | (1H-indazol-3-yl triazole with 4-(aminomethyl)phenyl) |

-continued

| Ex | compounds | ex | compounds |
|---|---|---|---|
| 13 | | 14 | |
| 15 | | 16 | |
| 17 | | 18 | |

-continued

| Ex | compounds | ex | compounds |
|---|---|---|---|
| 19 | | 20 | |
| 21 | | 22 | |
| 23 | | 24 | |

-continued

| Ex | compounds | ex | compounds |
|---|---|---|---|
| 25 | (structure) | 26 | (structure) |
| 27 | (structure) | 28 | (structure) |

| Ex | compounds | ex | compounds |
|---|---|---|---|
| 29 | | 30 | |
| 31 | | 32 | |

-continued

| Ex | compounds | ex | compounds |
|---|---|---|---|
| 33 | | 34 | |
| 35 | | 36 | |
| 37 | | 38 | |

-continued

| Ex | compounds | ex | compounds |
|---|---|---|---|
| 39 | | 40 | |
| 41 | | 42 | |

-continued

| Ex | compounds | ex | compounds |
|---|---|---|---|
| 43 | (structure) | 44 | (structure) |
| 45 | (structure) | 46 | (structure) |

-continued
| Ex | compounds | ex | compounds |
|---|---|---|---|
| 47 | 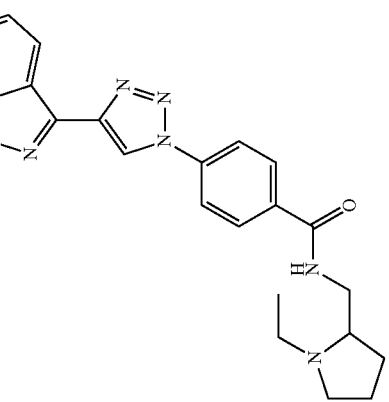 | 48 | 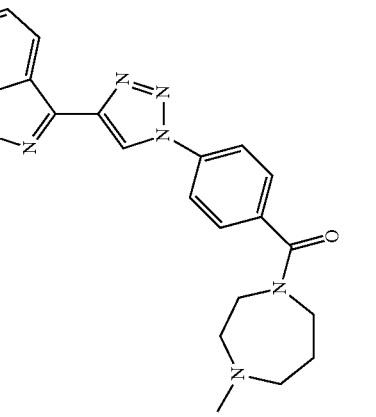 |
| 49 | 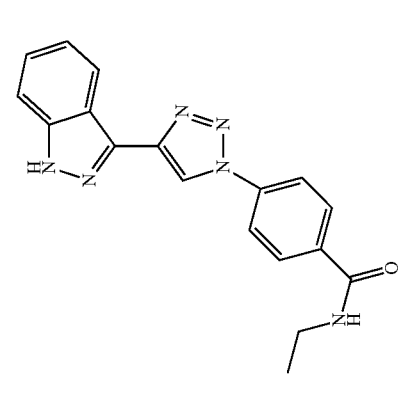 | 50 | 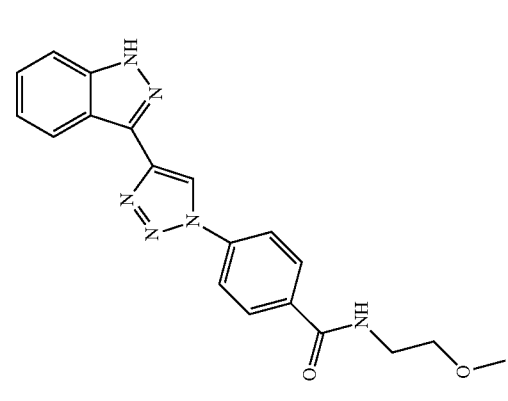 |

-continued

| Ex | compounds | ex | compounds |
|---|---|---|---|
| 51 | (structure) | 52 | (structure) |
| 53 | (structure) | 54 | (structure) |

| Ex | compounds | Ex | compounds |
|---|---|---|---|
| 55 | | 56 | |
| 57 | | 58 | |

-continued
| Ex | compounds |
|---|---|
| 59 | 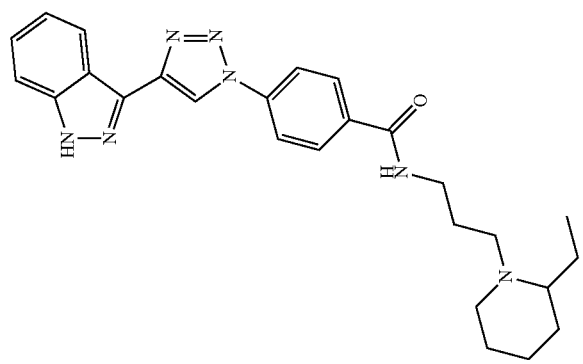 |
| 60 | 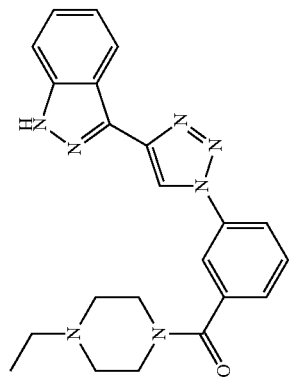 |

-continued

| Ex | ex | compounds | compounds |
|---|---|---|---|
| 61 | 62 | | |
| 63 | 64 | | |

-continued

| Ex | compounds | Ex | compounds |
|---|---|---|---|
| 65 | (structure) | 66 | (structure) |
| 67 | (structure) | 68 | (structure) |
| 69 | (structure) | 70 | (structure) |

-continued

| Ex | compounds | ex | compounds |
|---|---|---|---|
| 71 | | 72 | |
| 73 | | 74 | |

-continued
| Ex | compounds | ex | compounds |
|---|---|---|---|
| 75 | 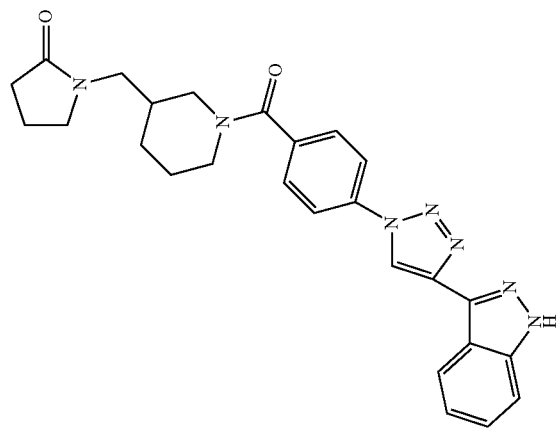 | 76 | 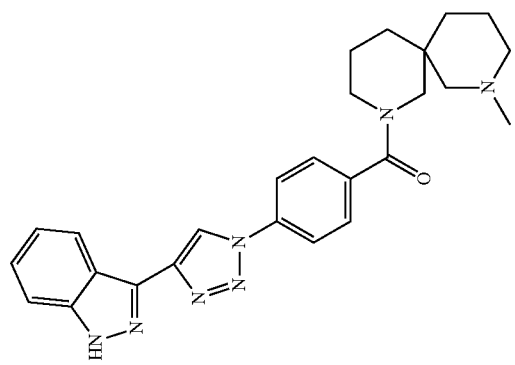 |

-continued
| Ex | compounds | ex | compounds |
|---|---|---|---|
| 77 | 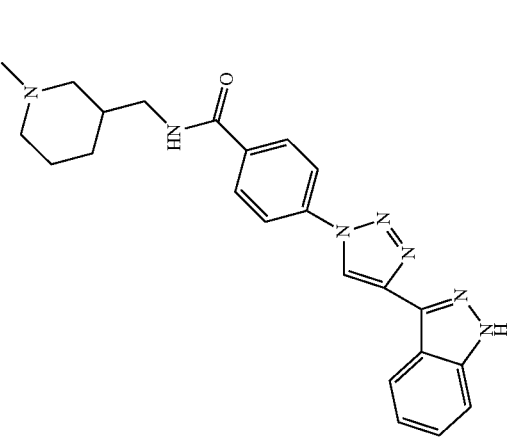 | 78 | 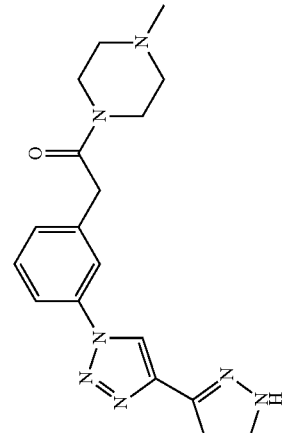 |
| 79 | 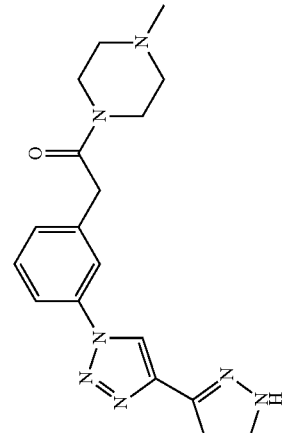 | 80 | 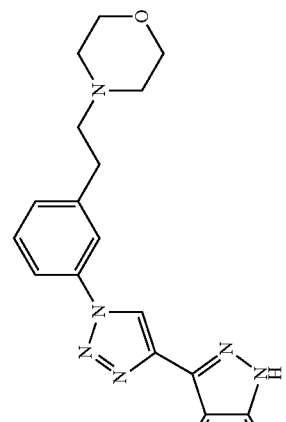 |

-continued

| Ex | compounds | ex | compounds |
|---|---|---|---|
| 81 | (structure: morpholine-C(=O)-2-fluoro-4-(triazolyl-indazole)phenyl) | 82 | (structure: pyrrolidine-C(=O)-CH2-3-(triazolyl-indazole)phenyl) |
| 83 | (structure: pyrrolidine-CH2CH2-3-(triazolyl-indazole)phenyl) | 84 | (structure: morpholine-C(=O)-4-(triazolyl-(6-piperidinyl)indazole)phenyl) |

| Ex | compounds | ex | compounds |
|---|---|---|---|
| 85 | | 86 | |
| 87 | | 88 | |

-continued

| Ex | compounds | ex | compounds |
|---|---|---|---|
| 89 | | 90 | |
| 91 | | 92 | |

| Ex | compounds |
|---|---|
| 93 | (structure of compound 93) |
| 94 | (structure of compound 94) |

| Ex | compounds |
|---|---|
| 95 | ![structure: morpholine-carbonyl-phenyl-triazole-indazole-CH2-pyridazinone] |
| 96 | ![structure: (3-hydroxypiperidin-1-yl)-carbonyl-phenyl-triazole-1H-indazole] |

-continued
| Ex | compounds | Ex | compounds |
|---|---|---|---|
| 97 | 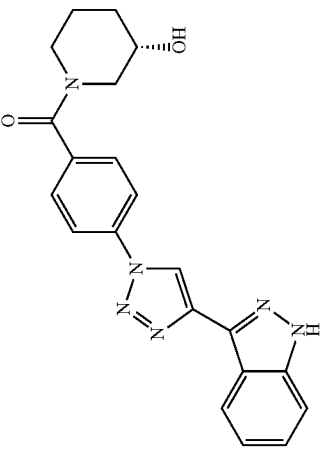 | 98 | 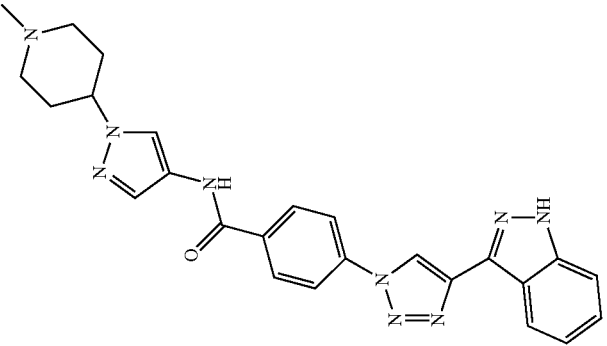 |
| 99 | 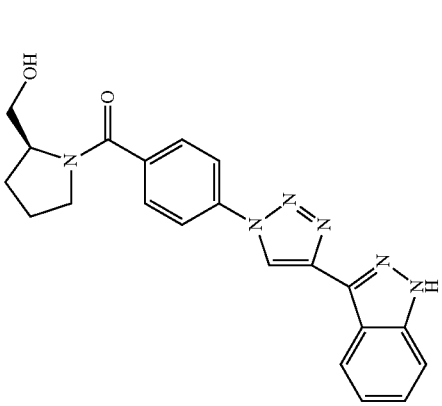 | 100 | 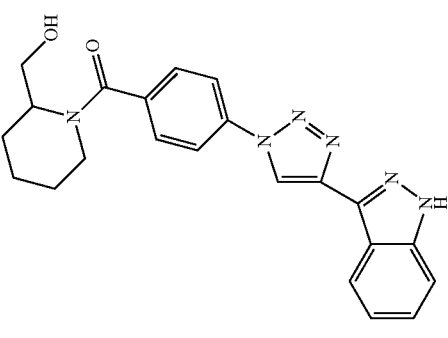 |

-continued

| Ex | compounds |
|---|---|
| 101 | (structure) |
| 102 | (structure) |
| 103 | (structure) |
| 104 | (structure) |

| Ex | ex | compounds |
|---|---|---|
| | 106 | 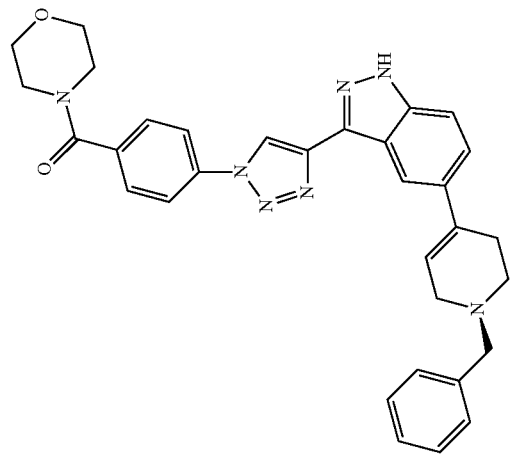 |
| 105 | | 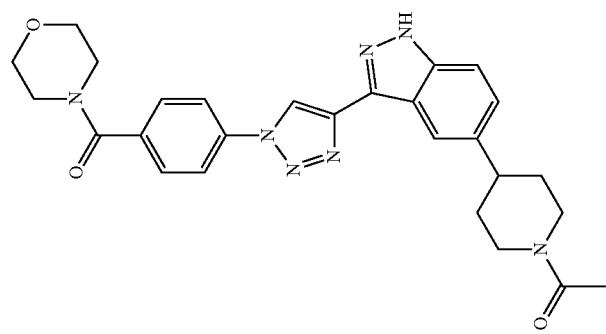 |

-continued

| Ex | compounds | ex | compounds |
|---|---|---|---|
| 107 | | 108 | |
| 109 | | 110 | |

-continued

| Ex | ex | compounds |
|---|---|---|
| 111 | | (structure: morpholine-ethyl-pyrazole-NH-C(O)-phenyl-pyrazole-indazole) |
| 112 | | (structure: 1-methylpyrrolidin-3-yl-pyrazole-NH-C(O)-phenyl-pyrazole-indazole) |

| Ex | compounds | ex | compounds |
|---|---|---|---|
| 113 | | 114 | |
| 115 | | 116 | |

-continued

| Ex | compounds |
|---|---|
| 117 | (structure) |
| 118 | (structure) |
| 119 | (structure) |
| 120 | (structure) |

-continued

| Ex | compounds | ex | compounds |
|---|---|---|---|
| 121 | | 122 | |
| 123 | | 124 | |

| Ex | compounds | ex | compounds |
|---|---|---|---|
| 125 | 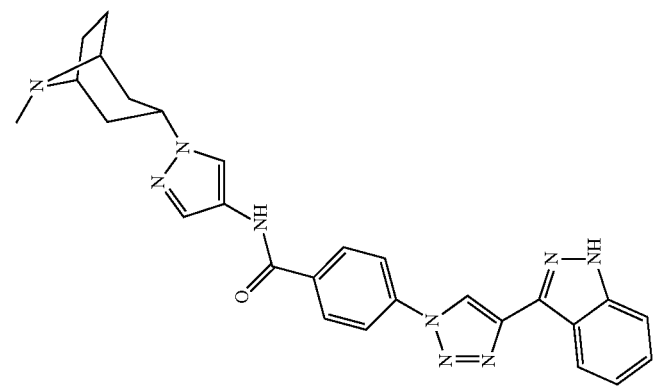 | 126 | 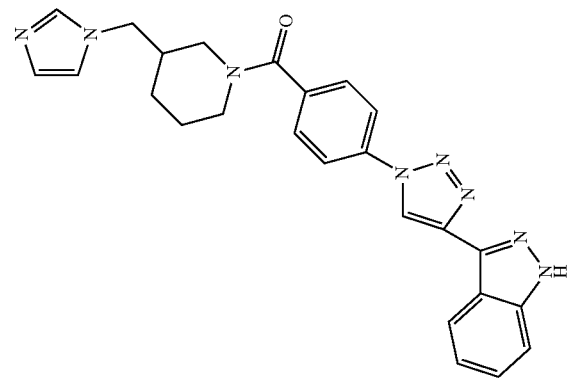 |

-continued

| Ex | compounds | Ex | compounds |
|---|---|---|---|
| 127 | (structure) | 128 | (structure) |
| 129 | (structure) | 130 | (structure) |

-continued
| Ex | compounds | Ex | compounds |
|---|---|---|---|
| 131 | 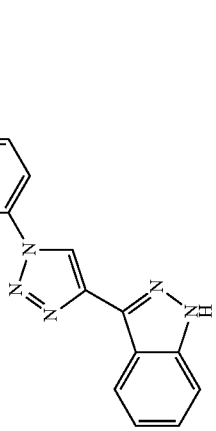 | 132 | 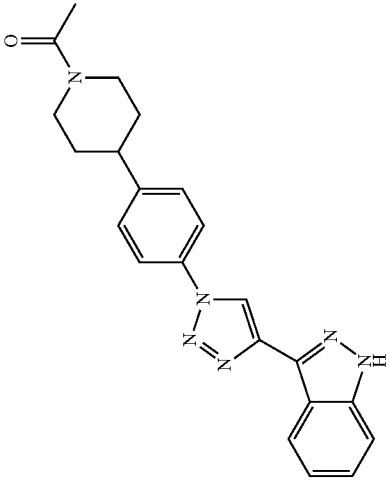 |
| 133 | 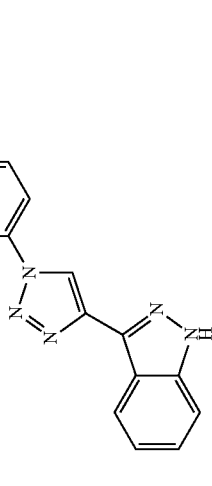 | 134 | 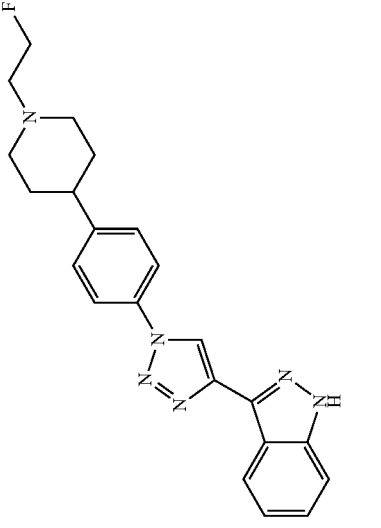 |

| Ex | compounds | ex | compounds |
|---|---|---|---|
| 135 | (structure) | 136 | (structure) |
| 137 | (structure) | 138 | (structure) |
| 139 | (structure) | 140 | (structure) |

| Ex | compounds | ex | compounds |
| --- | --- | --- | --- |
| 141 | | 142 | |
| 143 | | 144 | |

-continued

| Ex | compounds | ex | compounds |
|---|---|---|---|
| 145 | (structure) | 146 | (structure) |
| 147 | (structure) | 148 | (structure) |

| Ex | compounds | ex | compounds |
|---|---|---|---|
| 149 | | 150 | |
| 151 | | 152 | |

-continued
| Ex | compounds | Ex | compounds |
|---|---|---|---|
| 153 | 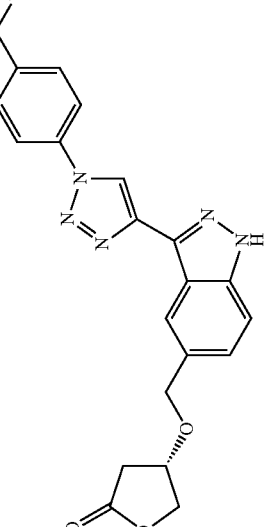 | 154 | 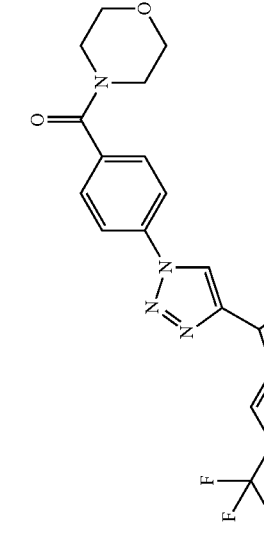 |
| 155 | 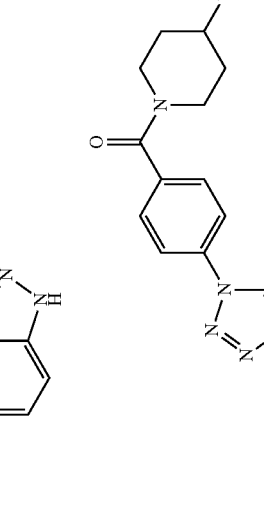 | 156 | 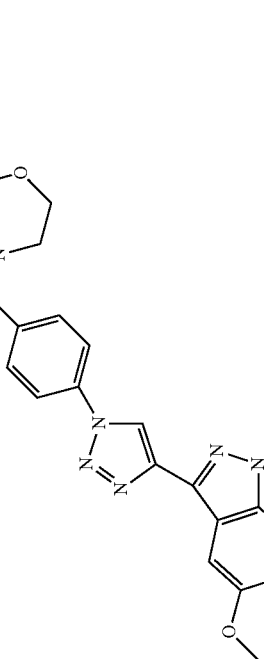 |
| 157 | 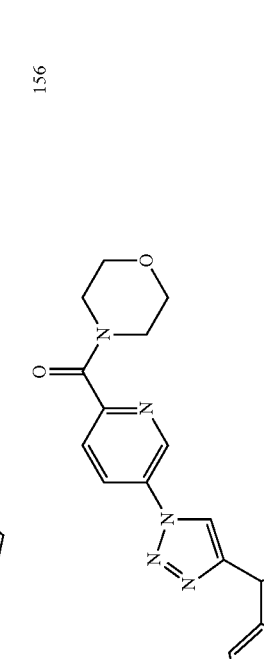 | 158 | 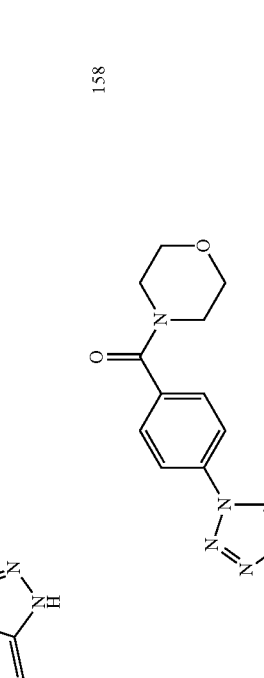 |

-continued

| Ex | compounds | ex | compounds |
|---|---|---|---|
| 159 | | 160 | |
| 161 | | 162 | |
| 163 | | 164 | |
| 165 | | 166 | |

-continued

| Ex | compounds | ex | compounds |
|---|---|---|---|
| 167 | | 168 | |
| 169 | | 170 | |
| 171 | | 172 | |

-continued

| Ex | compounds | Ex | compounds |
|---|---|---|---|
| 173 | | 174 | |
| 175 | | 176 | |
| 177 | | 178 | |

-continued
| Ex | compounds | ex | compounds |
|---|---|---|---|
| 179 | 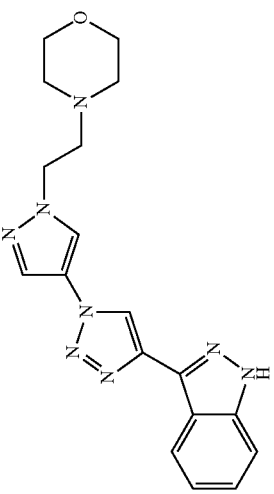 | 180 | 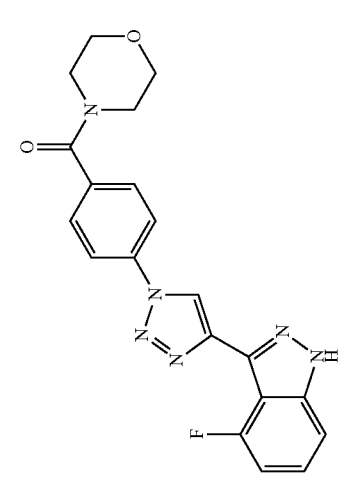 |
| 181 | 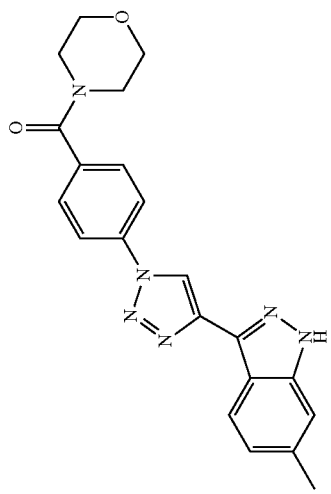 | 182 | 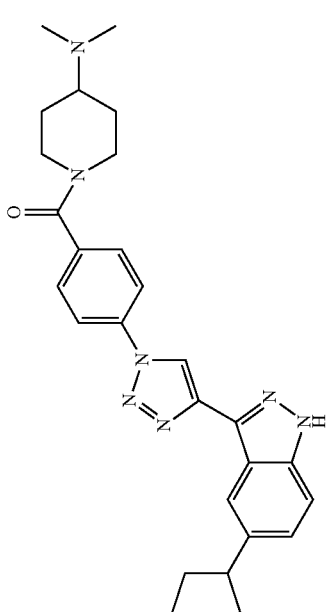 |
| 183 | 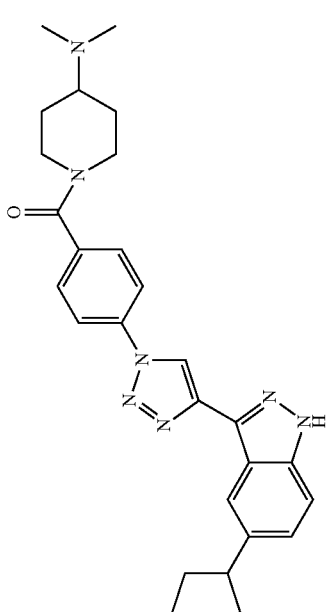 | 184 | |

-continued

| Ex | compounds | ex | compounds |
|---|---|---|---|
| 185 | (structure) | 186 | (structure) |
| 187 | (structure) | 188 | (structure) |
| 189 | (structure) | 190 | (structure) |

-continued
| Ex | compounds | Ex | compounds |
|---|---|---|---|
| 191 | 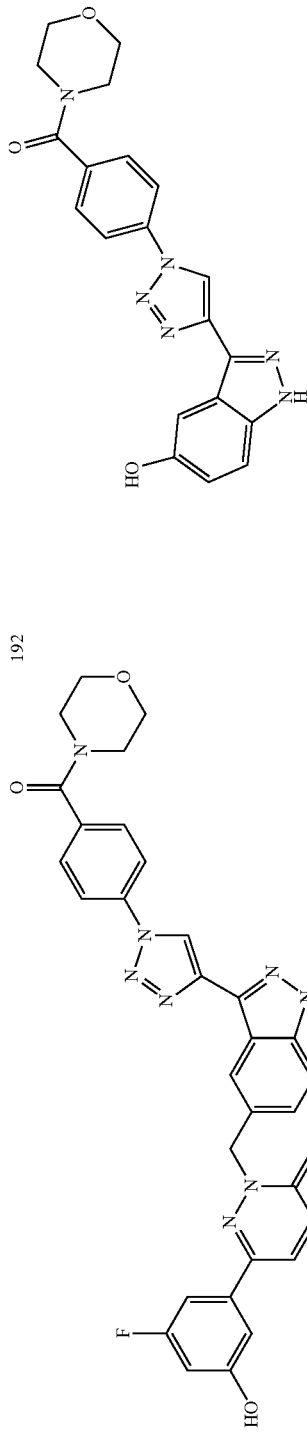 | 192 | 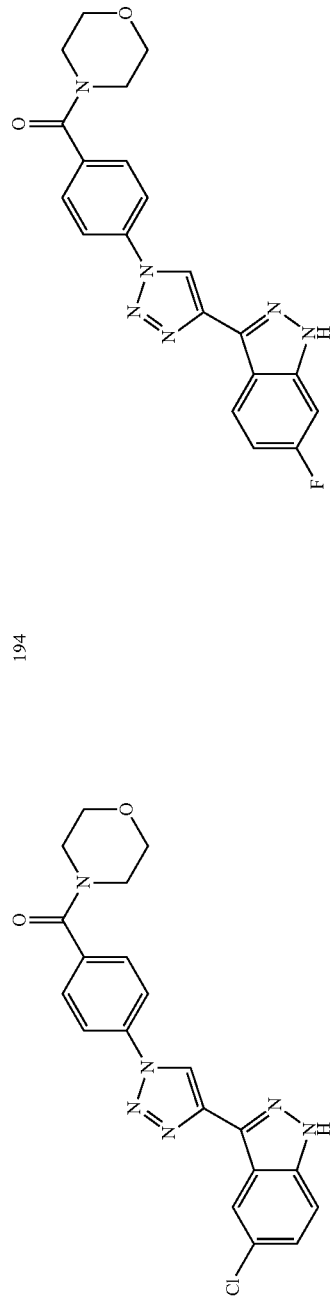 |
| 193 | | 194 | |
| 195 | | 196 | 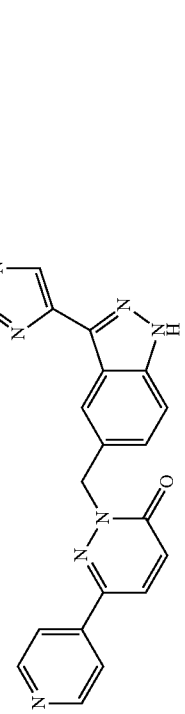 |

| Ex | compounds | ex | compounds |
|---|---|---|---|
| 197 | (structure) | 198 | (structure) |
| 199 | (structure) | 200 | (structure) |

-continued

| Ex | compounds |
|---|---|
| 201 | (structure) |
| 202 | (structure) |
| 203 | (structure) |
| 204 | (structure) |

| Ex | compounds | ex | compounds |
|---|---|---|---|
| 205 | (structure) | 206 | (structure) |
| 207 | (structure) | 208 | (structure) |

| Ex | compounds | ex | compounds |
|---|---|---|---|
| 209 | | 210 | |
| 211 | | 212 | |

| Ex | compounds | ex | compounds |
| --- | --- | --- | --- |
| 213 | (structure) | 214 | (structure) |
| 215 | (structure) | 216 | (structure) |

-continued

| Ex | compounds | ex | compounds |
|---|---|---|---|
| 217 | | 218 | |
| 219 | | 220 | |

| Ex | compounds | ex | compounds |
|---|---|---|---|
| 221 | | 222 | |
| 223 | | 224 | |
| 225 | | 226 | |

| Ex | compounds | ex | compounds |
|---|---|---|---|
| 227 | 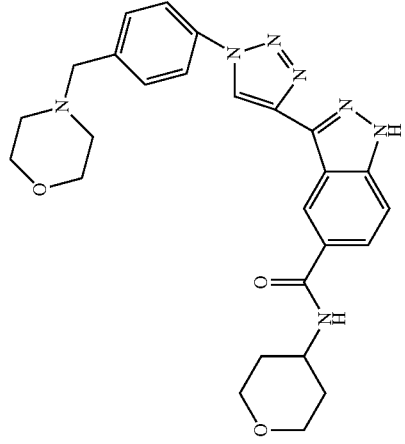 | 228 | 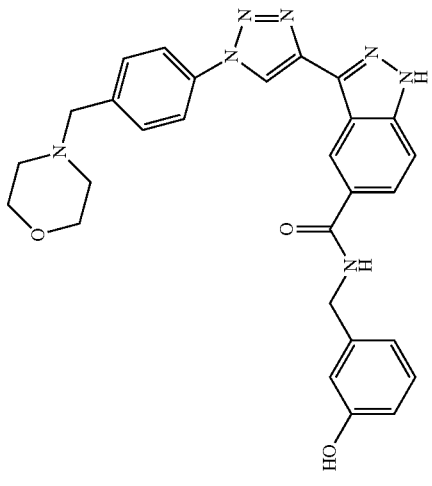 |
| 229 | 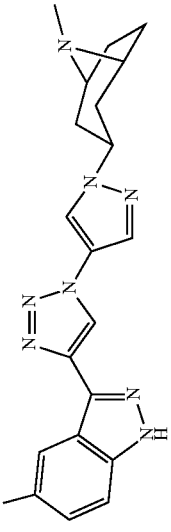 | 230 | 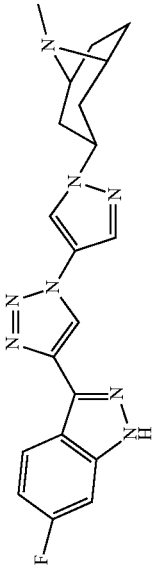 |

-continued

| Ex | compounds | ex | compounds |
|---|---|---|---|
| 231 | | 232 | |
| 233 | | 234 | |

-continued

| Ex | compounds |
|---|---|
| 235 | |
| 236 | |
| 237 | |
| 238 | |

| Ex | compounds | ex | compounds |
|---|---|---|---|
| 239 | (structure) | 240 | (structure) |
| 241 | (structure) | 242 | (structure) |
| 243 | (structure) | 244 | (structure) |

| Ex | compounds | ex | compounds |
|---|---|---|---|
| 245 | (morpholine carbonyl-phenyl-triazole-indazole with NH-CH(CH3)-CH2OH substituent) | 246 | (piperazine-phenyl-triazole-indazole) |
| 247 | (piperidine-CH2-phenyl-triazole-indazole) | 248 | (morpholine carbonyl-phenyl-triazole-indazole with NH-CH2-tetrahydropyran substituent) |

-continued

| Ex | compounds | ex | compounds |
|---|---|---|---|
| 249 | | 250 | |
| 251 | | 252 | |

| Ex | compounds | Ex | compounds |
|---|---|---|---|
| 253 | | 254 | |
| 255 | | 256 | |
| 257 | | 258 | |

| Ex | compounds | ex | compounds |
|---|---|---|---|
| 259 | 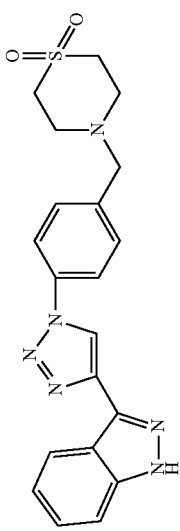 | 260 | 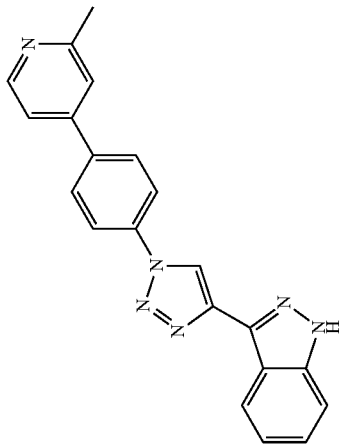 |
| 261 | 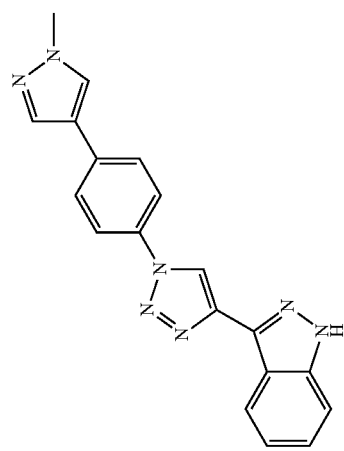 | 262 | 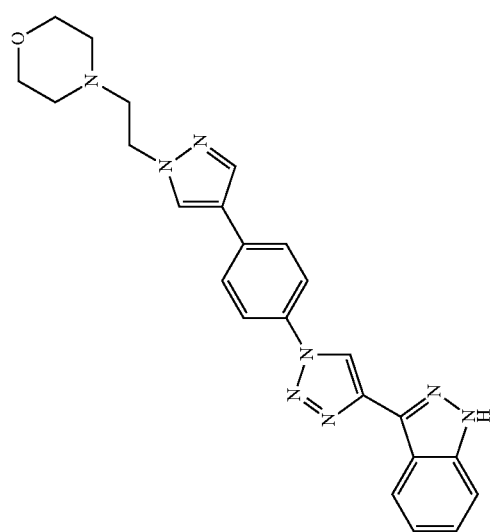 |

| Ex | compounds | ex | compounds |
|---|---|---|---|
| 263 | | 264 | |
| 265 | | 266 | |
| 267 | | 268 | |

-continued

| Ex | compounds | ex | compounds |
|---|---|---|---|
| 269 | | 270 | |
| 271 | | 272 | |

| Ex | compounds | ex | compounds |
|---|---|---|---|
| 273 | | 274 | |
| 275 | | 276 | |
| 277 | | 278 | |

-continued
| Ex | compounds | ex | compounds |
|---|---|---|---|
| 279 | 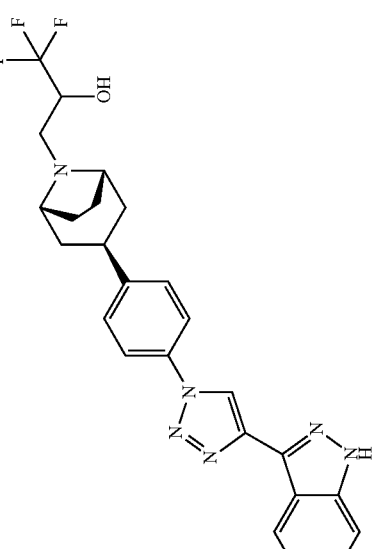 | 280 | 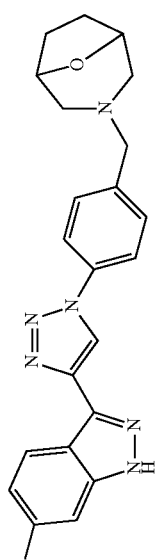 |
| 281 | 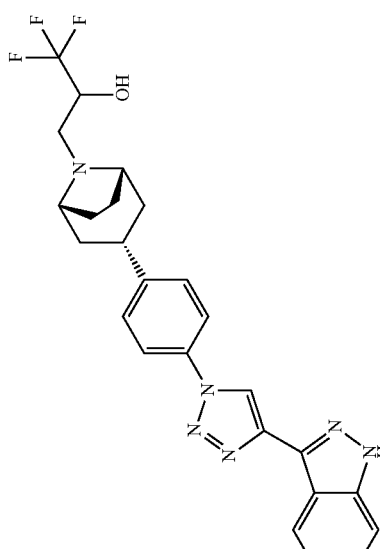 | 282 |  |
| 283 | 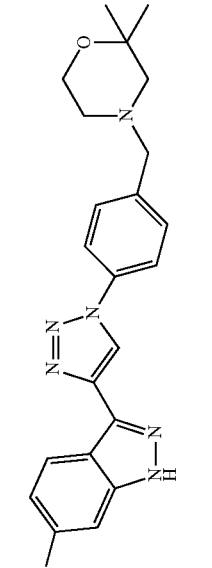 | 284 | 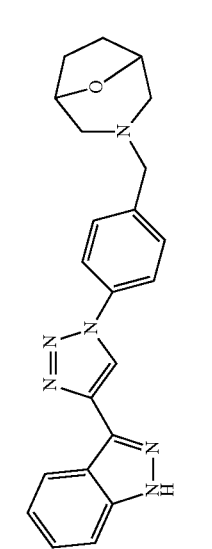 |

| Ex | compounds | ex | compounds |
|---|---|---|---|
| 285 | 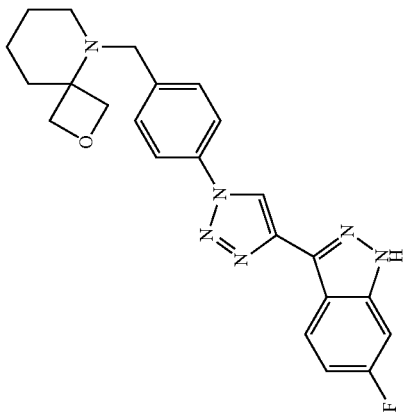 | 286 | 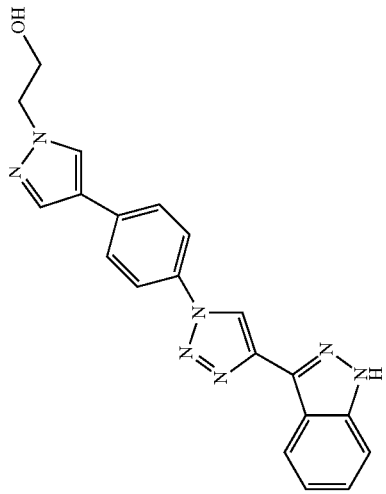 |
| 287 | 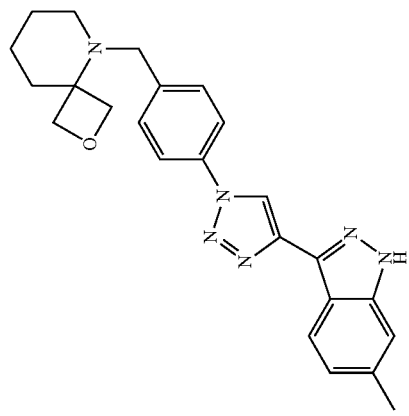 | 288 | 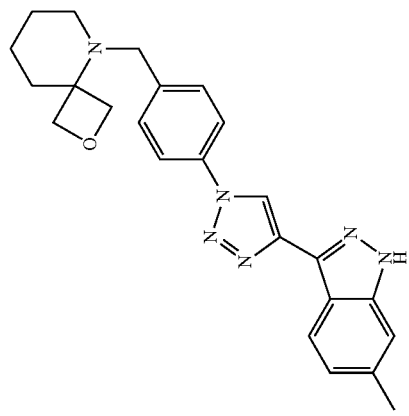 |

-continued

| Ex | compounds | ex | compounds |
|---|---|---|---|
| 289 | | 290 | |
| 291 | | 292 | |

| Ex | compounds | ex | compounds |
|---|---|---|---|
| 293 | | 294 | |
| 295 | | 296 | |

-continued

| Ex | compounds |
|---|---|
| 297 | (structure: 6-(trifluoromethyl)-1H-indazole linked to triazole linked to phenyl bearing morpholinomethyl) |
| 298 | (structure: 6-methyl-1H-indazole linked to triazole linked to phenyl bearing 4-(tetrahydropyran-4-yl)piperidin-1-yl) |
| 299 | (structure: 6-(trifluoromethyl)-1H-indazole linked to triazole linked to phenyl bearing piperidin-4-yl) |

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and aryl-sulfonyl, such as Mtr. Preferred amino-protecting groups are BOC and Mtr, further-more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methano/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl¬ formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60 and +30° C.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called pro¬ drug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a IRAK related disorder, comprising administering to said subject an effective amount of a compound of formula I and related formulae. The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality. The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkinson diseases, trauma, and chronic bacterial infection.

Preferably, disorders associated with IRAK are selected from Rheumatoid Arthritis Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Crohn's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adults onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, Cancer.

Preferred compounds of formula (I), and related formulae exhibit a IC50 for the binding to IRAK of less than about 5 µM, preferably less than about 1 µM and even more preferably less than about 0.100 µM.

Compounds according to formula (I), and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In general, the synthesis pathways for any individual compound of formula (I), and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula (I), and related formulae which contain a basic center may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), and related formulae, which contain an acid center, with a suitable base. Both types of salts may be formed or interconverted using ion-exchange resin techniques.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

In the following the present invention shall be illustrated by means of some examples, which are not construed to be viewed as limiting the scope of the invention.

General:

The HPLC data provided in the examples described below were obtained as followed.

Condition A: Column Waters Xbridge™ C8 50 mm×4.6 mm at a flow of 2 mL/min; 8 min gradient $H_2O:CH_3CN:TFA$ from 100:0:0.1% to 0:100:0.05%.

Condition B: Column Waters Xbridge™ C8 50 mm×4.6 mm at a flow of 2 mL/min; 8 min gradient $H_2O:CH_3CN$ from 100:0 to 0:100.

UV detection (maxplot) for all conditions.

The MS data provided in the examples described below were obtained as followed: Mass spectrum: LC/MS Waters ZMD (ESI).

The NMR data provided in the examples described below were obtained as followed: 1H-NMR: Bruker DPX-300 MHz or Bruker AV-400 MHz.

Preparative HPLC purifications were performed with a mass directed autopurification Fractionlynx from Waters equipped with a Sunfire Prep C18 OBD column 19×100 mm 5 μm, unless otherwise reported. All HPLC purifications were performed with a gradient of $ACN/H_2O$ or $ACN/H_2O/HCOOH$ (0.1%).

The microwave chemistry was performed on a single mode microwave reactor Emrys™ Optimiser or Initiator™ Sixty from Biotage.

The compounds of invention have been named according to the standards used in the program "ACD/Name Batch" from Advanced Chemistry Development Inc., ACD/Labs (7.00 Release). Product version: 7.10, build: 15 Sep. 2003

The compounds according to formula (I) can be prepared from readily available starting materials by several synthetic approaches, using both solution-phase and solid-phase chemistry protocols or mixed solution and solid phase protocols. Examples of synthetic pathways are described below in the examples. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich or Sigma or ABCR unless otherwise reported. SPE cartridges were purchased from IST and used following supplier recommendations.

Intermediate 1: 3-ethynyl-1H-indazole

Step a) Formation of tert-butyl 3-[(trimethylsilyl)ethynyl]-1H-indazole-1-carboxylate

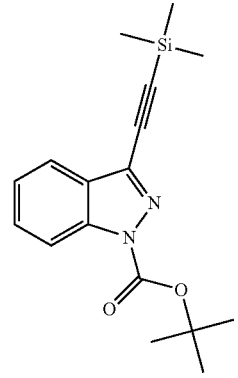 [SMILES: CC(C)(C)OC(=O)n1nc(C#C[Si](C)(C)C)c2ccccc21]

A mixture of tert-butyl 3-iodo-1H-indazole-1-carboxylate (prepared as described in J. Med. Chem. (2008), 51(12), 3460-3465); (34 g; 99 mmol; 1.00 eq.), (trimethylsilyl)acetylene (16.6 mL; 119 mmol; 1.20 eq.), $PdCl_2(PPh_3)_2$ (2.77 g; 3.95 mmol; 0.04 eq.) and TEA (41 mL) was heated overnight at 50° C. The reaction mixture was then diluted with DCM and washed three times with an aqueous saturated solution of $NH_4Cl$. Organic layer was dried over magnesium sulfate, filtered and concentrated. This crude was solubilized in DCM and the precipitate obtained was removed by filtration through a celite pad. Purification by flash chromatography on silica (Heptane/EtOAc; gradient from 98:2 to 2:98) afforded the title compound as a beige solid (20 g, 69% yield). 1H NMR (300 MHz, DMSO-d6) δ: 8.12 (d, J=8.5 Hz, 1H), 7.78 (d, J=8.5 Hz, 1H), 7.70 (m, 1H), 7.46 (m, 1H), 1.65 (s, 9H), 0.32 (s, 9H).

Step b) Formation of 3-ethynyl-1H-indazole

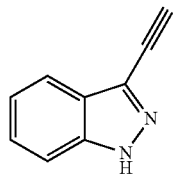

Potassium carbonate (880 mg, 6.4 mmol, 0.1 eq.) was added into a solution of tert-butyl 3-[(trimethylsilyl)ethynyl]-1H-indazole-1-carboxylate (20 g; 63.6 mmol; 1.0 eq.) in EtOH (400 mL) and the reaction mixture was stirred overnight at RT. Solvent was removed under vacuum while maintaining bath temperature below 25° C. The residue was dissolved in Et$_2$O, washed with water (twice) and brine (four times). Organic layer was dried over magnesium sulfate, filtered and concentrated to afford the title compound as a brown solid (7.1 g, 80%). $^1$H NMR (300 MHz, DMSO-d6) δ: 13.44 (s, 1H), 7.71 (d, J=8.5 Hz, 1H), 7.59 (d; J=8.5 Hz, 1H), 7.41 (m, 1H), 7.22 (m, 1H), 4.50 (s, 1H).

Intermediate 2: 3-ethynyl-5-methyl-1H-indazole

Step a) Formation of tert-butyl 3-iodo-5-methyl-1H-indazole-1-carboxylate

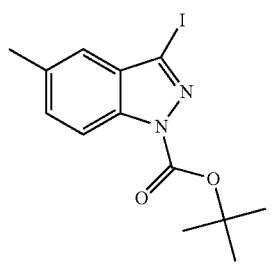 [SMILES: Cc1ccc2c(c1)c(I)nn2C(=O)OC(C)(C)C]

To a suspension of 3-iodo-5-methyl-1H-indazole (ChemBridge Corp.; 6.0 g; 23.3 mmol; 1.0 eq.) in acetonitrile (180 mL) were added DMAP (568 mg; 4.65 mmol; 0.20 eq.), di-tert-butyldicarbonate (6.1 g; 28 mmol; 1.2 eq.) and TEA (3.87 mL). The reaction mixture was stirred overnight at RT. Acetonitrile was removed under reduced pressure and the residue was dissolved in EtOAc. The resulting solution was washed with water and brine, dried over magnesium sulfate, filtered and concentrated to afford the title compound as a brown solid (8.32 g; 99.9%). $^1$H NMR (300 MHz, DMSO-d6) δ: 7.95 (d, J=8.7 Hz, 1H), 7.52 (dd, J=8.7, 1.4 Hz, 1H), 7.33-7.31 (1H, m), 2.47 (s, 3H), 1.64 (s, 9H).

Step b) Formation of tert-butyl 5-methyl-3-[(trimethylsilyl)ethynyl]-1H-indazole-1-carboxylate

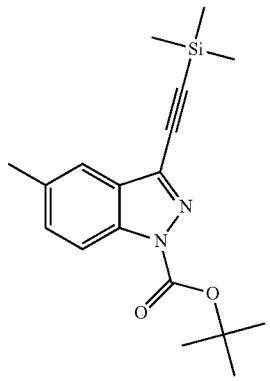 [SMILES: Cc1ccc2c(c1)c(C#C[Si](C)(C)C)nn2C(=O)OC(C)(C)C]

In a round bottom flask were introduced tert-butyl 3-iodo-5-methyl-1H-indazole-1-carboxylate (8.3 g; 23.2 mmol; 1.0 eq.), (trimethylsilyl)acetylene (6.8 mL; 48.8 mmol; 2.1 eq.), Pd(OAc)$_2$ (521 mg; 2.3 mmol; 0.1 eq.), triphenylphosphine (1.22 g; 4.65 mmol; 0.2 eq.) and copper iodide (442 mg; 2.32 mmol; 0.1 eq.) in TEA (57 mL). The reaction mixture was degassed and stirred at 80° C. under N2 for 1 hour. Et$_2$O was added and the reaction mixture was filtrated through a celite pad. The filtrate was then washed twice with an aqueous saturated solution of NH$_4$Cl and brine, dried over magnesium sulfate, filtered and concentrated. This crude was purified by flash chromatography on silica (Heptane/EtOAc, gradient from 100:0 to 10:90) to afford the title compound as a beige solid.

$^1$H NMR (300 MHz, DMSO-d6) δ: 8.00 (d, J=8.6 Hz, 1H), 7.56-7.55 (m, 1H), 7.50 (dd, J=8.6 Hz, 1.5 Hz, 1H), 2.47 (s, 3H), 1.64 (s, 9H), 0.33-0.31 (m, 9H).

Step c) Formation of 3-ethynyl-5-methyl-1H-indazole

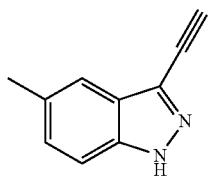

The title compound was obtained, following procedure described for intermediate 1, step b), but starting from 5-methyl-3-[(trimethylsilyl)ethynyl]-1H-indazole-1-carboxylate (2.63 g; 8.01 mmol; 1.0 eq.) as a beige solid (1.25 g, 100% yield). $^1$H NMR (300 MHz, DMSO-d6) δ 13.30 (brs, 1H), 7.49-7.46 (m, 2H), 7.25 (dd, J=8.7 Hz, 1.1 Hz, 1H), 4.46 (s, 1H), 2.42 (s, 3H). HPLC (Condition A): Rt 3.07 min (purity 96.4%).

Intermediate 3: 4-(4-azidobenzoyl)morpholine

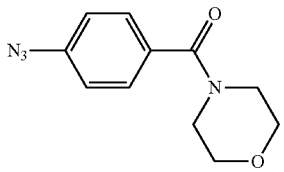 [SMILES: [N-]=[N+]=Nc1ccc(C(=O)N2CCOCC2)cc1]

TBTU (1.28 g; 3.98 mmol; 1.3 eq.) was added to a cooled (0° C.) solution of 4-azidobenzoic acid (500 mg; 3.06 mmol; 1.0 eq.) and DIEA (1.2 mL; 7.05 mmol; 2.3 eq.) in DMF (10 mL). After 15 min, morpholine (324 µl; 3.68 mmol; 1.2 eq.) was added and the reaction mixture was stirred at RT for 3 hours. The reaction mixture was diluted with EtOAc and washed twice with an aqueous saturated solution of $NaHCO_3$ then with brine. The organic layer was dried over magnesium sulfate, filtered and concentrated to afford the title compound as a beige solid (710 mg, 100%). $^1$H NMR (300 MHz, DMSO-d6) δ 7.46 (d, J=8.6 Hz, 2H), 7.18 (d, J=8.6 Hz, 2H), 3.59-3.47 (m, 8H). HPLC (Condition A): Rt 2.21 min (purity 98.2%).

Intermediate 4: 1-(4-azidobenzoyl)-3-(pyrrolidin-1-ylmethyl)piperidine

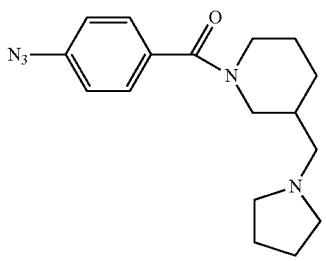 [SMILES: [N-]=[N+]=Nc1ccc(C(=O)N2CCCC(CN3CCCC3)C2)cc1]

The title compound was obtained, following procedure described for intermediate 3, but starting from 4-azidobenzoic acid (200 mg; 1.23 mmol; 1.0 eq.) and 3-Pyrrolidin-1-ylmethyl-piperidine dihydrochloride (Chemical Diversity Labs, 254 mg; 1.05 mmol; 0.86 eq.) as a beige oil (421 mg, 100%). MS (ESI+): 314.2 (purity 92%). $^1$H NMR (300 MHz, DMSO-d6) δ 7.51-7.37 (m, 2H), 7.20-7.08 (m, 2H), 2.69 (s, 2H), 2.50-2.10 (m, 6H), 1.92-1.32 (m, 10H), 1.25-1.12 (m, 1H).

Intermediate 5: 4-azido-N-{[(2R)-1-ethylpyrrolidin-2-yl]methyl}benzamide

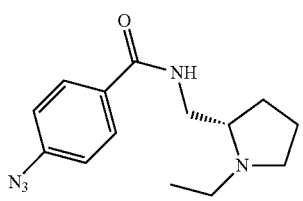 [SMILES: CCN1CCC[C@H]1CNC(=O)c1ccc(N=[N+]=[N-])cc1]

The title compound was obtained, following procedure described for intermediate 3, but starting from 4-azidobenzoic acid (305 mg; 1.87 mmol; 1.0 eq.) and 1-[(2R)-1-ethylpyrrolidin-2-yl]methanamine (TCI, 200. mg; 1.56 mmol; 1.0 eq.) as an oil. MS (ESI+): 274.1, (ESI−) 272.1 (purity 100%).

Intermediate 6: 4-azido-N-{[(2S)-1-ethylpyrrolidin-2-yl]methyl}benzamide

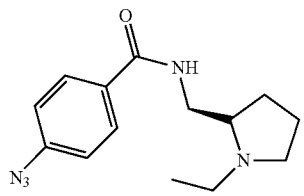

The title compound was obtained, following procedure described for intermediate 3, but starting from 4-azidobenzoic acid (305 mg; 1.87 mmol; 1.0 eq.) and 1-[(2S)-1-ethylpyrrolidin-2-yl]methanamine (TCI, 200 mg; 1.56 mmol; 1.0 eq.) as an oil. MS (ESI+): 274.1, (ESI−) 272.1 (purity 82%).

Intermediate 7: 4-[2-(4-azido-1H-pyrazol-1-yl)ethyl]pyridine

Step a) Formation of 4-[2-(4-nitro-1H-pyrazol-1-yl)ethyl]pyridine

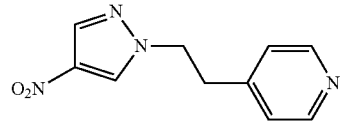 [SMILES: Nc1cnn(CCc2ccncc2)c1]

DIAD (7.27 mL; 37.2 mmol; 1.1 eq.) was added slowly into a solution of 4-(2-hydroxyethyl)pyridine (4.2 g; 34.1 mmol; 1.0 eq.), 4-nitro-1H-pyrazole (3.86 g; 34.1 mmol; 1.0 eq.) and triphenylphosphine (9.84 g; 37.5 mmol; 1.1 eq.) in THF (120 mL) maintained under nitrogen at 0° C. The reaction mixture was allowed to warm to RT and left O/N. THF was removed under reduced pressure and the crude was purified by flash chromatography on silica (EtOAc:heptane, gradient from 50:50 to 100:0) to afford the title compound in quantitative yield. MS (ESI+): 219.0, (ESI−) 272.1 (purity 92.2%). $^1$H NMR (400 Mz, DMSO-d6) δ 8.80 (s, 1H), 8.44-8.43 (m, 2H), 8.24 (s, 1H), 7.18-7.17 (m, 2H), 4.50-4.48 (t, J=7.04 Hz, 2H), 3.19-3.17 (t, J=7.0 Hz, 2H).

Step b) Formation of 1-(2-pyridin-4-ylethyl)-1H-pyrazol-4-amine

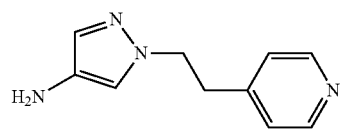

A solution of 4-[2-(4-nitro-1H-pyrazol-1-yl)ethyl]pyridine (9.9 g; 34 mmol; 1.0 eq.) in MeOH (250 mL) in presence of a catalytic amount of Pd/C was hydrogenated under 14 bars of H$_2$ at RT. After completion, the reaction mixture was filtered through a celite pad and concentrated. The crude was purified by flash chromatography on silica (DCM:MeOH, gradient from 100:0 to 80:20) to afford the title compound as a brown solid (3.26 g, 51%). MS (ESI+): 189.0 (purity 87.9%). $^1$H NMR (400 Mz, DMSO-d6) δ 842-8.41 (d, J=5.9 Hz, 2H), 7.15-7.14 (d, J=5.8 Hz, 2H), 6.96 (s, 1H), 6.91 (s, 1H), 4.21-4.19 (t, J=7.4 Hz, 2H), 3.99 (brs, 2H), 3.05-3.03 (t, J=7.1 Hz, 2H, t).

Step c) Formation of 4-[2-(4-azido-1H-pyrazol-1-yl)ethyl]pyridine

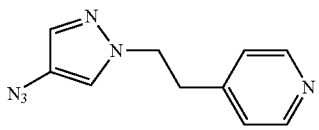

To a cooled solution (0° C.) of 1-(2-Pyridin-4-yl-ethyl)-1H-pyrazol-4-ylamine (300 mg; 2.66 mmol; 1.0 eq.) in AcOH (2.0 mL) and H$_2$SO$_4$ (1.0 mL) was added dropwise a solution of sodium nitrite (220 mg; 3.19 mmol; 1.2 eq.) in water (1.50 mL) and the reaction mixture was stirred at 0° C. for 1 hour. A solution of sodium azide (207 mg; 3.2 mmol; 1.2 eq.) in water (1.5 mL) was then added dropwise at 0° C. and the reaction mixture was stirred at 0° C. for 2 hours. The reaction mixture was then poured into ice water, basified to pH=10-11 with NaOH (5N) and extracted with EtOAc (twice). Combined organic layers were washed with brine, dried over magnesium sulfate, filtered and concentrated to afford the title compound as a dark oil, which was used without further purification in the next step. MS (ESI+): 215.0 (purity 98.7%).

Intermediate 8: 4-[4(5-methyl-1H-indazol-3-yl-1H-1,2,3-triazol-1-yl]benzaldehyde

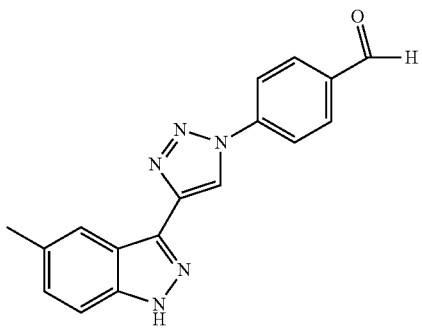 [SMILES: Cc1ccc2[nH]nc(-c3cn(-c4ccc(C=O)cc4)nn3)c2c1]

3-Ethynyl-5-methyl-1H-indazole (1.0 g; 6.4 mmol; 1.0 eq.) and 4-azidobenzaldehyde (prepared as described in Chem. Med. Chem. (2009), 4(7), 1182-1188; 1.30 g; 7.04 mmol; 1.1 eq.) were dissolved in 1,4-dioxane (15 mL). D-(−)-isoascorbic acid sodium salt (127 mg; 0.64 mmol; 0.10 eq.) followed by a solution of copper sulfate pentahydrate (32 mg; 0.13 mmol; 0.02 eq.) in water (1.5 mL) were added and the reaction mixture was stirred at 90° C. for 3.5 hours. To complete the reaction more D-(−)-isoascorbic acid sodium salt (127 mg; 0.64 mmol; 0.10 eq.) and copper sulfate pentahydrate (32 mg; 0.13 mmol; 0.02 eq.) were added again and the reaction mixture was heated at 10° C. for 8 h. 1,4-dioxane was removed under reduced pressure an the residue was sonicated in a mixture of EtOAc and water (1:1). The resulting solid was filtered and dried to afford the title compound as a beige solid (1.94 g, 100%). $^1$H NMR (300 MHz, DMSO-d6) δ: 13.29 (brs, 1H), 10.11 (s, 1H), 9.46 (s, 1H), 8.34 (d, J=8.6 Hz, 2H), 8.18 (d, J=8.6 Hz, 2H), 8.14 (m, 1H), 7.51 (d, J=8.4 Hz, 1H), 7.28 (dd, J=8.4 Hz, 1.4 Hz, 1H), 2.49 (s, 3H).

Intermediate 9: 3-[1-(6-chloropyridin-3-yl)-1H-1,2,3-triazol-4-yl]-1H-indazole

Step a) Formation of 5-azido-2-chloropyridine

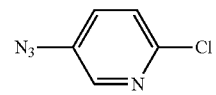

5-Amino-2-chloropyridine (2.28 g; 17.7 mmol; 1.0 eq.) was dissolved in TFA (7 mL). Sodium nitrite (1.35 g; 19.5 mmol; 1.1 eq.) was then added portion wise to this solution maintained at 0° C. Reaction mixture was stirred at 0° C. for 30 min before the addition of and ice-cold solution of sodium azide (1.15 g; 17.7 mmol; 1.0 eq.) in water (8 mL). It was stirred at 0° C. for 1 h. TFA was then removed and the residue was dissolved in EtOAc. Organic phase was washed with an aqueous saturated solution of NaHCO$_3$, brine, dried over magnesium sulfate, filtered and concentrated. The crude obtained was purified by flash chromatography on silica (heptane:EtOAc, gradient from 95:5 to 80:20) to afford the title compound as a brown oil (1.89 g, 69%). $^1$H NMR (300 Mz, DMSO-d6) δ 8.23 (dd, J=0.6, 2.9 Hz, 1H), 7.68 (dd, J=2.9, 8.6 Hz, 1H), 7.54 (dd, J=0.6, 8.6 Hz, 1H).

Step b) Formation of 3-[1-(6-chloropyridin-3-yl)-1H-1,2,3-triazol-4-yl]-1H-indazole

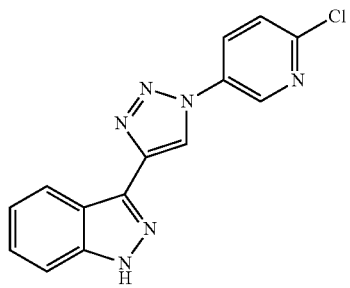 [SMILES: Clc1ccc(-n2cc(-c3n[nH]c4ccccc34)nn2)cn1]

3-Ethynyl-1H-indazole (249 mg; 1.75 mmol; 1.0 eq.) and 5-azido-2-chloropyridine (270 mg; 1.75 mmol; 1.0 eq.) were dissolved in 1,4-dioxane (11 mL). D-(−)-isoascorbic acid sodium salt (69 mg; 0.35 mmol; 0.2 eq.) was added followed by copper sulfate pentahydrate (17.5 mg; 0.07 mmol; 0.04 eq.) in water (3.7 mL) and the reaction mixture was heated at 80° C. for 2 days. The precipitate obtained was filtered, washed with water and EtOAc and dried under vacuum to afford the title compound as a beige powder. m.p.=272-280° C. $^1$H NMR (300 Mz, DMSO-d$_6$) δ 13.40 (s, 1H), 9.44 (s, 1H), 9.16 (d, J=2.8 Hz, 1H), 8.56 (dd, J=2.9, 8.8 Hz, 1H), 8.33

(d, J=8.1 Hz, 1H), 7.83 (d, J=8.9 Hz, 1H), 7.61 (d, J=8.5 Hz, 1H), 7.44 (m, 1H), 7.26 (m, 1H). HPLC (Condition A): Rt 3.30 min (purity 100%).

Intermediate 10: 3-{4-[4-(1H-indazol-3-yl)-1H-1,2, 3-triazol-1-yl]phenyl}propanoic acid

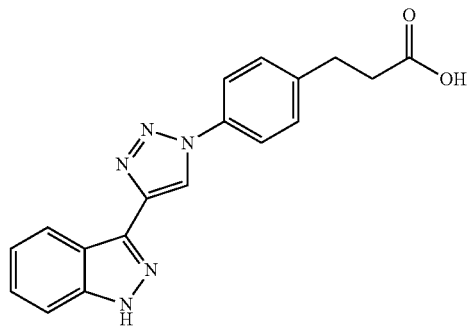 [SMILES: O=C(O)CCc1ccc(-n2cc(-c3n[nH]c4ccccc34)nn2)cc1]

3-(4-Azidophenyl)propanoic acid (Bachem, 672 mg; 3.5 mmol; 1.0 eq.) and 3-ethynyl-1H-indazole (500 mg; 3.5 mmol; 1.0 eq.) were dissolved in 1,4-dioxane (7.5 mL). D-(−)-isoascorbic acid sodium salt (139 mg; 0.70 mmol; 0.2 eq.) followed by a solution of copper sulfate pentahydrate (35 mg; 0.14 mmol; 0.04 eq.) in water (0.75 mL) were added. The reaction mixture was stirred at 90° C. for 48 h. Dioxane was partially removed under reduced pressure, water was added and the mixture was extracted with EtOAc (three times). Combined organic layers were washed with brine, dried over magnesium sulfate, filtered and concentrated. The crude obtained was sonicated in DCM (5 mL) and heptane (10 mL). The resulting solid was filtered and dried under high vacuum to afford the title compound as a brown solid (875 mg, 75%). $^1$H NMR (300 Mz, DMSO-d6) δ: 13.37 (brs, 1H), 9.27 (s, 1H), 8.35 (d, J=8.1 Hz, 1H), 7.95 (d, J=8.4 Hz, 2H), 7.61 (d, J=8.4 Hz, 1H), 7.49 (d, J=8.4 Hz, 2H), 7.46-7.41 (m, 1H), 7.27-7.22 (m, 1H), 2.92 (t, J=7.5 Hz, 2H), 2.60 (t, J=7.5 Hz, 2H). HPLC (Condition A): Rt 3.14 min (purity 93.5%). MS (ESI+): 334.2, MS (ESI−): 332.2.

Intermediate 11: 4-[4-(1H-indazol-3-yl)-1H-1,2,3-triazol-1-yl]benzoic acid

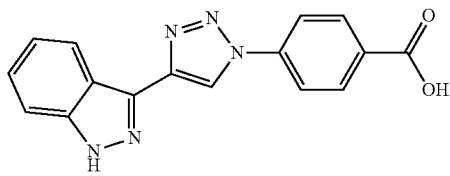 [SMILES: O=C(O)c1ccc(-n2cc(-c3n[nH]c4ccccc34)nn2)cc1]

4-azidobenzoic acid (252 mg; 1.55 mmol; 1.1 eq.) and 3-ethynyl-1H-indazole (200 mg; 1.4 mmol; 1.0 eq.) were dissolved in 1,4-dioxane (3 mL). D-(−)-isoascorbic acid sodium salt (28 mg; 0.14 mmol; 0.1 eq.) followed by a solution of copper sulfate pentahydrate (7 mg; 0.03 mmol; 0.02 eq.) in water (0.75 mL) were added and the reaction mixture was stirred at 900 for 48 h. Reaction mixture was diluted with EtOAc and extracted with a NaOH (0.1N). Aqueous phase was filtered, acidified to pH 4-5 by addition of HCl (5N) and the precipitate thus obtained, was filtered, washed with water and dried under reduced pressure at 50° C. to afford the title compound as a white solid (453 mg, 100%). $^1$H NMR (300 MHz, DMSO-d6) δ 13.53 (s, 1H), 9.57 (s, 1H), 8.49 (d, J=8.1 Hz, 1H), 8.42-8.24 (m, 3H), 8.13-8.03 (m, 1H), 7.74 (d, J=8.4 Hz, 1H), 7.63-7.50 (m, 1H), 7.45-7.29 (m, 2H).

Intermediate 12: 4-[4-(1H-indazol-3-yl)-1H-1,2,3-triazol-1-yl]-2-methoxybenzoic acid Step a) Formation of methyl 4-[4-(1H-indazol-3-yl)-1H-1,2,3-triazol-1-yl]-2-methoxybenzoate

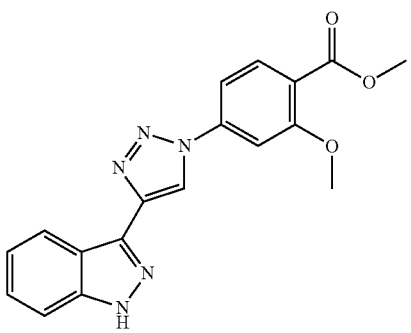

The title compound was prepared following procedure described for intermediate 10, but starting from Methyl 4-Azido-2-methoxybenzoic carboxylic acid (prepared as described in JOC, 1983, 48(25), p 5041-43; 324 mg; 1.41 mmol; 1.0 eq.) and 3-ethynyl-1H-indazole (200 mg; 1.41 mmol; 1.0 eq.) as a residue which was used directly in the next step (363 mg, 74%). MS (ESI+): 456.4, MS (ESI−): 454.5.

Step b) Formation of 4-[4-(1H-indazol-3-yl)-1H-1,2, 3-triazol-1-yl]-2-methoxybenzoic acid

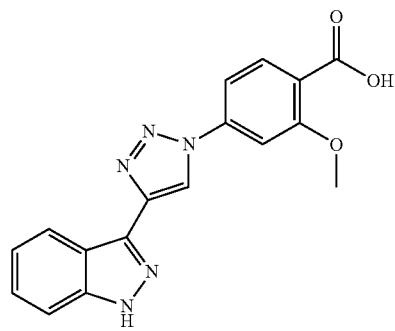 [SMILES: COc1cc(-n2cc(-c3n[nH]c4ccccc34)nn2)ccc1C(=O)O]

Methyl 4-[4-(1H-indazol-3-yl)-1H-1,2,3-triazol-1-yl]-2-methoxybenzoate (363 mg; 1.04 mmol; 1.0 eq.) suspended in MeOH (8 mL) was treated with sodium hydroxide (8.3 mL, 1N; 8.3 mmol; 8.0 eq.) and stirred at RT until all solid was dissolved (3 h). MeOH was removed under reduced pressure, the resulting solution was made acidic by addition of HCl 1N and extracted with DCM (3 times). Combined organic phases were washed with brine, dried over magnesium sulfate, filtered and concentrated to give the title compound as a beige solid (249 mg, 71%). MS (ESI+): 336.1, MS (ESI−): 334.2.

Intermediate 13:
[1-(4-azidobenzoyl)piperidin-3-yl]methanol

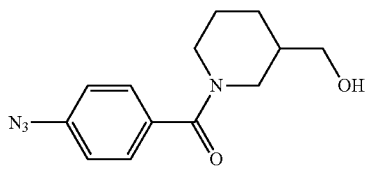 [SMILES: [N-]=[N+]=Nc1ccc(C(=O)N2CCCC(CO)C2)cc1]

The title compound was obtained following procedure described for intermediate 3, but starting from azidobenzoic acid (700 mg; 4.3 mmol; 1.0 eq.) and 3-(hydroxymethyl)piperidine (533 µl; 4.7 mmol; 1.1 eq.) as an oil (1.12 g; 100%). $^1$H NMR (300 MHz, DMSO-d6) δ: 7.41 (d, J=8.6 Hz, 2H), 7.17 (d, J=8.6 Hz, 2H), 4.56-4.28 (m, 2H), 3.68-3.47 (m, 1H), 3.29 (m, 1H), 3.12-2.94 (m, 1H), 2.82-2.54 (m, 2H), 1.74-1.39 (m, 4H), 1.26-1.13 (m, 1H). HPLC (Condition A): Rt 2.40 min (purity 89.4%). MS (ESI+): 261.1.

Intermediate 14:
[1-(4-azidobenzoyl)piperidin-3-yl]methanol

Step a) Formation of (4-azidophenyl)acetic acid

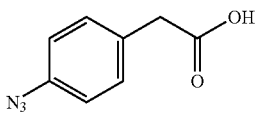 [SMILES: [N-]=[N+]=Nc1ccc(CC(=O)O)cc1]

The title compound was obtained, following procedure described for intermediate 7, step c), but starting from Methyl (4-aminophenyl)acetate (1.0 g; 6.05 mmol; 1.0 eq.) as a beige powder (790 mg, 74%). $^1$H NMR (300 MHz, DMSO-d6): 137.29 (d, J=8.5 Hz, 2H), 7.06 (d, J=8.5 Hz, 2H), 3.57 (s, 2H).

Step b) Formation of {4-[4-(1H-indazol-3-yl)-1H-1,2,3-triazol-1-yl]phenyl}acetic acid

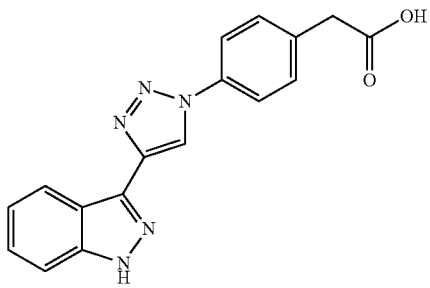 [SMILES: O=C(O)Cc1ccc(-n2cc(-c3n[nH]c4ccccc34)nn2)cc1]

The title compound was obtained, following procedure described for intermediate 10, but starting from 3-ethynyl-1H-indazole (300 mg; 2.11 mmol; 1.0 eq.) and (4-azidophenyl)acetic acid (374 mg; 2.11 mmol; 1.0 eq.) as a white solid (525 mg; 78%). $^1$H NMR (300 MHz, DMSO-d6): 13.35 (brs, 1H), 12.47 (bs, 1H), 9.29 (s, 1H), 8.36 (d, J=8.1 Hz, 1H), 8.00 (d, J=8.5 Hz, 2H), 7.601 (d, J=8.4 Hz, 1H), 7.51 (d, J=8.5 Hz, 2H), 7.47-7.41 (m, 1H), 7.28-7.232 (m, 1H), 3.71 (s, 2H). HPLC (Condition A): Rt 2.99 min (purity 93.1%).

Intermediate 15: {3-[4-(1H-indazol-3-yl-1H-1,2,3-triazol-1-yl]phenyl}acetic acid

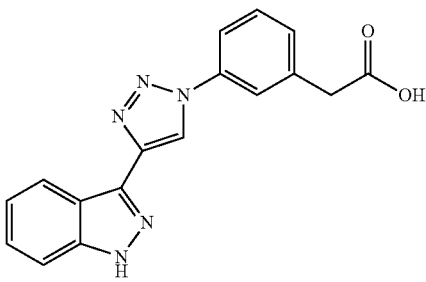 [SMILES: O=C(O)Cc1cccc(-n2cc(-c3n[nH]c4ccccc34)nn2)c1]

The title compound was obtained, following procedure described for intermediate 10, but starting from (3-azidophenyl)acetic acid (prepared as described in J. Med. Chem. (2005), 48(23), 7153-7165; 586 mg; 3.31 mmol; 1.0 eq.) and 3-ethynyl-1H-indazole (470 mg; 3.31 mmol; 1.0 eq.) as a brown solid (880 mg; 83.3%). $^1$H NMR (300 MHz, DMSO-d6): 13.36 (brs, 1H), 12.51 (brs, 1H), 9.31 (s, 1H), 8.36 (dt, J=8.2 Hz, 1.0 Hz, 1H), 8.01 (t, J=1.8 Hz, 1H), 7.96-7.93 (m, 1H), 7.63-7.55 (m, 2H), 7.47-7.41 (m, 2H), 7.28-7.23 (m, 1H), 3.76 (s, 2H).

Intermediate 16:
4-(4-azido-2-fluorobenzoyl)morpholine

Step a) Formation of
3-fluoro-4-(morpholin-4-ylcarbonyl)aniline

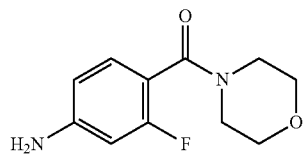

The title compound was obtained, following procedure described for intermediate 3, but starting from 4-amino-2-fluorobenzoic acid (150 mg; 0.97 mmol; 1.0 eq.) and morpholine (102 µl; 1.16 mmol; 1.2 eq.) as a pale orange oil (200 mg, 92.0%). $^1$H NMR (300 MHz, DMSO-d6) δ 7.04 (t, J=8.4 Hz, 1H), 6.41 (dd, J=8.4 Hz, 2.1 Hz, 1H), 6.31 (dd, J=13.0 Hz, 2.1 Hz, 1H), 3.26-3.36 (m, 8H). HPLC (Condition A): Rt 1.42 min (purity 96.3%).

Step b) Formation of
4-(4-azido-2-fluorobenzoyl)morpholine

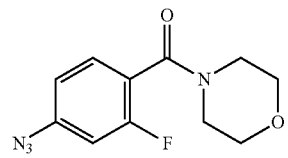 [SMILES: [N-]=[N+]=Nc1ccc(C(=O)N2CCOCC2)c(F)c1]

Tert-butyl nitrite (0.16 mL; 1.34 mmol; 1.5 eq.) was added to a solution of 3-fluoro-4-(morpholin-4-ylcarbonyl)aniline (200 mg; 0.89 mmol; 1.0 eq.) in AcOEt (6 mL) maintained at −10° C. The reaction mixture was stirred at −10° C. for 10 minutes before the addition of azidotrimethylsilane (0.14 mL; 1.07 mmol; 1.2 eq.). Reaction mixture was stirred at RT for 2 hours and concentrated under reduced pressure to give the title compound as a pale orange oil (220 mg, 99%). ¹H NMR (300 MHz, DMSO-d6): δ: 7.45 (t, J=8.0 Hz, 1H), 7.15 (dd, J=11.0 Hz, 2.1 Hz, 1H), 7.06 (dd, J=8.0 Hz, 2.1 Hz, 1H), 3.64-3.63 (m, 4H), 3.52 (t, J=4.6 Hz, 2H), 3.23 (t, J=4.6 Hz, 2H). MS (ES+): 2521.1; Rt 1.02 min (purity=92%).

Intermediate 17: tert-butyl 4-(3-ethynyl-1H-Indazol-5-yl)piperidine-1-carboxylate Step a) Formation of tert-butyl 4-(1H-indazol-5-yl)-3,6-dihydropyridine-1(2H)-carboxylate

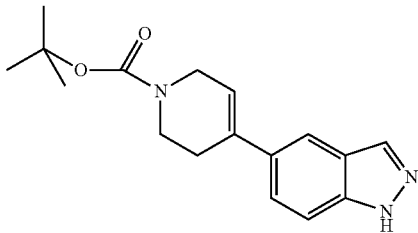 [SMILES: CC(C)(C)OC(=O)N1CC=C(c2ccc3[nH]ncc3c2)CC1]

A suspension of 5-bromoindazole (Combi-blocks; 3.0 g; 15.2 mmol; 1.0 eq.), tert-butyl 4-(4,4,5,5-tetramethyl-1,3,2-dioxaborolan-2-yl)-3,6-dihydropyridine-1(2H)-carboxylate (Frontier Scientific; 6.59 g; 21.3 mmol; 1.4 eq.), 1,1'-bis-(diphenylphosphino)ferrocene (1.11 g; 1.52 mmol; 0.1 eq.) and potassium carbonate (6.31 g; 45.7 mmol; 3.0 eq.) in degassed dioxane (60 mL) and water (30 mL) was heated at 90° C. for 24 h. The reaction mixture was cooled, diluted with DCM and filtered through a celite pad. Water was added to the filtrate and aqueous phase was extracted three times with DCM. Combined organic phases were washed with brine, dried over magnesium sulfate, filtered and concentrated. The crude was adsorbed on silica and purified by flash chromatography on silica (heptane/EtOAc, gradient from 80:20 to 30:70) to give the title compound as an off white solid. ¹H NMR (300 MHz, DMSO-d6) δ 13.04 (brs, 1H), 8.04 (s, 1H), 7.78-7.71 (m, 1H), 7.53-7.44 (m, 2H), 6.14 (s, 1H), 4.10-3.92 (m, 2H), 3.56 (t, J=5.7 Hz, 2H), 2.60-2.51 (m, 2H), 1.41 (s, 9H). HPLC (Condition A): Rt 4.42 min (purity 93.6%). MS (ES+): 341.2. MS (ES−): 298.2.

Step b) Formation of tert-butyl 4-(1H-indazol-5-yl)piperidine-1-carboxylate

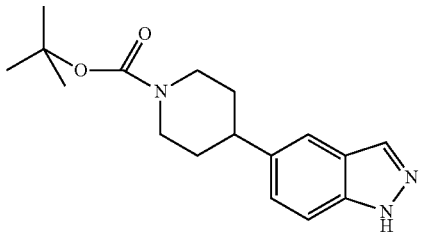 [SMILES: CC(C)(C)OC(=O)N1CCC(c2ccc3[nH]ncc3c2)CC1]

A solution of tert-butyl 4-(1H-indazol-5-yl)-3,6-dihydropyridine-1(2H)-carboxylate (200 mg; 0.67 mmol; 1.0 eq.) in MeOH (6 mL) was hydrogenated (10 bars) in a Paar instrument in presence of Pd/C (10% Pd moistened 50% H₂O; 7.11 mg; 0.07 mmol; 0.10 eq.) at RT. After 12 h, the reaction mixture was filtered through a celite pad and the filtrate was concentrated to dryness to give the title compound as a grey foam (200 mg; 99%). ¹H NMR (300 MHz, DMSO-d6) δ 12.94 (brs, 1H), 7.98 (s, 1H), 7.56 (s, 1H), 7.49-7.43 (m, 1H), 7.28-7.22 (m, 1H), 4.18-4.02 (m, 2H), 2.99-2.67 (m, 3H), 1.83-1.73 (m, 2H), 1.65-1.46 (m, 2H), 1.42 (s, 9H).

Step c) Formation of tert-butyl 4-(3-iodo-1H-indazol-5-yl)piperidine-1-carboxylate

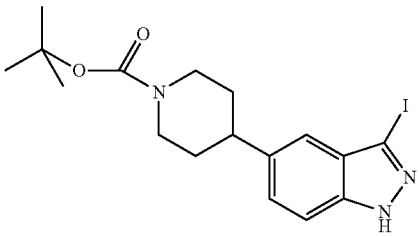 [SMILES: CC(C)(C)OC(=O)N1CCC(c2ccc3[nH]nc(I)c3c2)CC1]

KOH (141.5 mg; 2.52 mmol; 3.8 eq.) pellets were added in small portion during 10 min to a solution of tert-butyl 4-(1H-indazol-5-yl)piperidine-1-carboxylate (200 mg; 0.66 mmol; 1.0 eq.) and iodine (0.34 g; 1.33 mmol; 2.0 eq.) in dry DMF (6 mL). The reaction mixture was stirred O/N at RT. It was then poured into a saturated solution of Na₂S₂O₃ (100 mL) and extracted three times with ether. Combined organic layers were washed with water, brine, dried over magnesium sulfate, filtered and concentrated to give the title compound as a yellow foam (225 mg, 79%). ¹H NMR (300 MHz, DMSO-d6) δ 13.41 (brs, 1H), 7.48 (d, J=8.6 Hz, 1H), 7.35 (dd, J=8.7, 1.3 Hz, 1H), 7.20 (s, 1H), 4.26-3.94 (m, 2H), 2.93-2.74 (m, 3H), 1.99-1.70 (m, 2H), 1.67-1.47 (m, 2H), 1.42 (s, 9H). HPLC (Condition A): Rt 5.10 min (purity 100%).

Step d) Formation of tert-butyl 5-[1-(tert-butoxycarbonyl)piperidin-4-yl]-3-iodo-1H-indazole-1-carboxylate

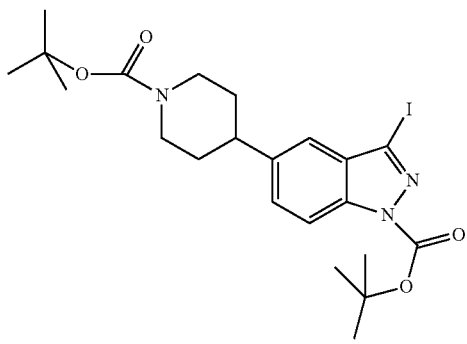 [SMILES: CC(C)(C)OC(=O)N1CCC(c2ccc3c(c2)c(I)nn3C(=O)OC(C)(C)C)CC1]

A solution of tert-butyl 4-(3-iodo-1H-indazol-5-yl)piperidine-1-carboxylate (218. mg; 0.51 mmol; 1.0 eq.), di-tert-butyldicarboxylate (145 mg; 0.66 mmol; 1.3 eq.), diméthylamino-4-pyridine (12.5 mg; 0.10 mmol; 0.20 eq.) and TEA (86.0 µl; 0.61 mmol; 1.2 eq.) in acetonitrile (6.5 mL) was stirred at RT O/N. Acetonitrile was removed under reduced pressure, the residue was diluted with water and extracted three times with Ether. Combined organic phases were washed with brine, dried over magnesium sulfate, filtered and concentrated. The crude was purified by flash chromatography on silica (heptane/EtOAc, gradient from 90:10 to 75:25) to give the title compound as a colorless oil (200 mg, 74%). $^1$H NMR (300 MHz, DMSO-d6) δ 7.99 (d, J=8.7 Hz, 1H), 7.62 (dd, J=1.6, 8.7 Hz, 1H), 7.35 (s, 1H), 4.18-4.03 (m, 2H), 2.96-2.73 (m, 3H), 1.87-1.75 (m, 2H), 1.64 (s, 9H). 1.61-1.48 (m, 2H), 1.42 (s, 9H). (Condition A): Rt 6.33 min (purity 99.8%).

Step e) Formation of tert-butyl 5-[1-(tert-butoxycarbonyl)piperidin-4-yl]-3-[(trimethylsilyl)ethynyl]-1H-indazole-1-carboxylate

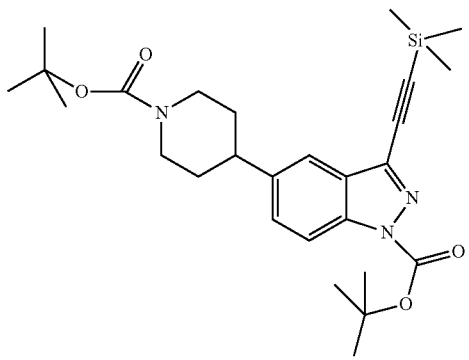 [SMILES: CC(C)(C)OC(=O)N1CCC(c2ccc3c(c2)c(C#C[Si](C)(C)C)nn3C(=O)OC(C)(C)C)CC1]

A suspension of tert-butyl 5-[1-(tert-butoxycarbonyl)piperidin-4-yl]-3-iodo-1H-indazole-1-carboxylate (200 mg; 0.38 mmol; 1.0 eq.), (Trimethylsilyl)acetylene (53 μl; 0.38 mmol; 1.0 eq.), TEA (158 μl) and bis(triphenylphosphine)palladium(II) chloride (10.7 mg; 0.02 mmol; 0.04 eq.) was heated at 70° C. overnight in a sealed tube. The reaction mixture was diluted with EtOAc and washed with a saturated solution of NH$_4$Cl and brine. The organic phase was dried over magnesium sulfate, filtered and concentrated to give the tittle compound as a brown gum (200 mg, 100%). $^1$H NMR (300 MHz, DMSO-d6) δ 8.04 (d, J=8.7 Hz, 1H), 7.63-7.54 (m, 2H), 4.15-4.04 (m, 2H), 2.99-2.74 (m, 3H), 1.86-1.74 (m, 2H), 1.64 (s, 9H), 1.61-1.52 (m, 2H), 1.42 (s, 9H), 0.32 (s, 9H).

Step f) Formation of tert-butyl 4-(3-ethynyl-1H-indazol-5-yl)piperidine-1-carboxylate

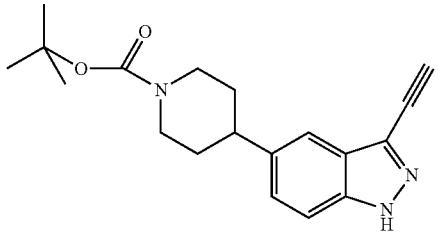 [SMILES: C#Cc1n[nH]c2ccc(C3CCN(C(=O)OC(C)(C)C)CC3)cc12]

A solution of tert-butyl 5-[1-(tert-butoxycarbonyl)piperidin-4-yl]-3-[(trimethylsilyl)ethynyl]-1H-indazole-1-carboxylate (189 mg; 0.38 mmol; 1.0 eq.) and potassium carbonate (5.3 mg; 0.04 mmol; 0.1 eq.) in EtOH (3.8 mL) was stirred at RT O/N. EtOH was removed under reduced pressure and the residue was diluted with ether, washed with water then brine, dried over magnesium sulfate, filtered and concentrated. The crude was purified by flash chromatography on silica (heptane/EtOAc, gradient from 90:10 to 60:40) to give the title compound as a beige solid (118 mg, 95%). $^1$H NMR (300 MHz, DMSO-d6) δ 13.35 (brs, 1H), 7.55-7.47 (m, 2H), 7.33 (dd, J=1.6, 8.6 Hz, 1H), 4.48 (s, 1H), 4.15-4.03 (m, 2H), 2.93-2.71 (m, 3H), 1.86-1.74 (m, 2H), 1.65-1.45 (m, 2H), 1.42 (s, 9H). HPLC (Condition A): Rt 4.78 min (purity 99.1%).

Intermediate 18: 3-{3-[4-(1H-indazol-3-yl)-1H-1,2,3-triazol-1-yl]phenyl}propanoic acid

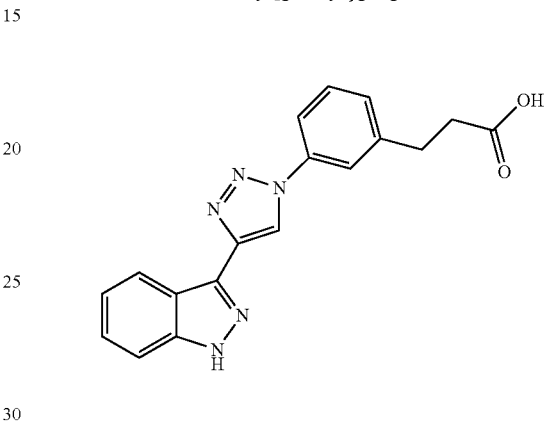

The title compound was obtained, following procedure described for intermediate 10, but starting from 3-(3-azidophenyl)propanoic acid (prepared as described in J. Med. Chem (1994), 37(12), 1841-1849, 570 mg; 2.98 mmol; 1.0 eq.) and 3-ethynyl-1H-indazole (424 mg; 2.98 mmol; 1.0 eq.) as a brown solid. $^1$H NMR (300 MHz, DMSO-d6): 13.36 (brs, 1H), 12.51 (brs, 1H), 9.32 (s, 1H), 8.36 (dt, J=1.0, 8.2 Hz, 1H), 7.96 (t, J=2.0 Hz, 1H), 7.90-7.87 (m, 1H), 7.61 (dt, J=8.4 Hz, 1.0 Hz, 1H), 7.54 (t, J=7.8 Hz, 1H), 7.47-7.38 (m, 2H), 7.28-7.23 (m, 1H), 2.97 (t, J=7.6 Hz, 2H), 2.68 (t, J=7.6 Hz, 2H).

Intermediate 19: 4-(4-azido-2-chlorobenzoyl)morpholine

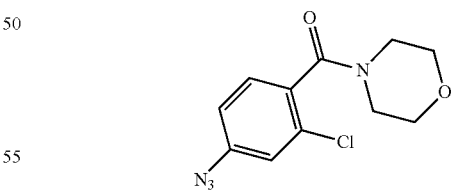

The title compound was obtained, following procedure described for intermediate 16, sep b), but starting from 3-chloro-4-(morpholin-4-ylcarbonyl)aniline (Enamine, 1.40 g; 5.8 mmol; 1.0 eq.) as a beige solid (1.5 g, 97%). $^1$H NMR (300 MHz, DMSO-d6) δ: 7.41 (d, J=8.3 Hz, 1H), 7.31 (d, J=2.2 Hz, 1H), 7.18 (dd, J=8.3 Hz, 2.2 Hz, 1H), 3.64-3.63 (m, 4H), 3.52 (t, J=4.7 Hz, 2H), 3.12 (t, J=4.7 Hz, 2H). HPLC (Condition A): Rt 2.81 min (purity 83%).

Intermediate 20: tert-butyl 3-ethynyl-5-(hydroxymethyl)-1H-indazole-1-carboxylate

Step a) Formation of tert-butyl 3-bromo-5-formyl-1H-indazole-1-carboxylate

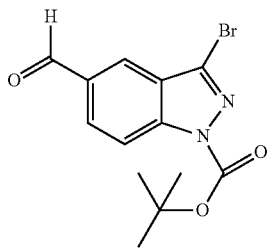 [SMILES: CC(C)(C)OC(=O)n1nc(Br)c2cc(C=O)ccc21]

The title compound was obtained, following procedure described for intermediate 17, step d), but starting from 3-bromo-1H-indazole-5-carboxaldehyde (1.09 g; 4.84 mmol; 1.0 eq.) as a white solid (1.2 g, 76%). $^1$H NMR (300 MHz, DMSO-d6) δ 10.16 (s, 1H), 8.38-8.33 (m, 1H), 8.26 (d, J=8.8 Hz, 1H), 8.17 (dd, J=1.5, 8.8 Hz, 1H), 1.66 (s, 9H). HPLC (Condition A): Rt 4.07 min (purity 96.6%). MS (ESI+): 325.1, 327.1.

Step b) Formation of tert-butyl 3-bromo-5-(hydroxymethyl)-1H-indazole-1-carboxylate

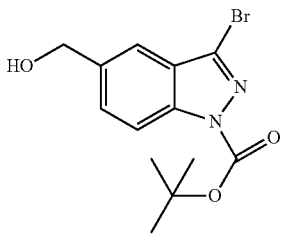 [SMILES: CC(C)(C)OC(=O)n1nc(Br)c2cc(CO)ccc21]

Sodium borohydride (395 mg; 10.4 mmol; 2.9 eq.) was added in one portion to a solution of tert-butyl-3-bromo-5-formyl-1H-indazole-1-carboxylate (1.20 g; 3.58 mmol; 1.0 eq.) in DMF (30 mL). The reaction mixture was stirred for 3 h then poured into HCl (0.1N solution) and extracted with EtOAc. Combined organic phases were washed with brine, dried over magnesium sulfate, filtered and concentrated to give the tittle compound as a yellow solid (1.19 g, 100%). $^1$H NMR (300 MHz, DMSO-d6) δ 8.05 (d, J=8.7 Hz, 1H), 7.69-7.60 (m, 2H), 4.66 (s, 2H), 1.65 (s, 9H). HPLC (Condition A): Rt 3.65 min (purity 81.6%). MS (ESI+): 327.1, 329.1.

Step c) Formation of tert-butyl 5-(hydroxymethyl)-3-[(trimethylsilyl)ethynyl]-1H-indazole-1-carboxylate

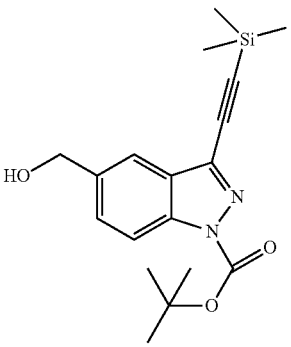 [SMILES: CC(C)(C)OC(=O)n1nc(C#C[Si](C)(C)C)c2cc(CO)ccc21]

A mixture of trimethylsilylacetylene (1.60 mL; 11.3 mmol; 2.1 eq.), tert-butyl 3-bromo-5-(hydroxymethyl)-1H-indazole-1-carboxylate (1.80 g; 5.50 mmol; 1.0 eq.), Pd(OAc)$_2$ (54 mg; 0.24 mmol; 0.04 eq.), triphenylphosphine (115 mg; 0.44 mmol; 0.08 eq.) and Copper iodide (62 mg; 0.33 mmol; 0.06 eq.) in TEA (50 mL) was degassed then heated at reflux for 3 h. After cooling, it was poured into HCl (0.1 N solution) and extracted with EtOAc. Combined organic phases were washed with brine, dried over magnesium sulfate, filtered and concentrated to give the title compound as a brown oil (2.6 g). $^1$H NMR (300 MHz, DMSO-d6) δ 8.06 (d, J=8.7 Hz, 1H), 7.71 (s, 1H), 7.60 (dd, J=1.6, 8.7 Hz, 1H), 5.41 (t, J=5.7 Hz, 1H), 4.66 (d, J=5.7 Hz, 2H), 1.65 (s, 9H), 0.32 (s, 9H). MS (ESI+): 345.2.

Step d) Formation of tert-butyl 3-ethynyl-5-(hydroxymethyl) 1H-indazole-1-carboxylate

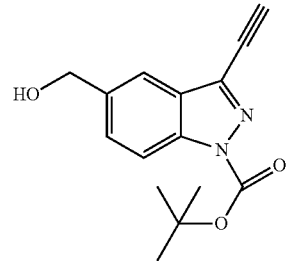 [SMILES: C#Cc1nn(C(=O)OC(C)(C)C)c2ccc(CO)cc12]

TBAF (10 mL of a 1.0 M solution in THF; 10 mmol; 2.5 eq.) was added in one portion to a solution of tert-butyl 5-(hydroxymethyl)-3-[(trimethylsilyl)ethynyl]-1H-indazole-1-carboxylate (2.6 g; 3.92 mmol; 1.0 eq.) in THF (30 mL). The reaction mixture was stirred at RT for 30 min and concentrated under reduced pressure. The crude residue was purified by flash chromatography on silica (n-heptane/EtOAc, gradient from 80:20 to 50:50) to give the title compound as a yellow solid. $^1$H NMR (300 MHz, DMSO-d6) δ 8.06 (d, J=8.7 Hz, 1H), 7.74 (s, 1H), 7.61 (dd, J=1.5, 8.7 Hz, 1H), 5.41 (t, J=5.6 Hz, 1H), 4.88 (s, 1H), 4.66 (d, J=5.6 Hz, 2H), 1.65 (s, 9H). HPLC (Condition A): Rt 3.29 min (purity 81.6%). MS (ESI+): 273.0.

Intermediate 21: tert-butyl 5-(bromomethyl)-3-{1-[4-(methoxycarbonyl)phenyl]-1H-1,2,3-triazol-4-yl}-1H-indazole-1-carboxylate

Step a) Formation of tert-butyl 3-ethynyl-5-methyl-1H-indazole-1-carboxylate

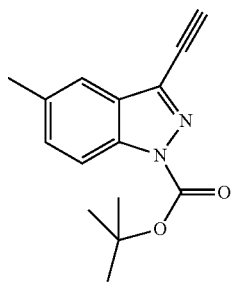 [SMILES: C#Cc1nn(C(=O)OC(C)(C)C)c2ccc(C)cc12]

The title compound was obtained, following procedure described for intermediate 17, step d), but starting from 3-ethynyl-5-methyl-1H-indazole (1.05 g; 6.72 mmol; 1.0 eq) as an orange solid (1.66 g, 96%). $^1$H NMR (300 MHz, DMSO-d6) δ 8.00 (d, J=8.7 Hz, 1H), 7.60 (s, 1H), 7.50 (dd, J=1.4, 8.7 Hz, 1H), 4.86 (s, 1H), 2.46 (s, 3H), 1.65 (s, 9H). HPLC (Condition A): Rt 4.56 min (purity 94.3%). MS (ESI+): 257.2.

Step b) Formation of tert-butyl 3-{1-[4-(methoxycarbonyl)phenyl]-1H-1,2,3-triazol-4-yl}-5-methyl-1H-indazole-1-carboxylate

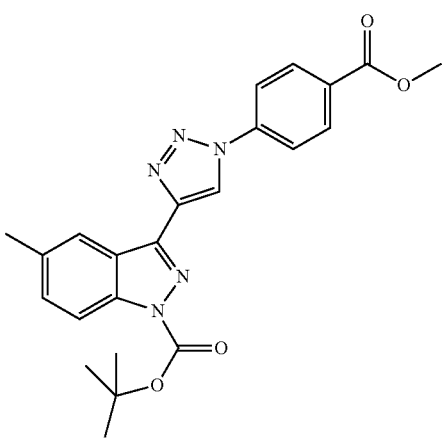

Copper sulfate pentahydrate (0.08 g; 0.33 mmol; 0.06 eq.) was added to a solution of tert-butyl-3-ethynyl-5-methyl-1H-indazole-1-carboxylate (1.55 g; 6.03 mmol; 1.0 eq.), methyl 4-azidobenzoate (prepared as described in JOC (2006), 71(15), 5822-5825; 1.20 g; 6.77 mmol; 1.1 eq.) and D-(−)-isoascorbic acid sodium salt (0.24 g; 1.22 mmol; 0.20 eq.) in DMF (15 mL) and water (0.50 mL). The reaction suspension was heated in MW at 80° C. for 45 min then poured into HCl (0.1 N solution) and extracted with EtOAc. Combined organic phases were washed with brine, dried over magnesium sulfate, filtered and concentrated. The crude was purified by flash chromatography on silica (n-heptane/EtOAc, gradient from 90:10 to 60:40) to give the title compound as a yellow solid. $^1$H NMR (300 MHz, DMSO) δ 9.66 (s, 1H), 8.35-8.25 (m, 3H), 8.20 (d, J=8.8 Hz, 2H), 8.05 (d, J=8.7 Hz, 1H), 7.54 (dd, J=1.5, 8.7 Hz, 1H), 3.91 (s, 3H), 2.53 (s, 3H), 1.69 (s, 9H). HPLC (Condition A): Rt 5.07 min (purity 96.8%). MS (ESI+): 434.4.

Step c) Formation of tert-butyl 5-(bromomethyl)-3-{1-[4-(methoxycarbonyl)phenyl]-1H-1,2,3-triazol-4-yl}-1H-indazole-1-carboxylate

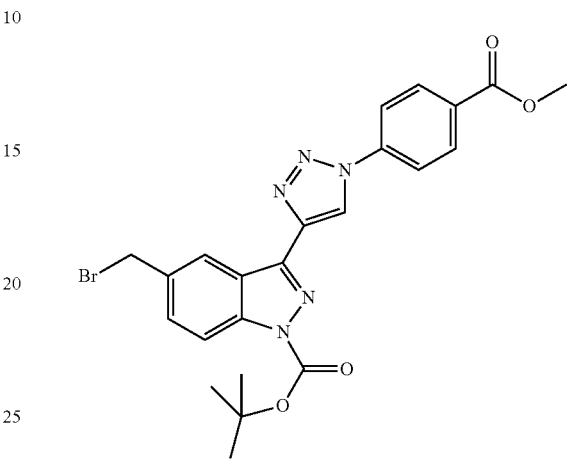

Zirconium tetrachloride (23 mg; 0.10 mmol; 0.1 eq.) was added in one portion to a solution of NBS (160 mg; 0.90 mmol; 0.9 eq.) in DCM (10 mL) at 0° C. A solution of tert-butyl 3-{1-[4-(methoxycarbonyl)phenyl]-1H-1,2,3-triazol-4-yl}-5-methyl-1H-indazole-1-carboxylate (434 mg; 1.00 mmol; 1.0 eq.) in DCM (10 mL) was then added dropwise to the reaction mixture which was subsequently stirred at RT for 16 h. The reaction mixture was then diluted with DCM and washed sequentially with saturated NaHCO$_3$ and brine, dried over magnesium sulfate, filtered and concentrated to give the title compound as a yellow solid (392 mg, 76%) $^1$H NMR (300 MHz, DMSO) δ 9.70 (s, 1H), 8.62 (d, J=1.0 Hz, 1H), 8.30 (d, J=8.8 Hz, 2H), 8.21 (d, J=8.8 Hz, 2H), 8.16 (d, J=8.8 Hz, 1H), 7.79 (dd, J=8.8 Hz, 1.7, 1H), 4.99 (s, 2H), 3.92 (s, 3H), 1.70 (s, 9H). MS (ESI+): 512.3.

Intermediate 22: tert-butyl 5-(hydroxymethyl)-3-{1-[4-(morpholin-4-ylcarbonyl)phenyl]-1H-1,2,3-triazol-4-yl}-1H-indazole-1-carboxylate

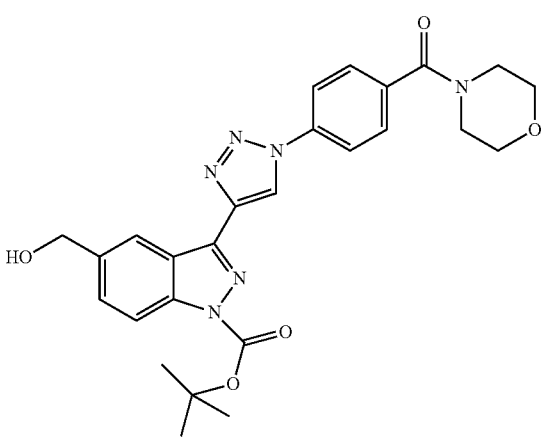 [SMILES: CC(C)(C)OC(=O)n1nc(-c2cn(-c3ccc(C(=O)N4CCOCC4)cc3)nn2)c2cc(CO)ccc21]

The title compound was obtained, following procedure described for intermediate 21, step b), but starting from tert-butyl-3-ethynyl-5-(hydroxymethyl)-1H-indazole-1-carboxylate (557 mg; 1.68 mmol; 1.0 eq.) as a yellow solid. ¹H NMR (300 MHz, DMSO-d6) δ 9.61 (s, 1H), 8.49 (s, 1H), 8.20 (d, J=8.6 Hz, 2H), 8.12 (d, J=8.8 Hz, 1H), 7.70 (d, J=8.6 Hz, 2H), 7.65 (dd, J=1.5, 8.7 Hz, 1H), 5.44 (t, J=5.7 Hz, 1H), 4.71 (d, J=5.7 Hz, 2H), 3.78-3.35 (m, 1H), 1.70 (s, 9H). HPLC (Condition A): Rt 3.42 min (purity 94.9%). MS (ESI+): 505.3.

Intermediate 23:
4-[4-azido-2-(trifluoromethyl)benzoyl]morpholine

Step a) Formation of 4-(morpholin-4-ylcarbonyl)-3-(trifluoromethyl)aniline

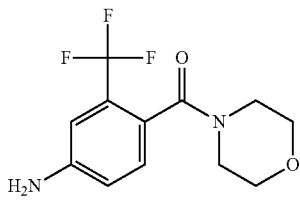 [SMILES: Nc1ccc(C(=O)N2CCOCC2)c(C(F)(F)F)c1]

The title compound was obtained, following procedure described for intermediate 3, but starting from 4-Amino-2-(trifluoromethyl)benzoic acid (1.00 g; 4.87 mmol; 1.0 eq.) and morpholine (515 µl; 5.85 mmol; 1.2 eq.) as an oil (1.36 g, 100%). ¹H NMR (300 MHz, DMSO-d6) δ 7.05 (d, J=8.2 Hz, 1H), 6.89 (s, 1H), 6.79 (d, J=8.2 Hz, 1H), 5.81 (brs, 2H), 3.74-3.35 (m, 6H), 3.29-2.97 (m, 2H).

Step b) Formation of 4-[4-azido-2-(trifluoromethyl)benzoyl]morpholine

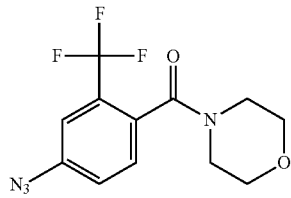 [SMILES: [N-]=[N+]=Nc1ccc(C(=O)N2CCOCC2)c(C(F)(F)F)c1]

The title compound was obtained, following procedure described for intermediate 16, step b), but starting from 4-(morpholin-4-ylcarbonyl)-3-(trifluoromethyl)aniline (730 mg; 2.66 mmol; 1.0 eq.) as an orange oil (837 mg, quantitative). HPLC (Condition A): Rt 3.56 min (purity 77.0%). MS (ESI+): 301.1.

Intermediate 24:
4-(4-azido-3-fluorobenzoyl)morpholine

Step a) Formation of 2-fluoro-4-(morpholin-4-ylcarbonyl)aniline

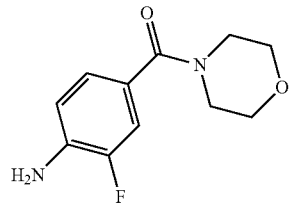 [SMILES: Nc1ccc(C(=O)N2CCOCC2)cc1F]

The title compound was obtained, following procedure described for intermediate 3, but starting from 4-Amino-3-fluorobenzenecarboxylic acid (Apollo Scientific, 500 mg; 3.22 mmol; 1.0 eq.) and morpholine (340 µl; 3.87 mmol; 1.2 eq.) as an orange solid (643 mg, 89%). ¹H NMR (300 MHz, DMSO-d6) δ 7.08 (dd, J=1.8, 12.0 Hz, 1H), 7.00 (dd, J=1.8, 8.2 Hz, 1H), 6.81-6.69 (m, 1H), 5.59 (brs, 2H), 3.66-3.53 (m, 4H), 3.53-3.43 (m, 4H). HPLC (Condition A): Rt 1.21 min (purity 96.7%).

Step b) Formation of 4-(4-azido-3-fluorobenzoyl)morpholine

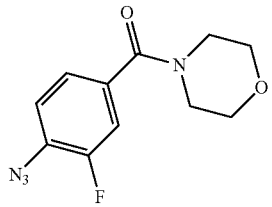 [SMILES: [N-]=[N+]=Nc1ccc(C(=O)N2CCOCC2)cc1F]

The title compound was obtained, following procedure described for intermediate 16, step b), but starting from 2-fluoro-4-(morpholin-4-ylcarbonyl)aniline (643 mg; 2.87 mmol; 1.0 eq.) as an orange oil (729 mg, 100%). ¹H NMR (300 MHz, DMSO-d6) δ 7.41-7.18 (m, 3H), 3.77-3.11 (m, 8H). HPLC (Condition A): Rt 3.02 min (purity 84.7%).

Intermediate 25:
1-(1-methylpyrrolidin-3-yl)-1H-pyrazol-4-amine

Step a) Formation of 4-nitro-1-pyrrolidin-3-yl-1H-pyrazole hydrochloride

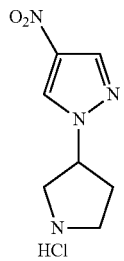 [SMILES: O=[N+]([O-])c1cnn(C2CCNC2)c1 ; Cl]

A solution of HCl (4N in dioxane, 50 mL, 150 mmol, 3.4 eq.) was added to a solution of tert-butyl-3-(4-nitro-1H-pyrazol-1-yl)pyrrolidine-1-carboxylate (prepared as described in *Tetrahedron Lett.* (2008), 49(18), 2996-2998, 13 g, 46 mmol, 1 eq.) in dry dioxane (75 mL) at 000° C. The reaction mixture was then stirred at RT for 5 h. It was concentrated under reduced pressure to give the title compound as an off-white solid (9.5 g, 95%). $^1$H NMR (400 MHz, DMSO-$d_6$) δ 9.73 (brs, 1H), 9.46 (brs, 1H), 9.07 (s, 1H), 8.37 (s, 1H), 5.24 (m, 1H), 3.50-3.72 (m, 3H), 2.28-2.49 (m, 3H).

Step b) Formation of 1-(1-Methylpyrrolidin-3-yl)-4-nitro-1H-pyrazole

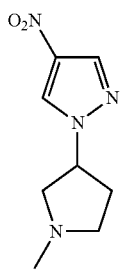

To a solution of Formic acid (50 ml) and Formaldehyde solution (50 mL) was added 4-Nitro-1-pyrrolidin-3-yl-1H-pyrazole hydrochloride (10 g). The reaction mixture was heated at 100° C. for 16 h. The reaction mixture was concentrated under reduced pressure. The residue was tarturated with acetonitrile (150 mL), filtered off solid and filtrate was concentrated. The crude material was basified with ammonia solution, extracted with ethyl acetate, dried over sodium sulphate and evaporated to afford (7 g, 78%) as pale yellow liquid. $^1$H NMR (400 Mz, DMSO-$d_6$) δ 8.85 (s, 1H), 8.24 (s, 1H), 5.24 (m, 1H), 2.75-2.81 (m, 3H), 2.33-2.49 (m, 2H), 2.27 (s, 3H), 2.12 (m, 1H).

Step c) Formation of 1-(1-Methylpyrrolidin-3-yl)-1H-pyrazol-4-amine

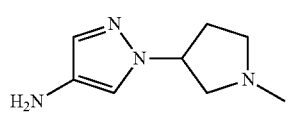

A solution of 1-(1-Methylpyrrolidin-3-yl)-4-nitro-1H-pyrazole (3.0 g, 18 mmol, 1 eq.) in methanol (40 mL) was hydrogenated (3 bars) in presence of Ra—Ni (1 g) at RT. After 3 h, the catalyst was filtered off and the filtrate was concentrated under reduced pressure to give the title compound as brown liquid. $^1$H NMR (400 MHz, DMSO-$d_6$) δ 7.06 (s, 1H), 6.85 (m, 1H), 4.67 (m, 1H), 3.82 (brs, 2H) 2.63-2.74 (m, 2H), 2.58-2.61 (m, 1H), 2.38-2.44 (m, 1H), 2.21-2.28 (m, 1H), 2.27 (s, 3H), 1.89-1.97 (m, 1H).

Intermediate 26: 3-ethynyl-5-bromo-1H-indazole

Step a) Formation of tert-butyl 5-bromo-3-[(trimethylsilyl)ethynyl]-1H-indazole-1-carboxylate

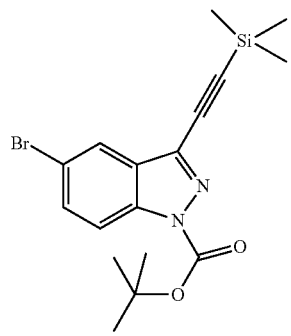 [SMILES: CC(C)(C)OC(=O)n1nc(C#C[Si](C)(C)C)c2cc(Br)ccc21]

The title compound was obtained, following procedure described for intermediate 2, step a), but starting from tert-Butyl 5-bromo-3-iodo-1H-indazole-1-carboxylate (J & W PharmLab, 16 g, 37 mmol) as a white solid (10 g, 67%): $^1$H NMR (400 MHz, DMSO-$d_6$) δ 8.05 (d, J=8.9 Hz, 1H), 7.97 (d, J=1.6 Hz, 1H), 7.81 (dd, J=1.9, 8.9 Hz, 1H), 1.63 (s, 9H), 0.31 (s, 9H).

Step b) Formation of 3-ethynyl-5-bromo-1H-indazole

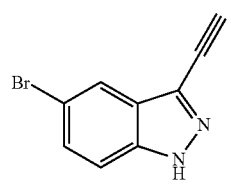

The title compound was obtained, following procedure described for intermediate 1, step b), but starting from of tert-butyl 5-bromo-3-[(trimethylsilyl)ethynyl]-1H-indazole-1-carboxylate (16 g, 0.04 mol) as a white solid (7 g, 78%). $^1$H NMR (400 MHZ, DMSO-d6) δ 13.63 (s, 1H), 7.87 (brs, 1H), 7.58 (d, J=8.8 Hz, 1H), 7.53 (dd, J=1.8, 8.8 Hz, 1H), 4.55 (s, 1H).

Intermediate 27: 3-(4-azido-1H-pyrazol-1-yl)-8-methyl-8-azabicyclo[3.2.1]octane

Step a) Formation of 8-Methyl-3-(4-nitro-1H-pyrazol-1-yl)-8-azabicyclo[3.2.1]octane

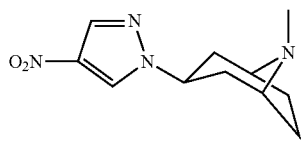 [SMILES: CN1C2CCC1CC(n1cc([N+](=O)[O-])cn1)C2]

To a solution of 4-Nitro-1H-pyrazole (10 g, 88.4 mmol) in DGM:DMF (3:1, 400 mL) were added Tropine (12.5 g, 88.4 mmol, 1 eq.), triphenyl phosphine (69.5 g, 265 mmol), followed by di-tert-butyl azodicarboxylate (61 g, 265 mmol) portionwise at 10-15° C. The reaction mixture was stirred at RT for 4 days. It was then concentrated under reduced pressure. The crude was purified by flash chromatography on silica (PetEther/EtOAc) to give the title compound as an off-white solid. $^1$H NMR (400 MHz, DMSO-$d_6$) δ 8.92 (s, 1H), 8.31 (s, 1H), 4.92-4.86 (m, 1H), 3.99 (m, 2H), 2.66-2.56 (m, 5H), 2.26-2.17 (m, 4H), 2.06-2.01 (m, 2H).

Step b) Formation of 1-(8-Methyl-8-azabicyclo[3.2.1]oct-3-yl)-1H-pyrazol-4-amine

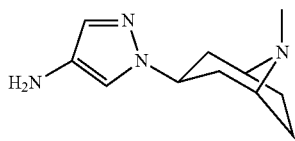

Ammonia was bubbled for 15 min in a solution of 8-Methyl-3-(4-nitro-1H-pyrazol-1-yl)-8-azabicyclo[3.2.1]octane (3.4 g, 14.4 mmol) in MeOH (300 mL). The solution was then hydrogenated (3 bars) in presence of Ra—Ni (2 g) at RT. After 2 h, the catalyst was filtered off and the filtrate was concentrated under reduced pressure. The solid was purified by trituration in acetonitrile (25 mL) to give the title compound as a white solid (2.2 g, 75%). $^1$H NMR (400 MHz, DMSO-$d_6$) δ 7.08 (brs, 1H), 6.87 (brs, 1H), 4.49 (brs, 1H), 3.84 (s, 2H), 2.61 (s, 3H), 2.42-2.36 (m, 2H), 2.19-2.16 (t, 2H), 2.06-1.97 (m, 4H).

Step c) Formation of 3-(4-azido-1H-pyrazol-1-yl)-8-azabicyclo[3.2.1]octane

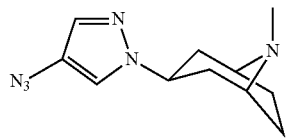 [SMILES: CN1C2CCC1CC(n1cc(N=[N+]=[N-])cn1)C2]

The title compound was prepared following procedure described for intermediate 7, step c), but starting from 1-(8-Methyl-8-aza-bicyclo[3.2.1]oct-3-yl)-1H-pyrazol-4-ylamine (124 mg; 0.60 mmol; 1.0 eq.) as a dark oil (139 mg; 100%) which was used without further purification in the next step. MS (ESI+): 233.0.

Intermediate 28: tert-butyl 4-(4-amino-1H-pyrazol-1-yl)azepane-1-carboxylate

Step a) Formation of tert-butyl 4-(4-nitro-1H-pyrazol-1-yl)azepane-1-carboxylate

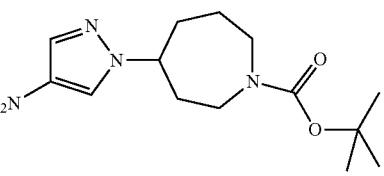

The title compound was obtained, following procedure described for intermediate 26, step a), but starting from 4-Nitro-1H-pyrazole (2.36 g, 20.9 mmol) and 4-hydroxyazepane-1-carboxylate (J & W PharmLab, 4.5 g, 20.9 mmol) as a white solid (4.5 g, 70%). $^1$H NMR: (400 MHz, DMSO-$d_6$) δ 8.91 (s, 1H), 8.25 (s, 1H), 4.49-4.41 (m, 1H), 3.60-3.53 (m, 1H), 3.41-3.38 (m, 2H), 3.27-3.31 (m, 1H), 2.08-2.01 (m, 2H), 1.97-1.90 (m, 2H), 1.87-1.83 (m, 1H), 1.66-1.63 (m, 1H), 1.40 (s, 9H).

Step b) Formation of tert-butyl 4-(4-amino-1H-pyrazol-1-yl)azepane-1-carboxylate

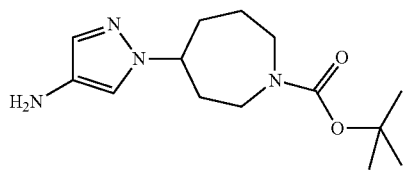 [SMILES: CC(C)(C)OC(=O)N1CCCC(n2cc([N+](=O)[O-])cn2)CC1]

A solution of tert-Butyl 4-(4-nitro-1H-pyrazol-1-yl)azepane-1-carboxylate (4.5 g, 15.5 mmol) in methanol (250 mL) was hydrogenated (3 bars) in presence of Palladium on Carbon (10%, 2 g) at RT. After 3 h, the reaction mixture was filtered through a celite pad and concentrated under reduced pressure to give the title compound as a brown solid (3.8 g, 95%). $^1$H NMR: (400 MHz, DMSO-$d_6$) δ 6.99 (s, 1H), 6.86 (s, 1H), 4.05 (m, 1H), 3.94 (m, 2H), 3.85 (m, 2H), 2.85 (brs, 2H), 1.86 (m, 2H), 1.65 (m, 2H), 1.40 (s, 9H).

Intermediate 29: 3-[1-(4-Bromo-phenyl)-1H-[1,2,3]triazol-4-yl]-1H-indazole

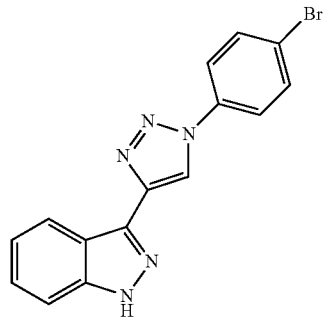 [SMILES: Brc1ccc(-n2cc(-c3n[nH]c4ccccc34)nn2)cc1]

To a solution of 3-Ethynyl-1H-indazole (6.0 g, 42.2 mmol) in Dioxane (60 mL) were added 4-Azidobromobenzene (Ukrorgsynthesis Ltd., 9.19 g, 46.4 mmol), D-(−)-Iso ascorbic acid sodium salt (0.83 g, 4.2 mmol) and a solution of CuSO$_4$.5H$_2$O (0.21 g, 0.8 mmol) in water (10 mL). The reaction mixture was heated at 80° C. for 3 days. After completion of the reaction, the reaction mixture was cooled to RT, diluted with ethyl acetate, washed with water and brine, dried over sodium sulfate and concentrated. The crude compound was recrystallized from methanol and dried under vacuum to afford the title compound as brown solid (9.0 g, 63%). $^1$H NMR (400 MHz, DMSO-$d_6$) δ 13.36 (s, 1H), 9.36 (s, 1H), 8.35-8.33 (d, J=8.1 Hz, 1H), 8.06-8.02 (m, 2H), 7.86-7.82 (m, 2H), 7.61-7.59 (d, J=8.4 Hz, 1H), 7.45-7.41 (m, 1H), 7.26-7.22 (m, 1H).

Intermediate 30: tert-butyl 4-{4-[4-(1H-indazol-3-yl)-1H-1,2,3-triazol-1-yl]phenyl}-3,6-dihydropyridine-1(2H)-carboxylate

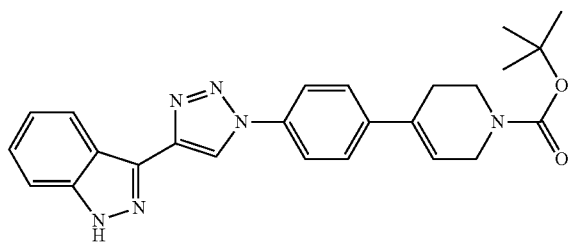 [SMILES: CC(C)(C)OC(=O)N1CC=C(c2ccc(-n3cc(-c4n[nH]c5ccccc45)nn3)cc2)CC1]

The title compound was obtained, following procedure described for intermediate 7, step a), but starting from 3-[1-(4-Bromo-phenyl)-1H-[1,2,3]triazol-4-yl]-1H-indazole (400 mg; 1.2 mmol; 1.0 eq.) and 1-N-Boc-(4,4,5,5-tetramethyl-[1,3,2]dioxaborolan-2-yl)-3,6-dihydro-2H-pyridine (545 mg; 1.76 mmol; 1.5 eq.) as a brown solid (515 mg, 99%). HPLC (max plot) 97.3%; Rt 4.95 min. UPLC/MS: (MS+) 443.3, (MS−) 441.3.

Intermediate 31: 4-(4-azidophenyl)-1-(3,3,3-trifluoropropyl)piperidine

Step a) Formation of tert-butyl 4-(4-nitrophenyl)-3,6-dihydropyridine-1(2H)-carboxylate

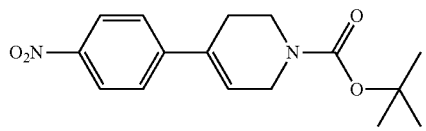 [SMILES: CC(C)(C)OC(=O)N1CC=C(c2ccc([N+](=O)[O-])cc2)CC1]

A mixture of 4-nitrophenylboronic acid pinacol ester (4.5 g; 18.1 mmol; 1.2 eq.), tert-butyl 4-{[(trifluoromethyl)sulfonyl]oxy}-3,6-dihydropyridine-1(2H)-carboxylate (5.0 g; 15.1 mmol; 1.0 eq.) and sodium carbonate (1.07 g, 10.1 mmol, 5 eq.) were dissolved in DME (50 mL) and water (25 mL). The mixture was degassed for 5 min with nitrogen before the addition of Pd(PPh$_3$)$_4$ (349 mg; 0.30 mmol; 0.02 eq.) and heated at 80° C. O/N. Water (100 mL) was added and aqueous phase was extracted with EtOAc (twice). Combined organic phases were washed with brine, dried over magnesium sulfate, filtered and concentrated. The crude was purified by flash chromatography on silica (EtOAc:heptane, 10.90) to give the title compound as a yellow solid (3.3 g, 72%). 1H NMR (300 MHz, DMSO-d$_6$) δ 8.24-8.17 (m, 2H), 7.65-7.68 (m, 2H), 6.45 (brs, 1H), 4.06 (m, 2H), 3.56 (t, 2H), 2.55-2.48 (m, 2H), 1.43 (s, 9H).

Step b) Formation of 4-(4-nitrophenyl)-1,2,3,6-tetrahydropyridinehydrochloride

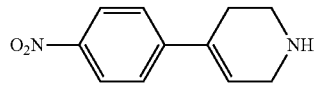

Hydrogen chloride (20 mL of a 4N solution in dioxane) was added dropwise to a solution of tert-butyl 4-(4-nitrophenyl)-3,6-dihydropyridine-1(2H)-carboxylate (3.0 g; 9.86 mmol; 1.0 eq.) in toluene (15 mL). The reaction mixture was stirred at RT for 3 h. The formed suspension was filtered, washed with toluene (10 mL) and dried under vacuum to give the title compound as a white solid (1.96 g, 97%). UPLC/MS: (MS+) 205.3.

Step c) Formation of 4-(4-nitrophenyl)-1-(3,3,3-trifluoropropyl)-1,2,3,6-tetrahydropyridine

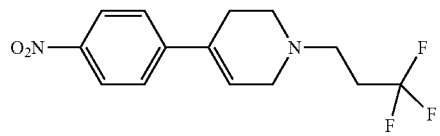 [SMILES: O=[N+]([O-])c1ccc(C2=CCN(CCC(F)(F)F)CC2)cc1]

Sodium triacetoxyborohydride (6.2 g, 29.4 mmol, 2 eq.) was added to a solution of 4-(4-nitrophenyl)-1,2,3,6-tetrahydropyridine (3.0 g; 14.7 mmol; 1.0 eq.), DIEA (2.5 mL; 14.7 mmol; 1.0 eq.) and 3,3,3-Trifluoropropanal (2.4 mL; 29.4 mmol; 2.0 eq.) in DCE (60 mL). The reaction mixture was heated at 50° C. for 2 h and quenched by addition of a saturated solution of NH$_4$Cl (50 mL). The phases were separated and organic phase was washed with water, dried over magnesium sulfate, filtered and concentrated to give a brown crude. Purification by flash chromatography on silica (EtOAc:heptane) afforded the title compound as a yellow solid (2.0 g, 45%). UPLC/MS: (MS+) 301.4.

Step d) Formation of 4-[1-(3,3,3-trifluoropropyl)piperidin-4-yl]aniline

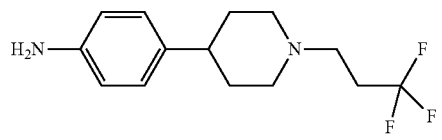 [SMILES: Nc1ccc(C2CCN(CCC(F)(F)F)CC2)cc1]

In Paar autoclave, a solution of 4-(4-nitrophenyl)-1-(3,3,3-trifluoropropyl)-1,2,3,6-tetrahydropyridine (2.6 g; 8.66 mmol; 1.0 eq.) in EtOAc (52 mL) was hydrogenated at 25 bars O/N in presence of Pd/C (moistened, 10%, 0.26 g; 2.44 mmol; 0.28 eq.). Reaction mixture was filtered through a celite pad. Filtrate was then concentrated under reduced pressure to give the title compound as a brown oil (2.33 g, 99%). UPLC/MS: (MS+) 273.4.

Step d) Formation of 4-(4-azidophenyl)-1-(3,3,3-trifluoropropyl)piperidine

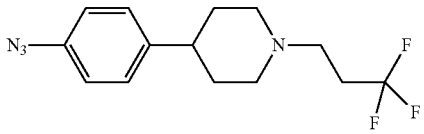 [SMILES: [N-]=[N+]=Nc1ccc(C2CCN(CCC(F)(F)F)CC2)cc1]

The title compound was obtained, following procedure described for intermediate 7, step c), but starting from 4-[1-(3,3,3-trifluoropropyl)piperidin-4-yl]aniline (500 mg; 1.84 mmol; 1.0 eq.) as an yellow oil (550 mg, 100%). UPLC/MS: (MS+) 299.4, (MS−) 301.4.

Intermediate 32: 3-[4-(4-azidophenyl)piperidin-1-yl]-1,1,1-trifluoropropan-2-ol

Step a) Formation of 1,1,1-trifluoro-3-[4-(4-nitrophenyl)-3,6-dihydropyridin-1(2H)-yl]propan-2-ol

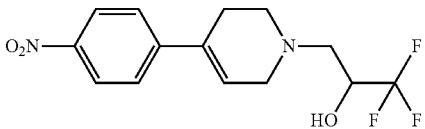 [SMILES: O=[N+]([O-])c1ccc(C2=CCN(CC(O)C(F)(F)F)CC2)cc1]

1,2-Epoxy-3,3,3-trifluoropropane, tech., 85% (2.32 g; 17.63 mmol; 1.20 eq.) was added to a suspension of 4-(4-nitrophenyl)-1,2,3,6-tetrahydropyridine (3.0 g; 14.7 mmol; 1.0 eq.) in DMF (60 mL) and DIEA (2.5 mL, 14.7 mmol, 1 eq.). The reaction mixture was heated at 45° C. for 4 h. It was then allowed to cool down to RT and diluted with water (50 mL) and EtOAc (100 mL). Organic layer was washed with a saturated solution of NH$_4$Cl (2×50 mL) and water, dried over magnesium sulfate, filtered and concentrated to give the expected compound as an orange solid (3.6 g, 77%). UPLC/MS: (MS+) 317.3, (MS−) 315.3.

Step b) Formation of 3-[4-(4-aminophenyl)piperidin-1-yl]-1,1,1-trifluoropropan-2-ol

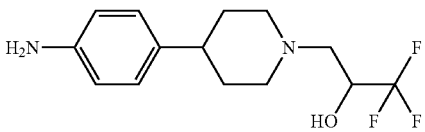

The title compound was obtained, following procedure described for intermediate 31, step d), but starting from 1,1,1-trifluoro-3-[4-(4-nitrophenyl)-3,6-dihydropyridin-1(2H)-yl]propan-2-ol (3.6 g; 11.4 mmol; 1.0 eq.) as a yellow solid (3.2 g, 98%). UPLC/MS: (MS+) 289.4.

Step c) Formation of 3-[4-(4-azidophenyl)piperidin-1-yl]-1,1,1-trifluoropropan-2-ol

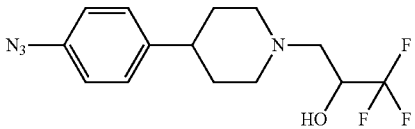 [SMILES: [N-]=[N+]=Nc1ccc(C2CCN(CC(O)C(F)(F)F)CC2)cc1]

The title compound was obtained, following procedure described for intermediate 7, step c), but starting from 3-[4-(4-aminophenyl)piperidin-1-yl]-1,1,1-trifluoropropan-2-ol (500 mg; 1.84 mmol; 1.0 eq.) as a brown oil (570 mg, 99%). UPLC/MS: (MS+) 315.4.

Intermediate 33: 1-(4-azidobenzoyl)-N,N-dimethylpiperidin-4-amine

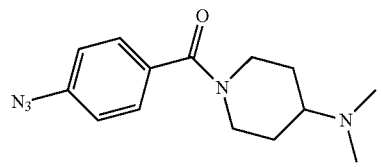 [SMILES: CN(C)C1CCN(C(=O)c2ccc(N=[N+]=[N-])cc2)CC1]

The title compound was obtained, following procedure described for intermediate 3, but starting from 4-Azidobenzoic acid (3.0 g; 18.4 mmol; 1.0 eq.) and 4-(dimethylamino)piperidine (2.36 g; 18.4 mmol; 1.0 eq.) as an orange oil (3.65 g, 73%). $^1$H NMR (300 MHz, DMSO-d6) δ 7.52-7.36 (m, 2H), 7.25-7.09 (m, 2H), 4.61-4.20 (m, 1H), 3.75-3.37 (m, 1H), 3.14-2.72 (m, 2H), 2.45-2.27 (m, 1H), 2.19 (s, 6H), 1.94-1.61 (m, 2H), 1.44-1.23 (m, 2H)

Intermediate 34: 1-{4-[4-(5-bromo-1H-indazol-3-yl)-1H-1,2,3-triazol-1-yl]benzoyl}-N,N-dimethylpiperidin-4-amine

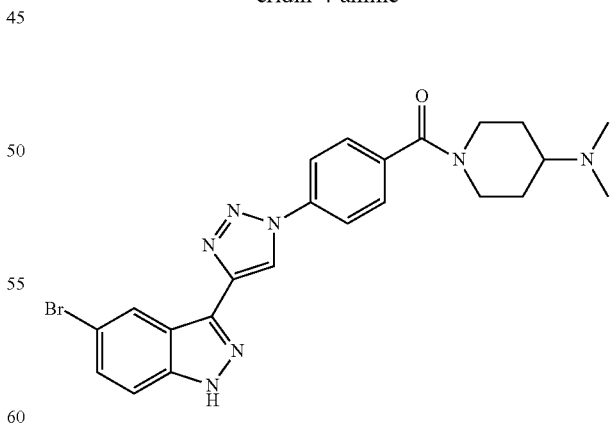

The title compound was obtained, following procedure described for intermediate 10 but starting from 5-Bromo-3-ethynyl-1H-indazole (1.5 g; 6.8 mmol; 1.0 eq.) and 1-(4-azidobenzoyl)-N,N-dimethylpiperidin-4-amine (1.85 g; 6.8 mmol; 1.0 eq.) as a yellow powder (1.36 g, 37%). HPLC (max plot) 99.8%; Rt 3.36 min. UPLC/MS: (MS+) 496.2.

Intermediate 35: 4-(4-azidobenzyl)morpholine

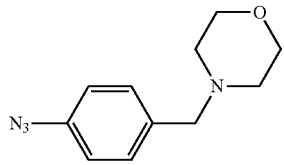 [SMILES: [N-]=[N+]=Nc1ccc(CN2CCOCC2)cc1]

The title compound was obtained, following procedure described for intermediate 7, step c), but starting from 4-morpholin-4-ylmethyl-phenylamine (1.06 g; 5.51 mmol; 1.0 eq.) as a yellow oil (1.21 g, 100%). 1H NMR (300 MHz, DMSO-d6) δ 7.34 (d, J=8.4 Hz, 2H), 7.07 (d, J=8.4 Hz, 2H), 3.62-3.49 (m, 4H), 3.43 (s, 2H), 2.41-2.23 (m, 4H). HPLC (max plot) 97.2%; Rt 1.36 min.

Intermediate 36: methyl 3-ethynyl-1H-indazole-5-carboxylate

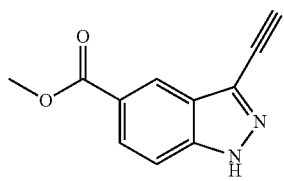

The title compound was obtained, following procedure described for intermediate 1 but starting from methyl 1H-indazole-5-carboxylate as a yellow solid (3.80 g; 91.11%). $^1$H NMR (400 MHz, DMSO) δ 13.78 (s, 1H), 8.33-8.32 (t, J=0.68 Hz, 1H), 7.97-7.95 (m, 1H), 7.70-7.67 (m, 1H), 4.64 (s, 1H), 3.87 (s, 3H).

Intermediate 37: tert-butyl 5-[(3-chloro-6-oxopyridazin-1(6H)-yl)methyl]-3-{1-[4-(morpholin-4-ylcarbonyl)phenyl]-1H-1,2,3-triazol-4-yl}-1H-indazole-1-carboxylate

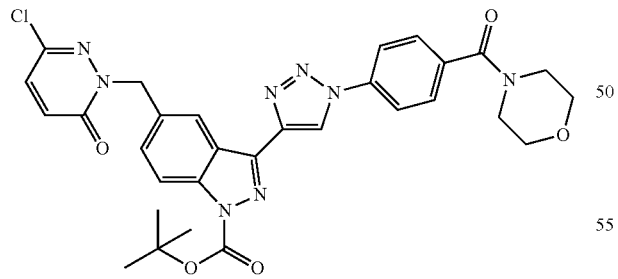

DIAD (0.35 mL; 1.80 mmol; 2.3 eq.) was added dropwise over 1 min to a solution of 6-chloropyridazin-3(2H)-one (153 mg; 1.17 mmol; 1.5 eq.), tert-butyl 5-(hydroxymethyl)-3-{1-[4-(morpholin-4-ylcarbonyl)phenyl]-1H-1,2,3-triazol-4-yl}-1H-indazole-1-carboxylate (393 mg; 0.78 mmol; 1.0 eq.) and triphenylphosphine (430 mg; 1.64 mmol; 2.1 eq.) in DCM (15 mL). The reaction mixture was stirred at RT for 16 h, then diluted with DCM and sequentially washed with a 1N HCl solution and brine, dried over magnesium sulfate, filtered and concentrated. The crude was purified by flash chromatography on silica (EtOAc: n-heptane, gradient from 30:70 to 90:10) to give the title compound as a white solid (316 mg, 66%).

1H NMR (300 MHz, DMSO-d6) δ 9.62 (s, 1H), 8.54 (s, 1H), 8.19 (d, J=8.6 Hz, 2H), 8.14 (d, J=8.8 Hz, 1H), 7.75-7.64 (m, 3H), 7.60 (d, J=9.7 Hz, 1H), 7.13 (d, J=9.7 Hz, 1H), 5.42 (s, 2H), 3.64 (s, 8H), 1.69 (s, 9H). HPLC (max plot) 98.6%; Rt 4.10 min. UPLC/MS: (MS+) 617.1, (MS−) 675.1.

Intermediate 38: (1S,4S)-5-(4-azidobenzyl-2-oxa-5-azabicyclo[2.2.1]heptane

Step a) Formation of (1S,4S)-5-(4-nitrobenzyl)-2-oxa-5-azabicyclo[2.2.1.]heptane

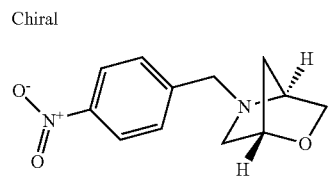 [SMILES: O=[N+]([O-])c1ccc(CN2C[C@@H]3C[C@H]2CO3)cc1]

The title compound was obtained, following procedure described for intermediate 31, step c), but starting 4-nitrobenzaldehyde (500 mg; 3.31 mmol; 1.0 eq.) and (1S,4S)-2-Oxa-5-azabicyclo2.2.1 heptane HCl (Activate scientific, 538 mg; 3.97 mmol; 1.20 eq.) as an yellow oil (843 mg, 100%). 1H NMR (300 MHz, DMSO-d6) δ 8.26-8.12 (m, 2H), 7.68-7.50 (m, 2H), 4.36 (brs, 1H), 3.93 (d, J=7.6 Hz, 1H), 3.86 (d, J=2.9 Hz, 2H), 3.54 (dd, J=7.5, 1.8 Hz, 1H), 3.47 (brs, 1H), 2.74 (dd, J=9.9, 1.7 Hz, 1H), 2.42 (d, J=9.9 Hz, 1H), 1.88-1.78 (m, 1H), 1.67-1.56 (m, 1H).

Step b) Formation of 4-[(1S,4S)-2-oxa-5-azabicyclo[2.2.1]hept-5-ylmethyl]aniline

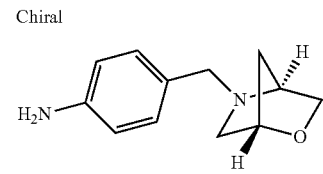 [SMILES: Nc1ccc(CN2C[C@@H]3C[C@H]2CO3)cc1]

A solution of (1S,4S)-5-(4-nitrobenzyl)-2-oxa-5-azabicyclo[2.2.1]heptane (943 mg; 4.03 mmol; 1.0 eq.) in EtOAc (10 mL) was hydrogenated under 10 bars H$_2$ in presence of Pd/C (moistened, 10%, 43 mg, 0.40 mmol; 0.1 eq.) O/N. The crude was filtered through a celite pad, concentrated under reduced pressure and purified by flash chromatography on silica (DCM:MeOH:NH$_4$OH, 96:3:1) to give the title compound as an yellow oil (80 mg, 10%). 1H NMR (300 MHz, DMSO-d6) δ 6.95 (d, J=8.4 Hz, 2H), 6.54-6.44 (m, 2H), 4.91 (s, 2H), 4.31 (s, 1H), 3.87 (d, J=7.4 Hz, 1H), 3.58-3.41 (m, 3H), 3.35 (d, J=8.1 Hz, 1H), 2.66 (dd, J=9.9, 1.7 Hz, 1H), 2.34 (d, J=10.0 Hz, 1H), 1.74 (dd, J=9.5, 2.1 Hz, 1H), 1.54 (d, J=9.5 Hz, 1H).

Step c) Formation of (1S,4S)-5-(4-azidobenzyl)-2-oxa-5-azabicyclo[2.2.1.]heptane

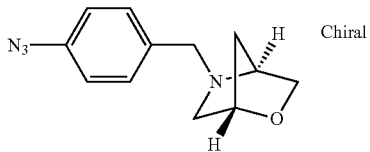

The title compound was obtained, following procedure described for intermediate 7, step c), but starting from 4-[(1S,4S)-2-oxa-5-azabicyclo[2.2.1]hept-5-ylmethyl]aniline (80 mg; 0.39 mmol; 1.0 eq.) as an yellow oil (110 mg, 100%). 1H NMR (300 MHz, CDCl3) δ 7.40-7.30 (m, 2H), 7.08-6.92 (m, 2H), 4.43 (brs, 1H), 4.12 (d, J=7.4 Hz, 1H), 3.75 (d, J=3.5 Hz, 2H), 3.66 (dd, J=7.8, 1.8 Hz, 1H), 3.46 (brs, 1H), 2.87 (dd, J=10.2, 1.7 Hz, 1H), 2.62-2.54 (m, 1H), 1.92 (dd, J=9.8, 2.1 Hz, 1H), 1.84-1.68 (m, 1H).

Intermediate 39: 3-(4-azidophenyl-8-cyclohexyl-8-azabicyclo[3.2.1]octane

Step a) Formation of tert-butyl 3-(4-nitrophenyl)-8-azabicyclo[3.2.1]oct-2-ene-8-carboxylate

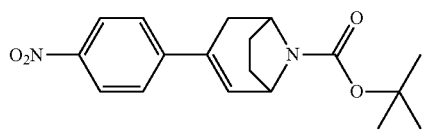

A mixture of 1-bromo-4-nitrobenzene (2.0 g; 9.9 mmol; 1.0 eq.), tert-butyl 3-(4,4,5,5-tetramethyl-1,3,2-dioxaborolan-2-yl)-8-azabicyclo[3.2.1]oct-2-ene-8-carboxylate (4.3 g; 12.9 mmol; 1.30 eq.), PdCl₂(dppf) (724 mg; 0.99 mmol; 0.1 eq.) and potassium carbonate (4.1 g; 29.7 mmol; 3.0 eq.) in Dioxane-1,4 (20 mL) and water (10 mL) was heated at 90° under nitrogen atmosphere O/N. The reaction mixture was filtered through a celite pad. The cake was rinsed with dichloromethane, phases were separated and organic phase was washed with water and brine. Organic phase was then dried over magnesium sulfate, filtered and concentrated. The crude was purified by flash chromatography on silica (heptane/EtOAc, gradient from 90:10 to 80:20) to give the title compound as a yellow solid (1.97 g; 60%). 1H NMR (300 MHz, DMSO-d6-d6) δ: 8.17 (d, J=9.0 Hz, 2H), 7.69 (d, J=9.0 Hz, 2H), 6.84 (d, J=5.3 Hz, 1H), 4.43 (t, J=5.3 Hz, 1H), 4.35 (m, 1H), 2.97 (d, J=17.5 Hz, 1H), 2.32 (d, J=17.5 Hz, 1H), 2.15 (m, 1H), 1.95-1.88 (m, 2H), 1.71-1.58 (m, 1H), 1.37 (s, 9H). HPLC (max plot) 89.0%; Rt %4.66 min. UPLC/MS: (MS+) 331.3.

Step b) Formation of 3-(4-nitrophenyl)-8-azabicyclo[3.2.1]oct-2-ene

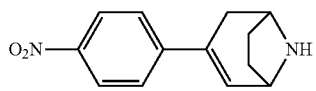 [SMILES: O=[N+]([O-])c1ccc(C2=CC3CCC(C2)N3)cc1]

Hydrogen chloride (22 mL of a solution 4N in dioxane) was added to a solution of tert-butyl 3-(4-nitrophenyl)-8-azabicyclo[3.2.1]oct-2-ene-8-carboxylate (1.97 g; 5.96 mmol; 1.0 eq.) in DCM (20 mL) and the reaction mixture was stirred at RT. After 1 h, the reaction mixture was diluted with DCM and organic phase was washed with NaOH 1N and brine, dried over magnesium sulfate, filtered and concentrated to give the title compound as a yellow solid (1.05 g, 76%). 1H NMR (300 MHz, DMSO-d6) δ 8.16 (d, J=9.0 Hz, 2H), 7.65 (d, J=9.0 Hz, 2H), 6.82 (dt, J=6.0 Hz, 1.5 Hz, 1H), 3.74-3.69 (m, 2H), 2.76 (dd, J=17.5 Hz, 4.5 Hz, 1H), 2.17 (dd, J=17.5 Hz, 1.5 Hz, 1H), 1.92-1.68 (m, 3H), 1.56-1.46 (m, 1H). HPLC (max plot) 91.7%; Rt %1.84 min. UPLC/MS: (MS+) 231.2.

Step c) Formation of 8-cyclohexyl-3-(4-nitrophenyl)-8-azabicyclo[3.2.1]oct-2-ene

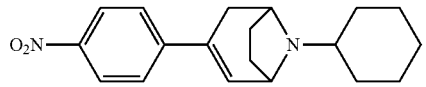 [SMILES: O=[N+]([O-])c1ccc(C2=CC3CCC(C2)N3C2CCCCC2)cc1]

Sodium triacetoxyborohydride (460 mg, 2.17 mmol, 2.0 eq.) was added to a solution of 3-(4-nitrophenyl)-8-azabicyclo[3.2.1]oct-2-ene (250 mg; 1.1 mmol; 1.0 eq.) and cyclohexanone (168 μl; 1.63 mmol; 1.5 eq.) in DCE (10.00 mL) and the reaction mixture was heated at 50° under nitrogen atmosphere. After 1 h, the reaction mixture was poured into a saturated solution of NaHCO₃. Aqueous phase was extracted twice with DCM and combined organic phases were washed with brine, dried over magnesium sulfate, filtered and concentrated. The crude was purified by flash chromatography on silica (DCM:MeOH, gradient from 100:0 to 90:10) to give the title compound as a beige solid (220 mg, 65%). 1H NMR (300 MHz, DMSO-d6) δ 8.17 (d, J=8.9 Hz, 2H), 7.68 (d, J=8.9 Hz, 2H), 6.68 (d, J=5.4 Hz, 1H), 3.79-3.68 (m, 2H), 2.80-2.75 (m, 1H), 2.31 (m, 1H), 2.07-1.66 (m, 8H), 1.52 (m, 2H), 1.23-1.09 (m, 5H). HPLC (max plot) 100.0%; Rt %3.01 min. UPLC/MS: (MS+) 313.4.

Step d) Formation of 4-(8-cyclohexyl-8-azabicyclo[3.2.1]oct-3-yl)aniline

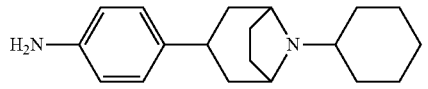 [SMILES: Nc1ccc(C2CC3CCC(C2)N3C2CCCCC2)cc1]

A solution of 8-cyclohexyl-3-(4-nitrophenyl)-8-azabicyclo[3.2.1]oct-2-ene (230 mg; 0.74 mmol; 1.0 eq.) in EtOH (7 mL) was passed twice at 1 mL/min through the H-Cube using a cartridge of Pd/C under full H₂ at 25°. The solution was then concentrated under reduced pressure to give the title compound as a 66:33 mixture of the endo:exo isomers (163 mg; 78%). 1H NMR (DMSO) δ 6.94 (d, J=8.3 Hz, 1.3H), 6.87 (d, J=8.3 Hz, 0.7H), 6.48-6.45 (m, 2H), 4.78 (bs, 2H), 3.47 (m, 2H), 2.84-2.70 (m, 1H), 2.19-2.07 (m, 2H), 1.90-1.82 (m, 3H), 1.72-1.63 (m, 5H), 1.54-1.46 (m, 2H), 1.40-1.33 (m, 2H), 1.27-0.98 (m, 5H). HPLC (max plot) 65.3%; Rt %2.25 min. UPLC/MS: (MS+) 285.4.

Step e) Formation of 3-(4-azidophenyl)-8-cyclo-hexyl-8-azabicyclo[3.2.1]octane

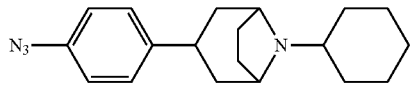 [SMILES: [N-]=[N+]=Nc1ccc(C2CC3CCC(C2)N3C2CCCCC2)cc1]

The title compound was obtained following procedure described for intermediate 7, step c), but starting from 4-(8-cyclohexyl-8-azabicyclo[3.2.1]oct-3-yl)aniline (175 mg; 0.62 mmol; 1.0 eq.) as a 66:33 mixture endo:exo isomers (140 mg, 73%). $^1$H NMR (300 MHz, DMSO-d6-d6): δ 7.37 (d, J=8.5 Hz, 1.3H), 7.30 (d, J=8.5 Hz, 0.7H), 7.05-7.00 (m, 2H), 3.53 (m, 2H), 3.00-2.89 (m, 1H), 2.28-2.19 (m, 2H), 1.95-1.85 (m, 3H), 1.72 (m, 5H), 1.59-1.49 (m, 2H), 1.39-1.35 (m, 2H), 1.28-1.11 (m, 5H). HPLC (max plot) 91.8%; Rt %3.08 min. UPLC/MS: (MS+) 311.4.

Intermediate 40

1-(4-methoxybenzyl)-3-{1-[4-(morpholin-4-ylcarbo-nyl)phenyl]-1H-1,2,3-triazol-4-yl}-1H-indazol-5-ol Step a) Formation of 5-bromo-1-(4-methoxybenzyl)-3-{1-[4-(morpholin-4-ylcarbonyl)phenyl]-1H-1,2,3-triazol-4-yl}-1H-indazole

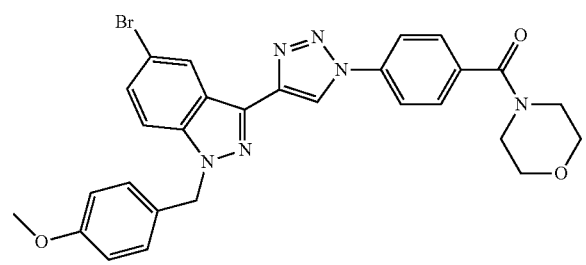 [SMILES: COc1ccc(Cn2nc(-c3cn(-c4ccc(C(=O)N5CCOCC5)cc4)nn3)c3cc(Br)ccc32)cc1]

4-methoxybenzylchloride (1.13 mL; 8.27 mmol; 1.5 eq.) was added dropwise to a solution of {4-[4-(5-Bromo-1H-indazol-3-yl)-[1,2,3]triazol-1-yl]-phenyl}-morpholin-4-yl-methanone (2.5 g; 5.5 mmol; 1.0 eq.) and KOH (0.34 g; 6.07 mmol; 1.1 eq.) in acetone (75 mL) and DMF (25 mL). The reaction mixture was stirred at RT O/N. It was then diluted with a 0.1N HCl solution and extracted three times with EtOAc. Combined organic phases were washed with brine, dried over magnesium sulfate, filtered and concentrated. The crude was purified by flash chromatography on silica (DCM:MeOH, gradient from 100:0 to 90:10) to give the title compound as an orange oil (4.1 g, 100%). UPLC/MS: (MS+) 573.0.

Step b) Formation of 1-(4-methoxybenzyl)-3-{1-[4-(morpholin-4-ylcarbonyl)phenyl]-1H-1,2,3-triazol-4-yl}-5-(4,4,5,5-tetramethyl-1,3,2-dioxaborolan-2-yl)-1H-indazole

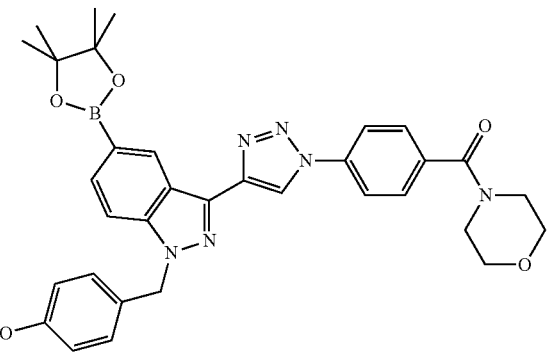

A mixture of 5-bromo-1-(4-methoxybenzyl)-3-{1-[4-(morpholin-4-ylcarbonyl)phenyl]-1H-1,2,3-triazol-4-yl}-1H-indazole (200 mg; 0.35 mmol; 1.0 eq.), bis-(pinacolato) diboron (133 mg; 0.52 mmol; 1.5 eq.), potassium acetate (103 mg; 1.05 mmol; 3.0 eq.) and PdCl$_2$(dppf) (25 mg, 0.03 mmol, 0.1 eq.) in dioxane (5 mL) was heated O/N in a sealed tube at 90° C. Solvent was then removed under reduced pressure and the crude was purified by flash chromatography on silica (DCM:MeOH) to give the title compound as a brown solid (220 mg, 100%). UPLC/MS: (MS+) 624.2.

Step c) Formation of 1-(4-methoxybenzyl)-3-{1-[4-(morpholin-4-ylcarbonyl)phenyl]-1H-1,2,3-triazol-4-yl}-1H-indazol-5-ol

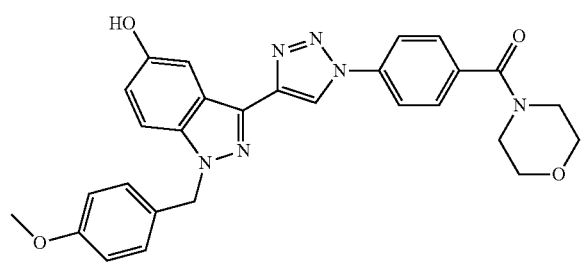 [SMILES: COc1ccc(Cn2nc(-c3cn(-c4ccc(C(=O)N5CCOCC5)cc4)nn3)c3cc(O)ccc32)cc1]

A solution of 1-(4-methoxybenzyl)-3-{1-[4-(morpholin-4-ylcarbonyl)phenyl]-1H-1,2,3-triazol-4-yl}-5-(4,4,5,5-tetramethyl-1,3,2-dioxaborolan-2-yl)-1H-indazole (239 mg; 0.39 mmol; 1.0 eq.) and hydrogen peroxide (52 mg, 1.54 mmol, 4 eq.) in EtOAc (4.8 mL) was stirred O/N at RT. Solvent was removed under reduced pressure and the crude was purified by preparative HPLC to give the title compound as a white powder (135 mg, 69%). UPLC/MS: (MS+) 511.1.

Intermediate 41

[3-{1-[4-(morpholin-4-ylcarbonyl)phenyl]-1H-1,2,3-triazol-4-yl}-1-(tetrahydro-2H-pyran-2-yl)-1H-indazol-5-yl]methanol

Step a) Formation of methyl 3-ethynyl-1-(tetrahydro-2H-pyran-2-yl)-1H-indazole-5-carboxylate

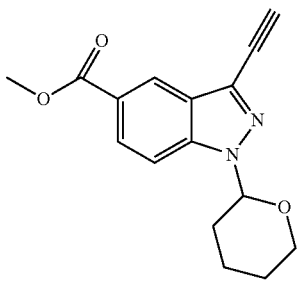 [SMILES: C#Cc1nn(C2CCCCO2)c2ccc(C(=O)OC)cc12]

PTSA (0.99 g; 5.77 mmol; 0.11 eq.) was added to a solution of 3-Ethynyl-1H-indazole-5-carboxylic acid methyl ester (10.1 g; 50.2 mmol; 1.0 eq.) and 3,4-dihydro-2H-pyran (10.5 mL; 116 mmol; 2.3 eq.) in DME (100 mL). The reaction mixture was refluxed for 3 h, then cooled and concentrated. The residue was redissolved in DCM and washed sequentially with NaHCO$_3$ (sat) and NaCl (sat) solutions, dried over magnesium sulfate, filtered and concentrated. The crude was triturated with Et$_2$O to give the title compound as a yellow solid
(7.9 g; 54%). 1H NMR (300 MHz, DMSO-d6) δ 8.33 (dd, J=1.5, 0.8 Hz, 1H), 8.05 (dd, J=8.9, 1.5 Hz, 1H), 7.94 (dd, J=8.9, 0.8 Hz, 1H), 5.96 (dd, J=9.5, 2.4 Hz, 1H), 4.75 (s, 1H), 3.95-3.84 (m, 4H), 3.82-3.70 (m, 1H), 2.43-2.26 (m, 1H), 2.09-1.94 (m, 2H), 1.84-1.65 (m, 1H), 1.65-1.50 (m, 2H). HPLC (max plot) 98.4%; Rt %3.92 min. UPLC/MS: (MS+) 201.2.

Step b) Formation of 3-ethynyl-1-(tetrahydro-2H-pyran-2-yl)-1H-indazole-5-carboxylic acid

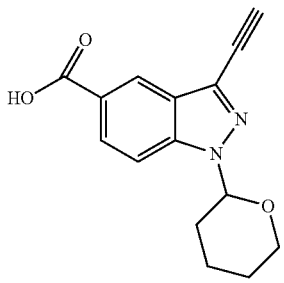 [SMILES: C#Cc1nn(C2CCCCO2)c2ccc(C(=O)O)cc12]

Sodium hydroxide (100 mL; 5.0 M; 500 mmol; 18.1 eq.) was added in one portion to a solution of methyl 3-ethynyl-1-(tetrahydro-2H-pyran-2-yl)-1H-indazole-5-carboxylate (7.9 g; 27.7 mmol; 1.0 eq.) in DMF (100 mL) and MeOH (100 mL). The reaction mixture was stirred at RT for 1 h, then poured into a 1N HCl solution (pH 1) and extracted with DCM. Combined organic phases were washed with brine, dried over magnesium sulfate, filtered and concentrated. The brown solid obtained was triturated with MeOH to give the title compound as a red solid (4.83 g, 65%). 1H NMR (300 MHz, DMSO-d6) δ 13.09 (s, 1H), 8.35-8.28 (m, 1H), 8.04 (dd, J=8.9, 1.5 Hz, 1H), 7.90 (dd, J=8.9, 0.6 Hz, 1H), 5.95 (dd, J=9.5, 2.3 Hz, 1H), 4.73 (s, 1H), 3.94-3.84 (m, 1H), 3.83-3.69 (m, 1H), 2.43-2.27 (m, 1H), 2.09-1.93 (m, 2H), 1.83-1.65 (m, 1H), 1.64-1.52 (m, 2H). HPLC (max plot) 99.5%; Rt %3.17 min. UPLC/MS: (MS−) 269.3.

Step c) Formation of [3-ethynyl-1-(tetrahydro-2H-pyran-2-yl)-1H-indazol-5-yl]methanol

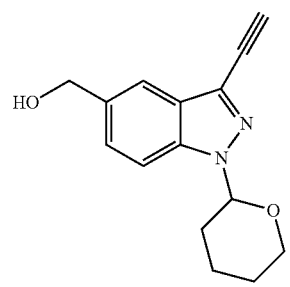 [SMILES: C#Cc1nn(C2CCCCO2)c2ccc(CO)cc12]

BOP (3.18 g; 7.19 mmol; 1.20 eq.) was added to a solution of 3-ethynyl-1-(tetrahydro-2H-pyran-2-yl)-1H-indazole-5-carboxylic acid (1.97 g; 5.97 mmol; 1.0 eq.) in DIEA (7 mL; 41.2 mmol; 6.9 eq.) and THF (350 mL). After 1 h, DMA (100 mL) was added in one portion followed by sodium borohydride (0.70 g; 18.5 mmol; 3.1 eq.). The reaction mixture was stirred at RT for 20 min, diluted with EtOAc and washed sequentially with 1 N HCl, NaHCO$_3$ (sat) and NaCl (sat) solutions, dried over magnesium sulfate, filtered and concentrated. Purification by flash chromatography on silica (EtOAc: n-heptane, gradient from 10:90 to 50:50) gave the title compound as a clear oil (1.26 g; 78.2%). 1H NMR (300 MHz, DMSO-d6) δ 7.75 (d, J=8.7 Hz, 1H), 7.65 (d, J=0.6 Hz, 1H), 7.43 (dd, J=8.7, 1.5 Hz, 1H), 5.87 (dd, J=9.5, 2.3 Hz, 1H), 5.29 (t, J=5.8 Hz, 1H), 4.62 (d, J=5.8 Hz, 2H), 4.58 (s, 1H), 3.93-3.82 (m, 1H), 3.80-3.68 (m, 1H), 2.44-2.27 (m, 1H), 2.08-1.91 (m, 2H), 1.83-1.64 (m, 1H), 1.63-1.51 (m, 2H). HPLC (max plot) 95.2%; Rt %2.78 min. UPLC/MS: (MS+) 257.2.

Step d) Formation of [3-{1-[4-(morpholin-4-ylcarbonyl)phenyl]-1H-1,2,3-triazol-4-yl}-1-(tetrahydro-2H-pyran-2-yl)-1H-indazol-5-yl]methanol

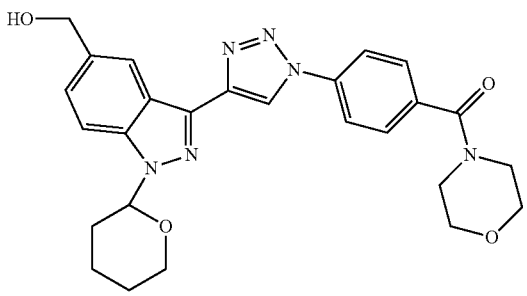 [SMILES: O=C(c1ccc(-n2cc(-c3nn(C4CCCCO4)c4ccc(CO)cc34)nn2)cc1)N1CCOCC1]

The title compound was obtained, following procedure described for intermediate 10, but starting from [3-ethynyl-1-(tetrahydro-2H-pyran-2-yl)-1H-indazol-5-yl]methanol (1.39 g; 5.42 mmol; 1.0 eq.) and 4-(4-azidobenzoyl)morpholine (1.89 g; 8.14 mmol; 1.5 eq) as a yellow solid (1.87 g, 71%). 1H NMR (300 MHz, DMSO-d6) δ 9.41 (s, 1H), 8.33 (d, J=0.6 Hz, 1H), 8.18 (d, J=8.7 Hz, 2H), 7.77 (d, J=8.7 Hz, 1H), 7.69 (d, J=8.7 Hz, 2H), 7.47 (dd, J=8.7, 1.5 Hz, 1H), 5.98-5.90 (m, 1H), 5.31 (t, J=5.7 Hz, 1H), 4.67 (d, J=5.7 Hz, 2H), 3.98-3.89 (m, 1H), 3.85-3.73 (m, 1H), 3.71-3.36 (m, 8H), 2.59-2.42 (m, 1H), 2.15-1.97 (m, 2H), 1.88-1.71 (m, 1H), 1.68-1.51 (m, 2H). HPLC (max plot) 92.9%; Rt %2.99 min. UPLC/MS: (MS+) 489.5.

Example 1

3-{1-[4-(morpholin-4-ylcarbonyl)phenyl]-1H-1,2,3-triazol-4-yl}-1H-indazole

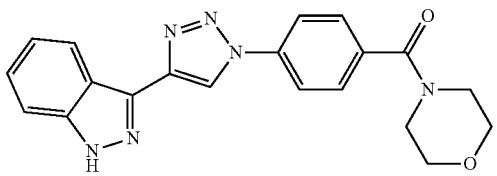 [SMILES: O=C(c1ccc(-n2cc(-c3n[nH]c4ccccc34)nn2)cc1)N1CCOCC1]

The title compound was obtained, following procedure described for intermediate 10, but starting from 4-(4-azidobenzoyl)morpholine (710 mg; 3.1 mmol; 1.0 eq.) and 3-ethynyl-1H-indazole (435 mg; 3.1 mmol; 1.0 eq.). After purification by preparative HPLC, it was obtained as a white solid. ¹H NMR (300 Mz, DMSO-d6) δ: 13.39 (brs, 1H), 9.40 (s, 1H), 8.37 (dt, J=8.2, 1.0 Hz, 1H), 8.16 (d, J=8.6 Hz, 2H), 7.69 (d, J=8.6 Hz, 2H), 7.62 (dt, J=8.4, 1.0 Hz, 1H), 7.48-7.42 (m, 1H), 7.29-7.24 (m, 1H), 3.64 (m, 6H), 3.41 (m, 2H). HPLC (Condition A): Rt 2.90 min (purity 99.3%). MS (ESI+): 375.2, MS (ESI−): 373.2.

Example 2

3-[1-(4-{[3-(pyrrolidin-1-ylmethyl)piperidin-1-yl]carbonyl}phenyl)-1H-1,2,3-triazol-4-yl]-1H-indazole

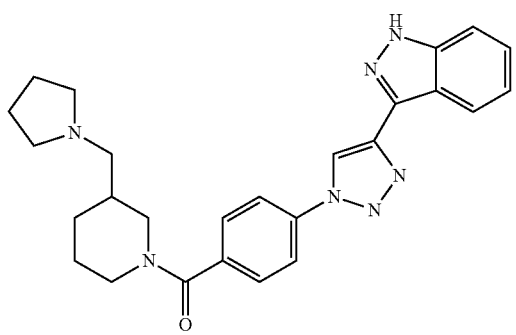

The title compound was prepared following procedure described for intermediate 10, but starting from 1-(4-azidobenzoyl)-3-(pyrrolidin-1-ylmethyl)piperidine (420 mg; 1.34 mmol; 1.0 eq.) and 3-ethynyl-1H-indazole (190 mg; 1.34 mmol; 1.0 eq.). After purification by preparative HPLC, it was obtained as the formic acid salt. The salt was solubilized in DCM and washed with a saturated solution of NaHCO₃ then brine. Organic phase was dried over magnesium sulfate, filtered and concentrated. The resulting oil was suspended in EtOH, and concentrated to dryness to afford the title compound as a yellow powder. ¹H NMR (300 Mz, DMSO-d6) δ: 13.37 (s, 1H), 9.37 (s, 1H), 8.36 (d, J=8.1 Hz, 1H), 8.15 (d, J=8.7 Hz, 2H), 7.61 (m, 3H), 7.43 (m, 1H), 7.26 (m, 1H), 4.48 (m, 0.4H), 4.25 (m, 0.6H), 3.70 (m, 0.6H), 3.52 (m, 0.4H), 3.04 (m, 0.4H), 2.91 (m, 0.6H), 2.74 (m, 0.4H), 2.20-2.43 (m, 4H), 2.02 (m, 0.6H), 1.69 (m, 6H), 1.48 (m, 4H), 1.20 (m, 1H). HPLC (Condition A): Rt 2.69 min (purity 99.9%). MS (ESI+): 456.4, MS (ESI−): 454.5.

Example 3

N-{[(2R)-1-ethylpyrrolidin-2-yl]methyl}-4-[4-(5-methyl-1H-indazol-3-yl)-1H-1,2,3-triazol-1-yl]benzamide

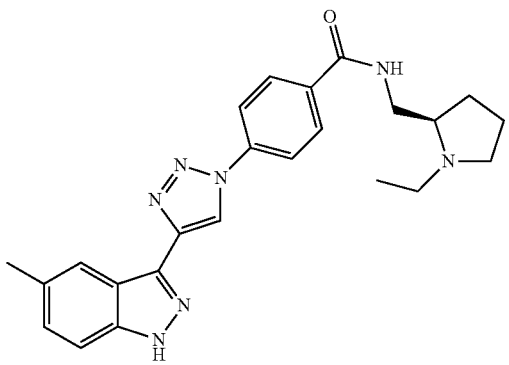 [SMILES: CCN1CCC[C@@H]1CNC(=O)c1ccc(-n2cc(-c3n[nH]c4ccc(C)cc34)nn2)cc1]

The title compound was obtained, following procedure described for intermediate 10, but starting from 4-azido-N-{[(2R)-1-ethylpyrrolidin-2-yl]methyl}benzamide (158 mg; 0.58 mmol; 1.0 eq.) and 3-ethynyl-5-methyl-1H-indazole (90 mg; 0.58 mmol; 1.0 eq.). After purification by preparative HPLC, it was obtained as a white powder. ¹H NMR (300 Mz, DMSO-d6) δ: 13.36 (brs, 1H), 9.43 (s, 1H), 8.61 (t, J=6.0 Hz, 1H), 8.2-8.07 (m, 5H), 7.51 (d, J=8.5 Hz, 1H), 7.28 (dd, J=8.5 Hz, 1.5 Hz, 1H), 3.50-3.41 (m, 1H), 3.16-3.03 (m, 2H), 2.93-2.81 (m, 1H), 2.70-2.59 (m, 1H), 2.37-2.26 (m, 1H), 2.16 (dd, J=16.8, 8.6 Hz, 1H), 1.88-1.78 (m, 1H), 1.71-1.57 (m, 3H), 1.07 (t, J=7.2 Hz, 3H). HPLC (Condition B): Rt 1.61 min (purity 95.0%). MS (ESI+): 430.4, MS (ESI−): 428.4.

Example 4

N-{[(2S)-1-ethylpyrrolidin-2-yl]methyl}-4-[4-(5-methyl-1H-indazol-3-yl)-1H-1,2,3-triazol-1-yl]benzamide

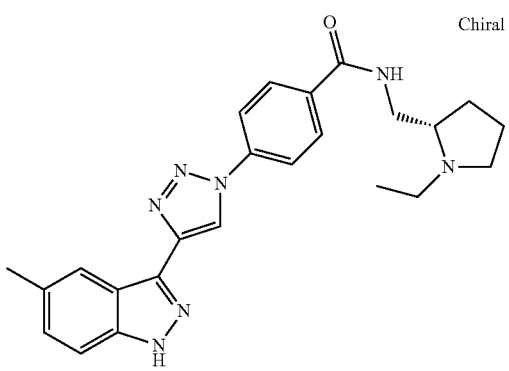 [SMILES: CCN1CCC[C@H]1CNC(=O)c1ccc(-n2cc(-c3n[nH]c4ccc(C)cc34)nn2)cc1]

The title compound was obtained, following procedure described for intermediate 10, but starting from 4-azido-N-{[(2S)-1-ethylpyrrolidin-2-yl]methyl}benzamide (197 mg;

0.58 mmol; 1.0 eq.) and 3-ethynyl-5-methyl-1H-indazole (90 mg; 0.58 mmol; 1.0 eq.). After purification by preparative HPLC, it was obtained as a white powder. ¹H NMR (300 Mz, DMSO-d6): δ: 13.28 (brs, 1H), 9.40 (s, 1H), 8.60 (t, J=6.0 Hz, 1H), 8.20-8.07 (m, 5H), 7.51 (d, J=8.5 Hz, 1H), 7.28 (dd, J=8.5 Hz, 1.5 Hz, 1H), 3.50-3.41 (m, 1H), 3.15-3.01 (m, 2H), 2.92-2.80 (m, 1H), 2.65-2.58 (m, 1H), 2.35-2.24 (m, 1H), 2.13 (dd, J=16.8 Hz, 8.6 Hz, 1H), 1.86-1.77 (m, 1H), 1.71-1.57 (m, 3H), 1.07 (t, J=7.2 Hz, 3H). HPLC (Condition A): Rt 2.81 min (purity 100.0%). MS (ESI+): 430.4, MS (ESI−): 428.4.

Example 5

3-{1-[1-(2-pyridin-4-ylethyl)-1H-pyrazol-4-yl]-1H-1,2,3-triazol-4-yl}-1H-indazole

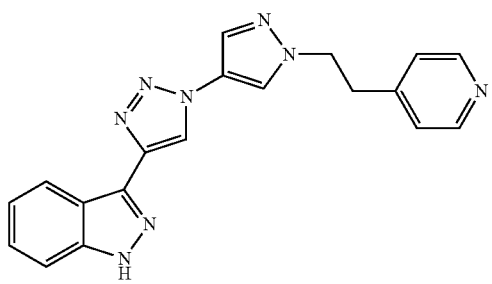 [SMILES: c1ccc2c(-c3cn(-c4cnn(CCc5ccncc5)c4)nn3)n[nH]c2c1]

The title compound was obtained, following procedure described for intermediate 10, but starting from 4-[2-(4-azido-1H-pyrazol-1-yl)ethyl]pyridine (136 mg; 0.63 mmol; 1.0 eq.) and 3-ethynyl-1H-indazole (90 mg; 0.63 mmol; 1.0 eq.). After purification by preparative HPLC, it was obtained as a beige powder. ¹H NMR (300 Mz, DMSO-d6): 13.32 (s, 1H), 9.04 (s, 1H), 8.48-8.46 (m, 3H), 8.32 (d, J=8.2 Hz, 1H), 8.11 (d, J=0.6 Hz, 1H), 7.60 (d, J=8.5 Hz, 1H), 7.43 (ddd, J=8.0, 5.8, 1.0 Hz, 1H), 7.27-7.22 (m, 3H), 4.52 (t, J=7.1 Hz, 2H), 3.28 (t, J=7.1 Hz, 2H). HPLC (Condition A): Rt 2.12 min (purity 100.0%). MS (ESI+): 357.2, MS (ESI−): 355.2.

Example 6

5-methyl-3-{1-[4-(pyrrolidin-1-ylmethyl)phenyl]-1H-1,2,3-triazol-4-yl}-1H-indazole

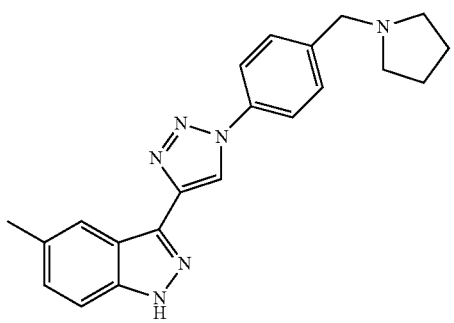 [SMILES: Cc1ccc2[nH]nc(-c3cn(-c4ccc(CN5CCCC5)cc4)nn3)c2c1]

Sodium cyanoborohydride (166 mg; 2.64 mmol; 4.0 eq.) was added to a solution of 4-[4-(5-methyl-1H-indazol-3-yl)-1H-1,2,3-triazol-1-yl]benzaldehyde (200 mg; 0.66 mmol; 1.0 eq.) and pyrrolidine (1.64 mL; 19.8 mmol; 30 eq.) in DMA (4 mL) and the reaction mixture was stirred at RT. After 12 h, as no product was detected, sodium borohydride was added (100 mg; 2.64 mmol; 4.0 eq.) and the reaction mixture was stirred at RT for 1 hour. Reaction was quenched with water and extracted with EtOAc (twice). Combined organic phases were washed with brine, dried over magnesium sulfate, filtered and concentrated. Purification by preparative HPLC afforded the title compound as a formic acid salt. It was dissolved in MeOH and passed through a SPE-NH₂ cartridge. The fractions containing the desired compound were concentrated to dryness affording a yellow gum, which was twice sonicated in 3 mL of Et₂O. The suspension obtained was concentrated then dried overnight under high vacuum to afford the title compound as a beige solid. ¹H NMR (300 Mz, DMSO-d6) δ: 13.245 (brs, 1H), 9.26 (s, 1H), 8.14-8.13 (m, 1H), 7.99 (d, J=8.5 Hz, 2H), 7.55 (d, J=8.5 Hz, 2H), 7.50 (d, J=8.5 Hz, 1H), 7.27 (dd, J=8.5 Hz, 1.5 Hz, 1H), 3.67 (s, 2H), 2.49-2.45 (m, 7H), 1.74-1.70 (m, 4H). HPLC (Condition A): Rt 2.63 min (purity 99.5%). MS (ESI+): 359.2, MS (ESI−): 357.3.

Example 7

5-methyl-3-{1-[4-(morpholin-4-ylmethyl)phenyl]-1H-1,2,3-triazol-4-yl}-1H-indazole

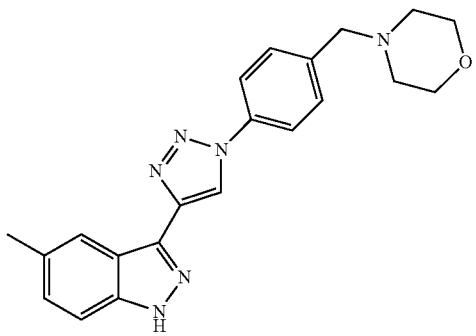 [SMILES: Cc1ccc2[nH]nc(-c3cn(-c4ccc(CN5CCOCC5)cc4)nn3)c2c1]

The title compound was obtained, following procedure described for example 6, but starting from 4-[4-(5-methyl-1H-indazol-3-yl)-1H-1,2,3-triazol-1-yl]benzaldehyde (200 mg; 0.66 mmol; 1.0 eq.) and morpholine (1.7 mL; 19.8 mmol; 30 eq.) as a beige solid. ¹H NMR (300 Mz, DMSO-d6) δ: 13.23 (brs, 1H), 9.26 (s, 1H), 8.14-8.13 (m, 1H), 8.01 (d, J=8.5 Hz, 2H), 7.56 (d, J=8.5 Hz, 2H), 7.50 (d, J=8.5 Hz, 1H), 7.27 (dd, J=8.5, 1.5 Hz, 1H), 3.60 (t, J=4.5 Hz, 4H), 3.56 (s, 2H), 2.47 (s, 3H), 2.40 (t, J=4.5 Hz, 4H). HPLC (Condition A): Rt 2.54 min (purity 98.6%). MS (ESI+): 375.2, MS (ESI−): 373.3.

Example 8

N-methyl-1-{4-[4-(5-methyl-1H-indazol-3-yl)-1H-1,2,3-triazol-1-yl]phenyl}methanamine

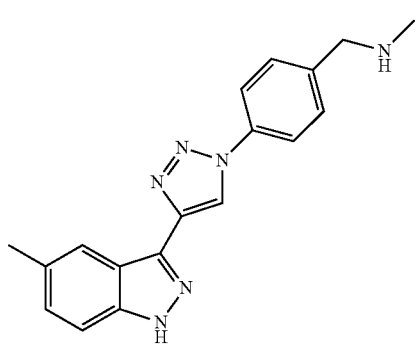

The title compound was obtained following procedure described for example 6, but starting from 4-[4-(5-methyl-1H-indazol-3-yl)-1H-1,2,3-triazol-1-yl]benzaldehyde (200 mg; 0.66 mmol; 1.0 eq.) and methylamine (6.6 mL of a 2.00 M solution in THF; 13.2 mmol; 20 eq.) as a white solid. $^1$H NMR (300 Mz, DMSO-d6) δ: 13.25 (brs, 1H), 9.27 (s, 1H), 8.28 (brs, 1H), 8.14-8.13 (m, 1H), 8.03 (d, J=8.5 Hz, 2H), 7.61 (d, J=8.5 Hz, 2H), 7.50 (d, J=8.5 Hz, 1H), 7.27 (dd, J=8.5 Hz, 1.5 Hz, 1H), 3.87 (s, 2H), 2.48 (s, 3H), 2.37 (s, 3H). HPLC (Condition A): Rt 2.45 min (purity 98.4%). MS (ESI+): 319.1, MS (ESI−): 317.2.

Example 9

5-methyl-3-(1-{4-[(4-methylpiperazin-1-yl)methyl]phenyl}-1H-1,2,3-triazol-4-yl)-1H-indazole

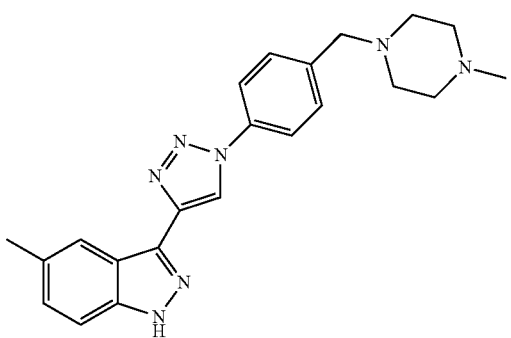

The title compound was obtained following procedure described for example 6, but starting from 4-[4-(5-methyl-1H-indazol-3-yl)-1H-1,2,3-triazol-1-yl]benzaldehyde (200 mg; 0.66 mmol; 1.0 eq.) and methyl piperazine (2.2 mL; 19.8 mmol; 30 eq.) as a beige solid. $^1$H NMR (DMSO-d6) δ: 13.21 (brs, 1H), 9.25 (s, 1H), 8.14-8.13 (m, 1H), 8.00 (d, J=8.5 Hz, 2H), 7.54 (d, J=8.5 Hz, 2H), 7.50 (d, J=8.5 Hz, 1H), 7.27 (dd, J=8.5, 1.5 Hz, 1H), 3.55 (s, 2H), 2.47 (s, 3H), 2.40-2.34 (m, 8H), 2.16 (s, 3H). HPLC (Condition A): Rt 2.29 min (purity 90.9%). MS (ESI+): 388.3, MS (ESI−): 386.4.

Example 10

N,N-dimethyl-1-{4-[4-(5-methyl-1H-indazol-3-yl)-1H-1,2,3-triazol-1-yl]phenyl}methanamine

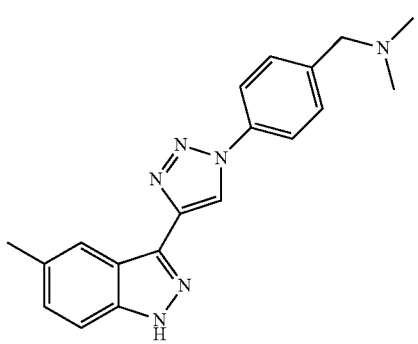

The title compound was obtained following procedure described for example 6, but starting from 4-[4-(5-methyl-1H-indazol-3-yl)-1H-1,2,3-triazol-1-yl]benzaldehyde (180 mg; 0.59 mmol; 1.0 eq.) and dimethylamine (8.9 mL of a 2M solution in THF; 17.8 mmol; 30 eq.) as a beige solid. $^1$H NMR (300 Mz, DMSO-d6) δ: 13.23 (brs, 1H), 9.27 (s, 1H), 8.14 (m, 1H), 8.01 (d, J=8.6 Hz, 2H), 7.54 (d, J=8.6 Hz, 2H), 7.50 (d, J=8.6 Hz, 1H), 7.27 (d, J=8.6 Hz, 1.5 Hz, 1H), 3.48 (s, 2H), 2.48 (s, 3H), 2.19 (s, 6H). HPLC (Condition A): Rt 2.53 min (purity 97.3%). MS (ESI+): 333.2, MS (ESI−): 331.3.

Example 11

5-methyl-3-{1-[4-(piperazin-1-ylmethyl)phenyl]-1H-1,2,3-triazol-4-yl}-1H-indazole

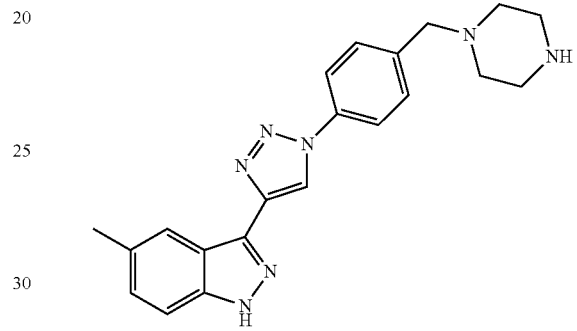

Sodium triacetoxyborohydride (279 mg; 1.32 mmol; 2.0 eq.) was added to a solution of tert-butyl-1-piperazinecarboxylate (1.22 g; 6.59 mmol; 10 eq.) and 4-[4-(5-methyl-1H-indazol-3-yl)-1H-1,2,3-triazol-1-yl]benzaldehyde (200 mg; 0.66 mmol; 1.0 eq.) in DMA (4 mL) and the reaction mixture was stirred overnight at RT. Sodium triacetoxyborohydride (279 mg; 1.32 mmol; 2.0 eq.) and glacial acetic acid (75.42 μl; 1.32 mmol; 2.00 eq.) then sodium cyanoborohydride (83 mg; 1.32 mmol; 2. eq.) were added to complete the reaction which was quenched with water and extracted with EtOAc (twice). Combined organic phases were washed with brine, dried over magnesium sulfate, filtered and concentrated. The resulting gum was stirred at RT in a solution of HCl in dioxane (5 mL, 4N) for 2 hours. The reaction mixture was basified to pH=9-10 and extracted with EtOAc. Organic layer was dried over magnesium sulfate, filtered and concentrated. Purification by preparative HPLC afforded the title compound as a formic acid salt. It was dissolved in MeOH and passed through a SPE-NH2 cartridge. The fractions containing the desired compound were concentrated to dryness affording a yellow gum, which was twice sonicated in 3 mL of Et$_2$O. The suspension obtained was concentrated then dried overnight under high vacuum to afford the title compound as a beige solid. $^1$H NMR (300 Mz, DMSO-d6) δ: 13.23 (brs, 1H), 9.25 (s, 1H), 8.14-8.13 (m, 1H), 8.00 (d, J=8.5 Hz, 2H), 7.54 (d, J=8.5 Hz, 2H), 7.50 (d, J=8.5 Hz, 1H), 7.28 (dd, J=8.5 Hz, 1.5 Hz, 1H), 3.52 (s, 2H), 2.72-2.69 (m, 4H), 2.487 (s, 3H), 2.32-2.30 (m, 4H). HPLC (Condition A): Rt 2.22 min (purity 95.4%). MS (ESI+): 374.3, MS (ESI−): 372.3.

Example 12

1-{4-[4-(1H-indazol-3-yl)-1H-1,2,3-triazol-1-yl]phenyl}methanamine

Step a) Formation of tert-butyl {4-[4-(1H-indazol-3-yl)-1H-1,2,3-triazol-1-yl]benzyl}carbamate

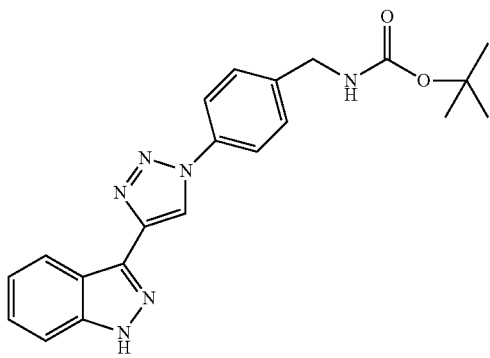 [SMILES: CC(C)(C)OC(=O)NCc1ccc(-n2cc(-c3n[nH]c4ccccc34)nn2)cc1]

The title compound was obtained, following procedure described for intermediate 10, but starting from tert-butyl 4-azidobenzyl)carbamate (prepared as described in Organic Letters (2003), 5(14), 2571-2572; 1.12 g; 4.51 mmol; 1.0 eq.) and 3-ethynyl-1H-indazole (641 mg; 4.51 mmol; 1.0 eq.) as a white powder. $^1$H NMR (DMSO-d6) δ 13.35 (brs, 1H), 9.28 (s, 1H), 8.36 (d, J=8.2, 1H), 8.00 (d, J=8.4 Hz, 2H), 7.60 (d, J=8.4 Hz, 1H), 7.54-7.41 (m, 4H), 7.28-7.20 (m, 1H), 4.22 (d, J=6.0 Hz, 2H), 1.41 (s, 9H). HPLC (Condition A): Rt 3.95 min (purity 95.1%). MS (ESI+): 391.3, MS (ESI−): 389.3.

Step b) Formation of 1-{4-[4-(1H-indazol-3-yl)-1H-1,2,3-triazol-1-yl]phenyl}methanamine hydrochloride

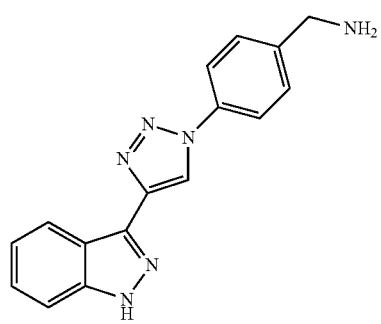 [SMILES: NCc1ccc(-n2cc(-c3n[nH]c4ccccc34)nn2)cc1]

A solution of tert-butyl {4-[4-(1H-indazol-3-yl)-1H-1,2,3-triazol-1-yl]benzyl}carbamate (1.17 g; 3.00 mmol; 1.0 eq.) in HCl solution in 1,4-dioxane (7.5 mL, 4N) was stirred at RT. After 48 h, the reaction mixture was concentrated to dryness affording a sticky solid, which was sonicated in a 1:1 mixture of DCM/MeOH. The suspension obtained was concentrated to dryness to afford the title compound as a beige solid (967 mg, 98%). HPLC (Condition A): Rt 2.08 min (purity 95.3%). MS (ESI+): 291.1, MS (ESI−): 289.2. Purification by preparative HPLC of 50 mg of this crude by afforded a pure sample (35 mg): $^1$H NMR (300 Mz, DMSO-d6) δ: 13.40 (brs, 1H), 9.33 (s, 1H), 8.36 (dt, J=8.2 Hz, J=1.0 Hz, 1H), 8.07 (d, J=8.5 Hz, 2H), 7.68 (d, J=8.5 Hz, 2H), 7.62 (dt, J=8.2 Hz, 1.0 Hz, 1H), 7.47-7.42 (m, 1H), 7.29-7.24 (m, 1H), 4.02 (s, 2H). HPLC (Condition A): Rt 2.06 min (purity 97.5%). MS (ESI+): 291.1, MS (ESI−): 289.1.

Example 13

N-{4-[4-(1H-indazol-3-yl)-1H-1,2,3-triazol-1-yl]benzyl}cyclopentanecarboxamide

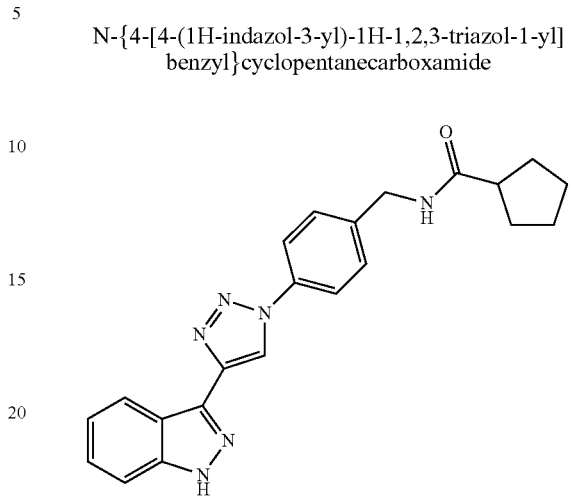

TBTU (185 mg; 0.58 mmol; 1.3 eq.) was added to a cooled (0° C.) solution of cyclopentane carboxylic acid (53 µl; 0.49 mmol; 1.1 eq.) in DMF (2.9 mL). After 10 min, a solution of 1-{4-[4-(1H-indazol-3-yl)-1H-1,2,3-triazol-1-yl]phenyl}methanamine (145 mg; 0.44 mmol; 1.0 eq.) and DIEA (174 µl; 1.02 mmol; 2.3 eq.) in DMF (2.9 mL) was added and the reaction mixture was stirred overnight at RT. DCM was added and the reaction mixture was washed with an aqueous saturated solution of NH$_4$Cl and brine. The organic layer was dried over magnesium sulfate, filtered and concentrated. The crude was purified by preparative HPLC to afford the title compound as a white solid. $^1$H NMR (300 Mz, DMSO-d 6) δ: 13.36 (brs, 1H), 9.28 (s, 1H), 8.41 (t, J=6.0 Hz, 1H), 8.36 (dt, J=8.2 Hz, 1.0 Hz, 1H), 8.00 (d, J=8.6 Hz, 2H), 7.60 (dt, J=8.2 Hz, 1.0 Hz, 1H), 7.49-7.41 (m, 3H); 7.28-7.23 (m, 1H), 4.35 (d, J=6.0 Hz, 2H), 2.70-2.59 (m, 1H), 1.84-1.49 (m, 8H). HPLC (Condition A): Rt 3.59 min (purity 97.6%). MS (ESI+): 387.3, MS (ESI−): 385.4.

Example 14

N-{4-[4-(1H-indazol-3-yl)-1H-1,2,3-triazol-1-yl]benzyl}acetamide

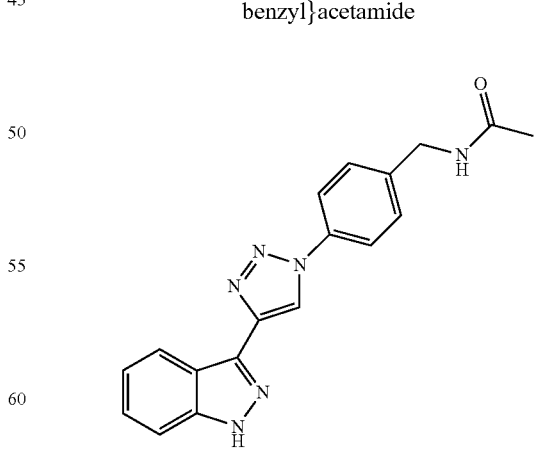

To a solution of 1-{4-[4-(1H-indazol-3-yl)-1H-1,2,3-triazol-1-yl]phenyl}methanamine (190 mg; 0.58 mmol; 1.0 eq.) and TEA (242 µl; 1.74 mmol; 3.0 eq.) in DMF (3.8 mL) was added acetyl chloride (46 µl; 0.70 mmol; 1.2 eq.) and the reaction mixture was stirred overnight at RT. Reaction mixture was diluted with DCM and washed with water and brine. The organic phase was dried over magnesium sulfate, filtered and concentrated. Purification by preparative HPLC afforded the title compound as a white solid. $^1$H NMR (300 Mz, DMSO) δ: 13.36 (brs, 1H), 8.29 (s, 1H), 8.47 (t, J=5.9 Hz, 1H), 8.36 (dt, J=8.0 Hz, J=1.0 Hz, 1H), 8.01 (d, J=8.6 Hz, 2H), 7.60 (dt, J=8.4 Hz, J=1.0 Hz, 1H), 7.49 (d, J=8.6 Hz, 2H), 7.47-7.41 (m, 1H), 7.28-7.23 (m, 1H), 4.34 (d, J=5.9 Hz, 2H), 1.90 (s, 3H). HPLC (Condition A): Rt 2.81 min (purity 97.7%). MS (ESI+): 333.2, MS (ESI−): 331.2.

Example 15

N-{4-[4(1H-indazol-3-yl)-1H-1,2,3-triazol-1-yl)benzyl}isonicotinamide

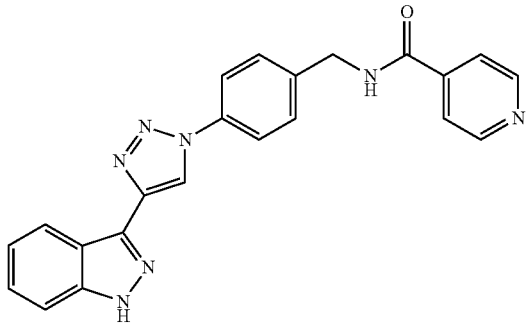 [SMILES: O=C(NCc1ccc(-n2cc(-c3n[nH]c4ccccc34)nn2)cc1)c1ccncc1]

The title compound was obtained following procedure described for example 14, but starting from 1-{4-[4-(1H-indazol-3-yl)-1H-1,2,3-triazol-1-yl]phenyl}methanamine (190 mg; 0.58 mmol; 1.0 eq.) and isonicotinoyl chloride hydrochloride (124. mg; 0.70 mmol; 1.2 eq.) as a white solid. $^1$H NMR (300 Mz, DMSO): 13.36 (brs, 1H), 9.45 (t, J=6.0 Hz, 1H), 9.29 (s, 1H), 8.77-8.75 (m, 2H), 8.36 (dt, J=8.0 Hz, 1.0 Hz, 1H), 8.03 (d, J=8.6 Hz, 2H), 7.84-7.82 (m, 2H), 7.62-7.52 (m, 3H), 7.46-7.41 (m, 1H), 7.28-7.23 (m, 1H), 4.60 (d, J=6.0 Hz, 2H). HPLC (Condition A): Rt 2.49 min (purity 100.0%). MS (ESI+): 396.3, MS (ESI−): 394.3.

Example 16

N-{4-[4-(1H-indazol-3-yl)-1H-1,2,3-triazol-1-yl]benzyl}-2-morpholin-4-ylacetamide

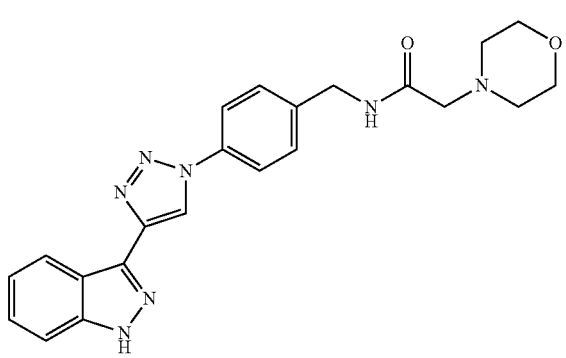 [SMILES: O=C(CN1CCOCC1)NCc1ccc(-n2cc(-c3n[nH]c4ccccc34)nn2)cc1]

The title compound was obtained following procedure described for example 13, but starting from 1-{4-[4-(1H-indazol-3-yl)-1H-1,2,3-triazol-1-yl]phenyl}methanamine (150 mg; 0.46 mmol; 1.0 eq.) and 4-morpholinoacetic acid (Matrix scientific, 73 mg; 0.50 mmol; 1.1 eq.) as a white solid. $^1$H NMR (300 Mz, DMSO-d6): 13.36 (brs, 1H), 9.29 (s, 1H), 8.45 (t, J=6.0 Hz, 1H), 8.36 (d, J=8.0 Hz, 1H), 8.00 (d, J=8.6 Hz, 2H), 7.61 (d, J=8.4 Hz, 1H), 7.50 (d, J=8.6 Hz, 2H), 7.47-7.41 (m, 1H), 7.28-7.23 (m, 1H), 4.39 (d, J=6.0 Hz, 2H), 3.63 (t, J=4.6 Hz, 4H), 3.01 (s, 2H), 2.45 (t, J=4.6 Hz, 4H). HPLC (Condition A): Rt 2.50 min (purity 99.6%). MS (ESI+): 418.4, MS (ESI−): 416.5.

Example 17

N-{4-[4-(1H-indazol-3-yl)-1H-1,2,3-triazol-1-yl]benzyl}tetrahydro-2H-pyran-4-carboxamide

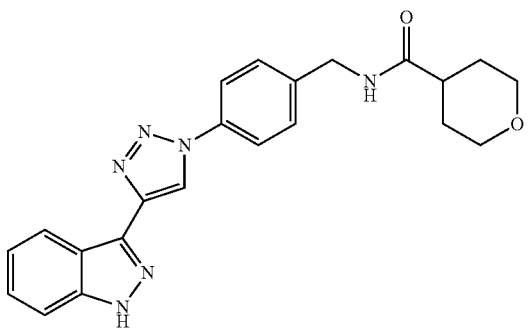

The title compound was obtained following procedure described for example 14, but starting from 1-{4-[4-(1H-indazol-3-yl)-1H-1,2,3-triazol-1-yl]phenyl}methanamine (190 mg; 0.58 mmol; 1.0 eq.) and tetrahydro-2H-pyran-4-carbonyl chloride (104 mg; 0.70 mmol; 1.2 eq.) as a white solid. $^1$H NMR (300 Mz, DMSO-d6) δ: 13.36 (brs, 1H), 9.29 (s, 1H), 8.45 (t, J=6.0 Hz, 1H), 8.35 (dt, J=8.1 Hz, 1.0 Hz, 1H), 8.00 (d, J=8.6 Hz, 2H), 7.61 (dt, J=8.5 Hz, 1.0 HZ, 1H), 7.49-7.71 (m, 3H), 7.28-7.23 (m, 1H), 4.36 (d, J=6.0 Hz, 2H), 3.91-3.85 (m, 2H), 3.36-3.28 (m, 2H), 2.46-2.39 (m, 1H), 1.67-1.59 (m, 4H). HPLC (Condition A): Rt 2.93 min (purity 98.9%). MS (ESI+): 403.3, MS (ESI−): 401.3.

Example 18

3-{1-[4-(2-morpholin-4-yl-2-oxoethyl)phenyl]-1H-1,2,3-triazol-4-yl}-1H-indazole

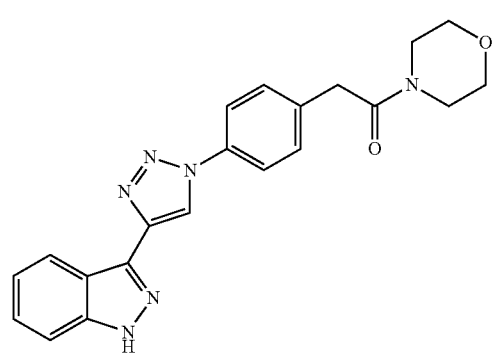 [SMILES: O=C(Cc1ccc(-n2cc(-c3n[nH]c4ccccc34)nn2)cc1)N1CCOCC1]

COMU (151 mg; 0.41 mmol; 1.3 eq.) was added into a solution of {4-[4-(1H-indazol-3-yl)-1H-1,2,3-triazol-1-yl]phenyl}acetic acid (100 mg; 0.31 mmol; 1.0 eq.) and DIEA (69 µl; 0.41 mmol; 1.3 eq.) in DMF (4 mL). After 1-2 min, morpholine (33 µl; 0.38 mmol; 1.2 eq.) was added and the reaction mixture was stirred overnight at RT. EtOAc was added and the reaction mixture was washed twice with an aqueous saturated solution of NaHCO$_3$. The organic layer was dried over magnesium sulfate, filtered and concentrated. Purification by preparative HPLC afforded the tittle compound as a white solid. $^1$H NMR (300 Mz, DMSO-d6) δ: 13.36 (brs, 1H), 9.29 (s, 1H), 8.36 (d, J=8.1 Hz, 1H), 7.99 (d, J=8.5 Hz, 2H), 7.61 (d, J=8.5 Hz, 1H), 7.49-7.41 (m, 3H), 7.28-7.23 (m, 1H), 3.84 (s, 2H), 3.58-3.55 (m, 6H), 3.49-3.46 (m, 2H). HPLC (Condition A): Rt 2.97 min (purity 98.8%). MS (ESI+): 389.3, MS (ESI−): 387.3.

Example 19

3-{1-[4-(2-oxo-2-pyrrolidin-1-ylethyl)phenyl]-1H-1,2,3-triazol-4-yl}-1H-indazole

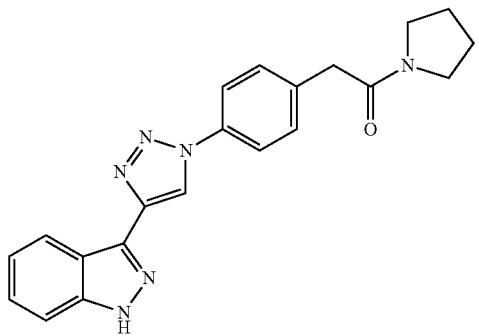 [SMILES: O=C(Cc1ccc(-n2cc(-c3n[nH]c4ccccc34)nn2)cc1)N1CCCC1]

The title compound was obtained following procedure described for example 18, but starting from {4-[4-(1H-indazol-3-yl)-1H-1,2,3-triazol-1-yl]phenyl}acetic acid (120 mg; 0.38 mmol; 1.0 eq.) and pyrrolidine (37 µl; 0.45 mmol; 1.2 eq.) as a beige solid. $^1$H NMR (300 Mz, DMSO-d6) δ: 13.35 (brs, 1H), 9.29 (s, 1H), 8.36 (d, J=8.1 Hz, 1H), 7.98 (d, J=8.5 Hz, 2H), 7.60 (d, J=8.4 Hz, 1H), 7.49-7.42 (m, 3H), 7.28-7.23 (m, 1H), 3.74 (s, 2H), 3.52 (t, J=6.7 Hz, 2H), 3.32 (t, J=6.7 Hz, 2H), 1.90 (quint., J=6.7 Hz, 2H), 1.78 (quint., J=6.7 Hz, 2H). HPLC (Condition A): Rt 3.29 min (purity 94.3%). MS (ESI+): 373.25, MS (ESI−): 371.3.

Example 20

3-[1-(6-morpholin-4-ylpyridin-3-yl)-1H-1,2,3-triazol-4-yl]-1H-indazole

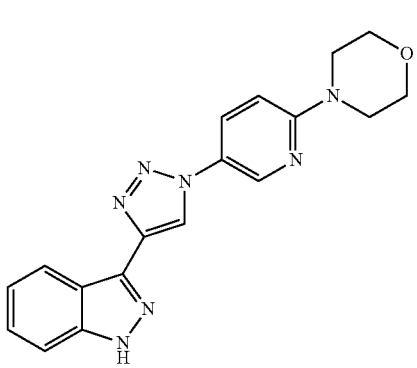 [SMILES: c1ccc2c(-c3cn(-c4ccc(N5CCOCC5)nc4)nn3)n[nH]c2c1]

A suspension of 3-[1-(6-chloropyridin-3-yl)-1H-1,2,3-triazol-4-yl]-1H-indazole (13 mg; 0.04 mmol; 1.0 eq.) in morpholine (0.5 mL) was heated in MW at 120° C. for 4.5 h. The precipitate obtained was filtered, washed with Et$_2$O and dried under vacuum at 50° C. to afford the title compound as a beige solid. $^1$H NMR (DMSO-d6) δ: 13.33 (s, 1H), 9.18 (s, 1H), 8.74 (d, J=2.8 Hz, 1H), 8.34 (d, J=8.0 Hz, 1H), 8.16 (dd, J=2.6, 9.1 Hz, 1H), 7.59 (d, J=8.4 Hz, 1H), 7.43 (m, 1H), 7.23 (m, 1H), 7.07 (d, J=9.1 Hz, 1H), 3.72 (m, 4H), 3.55 (m, 4H). HPLC (Condition A): Rt 3.21 min (purity 97.3%). MS (ESI+): 348.3, MS (ESI−): 346.3.

Example 21

3-{4-[4-(1H-indazol-3-yl)-1H-1,2,3-triazol-1-yl]phenyl}-N,N-dimethylpropanamide

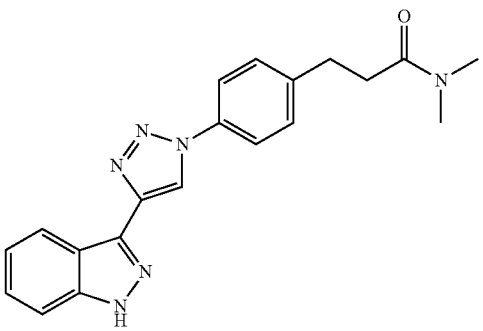 [SMILES: CN(C)C(=O)CCc1ccc(-n2cc(-c3n[nH]c4ccccc34)nn2)cc1]

TBTU (188 mg; 0.58 mmol; 1.3 eq.) was added to a cooled (0° C.) solution of 3-{4-[4-(1H-indazol-3-yl)-1H-1,2,3-triazol-1-yl]phenyl}propanoic acid (150 mg; 0.45 mmol; 1.0 eq.) and DIEA (176 µl; 1.03 mmol; 2.3 eq.) in DMF (3 mL). After 10 min, dimethylamine (270 µl of a 2.00 M in THF; 0.54 mmol; 1.20 eq.) was added and the reaction mixture was stirred overnight at RT. The resulting solid was filtered off and purified by preparative HPLC to afford the title compound as a brown solid. $^1$H NMR (300 Mz, DMSO-d6) δ: 13.34 (brs, 1H), 9.26 (s, 1H), 8.36 (d, J=8.1 Hz, 1H), 7.94 (d, J=8.5 Hz, 2H), 7.62-7.59 (m, 1H), 7.50 (d, J=8.5 Hz, 2H), 7.46-7.41 (m, 1H), 7.28-7.23 (m, 1H), 2.96 (s, 3H), 2.93-2.88 (m, 2H), 2.83 (s, 3H), 2.70-2.65 (m, 2H). HPLC (Condition A): Rt 3.23 min (purity 92.2%). MS (ESI+): 361.3, MS (ESI−): 359.3.

Example 22

3-{1-[4-(3-morpholin-4-yl-3-oxopropyl)phenyl]-1H-1,2,3-triazol-4-yl}-1H-indazole

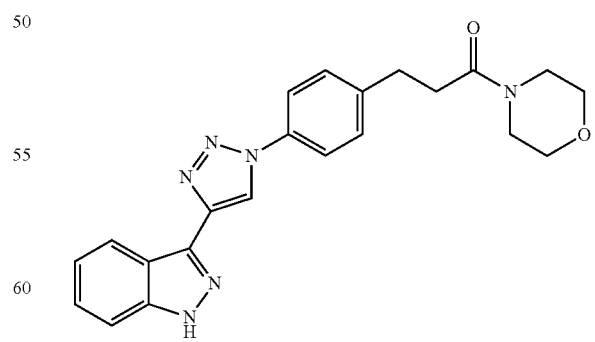

The title compound was obtained following procedure described for example 21, but starting from 3-{4-[4-(1H-indazol-3-yl)-1H-1,2,3-triazol-1-yl]phenyl}propanoic acid (150 mg; 0.45 mmol; 1.0 eq.) and morpholine (47 µl; 0.54 mmol; 1.2 eq.) as a brown solid. ¹H NMR (300 Mz, DMSO-d6) δ: 13.35 (brs, 1H), 9.27 (s, 1H), 8.36 (d, J=8.21 Hz, 1H), 7.95 (d, J=8.6 Hz, 2H), 7.60 (dt, J=8.5 Hz, 1.0 Hz, 1H), 7.50 (d, J=8.6 Hz, 2H), 7.47-7.41 (m, 1H), 7.28-7.23 (m, 1H), 3.54-3.51 (m, 4H), 3.46-3.43 (m, 4H), 2.95-2.90 (m, 2H), 2.73-2.68 (m, 2H). HPLC (Condition A): Rt 3.14 min (purity 98.2%). MS (ESI+): 403.3, MS (ESI−): 401.5.

Example 23

3-{1-[4-(3-oxo-3-pyrrolidin-1-ylpropyl)phenyl]-1H-1,2,3-triazol-4-yl}-1H-indazole

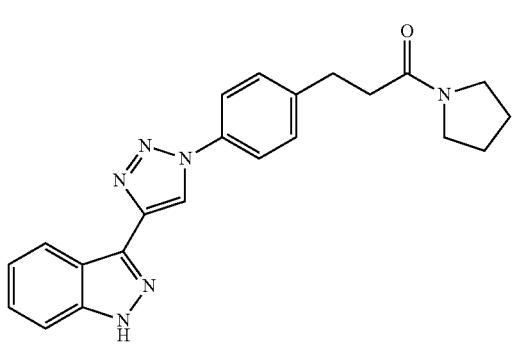 [SMILES: O=C(CCc1ccc(-n2cc(-c3n[nH]c4ccccc34)nn2)cc1)N1CCCC1]

The title compound was obtained following procedure described for example 13, but starting from 3-{4-[4-(1H-indazol-3-yl)-1H-1,2,3-triazol-1-yl]phenyl}propanoic acid (150 mg; 0.45 mmol; 1.0 eq.) and pyrrolidine (45 µl; 0.54 mmol; 1.2 eq.) as a beige solid. ¹H NMR (300 Mz, DMSO-d6) δ: 13.35 (brs, 1H), 9.27 (s, 1H), 8.35 (dt, J=8.1 Hz, 1.0 Hz, 1H), 7.94 (d, J=8.5 Hz, 2H), 7.61 (dt, J=8.5 Hz, 1.0 Hz, 1H), 7.50 (d, J=8.5 Hz, 2H), 7.46-7.41 (m, 1H), 7.28-7.23 (m, 1H), 3.38 (t, J=6.7 Hz, 2H), 3.29 (t, J=6.7 Hz, 2H), 2.92 (t, J=7.5 Hz, 2H), 2.61 (t, J=7.5 Hz, 2H), 1.89-1.71 (m, 4H). HPLC (Condition A): Rt 3.49 min (purity 99.3%). MS (ESI+): 387.3, MS (ESI−): 385.4.

Example 24

3-(1-{4-[3-(4-methylpiperazin-1-yl)-3-oxopropyl]phenyl}-1H-1,2,3-triazol-4-yl)-1H-indazole

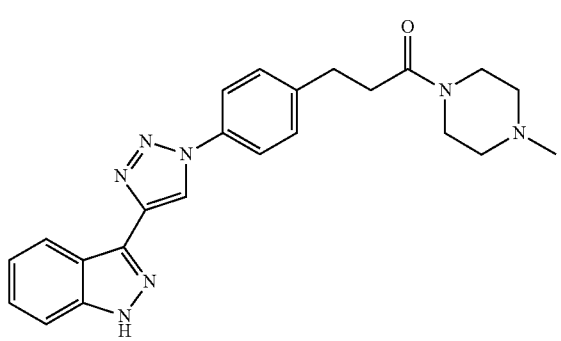 [SMILES: CN1CCN(C(=O)CCc2ccc(-n3cc(-c4n[nH]c5ccccc45)nn3)cc2)CC1]

The title compound was obtained following procedure described for example 13, but starting from 3-{4-[4-(1H-indazol-3-yl)-1H-1,2,3-triazol-1-yl]phenyl}propanoic acid (150 mg; 0.45 mmol; 1.0 eq.), 1-methylpiperazine (60 µl; 0.54 mmol; 1.2 eq.) as a beige solid. ¹H NMR (300 Mz, DMSO-d6) δ: 13.35 (brs, 1H), 9.27 (s, 1H), 8.35 (d, J=8.1 Hz, 1H), 7.95 (d, J=8.5 Hz, 2H), 7.60 (d, J=8.5 Hz, 1H), 7.50 (d, J=8.5 Hz, 2H), 7.46-7.41 (m, 1H), 7.28-7.23 (m, 1H), 3.43 (m, 4H), 2.94-2.89 (m, 2H), 2.72-2.67 (m, 2H), 2.27 (m, 4H), 2.18 (s, 3H). HPLC (Condition A): Rt 2.45 min (purity 99.5%). MS (ESI+): 416.4, MS (ESI−): 414.4.

Example 25

4-[4-(1H-indazol-3-yl)-1H-1,2,3-triazol-1-yl]-2-methoxy-N,N-dimethylbenzamide

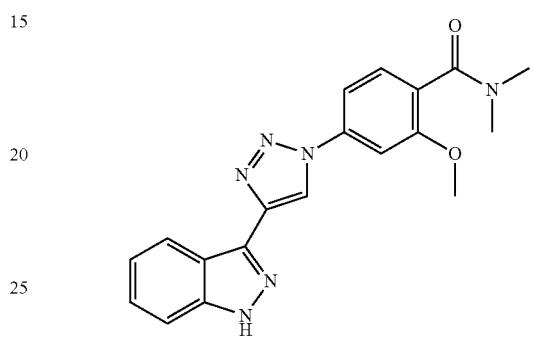

The title compound was obtained following procedure described for example 13, but starting from 4-[4-(1H-indazol-3-yl)-1H-1,2,3-triazol-1-yl]-2-methoxybenzoic acid (70 mg; 0.21 mmol; 1.0 eq.) and dimethylamine (156 µl of a 2.0 M solution in THF; 0.31 mmol; 1.5 eq.) as a white sticky solid. ¹H NMR (300 Mz, DMSO-d6) δ: 13.39 (s, 1H), 9.46 (s, 1H), 8.37 (d, J=8.1 Hz, 1H), 7.76 (d, J=1.9 Hz, 1H), 7.71 (dd, J=8.1 Hz, 1.9 Hz, 1H), 7.62 (d, J=8.4 Hz, 1H), 7.48-7.41 (m, 2H), 7.27 (ddd, J=8.4, 6.8, 0.7 Hz, 1H), 3.97 (s, 3H), 3.02 (s, 3H), 2.82 (s, 3H). HPLC (Condition A): Rt 3.05 min (purity 99.7%). MS (ESI+): 363.2, MS (ESI−): 361.3.

Example 26

1-{4-[4-(1H-indazol-3-yl)-1H-1,2,3-triazol-1-yl]benzoyl}pyrrolidin-3-ol

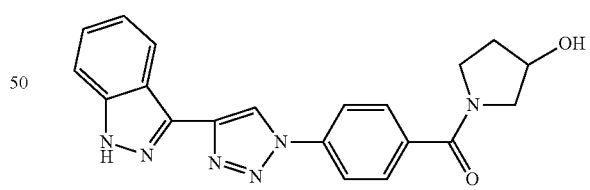

A solution of TBTU (137 mg; 0.33 mmol; 1.3 eq.) and 4-[4-(1H-indazol-3-yl)-1H-1,2,3-triazol-1-yl]benzoic acid (100 mg; 0.33 mmol; 1.0 eq.) in DMF (2 mL) was stirred for 1 h at RT before the addition of DIEA (111 µl; 0.66 mmol; 2.0 eq.) and 3-pyrrolidinol (43 mg; 0.49 mmol.; 1.5 eq.). The reaction mixture was stirred at RT overnight. It was then diluted with DCM and washed with an aqueous saturated solution of NaHCO₃. Organic phase was dried over magnesium sulfate, filtered and concentrated. The crude was purified by preparative HPLC to afford the title compound as a yellow solid. ¹H NMR (300 Mz, DMSO-d6) δ 13.38 (s, 1H), 9.41 (s, 1H), 8.37 (d, J=8.1 Hz, 1H), 8.15 (d, J=8.7 Hz, 2H), 7.78 (dd, J=3.2, 8.6 Hz, 2H), 7.62 (d, J=8.4 Hz, 1H), 7.51-7.39 (m, 1H), 7.27 (t, J=7.1 Hz, 1H), 4.32 (brd, J=26.0 Hz, 1H), 3.76-3.54 (m, 2H), 3.54-3.20 (m, 3H), 2.06-1.75 (m, 2H). HPLC (Condition A): Rt 2.58 min (purity 96.7%). MS (ESI+): 375.2, MS (ESI−): 373.2.

Example 27

1-{4-[4-(1H-indazol-3-yl)-1H-1,2,3-triazol-1-yl]benzoyl}-N,N-dimethylpyrrolidin-3-amine

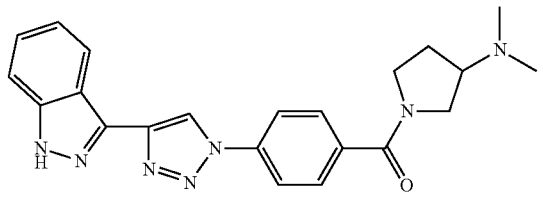 [SMILES: CN(C)C1CCN(C(=O)c2ccc(-n3cc(-c4n[nH]c5ccccc45)nn3)cc2)C1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-dimethylamino pyrrolidine (56 mg, 0.49, 1.5 eq.). Purification by flash chomatography on silica (DCM:MeOH:NH$_4$OH, gradient from 100:0:0 to 90:10:0.1) afforded the title compound as a yellow powder. $^1$H NMR (300 Mz, DMSO-d6) δ 13.37 (s, 1H), 9.39 (s, 1H), 8.36 (d, J=8.2 Hz, 1H), 8.13 (d, J=8.3 Hz, 2H), 7.83-7.72 (m, 2H), 7.61 (d, J=8.4 Hz, 1H), 7.53-7.36 (m, 1H), 7.33-7.19 (m, 1H), 3.77-3.18 (m, 5H), 2.78-2.60 (m, 1H), 2.24-1.92 (m, 6H), 1.82-1.69 (m, 1H). HPLC (Condition A): Rt 2.20 min (purity 90.1%). MS (ESI+): 402.3, MS (ESI−): 400.3.

Example 28

(1-{4-[4-(1H-indazol-3-yl)-1H-1,2,3-triazol-1-yl]benzoyl}piperidin-4-yl)methanol

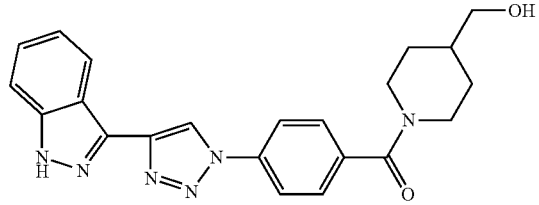 [SMILES: O=C(c1ccc(-n2cc(-c3n[nH]c4ccccc34)nn2)cc1)N1CCC(CO)CC1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 4-piperinyl methanol (Alfa Aesar, 57 mg, 0.49 mmol, 1.5 eq.). Purification by flash chromatography on silica (DCM:MeOH:NH$_4$OH, gradient from 100:0:0 to 90:10:0.1) afforded the title compound as a beige powder. $^1$H NMR (300 Mz, DMSO-d6) δ 13.37 (s, 1H), 9.38 (s, 1H), 8.36 (d, J=8.3 Hz, 1H), 8.13 (d, J=8.6 Hz, 2H), 7.67-7.56 (m, 3H), 7.50-7.38 (m, 1H), 7.31-7.19 (m, 1H), 4.52 (t, J=5.1 Hz, 1H), 3.71-3.52 (m, 1H), 3.39-3.22 (m, 2H), 1.92-1.51 (m, 4H), 1.30-1.01 (m, 4H). HPLC (Condition A): Rt 2.84 min (purity 91.8%). MS (ESI+): 403.3, MS (ESI−): 401.2.

Example 29

1-(1-{4-[4-(1H-indazol-3-yl)-1H-1,2,3-triazol-1-yl]benzoyl}piperidin-3-yl)-N,N-dimethylmethanamine

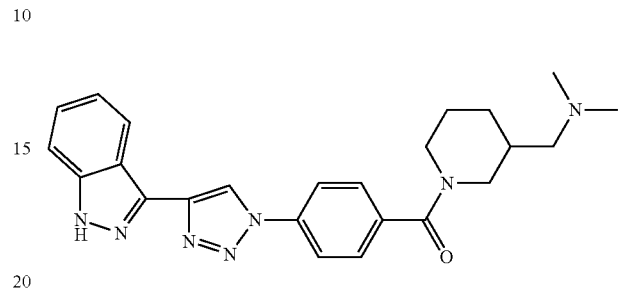

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and N-Dimethyl-1-piperidin-3-ylmethanamine (Matrix scientific, 70 mg, 0.49, 1.5 eq.). Purification by flash chomatography on silica (DCM:MeOH:NH$_4$OH, gradient from 100:0:0 to 90:10:0.1) afforded the title compound as a yellow powder. $^1$H NMR (300 Mz, DMSO-d6) δ 13.37 (s, 1H), 9.39 (s, 1H), 8.36 (d, J=8.1 Hz, 1H), 8.14 (d, J=8.6 Hz, 2H), 7.70-7.56 (m, 3H), 7.50-7.36 (m, 1H), 7.25 (t, J=7.5 Hz, 1H), 3.31 (s, 6H), 2.45-1.90 (m, 6H), 1.89-1.32 (m, 4H), 1.31-1.08 (m, 1H). HPLC (Condition A): Rt 2.43 min (purity 96.2%). MS (ESI+): 430.4, MS (ESI−): 428.3.

Example 30

1-{4-[4-4H-indazol-3-yl)-1H-1,2,3-triazol-1-yl]benzoyl}piperidin-3-ol

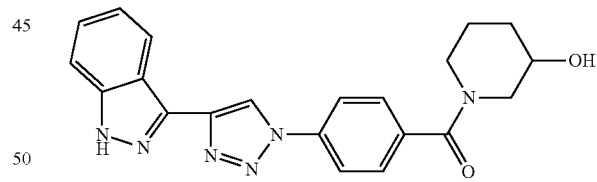

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-hydroxypiperidine (50 mg, 0.49, 1.5 eq.). The crude obtained was suspended in acetonitrile, filtered and dried to afford the title compound as a beige powder. $^1$H NMR (300 Mz, DMSO-d6) δ 13.38 (s, 1H), 9.39 (s, 1H), 8.37 (d, J=7.9 Hz, 1H), 8.14 (d, J=8.6 Hz, 2H), 7.75-7.57 (m, 3H), 7.51-7.39 (m, 1H), 7.27 (t, J=7.5 Hz, 1H), 5.10-4.81 (m, 1H), 4.21 (brs, 0.5H), 3.77 (brs, 0.5H), 3.62-3.37 (m, 1H), 3.09 (brs, 1H), 2.01-1.26 (m, 6H). HPLC (Condition A): Rt 2.79 min (purity 93.7%). MS (ESI+): 389.3, MS (ESI−): 387.3.

Example 31

4-[4-(1H-indazol-3-yl)-1H-1,2,3-triazol-1-yl]-N-(1-methyl-2-oxopyrrolidin-3-yl)benzamide

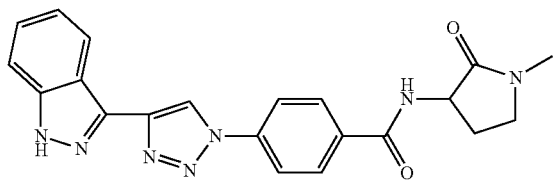 [SMILES: CN1CCC(NC(=O)c2ccc(-n3cc(-c4n[nH]c5ccccc45)nn3)cc2)C1=O]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-amino-1-methylpyrrolidin-2-one (Chem Bridge Corp., 56 mg, 0.49 mmol, 1.5 eq.). The crude obtained was suspended in acetonitrile, filtered and dried to afford the title compound as a beige powder. $^1$H NMR (300 Mz, DMSO-d6) δ 13.38 (s, 1H), 9.43 (s, 1H), 8.94 (d, J=8.4 Hz, 1H), 8.36 (d, J=8.1 Hz, 1H), 8.21 (d, J=8.8 Hz, 2H), 8.11 (d, J=8.8 Hz, 2H), 7.61 (d, J=8.4 Hz, 1H), 7.50-7.38 (m, 1H), 7.31-7.15 (m, 1H), 4.74-4.52 (m, 1H), 3.42-3.32 (m, 2H), 2.77 (s, J=7.8 Hz, 3H), 2.44-2.27 (m, 1H), 2.13-1.85 (m, 1H). HPLC (Condition A): Rt 2.69 min (purity 92.2%). MS (ESI+): 402.3, MS (ESI-): 400.3.

Example 32

5-methyl-3-{1-[4-(morpholin-4-ylcarbonyl)phenyl]-1H-1,2,3-triazol-4-yl}-1H-indazole

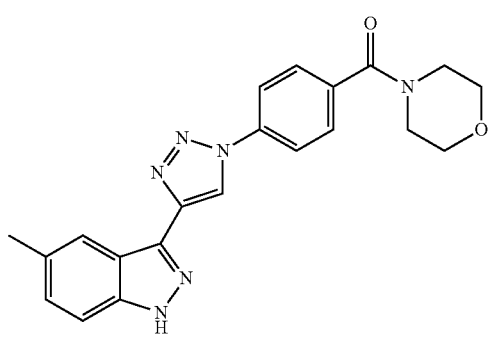 [SMILES: Cc1ccc2[nH]nc(-c3cn(-c4ccc(C(=O)N5CCOCC5)cc4)nn3)c2c1]

Copper sulfate pentahydrate (70 mg; 0.28 mmol; 0.07 eq.) was added to a solution of 3-ethynyl-5-methyl-1H-indazole (665 mg; 4.26 mmol; 1.00 eq.), 4-(4-azidobenzoyl)morpholine (987 mg; 4.25 mmol; 1.0 eq.) and D-(-)-isoascorbic acid sodium salt (283 mg; 1.43 mmol; 0.34 eq.) in DMF (15 mL) and water (0.5 mL). The reaction suspension was heated in MW at 80° C. for 40 min then poured into HCl solution (1N) and extracted with EtOAc (twice). Combined organic phases were washed with brine, dried over magnesium sulfate, filtered and concentrated to give a yellow solid (1.38 g, 83%). $^1$H NMR (300 Mz, DMSO-d6) δ: 13.25 (s, 1H), 9.36 (s, 1H), 8.20-8.10 (m, 3H), 7.68 (d, J=108.7 Hz, 2H), 7.51 (d, J=8.6 Hz, 1H), 7.28 (dd, J=1.4, 8.6 Hz, 1H), 3.74-3.36 (m, 8H), 2.48 (s, 3H). HPLC (Condition A): Rt 3.21 min (purity 98.6%). MS (ESI+): 389.2, MS (ESI-): 387.2.

Example 33

(1-{4-[4(1H-indazol-3-yl-1H-1,2,3-triazol-1-yl]benzoyl}piperidin-3-yl)methanol

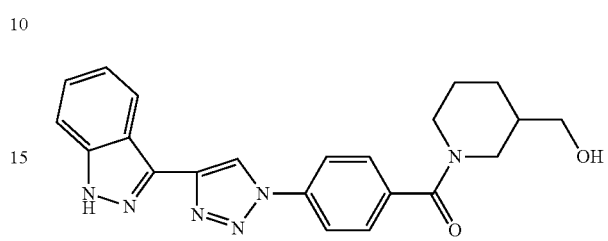

The title compound was obtained following procedure described for intermediate 10, but starting from (4-azidobenzoyl)piperidin-3-yl]methanol (1.12 g; 4.30 mmol; 1.0 eq.) and 3-ethynyl-1H-indazole (612 mg; 4.30 mmol; 1.0 eq.) as a white solid. $^1$H NMR (300 Mz, DMSO-d6): 13.38 (brs, 1H), 9.39 (s, 1H), 8.36 (dt, J=8.1 Hz, 1.0 Hz, 1H), 8.14 (d, J=8.6 Hz, 2H), 7.65-7.60 (m, 3H), 7.47-7.42 (m, 1H), 7.28-7.23 (m, 1H), 4.62-4.35 (m, 2H), 3.74-3.53 (m, 1H), 3.38-3.25 (m, 1H), 3.10-2.56 (m, 3H), 1.77-1.47 (m, 4H), 1.28-1.12 (m, 1H). HPLC (Condition A): Rt 2.93 min (purity 97.2%). MS (ESI+): 403.3, MS (ESI-): 401.4.

Example 34

3-{1-[3-methoxy-4-(morpholin-4-ylcarbonyl)phenyl]-1H-1,2,3-triazol-4-yl}-1H-indazole

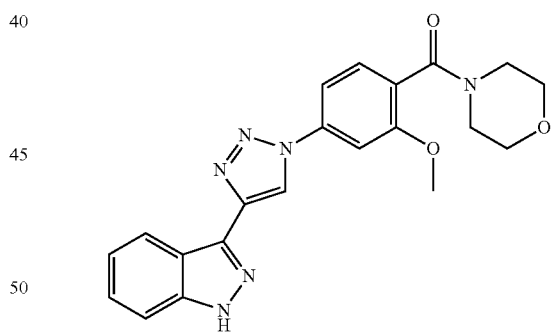

The title compound was obtained following procedure described for example 14, but starting from 4-[4-(1H-indazol-3-yl)-1H-1,2,3-triazol-1-yl]-2-methoxybenzoic acid (70 mg; 0.21 mmol; 1.0 eq.) and morpholine (27 μl; 0.31 mmol; 1.5 eq.) as a white solid. $^1$H NMR (300 Mz, DMSO-d6) δ: 13.41 (s, 1H), 9.46 (s, 1H), 8.37 (d, J=8.1 Hz, 1H), 7.76 (d, J=1.9 Hz, 1H), 7.71 (dd, J=8.1, 1.9 Hz, 1H), 7.62 (d, J=8.4 Hz, 1H), 7.48-7.42 (m, 2H), 7.27 (ddd, J=8.4, 6.8, 0.7 Hz, 1H), 3.97 (s, 3H), 3.65 (bs, 4H), 3.55 (t, J=4.6 Hz, 2H), 3.22-3.18 (m, 2H). HPLC (Condition A): Rt 3.02 min (purity 99.3%). MS (ESI+): 405.3, MS (ESI-): 403.3.

Following compounds were prepared according to procedures described for example 1 or example 26 above:

| Example | Structure | Name | LCMS Purity max plot | Mass peak [M]+ |
|---|---|---|---|---|
| 35 | 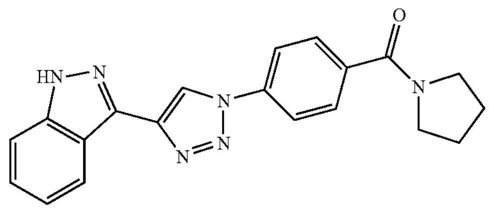 [SMILES: O=C(c1ccc(-n2cc(-c3n[nH]c4ccccc34)nn2)cc1)N1CCCC1] | 3-{1-[4-(pyrrolidin-1-ylcarbonyl)phenyl]-1H-1,2,3-triazol-4-yl}-1H-indazole | 97.5 | 359.5 |
| 36 | 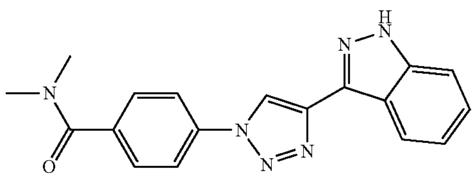 [SMILES: CN(C)C(=O)c1ccc(-n2cc(-c3n[nH]c4ccccc34)nn2)cc1] | 4-[4-(1H-indazol-3-yl)-1H-1,2,3-triazol-1-yl]-N,N-dimethylbenzamide | 100 | 333.1 |
| 37 | 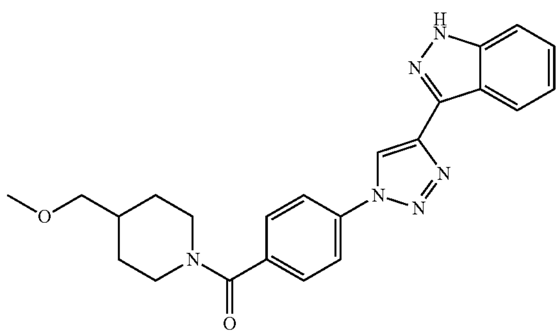 [SMILES: COCC1CCN(C(=O)c2ccc(-n3cc(-c4n[nH]c5ccccc45)nn3)cc2)CC1] | 3-[1-(4-{[4-(methoxymethyl)piperidin-1-yl]carbonyl}phenyl)-1H-1,2,3-triazol-4-yl]-1H-indazole | 94.8 | 417.1 |
| 38 | 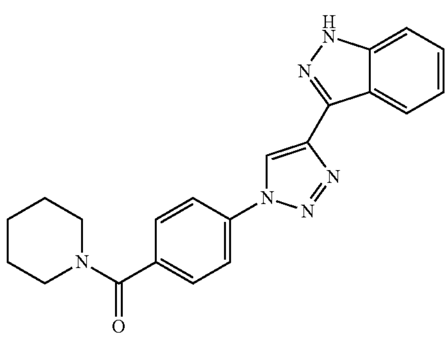 [SMILES: O=C(c1ccc(-n2cc(-c3n[nH]c4ccccc34)nn2)cc1)N1CCCCC1] | 3-{1-[4-(piperidin-1-ylcarbonyl)phenyl]-1H-1,2,3-triazol-4-yl}-1H-indazole | 100 | 373.2 |
| 39 | 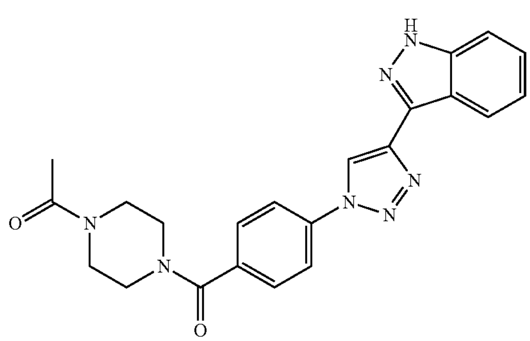 [SMILES: CC(=O)N1CCN(C(=O)c2ccc(-n3cc(-c4n[nH]c5ccccc45)nn3)cc2)CC1] | 3-(1-{4-[(4-acetylpiperazin-1-yl)carbonyl]phenyl}-1H-1,2,3-triazol-4-yl)-1H-indazole | 100 | 416.1 |

-continued

| Example | Structure | Name | LCMS Purity max plot | Mass peak [M]+ |
|---|---|---|---|---|
| 40 | 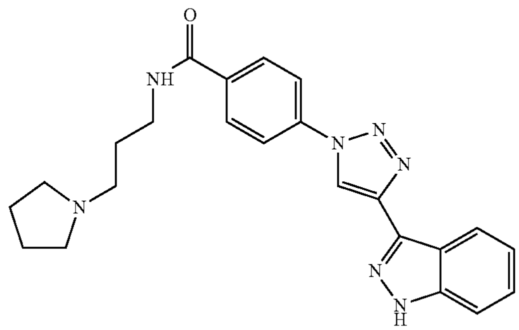 [SMILES: O=C(NCCCN1CCCC1)c1ccc(-n2cc(-c3n[nH]c4ccccc34)nn2)cc1] | 4-[4-(1H-indazol-3-yl)-1H-1,2,3-triazol-1-yl]-N-(3-pyrrolidin-1-ylpropyl)benzamide | 91.6 | 416.1 |
| 41 | 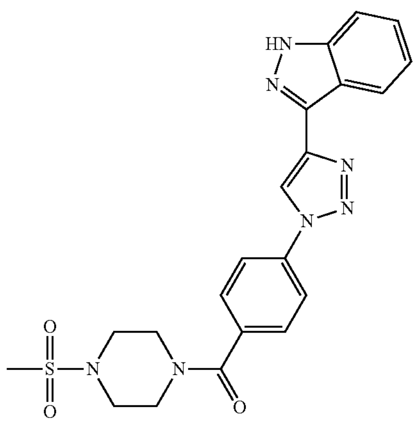 [SMILES: CS(=O)(=O)N1CCN(C(=O)c2ccc(-n3cc(-c4n[nH]c5ccccc45)nn3)cc2)CC1] | 3-[1-(4-{[4-(methylsulfonyl)piperazin-1-yl]carbonyl}phenyl)-1H-1,2,3-triazol-4-yl]-1H-indazole | 96.5 | 451.9 |
| 42 | 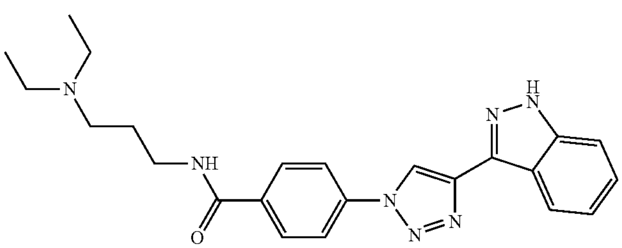 [SMILES: CCN(CC)CCCNC(=O)c1ccc(-n2cc(-c3n[nH]c4ccccc34)nn2)cc1] | N-[3-(diethylamino)propyl]-4-[4-(1H-indazol-3-yl)-1H-1,2,3-triazol-1-yl]benzamide | 100 | 418.2 |
| 43 | 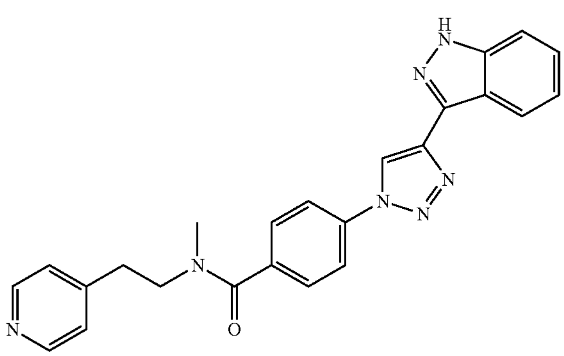 [SMILES: CN(CCc1ccncc1)C(=O)c1ccc(-n2cc(-c3n[nH]c4ccccc34)nn2)cc1] | 4-[4-(1H-indazol-3-yl)-1H-1,2,3-triazol-1-yl]-N-methyl-N-(2-pyridin-4-ylethyl)benzamide | 100 | 424.1 |

-continued

| Example | Structure | Name | LCMS Purity max plot | Mass peak [M]+ |
|---|---|---|---|---|
| 44 | 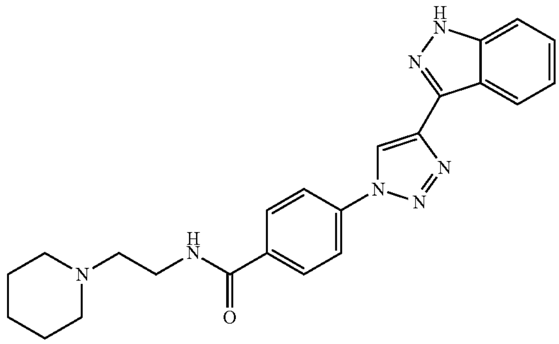 [SMILES: O=C(NCCN1CCCCC1)c1ccc(-n2cc(-c3n[nH]c4ccccc34)nn2)cc1] | 4-[4-(1H-indazol-3-yl)-1H-1,2,3-triazol-1-yl]-N-(2-piperidin-1-ylethyl)benzamide | 100 | 416.2 |
| 45 | 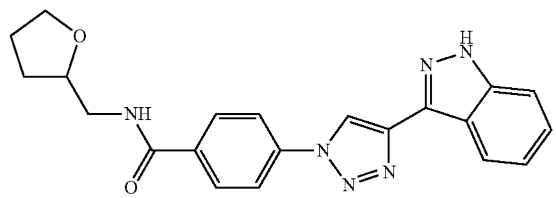 [SMILES: O=C(NCC1CCCO1)c1ccc(-n2cc(-c3n[nH]c4ccccc34)nn2)cc1] | 4-[4-(1H-indazol-3-yl)-1H-1,2,3-triazol-1-yl]-N-(tetrahydrofuran-2-ylmethyl)benzamide | 100 | 389.1 |
| 46 | 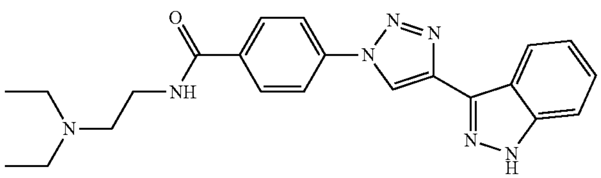 [SMILES: CCN(CC)CCNC(=O)c1ccc(-n2cc(-c3n[nH]c4ccccc34)nn2)cc1] | N-[2-(diethylamino)ethyl]-4-[4-(1H-indazol-3-yl)-1H-1,2,3-triazol-1-yl]benzamide | 87.8 | 404.2 |
| 47 | 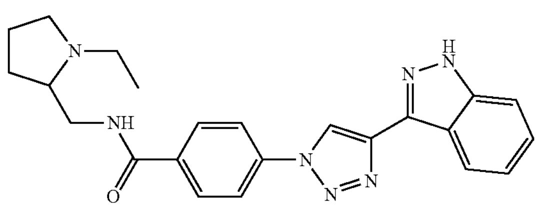 [SMILES: CCN1CCCC1CNC(=O)c1ccc(-n2cc(-c3n[nH]c4ccccc34)nn2)cc1] | N-[(1-ethylpyrrolidin-2-yl)methyl]-4-[4-(1H-indazol-3-yl)-1H-1,2,3-triazol-1-yl]benzamide | 100 | 416.1 |
| 48 | 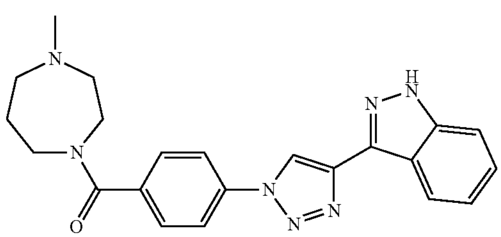 [SMILES: CN1CCCN(C(=O)c2ccc(-n3cc(-c4n[nH]c5ccccc45)nn3)cc2)CC1] | 3-(1-{4-[(4-methyl-1,4-diazepan-1-yl)carbonyl]phenyl}-1H-1,2,3-triazol-4-yl)-1H-indazole | 96.3 | 402.2 |
| 49 | 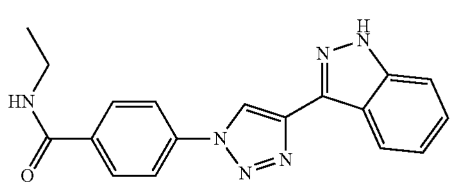 [SMILES: CCNC(=O)c1ccc(-n2cc(-c3n[nH]c4ccccc34)nn2)cc1] | N-ethyl-4-[4-(1H-indazol-3-yl)-1H-1,2,3-triazol-1-yl]benzamide | 93.4 | 333.1 |
| 50 | 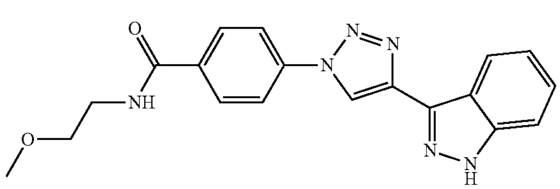 [SMILES: COCCNC(=O)c1ccc(-n2cc(-c3n[nH]c4ccccc34)nn2)cc1] | 4-[4-(1H-indazol-3-yl)-1H-1,2,3-triazol-1-yl]-N-(2-methoxyethyl)benzamide | 89.3 | 363.1 |

-continued

| Example | Structure | Name | LCMS Purity max plot | Mass peak [M]+ |
|---|---|---|---|---|
| 51 | 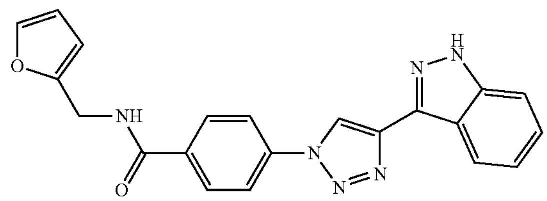 [SMILES: O=C(NCc1ccco1)c1ccc(-n2cc(-c3n[nH]c4ccccc34)nn2)cc1] | N-(2-furylmethyl)-4-[4-(1H-indazol-3-yl)-1H-1,2,3-triazol-1-yl]benzamide | 91.9 | 385.1 |
| 52 | 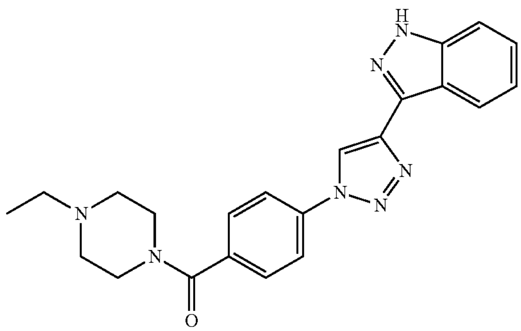 [SMILES: CCN1CCN(C(=O)c2ccc(-n3cc(-c4n[nH]c5ccccc45)nn3)cc2)CC1] | 3-(1-{4-[(4-ethylpiperazin-1-yl)carbonyl]phenyl)-1H-1,2,3-triazol-4-yl)-1H-indazole | 93.5 | 402.1 |
| 53 | 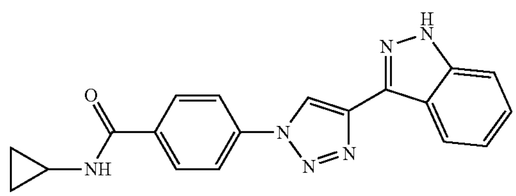 [SMILES: O=C(NC1CC1)c1ccc(-n2cc(-c3n[nH]c4ccccc34)nn2)cc1] | N-cyclopropyl-4-[4-(1H-indazol-3-yl)-1H-1,2,3-triazol-1-yl]benzamide | 95.5 | 345.1 |
| 54 | 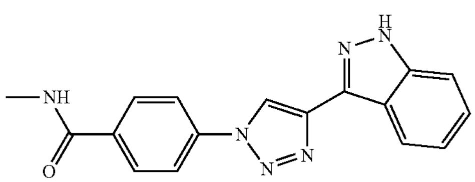 [SMILES: CNC(=O)c1ccc(-n2cc(-c3n[nH]c4ccccc34)nn2)cc1] | 4-[4-(1H-indazol-3-yl)-1H-1,2,3-triazol-1-yl]-N-methylbenzamide | 100 | 319.1 |
| 57 | 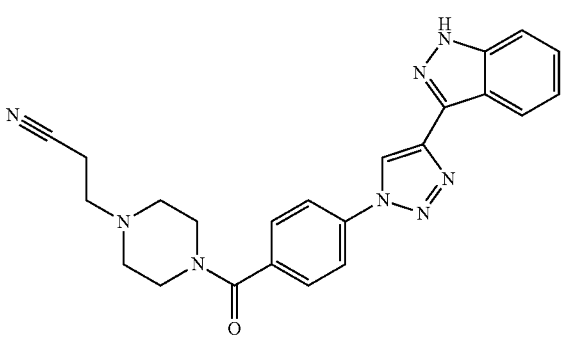 [SMILES: N#CCCN1CCN(C(=O)c2ccc(-n3cc(-c4n[nH]c5ccccc45)nn3)cc2)CC1] | 3-(4-(4-[4-(1H-indazol-3-yl)-1H-1,2,3-triazol-1-yl]benzoyl}piperazin-1-yl)propanenitrile | 97 | 427.1 |

| Example | Structure | Name | LCMS Purity max plot | Mass peak [M]+ |
|---|---|---|---|---|
| 58 | 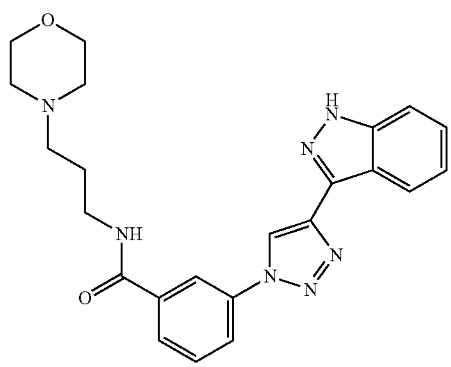 [SMILES: O=C(NCCCN1CCOCC1)c1cccc(-n2cc(-c3n[nH]c4ccccc34)nn2)c1] | 3-[4-(1H-indazol-3-yl)-1H-1,2,3-triazol-1-yl]-N-(3-morpholin-4-ylpropyl)benzamide | 100 | 432.1 |
| 59 | 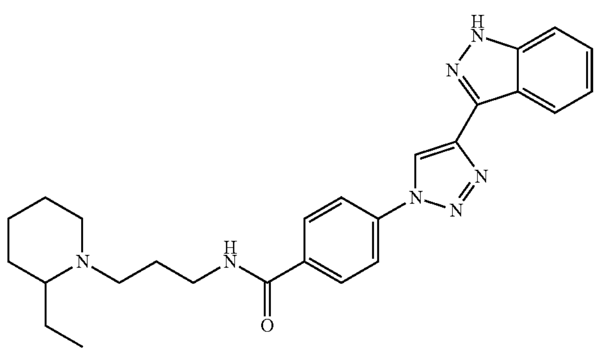 [SMILES: CCC1CCCCN1CCCNC(=O)c1ccc(-n2cc(-c3n[nH]c4ccccc34)nn2)cc1] | N-[3-(2-ethylpiperidin-1-yl)propyl]-4-[4-(1H-indazol-3-yl)-1H-1,2,3-triazol-1-yl]benzamide | 87.3 | 458.2 |
| 60 | 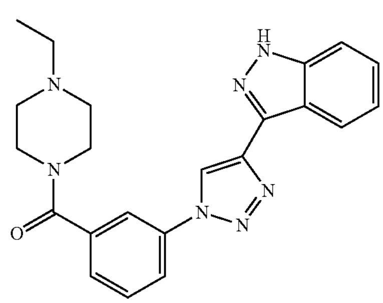 [SMILES: CCN1CCN(C(=O)c2cccc(-n3cc(-c4n[nH]c5ccccc45)nn3)c2)CC1] | 3-(1-{3-[(4-ethylpiperazin-1-yl)carbonyl]phenyl}-1H-1,2,3-triazol-4-yl)-1H-indazole | 79.8 | 402.2 |
| 61 | 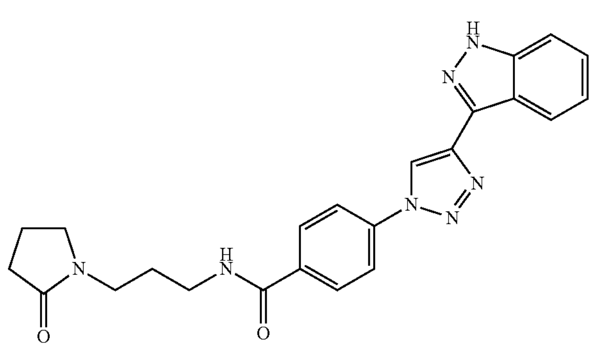 [SMILES: O=C(NCCCN1CCCC1=O)c1ccc(-n2cc(-c3n[nH]c4ccccc34)nn2)cc1] | 4-[4-(1H-indazol-3-yl)-1H-1,2,3-triazol-1-yl]-N-[3-(2-oxopyrrolidin-1-yl)propyl]benzamide | 100 | 430.1 |

-continued

| Example | Structure | Name | LCMS Purity max plot | Mass peak [M]+ |
|---|---|---|---|---|
| 62 | 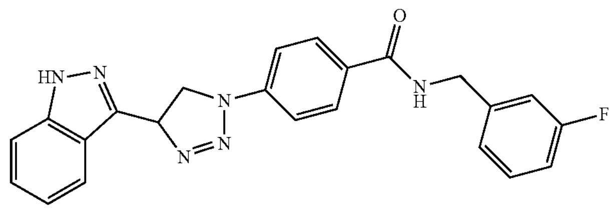 [SMILES: O=C(NCc1cccc(F)c1)c1ccc(N2CC(c3n[nH]c4ccccc34)N=N2)cc1] | N-(3-fluorobenzyl)-4-[4-(1H-indazol-3-yl)-1H-1,2,3-triazol-1-yl]benzamide | 92.8 | 413.5 |
| 63 | 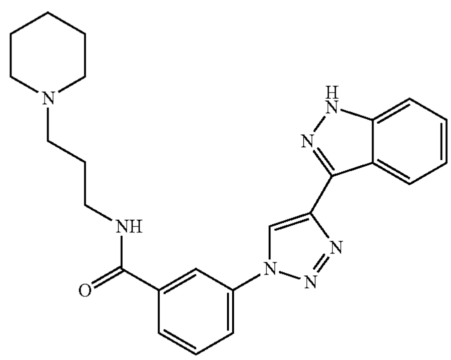 [SMILES: O=C(NCCCN1CCCCC1)c1cccc(-n2cc(-c3n[nH]c4ccccc34)nn2)c1] | 3-[4-(1H-indazol-3-yl)-1H-1,2,3-triazol-1-yl]-N-(3-piperidin-1-ylpropyl)benzamide | 97.2 | 430.1 |
| 64 | 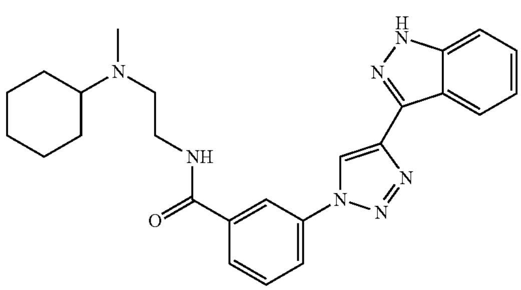 [SMILES: CN(CCNC(=O)c1cccc(-n2cc(-c3n[nH]c4ccccc34)nn2)c1)C1CCCCC1] | N-{2-[cyclohexyl(methyl)amino]ethyl}-3-[4-(1H-indazol-3-yl)-1H-1,2,3-triazol-1-yl]benzamide | 88.2 | 444.1 |
| 65 | 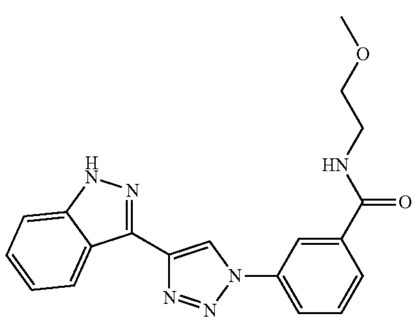 [SMILES: COCCNC(=O)c1cccc(-n2cc(-c3n[nH]c4ccccc34)nn2)c1] | 3-[4-(1H-indazol-3-yl)-1H-1,2,3-triazol-1-yl]-N-(2-methoxyethyl)benzamide | 96.9 | 363.0 |
| 66 | 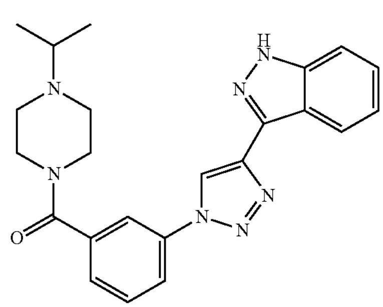 [SMILES: CC(C)N1CCN(C(=O)c2cccc(-n3cc(-c4n[nH]c5ccccc45)nn3)c2)CC1] | 3-(1-{3-[(4-isopropylpiperazin-1-yl)carbonyl]phenyl}-1H-1,2,3-triazol-4-yl)-1H-indazole | 88 | 416.1 |

| Example | Structure | Name | LCMS Purity max plot | Mass peak [M]+ |
|---|---|---|---|---|
| 67 | 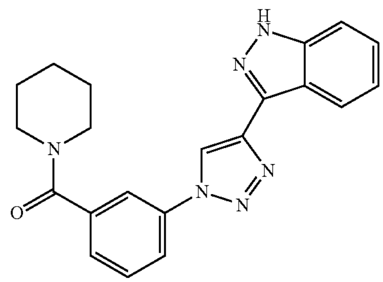 [SMILES: O=C(c1cccc(-n2cc(-c3n[nH]c4ccccc34)nn2)c1)N1CCCCC1] | 3-{1-[3-(piperidin-1-ylcarbonyl)phenyl]-1H-1,2,3-triazol-4-yl}-1H-indazole | 100 | 373.1 |
| 68 | 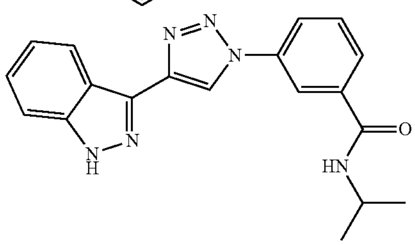 | 3-[4-(1H-indazol-3-yl)-1H-1,2,3-triazol-1-yl]-N-isopropylbenzamide | 95.3 | 347.2 |
| 69 | 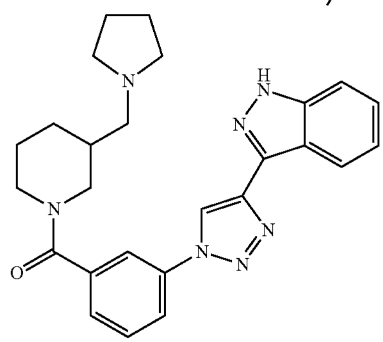 | 3-[1-(3-{[3-(pyrrolidin-1-ylmethyl)piperidin-1-yl]carbonyl}phenyl)-1H-1,2,3-triazol-4-yl]-1H-indazole | 83.5 | 456.2 |

Example 70

3-(1-{4-[2-(4-methylpiperazin-1-yl)-2-oxoethyl]phenyl-1H-1,2,3-triazol-4-yl}-1H-indazole

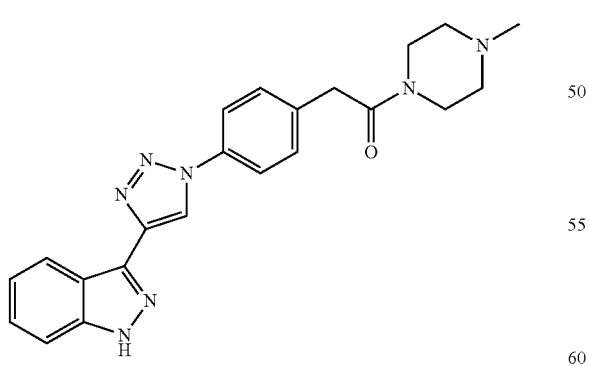

The title compound was obtained, following procedure described for example 18, but starting from {4-[4-(1H-indazol-3-yl)-1H-1,2,3-triazol-1-yl]phenyl}acetic acid (120 mg; 0.38 mmol; 1.0 eq.) and N-methyl piperazine (50 µl; 0.45 mmol; 1.2 eq.). The reaction mixture was eluted through a SPE-NH2 column before purification by preparative HPLC which afforded the title compound as beige powder. ¹H NMR (300 MHz, DMSO-d6) δ 13.36 (brs, 1H), 9.30 (s, 1H), 8.36 (d, J=8.2 Hz, 1H), 8.00 (d, J=8.5 Hz, 2H), 7.61 (d, J=8.5 Hz, 1H), 7.48-7.41 (m, 3H), 7.28-7.23 (m, 1H), 3.86 (s, 2H), 3.67 (m, 4H), 2.73 (m, 4H), 2.48 (m, 3H). HPLC (Condition A): Rt 2.30 min (purity 99.4%). MS (ESI+): 402.3, MS (ESI−): 400.4.

Example 71

1-{4-[4(1H-indazol-3-yl)-1H-1,2,3-triazol-1-yl]benzoyl}piperidin-ol

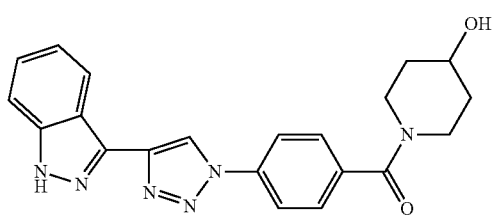 [SMILES: O=C(c1ccc(-n2cc(-c3n[nH]c4ccccc34)nn2)cc1)N1CCC(O)CC1]

The title compound was obtained, following procedure described for example 26, but starting from 4-[4-(1H-indazol-3-yl)-1H-1,2,3-triazol-1-yl]benzoic acid (100 mg; 0.33 mmol; 1.0 eq.) and 4-hydroxypiperidine (50 mg, 0.49 mmol, 1.5 eq.) as a brown oil. ¹H NMR (300 MHz, DMSO-d6) δ 13.37 (s, 1H), 9.38 (s, 1H), 8.36 (d, J=8.2 Hz, 1H), 8.18-8.08 (m, 2H), 7.68-7.56 (m, 3H), 7.50-7.37 (m, 1H), 7.30-7.18 (m, 1H), 4.82 (d, J=3.9 Hz, 1H), 4.01 (brs, 1H), 3.83-3.65 (m, 1H), 3.51 (brs, 1H), 3.24 (brs, J=12.5 Hz, 2H), 1.77 (brs, 2H), 1.39 (brs, 2H). HPLC (Condition A): Rt 2.65 min (purity 92.6%). MS (ESI+): 389.3, MS (ESI−): 387.2.

Example 72

1-{4-[4-(1H-indazol-3-yl)-1H-1,2,3-triazol-1-yl]benzoyl}-N,N-dimethylpiperidin-4-amine

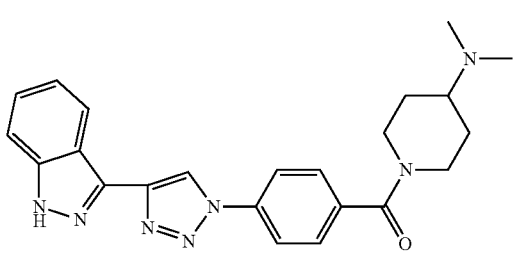 [SMILES: CN(C)C1CCN(C(=O)c2ccc(-n3cc(-c4n[nH]c5ccccc45)nn3)cc2)CC1]

The title compound was obtained, following procedure described for example 26, but starting from 4-[4-(1H-indazol-3-yl)-1H-1,2,3-triazol-1-yl]benzoic acid (100 mg; 0.33 mmol; 1.0 eq.) and 4-dimethylaminopiperidine (Fluoro-Chem, 63 mg, 0.49 mmol, 1.5 eq.) as a colorless oil. ¹H NMR (300 MHz, DMSO-d6) δ 13.39 (s, 1H), 9.40 (s, 1H), 8.37 (d, J=8.1 Hz, 1H), 8.23-8.10 (m, 3H), 7.71-7.57 (m, 3H), 7.51-7.39 (m, 1H), 7.32-7.20 (m, 1H), 4.47 (brs, 1H), 3.66 (brs, 1H), 3.22-2.72 (m, 2H), 2.62-2.43 (m, 1H), 2.27 (s, 6H), 1.99-1.64 (m, 2H), 1.54-1.26 (m, 2H). HPLC (Condition A): Rt 2.27 min (purity 99.6%). MS (ESI+): 416.3, MS (ESI−): 414.3.

Example 73

3-[1-(4-{[3-(pyrrolidin-1-ylcarbonyl)piperidin-1-yl]carbonyl}phenyl)-1H-1,2,3-triazol-4-yl]-1H-indazole

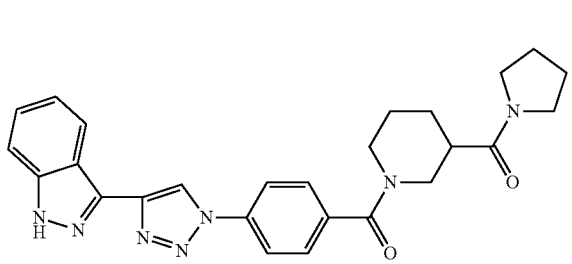 [SMILES: O=C(c1ccc(-n2cc(-c3n[nH]c4ccccc34)nn2)cc1)N1CCCC(C(=O)N2CCCC2)C1]

The title compound was obtained, following procedure described for example 26, but starting from 4-[4-(1H-indazol-3-yl)-1H-1,2,3-triazol-1-yl]benzoic acid (100 mg; 0.33 mmol; 1.0 eq.) and 3-Piperidinyl(1-pyrrolidinyl)methanone (90 mg, 0.49 mmol, 1.5 eq.) as white solid. ¹H NMR (DMSO) δ 1H NMR (300 MHz, DMSO-d6) δ 13.38 (s, 1H), 9.39 (s, 1H), 8.37 (d, J=8.1 Hz, 1H), 8.15 (d, J=8.5 Hz, 2H), 7.72-7.57 (m, 3H), 7.51-7.39 (m, 1H), 7.32-7.21 (m, 1H), 4.57-4.28 (m, 1H), 3.70-3.37 (m, 2H), 3.31-3.03 (m, 4H), 2.99-2.58 (m, 2H), 2.02-1.40 (m, 8H). HPLC (Condition A): Rt 3.26 min (purity 99.3%).

Example 74

3-[1-(4-{[3-(morpholin-4-ylmethylpiperidin-1-yl]carbonyl}phenyl)-1H-1,2,3-triazol-4-yl]-1H-indazole

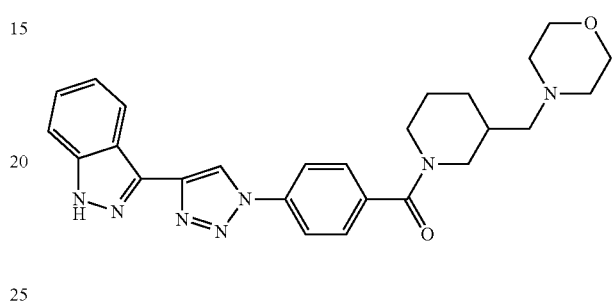

The title compound was obtained, following procedure described for example 26, but starting from 4-[4-(1H-indazol-3-yl)-1H-1,2,3-triazol-1-yl]benzoic acid (100 mg; 0.33 mmol; 1.0 eq.) and 4-Piperidin-3-ylmethyl-morpholine; dihydrochloride (126 mg, 0.49 mmol, 1.5 eq.) as a brown solid. ¹H NMR (300 MHz, DMSO-d6) δ 13.39 (s, 1H), 9.40 (s, 1H), 8.38 (d, J=8.1 Hz, 1H), 8.14 (d, J=8.6 Hz, 2H), 7.69-7.57 (m, 3H), 7.51-7.39 (m, 1H), 7.27 (t, J=7.5 Hz, 1H), 4.56-4.21 (m, 1H), 3.80-3.46 (m, 2H), 3.46-3.21 (m, 2H), 3.12-2.56 (m, 2H), 2.45-1.94 (m, 6H), 1.91-1.04 (m, 6H). HPLC (Condition A): Rt 2.47 min (purity 97.9%).

Example 75

1-[(1-{4-[4-(1H-indazol-3-yl)-1H-1,2,3-triazol-1-yl]benzoyl}piperidin-3-yl)methyl]pyrrolidin-2

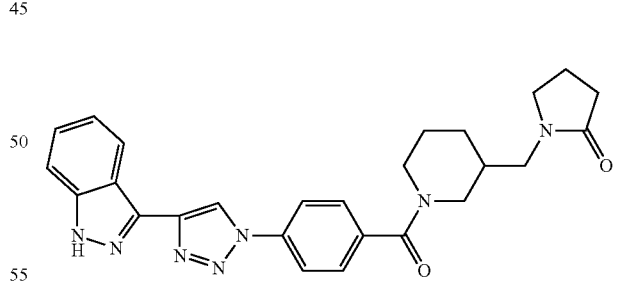

The title compound was obtained, following procedure described for example 26, but starting from 4-[4-(1H-indazol-3-yl)-1H-1,2,3-triazol-1-yl]benzoic acid (100 mg; 0.33 mmol; 1.0 eq.) and 1-(3-Piperidinylmethyl)-2-pyrrolidinone (90 mg, 0.49 mmol, 1 eq.) as a brown solid. ¹H NMR (300 MHz, DMSO-d6) δ 13.39 (s, 1H), 9.39 (s, 1H), 8.36 (d, J=8.2 Hz, 1H), 8.14 (d, J=8.5 Hz, 2H), 7.72-7.57 (m, 3H), 7.48-7.37 (m, 1H), 7.25 (t, J=7.5 Hz, 1H), 4.40-4.15 (m, 1H), 3.61-3.26 (m, 3H), 3.24-2.59 (m, 5H), 2.34-1.56 (m, 6H), 1.56-1.07 (m, 2H). HPLC (Condition A): Rt 3.12 min (purity 91.6%).

Example 76

2-{4-[4-(1H-indazol-3-yl)-1H-1,2,3-triazol-1-yl]benzoyl}-8-methyl-2,8-diazaspiro[5.5]undecane

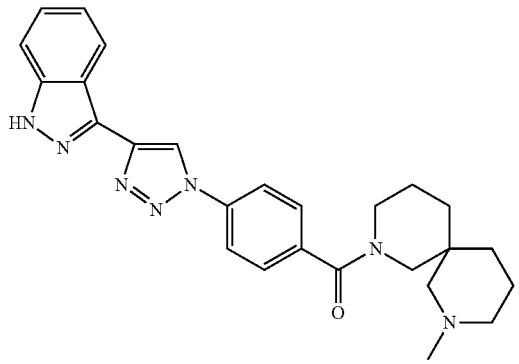 [SMILES: CN1CCCC2(CCCN(C(=O)c3ccc(-n4cc(-c5n[nH]c6ccccc56)nn4)cc3)C2)C1]

The title compound was obtained, following procedure described for example 26, but starting from 4-[4-(1H-indazol-3-yl)-1H-1,2,3-triazol-1-yl]benzoic acid (100 mg; 0.33 mmol; 1.0 eq.) and 2-Methyl-2,8-diazaspiro[5.5]undecane (83 mg, 0.49 mmol, 1.5 eq.) as a brown solid. $^1$H NMR (300 MHz, DMSO-d6) δ 13.38 (s, 1H), 9.40 (s, 1H), 8.36 (d, J=8.2 Hz, 1H), 8.13 (d, J=8.6 Hz, 2H), 7.62 (t, J=8.0 Hz, 3H), 7.50-7.37 (m, 1H), 7.25 (t, J=7.6 Hz, 1H), 4.05-3.63 (m, 1H), 3.57-3.09 (m, 4H), 2.45-0.73 (m, 14H). HPLC (Condition A): Rt 2.60 min (purity 92.2%).

Example 77

4-[4-(1H-indazol-3-yl)-1H-1,2,3-triazol-1-yl]-N-[(1-methylpiperidin-3-yl)methyl]benzamide

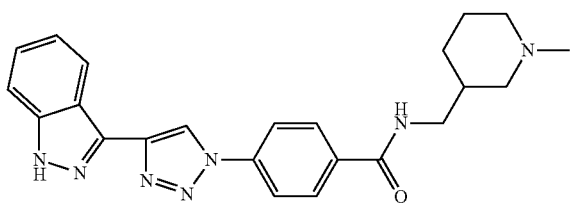 [SMILES: CN1CCCC(CNC(=O)c2ccc(-n3cc(-c4n[nH]c5ccccc45)nn3)cc2)C1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-(Aminomethyl)-1-methylpiperidine (63 mg, 0.49 mmol, 1.5 eq.) as a white solid. $^1$H NMR (300 MHz, DMSO-d6) δ 13.39 (s, 1H), 9.42 (s, 1H), 8.65 (t, J=5.7 Hz, 1H), 8.36 (d, J=8.2 Hz, 1H), 8.18 (d, J=8.8 Hz, 2H), 8.08 (d, J=8.8 Hz, 2H), 7.61 (d, J=8.4 Hz, 1H), 7.50-7.38 (m, 1H), 7.25 (t, J=7.5 Hz, 1H), 3.27-3.05 (m, 2H), 2.66 (dd, J=9.3, 31.9 Hz, 2H), 2.12 (s, 3H), 1.93-1.53 (m, 5H), 1.53-1.33 (m, 1H), 1.04-0.81 (m, 1H). HPLC (Condition A): Rt 2.43 min (purity 86.1%). MS (ESI+): 416.3, MS (ESI−): 414.3.

Example 78

3-{1-[3-(2-morpholin-4-yl-2-oxoethyl)phenyl]-1H-1,2,3-triazol-4-yl}-1H-indazole

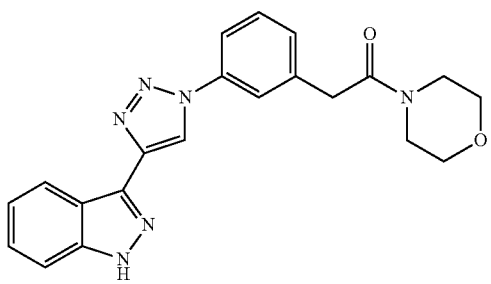 [SMILES: O=C(Cc1cccc(-n2cc(-c3n[nH]c4ccccc34)nn2)c1)N1CCOCC1]

The title compound was obtained following procedure described for example 70, but starting from {3-[4-(1H-indazol-3-yl)-1H-1,2,3-triazol-1-yl]phenyl}acetic acid (200 mg; 0.63 mmol; 1.0 eq.) and morpholine (66 μl; 0.75 mmol; 1.2 eq.) as a white powder. $^1$H NMR (300 MHz, DMSO-d6) δ 13.36 (brs, 1H), 9.30 (s, 1H), 8.36 (dt, J=8.0 Hz, 1.0 Hz, 1H), 7.96-7.90 (m, 2H), 7.63-7.54 (m, 2H), 7.47-7.41 (m, 1H), 7.37 (dt, J=1.0, 8.0 Hz, 1H), 7.28-7.23 (m, 1H), 3.88 (s, 2H), 3.58-3.55 (m, 6H), 3.50-3.47 (m, 2H). HPLC (Condition A): Rt 3.01 min (purity 99.0%). MS (ESI−): 387.4.

Example 79

3-(1-{3-[2-(4-methylpiperazin-1-yl)-2-oxoethyl]phenyl}-1H-1,2,3-triazol-4-yl)-1H-indazole

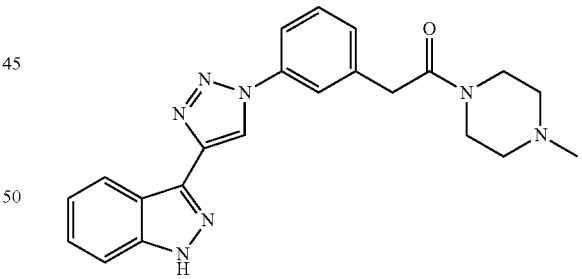

The title compound was obtained following procedure described for example 70, but starting from {3-[4-(1H-indazol-3-yl)-1H-1,2,3-triazol-1-yl]phenyl}acetic acid (200 mg; 0.63 mmol; 1.0 eq.) 1-methylpiperazine (84 μl; 0.75 mmol; 1.2 eq.) as a beige powder. $^1$H NMR (300 Mhz, DMSO-d6) δ 13.37 (brs, 1H), 9.30 (s, 1H), 8.36 (dt, J=8.1 Hz, 1.0 Hz, 1H), 7.96 (m, 1H), 7.93-7.90 (m, 1H), 7.61 (dt, J=8.4 Hz, 1.0 Hz, 1H), 7.56 (t, J=8.0 Hz, 1H), 7.47-7.41 (m, 1H), 7.37-7.35 (m, 1H), 7.28-7.23 (m, 1H), 3.87 (s, 2H), 3.55 (t, J=4.8 Hz, 2H), 3.49 (t, J=4.8 Hz, 2H), 2.31-2.26 (m, 4H), 2.18 (s, 3H). HPLC (Condition A): Rt 2.31 min (purity 98.9%). MS (ESI+): 402.3, MS (ESI−): 400.3.

Example 80

3-{1-[3-(2-morpholin-4-ylethyl)phenyl]-1H-1,2,3-triazol-4-yl}-1H-indazole

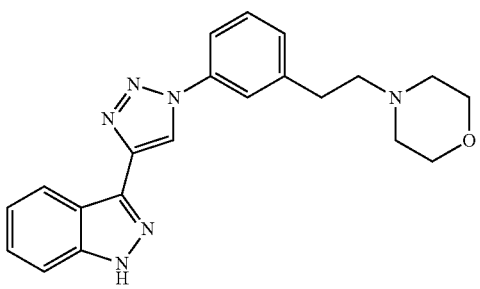 [SMILES: c1cc(CCN2CCOCC2)cc(-n2cc(-c3n[nH]c4ccccc34)nn2)c1]

LAH (1M in THF, 107 µl; 0.26 mmol; 2.0 eq.) was added dropwise to a cooled (0° C.) solution of 3-{1-[3-(2-morpholin-4-yl-2-oxoethyl)phenyl]-1H-1,2,3-triazol-4-yl}-1H-indazole (50 mg, 0.13 mmol, 1 eq.) in dry THF (1 mL). The reaction mixture was allowed to warm to RT and stirred overnight. Water was added and the reaction mixture was extrated three times with EtOAc. Combined organic phases were dried over magnesium sulfate, filtered and concentratd. The crude was purified by preparative HPLC to give the title compound as a beige powder. $^1$H NMR (300 MHz, DMSO-d6) δ 13.37 (brs, 1H), 9.31 (s, 1H), 8.37 (dt, J=8.2 Hz, 1.0 Hz, 1H), 7.96 (t, J=1.5 Hz, 1H), 7.90-7.87 (m, 1H), 7.61 (dt, J=1.0, 8.4 Hz, 1H), 7.53 (t, J=7.9 Hz, 1H), 7.47-7.41 (m, 1H), 7.40-7.38 (m, 1H), 7.28-7.23 (m, 1H), 3.59 (t, J=4.6 Hz, 4H), 2.91-2.86 (m, 2H), 2.64-2.59 (m, 2H), 2.47 (t, J=4.6 Hz, 4H). HPLC (Condition A): Rt 2.47 min (purity 95.5%). MS (ESI+): 375.2, MS (ESI−): 373.3.

Example 81

3-{1-[3-fluoro-4-(morpholin-4-ylcarbonyl)phenyl]-1H-1,2,3-triazol-4-yl}-1H-indazole

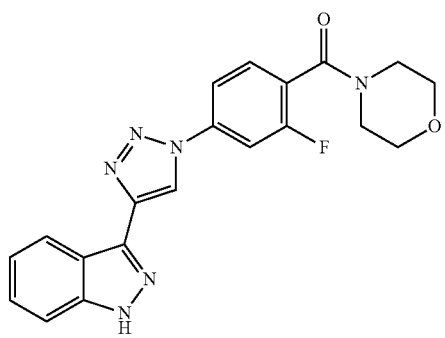 [SMILES: O=C(c1ccc(-n2cc(-c3n[nH]c4ccccc34)nn2)cc1F)N1CCOCC1]

The title compound was obtained following procedure described for intermediate 10, but starting from 3-ethynyl-1H-indazole (114 mg; 0.80 mmol; 1.0 eq.) and 4-(4-azido-2-fluorobenzoyl)morpholine (200 mg; 0.80 mmol; 1.0 eq.) as a yellow powder. $^1$H NMR (300 MHz, DMSO) δ: 13.41 (brs, 1H), 9.44 (s, 1H), 8.36 (dt, J=8.2 Hz, 1.0 Hz, 1H), 8.14 (dd, J=10.5 Hz, 2.0 Hz, 1H), 8.06 (dd, J=8.2 Hz, 2.0 Hz, 1H), 7.71 (t, J=7.8 Hz, 1H), 7.62 (dt, J=8.5 Hz, 1.0 Hz, 1H), 7.47-7.43 (m, 1H), 7.29-7.24 (m, 1H), 3.68 (m, 1H), 3.68 (m, 4H), 3.57 (t, J=4.5 Hz, 2H), 3.32 (m, 2H). HPLC (Condition A): Rt 3.22 min (purity 100.0%). MS (ESI+): 393.3, MS (ESI−): 391.3.

Example 82

3-{1-[3-(2-oxo-2-pyrrolidin-1-ylethyl)phenyl]-1H-1,2,3-triazol-4-yl}-1H-indazole

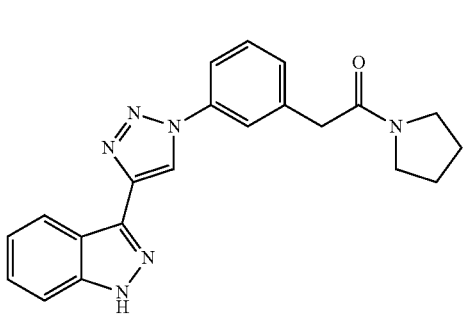 [SMILES: O=C(Cc1cccc(-n2cc(-c3n[nH]c4ccccc34)nn2)c1)N1CCCC1]

The title compound was obtained following procedure described for example 70, but starting from {3-[4-(1H-indazol-3-yl)-1H-1,2,3-triazol-1-yl]phenyl}acetic acid (200 mg; 0.63 mmol; 1.0 eq.) and pyrrolidine (62 µl; 0.75 mmol; 1.2 eq.) as a white solid. $^1$H NMR (300 MHz, DMSO-d6): 13.37 (brs, 1H), 9.29 (s, 1H), 8.36 (dt, J=8.1 Hz, 1.0 Hz, 1H), 7.96 (t, J=1.8 Hz, 1H), 7.93-7.90 (m, 1H), 7.61 (d, J=8.5 Hz, 1H), 7.56 (t, J=7.8 Hz, 1H), 7.47-7.41 (m, 1H), 7.38 (d, J=7.8 Hz, 1H), 7.28-7.23 (m, 1H), 3.79 (s, 2H), 3.54 (t, J=6.7 Hz, 2H), 3.32 (t, J=6.7 Hz, 2H), 1.90 (quint., J=6.7 Hz, 2H), 1.79 (quint., J=6.7 Hz, 2H).

Example 83

3-{1-[3-(2-pyrrolidin-1-ylethyl)phenyl]-1H-1,2,3-triazol-4-yl}-1H-indazole

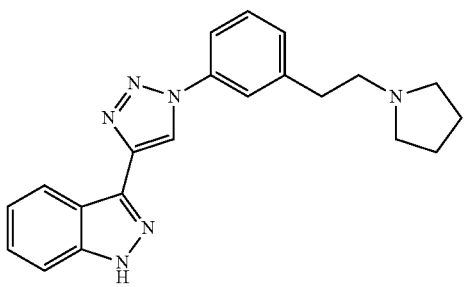 [SMILES: c1cc(CCN2CCCC2)cc(-n2cc(-c3n[nH]c4ccccc34)nn2)c1]

The title compound was obtained following procedure described for example 80, but starting from 3-{1-[3-(2-oxo-2-pyrrolidin-1-ylethyl)phenyl]-1H-1,2,3-triazol-4-yl}-1H-indazole (40 mg; 0.11 mmol; 1.00 eq.) as a white solid. $^1$H NMR (300 MHz, DMSO-d6) δ 13.55 (brs, 1H), 9.33 (s, 1H), 8.37 (dt, J=8.0 Hz, 1.0 Hz, 1H), 8.27 (s, 1H), 7.98 (t, J=1.78 Hz, 1H), 7.92-7.89 (m, 1H), 7.62 (dt, J=8.4 Hz, 1.0 Hz, 1H), 7.55 (t, J=8.0 Hz, 1H), 7.47-7.39 (m, 2H), 7.29-7.24 (m, 1H), 2.94 (m, 4H), 2.76-2.72 (m, 4H), 1.78-1.74 (m, 4H). HPLC (Condition A): Rt 2.56 min (purity 95.8%). MS (ESI+): 359.2, MS (ESI−): 357.3.

Example 84

3-{1-[4-(morpholin-4-ylcarbonyl)phenyl]-1H-1,2,3-triazol-4-yl}-5-piperidin-4-yl-1H-indazole Step a) Formation of tert-butyl 4-(3-{1-[4-(morpholin-4-ylcarbonyl)phenyl]-1H-1,2,3-triazol-4-yl}-1H-indazol-5-yl)piperidine-1-carboxylate hydrochloride

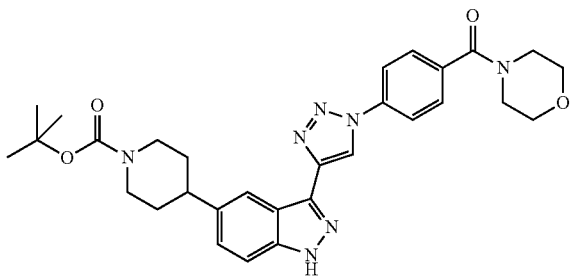 [SMILES: CC(C)(C)OC(=O)N1CCC(c2ccc3[nH]nc(-c4cn(-c5ccc(C(=O)N6CCOCC6)cc5)nn4)c3c2)CC1]

The title compound was obtained following procedure described for Intermediate 10, but starting from 4-(4-azidobenzoyl)morpholine (83 mg; 0.36 mmol; 1.0 eq.) and tert-butyl 4-(3-ethynyl-1H-indazol-5-yl)piperidine-1-carboxylate (116 mg; 0.36 mmol; 1.0 eq.) as a brown gum. $^1$H NMR (300 MHz, DMSO-d6) δ 13.30 (brs, 1H), 9.37 (s, 1H), 8.20-8.10 (m, 3H), 7.74-7.64 (m, 2H), 7.54 (d, J=8.5 Hz, 1H), 7.37 (dd, J=8.6, 1.6 Hz, 1H), 4.23-4.02 (m, 2H), 3.79-3.35 (m, 8H), 3.01-2.71 (m, 3H), 1.94-1.77 (m, 2H), 1.70-1.49 (m, 2H), 1.43 (s, 9H). HPLC (Condition A): Rt 4.53 min (purity 100.0%).

Step b) Formation of 3-{1-[4-(morpholin-4-ylcarbonyl)phenyl]-1H-1,2,3-triazol-4-yl}-5-piperidin-4-yl-1H-indazole hydrochloride

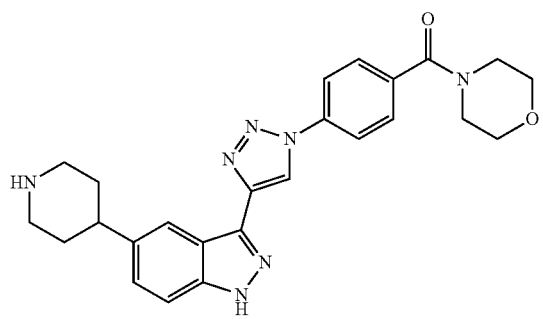 [SMILES: O=C(c1ccc(-n2cc(-c3n[nH]c4ccc(C5CCNCC5)cc34)nn2)cc1)N1CCOCC1]

To a solution of tert-butyl 4-(3-{1-[4-(morpholin-4-ylcarbonyl)phenyl]-1H-1,2,3-triazol-4-yl}-1H-indazol-5-yl)piperidine-1-carboxylate (40 mg; 0.07 mmol; 1.0 eq.) in Dioxane-1,4 (3.0 mL) and water (1.0 mL) was added Hydrogen chloride (1 mL of a 4N solution in dioxane, 4.00 mmol; 56 eq.). The resulting solution was stirred at RT for 12 h. Solvent was removed under reduced pressure, the residue was redissolved in ACN and water and lyophilized to give the title compound as a yellow solid (40 mg, 100%). $^1$H NMR (300 MHz, DMSO) δ 13.38 (brs, 1H), 9.37 (s, 1H), 8.96 (brs, 1H), 8.76 (brs, 1H), 8.23 (s, 1H), 8.19-8.09 (m, 2H), 7.75-7.53 (m, 3H), 7.34 (dd, J=1.4, 8.7 Hz, 1H), 3.80-3.52 (m, 5H), 3.53-3.21 (m, 3H), 3.04 (d, J=5.3 Hz, 4H), 2.15-1.75 (m, 5H). HPLC (Condition A): Rt 2.44 min (purity 93.2%). MS (ES+): 458.5, MS (ESI−): 456.5.

Example 85

3-{1-[3-(3-morpholin-4-yl-3-oxopropyl)phenyl]-1H-1,2,3-triazol-4-yl}-1H-indazole

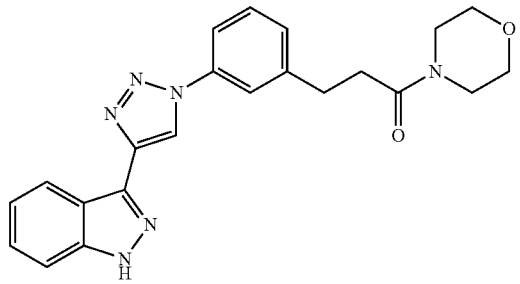 [SMILES: O=C(CCc1cccc(-n2cc(-c3n[nH]c4ccccc34)nn2)c1)N1CCOCC1]

The title compound was obtained following procedure described for example 70, but starting from 3-{3-[4-(1H-indazol-3-yl)-1H-1,2,3-triazol-1-yl]phenyl}propanoic acid (200 mg; 0.60 mmol; 1.0 eq.) and morpholine (63 µl; 0.72 mmol; 1.2 eq.) as a beige solid. $^1$H NMR (300 MHz, DMSO-d6): 13.36 (brs, 1H), 9.31 (s, 1H), 8.36 (d, J=8.0 Hz, 1H), 7.97 (t, J=1.7 Hz, 1H), 7.89-7.86 (m, 1H), 7.61 (dt, J=8.4 Hz, 1.0 Hz, 1H), 7.54 (t, J=8.0 Hz, 1H), 7.47-7.39 (m, 2H), 7.28-7.23 (m, 1H), 73.53-3.50 (m, 4H), 3.46-3.44 (m, 4H), 2.98-2.93 (m, 2H), 2.77-2.72 (m, 2H). HPLC (Condition A): Rt 3.21 min (purity 99.2%). MS (ESI+): 403.3, MS (ESI−): 401.4.

Example 86

3-{1-[3-(3-morpholin-4-ylpropyl)phenyl]-1H-1,2,3-triazol-4-yl}-1H-indazole

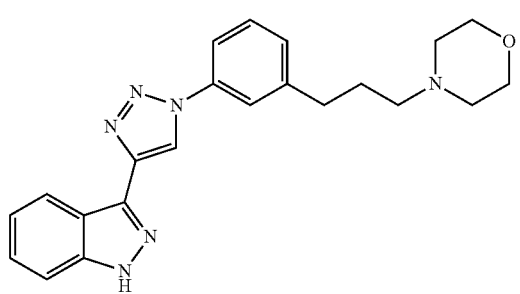 [SMILES: c1cc(CCCN2CCOCC2)cc(-n2cc(-c3n[nH]c4ccccc34)nn2)c1]

The title compound was obtained following procedure described for example 80, but starting from 3-{1-[3-(3-morpholin-4-yl-3-oxopropyl)phenyl]-1H-1,2,3-triazol-4-yl}-1H-indazole (75 mg; 0.17 mmol; 1.0 eq.) as a yellow solid. $^1$H NMR (300 MHz, DMSO-d6): 11.30 (bs, 1H), 9.32 (s, 1H), 8.36 (dt, J=8.0 Hz, 1.0 Hz, 1H), 7.99 (m, 1H), 7.93 (d, J=8.0 Hz, 1H), 7.63-7.55 (m, 2H), 7.46-7.40 (m, 2H), 7.28-7.23 (m, 1H), 3.96-3.80 (m, 4H), 3.45-3.41 (m, 2H), 3.15-2.99 (m, 4H), 2.80 (t, J=7.6 Hz, 2H), 2.20-2.10 (m, 2H). HPLC (Condition A): Rt 2.65 min (purity 97.3%). MS (ESI+): 389.3, MS (ESI−): 387.4.

Example 87

3-{1-[3-(3-oxo-3-pyrrolidin-1-ylpropyl)phenyl]-1H-1,2,3-triazol-4-yl}-1H-indazole

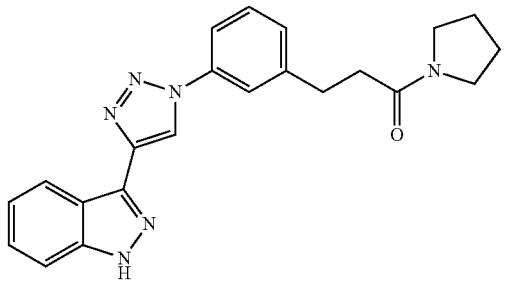 [SMILES: O=C(CCc1cccc(-n2cc(-c3n[nH]c4ccccc34)nn2)c1)N1CCCC1]

The title compound was obtained following procedure described for example 70, but starting from 3-{3-[4-(1H-indazol-3-yl)-1H-1,2,3-triazol-1-yl]phenyl}propanoic acid (200 mg; 0.60 mmol; 1.0 eq.) and pyrrolidine (59 μl; 0.72 mmol; 1.2 eq.) as a beige solid. $^1$H NMR (300 MHz, DMSO-d6): 13.36 (bs, 1H), 9.301 (s, 1H), 8.36 (d, J=8.0 Hz, 1H), 7.96 (t, J=1.8 Hz, 1H), 7.89-7.86 (m, 1H), 7.61 (dt, J=8.6 Hz, 1.0 Hz, 1H), 7.53 (t, J=8.0 Hz, 1H), 7.47-7.39 (m, 2H), 7.31-7.23 (m, 1H), 3.39 (t, J=6.7 Hz, 2H), 3.29 (t, J=6.7 Hz, 2H), 2.98-2.93 (m, 2H), 2.68-2.63 (m, 2H), 1.89-1.80 (m, 2H), 1.79-1.70 (m, 2H). HPLC (Condition A): Rt 3.50 min (purity 97.7%). MS (ESI+): 387.3, MS (ESI−): 385.3.

Example 88

3-{1-[3-(3-pyrrolidin-1-ylpropyl)phenyl]-1H-1,2,3-triazol-4-yl}-1H-indazole

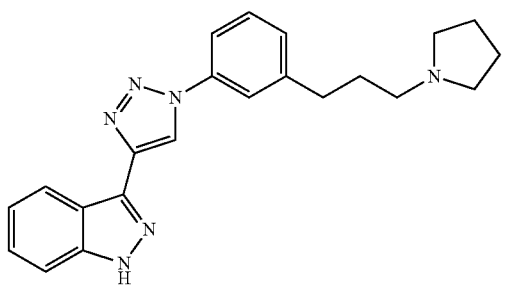 [SMILES: c1cc(CCCN2CCCC2)cc(-n2cc(-c3n[nH]c4ccccc34)nn2)c1]

The title compound was obtained following procedure described for example 80, but starting from 3-{1-[3-(3-oxo-3-pyrrolidin-1-ylpropyl)phenyl]-1H-1,2,3-triazol-4-yl}-1H-indazole (80 mg; 0.18 mmol; 1.0 eq.) as a yellow solid. $^1$H NMR (300 MHz, DMSO-d6): 13.40 (bs, 1H), 10.83 (bs, 1H), 9.33 (s, 1H), 8.36 (dt, J=8.0 Hz, 1.0 Hz, 1H), 7.98 (m, 1H), 7.93-7.90 (m, 1H), 7.63-7.55 (m, 2H), 7.47-7.40 (m, 2H), 7.28-7.23 (m, 1H), 3.56-3.50 (m, 2H), 3.17-3.10 (m, 2H), 2.99-2.93 (m, 2H), 2.81 (t, J=7.5 Hz, 2H), 2.14-1.84 (m, 6H). HPLC (Condition A): Rt 2.75 min (purity 98.3%). MS (ESI+): 373.3, MS (ESI−): 371.4.

Example 89

3-{1-[3-chloro-4-(morpholin-4-ylcarbonyl)phenyl]-1H-1,2,3-triazol-4-yl}-1H-indazole

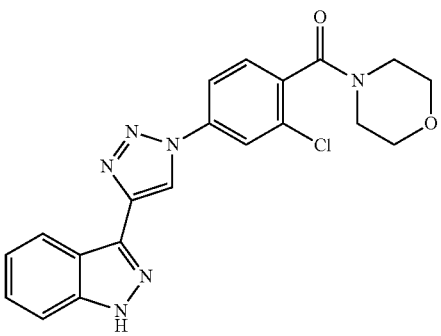

The title compound was obtained following procedure described for Intermediate 10, but starting from 4-(4-azido-2-chlorobenzoyl)morpholine (1.50 g; 5.62 mmol; 1.0 eq.) and 3-ethynyl-1H-indazole (0.80 g; 5.62 mmol; 1.0 eq.) as a beige powder. $^1$H NMR (300 MHz, DMSO-d6) δ: 13.41 (brs, 1H), 9.46 (s, 1H), 8.37-8.33 (m, 2H), 8.17 (dd, J=8.4 Hz, 2.1 Hz, 1H), 7.69 (d, J=8.4 Hz, 1H), 7.62 (dt, J=1.0, 8.4 Hz, 1H), 7.47-7.42 (m, 1H), 7.29-7.24 (m, 1H), 3.73-3.65 (m, 4H), 3.57 (t, J=4.5 Hz, 2H), 3.22 (t, J=4.5 Hz, 2H). HPLC (Condition A): Rt 3.42 min (purity 98.8%). MS (ESI+): 409.3, MS (ESI−): 407.3.

Example 90

4-[4-(1H-indazol-3-yl)-1H-1,2,3-triazol-1-yl]-N-[2-(1-methylpyrrolidin-2-yl)ethyl]benzamide

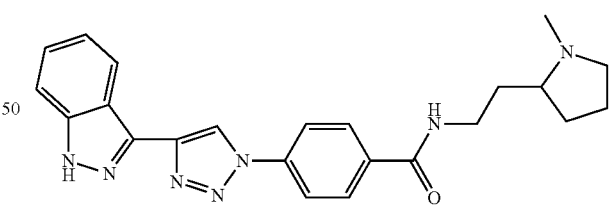

The title compound was obtained following procedure described for example 70, but starting from 4-[4-(1H-indazol-3-yl)-1H-1,2,3-triazol-1-yl]benzoic acid (150 mg; 0.49 mmol; 1.0 eq.) and 1-(pyridin-4-yl)-1H-pyrazol-4-amine (60 mg mg; 0.47 mmol; 0.95 eq.) as a white powder. $^1$H NMR (300 MHz, DMSO-d6) δ 13.40 (s, 1H), 9.42 (s, 1H), 8.74 (t, J=4.3 Hz, 1H), 8.34 (d, J=7.8 Hz, 1H), 8.20 (d, J=7.8 Hz, 2H), 8.09 (d, J=7.8 Hz, 2H), 7.61 (d, J=8.5 Hz, 1H), 7.44 (t, J=7.1 Hz, 1H), 7.25 (t, J=6.4 Hz, 1H), 3.37 (m, 3H), 2.95 (m, 1H), 2.79 (m, 1H), 2.64 (s, 3H), 2.21 (m, 1H), 2.07 (m, 1H), 1.85 (m, 2H), 1.63 (m, 2H). HPLC (Condition A): Rt 2.51 min (purity 99.2%). MS (ESI+): 416.3, MS (ESI−): 414.4.

Example 91

1-(1-{4-[4(1H-indazol-3-yl)-1H-1,2,3-triazol-1-yl]benzoyl}piperidin-4-yl)-N,N-dimethylmethanamine

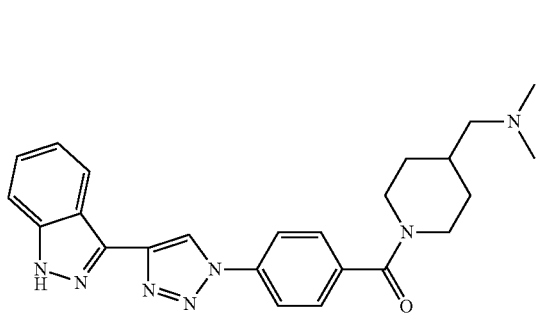 [SMILES: CN(C)CC1CCN(C(=O)c2ccc(-n3cc(-c4n[nH]c5ccccc45)nn3)cc2)CC1]

The title compound was obtained following procedure described for example 70, but starting from 4-[4-(1H-indazol-3-yl)-1H-1,2,3-triazol-1-yl]benzoic acid (150 mg; 0.49 mmol; 1.0 eq.) and 1-(pyridin-4-yl)-1H-pyrazol-4-amine (66 mg; 0.47 mmol; 0.95 eq.) as a white powder. $^1$H NMR (300 MHz, DMSO-d6) δ 13.38 (s, 1H), 9.39 (s, 1H), 8.35 (d, J=7.9 Hz, 1H), 8.14 (d, J=8.8 Hz, 2H), 7.63 (d, J=8.4 Hz, 2H), 7.60 (d, J=8.4 Hz, 1H), 7.43 (t, J=7.8 Hz, 1H), 7.25 (t, J=7.6 Hz, 1H), 4.48 (brs, 1H), 3.60 (m, 2H), 270-2.83 (m, 3H), 2.58 (s, 6H), 1.96 (m, 1H), 1.75 (m, 2H), 1.16 (m, 2H). HPLC (Condition A): Rt 2.86 min (purity 93.1%). MS (ESI+): 430.4, MS (ESI−): 428.4.

Example 92

2-(1-{4-[4-(1H-indazol-3-yl-1H-1,2,3-triazol-1-yl]benzoyl}piperidin-2-yl-N,N-dimethylethanamine

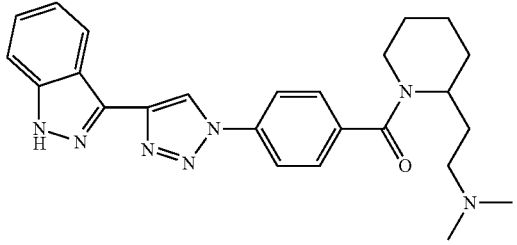 [SMILES: CN(C)CCC1CCCCN1C(=O)c1ccc(-n2cc(-c3n[nH]c4ccccc34)nn2)cc1]

The title compound was obtained following procedure described for example 70, but starting from 4-[4-(1H-indazol-3-yl)-1H-1,2,3-triazol-1-yl]benzoic acid (150 mg; 0.49 mmol; 1.0 eq.) and 1-(pyridin-4-yl)-1H-pyrazol-4-amine (73 mg; 0.47 mmol; 0.95 eq.) as a white powder. $^1$H NMR (300 MHZ, DMSO) δ 13.37 (s, 1H), 9.39 (s, 1H), 9.14 (brs, 1H), 8.34 (d, J=8.3 Hz, 1H), 8.14 (d, J=8.1 Hz, 2H), 7.65 (d, J=8.2 Hz, 1H), 7.60 (d, J=8.2 Hz, 2H), 7.43 (t, J=7.4 Hz, 1H), 7.25 (t, J=7.4 Hz, 1H), 4.75 (s, 1H), 3.08 (m, 4H), 2.82 (s, 6H), 2.24 (m, 1H), 1.43-1.84 (m, 7H). HPLC (Condition A): Rt 2.12 min (purity 96.9%). MS (ESI+): 444.4, MS (ESI−): 442.4.

Example 93

(3-{1-[4(morpholin-4-ylcarbonyl)phenyl]-1H-1,2,3-triazol-4-yl}-1H-indazol-5-yl)methanol

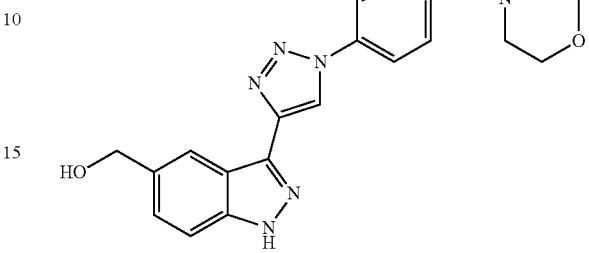

The title compound was obtained following procedure described for example 21, step b), but starting from tert-butyl 3-ethynyl-5-(hydroxymethyl)-1H-indazole-1-carboxylate (557 mg; 1.68 mmol; 1.0 eq.) and 4-(4-azidobenzoyl)morpholine (390 mg, 1.51 mmol, 0.9 eq.) as a white solid. $^1$H NMR (300 MHz, DMSO-d6) δ 13.32 (s, 1H), 9.37 (s, 1H), 8.31 (s, 1H), 8.15 (d, J=8.5 Hz, 2H), 7.69 (d, J=8.5 Hz, 2H), 7.56 (d, J=8.6 Hz, 1H), 7.41 (d, J=8.6 Hz, 1H), 4.66 (s, 2H), 3.86-3.25 (m, 8H). HPLC (Condition A): Rt 2.25 min (purity 95.4%). MS (ESI+): 405.3, MS (ESI−): 403.3.

Example 94

6-(3,5-difluorophenyl)-2-[(3-{1-[4-(morpholin-4-ylcarbonyl)phenyl]-1H-1,2,3-triazol-4-yl}-1H-indazol-5-yl)methyl]pyridazin-3(2H)-one Step a) Formation of 4-[4-(5-{[3-(3,5-difluorophenyl)-6-oxopyridazin-1(6H)-yl]methyl}-1H-indazol-3-yl)-1H-1,2,3-triazol-1-yl]benzoic acid

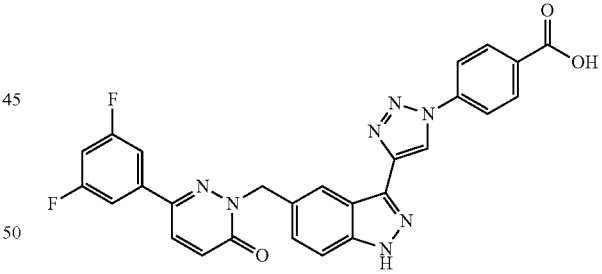

Sodium hydride (34. mg; 0.78 mmol; 2.0 eq.) was added in one portion to a solution of 6-(3,5-Difluoro-phenyl)-2H-pyridazin-3-one (106 mg; 0.51 mmol; 1.3 eq.) in DMF (3 mL). After 10 min a solution of tert-butyl 5-(bromomethyl)-3-{1-[4-(methoxycarbonyl)phenyl]-1H-1,2,3-triazol-4-yl}-1H-indazole-1-carboxylate (392 mg; 0.38 mmol; 1.0 eq.) in DMF (3 mL) was added dropwise over 2 min and the reaction solution stirred for 4 h at RT. The reaction mixture was then poured into saturated solution of NaHCO$_3$ and extracted with EtOAc. Combined organic phases were dried over magnesium sulfate, filtered and concentrated to give a yellow solid. This solid was redissolved in NaOH (5N, 0.5 mL) and DMSO (2 mL) and heated in MW for 10 min at 80° C. Reaction mixture was poured in a saturated solution of NaHCO$_3$ and washed with EtOAc. The basic aqueous phase was acidified to pH 1 with 1N HCl and extracted with EtOAc. Combined organic phases were washed with brine, dried over magnesium sulfate, filtered and concentrated to give the title compound as a yellow solid (218 mg, 100%). $^1$H NMR (300 MHz, DMSO-d6) δ 13.43 (s, 1H), 9.44 (s, 1H), 8.47 (s, 1H), 8.29-8.09 (m, 6H), 7.68 (d, J=7.2 Hz, 2H), 7.63-7.47 (m, 2H), 7.40-7.30 (m, 1H), 7.14 (d, J=9.8 Hz, 1H), 5.52 (s, 2H). HPLC (Condition A): Rt 3.87 min (purity 52.8%). MS (ESI+): 526.2, MS (ESI−): 524.2.

Step b) Formation of 6-(3,5-difluorophenyl)-2-[(3-{1-[4-(morpholin-4-ylcarbonyl)phenyl]-1H-1,2,3-triazol-4-yl}-1H-indazol-5-yl)methyl]pyridazin-3(2H)-one

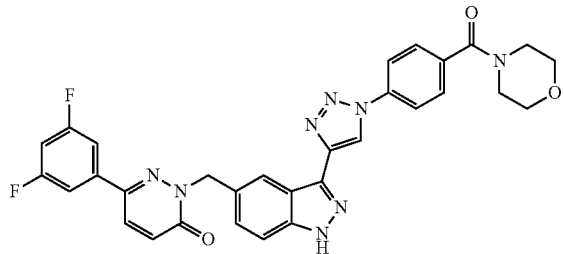 [SMILES: O=C(c1ccc(-n2cc(-c3n[nH]c4ccc(Cn5nc(-c6cc(F)cc(F)c6)ccc5=O)cc34)nn2)cc1)N1CCOCC1]

4-[4-(5-{[3-(3,5-difluorophenyl)-6-oxopyridazin-1(6H)-yl]methyl}-1H-indazol-3-yl)-1H-1,2,3-triazol-1-yl]benzoic acid (218 mg; 0.22 mmol; 1.0 eq.) was added in one portion to a suspension of 1,1'-carbonyldiimidazole (97 mg; 0.60 mmol; 2.7 eq.) in DMF (20 mL). The reaction suspension was heated at 10° C. for 20 min then morpholine (100 μl; 1.15 mmol; 5.2 eq.) was added in one portion. The reaction mixture was heated at 100° C. for 16 h. It was allowed to cool to RT, poured into HCl (1N solution) and extracted with EtOAc. Combined organic phases were washed sequentially with an aqueous saturated solution of NaHCO$_3$ and brine, dried over magnesium sulfate, filtered and concentrated. The crude was purified by preparative HPLC to give the title compound a a white solid. $^1$H NMR (300 MHz, DMSO-d6) δ 13.42 (s, 1H), 9.38 (s, 1H), 8.48 (s, 1H), 8.23-8.08 (m, 3H), 7.75-7.64 (m, 4H), 7.61 (d, J=8.6 Hz, 1H), 7.57-7.48 (m, 1H), 7.42-7.28 (m, 1H), 7.13 (d, J=9.8 Hz, 1H), 5.51 (s, 2H), 3.64 (s, 8H). HPLC (Condition A): Rt 3.78 min (purity 97.7%). MS (ESI−): 593.7.

Example 95

2-[(3-{1-[4-(morpholin-4-ylcarbonyl)phenyl]-1H-1,2,3-triazol-4-yl}-1H-indazol-5-yl)methyl]pyridazin-3(2H)-one Step a) Formation of tert-butyl 3-{1-[4-(morpholin-4-ylcarbonyl)phenyl]-1H-1,2,3-triazol-4-yl}-5-[(6-oxopyridazin-1(6H)-yl)methyl]-1H-indazole-1-carboxylate

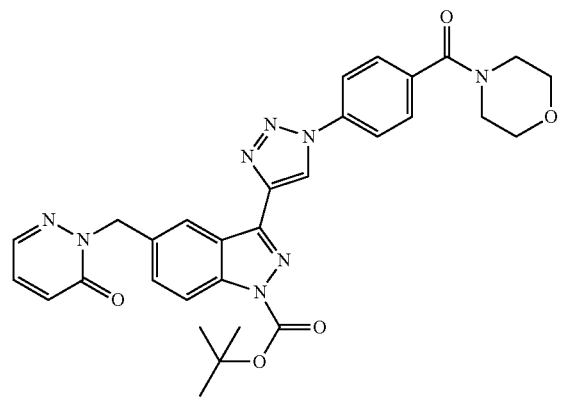 [SMILES: CC(C)(C)OC(=O)n1nc(-c2cn(-c3ccc(C(=O)N4CCOCC4)cc3)nn2)c2cc(Cn3ncccc3=O)ccc21]

DIAD (0.30 mL; 1.54 mmol; 2.3 eq.) was added dropwise over 1 min to a solution of tert-butyl 5-(hydroxymethyl)-3-{1-[4-(morpholin-4-ylcarbonyl)phenyl]-1H-1,2,3-triazol-4-yl}-1H-indazole-1-carboxylate (340 mg; 0.67 mmol; 1.0 eq.), 3(2H)-pyridazinone (100 mg; 1.04 mmol; 1.5 eq.) and triphenylphosphine (354 mg; 1.35 mmol; 2.0 eq.) in DCM (15 mL). The reaction mixture was stirred for 4 h at RT then poured into HCl (0.1N solution) and extracted with DCM. Combine organic phases were washed with brine, dried over magnesium sulfate, filtered and concentrated. The crude was purified by flash chromatography on silica (gradient 20:80 to 90:10, MeOH pure) to give the title compound as a yellow solid. $^1$H NMR (300 MHz, DMSO-d6) δ 9.61 (s, 1H), 8.52 (s, 1H), 8.19 (d, J=8.6 Hz, 2H), 8.13 (d, J=8.7 Hz, 1H), 7.98 (dd, J=1.6, 3.9 Hz, 1H), 7.77-7.61 (m, 3H), 7.45 (dd, J=3.9 Hz, 1H), 7.01 (dd, J=9.5 Hz, 1.6, 1H), 5.46 (s, 2H), 3.76-3.35 (m, 8H), 1.69 (s, 9H). HPLC (Condition A): Rt 3.74 min (purity 91.1%). MS (ESI−): 483.4.

Step b) Formation of 2-[(3-{1-[4-(morpholin-4-ylcarbonyl)phenyl]-1H-1,2,3-triazol-4-yl}-1H-indazol-5-yl)methyl]pyridazin-3(2H)-one

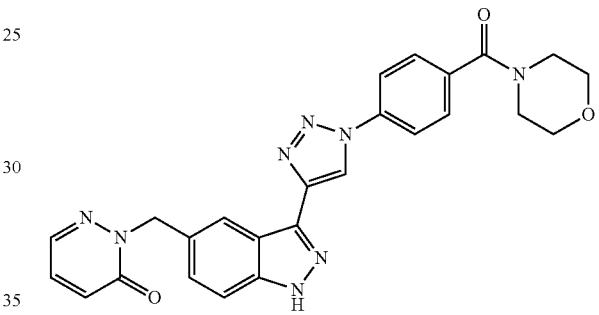

A solution of tert-butyl 3-{1-[4-(morpholin-4-ylcarbonyl)phenyl]-1H-1,2,3-triazol-4-yl}-5-[(6-oxopyridazin-1(6H)-yl)methyl]-1H-indazole-1-carboxylate (202 mg; 0.32 mmol; 1.00 eq.) and HCl (6.00 mL of a 4 N solution in dioxane; 24 mmol; 76 eq.) in MeOH (4 mL) was stirred at RT for 3 h. The reaction mixture was then concentrated under reduced pressure and the residue was purified by preparative HPLC to give the title compound as a white solid. HPLC (Condition A): Rt 2.67 min (purity 98.1%). MS (ESI+): 483.3, MS (ESI−): 481.3.

Example 96

(3R)-1-{4-[4-(1H-indazol-3-yl)-1H-1,2,3-triazol-1-yl]benzoyl}piperidin-3-ol

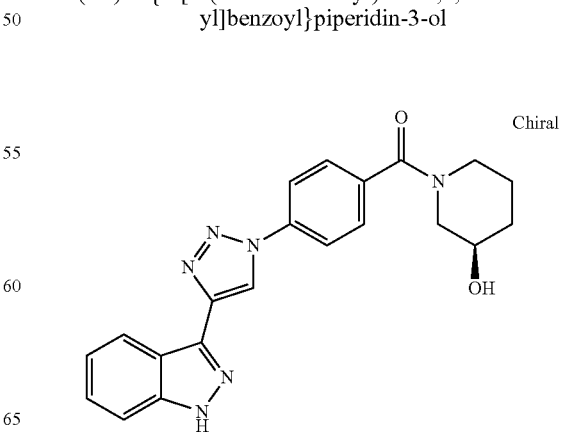

The title compound was obtained following procedure described for example 26, but starting from 4-[4-(1H-indazol-3-yl)-1H-1,2,3-triazol-1-yl]benzoic acid (153 mg; 0.50 mmol; 1.0 eq.) and (R)-(+)-3-hydroxypiperidine hydrochlorid (83 mg; 0.60 mmol; 1.2 eq.) as a white solid. $^1$H NMR (300 MHz, DMSO-d6) δ 13.39 (brs, 1H), 9.39 (brs, 1H), 8.37 (d, J=8.1 Hz, 1H), 8.14 (d, J=8.6 Hz, 2H), 7.73-7.57 (m, 3H), 7.51-7.39 (m, 1H), 7.27 (t, J=7.5 Hz, 1H), 5.15-4.78 (m, 1H), 4.34-3.68 (m, 1H), 3.63-3.36 (m, 2H), 3.20-2.85 (m, 2H), 2.06-1.59 (m, 2H), 1.56-1.28 (m, 2H). HPLC (Condition A): Rt 3.27 min (purity 92.6%). HPLC (Condition C): Rt 12.69 min (purity 96.9%). MS (ESI+): 389.3, MS (ESI−): 387.4.

Example 97

(3S)-1-{4-[4-(1H-indazol-3-yl)-1H-1,2,3-triazol-1-yl]benzoyl}piperidin-3-ol

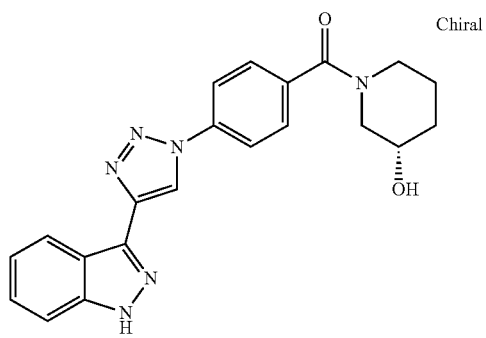 [SMILES: O=C(c1ccc(-n2cc(-c3n[nH]c4ccccc34)nn2)cc1)N1CCC[C@H](O)C1]

The title compound was obtained following procedure described for example 26, but starting from 4-[4-(1H-indazol-3-yl)-1H-1,2,3-triazol-1-yl]benzoic acid (153 mg; 0.50 mmol; 1.0 eq.) and (S)-3-Hydroxypiperidine hydrochloride (83 mg; 0.60 mmol; 1.2 eq.) as a white solid. $^1$H NMR (300 MHz, DMSO-d6) δ 13.39 (brs, 1H), 9.39 (brs, 1H), 8.37 (d, J=8.1 Hz, 1H), 8.14 (d, J=8.6 Hz, 2H), 7.73-7.57 (m, 3H), 7.51-7.39 (m, 1H), 7.27 (t, J=7.5 Hz, 1H), 5.15-4.78 (m, 1H), 4.34-3.68 (m, 1H), 3.63-3.36 (m, 2H), 3.20-2.85 (m, 2H), 2.06-1.59 (m, 2H), 1.56-1.28 (m, 2H). HPLC (Condition A): Rt 3.25 min (purity 88.1%). MS (ESI+): 389.3, MS (ESI−): 387.4.

Example 98

4-[4-(1H-indazol-3-yl)-1H-1,2,3-triazol-1-yl]-N-[1-(1-methylpiperidin-4-yl)-1H-pyrazol-4-yl]benzamide

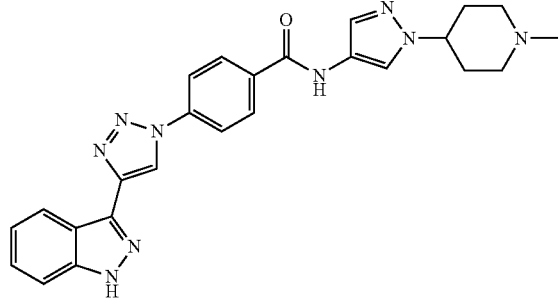 [SMILES: CN1CCC(n2cc(NC(=O)c3ccc(-n4cc(-c5n[nH]c6ccccc56)nn4)cc3)cn2)CC1]

The title compound was obtained following procedure described for example 70, but starting from 4-[4-(1H-indazol-3-yl)-1H-1,2,3-triazol-1-yl]benzoic acid (183 mg; 0.60 mmol; 1.0 eq.) and 1-(1-Methyl-piperidin-4-yl)-1H-pyrazol-4-ylamine (130 mg; 0.72 mmol; 1.2 eq.) as a white solid. $^1$H NMR (300 MHz, DMSO-d6) δ 13.41 (brs, 1H), 10.62 (brs, 1H), 9.46 (s, 1H), 8.38 (d, J=8.2 Hz, 1H), 8.32-8.14 (m, 4H), 8.10 (s, 1H), 7.69-7.58 (m, 2H), 7.46 (t, J=7.1 Hz, 1H), 7.28 (t, J=7.6 Hz, 1H), 4.25-3.99 (m, 1H), 2.87 (d, J=13.7 Hz, 2H), 2.21 (s, 3H), 2.15-1.86 (m, 6H). HPLC (Condition A): Rt 3.07 min (purity 98.6%). MS (ESI+): 468.3, MS (ESI−): 466.3.

Example 99

((2S)-1-{4-[4-(1H-indazol-3-yl-1H-1,2,3-triazol-1-yl]benzoyl}pyrrolidin-2-yl)methanol

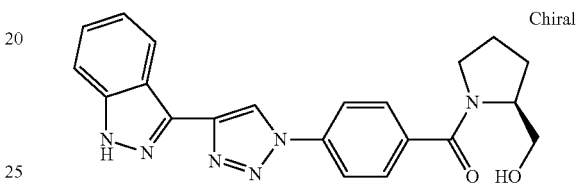

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and L-prolinol (50 mg, 0.49 mmol, 1.5 eq.) as a white solid. $^1$H NMR (300 MHz, DMSO-d6) δ 13.38 (s, 1H), 9.40 (s, 1H), 8.37 (d, J=8.1 Hz, 1H), 8.15 (d, J=8.5 Hz, 2H), 7.87-7.67 (m, 2H), 7.62 (d, J=8.4 Hz, 1H), 7.51-7.39 (m, 1H), 7.27 (t, J=7.5 Hz, 1H), 4.83 (t, J=5.7 Hz, 1H), 4.27-4.09 (m, 1H), 3.73-3.35 (m, 3H), 3.10 (s, 1H), 2.07-1.60 (m, 4H). HPLC (Condition A): Rt 3.07 min (purity 99.2%). MS (ESI+): 389.3, MS (ESI−): 387.3.

Example 100

(1-{4-[4-(1H-indazol-3-yl)-1H-1,2,3-triazol-1-yl]benzoyl}piperidin-2-yl)methanol

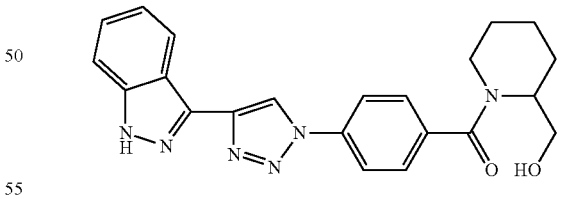

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 2-piperidine methanol (57 mg, 0.49 mmol, 1.5 eq.) as a beige oil. $^1$H NMR (300 MHz, DMSO-d6) δ 13.38 (s, 1H), 9.38 (s, 1H), 8.37 (d, J=8.0 Hz, 1H), 8.12 (d, J=8.5 Hz, 2H), 7.73-7.57 (m, 3H), 7.57-7.39 (m, 1H), 7.36-7.21 (m, 1H), 4.92-4.77 (m, 1H), 4.55-4.19 (m, 1H), 3.85-3.57 (m, 2H), 3.01-2.66 (m, 1H), 2.03-1.10 (m, 7H). HPLC (Condition A): Rt 3.05 min (purity 94.3%). MS (ESI+): 403.3, MS (ESI−): 401.3.

Example 101

3-{1-[4-(morpholin-4-ylcarbonyl)-3-(trifluoromethyl)phenyl]-1H-1,2,3-triazol-4-yl}-1H-indazole

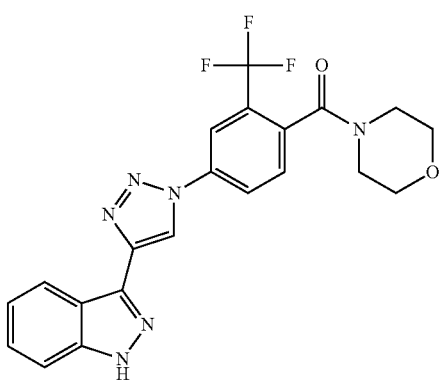 [SMILES: O=C(c1ccc(-n2cc(-c3n[nH]c4ccccc34)nn2)cc1C(F)(F)F)N1CCOCC1]

The title compound was obtained following procedure described for intermediate 10, but starting from 4-[4-azido-2-(trifluoromethyl)benzoyl]morpholine (244 mg; 0.57 mmol; 1.0 eq.) and 3-ethynyl-1H-indazole (81 mg; 0.57 mmol; 1.0 eq.) as a white solid. $^1$H NMR (300 MHz, DMSO-d6): 13.42 (brs, 1H), 9.58 (s, 1H), 8.54 (d, J=2.0 Hz, 1H), 8.47 (dd, J=8.3 Hz, 2.0 Hz, 1H), 8.36 (dt, J=8.0 Hz, 1.0 Hz, 1H), 7.82 (d, J=8.3 Hz, 1H), 7.62 (dt, J=8.3 Hz, 1.0 Hz, 1H), 7.48-7.43 (m, 1H), 7.30-7.25 (m, 1H), 3.75-3.57 (m, 5H), 3.47-3.40 (m, 1H), 3.27-3.13 (m, 2H). HPLC (Condition A): Rt 3.43 min (purity 99.3%). MS (ESI+): 443.3, MS (ESI−): 413.3.

Example 102

3-{1-[2-fluoro-4-(morpholin-4-ylcarbonyl)phenyl]-1H-1,2,3-triazol-4-yl}-1H-indazole

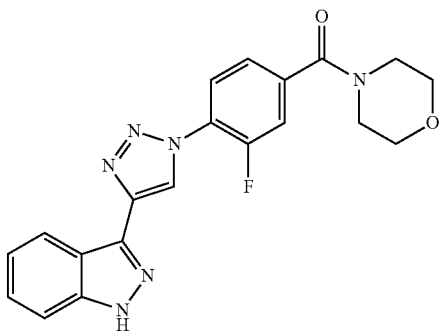 [SMILES: O=C(c1ccc(-n2cc(-c3n[nH]c4ccccc34)nn2)c(F)c1)N1CCOCC1]

The title compound was obtained following procedure described for intermediate 10, but starting from 4-(4-azido-3-fluorobenzoyl)morpholine (143 mg; 0.57 mmol; 1.0 eq.) and 3-ethynyl-1H-indazole (81 mg; 0.57 mmol; 1.0 eq.) as a beige solid. $^1$H NMR (300 MHz, DMSO-d6): 12.39 (brs, 1H), 9.10 (d, J=2.0 Hz, 1H), 8.34 (dt, J=8.0 Hz, 1.0 Hz, 1H), 8.04 (t, J=8.0 Hz, 1H), 7.73 (dd, J=1.5, 10.1 Hz, 1H), 7.62 (dt, J=1.0, 8.5 Hz, 1H), 7.52 (dd, J=1.5, 8.0 Hz, 1H), 7.47-7.42 (m, 1H), 7.29-7.24 (m, 1H), 3.67-3.60 (m, 6H), 3.42 (m, 2H). HPLC (Condition A): Rt 2.99 min (purity 99.6%). MS (ESI+): 393.2, MS (ESI−): 391.2.

Example 103

2-[(3-{1-[4-(morpholin-4-ylcarbonyl)phenyl]-1H-1,2,3-triazol-4-yl}-1H-indazol-5-yl)methyl]-6-pyridin-4-ylpyridazin-3(2H)-one Step a) Formation of tert-butyl 3-{1-[4-(methoxycarbonyl)phenyl]-1H-1,2,3-triazol-4-yl}-5-[(6-oxo-3-pyridin-4-ylpyridazin-1(6H)-yl)methyl]-1H-indazole-1-carboxylate

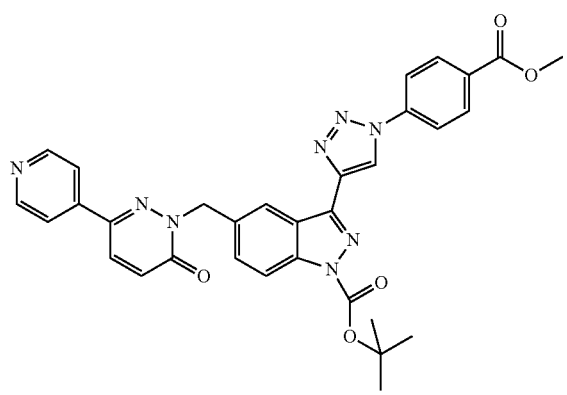 [SMILES: COC(=O)c1ccc(-n2cc(-c3nn(C(=O)OC(C)(C)C)c4ccc(Cn5nc(-c6ccncc6)ccc5=O)cc34)nn2)cc1]

Sodium hydride (106 mg; 2.43 mmol; 7.4 eq.) was added in one portion to a solution of 6-pyridin-4-ylpyridazin-3(2H)-one (176 mg; 1.02 mmol; 3.1 eq.) in DMF (6 mL). After 10 min a solution of tert-butyl 5-(bromomethyl)-3-{1-[4-(methoxycarbonyl)phenyl]-1H-1,2,3-triazol-4-yl}-1H-indazole-1-carboxylate (565 mg; 0.33 mmol; 1.0 eq.) in DMF (6 mL) was added dropwise over 2 min and the reaction solution stirred for 4 h at RT. The reaction mixture was then poured into saturated solution of NaHCO$_3$ and extracted with EtOAc. Combined organic phases were dried over magnesium sulfate, filtered and concentrated. The crude was purified by preparative HPLC to give the title compound as a yellow solid. $^1$H NMR (300 MHz, DMSO-d6) δ 9.69 (s, 1H), 8.75-8.62 (m, 3H), 8.30 (d, J=8.8 Hz, 2H), 8.24-8.18 (m, 3H), 8.15 (d, J=9.2 Hz, 1H), 7.93 (dd, J=1.6, 4.6 Hz, 2H), 7.78-7.72 (m, 1H), 7.19 (d, J=9.8 Hz, 1H), 5.59 (s, 2H), 3.92 (s, 3H), 1.68 (s, 9H). MS (ESI+): 605.3.

Step b) Formation of 4-(4-{5-[(6-oxo-3-pyridin-4-ylpyridazin-1(6H)-yl)methyl]-1H-indazol-3-yl}-1H-1,2,3-triazol-1-yl)benzoic acid

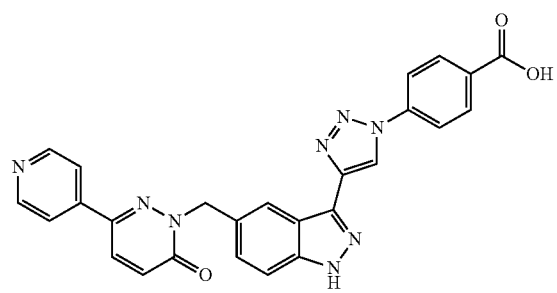 [SMILES: O=C(O)c1ccc(-n2cc(-c3n[nH]c4ccc(Cn5nc(-c6ccncc6)ccc5=O)cc34)nn2)cc1]

tert-butyl 3-{1-[4-(methoxycarbonyl)phenyl]-1H-1,2,3-triazol-4-yl}-5-[(6-oxo-3-pyridin-4-ylpyridazin-1(6H)-yl)methyl]-1H-indazole-1-carboxylate (88 mg; 0.10 mmol; 1.0 eq.) was suspended in NaOH (5N solution, 0.50 mL), DMF (6 mL) and EtOH (6 mL). The suspension was heated in MW at 80° C. for 10 min. The reaction mixture was allowed to cool to RT and brought to pH 6 by addition HCl (1N solution). The resulting solution was passed through an SCX-2 column and concentrated to give the title compound as a yellow solid (65 mg, 100%). $^1$H NMR (300 MHz, DMSO-d6) δ 13.41 (brs, 1H), 9.28 (s, 1H), 8.70 (dd, J=1.6, 4.5 Hz, 2H), 8.50 (s, 1H), 8.17 (d, J=9.8 Hz, 1H), 8.04 (d, J=8.7 Hz, 2H), 7.99-7.88 (m, 4H), 7.58 (d, J=9.0 Hz, 2H), 7.55-7.47 (m, 1H), 7.17 (d, J=9.8 Hz, 1H), 5.54 (s, 2H). HPLC (Condition A): Rt 2.34 min (purity 93.1%). MS (ESI+): 491.3, MS (ESI−): 489.4.

Step c) Formation of 2-[(3-{1-[4-(morpholin-4-ylcarbonyl)phenyl]-1H-1,2,3-triazol-4-yl}-1H-indazol-5-yl)methyl]-6-pyridin-4-ylpyridazin-3(2H)-one

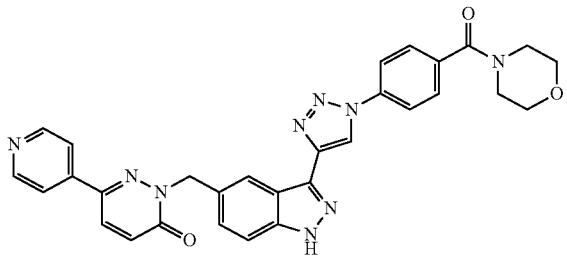 [SMILES: O=C(c1ccc(-n2cc(-c3n[nH]c4ccc(Cn5nc(-c6ccncc6)ccc5=O)cc34)nn2)cc1)N1CCOCC1]

The title compound was obtained following procedure described for example 94, step b), but starting from 4-(4-{5-[(6-oxo-3-pyridin-4-ylpyridazin-1(6H)-yl)methyl]-1H-indazol-3-yl}-1H-1,2,3-triazol-1-yl)benzoic acid (65 mg; 0.12 mmol; 1.0 eq.) and morpholine (4 mL; 46 mmol; 372 eq.) to give the title compound as a white solid. $^1$H NMR (300 MHz, DMSO-d6) δ 13.42 (s, 1H), 9.38 (s, 1H), 8.70 (dd, J=1.6, 4.6 Hz, 2H), 8.50 (s, 1H), 8.16 (d, J=6.0 Hz, 1H), 8.14 (d, J=3.0 Hz, 1H), 7.92 (dd, J=1.6, 4.6 Hz, 2H), 7.69 (d, J=8.6 Hz, 2H), 7.61 (d, J=8.7 Hz, 1H), 7.54 (d, J=8.7 Hz, 1H), 7.17 (d, J=9.8 Hz, 1H), 5.53 (s, 2H), 3.64 (s, 8H). HPLC (Condition A): Rt 2.24 min (purity 98.8%). MS (ESI+): 560.3, MS (ESI−): 558.2.

Example 104

5-(1-methyl-1,2,3,6-tetrahydropyridin-4-yl)-3-{1-[4-(morpholin-4-ylcarbonyl)phenyl]-1H-1,2,3-triazol-4-yl}-1H-indazole

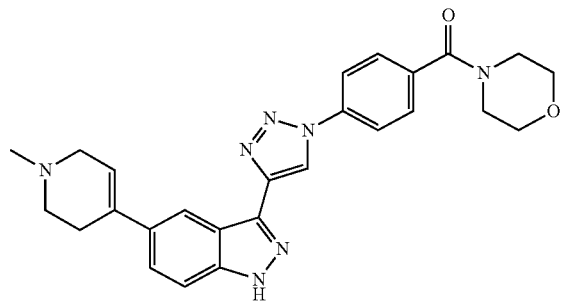 [SMILES: CN1CC=C(c2ccc3[nH]nc(-c4cn(-c5ccc(C(=O)N6CCOCC6)cc5)nn4)c3c2)CC1]

A suspension of {4-[4-(5-Bromo-1H-indazol-3-yl)-[1,2,3]triazol-1-yl]-phenyl}-morpholin-4-yl-methanone (150 mg; 0.33 mmol; 1.0 eq.), 1-Methyl-1,2,3,6-tetrahydropyridine-4-boronic acid, pinacol ester (Boron Molecular, 221 mg; 0.99 mmol; 3.0 eq.), PdCl$_2$(PPh$_3$)$_2$ (23 mg; 0.03 mmol; 0.10 eq.), cesium fluoride (151 mg; 0.99 mmol; 3.0 eq.) in dioxane (3 mL) and water (1.5 mL) was degassed with nitrogen flow and heat in MW at 150° C. for 10 min. The reaction mixture was filtered through a celite pad, water was added to the filtrate. Aqueous phase was extracted three time with DCM using separators tubes. Combined organic phases were concentrated under reduced pressure and the crude was purified by flash chromatography on silica (DCM/MeOH, gradient from 100:0 to 90:10) to give the title compound as a yellow powder. $^1$H NMR (300 MHz, DMSO) δ 13.36 (brs, 1H), 9.39 (s, 1H), 8.31 (s, 1H), 8.15 (d, J=8.0 Hz, 2H), 7.78-7.47 (m, 4H), 6.32-6.11 (m, 1H), 3.84-3.49 (m, 6H), 3.46-3.25 (m, 2H), 3.11-2.98 (m, 2H), 2.71-2.58 (m, 4H), 2.30 (s, 3H). HPLC (Condition A): Rt 2.22 min (purity 94.5%). MS (ESI+): 470.3, MS (ESI−): 468.3.

Example 105

5-(1-acetylpiperidin-4-yl)-3-{1-[4-(morpholin-4-ylcarbonyl)phenyl]-1H-1,2,3-triazol-4-yl}-1H-indazole

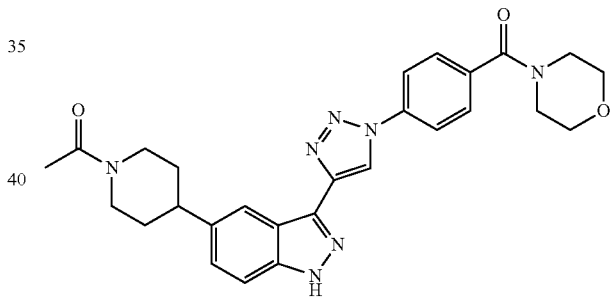

To a solution of 3-{1-[4-(morpholin-4-ylcarbonyl)phenyl]-1H-1,2,3-triazol-4-yl}-5-piperidin-4-yl-1H-indazole (100 mg; 0.22 mmol; 1.0 eq.) in Pyridine (1.5 mL) was added acetyl chlorid (15 μl; 0.22 mmol; 1.0 eq.). The reaction mixture was stirred at room temperature O/N. Acetyl chlorid (15 μl; 0.22 mmol; 1.0 eq.) was added again to the reaction mixture to complete the reaction. Pyridine was removed under reduced pressure and DCM was added to the residue. DCM phase was washed with a saturated solution of NH$_4$Cl and brine, dried over magnesium sulfate, flittered and concentrated. The crude was purified by preparative chromatography to give the title compound as a white foam. $^1$H NMR (300 MHz, DMSO-d6) δ 13.30 (brs, 1H), 9.37 (s, 1H), 8.23-8.07 (m, 3H), 7.74-7.64 (m, 2H), 7.55 (d, J=8.6 Hz, 1H), 7.37 (dd, J=8.7 Hz, 1.4, 1H), 4.66-4.50 (m, 1H), 3.97 (d, J=13.2 Hz, 1H), 3.79-3.34 (m, 8H), 3.25-3.09 (m, 1H), 3.03-2.86 (m, 1H), 2.72-2.55 (m, 1H), 2.06 (s, 3H), 1.96-1.44 (m, 4H). HPLC (Condition A): Rt 3.09 min (purity 94.3%). MS (ESI+): 500.3, MS (ESI−): 498.3.

Example 106

5-(1-benzyl-1,2,3,6-tetrahydropyridin-4-yl)-3-{1-[4-(morpholin-4-ylcarbonyl)phenyl]-1H-1,2,3-triazol-4-yl}-1H-indazole

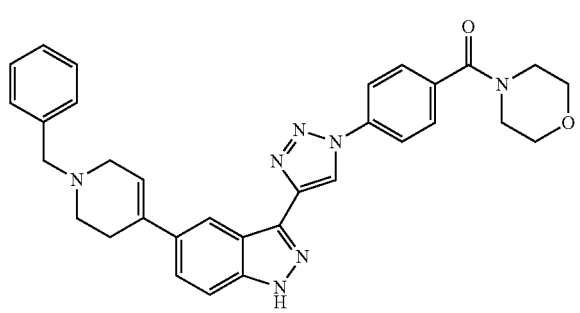 [SMILES: O=C(c1ccc(-n2cc(-c3n[nH]c4ccc(C5=CCN(Cc6ccccc6)CC5)cc34)nn2)cc1)N1CCOCC1]

A suspension of {4-[4-(5-Bromo-1H-indazol-3-yl)-[1,2,3]triazol-1-yl]-phenyl}-morpholin-4-yl-methanone (100 mg; 0.22 mmol; 1.0 eq.), 1-Benzyl-4-(4,4,5,5-tetramethyl-[1,3,2]dioxaborolan-2-yl)-1,2,3,6-tetrahydro-pyridine; hydrochloride (J&W Pharm Lab, 222 mg; 0.66 mmol; 3.00 eq.), $Pd_2Cl_2(PPh_3)_2$ (15 mg; 0.02 mmol; 0.1 eq.), potassium carbonate (91 mg; 0.66 mmol; 3.0 eq.) in dioxane (2 mL) and water (1 mL) was degassed with nitrogen flow and heated in MW at 150° C. for 10 min. The reaction mixture was filtered through a celite pad, water was added to the filtrate. Aqueous phase was extracted three times with DCM using separators tubes. Combined organic phases were concentrated under reduced pressure and the crude was purified by flash chromatography on silica (DCM/MeOH, gradient from 100:0 to 90:10) to give the title compound as yellow powder. $^1$H NMR (300 MHz, DMSO-d6) δ 13.37 (brs, 1H), 9.39 (s, 1H), 8.30 (s, 1H), 8.22-8.10 (m, 2H), 7.76-7.65 (m, 2H), 7.65-7.50 (m, 2H), 7.42-7.31 (m, 4H), 7.31-7.22 (m, 1H), 6.30-6.10 (m, 1H), 3.78-3.50 (m, 8H), 3.47-3.37 (m, 2H), 3.18-3.07 (m, 2H), 2.77-2.56 (m, 4H). HPLC (Condition A): Rt 2.87 min (purity 97.5%). MS (ESI+): 546.4, MS (ESI−): 544.3.

Example 107

N-cyclohexyl-N-(2-hydroxyethyl)-4-[4-(1H-indazol-3-yl)-1H-1,2,3-triazol-1-yl]benzamide

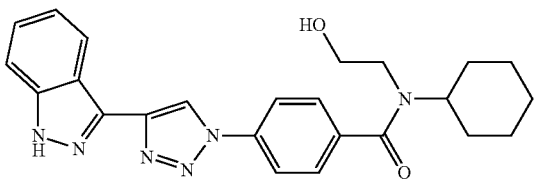 [SMILES: O=C(c1ccc(-n2cc(-c3n[nH]c4ccccc34)nn2)cc1)N(CCO)C1CCCCC1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and N-cyclohexylethanolamine (70 mg, 0.49 mmol, 1.5 eq.) as a white solid. $^1$H NMR (300 MHz, DMSO-d6) δ 13.38 (s, 1H), 9.40 (s, 1H), 8.37 (d, J=8.2 Hz, 1H), 8.14 (d, J=8.3, 2H), 7.67-7.54 (m, 3H), 7.51-7.39 (m, 1H), 7.35-7.21 (m, 1H), 4.86-4.70 (m, 1H), 3.56 (brs, 2H), 3.47-3.26 (m, 3H), 1.90-1.33 (m, 8H), 1.11-0.90 (m, 2H). HPLC (Condition A): Rt 3.58 min (purity 99.6%). MS (ESI+): 431.3, MS (ESI−): 429.3.

Example 108

3-[1-(4-{[(2S)-2-(methoxymethyl)pyrrolidin-1-yl]carbonyl}phenyl)-1H-1,2,3-triazol-4-yl]-1H-indazole

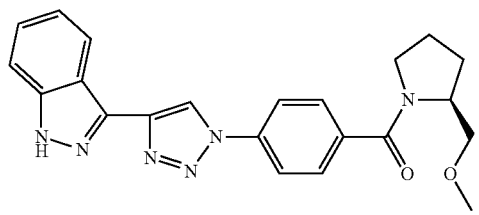 [SMILES: COC[C@@H]1CCCN1C(=O)c1ccc(-n2cc(-c3n[nH]c4ccccc34)nn2)cc1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and (S)-(+)-2-(methoxymethyl)pyrrolidine (56 mg, 0.49 mmol, 1.5 eq.) as a white solid. $^1$H NMR (300 MHz, DMSO-d6) δ 13.39 (s, 1H), 9.41 (s, 1H), 8.37 (d, J=8.1 Hz, 1H), 8.15 (d, J=8.6 Hz, 2H), 7.74 (d, J=8.4, 2H), 7.62 (d, J=8.4 Hz, 1H), 7.51-7.39 (m, 1H), 7.27 (t, J=7.5 Hz, 1H), 4.29 (brs, 1H), 3.67-3.57 (m, 1H), 3.57-3.21 (m, 5H), 3.04 (brs, 1H), 2.11-1.62 (m, 4H). HPLC (Condition A): Rt 3.33 min (purity 99.8%). MS (ESI+): 403.3, MS (ESI−): 401.3.

Example 109

3-(1-{4-[(4-methoxypiperidin-1-yl)carbonyl]phenyl}-1H-1,2,3-triazol-4-yl)-1H-indazole

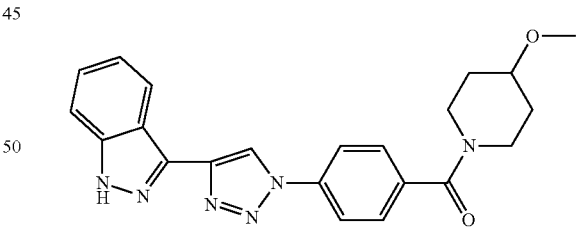

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 4-methoxy-piperidine (567 mg, 0.49 mmol, 1.5 eq.) as a white solid. $^1$H NMR (300 MHz, DMSO-d6) δ 13.39 (s, 1H), 9.40 (s, 1H), 8.37 (d, J=8.0 Hz, 1H), 8.14 (d, J=8.6 Hz, 2H), 7.71-7.57 (m, 3H), 7.51-7.39 (m, 1H), 7.27 (t, J=7.5 Hz, 1H), 3.94 (brs, 1H), 3.61-3.41 (m, 2H), 3.39-3.17 (m, 2H), 3.28 (s, 3H), 1.88 (brs, 2H), 1.49 (brs, 2H). HPLC (Condition A): Rt 3.19 min (purity 99.8%). MS (ESI+): 403.3, MS (ESI−): 401.2.

Example 110

6-methyl-2-[3-{1-[4-(morpholin-4-ylcarbonyl)phenyl]-1H-1,2,3-triazol-4-yl}-1H-indazol-5-yl)methyl]pyridazin-3(2H)-one Step a) Formation of 4-(4-{5-[(3-methyl-6-oxopyridazin-1(6H)-yl)methyl]-1H-indazol-3-yl}-1H-1,2,3-triazol-1-yl)benzoic acid

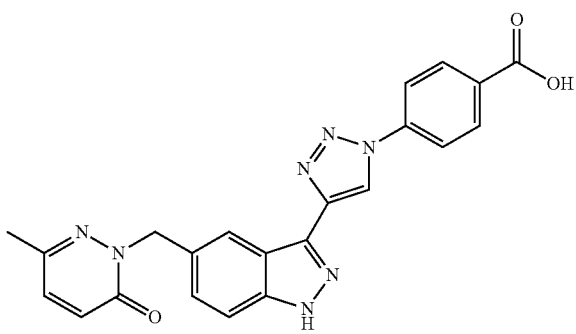 [SMILES: Cc1ccc(=O)n(Cc2ccc3[nH]nc(-c4cn(-c5ccc(C(=O)O)cc5)nn4)c3c2)n1]

The title compound was obtained following procedure described for example 94, step a), but starting from 6-methyl-3(2H)-pyridazinone (107 mg; 0.97 mmol; 2.9 eq.) and tert-butyl 5-(bromomethyl)-3-{1-[4-(methoxycarbonyl)phenyl]-1H-1,2,3-triazol-4-yl}-1H-indazole-1-carboxylate (565 mg; 0.33 mmol; 1.0 eq.) as a yellow solid. $^1$H NMR (300 MHz, DMSO-d6) δ 13.44 (s, 1H), 9.40 (s, 1H), 8.35 (s, 1H), 8.23-8.12 (m, 4H), 7.58 (d, J=8.7, 1H), 7.43 (dd, J=8.7, 1.5, 1H), 7.35 (d, J=9.5, 1H), 6.93 (d, J=9.5, 1H), 5.35 (s, 2H), 2.26 (s, 3H). HPLC (Condition A): Rt 3.07 min (purity 77.9%). MS (ESI−): 426.4.

Step b) Formation of 6-methyl-2-[(3-{1-[4-(morpholin-4-ylcarbonyl)phenyl]-1H-1,2,3-triazol-4-yl}-1H-indazol-5-yl)methyl]pyridazin-3(2H)-one

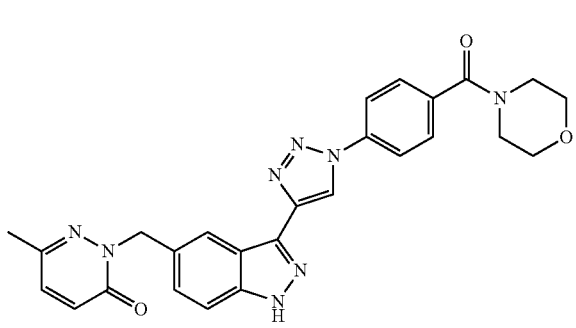 [SMILES: Cc1ccc(=O)n(Cc2ccc3[nH]nc(-c4cn(-c5ccc(C(=O)N6CCOCC6)cc5)nn4)c3c2)n1]

The title compound was obtained following procedure described for example 94, step b), but starting from 4-(4-{5-[(3-methyl-6-oxopyridazin-1(6H)-yl)methyl]-1H-indazol-3-yl}-1H-1,2,3-triazol-1-yl)benzoic acid (35 mg; 0.06 mmol; 1.0 eq.) as a white solid. HPLC (Condition A): Rt 2.98 min (purity 97.5%). MS (ESI+): 357.2, MS (ESI−): 355.2.

Example 111

4-[4-(1H-indazol-3-yl)-1H-1,2,3-triazol-1-yl]-N-[1-(2-morpholin-4-ylethyl)-1H-pyrazol-4-yl]benzamide

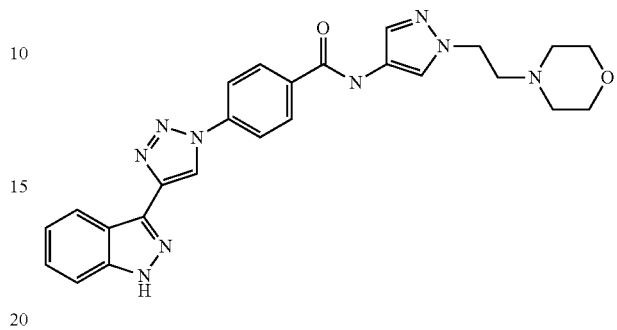

The title compound was obtained following procedure described for example 70, but starting from 4-[4-(1H-indazol-3-yl)-1H-1,2,3-triazol-1-yl]benzoic acid (101 mg; 0.33 mmol; 1.0 eq.) and 1-(2-Morpholin-4-yl-ethyl)-1H-pyrazol-4-ylamine; dihydrochloride (purchased from UkrOrgSynthesis Building Blocks, 107 mg; 0.40 mmol; 1.2 eq.) as a white solid. $^1$H NMR (300 MHz, DMSO-d6) δ 13.42 (brs, 1H), 10.62 (brs, 1H), 9.46 (s, 1H), 8.38 (d, J=8.1 Hz, 1H), 8.24 (q, J=8.9 Hz, 4H), 8.14 (s, 1H), 7.62 (d, J=7.3 Hz, 2H), 7.52-7.39 (m, 1H), 7.28 (t, J=7.5 Hz, 1H), 4.24 (t, J=6.5 Hz, 2H), 3.63-3.48 (m, 4H), 2.71 (t, J=6.5 Hz, 2H), 2.47-2.34 (m, 4H). HPLC (Condition A): Rt 3.06 min (purity 94.0%). MS (ESI+): 484.3, MS (ESI−): 482.2.

Example 112

4-[4-(1H-indazol-3-yl)-1H-1,2,3-triazol-1-yl]-N-[1-(1-methylpyrrolidin-3-yl)-1H-pyrazol-4-yl]benzamide

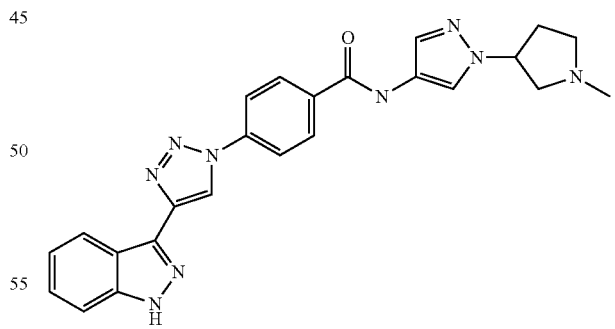

The title compound was obtained following procedure described for example 70, but starting from 4-[4-(1H-indazol-3-yl)-1H-1,2,3-triazol-1-yl]benzoic acid (101 mg; 0.33 mmol; 1.0 eq.) and 1-(1-Methyl-pyrrolidin-3-yl)-1H-pyrazol-4-ylamine (66 mg; 0.40 mmol; 1.2 eq.) as a beige powder. $^1$H NMR (300 MHz, DMSO-d6) δ 13.41 (brs, 1H), 10.63 (brs, 1H), 9.46 (s, 1H), 8.38 (d, J=8.1 Hz, 1H), 8.32-8.12 (m, 5H), 7.63 (t, J=4.2 Hz, 2H), 7.52-7.39 (m, 1H), 7.28 (t, J=7.6 Hz, 1H), 4.99-4.81 (m, 1H), 2.86-2.67 (m, 3H), 2.48-2.33 (m,

Example 113

3-[1-(4-{[3-(2-methoxyethyl)piperidin-1-yl]carbonyl}phenyl-1H-1,2,3-triazol-4-yl]-1H-indazole

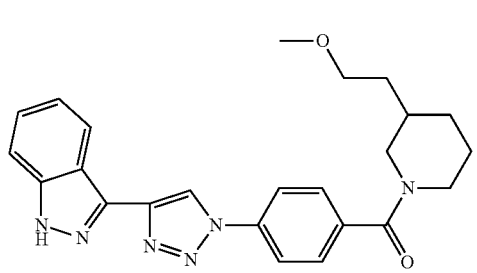 [SMILES: COCCC1CCCN(C(=O)c2ccc(-n3cc(-c4n[nH]c5ccccc45)nn3)cc2)C1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-(2-methoxyethyl)piperidine. HCl (ChemBridge Corporation, 70 mg; 0.49 mmol; 1.5 eq.) as a white solid. $^1$H NMR (300 MHz, DMSO-d6) δ 13.38 (s, 1H), 9.40 (s, 1H), 8.37 (d, J=8.2 Hz, 1H), 8.15 (d, J=8.4 Hz, 2H), 7.73-7.57 (m, 3H), 7.51-7.38 (m, 1H), 7.33-7.20 (m, 1H), 4.45-4.23 (m, 1H), 3.48-3.39 (m, 1H), 3.34 (s, 3H), 3.29-2.98 (m, 4H), 1.84 (brd, J=11.7 Hz, 1H), 1.78-1.56 (m, 2H), 1.56-1.11 (m, 4H). HPLC (Condition A): Rt 3.62 min (purity 100.0%). MS (ESI+): 431.3, MS (ESI−): 429.3.

Example 114

1-{4-[4-(1H-indazol-3-yl)-1H-1,2,3-triazol-1-yl]benzoyl}azetidin-3-ol

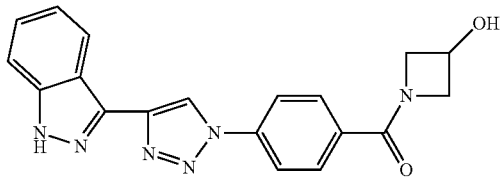 [SMILES: O=C(c1ccc(-n2cc(-c3n[nH]c4ccccc34)nn2)cc1)N1CC(O)C1]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-hydroxyazetidine hydrochloride (ChemBridge Corporation, 54 mg; 0.49 mmol; 1.5 eq.) as a white powder. $^1$H NMR (300 MHz, DMSO-d6) δ 13.39 (s, 1H), 9.42 (s, 1H), 8.37 (d, J=8.3 Hz, 1H), 8.17 (d, J=8.7 Hz, 2H), 7.88 (d, J=8.7 Hz, 2H), 7.62 (d, J=8.4 Hz, 1H), 7.51-7.39 (m, 1H), 7.27 (t, J=7.5 Hz, 1H), 5.81 (d, J=5.8 Hz, 1H), 4.62-4.43 (m, 2H), 4.39-4.23 (m, 1H), 4.19-4.03 (m, 1H), 3.83 (brd, J=8.4 Hz, 1H). HPLC (Condition A): Rt 2.59 min (purity 100.0%). MS (ESI+): 361.2, MS (ESI−): 359.1.

Example 115

3-{1-[4-({3-[(2-methyl-1H-imidazol-1-yl)methyl]piperidin-1-yl}carbonyl)phenyl]-1H-1,2,3-triazol-4-yl}-1H-indazole

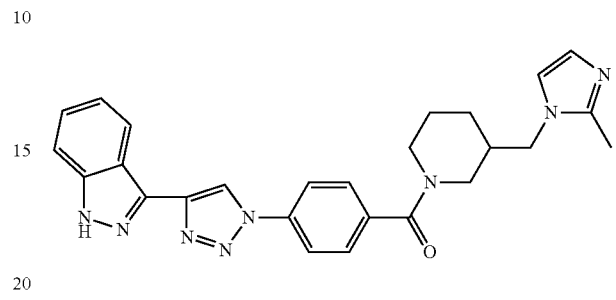

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-[(2-Methyl-1H-imidazol-1-yl)methyl]piperidine (88 mg; 0.49 mmol; 1.5 eq.) as a white solid. $^1$H NMR (DMSO-d6) δ 13.41 (s, 1H), 9.40 (s, 1H), 8.37 (d, J=8.1 Hz, 1H), 8.14 (brs, 2H), 7.62 (m, 3H), 7.51-7.38 (m, 1H), 7.27 (m, 2.5H), 7.00 (m, 1.5H), 4.53-2.73 (m, 6H), 2.46-2.20 (m, 3H), 2.04 (brs, 1H), 1.90-1.59 (m, 2H), 1.59-1.10 (m, 2H). HPLC (Condition A): Rt 2.59 min (purity 98.5%). MS (ESI+): 467.3, MS (ESI−): 465.2.

Example 116

4-[4-(1H-indazol-3-yl)-1H-1,2,3-triazol-1-yl]-N-(1-methylpiperidin-4-yl)benzamide

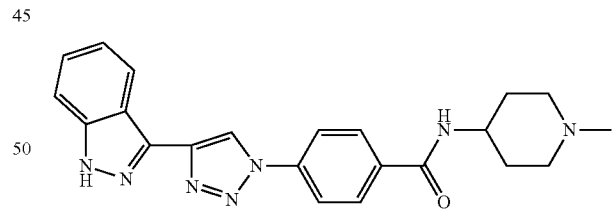

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 4-amino-1-methylpiperidine (56 mg; 0.49 mmol; 1.5 eq.) as a white solid. $^1$H NMR (DMSO-d6) δ 13.41 (s, 1H), 9.46 (s, 1H), 8.65 (d, J=7.5 Hz, 1H), 8.37 (d, J=8.0 Hz, 1H), 8.22 (d, J=8.8 Hz, 2H), 8.12 (d, J=8.8 Hz, 2H), 7.63 (d, J=8.5 Hz, 1H), 7.50-7.40 (m, 1H), 7.32-7.20 (m, 1H), 4.07 (brs, 1H), 3.49 (d, J=11.4 Hz, 2H), 3.23-3.03 (m, 2H), 2.86-2.71 (m, 3H), 2.08 (m, 2H), 1.86-1.66 (m, 2H). HPLC (Condition A): Rt 2.39 min (purity 97.9%). MS (ESI+): 402.3, MS (ESI−): 400.3.

Example 117

2-(1-{4-[4-(1H-indazol-3-yl)-1H-1,2,3-triazol-1-yl]benzoyl}piperidin-2-yl)ethanol

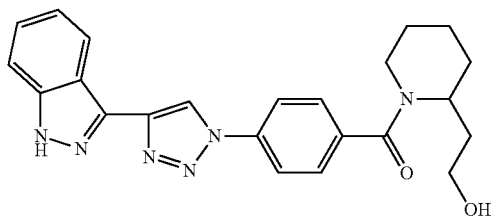 [SMILES: O=C(c1ccc(-n2cc(-c3n[nH]c4ccccc34)nn2)cc1)N1CCCCC1CCO]

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 2-piperidine ethanol (63 mg; 0.49 mmol; 1.5 eq.) as a white solid. $^1$H NMR (300 MHz, DMSO-d6) δ 13.21 (s, 1H), 9.22 (s, 1H), 8.20 (d, J=8.0 Hz, 1H), 7.96 (d, J=8.4 Hz, 2H), 7.52-7.38 (m, 3H), 7.35-7.22 (m, 1H), 7.16-7.01 (m, 1H), 4.77-4.53 (m, 1H), 4.37-4.11 (m, 2H), 3.39-3.08 (m, 2H), 2.50-2.21 (m, 1H), 1.89-1.19 (m, 6H), 1.13-1.02 (m, 2H). HPLC (Condition A): Rt 3.17 min (purity 94.4%). MS (ESI+): 417.2, MS (ESI−): 415.2.

Example 118

3-[1-(4-{[3-(methoxymethyl)piperidin-1-yl]carbonyl}phenyl)-1H-1,2,3-triazol-4-yl]-1H-indazole

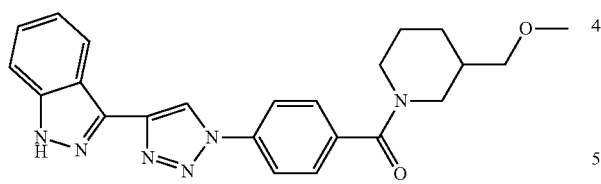

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-Methoxymethyl-piperidine hydrochloride (81 mg; 0.49 mmol; 1.5 eq.) as a white solid. $^1$H NMR (300 MHz, DMSO-d6) δ 13.39 (s, 1H), 9.40 (s, 1H), 8.37 (d, J=8.1 Hz, 1H), 8.15 (d, J=8.0 Hz, 2H), 7.73-7.56 (m, 3H), 7.55-7.35 (m, 1H), 7.27 (t, J=7.5 Hz, 1H), 4.55-4.16 (m, 1H), 3.79-3.45 (m, 1H), 3.42-2.81 (m, 7H), 2.79-2.59 (m, 1H), 1.92-1.14 (m, 4H). HPLC (Condition A): Rt 3.49 min (purity 98.9%). MS (ESI+): 417.2, MS (ESI−): 415.2.

Example 119

N-(2-hydroxybutyl)-4-[4-(1H-indazol-3-yl)-1H-1,2,3-triazol-1-yl]benzamide

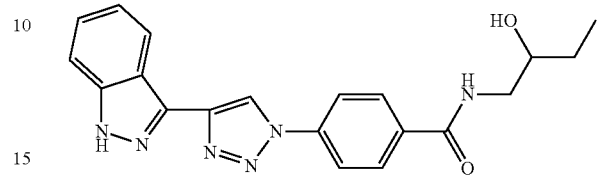

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 1-amino-2-butanol (44 mg; 0.49 mmol; 1.5 eq.) as a white solid. $^1$H NMR (300 MHz, DMSO-d6) δ δ 13.41 (s, 1H), 9.42 (s, 1H), 8.61 (t, J=5.7 Hz, 1H), 8.37 (d, J=8.2 Hz, 1H), 8.18 (d, J=8.8 Hz, 2H), 8.12 (d, J=8.8 Hz, 2H), 7.62 (d, J=8.4 Hz, 1H), 7.51-7.39 (m, 1H), 7.27 (t, J=7.5 Hz, 1H), 4.78 (d, J=5.2 Hz, 1H), 3.58 (m, 1H), 3.35 (m, 1H), 3.22 (m, 1H), 1.48 (m, 1H), 1.34 (m, 1H), 0.92 (t, J=7.4 Hz, 3H). HPLC (Condition A): Rt 2.91 min (purity 100.0%). MS (ESI+): 377.2, MS (ESI−): 375.2.

Example 120

3-(1-{4-[(4-pyrrolidin-1-ylpiperidin-1-yl)carbonyl]phenyl}-1H-1,2,3-triazol-4-yl)-1H-indazole

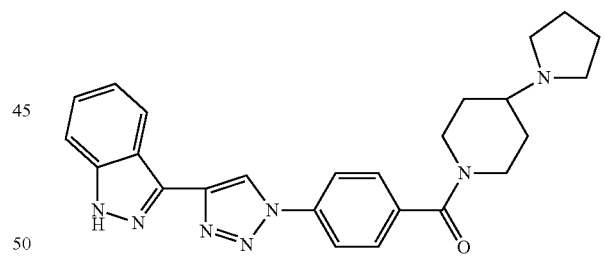

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 4-(1-pyrrolidinyl)piperidine (76 mg; 0.49 mmol; 1.5 eq.) as a white solid.

$^1$H NMR (300 MHz, DMSO-d6) δ 13.39 (s, 1H), 9.40 (s, 1H), 8.37 (d, J=8.1 Hz, 1H), 8.19-8.07 (m, 2H), 7.72-7.57 (m, 3H), 7.52-7.39 (m, 1H), 7.27 (t, J=7.5 Hz, 1H), 4.38-4.15 (m, 1H), 3.71-3.49 (m, 1H), 3.23-2.91 (m, 2H), 2.57-2.42 (m, 4H), 2.33-2.17 (m, 1H), 2.02-1.73 (m, 2H), 1.73-1.59 (m, 4H), 1.42 (d, J=9.8 Hz, 2H). HPLC (Condition A): Rt 2.43 min (purity 98.2%). MS (ESI+): 442.3, MS (ESI−): 440.3.

Example 121

5-[1-(2-fluoroethyl)piperidin-4-yl]-3-{1-[4-(morpholin-4-ylcarbonyl)phenyl]-1H-1,2,3-triazol-4-yl}-1H-indazole

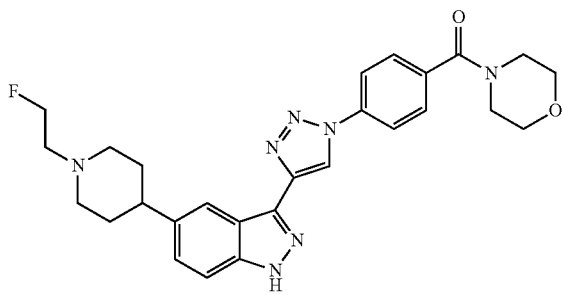 [SMILES: O=C(c1ccc(-n2cc(-c3n[nH]c4ccc(C5CCN(CCF)CC5)cc34)nn2)cc1)N1CCOCC1]

A suspension of 1-bromo-2-fluoro-ethane (Avocado Research, 26 mg; 0.21 mmol; 0.95 eq.), 3-{1-[4-(morpholin-4-ylcarbonyl)phenyl]-1H-1,2,3-triazol-4-yl)-5-piperidin-4-yl}-1H-indazole (100 mg; 0.22 mmol; 1.0 eq.) and NaHCO$_3$ (257 mg; 3.06 mmol; 14 eq.) in dry DMF (2 mL) was heated in MW at 100° C. for 3 h. EtOAc and water were added to the reaction mixture. The two phases were separated and the aqueous phase was extracted with EtOAc twice. Combined organic phases were washed with brine, dried over magnesium sulfate, filtered and concentrated. The crude was purified by flash chromatography on silica (DCM/MeOH, gradient from 100:0 to 90:10) to give the title compound as a beige solid. $^1$H NMR (300 MHz, DMSO-d6) δ 13.29 (brs, 1H), 9.38 (s, 1H), 8.28-8.05 (m, 3H), 7.69 (d, J=8.0 Hz, 2H), 7.54 (d, J=8.7 Hz, 1H), 7.37 (d, J=8.8 Hz, 1H), 4.57 (dt, J=48.0 Hz, 4.8, 2H), 3.88-3.37 (m, 8H), 3.18-2.91 (m, 2H), 2.85-2.56 (m, 3H), 2.28-2.06 (m, 2H), 1.94-1.61 (m, 4H). HPLC (Condition A): Rt 5.96 min (purity 93.8%). MS (ESI+): 504.3, MS (ESI−): 502.3.

Example 122

5-bromo-3-{1-[4-(morpholin-4-ylcarbonyl)phenyl]-1H-1,2,3-triazol-4-yl}-1H-indazole

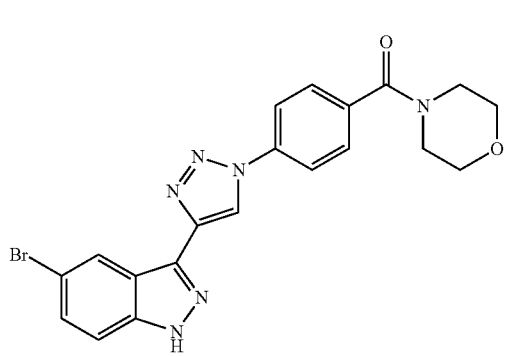 [SMILES: O=C(c1ccc(-n2cc(-c3n[nH]c4ccc(Br)cc34)nn2)cc1)N1CCOCC1]

The title compound was obtained following procedure described for intermediate 21, step b), but starting from 4-(4-azidobenzoyl)morpholine (3.47 g; 15 mmol; 1.1 eq.) and 5-Bromo-3-ethynyl-1H-indazole (3.0 g; 13.6 mmol; 1.0 eq.) as a yellow solid. $^1$H NMR (300 MHz, DMSO-d6) δ 13.60 (s, 1H), 9.45 (s, 1H), 8.55 (s, 1H), 8.15 (d, J=8.1 Hz, 2H), 7.69 (d, J=8.1 Hz, 2H), 7.65-7.53 (m, 2H), 3.79-3.35 (m, 8H). HPLC (Condition A): Rt 3.50 min (purity 99.1%). MS (ESI+): 453.3, 455.3, MS (ESI−): 451.3, 453.3.

Example 123

5-(1-methyl-1H-pyrazol-4-yl)-3-{1-[4-(morpholin-4-ylcarbonyl)phenyl]-1H-1,2,3-triazol-4-yl}-1H-indazole

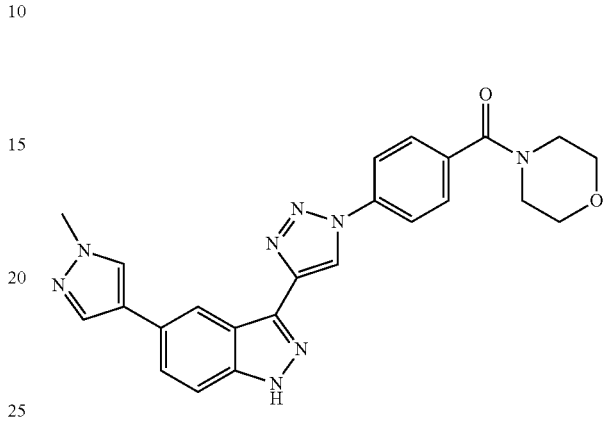

The title compound was obtained following procedure described for example 104, but starting from {4-[4-(5-Bromo-1H-indazol-3-yl)-[1,2,3]triazol-1-yl]-phenyl}-morpholin-4-yl-methanone (120 mg; 0.26 mmol; 1.0 eq.) and 1-methyl-4-(4,4,5,5-tetramethyl-1,3,2-dioxaborolan-2-yl)-1H-pyrazole (83 mg; 0.40 mmol; 1.5 eq.) as a beige powder (87 mg, 72%). $^1$H NMR (300 MHz, DMSO-d6) δ 13.37 (brs, 1H), 9.41 (s, 1H), 8.42 (s, 1H), 8.24-8.10 (m, 3H), 7.91 (s, 1H), 7.77-7.56 (m, 4H), 3.90 (s, 3H), 3.77-3.36 (m, 8H). HPLC (Condition A): Rt 3.25 min (purity 98.7%). MS (ESI+): 455.3, MS (ESI−): 453.3.

Example 124

5-(1-methylpiperidin-4-yl)-3-{1-[4-(morpholin-4-ylcarbonyl)phenyl]-1H-1,2,3-triazol-4-yl}-1H-indazole

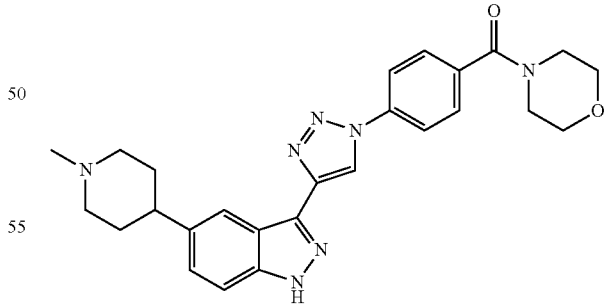

5-(1-methyl-1,2,3,6-tetrahydropyridin-4-yl)-3-{1-[4-(morpholin-4-ylcarbonyl)phenyl]-1H-1,2,3-triazol-4-yl}-1H-indazole (20 mg; 0.04 mmol; 1.0 eq.) was dissolved in MeOH (3 mL) and Pd/C (moistened, 50% water; 100 mg) was added. The reaction mixture was hydrogenenated at RT for two days in a Parr instrument (35 bars). Reaction mixture was filtered through a celite pad and dried under vacuum to give the title compound as a beige solid (14 mg, 70%). $^1$H NMR (300 MHz, DMSO-d6) δ 9.37 (s, 1H), 8.25-8.09 (m, 3H), 7.73-7.62 (m, 2H), 7.64-7.49 (m, 1H), 7.40-7.29 (m, 1H), 3.81-3.39 (m, 8H), 2.98-2.56 (m, 4H), 2.22 (s, 3H), 2.06-1.66 (m, 5H). HPLC (Condition A): Rt 3.86 min (purity 87.8%). MS (ESI+): 472.3, MS (ESI−): 470.2.

Example 125

4-[4-(1H-indazol-3-yl)-1H-1,2,3-triazol-1-yl]-N-[1-(8-methyl-8-azabicyclo[3.2.1]oct-3-yl)-1H-pyrazol-4-yl]benzamide

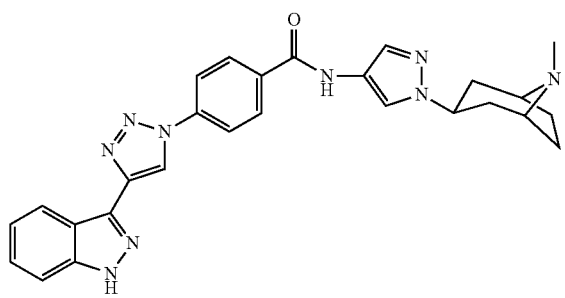 [SMILES: CN1C2CCC1CC(n1cc(NC(=O)c3ccc(-n4cc(-c5n[nH]c6ccccc56)nn4)cc3)cn1)C2]

The title compound was obtained following procedure described for example 70, but starting from 4-[4-(1H-indazol-3-yl)-1H-1,2,3-triazol-1-yl]benzoic acid (101 mg; 0.33 mmol; 1.0 eq.) and 1-(8-Methyl-8-aza-bicyclo[3.2.1]oct-3-yl)-1H-pyrazol-4-ylamine (82 mg; 0.40 mmol; 1.2 eq.) as a beige solid. $^1$H NMR (300 MHz, DMSO-d6) δ 13.42 (br s, 1H), 10.63 (br s, 1H), 9.46 (s, 1H), 8.38 (d, J=8.2 Hz, 1H), 8.23 (q, J=8.9 Hz, 4H), 8.13 (s, 1H), 7.68-7.58 (m, 2H), 7.52-7.39 (m, 1H), 7.27 (t, J=7.4 Hz, 1H), 4.64-4.46 (m, 1H), 3.33 (d, J=13.3 Hz, 2H), 2.35 (s, 3H), 2.22-1.95 (m, 4H), 1.91-1.69 (m, 4H). HPLC (Condition A): Rt 3.18 min (purity 88.1%). MS (ESI+): 494.3, MS (ESI−): 492.4.

Example 126

3-[1-(4-{[3-(1H-imidazol-1-ylmethyl)piperidin-1-yl]carbonyl}phenyl)-1H-1,2,3-triazol-4-yl]-1H-indazole

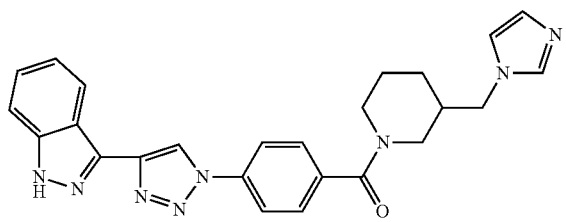

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-Imidazol-1-ylmethyl-piperidine; dihydrochloride (117 mg; 0.49 mmol; 1.5 eq.) as a white solid. $^1$H NMR (DMSO-d6) δ 13.41 (s, 1H), 9.42 (s, 1H), 8.37 (d, J=8.2 Hz, 1H), 8.12 (m, 2H), 7.65 (m, 3H), 7.62 (d, J=8.4 Hz, 1H), 7.45 (m, 1H), 7.27 (m, 1.5H), 6.74-7.15 (m, 1.5H), 2.70-4.5 (m, 6H), 2.03 (m, 1H), 1.67 (m, 2H), 1.45 (m, 1H), 1.24 (m, 1H). HPLC (Condition A): Rt 2.55 min (purity 97.8%). MS (ESI+): 453.3, MS (ESI−): 451.3.

Example 127

3-(1-{4-[(3-methoxypiperidin-1-yl)carbonyl]phenyl}-1H-1,2,3-triazol-4-yl)-1H-indazole

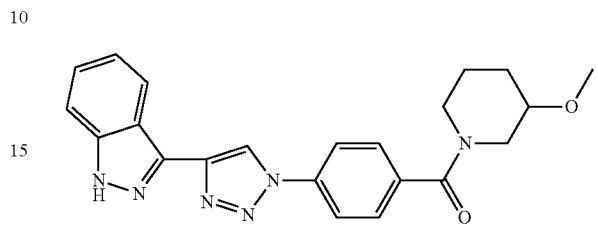

The title compound was obtained following procedure described for example 26, but starting from 4-[4-(1H-indazol-3-yl)-1H-1,2,3-triazol-1-yl]benzoic acid (100 mg; 0.33 mmol; 1.0 eq.) and 3-Methoxy-piperidine; hydrochloride (ChemCollect GmbH, 74 mg; 0.49 mmol; 1.5 eq.) as a white solid. $^1$H NMR (300 MHz, DMSO) δ 13.38 (s, 1H), 9.40 (s, 1H), 8.37 (d, J=8.3 Hz, 1H), 8.15 (d, J=8.3 Hz, 2H), 7.72-7.55 (m, 3H), 7.45 (t, J=7.5 Hz, 1H), 7.27 (t, J=7.4 Hz, 1H), 4.09-3.65 (m, 1H), 3.57-3.18 (m, 5H), 3.10 (brs, 1H), 2.03-1.21 (m, 5H). HPLC (Condition A): Rt 3.22 min (purity 99.5%). MS (ESI+): 403.2, MS (ESI−): 401.2.

Example 128

4-[4-(1H-indazol-3-yl)-1H-1,2,3-triazol-1-yl]-N-(1-piperidin-4-yl-1H-pyrazol-4-yl)benzamide hydrochloride Step a) Formation of tert-butyl 4-[4-({4-[4-(1H-indazol-3-yl)-1H-1,2,3-triazol-1-yl]benzoyl}amino)-1H-pyrazol-1-yl]piperidine-1-carboxylate

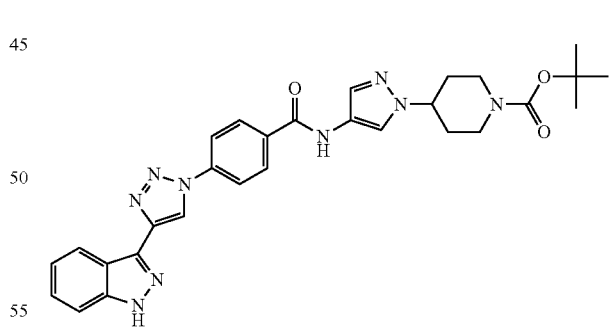

The title compound was obtained following procedure described for example 70, but starting from 4-[4-(1H-indazol-3-yl)-1H-1,2,3-triazol-1-yl]benzoic acid (101 mg; 0.33 mmol; 1.0 eq.) and 4-(4-Amino-pyrazol-1-yl)-piperidine-1-carboxylic acid tert-butyl ester (105 mg; 0.40 mmol; 1.2 eq.) as pink powder. $^1$H NMR (300 MHz, DMSO-d6) δ 13.41 (brs, 1H), 10.63 (brs, 1H), 9.46 (s, 1H), 8.38 (d, J=8.3 Hz, 1H), 8.23 (dd, J=8.4, 18.6 Hz, 4H), 8.12 (s, 1H), 7.71-7.56 (m, 2H), 7.46 (t, J=7.7 Hz, 1H), 7.27 (t, J=7.5 Hz, 1H), 4.38 (s, 1H), 4.05 (d, J=13.3 Hz, 2H), 2.91 (brs, 2H), 2.09-1.92 (m, 2H), 1.90-1.66

(m, 2H), 1.43 (s, 9H). HPLC (Condition A): Rt 4.60 min (purity 95.7%). MS (ESI+): 554.3, MS (ESI−): 552.3.

Step b) Formation of 4-[4-(1H-indazol-3-yl)-1H-1,2,3-triazol-1-yl]-N-(1-piperidin-4-yl-1H-pyrazol-4-yl)benzamide hydrochloride

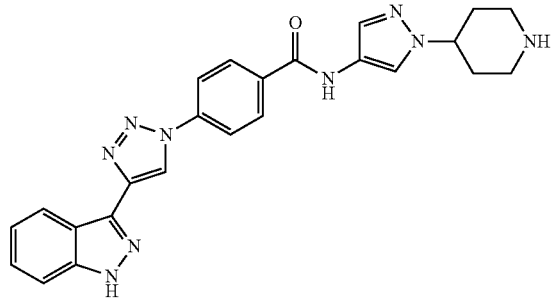 [SMILES: O=C(Nc1cnn(C2CCNCC2)c1)c1ccc(-n2cc(-c3n[nH]c4ccccc34)nn2)cc1]

To a solution of tert-butyl 4-[4-({4-[4-(1H-indazol-3-yl)-1H-1,2,3-triazol-1-yl]benzoyl}amino)-1H-pyrazol-1-yl]piperidine-1-carboxylate (100 mg; 0.18 mmol; 1.0 eq.) in Dioxane (3 mL) was added HCl 4N solution in 1,4-dioxane (450 µl of a 4N solution in dioxane; 1.80 mmol; 10 eq.) and one drop of water. The resulting suspension was stirred at RT O/N. Solvent were removed under reduced pressure and the residue was suspended in ACN and filtered to afford the title compound as a beige solid (64 mg; 72%). $^1$H NMR (300 MHz, DMSO-d6) δ 13.45 (brs, 1H), 10.75 (s, 1H), 9.46 (s, 1H), 9.19-8.73 (m, 2H), 8.38 (d, J=8.1 Hz, 1H), 8.32-8.18 (m, 4H), 8.15 (s, 1H), 7.71 (s, 1H), 7.63 (d, J=8.4 Hz, 1H), 7.52-7.39 (m, 1H), 7.27 (t, J=7.5 Hz, 1H), 4.64-4.42 (m, 1H), 3.48-3.30 (m, 2H), 3.05 (s, 2H), 2.27-2.05 (m, 4H). HPLC (Condition A): Rt 3.06 min (purity 95.7%). MS (ESI+): 454.4, MS (ESI−): 452.3.

Example 129

N-(1-azepan-4-yl-1H-pyrazol-4-yl)-4-[4-(1H-indazol-3-yl)-1H-1,2,3-triazol-1-yl]benzamide hydrochloride Step a) Formation of tert-butyl 4-[4-({4-[4-(1H-indazol-3-yl)-1H-1,2,3-triazol-1-yl]benzoyl}amino)-1H-pyrazol-1-yl]azepane-1-carboxylate

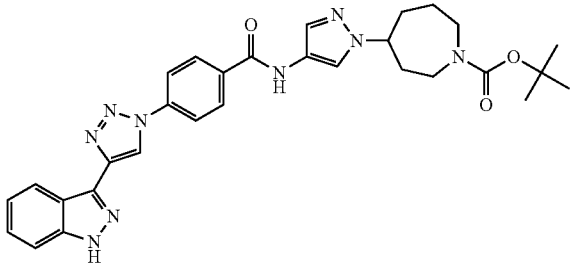 [SMILES: CC(C)(C)OC(=O)N1CCCC(n2cc(NC(=O)c3ccc(-n4cc(-c5n[nH]c6ccccc56)nn4)cc3)cn2)CC1]

The title compound was obtained following procedure described for example 70, but starting from 4-[4-(1H-indazol-3-yl)-1H-1,2,3-triazol-1-yl]benzoic acid (101 mg; 0.33 mmol; 1.0 eq.) and 4-(4-Amino-pyrazol-1-yl)-azepane-1-carboxylic acid tert-butyl ester (111 mg; 0.40 mmol; 1.2 eq.) as a beige solid. $^1$H NMR (300 MHz, DMSO-d6) δ 13.41 (brs, 1H), 10.62 (brs, 1H), 9.46 (s, 1H), 8.38 (d, J=8.2 Hz, 1H), 8.23 (dd, J=8.8, 19.4 Hz, 4H), 8.09 (s, 1H), 7.62 (d, J=6.2 Hz, 2H), 7.46 (t, J=7.4 Hz, 1H), 7.28 (t, J=7.5 Hz, 1H), 4.34 (s, 1H), 3.70-3.50 (m, 1H), 3.48-3.35 (m, 2H), 3.32-3.15 (m, 1H), 2.16-1.55 (m, 6H), 1.44 (s, 9H). HPLC (Condition A): Rt 4.69 min (purity 99.0%). MS (ESI+): 568.3, MS (ESI−): 566.3.

Step b) Formation of N-(1-azepan-4-yl-1H-pyrazol-4-yl)-4-[4-(1H-indazol-3-yl)-1H-1,2,3-triazol-1-yl]benzamide hydrochloride

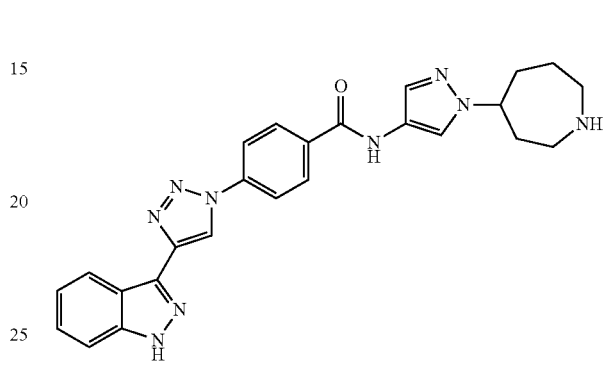

The title compound was obtained following procedure described for example 128, step b), but starting from tert-butyl 4-[4-({4-[4-(1H-indazol-3-yl)-1H-1,2,3-triazol-1-yl]benzoyl}amino)-1H-pyrazol-1-yl]azepane-1-carboxylate (100 mg; 0.18 mmol; 1.0 eq.) as a beige solid (84 mg, 95%). $^1$H NMR (300 MHz, DMSO-d6) δ 13.43 (brs, 1H), 10.72 (brs, 1H), 9.46 (s, 1H), 9.25-8.88 (m, 2H), 8.38 (d, J=8.1 Hz, 1H), 8.33-8.09 (m, 5H), 7.71-7.58 (m, 2H), 7.52-7.40 (m, 1H), 7.27 (t, J=7.5 Hz, 1H), 4.56 (d, J=5.4 Hz, 1H), 3.45-3.02 (m, 4H), 2.40-2.10 (m, 4H), 2.05-1.71 (m, 2H). HPLC (Condition A): Rt 3.12 min (purity 96.1%). MS (ESI+): 468.3, MS (ESI−): 466.4.

Example 131 tert-butyl 4-{4-[4-(1H-indazol-3-yl)-1H-1,2,3-triazol-1-yl]phenyl}-3,6-dihydropyridine-1(2H)-carboxylate hydrochloride

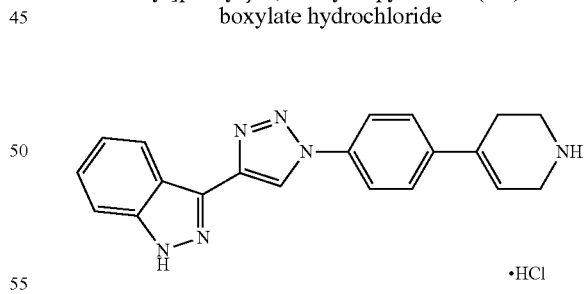

Hydrogen chloride (6.0 mL of a 4N solution in dioxane) was added to a suspension of tert-butyl 4-{4-[4-(1H-indazol-3-yl)-1H-1,2,3-triazol-1-yl]phenyl}-3,6-dihydropyridine-1(2H)-carboxylate (505 mg; 1.14 mmol; 1.0 eq.) in Dioxane (6.0 mL). The resulting light brown suspension was stirred at 350 for 3 h. It was then concentrated to dryness and the resulting beige solid was suspended in dioxane, filtered, rinsed several times with Et$_2$O and dried under vacuum at 400 to give the title compound as a beige solid (379 mg; 87.7%). 1H NMR (300 MHz, DMSO-d6) δ 13.43 (brs, 1H), 9.52-9.14 (m, 3H), 8.36 (d, J=8.1, 1H), 8.10 (d, J=8.0, 2H), 7.75 (d, J=8.1, 2H), 7.62 (d, J=8.5, 1H), 7.44 (t, J=7.6, 1H), 7.26 (t, J=7.2, 1H), 6.37 (s, 1H), 3.96-3.67 (m, 2H), 3.45-3.18 (m, 2H), 2.93-2.57 (m, 2H).

Example 132

3-[1-(4-piperidin-4-ylphenyl)-1H-1,2,3-triazol-4-yl]-1H-indazole hydrochloride

Step a) Formation of tert-butyl 4-{4-[4-(1H-indazol-3-yl)-1H-1,2,3-triazol-1-yl]phenyl}piperidine-1-carboxylate

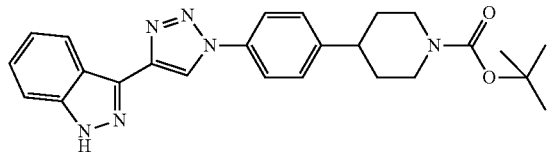 [SMILES: CC(C)(C)OC(=O)N1CCC(c2ccc(-n3cc(-c4n[nH]c5ccccc45)nn3)cc2)CC1]

In a Parr reactor, Pd/C (10% Pd moistened, 50% water, 24 mg, 0.23 mmol, 0.1 eq.) was suspended in a solution of tert-butyl 4-{4-[4-(1H-indazol-3-yl)-1H-1,2,3-triazol-1-yl]phenyl}-3,6-dihydropyridine-1(2H)-carboxylate (1.0 g; 2.26 mmol; 1.0 eq.) and ammonium formate (2.85 g; 45.2 mmol; 20 eq.) in THF (55 mL). The reaction mixture was stirred for 48 h at 70° C. It was then filtered through a celite pad, the cake was rinsed several times with THF and the filtrate was concentrated to dryness. The resulting residue was partitioned between DCM and water. Organic phase was washed with brine, dried over magnesium sulfate, filtered and concentrated. Purification by flash chromatography on silica (DCM: MeOH, gradient from 100:0 to 95:5) gave the title compound as a white foam (950 mg g; 94.5%). 1H NMR (300 MHz, DMSO-d6) δ 13.36 (brs, 1H), 9.27 (s, 1H), 8.36 (d, J=8.2 Hz, 1H), 8.01-7.93 (m, 2H), 7.61 (d, J=8.4 Hz, 1H), 7.56-7.39 (m, 3H), 7.30-7.20 (m, 1H), 4.27-3.94 (m, 2H), 3.01-2.63 (m, 3H), 1.96-1.70 (m, 2H), 1.69-1.47 (m, 2H), 1.43 (s, 9H). 1H HPLC (max plot) 97.2%; Rt 5.33 min. UPLC/MS: (MS+) 445.2, (MS−) 443.2.

Step b) Formation of 3-[1-(4-piperidin-4-ylphenyl)-1H-1,2,3-triazol-4-yl]-1H-indazole hydrochloride

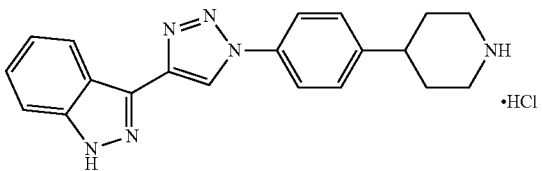 [SMILES: c1ccc2c(-c3cn(-c4ccc(C5CCNCC5)cc4)nn3)n[nH]c2c1 ; Cl]

The title compound was obtained, following procedure described for example 131, but starting from tert-butyl 4-{4-[4-(1H-indazol-3-yl)-1H-1,2,3-triazol-1-yl]phenyl}piperidine-1-carboxylate (900 mg; 2.02 mmol; 1.0 eq.) as a white powder (700 mg; 90.8%). 1H NMR (300 MHz, DMSO-d6) δ 13.43 (brs, 1H), 9.29 (s, 1H), 9.17-8.72 (m, 2H), 8.36 (d, J=8.1 Hz, 1H), 8.07-7.94 (m, 2H), 7.67-7.56 (m, 1H), 7.55-7.38 (m, 3H), 7.32-7.19 (m, 1H), 3.51-3.24 (m, 2H), 3.19-2.84 (m, 3H), 2.15-1.73 (m, 4H). HPLC (max plot) 99.4%; Rt 2.62 min. UPLC/MS: (MS+) 345.2, (MS−) 343.1.

Example 133

3-(1-{4-[1-(2-fluoroethyl)piperidin-4-yl]phenyl}-1H-1,2,3-triazol-4-yl)-1H-indazole

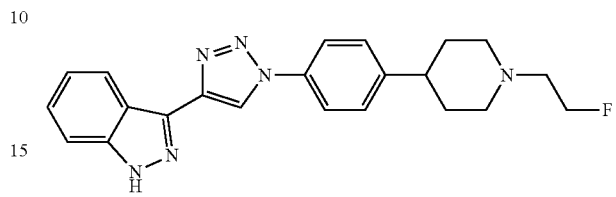

1-bromo-2-fluoroethane (30 mg; 0.24 mmol; 0.9 eq.) was added to a suspension of 3-[1-(4-piperidin-4-ylphenyl)-1H-1,2,3-triazol-4-yl]-1H-indazole (100 mg; 0.26 mmol; 1.0 eq.) and NaHCO₃ (331 mg; 3.94 mmol; 15 eq.) in dry DMF (2 mL). The reaction mixture was heated in MW at 100° C. for 3 h. It was then diluted with water and extracted with EtOAc. Combined organic phases were washed with brine, dried over magnesium sulfate, filtered and concentrated. Purification by flash chromatography on silica (DCM: MeOH, gradient from 100:0 to 90:10) gave the title compound as a white solid (40 mg, 39%). 1H NMR (300 MHz, DMSO-d6) δ 13.36 (brs, 1H), 9.27 (s, 1H), 8.41-8.31 (m, 1H), 8.01-7.92 (m, 2H), 7.64-7.58 (m, 1H), 7.55-7.38 (m, 3H), 7.30-7.20 (m, 1H), 4.56 (dt, J=47.8, 4.9 Hz, 2H), 3.09-2.96 (m, 2H), 2.75-2.54 (m, 3H), 2.22-2.07 (m, 2H), 1.88-1.61 (m, 4H). HPLC (max plot) 99.8%; Rt 2.64 min. UPLC/MS: (MS+) 391.1, (MS−) 389.2

Example 134

3-{1-[4-(1-acetylpiperidin-4-yl)phenyl]-1H-1,2,3-triazol-4-yl}-1H-indazole

Step a) Formation of 1-acetyl-3-{1-[4-(1-acetylpiperidin-4-yl)phenyl]-1H-1,2,3-triazol-4-yl}-1H-indazole

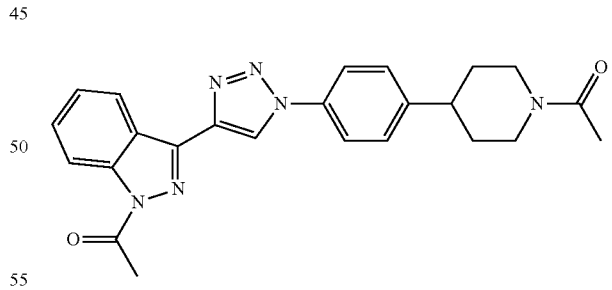

Acetyl chloride (17 μl; 0.25 mmol; 0.95 eq.) was added to a solution of 3-[1-(4-piperidin-4-ylphenyl)-1H-1,2,3-triazol-4-yl]-1H-indazole (100 mg; 0.26 mmol; 1.0 eq.) in pyridine (1.50 mL). the reaction mixture was stirred at RT for 1 h. Acetyl chloride (9 μl; 0.13 mmol; 0.5 eq.) was added again and the reaction mixture was stirred at RT for 1 h. It was the concentrated under reduced pressure and the residue was diluted with DCM. Water was added, the two phases were separated and aqueous phase was extracted with DCM. Combined organic phases were washed with brine, dried over magnesium sulfate, filtered and concentrated. Purification by flash chromatography on silica (DCM:MeOH, gradient 100:0 to 90:10) gave the title compound as a beige solid (85 mg, 76%). HPLC (max plot) 96.2%; Rt 4.08 min. UPLC/MS: (MS+) 429.2.

Step b) Formation of 3-{1-[4-(1-acetylpiperidin-4-yl)phenyl]-1H-1,2,3-triazol-4-yl}-1H-indazole

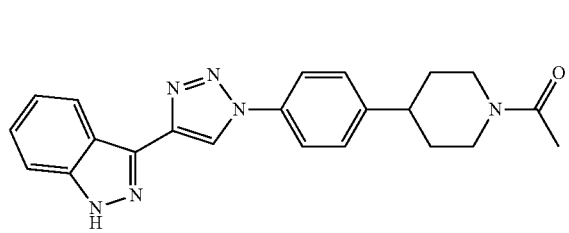 [SMILES: CC(=O)N1CCC(c2ccc(-n3cc(-c4n[nH]c5ccccc45)nn3)cc2)CC1]

A solution of 1-acetyl-3-{1-[4-(1-acetylpiperidin-4-yl)phenyl]-1H-1,2,3-triazol-4-yl}-1H-indazole (85 mg; 0.20 mmol; 1.0 eq.) and potassium carbonate (274 mg; 1.98 mmol; 10 eq.).

in MeOH (1.0 mL) and DCM (1.00 mL) was stirred at RT for 1 h. It was then diluted with water. Aqueous phase was separated and extracted with DCM. Combined organic phases were washed with brine, dried over magnesium sulfate, filtered and concentrated to give the title compound as a white powder (35 mg, 46%). 1H NMR (300 MHz, DMSO-d6) δ 13.35 (brs, 1H), 9.28 (s, 1H), 8.41-8.31 (m, 1H), 8.03-7.93 (m, 2H), 7.64-7.58 (m, 1H), 7.55-7.39 (m, 3H), 7.30-7.20 (m, 1H), 4.64-4.47 (m, 1H), 4.02-3.84 (m, 1H), 3.23-3.07 (m, 1H), 2.98-2.81 (m, 1H), 2.68-2.54 (m, 1H), 2.05 (s, 3H), 1.92-1.76 (m, 2H), 1.74-1.39 (m, 2H). HPLC (max plot) 98.5%; Rt 3.90 min. UPLC/MS: (MS+) 387.2, (MS−) 385.2.

Example 135

6-fluoro-3-(1-{4-[1-(3,3,3-trifluoropropyl)piperidin-4-yl]phenyl}-1H-1,2,3-triazol-4-yl)-1H-indazole

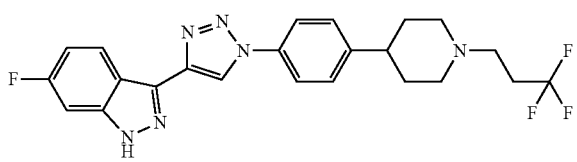 [SMILES: Fc1ccc2c(-c3cn(-c4ccc(C5CCN(CCC(F)(F)F)CC5)cc4)nn3)n[nH]c2c1]

The title compound was obtained, following procedure described for intermediate 10, but starting from 3-ethynyl-6-fluoro-1H-indazole (60 mg; 0.37 mmol; 1.0 eq.) and 4-(4-azidophenyl)-1-(3,3,3-trifluoropropyl)piperidine (112 mg; 0.37 mmol; 1.0 eq.) as an amorphous beige foam (38 mg; 22%). 1H NMR (300 MHz, DMSO-d6-d6) δ: 13.43 (brs, 1H), 9.29 (s, 1H), 8.38 (dd, J=8.9, 5.4 Hz, 1H), 8.07-7.89 (m, 2H), 7.61-7.43 (m, 2H), 7.40 (dd, J=9.5, 1.9 Hz, 1H), 7.15 (td, J=9.3, 2.1 Hz, 1H), 3.18-2.99 (m, 2H), 2.85-2.52 (m, 5H), 2.34-2.11 (m, 2H), 1.95-1.54 (m, 4H). HPLC (Condition A): Rt 3.21 min (purity 93.0%). UPLC/MS: (MS+) 459.5, (MS−) 457.5.

Example 136

1,1,1-trifluoro-3-(4-{4-[4-(6-methyl-1H-indazol-3-yl)-1H-1,2,3-triazol-1-yl]phenyl}piperidin-1-yl)propan-2-ol

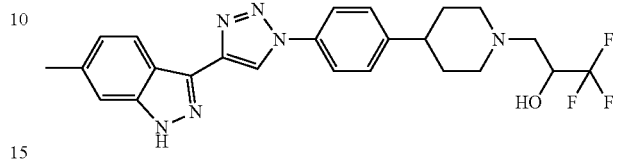

The title compound was obtained, following procedure described for intermediate 10, but starting from 3-ethynyl-6-methyl-1H-indazole (60 mg; 0.38 mmol; 1.0 eq.) and 3-[4-(4-azidophenyl)piperidin-1-yl]-1,1,1-trifluoropropan-2-ol (121 mg; 0.38 mmol; 1.0 eq.) as a white foam (53 mg; 29%). 1H NMR (300 MHz, DMSO-d6-d6) δ 13.18 (brs, 1H), 9.24 (s, 1H), 8.22 (d, J=8.3 Hz, 1H), 8.01-7.90 (m, 2H), 7.57-7.45 (m, 2H), 7.37 (s, 1H), 7.09 (d, J=8.4 Hz, 1H), 4.27-4.06 (m, 1H), 3.12-2.92 (m, 3H), 2.70-2.52 (m, 3H), 2.48 (s, 3H), 2.29-2.07 (m, 2H), 1.89-1.58 (m, 4H). HPLC (Condition A): Rt 3.22 min (purity 94.7%). UPLC/MS: (MS+) 471.5, (MS−) 469.5.

Example 137

4-{4-[4-(1H-indazol-3-yl)-1H-1,2,3-triazol-1-yl]phenyl}piperidin-3-ol hydrochloride Step a) Formation of tert-butyl 3-hydroxy-4-{4-[4-(1H-indazol-3-yl)-1H-1,2,3-triazol-1-yl]phenyl}piperidine-1-carboxylate

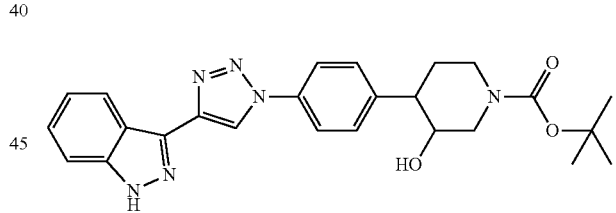

To a stirred solution of borane-methyl sulfide complex (587 μl of a 2.0 M solution in THF; 1.18 mmol; 1.3 eq.) in THF (6.0 mL) maintained at 0° C. under nitrogen atmosphere, was added dropwise a solution of tert-butyl 4-{4-[4-(1H-indazol-3-yl)-1H-1,2,3-triazol-1-yl]phenyl}-3,6-dihydropyridine-1(2H)-carboxylate (400 mg; 0.90 mmol; 1.0 eq.) in THF (6.0 mL). The reaction mixture was stirred at RT for 12 h. Further borane-methyl sulfide complex (135 μl of a 2.00 M solution in THF; 0.27 mmol; 0.3 eq.) was added and the reaction mixture was stirred at RT for 1 more hour. The reaction mixture was then cooled down to 0° C. before the dropwise addition of NaOH (3.6 mL) followed by hydrogen peroxide (615 μl). It was then allowed to warm to RT and stir O/N. The reaction mixture was then diluted with water and extracted with DCM (four times). The combined organic phases were washed with brine, dried over magnesium sulfate, filtered and concentrated. Purification by flash chromatography on silica (EtOAc:heptanes, gradient from 90:10 to 40:60) to give the title compound as a white foam (90 mg, 22%). HPLC (max plot) 96.4%; Rt % 4.16 min. UPLC/MS: (MS+) 461.4, (MS−) 459.5.

Step b) Formation of 4-{4-[4-(1H-indazol-3-yl)-1H-1,2,3-triazol-1-yl]phenyl}piperidin-3-ol hydrochloride

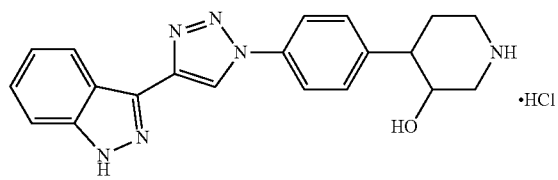 [SMILES: OC1CNCCC1c1ccc(-n2cc(-c3n[nH]c4ccccc34)nn2)cc1 ; Cl]

The title compound was obtained, following procedure described for example 131, but starting from tert-butyl 3-hydroxy-4-{4-[4-(1H-indazol-3-yl)-1H-1,2,3-triazol-1-yl]phenyl}piperidine-1-carboxylate (85 mg; 0.18 mmol; 1.0 eq.) as a white solid (70 mg, 96%). 9:1 mixture of cis and trans isomer: 1H NMR (300 MHz, DMSO-d6) δ 13.41 (brs, 1H), 9.29 (s, 1H), 9.27-9.04 (m, 2H), 8.37 (d, J=8.1 Hz, 1H), 8.13-7.95 (m, 2H), 7.66-7.57 (m, 1H), 7.52-7.39 (m, 2H), 7.32-7.19 (m, 1H), 4.61 (brs, 1H), 3.98 (td, J=10.6, 4.4 Hz, 1H), 3.47-2.56 (m, 6H), 2.13-1.71 (m, 2H). HPLC (max plot) 96.0%; Rt % 2.36 min. UPLC/MS: (MS+) 361.3, (MS−) 359.4.

Example 138

N,N-dimethyl-1-(4-{4-[5-(2-methylprop-1-en-1-yl)-1H-indazol-3-yl]-1H-1,2,3-triazol-1-yl}benzoyl)piperidin-4-amine

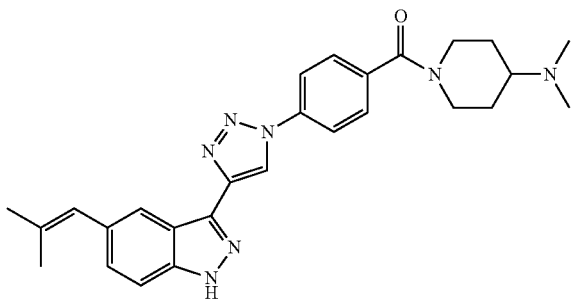 [SMILES: CC(C)=Cc1ccc2[nH]nc(-c3cn(-c4ccc(C(=O)N5CCC(N(C)C)CC5)cc4)nn3)c2c1]

A mixture of 1-{4-[4-(5-bromo-1H-indazol-3-yl)-1H-1,2,3-triazol-1-yl]benzoyl}-N,N-dimethylpiperidin-4-amine (160 mg; 0.32 mmol; 1.0 eq.), 1-{4-[4-(5-bromo-1H-indazol-3-yl)-1H-1,2,3-triazol-1-yl]benzoyl}-N,N-dimethylpiperidin-4-amine (160 mg; 0.32 mmol; 1.0 eq.), PdCl₂dppf (24 mg; 0.03 mmol; 0.1 eq.) and potassium carbonate (224 mg; 1.62 mmol; 5.0 eq.) in dioxane (1 mL) and water (1 mL) was heated at 80° C. O/N in a sealed tube. The reaction mixture was then filtered through a celite pad and filtrate was extracted twice with DCM. Combined organic phases were washed with brine, dried over magnesium sulfate, filtered and concentrated. Purification by flash chromatography on silica (DCM:MeOH, gradient form 90:10 to 50:50) gave the title compound as a brown powder (68 mg, 45%).

1H NMR (DMSO) δ 13.35 (s, 1H), 9.37 (s, 1H), 8.21 (s, 1H), 8.17-8.11 (m, 2H), 7.68-7.62 (m, 2H), 7.55 (d, J=8.7 Hz, 1H), 7.35-7.29 (m, 1H), 6.47-6.43 (m, 1H), 4.54-4.38 (m, 1H), 3.73-3.55 (m, 1H), 3.18-2.74 (m, 2H), 2.42-2.29 (m, 1H), 2.19 (s, 6H), 1.93 (s, 3H), 1.90 (s, 3H), 1.88-1.61 (m, 2H), 1.47-1.29 (m, 2H). HPLC (max plot) 98.0%; Rt 3.71 min. UPLC/MS: (MS+) 470.3, (MS−) 468.3.

Example 139

1-{4-[4(5-isobutyl-1H-indazol-3-yl)-1H-1,2,3-triazol-1-yl]benzoyl}-N,N-dimethylpiperidin-4-amine

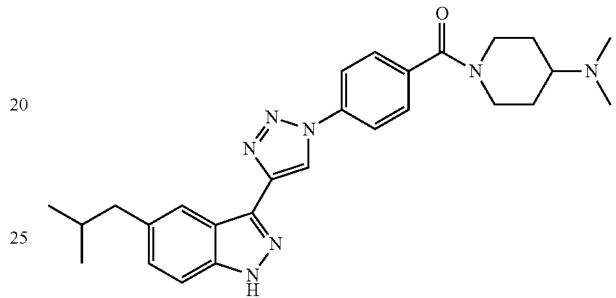

The title compound was obtained, following procedure described for example 132, but starting from N,N-dimethyl-1-(4-{4-[5-(2-methylprop-1-en-1-yl)-1H-indazol-3-yl]-1H-1,2,3-triazol-1-yl}benzoyl)piperidin-4-amine (65 mg; 0.14 mmol; 1.0 eq.) as a white foam (26 mg, 40%). 1H NMR (300 MHz, DMSO-d6) δ 13.28 (brs, 1H), 9.35 (s, 1H), 8.17-8.06 (m, 3H), 7.73-7.60 (m, 2H), 7.52 (d, J=8.5 Hz, 1H), 7.27 (dd, J=9.8 Hz, 1H), 4.59-4.35 (m, 1H), 3.90-3.25 (m, 1H), 3.26-2.72 (m, 2H), 2.62 (d, J=7.1 Hz, 2H), 2.47-2.35 (m, 1H), 2.22 (s, 6H), 2.03-1.63 (m, 3H), 1.53-1.28 (m, 2H), 0.91 (d, J=6.6 Hz, 6H). HPLC (max plot) 98.0%; Rt 3.82 min. UPLC/MS: (MS+) 472.3, (MS−) 470.3.

Example 140

3-{1-[1-(8-methyl-8-azabicyclo[3.2.1]oct-3-yl)-1H-pyrazol-4-yl]-1H-1,2,3-triazol-4-yl}-1H-indazole

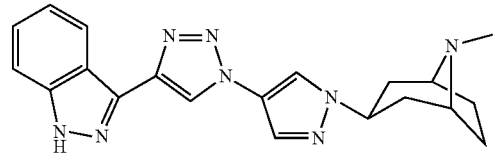 [SMILES: CN1C2CCC1CC(n1cc(-n3cc(-c4n[nH]c5ccccc45)nn3)cn1)C2]

The title compound was obtained, following procedure described for intermediate 10, but starting from 3-(4-azido-1H-pyrazol-1-yl)-8-methyl-8-azabicyclo[3.2.1]octane (139 mg; 0.6 mmol; 1.0 eq.) and 3-ethynyl-1H-indazole (85 mg; 0.60 mmol; 1.00 eq.) as a yellow solid (40 mg, 16%). 1H NMR (300 MHz, DMSO-d6) δ 13.33 (s, 1H), 9.05 (s, 1H), 8.56 (s, 1H), 8.33 (d, J=8.1 Hz, 1H), 8.23 (s, 1H), 8.11 (s, 1H), 7.60 (d, J=8.4 Hz, 1H), 7.49-7.38 (m, 1H), 7.25 (t, J=7.4 Hz, 1H), 4.76-4.54 (m, 1H), 3.43 (br s, 2H), 2.39 (s, 3H), 2.22 (t, J=11.9 Hz, 2H), 2.08 (d, J=10.1 Hz, 2H), 1.96 (d, J=10.2 Hz, 2H), 1.86-1.71 (m, 2H). HPLC (max plot) 98.5%; Rt 2.70 min. UPLC/MS: (MS+) 375.2, (MS−) 373.1.

Example 141

3-{1-[4-(morpholin-4-ylcarbonyl)phenyl]-1H-1,2,3-triazol-4-yl}-5-(piperidin-4-ylmethyl)-1H-indazole hydrochloride Step a) Formation of tert-butyl 4-[(3-{1-[4-(morpholin-4-ylcarbonyl)phenyl]-1H-1,2,3-triazol-4-yl}-1H-indazol-5-yl)methyl]piperidine-1-carboxylate

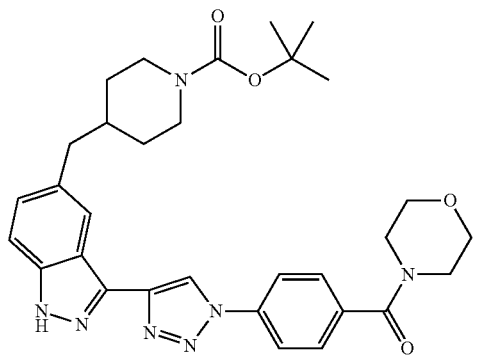 [SMILES: CC(C)(C)OC(=O)N1CCC(Cc2ccc3[nH]nc(-c4cn(-c5ccc(C(=O)N6CCOCC6)cc5)nn4)c3c2)CC1]

A degassed solution of 1-N-Boc-4-methylene-piperidine (48 mg; 0.24 mmol; 1.1 eq.) and 9-BBN (0.5 M 0.44 mL of a 0.5 M solution in THF; 0.22 mmol; 1.0 eq.) in THF (0.5 mL) was heated at 800 for 1 h in a sealed tube. This solution was allowed to cool to RT and cannulated to a degassed mixture of 5-bromo-3-{1-[4-(morpholin-4-ylcarbonyl)phenyl]-1H-1,2,3-triazol-4-yl}-1H-indazole (100 mg; 0.22 mmol; 1.0 eq.), PdCl$_2$dppf (1 mg; 0.001 mmol; 0.01 eq.) and potassium carbonate (76 mg; 0.55 mmol; 2.5 eq.) in DMF (1 mL) and water (0.1 mL). The resulting mixture was heated at 65° C. O/N. As the reaction was not complete, a second solution of borane was prepared (from 0.24 mmol of 1-N-Boc-4-methylene-piperidine) and added to the reaction mixture which was heated at 65° C. for one more night. The reaction mixture was poured into water and extracted twice with EtOAc. Combined organic phases were washed with brine, dried over magnesium sulfate, filtered and concentrated. Purification by flash chromatography on silica (DCM:MeOH, gradient from 100:0 to 90:10) gave the title compound as a yellow powder (110 mg, 87%). 1H NMR (300 MHz, DMSO-d6) δ 13.29 (brs, 1H), 9.36 (s, 1H), 8.21-8.08 (m, 3H), 7.74-7.65 (m, 2H), 7.56-7.48 (m, 1H), 7.32-7.23 (m, 1H), 4.04-3.81 (m, 2H), 3.79-3.36 (m, 8H), 2.83-2.56 (m, 3H), 1.84-1.50 (m, 3H), 1.49-1.39 (m, 1H), 1.37 (s, 9H), 1.21-0.91 (m, 2H). HPLC (max plot) 86.0%; Rt 4.36 min. UPLC/MS: (MS−) 470.2 (M-tBuOCO).

Step b) Formation of 3-{1-[4-(morpholin-4-ylcarbonyl)phenyl]-1H-1,2,3-triazol-4-yl}-5-(piperidin-4-ylmethyl)-1H-indazole hydrochloride

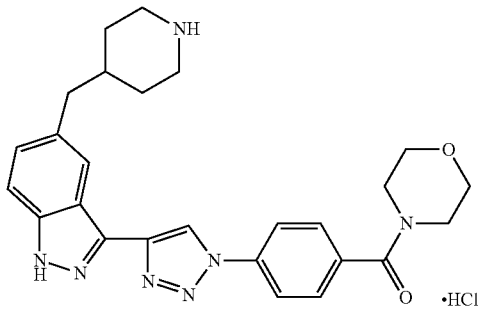 [SMILES: O=C(c1ccc(-n2cc(-c3n[nH]c4ccc(CC5CCNCC5)cc34)nn2)cc1)N1CCOCC1 ; Cl]

The title compound was obtained, following procedure described for example 131, but starting from tert-butyl 4-[(3-{1-[4-(morpholin-4-ylcarbonyl)phenyl]-1H-1,2,3-triazol-4-yl}-1H-indazol-5-yl)methyl]piperidine-1-carboxylate (100 mg; 0.17 mmol; 1.0 eq.) as a beige solid (31 mg, 35%). 1H NMR (300 MHz, DMSO-d6) δ 13.34 (brs, 1H), 9.37 (s, 1H), 8.84-8.66 (m, 1H), 8.57-8.35 (m, 1H), 8.15 (d, J=7.7 Hz, 3H), 7.69 (d, J=8.4 Hz, 2H), 7.55 (d, J=8.4 Hz, 1H), 7.28 (d, J=8.9 Hz, 1H), 3.92-3.30 (m, 8H), 3.23 (d, J=11.1 Hz, 2H), 2.50 (s, 4H), 1.99-1.65 (m, 3H), 1.51-1.28 (m, 2H). HPLC (max plot) 93.2%; Rt 2.21 min. UPLC/MS: (MS−) 470.2.

Example 142 methyl 3-{1-[4-(morpholin-4-ylmethyl)phenyl]-1H-1,2,3-triazol-4-yl}-1H-indazole-5-carboxylate

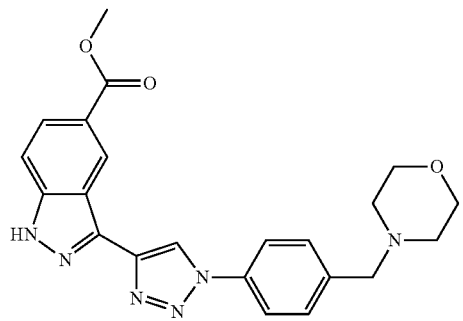 [SMILES: COC(=O)c1ccc2[nH]nc(-c3cn(-c4ccc(CN5CCOCC5)cc4)nn3)c2c1]

The title compound was obtained, following procedure described for intermediate 10, but starting from 5-(benzyloxy)-3-ethynyl-1-{[2-(trimethylsilyl)ethoxy]methyl}-1H-indazole (400 mg; 2.0 mmol; 1.0 eq.) and 4-(4-azidobenzoyl)morpholine (436 µl; 2.0 mmol; 1.0 eq.) as a white solid (508 mg, 61%). 1H NMR (300 MHz, DMSO-d6) δ 13.73 (s, 1H), 9.38 (s, 1H), 9.10 (s, 1H), 8.07-7.96 (m, 3H), 7.71 (dd, J=8.8, 0.7 Hz, 1H), 7.57 (d, J=8.5 Hz, 2H), 3.92 (s, 3H), 3.68-3.52 (m, 6H), 2.46-2.29 (m, 4H). HPLC (max plot) 97.7%; Rt 2.45 min. UPLC/MS: (MS+) 419.1, (MS−) 417.1.

Example 143

N-(1-methylpiperidin-4-yl)-3-{1-[4-(morpholin-4-ylmethyl)phenyl]-1H-1,2,3-triazol-4-yl}-1H-indazole-5-carboxamide

Step a) Formation of 3-{1-[4-(morpholin-4-ylmethyl)phenyl]-1H-1,2,3-triazol-4-yl}-1H-indazole-5-carboxylic acid

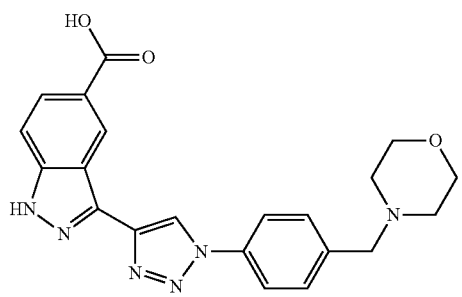 [SMILES: O=C(O)c1ccc2[nH]nc(-c3cn(-c4ccc(CN5CCOCC5)cc4)nn3)c2c1]

A solution of methyl 3-{1-[4-(morpholin-4-ylmethyl)phenyl]-1H-1,2,3-triazol-4-yl}-1H-indazole-5-carboxylate (351 mg; 0.84 mmol; 1.0 eq.) and lithium hydroxide (201 mg; 8.4 mmol; 10 eq.) in THF (3.5 mL) and water (3.5 mL) was stirred O/N at 40° C. A 5N solution of HCl was then added and the precipitate was filtered, rinsed with water and dried under reduced pressure at 40° C. O/N to give the title compound as a white powder (366 mg, 100%). UPLC/MS: (MS+) 405.1, (MS−) 403.1.

Step b) Formation of N-(1-methylpiperidin-4-yl)-3-{1-[4-(morpholin-4-ylmethyl)phenyl]-1H-1,2,3-triazol-4-yl}-1H-indazole-5-carboxamide

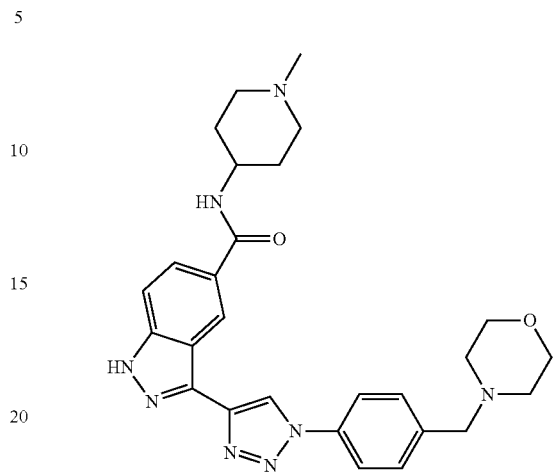

The title compound was obtained, following procedure described for intermediate 3, but starting from 3-{1-[4-(morpholin-4-ylmethyl)phenyl]-1H-1,2,3-triazol-4-yl}-1H-indazole-5-carboxylic acid (50 mg; 0.12 mmol; 1.0 eq.) and 4-amino-1-methylpiperidine (64 mg; 0.56 mmol; 4.5 eq.) as a white solid (33 mg, 53%). 1H NMR (300 MHz, DMSO-d6) δ 13.61 (s, 1H), 9.41 (s, 1H), 8.90 (s, 1H), 8.67 (d, J=6.9 Hz, 1H), 8.04 (d, J=8.5 Hz, 2H), 7.95 (dd, J=8.8, 1.5 Hz, 1H), 7.65 (d, J=8.8 Hz, 1H), 7.58 (d, J=8.5 Hz, 2H), 4.18-3.99 (m, 1H), 3.68-3.53 (m, 4H), 3.47-3.25 (m, 6H), 3.13-2.91 (m, 2H), 2.72 (s, 3H), 2.47-2.32 (m, 2H), 2.11-1.80 (m, 4H). HPLC (max plot) 100.0%; Rt % 1.60 min. UPLC/MS: (MS+) 501.2, (MS−) 499.2.

Example 144

6-(4-hydroxyphenyl)-2-[(3-{1-[4-(morpholin-4-ylcarbonyl)phenyl]-1H-1,2,3-triazol-4-yl}-1H-indazol-5-yl)methyl]pyridazin-3(2H)-one

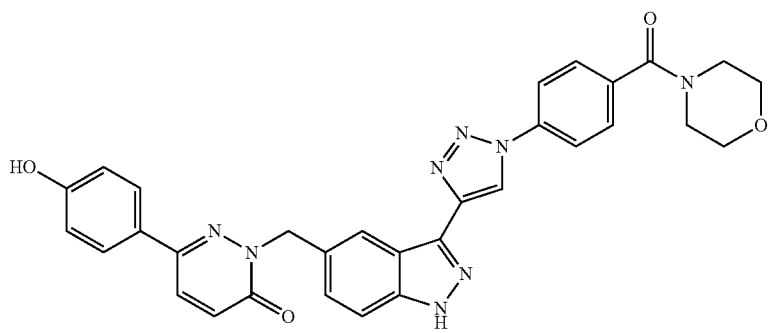 [SMILES: O=C(c1ccc(-n2cc(-c3n[nH]c4ccc(Cn5nc(-c6ccc(O)cc6)ccc5=O)cc34)nn2)cc1)N1CCOCC1]

A suspension of PdCl$_2$(PPh$_3$)$_2$ (10 mg; 0.01 mmol; 0.11 eq.), tert-butyl 5-[(3-chloro-6-oxopyridazin-1(6H)-yl)methyl]-3-{1-[4-(morpholin-4-ylcarbonyl)phenyl]-1H-1,2,3-triazol-4-yl}-1H-indazole-1-carboxylate (79 mg; 0.13 mmol; 1.0 eq.), 4-hydroxyphenylboronic acid (35 mg; 0.25 mmol; 2.0 eq.) and cesium fluoride (65 mg; 0.43 mmol; 3.3 eq.) in DMF (2.0 mL) and water (1.0 mL) was degassed with argon in a sealed tube and heated in MW at 120° C. for 1.5 h. The mixture was then filtered through a celite pad. The filtrate was diluted with EtOAc. The phases were separated and organic phase was washed with a 1 N solution of HCl, dried over magnesium sulfate, filtered and concentrated. Purification of the crude by preparative HPLC gave the title compound as a white solid (9 mg, 9%). 1H NMR (300 MHz, DMSO-d6) δ 13.40 (s, 1H), 9.85 (br, 1H), 9.38 (s, 1H), 8.46 (s, 1H), 8.18-8.12 (m, 2H), 7.98 (d, J=9.8 Hz, 1H), 7.76 (d, J=8.7 Hz, 2H), 7.69 (d, J=8.6 Hz, 2H), 7.59 (d, J=8.6 Hz, 1H), 7.54-7.46 (m, 1H), 7.05 (d, J=9.7 Hz, 1H), 6.85 (d, J=8.7 Hz, 2H), 5.46 (s, 2H), 3.75-3.43 (m, 8H). HPLC (max plot) 98.6%; Rt 3.14 min. UPLC/MS: (MS+) 575.1, (MS−) 573.0.

Example 145

3-(1-{4[(1S,4S)-2-oxa-5-azabicyclo[2.2.1]hept-5-ylmethyl]phenyl}-1H-1,2,3-triazol-4-yl)-1H-indazole

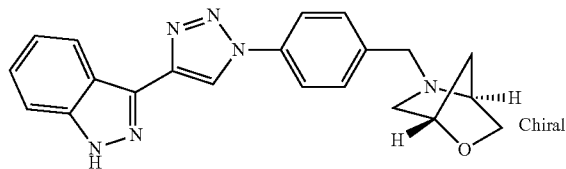 [SMILES: c1ccc2c(-c3cn(-c4ccc(CN5C[C@@H]6C[C@H]5CO6)cc4)nn3)n[nH]c2c1]

The title compound was obtained, following procedure described for intermediate 10, but starting from 3-Ethynyl-1H-indazole (74 mg; 0.52 mmol; 1.0 eq.) and (1S,4S)-5-(4-azidobenzyl)-2-oxa-5-azabicyclo[2.2.1]heptane (120 mg; 0.52 mmol; 1.0 eq.) as a yellow solid (79 mg, 40%). 1H NMR (300 MHz, DMSO-d6) δ 13.36 (s, 1H), 9.29 (s, 1H), 8.37 (d, J=8.1 Hz, 1H), 8.00 (d, J=8.6 Hz, 2H), 7.66-7.53 (m, 3H), 7.49-7.39 (m, 1H), 7.30-7.20 (m, 1H), 4.38 (brs, 1H), 3.96 (d, J=7.4 Hz, 1H), 3.82 (d, J=3.3 Hz, 2H), 3.56 (dd, J=7.5, 1.8 Hz, 1H), 3.49 (brs, 1H), 2.77 (dd, J=9.9, 1.6 Hz, 1H), 2.45 (d, J=9.9 Hz, 1H), 1.84 (dd, J=9.4, 1.8 Hz, 1H), 1.62 (d, J=9.6 Hz, 1H). HPLC (max plot) 98.4%; Rt 2.32 min. UPLC/MS: (MS+) 373.3, (MS−) 371.2.

Example 146

3-(3-{1-[4-(morpholin-4-ylcarbonyl)phenyl]-1H-1,2,3-triazol-4-yl}-1H-indazol-6-yl)prop-2-yn-1-ol

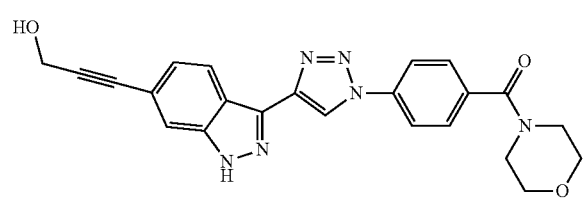 [SMILES: O=C(c1ccc(-n2cc(-c3n[nH]c4cc(C#CCO)ccc34)nn2)cc1)N1CCOCC1]

A mixture of {4-[4-(6-Bromo-1H-indazol-3-yl)-[1,2,3]triazol-1-yl]-phenyl}-morpholin-4-yl-methanone (150 mg; 0.33 mmol; 1.0 eq.), propargyl alcohol (39 µl; 0.66 mmol; 2.0 eq.) and Pd(PPh$_3$)$_4$ (19 mg, 0.02 mmol, 0.05 eq.) in pyrrolidine (1.5 mL) was heated O/N at 80° C. in a sealed tube. The reaction mixture was then diluted with DCM and washed with a saturated solution of NH$_4$Cl (three times) and brine. Organic phase was dried over magnesium sulfate, filtered and concentrated. Purification by preparative HPLC gave the title compound as a beige solid (40 mg, 28%). 1H NMR (300 MHz, DMSO-d6-d6): 13.50 (brs, 1H), 9.42 (s, 1H), 8.34 (dd, J=8.5 Hz, 1.0 Hz, 1H), 8.15 (d, J=8.6 Hz, 2H), 7.70-7.67 (m, 3H), 7.28 (dd, J=8.5 Hz, 1.0 Hz, 1H), 5.40 (t, J=6.0 Hz, 1H), 4.35 (d, J=6.0 Hz, 2H), 3.64 (m, 6H), 3.47 (m, 2H).

HPLC (max plot) 94.4%; Rt % 2.65 min. UPLC/MS: (MS+) 429.1, (MS−) 427.2.

Example 147

3-(3-{1-[4-(morpholin-ylcarbonyl)phenyl]-1H-1,2,3-triazol-4-yl}-1H-indazol-6-yl)propan-1-ol

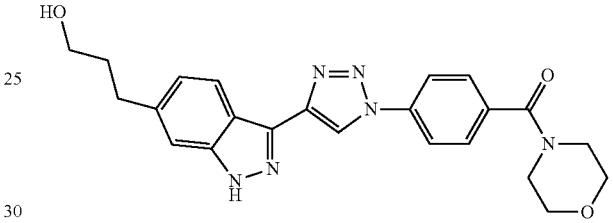

A solution of 3-(3-{1-[4-(morpholin-4-ylcarbonyl)phenyl]-1H-1,2,3-triazol-4-yl}-1H-indazol-6-yl)prop-2-yn-1-ol (40 mg; 0.09 mmol; 1.0 eq.) in DCM (2.0 mL) and MeOH (2.0 mL) was passed through a Pd/C cartridge at RT with full H$_2$ at 1 mL/min in the H-cube. Solvents were removed under reduced pressure and the crude obtained was purified by preparative HPLC to give the title compound as a white solid (15 mg, 37%). 1H NMR (300 MHz, DMSO-d6) δ 13.23 (brs, 1H), 9.37 (s, 1H), 8.24 (d, J=8.3 Hz, 1H), 8.15 (d, J=8.6 Hz, 2H), 7.68 (d, J=8.6 Hz, 2H), 7.37 (m, 1H), 7.12 (dd, J=8.3 Hz, 1.1 Hz, 1H), 4.52 (t, J=5.1 Hz, 1H), 3.64 (m, 6H), 3.42 (m, 2H), 2.94-2.75 (m, 4H), 1.85-1.72 (m, 2H). HPLC (max plot) 98.3%; Rt % 2.69 min. UPLC/MS: (MS+) 433.1, (MS−) 431.2.

Example 148

N-(1-methylpiperidin-3-yl)-3-{1-[4-(morpholin-4-ylcarbonyl)phenyl]-1H-1,2,3-triazol-4-yl}-1H-indazol-5-amine

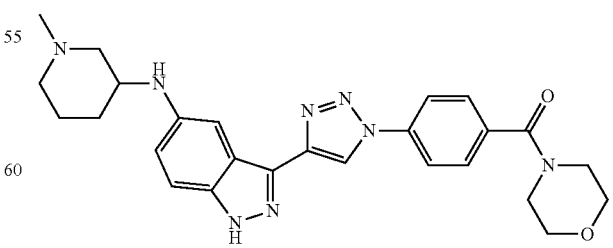

LiHMDS (1.99 mL of a 1.0 M in THF; 1.99 mmol; 4.5 eq.) was added to a degassed suspension of {4-[4-(5-Bromo-1H-indazol-3-yl)-[1,2,3]triazol-1-yl]-phenyl}-morpholin-4-ylmethanone (200 mg; 0.44 mmol; 1.0 eq.), 3-Amino-1-methylpiperidine dihydrochloride, 98% (99 mg; 0.53 mmol; 1.2 eq.), Chloro[2-(dicyclohexylphosphino)-3,6-dimethoxy-2'-4'-6'-tri-1-propyl-1,1'-biphenyl][2-(2-aminoethyl)phenyl] palladium(II), (7.0 mg; 0.01 mmol; 0.02 eq.) and dicyclohexyl-(2',4',6'-triisopropyl-3,6-dimethoxy-biphenyl-2-yl)-phosphane (5.0 mg; 0.01 mmol; 0.02 eq.) in DMF (500 μl). The reaction mixture was then heated at 70° C. O/N. As the reaction was not completed, further 3-Amino-1-methylpiperidine dihydrochloride (99 mg; 0.53 mmol; 1.2 eq.), Chloro[2-(dicyclohexylphosphino)-3,6-dimethoxy-2'-4'-6'-tri-1-propyl-1,1'-biphenyl][2-(2-aminoethyl)phenyl]palladium (II) (7.0 mg; 0.01 mmol; 0.02 eq.), dicyclohexyl-(2',4',6'-triisopropyl-3,6-dimethoxy-biphenyl-2-yl)-phosphane (5.0 mg; 0.01 mmol; 0.02 eq.) and LiHMDS (1.99 mL of a 1.0 M in THF; 1.99 mmol; 4.5 eq.) were added and the reaction mixture was heated again at 70° C. for 12 h. It was diluted with DCM and washed with water. The organic phase was dried over magnesium sulfate, filtered and concentrated. Purification by preparative HPLC gave the title compound as a brown solid (10 mg; 5%). 1H NMR (300 MHz, DMSO-d6-d6): 12.96 (brs, 1H), 9.26 (s, 1H), 8.14 (d, J=8.6 Hz, 2H), 7.68 (d, J=8.6 Hz, 2H), 7.36-7.33 (m, 1H), 6.96-6.92 (m, 2H), 5.36 (m, 1H), 3.64-3.55 (m, 1H), 3.00 (m, 1H), 2.73 (m, 1H), 2.23 (m, 3H), 1.99-1.59 (m, 3H), 1.30 (m, 1H). HPLC (max plot) 94.3%; Rt % 1.99 min. UPLC/MS: (MS+) 487.3, (MS−) 485.3.

Example 149

N,N-dimethyl-1-(3-{1-[4-(morpholin-4-ylcarbonyl)phenyl]-1H-1,2,3-triazol-4-yl}-1H-indazol-5-yl)pyrrolidin-3-amine Step a) formation of (4-{4-[5-Bromo-1-(tetrahydro-pyran-2-yl)-1H-indazol-3-yl]-[1,2,3]triazol-1-yl}-phenyl)-morpholin-4-yl-methanone

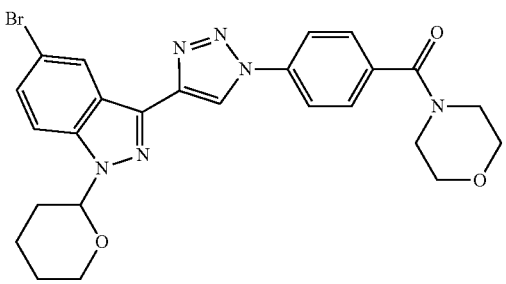 [SMILES: O=C(c1ccc(-n2cc(-c3nn(C4CCCCO4)c4ccc(Br)cc34)nn2)cc1)N1CCOCC1]

The title compound was obtained, following procedure described for intermediate 41, step a), but starting {4-[4-(5-Bromo-1H-indazol-3-yl)-[1,2,3]triazol-1-yl]-phenyl}-morpholin-4-yl-methanone (1.8 g; 3.99 mmol; 1.0 eq.) as a white solid (1.61 g, 75%). 1H NMR (300 MHz, DMSO-d6) δ 9.50 (s, 1H), 8.57 (d, J=1.5 Hz, 1H), 8.24-8.13 (m, 2H), 7.86 (d, J=8.9 Hz, 1H), 7.73-7.68 (m, 2H), 7.68-7.63 (m, 1H), 6.04-5.93 (m, 1H), 3.94 (d, J=11.7 Hz, 1H), 3.86-3.75 (m, 1H), 3.53 (d, J=68.4 Hz, 8H), 2.47-2.37 (m, 1H), 2.16-1.97 (m, 2H), 1.88-1.70 (m, 1H), 1.68-1.55 (m, 2H). UPLC/MS: (MS+) 537.4.

Step b) Formation of N,N-dimethyl-1-[3-{1-[4-(morpholin-4-ylcarbonyl)phenyl]-1H-1,2,3-triazol-4-yl}-1-(tetrahydro-2H-pyran-2-yl)-1H-indazol-5-yl]pyrrolidin-3-amine

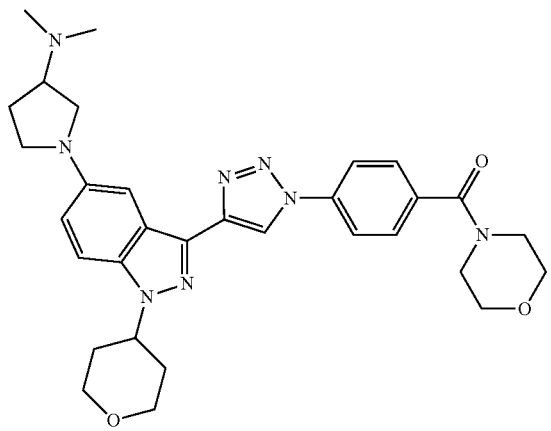 [SMILES: CN(C)C1CCN(c2ccc3c(c2)c(-c2cn(-c4ccc(C(=O)N5CCOCC5)cc4)nn2)nn3C2CCOCC2)C1]

A mixture of 4-{4-[5-Bromo-1-(tetrahydro-pyran-2-yl)-1H-indazol-3-yl]-[1,2,3]triazol-1-yl}-phenyl)-morpholin-4-yl-methanone (150 mg; 0.28 mmol; 1.0 eq.), 3-(dimethylamino)pyrrolidine (38 mg; 0.33 mmol; 1.2 eq.), 2-2-dicyclohexylphosphino-2',6'-di-i-propoxy-1,1'-biphenyl (13 mg; 0.03 mmol; 0.1 eq.), Chloro(2-dicyclohexylphosphino-2',6'-di-i-propoxy-1,1'-biphenyl)[2-(2-aminoethylphenyl)]palladium(II), methyl-t-butylether (23 mg; 0.03 mmol; 0.1 eq.) and sodium tert-butoxide (134 mg; 1.40 mmol; 5.0 eq.) in dry THF (3.0 mL) was heated in a sealed tube in MW at 100° C. for 15 min. It was diluted with DCM and washed with water. The organic phase was dried over magnesium sulfate, filtered and concentrated. purification by flash chromatography (DCM:MeOH, gradient from 100:0 to 90:10) gave the title compound as a brown liquid (110 mg, 69%). 1H NMR (DMSO) δ 9.32 (s, 1H), 8.16 (d, J=8.7 Hz, 2H), 7.69-7.63 (m, 3H), 7.26 (d, J=2.0 Hz, 1H), 6.99 (dd, J=9.0 Hz, 2.0 Hz, 1H), 5.84 (dd, J=10.0 Hz, 2.0 Hz, 1H), 3.95-3.91 (m, 1H), 3.82-3.30 (m, 13H), 2.88-2.80 (m, 1H), 2.50-2.41 (m, 1H), 2.23 (s, 6H), 2.19 (m, 1H), 2.08-2.01 (m, 2H), 1.94-1.75 (m, 2H), 1.60 (m, 2H). HPLC (max plot) 98.8%; Rt % 2.74 min. UPLC/MS: (MS+) 571.6.

Step c) Formation of N,N-dimethyl-1-(3-{1-[4-(morpholin-4-ylcarbonyl)phenyl]-1H-1,2,3-triazol-4-yl}-1H-indazol-5-yl)pyrrolidin-3-amine

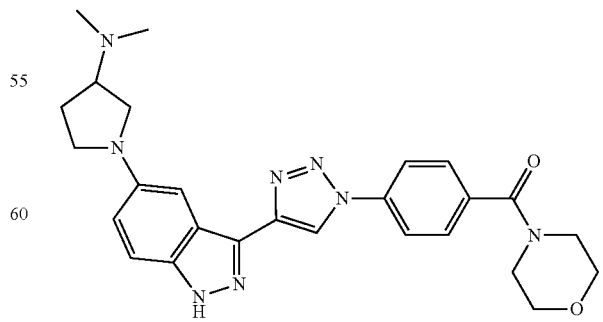

Hydrogen chloride (0.72 mL of a 4 N solution in dioxane) was added to a solution of N,N-dimethyl-1-[3-{1-[4-(morpholin-4-ylcarbonyl)phenyl]-1H-1,2,3-triazol-4-yl}-1-(tetrahydro-2H-pyran-2-yl)-1H-indazol-5-yl]pyrrolidin-3-amine (110 mg; 0.19 mmol; 1.0 eq.) in DCM (1.1 mL) and MeOH (0.55 mL). The reaction mixture was stirred at RT O/N. Solvents were then removed under reduced pressure and the residue was purified by preparative HPLC to give the title compound as a yellow powder (65 mg, 69%). 1H NMR (300 MHz, MeOD): 8.98 (s, 1H), 8.14 (d, J=8.7 Hz, 2H), 7.73 (d, J=8.7 Hz, 2H), 7.53 (d, J=9.1 Hz, 1H), 7.48 (d, J=2.0 Hz, 1H), 7.13 (dd, J=8.1 Hz, 2.0 Hz, 1H), 3.80-3.68 (m, 9H), 3.63-3.43 (m, 4H), 2.84 (s, 6H), 2.61-2.51 (m, 1H), 2.30-2.21 (m, 1H). HPLC (max plot) 96.0%; Rt %2.12 min. UPLC/MS: (MS+) 487.4, (MS−) 485.3.

Example 150

2,2,2-trifluoro-1-{4-[4-(1H-indazol-3-yl)-1H-1,2,3-triazol-1-yl]phenyl}ethanol

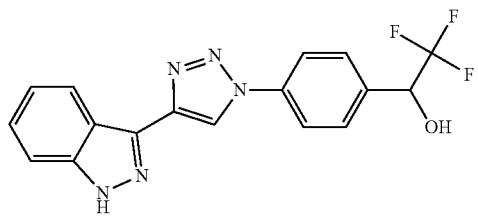 [SMILES: OC(c1ccc(-n2cc(-c3n[nH]c4ccccc34)nn2)cc1)C(F)(F)F]

A mixture of 1-(4-bromophenyl)-2,2,2-trifluoroethan-1-ol (296 mg; 1.16 mmol; 1.1 eq.), 3-Ethynyl-1H-indazole (150 mg; 1.06 mmol; 1.0 eq.), sodium azide (75 mg; 1.16 mmol; 1.1 eq.), D-(−)-isoascorbic acid sodium salt (21 mg; 0.11 mmol; 0.1 eq.), copper iodide (20 mg; 0.11 mmol; 0.1 eq.) and trans-1,2-bis(methylamino)cyclohexane (22 mg; 0.16 mmol; 0.15 eq.) in DMSO (2.6 mL) and WATER (0.5 mL) was heated in a sealed tube at 70° C. for 48 h. The reaction mixture was poured into a solution of saturated NH$_4$OH and extracted with DCM (twice). Combined organic phases were washed with brine, dried over magnesium sulfate, filtered and concentrated. Purification by preparative HPLC gave the title compound as a beige solid (100 mg, 26%). 1H NMR (DMSO) δ 13.38 (brs, 1H), 9.33 (s, 1H), 8.36 (dt, J=8.0 Hz, 1.0 Hz, 1H), 8.12 (d, J=8.7 Hz, 2H), 7.75 (d, J=8.7 Hz, 2H), 7.61 (dt, J=8.4 Hz, 1.0 Hz, 1H), 7.47-7.42 (m, 1H), 7.29-7.23 (m, 1H), 7.05 (bs, 1H), 5.34 (q, J=7.2 Hz, 1H). HPLC (max plot) 100.0%; Rt %3.83 min. UPLC/MS: (MS+) 360.4, (MS−) 358.4.

Example 151 & 152

3-(1-{4-[(3-exo)-8-cyclohexyl-8-azabicyclo[3.2.1]oct-3-yl]phenyl}-1H-1,2,3-triazol-4-yl)-1H-indazole and 3-(1-{4-[(3-endo)-8-cyclohexyl-8-azabicyclo[3.2.1]oct-3-yl]phenyl}-1H-1,2,3-triazol-4-yl)-1H-indazole

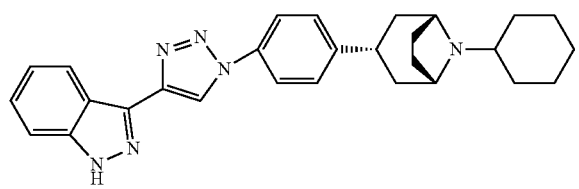

-continued

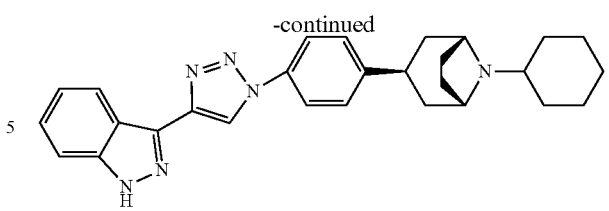

The title compound was obtained following procedure described for intermediate 10, but starting from 3-(4-azidophenyl)-8-cyclohexyl-8-azabicyclo[3.2.1]octane (135 mg; 0.43 mmol; 1.0 eq.) and 3-Ethynyl-1H-indazole (62 mg; 0.43 mmol; 1.0 eq.) as a 70:30 mixture of the endo:exo isomer (110.00 mg; 38%). The two isomers were separated by SFC using a chiralpak IA column (250×20 mm, 5 μm) with 50% EtOH containing 0.1% DIEA at 80 mL/min.

First eluting compound: exo isomer, beige solid, 20 mg. $^1$H NMR (300 MHz, DMSO-d6-d6): 13.36 (brs, 1H), 9.27 (s, 1H), 8.35 (d, J=8.1 Hz, 1H), 7.98 (d, J=8.1 Hz, 2H), 7.60 (d, J=8.4 Hz, 1H), 7.54 (d, J=8.1 Hz, 2H), 7.47-7.41 (m, 1H), 7.28-7.23 (m, 1H), 4.40-3.61 (m, 2H), 3.15 (m 1H), 2.10-1.69 (m, 10H), 1.58 (m, 3H), 1.31-1.08 (m, 6H).

Second eluting compound: endo isomer, beige solid, 40 mg. $^1$H NMR (300 MHz, DMSO-d6-d6): 13.35 (brs, 1H), 9.27 (s, 1H), 8.36 (d, J=8.1 Hz, 1H), 7.94 (d, J=8.6 Hz, 2H), 7.62-7.57 (m, 3H), 7.46-7.41 (m, 1H), 7.28-7.22 (m, 1H), 3.56 (m, 2H), 3.09 (quint., J=7.2 Hz, 1H), 2.36-2.20 (m, 3H), 1.90-1.86 (m, 2H), 1.79-1.72 (m, 4H), 1.62-1.57 (m, 2H), 1.45-1.41 (m, 2H), 1.29-1.06 (m, 6H).

Example 153

3-[(3-{1-[4-(morpholin-4-ylcarbonyl)phenyl]-1H-1,2,3-triazol-4-yl}-1H-indazol-5-yl)oxy]propan-1-ol Step a) Formation of 3-[(1-(4-methoxybenzyl)-3-{1-[4-(morpholin-4-ylcarbonyl)phenyl]-1H-1,2,3-triazol-4-yl}-1H-indazol-5-yl)oxy]propan-1-ol

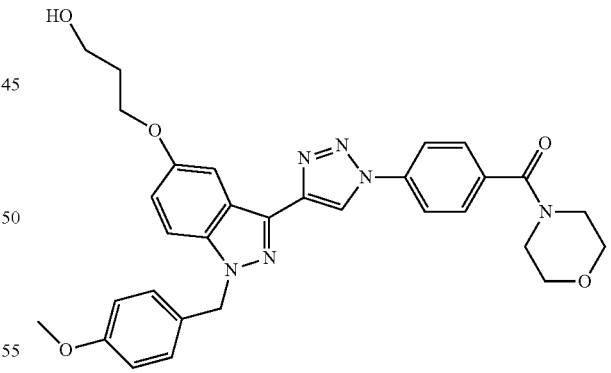

A solution of 1-(4-methoxybenzyl)-3-{1-[4-(morpholin-4-ylcarbonyl)phenyl]-1H-1,2,3-triazol-4-yl}-1H-indazol-5-ol (60 mg; 0.12 mmol; 1.0 eq.), 3-bromo-1-propanol (24 mg; 0.18 mmol; 1.5 eq.) and cesium carbonate (77 mg; 0.24 mmol; 2.0 eq.) in DMF (1.2 mL) was stirred at RT O/N. The reaction mixture was then diluted with DCM and washed with brine. Organic phase was dried over magnesium sulfate, filtered and concentrated. Purification of the crude by preparative HPLC gave the title compound as a white powder (43 mg, 64%).

UPLC/MS: (MS+) 569.2.

Step b) Formation of: 3-[(3-{1-[4-(morpholin-4-ylcarbonyl)phenyl]-1H-1,2,3-triazol-4-yl}-1H-indazol-5-yl)oxy]propan-1-ol

Example 154

(4S)-4-[(3-{1-[4-(morpholin-4-ylcarbonyl)phenyl]-1H-1,2,3-triazol-4-yl}-1H-indazol-5-yl)methoxy]dihydrofuran-2(3H)-one

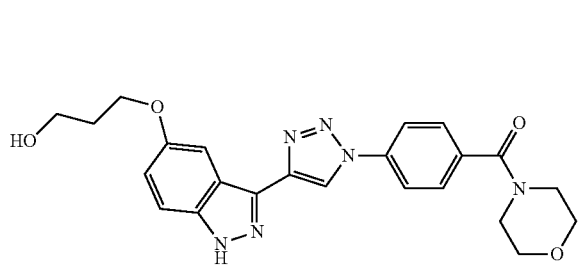 [SMILES: O=C(c1ccc(-n2cc(-c3n[nH]c4ccc(OCCCO)cc34)nn2)cc1)N1CCOCC1]

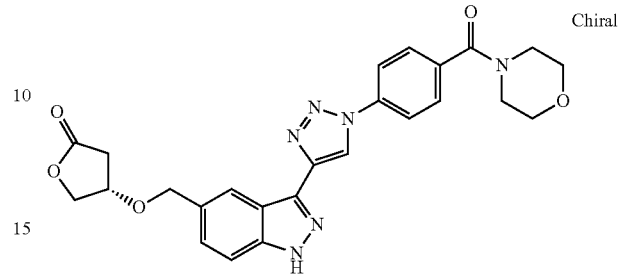

A solution of 3-[(1-(4-methoxybenzyl)-3-{1-[4-(morpholin-4-ylcarbonyl)phenyl]-1H-1,2,3-triazol-4-yl}-1H-indazol-5-yl)oxy]propan-1-ol (43 mg; 0.08 mmol; 1.0 eq.) and anisole (124 mL, 1.13 mmol, 15 eq.) in TFA (2 mL) and water (2.7 mL) was stirred at RT for 48 h. Reaction mixture was concentrated under reduced pressure and purified by preparative HPLC to give the title compound as a brown gum (10.5 mg, 31%). 1H NMR (300 MHz, DMSO-d6) δ 13.25 (s, 1H), 9.35 (s, 1H), 8.15 (d, J=8.6 Hz, 2H), 7.77-7.72 (m, 1H), 7.69 (d, J=8.6 Hz, 2H), 7.52 (d, J=9.0 Hz, 1H), 7.10 (dd, J=9.0, 2.4 Hz, 1H), 4.61 (t, J=5.2 Hz, 1H), 4.21-4.06 (m, 2H), 3.78-3.24 (m, 10H), 2.02-1.82 (m, 2H). HPLC (max plot) 97.2%; Rt %2.63 min. UPLC/MS: (MS+) 449.1, (MS−) 447.1.

A solution of methanesulfonic anhydride (113 mg; 0.65 mmol; 1.6 eq.) in DCM (3.0 mL) was added dropwise over 1 min to a solution of [3-{1-[4-(morpholin-4-ylcarbonyl)phenyl]-1H-1,2,3-triazol-4-yl}-1-(tetrahydro-2H-pyran-2-yl)-1H-indazol-5-yl]methanol (194 mg; 0.40 mmol; 1.0 eq.) in DIEA (1.0 mL; 5.9 mmol; 15 eq.) and DCM (3.0 mL) containing activated molecular sieves. After 10 min, a solution of (S)-3-hydroxy-g-butyrolactone (160 mg; 1.57 mmol; 4 eq.) in DCM (1.0 mL) was added dropwise over 2 min. The reaction mixture was then stirred for 16 h at RT. It was filtered through a celite pad and the filtrate was concentrated under reduced pressure. The residue was redissolved in MeOH (2 mL) and hydrogen chloride (8 mL of a 4N solution in dioxane) was added. The reaction mixture was stirred at RT for 3 h and then concentrated under reduced pressure. Purification by preparative HPLC gave the title compound as a white solid (14 mg, 7%). 1H NMR (300 MHz, DMSO-d6) δ 13.41 (s, 1H), 9.38 (s, 1H), 8.33 (s, 1H), 8.15 (d, J=8.5 Hz, 2H), 7.69 (d, J=8.5 Hz, 2H), 7.61 (d, J=8.6 Hz, 1H), 7.49-7.37 (m, 1H), 4.69 (s, 2H), 4.47-4.34 (m, 3H), 3.82-3.40 (m, 8H), 2.88 (dd, J=17.8, 5.7 Hz, 1H), 2.56 (d, J=17.8 Hz, 1H). HPLC (max plot) 96.5%; Rt %2.59 min. UPLC/MS: (MS+) 489.5, (MS−) 487.6.

Examples 155 to 299 described in table 1 can be prepared following methods and techniques described in the above examples.

TABLE 1

| 155 | 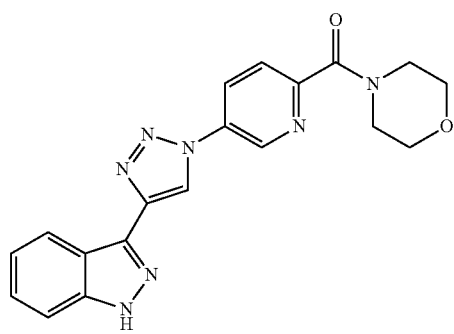 [SMILES: O=C(c1ccc(-n2cc(-c3n[nH]c4ccccc34)nn2)cn1)N1CCOCC1] | beige powder, 1H NMR (300 MHz, DMSO) δ 13.42 (br s, 1H), 9.50 (s, 1H), 9.33 (d, J = 2.3, 1H), 8.63 (dd, J = 8.5, 2.6, 1H), 8.37 (d, J = 8.2, 1H), 7.91 (d, J = 8.5, 1H), 7.63 (d, J = 8.4, 1H), 7.52-7.40 (m, 1H), 7.28 (t, J = 7.5, 1H), 3.87-3.42 (m, 8H). HPLC (max plot) 93.3%; Rt 2.84 min. UPLC/MS: (MS+) 376.2, (MS−) 346.2 |
|---|---|---|

TABLE 1-continued

| 156 | 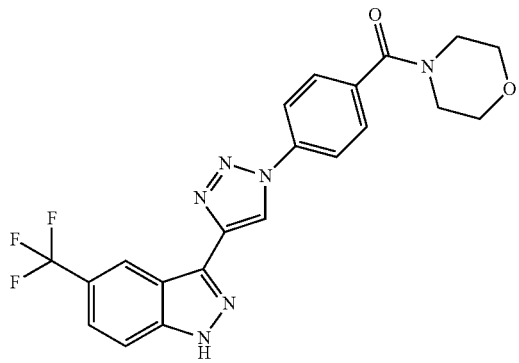 [SMILES: O=C(c1ccc(-n2cc(-c3n[nH]c4ccc(C(F)(F)F)cc34)nn2)cc1)N1CCOCC1] | yellow amorphous solid, 1H NMR (DMSO) δ 13.85 (bs, 1H), 9.51 (bs, 1H), 8.74 (m, 1H), 8.15 (d, J = 8.6 Hz, 2H), 7.85 (d, J = 8.9 Hz, 1H), 7.74 (dd, J = 8.9 Hz, 1.5 Hz, 1H), 7.70 (d, J = 8.6 Hz, 2H), 3.64 (m, 6H), 3.40 (m, 2H). HPLC (max plot) 98.9%; Rt 3.86 min. UPLC/MS: (MS+) 443.1, (MS−) 441.2 |
| --- | --- | --- |
| 157 | 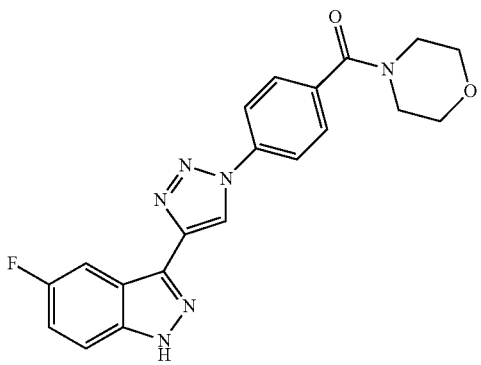 [SMILES: O=C(c1ccc(-n2cc(-c3n[nH]c4ccc(F)cc34)nn2)cc1)N1CCOCC1] | white solid, 1H NMR (DMSO) δ 13.54 (bs, 1H), 9.42 (s, 1H), 8.15 (d, J = 8.0 Hz, 2H), 8.05 (d, J = 9.5 Hz, 1H), 7.70-7.65 (m, 3H), 7.39-7.33 (m, 1H), 3.64-3.40 (m, 8H). HPLC (max plot) 93.7%; Rt 3.29 min. UPLC/MS: (MS+) 393.1, (MS−) 391.2 |
| 158 | 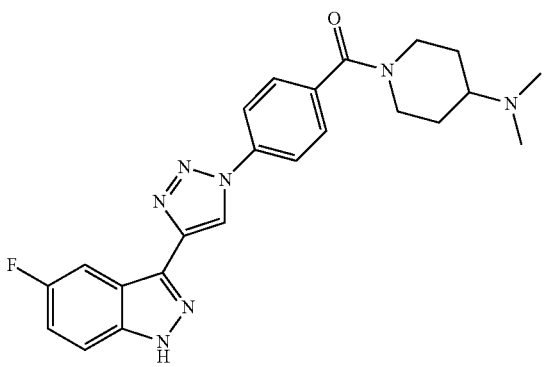 | white amorphous solid, 1H NMR (DMSO) δ 13.54 (bs, 1H), 9.41 (s, 1H), 8.14 (d, J = 8.0 Hz, 2H), 8.04 (d, J = 9.0 Hz, 1H), 7.69-7.64 (m, 3H), 7.36 (t, J = 9.0 Hz, 1H), 4.46 (m, 1H), 3.63 (m, 1H), 3.08-2.85 (m, 2H), 2.39-2.32 (m, 1H), 2.18 (s, 6H), 1.86-1.74 (m, 2H), 1.43-1.31 (m, 2H). HPLC (max plot) 98.3%; Rt 2.57 min. UPLC/MS: (MS+) 393.1, (MS−) 391.1 |
| 159 | 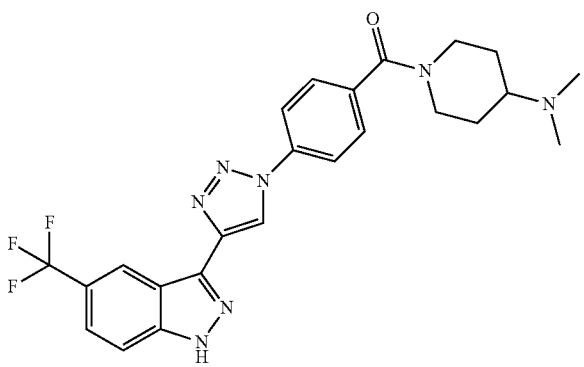 [SMILES: CN(C)C1CCN(C(=O)c2ccc(-n3cc(-c4n[nH]c5ccc(C(F)(F)F)cc45)nn3)cc2)CC1] | brown amorphous solid, 1H NMR (DMSO) δ 13.85 (bs, 1H), 9.49 (s, 1H), 8.74 (s, 1H), 8.14 (d, J = 7.8 Hz, 2H), 7.85 (d, J = 8.7 Hz, 1H), 7.73 (d, J = 8.7 Hz, 1H), 7.664 (d J = 7.8 Hz, 2H), 4.46 (m, 1H), 3.61 (m, 1H), 3.07-2.85 (m, 2H), 2.42-2.35 (m, 1H), 2.20 (s, 6H), 1.83-1.73 (m, 2H), 1.41-1.37 (m, 2H). HPLC (max plot) 89.8%; Rt 3.51 min. UPLC/MS: (MS+) 484.2, (MS−) 482.3 |

TABLE 1-continued

| 160 | 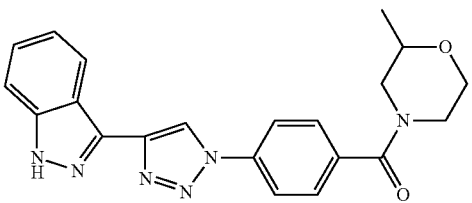 [SMILES: CC1CN(C(=O)c2ccc(-n3cc(-c4n[nH]c5ccccc45)nn3)cc2)CCO1] | white solid, 1H NMR (300 MHz, DMSO) δ 13.39 (s, 1H), 9.41 (s, 1H), 8.37 (d, J = 8.1 Hz, 1H), 8.16 (d, J = 8.6 Hz, 2H), 7.69 (d, J = 8.6 Hz, 2H), 7.62 (d, J = 8.4 Hz, 1H), 7.51-7.39 (m, 1H), 7.27 (t, J = 7.5 Hz, 1H), 4.47-4.18 (m, 1H), 3.84 (brd, J = 34.0 Hz, 2H), 3.62-3.38 (m, 3H), 2.95 (brs, 1H), 1.09 (brd, J = 35.7 Hz, 3H). HPLC (max plot) 97.9%; Rt 3.12 min. UPLC/MS: (MS+) 389.2. |
| --- | --- | --- |
| 161 | 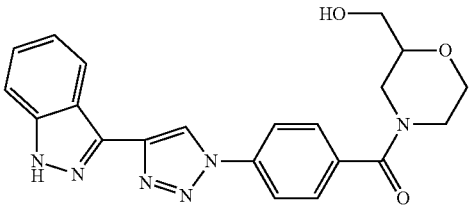 [SMILES: O=C(c1ccc(-n2cc(-c3n[nH]c4ccccc34)nn2)cc1)N1CCOC(CO)C1] | white solid, 1H NMR (300 MHz, DMSO) δ 13.39 (s, 1H), 9.41 (s, 1H), 8.37 (d, J = 8.1 Hz, 1H), 8.16 (d, J = 8.1 Hz, 2H), 7.69 (d, J = 8.0 Hz, 2H), 7.62 (d, J = 8.4 Hz, 1H), 7.45 (t, J = 7.6 Hz, 1H), 7.27 (t, J = 7.5 Hz, 1H), 4.81 (brd, J = 21.8 Hz, 1H), 4.39 (brd, J = 37.4 Hz, 1H), 3.87 (brd, J = 40.5 Hz, 1H), 3.49 (brs, 1H), 3.34 (s, 4H), 3.02 (brs, 1H), 2.73 (brs, 1H). HPLC (max plot) 99.0%; Rt 2.61 min. UPLC/MS: (MS+) 405.3, (MS−) 403.3 |
| 162 | 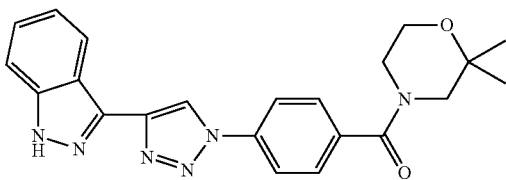 [SMILES: CC1(C)CN(C(=O)c2ccc(-n3cc(-c4n[nH]c5ccccc45)nn3)cc2)CCO1] | white solid, δ 1H NMR (300 MHz, DMSO) δ 13.39 (s, 1H), 9.41 (s, 1H), 8.37 (d, J = 8.1 Hz, 1H), 8.17 (d, J = 8.6 Hz, 2H), 7.78-7.57 (m, 3H), 7.51-7.39 (m, 1H), 7.27 (t, J = 7.5 Hz, 1H), 3.65 (brs, 3H), 3.49 (brs, 1H), 3.33 (brs, 1H), 3.19 (brs, 1H), 1.16 (brd, J = 35.6 Hz, 6H). HPLC (max plot) 99.4%; Rt 3.24 min. UPLC/MS: (MS+) 403.3, (MS−) 401.3 |
| 163 | 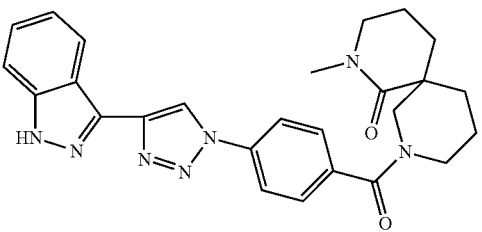 [SMILES: CN1CCCC2(CCCN(C(=O)c3ccc(-n4cc(-c5n[nH]c6ccccc56)nn4)cc3)C2)C1=O] | beige solid, 1H NMR (300 MHz, DMSO) δ 13.39 (s, 1H), 9.41 (s, 1H), 8.37 (d, J = 7.9 Hz, 1H), 8.15 (d, J = 8.0 Hz, 2H), 7.74-7.56 (m, 3H), 7.54-7.39 (m, 1H), 7.34-7.19 (m, 1H), 4.50-4.20 (m, 1H), 3.69-3.43 (m, 1H), 3.43-3.22 (m, 2H), 3.22-3.00 (m, 2H), 2.89-2.60 (m, 2H), 2.20-1.94 (m, 1H), 1.95-1.75 (m, 2H), 1.75-1.42 (m, 5H), 1.35-1.08 (m, 1H). 1H NMR (DMSO) δ. HPLC (max plot) 92.5%; Rt 3.22 min. UPLC/MS: (MS+) 470.2, (MS−) 468.2. |
| 164 | 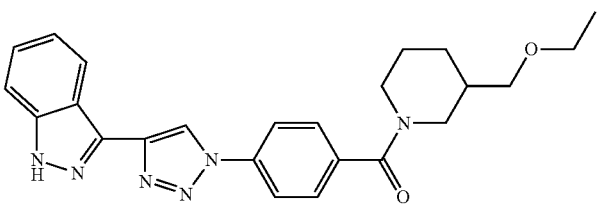 | beige solid, 1H NMR (300 MHz, DMSO) δ 13.39 (s, 1H), 9.40 (s, 1H), 8.37 (d, J = 8.2 Hz, 1H), 8.15 (d, J = 8.6 Hz, 2H), 7.70-7.57 (m, 3H), 7.51-7.39 (m, 1H), 7.27 (t, J = 7.5 Hz, 1H), 4.34 (brd, J = 77.0 Hz, 2H), 3.73-3.38 (m, 2H), 3.37-3.24 (m, 2H), 3.24-2.87 (m, 2H), 2.79-2.58 (m, 1H), 1.77 (brd, J = 14.7 Hz, 3H), 1.55-1.37 (m, 1H), 1.37-1.20 (m, 1H), 1.20-1.08 (m, 1H), 1.04-0.87 (m, 1H). HPLC (max plot) 98.8%; Rt 3.74 min. UPLC/MS: (MS+) 431.2, (MS−) 429.2. |
| 165 | 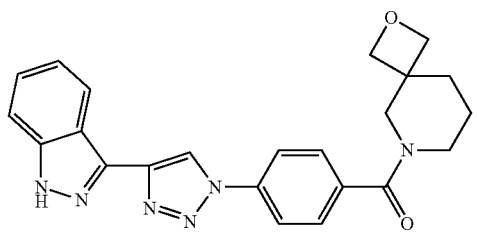 [SMILES: O=C(c1ccc(-n2cc(-c3n[nH]c4ccccc34)nn2)cc1)N1CCCC2(COC2)C1] | white solid, 1H NMR (300 MHz, DMSO) δ 13.39 (s, 1H), 9.41 (s, 1H), 8.37 (d, J = 8.1 Hz, 1H), 8.24-8.07 (m, 2H), 7.76-7.56 (m, 3H), 7.49-7.39 (m, 1H), 7.32-7.21 (m, 1H), 4.49-4.16 (m, 4H), 4.14-3.97 (m, 1H), 3.97-3.75 (m, 1H), 3.72-3.45 (m, 2H), 1.95-1.79 (m, 2H), 1.58-1.38 (m, 2H). HPLC (max plot) 99.3%; Rt 3.10 min. UPLC/MS: (MS+) 415.2, (MS−) 413.1. |

TABLE 1-continued

| 166 | 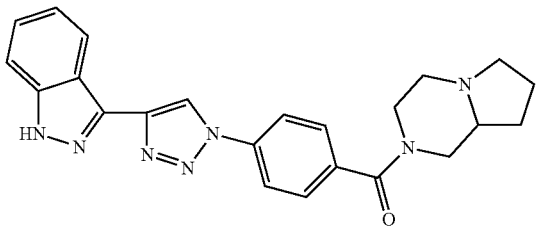 [SMILES: O=C(c1ccc(-n2cc(-c3n[nH]c4ccccc34)nn2)cc1)N1CCN2CCCC2C1] | yellow powder, 1H NMR (300 MHz, DMSO) δ 13.39 (s, 1H), 9.40 (s, 1H), 8.37 (d, J = 7.9 Hz, 1H), 8.21-8.10 (m, 2H), 7.75-7.54 (m, 3H), 7.52-7.40 (m, 1H), 7.33-7.19 (m, 1H), 4.78-4.32 (m, 2H), 3.80-3.48 (m, 2H), 3.15-2.82 (m, 3H), 2.31-2.05 (m, 2H), 2.05-1.80 (m, 1H), 1.82-1.55 (m, 3H). 1H NMR (DMSO) δ. HPLC (max plot) 98.7%; Rt 2.31 min. UPLC/MS: (MS+) 414.2, (MS−) 412.2. |
| 167 | 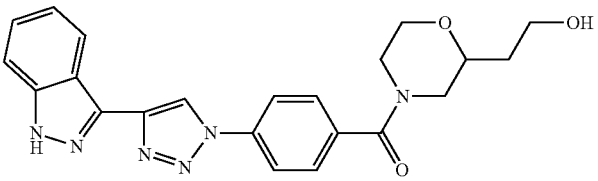 [SMILES: O=C(c1ccc(-n2cc(-c3n[nH]c4ccccc34)nn2)cc1)N1CCOC(CCO)C1] | white solid, 1H NMR (300 MHz, DMSO) δ 13.39 (s, 1H), 9.41 (s, 1H), 8.37 (d, J = 8.0 Hz, 1H), 8.16 (d, J = 8.6 Hz, 2H), 7.68 (d, J = 8.5 Hz, 2H), 7.62 (d, J = 8.4 Hz, 1H), 7.51-7.39 (m, 1H), 7.27 (t, J = 7.2 Hz, 1H), 4.63-4.22 (m, 2H), 4.02-3.68 (m, 1H), 3.65-3.37 (m, 5H), 3.11-2.84 (m, 1H), 2.81-2.58 (m, 1H), 1.78-1.32 (m, 2H). HPLC (max plot) 91.6%; Rt 2.70 min. UPLC/MS: (MS+) 419.2, (MS−) 417.2. |
| 168 | 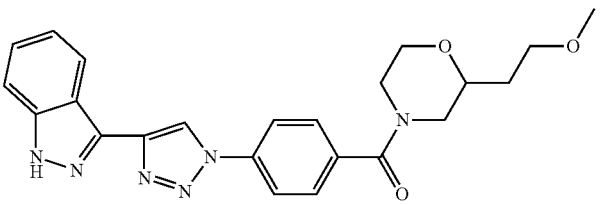 | beige solid, 1H NMR (300 MHz, DMSO) δ 13.41 (s, 1H), 9.41 (s, 1H), 8.37 (d, J = 8.2 Hz, 1H), 8.16 (d, J = 8.5 Hz, 2H), 7.68 (d, J = 8.5 Hz, 2H), 7.62 (d, J = 8.4 Hz, 1H), 7.51-7.40 (m, 1H) 7.31-7.21 (m, 1H), 4.41 (s, 1H), 3.76 (s, 1H), 3.66-3.07 (m, 6H), 3.06-2.80 (m, 1H), 1.88-1.41 (m, 4H), 1.35-1.14 (m, 1H). HPLC (max plot) 95.3%; Rt 3.67 min. UPLC/MS: (MS+) 433.2, (MS−) 431.2. |
| 169 | 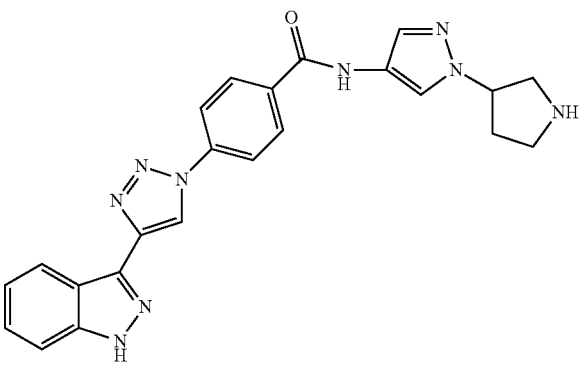 [SMILES: O=C(Nc1cnn(C2CCNC2)c1)c1ccc(-n2cc(-c3n[nH]c4ccccc34)nn2)cc1] | black solid, 1H NMR (300 MHz, DMSO) δ 13.44 (brs, 1H), 10.78 (brs, 1H), 9.52-9.15 (m, 3H), 8.38 (d, J = 8.1 Hz, 1H), 8.32-8.16 (m, 4H), 7.77 (s, 1H), 7.63 (d, J = 8.4 Hz, 1H), 7.53-7.40 (m, 1H), 7.28 (t, J = 7.8 Hz, 1H), 5.31-5.14 (m, 1H), 3.71-3.23 (m, 4H), 2.48-2.14 (m, 2H). HPLC (max plot) 91.0%; Rt 2.62 min. UPLC/MS: (MS+) 440.2, (MS−) 438.3. |
| 170 | 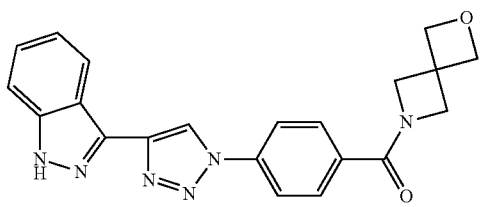 [SMILES: O=C(c1ccc(-n2cc(-c3n[nH]c4ccccc34)nn2)cc1)N1CC2(COC2)C1] | white solid, 1H NMR (300 MHz, DMSO) δ 13.40 (s, 1H), 9.43 (s, 1H), 8.37 (d, J = 8.0 Hz, 1H), 8.17 (d, J = 8.7 Hz, 2H), 7.87 (d, J = 8.7 Hz, 2H), 7.62 (d, J = 8.4 Hz, 1H), 7.51-7.40 (m, 1H), 7.27 (t, J = 7.5 Hz, 1H), 4.71 (s, 4H), 4.56 (s, 2H), 4.26 (s, 2H). HPLC (max plot) 96.4%; Rt 2.84 min. UPLC/MS: (MS+) 387.1, (MS−) 385.2. |
| 171 | 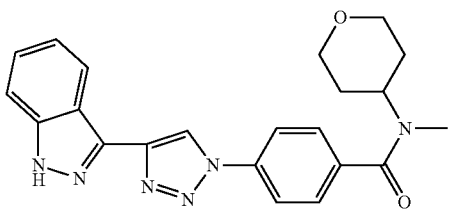 [SMILES: CN(C(=O)c1ccc(-n2cc(-c3n[nH]c4ccccc34)nn2)cc1)C1CCOCC1] | beige powder, 1H NMR (300 MHz, DMSO) δ 13.39 (s, 1H), 9.41 (s, 1H), 8.37 (d, J = 8.1 Hz, 1H), 8.15 (d, J = 8.5 Hz, 2H), 7.79-7.56 (m, 3H), 7.51-7.39 (m, 1H), 7.27 (t, J = 7.4 Hz, 1H), 4.56 (brs, 1H), 4.07-3.77 (m, 2H), 3.54-3.38 (m, 1H), 3.26-3.00 (m, 1H), 2.89 (brs, 3H), 1.98-1.71 (m, 2H), 1.71-1.52 (m, 2H). HPLC (max plot) 99.1%; Rt % 3.09 min. UPLC/MS: (MS+) 403.1. |

| | | |
|---|---|---|
| 172 | 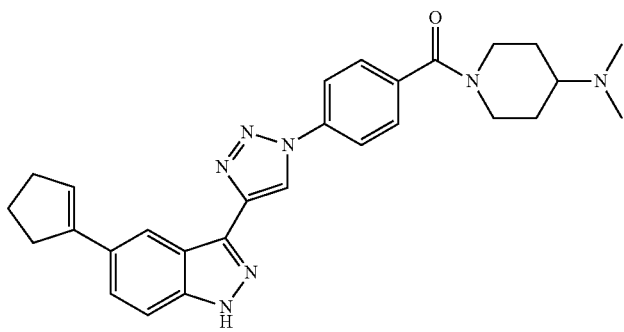 [SMILES: CN(C)C1CCN(C(=O)c2ccc(-n3cc(-c4n[nH]c5ccc(C6=CCCC6)cc45)nn3)cc2)CC1] | greenish electrostatic powder, 1H NMR (DMSO) δ 13.44 (s, 1H), 9.41 (s, 1H), 8.25 (s, 1H), 8.16-8.10 (m, 2H), 7.72 (dd, J = 8.7-1.6 Hz, 1H), 7.68-7.62 (m, 2H), 7.56 (d, J = 8.7 Hz, 1H), 6.33-6.28 (m, 1H), 4.54-4.35 (m, 1H), 3.73-3.55 (m, 1H), 3.18-2.97 (m, 1H), 2.96-2.75 (m, 3H), 2.59-2.51 (m, 2H), 2.09-1.94 (m, 2H), 2.18 (s, 6H), 1.92-1.64 (m, 2H), 1.47-1.29 (m, 2H), 2.43-2.29 (m, 1H). HPLC (max plot) 96.5%; Rt 3.79 min. UPLC/MS: (MS+) 482.2. |
| 173 | 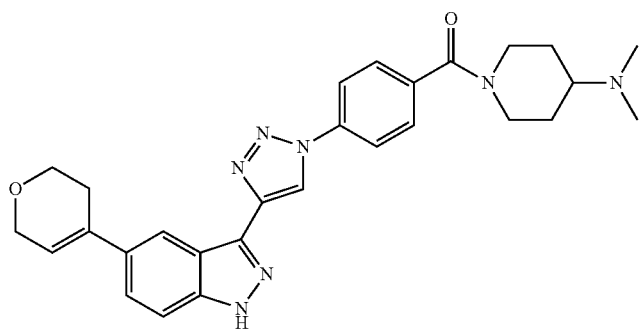 [SMILES: CN(C)C1CCN(C(=O)c2ccc(-n3cc(-c4n[nH]c5ccc(C6=CCOCC6)cc45)nn3)cc2)CC1] | greenish electrostatic powder, 1H NMR (DMSO) δ 13.40 (s, 1H), 9.41 (s, 1H), 8.33 (s, 1H), 8.17-8.10 (m, 2H), 7.70-7.59 (m, 4H), 6.33-6.29 (m, 1H), 4.54-4.38 (m, 1H), 4.31-4.24 (m, 2H), 3.93-3.84 (m, 2H), 3.73-3.55 (m, 1H), 3.18-2.74 (m, 2H), 2.64-2.54 (m, 2H), 2.19 (s, 6H), 1.93-1.61 (m, 2H), 1.47-1.29 (m, 2H), 2.42-2.30 (m, 1H). HPLC (max plot) 93.7%; Rt 2.98 min. UPLC/MS: (MS+) 498.2, (MS−) 496.3. |
| 174 | 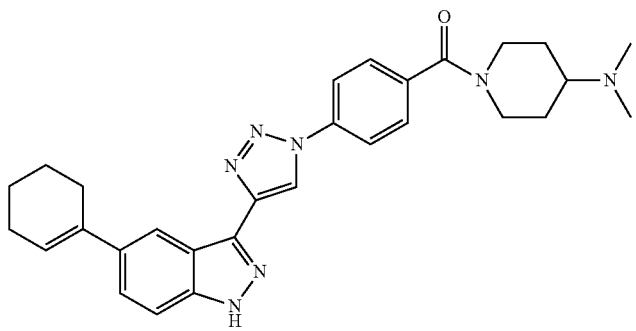 [SMILES: CN(C)C1CCN(C(=O)c2ccc(-n3cc(-c4n[nH]c5ccc(C6=CCCCC6)cc45)nn3)cc2)CC1] | brown electrostatic powder, 1H NMR (300 MHz, DMSO) δ 13.35 (brs, 1H), 9.38 (s, 1H), 8.33-8.25 (m, 1H), 8.20-8.07 (m, 2H), 7.70-7.61 (m, 2H), 7.60-7.48 (m, 2H), 6.25-6.16 (m, 1H), 4.57-4.32 (m, 1H), 3.77-3.49 (m, 1H), 3.21-2.75 (m, 2H), 2.56-2.45 (m, 2H), 2.43-2.28 (m, 1H), 2.28-2.20 (m, 2H), 2.19 (s, 6H), 1.98-1.57 (m, 6H), 1.50-1.27 (m, 2H). 1H NMR (DMSO) δ. HPLC (max plot) 96.1%; Rt 3.99 min. UPLC/MS: (MS+) 496.3, (MS−) 494.3. |
| 175 | 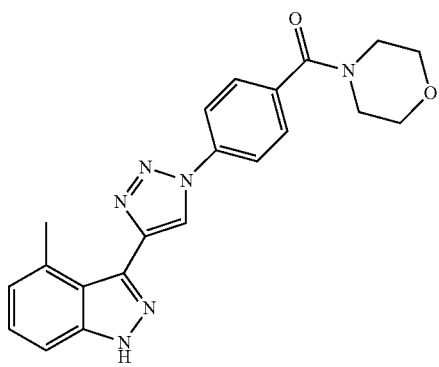 [SMILES: Cc1cccc2[nH]nc(-c3cn(-c4ccc(C(=O)N5CCOCC5)cc4)nn3)c12] | white amorphous solid, 1H NMR (DMSO) δ 13.42 (bs, 1H), 9.25 (s, 1H), 8.12 (d, J = 8.6 Hz, 2H), 7.68 (d, J = 8.6 Hz, 2H), 7.43 (d, J = 8.3 Hz, 1H), 7.30 (dd, J = 8.3 Hz, 6.9 Hz, 1H), 6.95 (d, J = 6.9 Hz, 1H), 3.64 (m, 6H), 3.41 (m, 2H), 2.58 (s, 3H). HPLC (max plot) 100.0%; Rt 3.00 min. UPLC/MS: (MS+) 389.1, (MS−) 387.2. |

| | | |
|---|---|---|
| 176 | 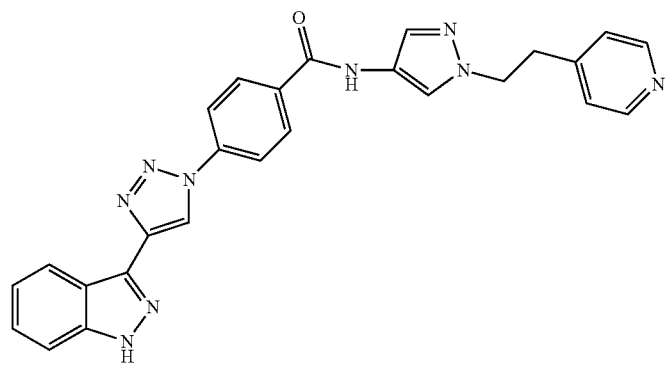 [SMILES: O=C(Nc1cnn(CCc2ccncc2)c1)c1ccc(-n2cc(-c3n[nH]c4ccccc34)nn2)cc1] | grey powder, 1H NMR (300 MHz, DMSO) δ 13.40 (brs, 1H), 10.60 (s, 1H), 9.46 (s, 1H), 8.46 (dd, J = 4.4, 1.5 Hz, 2H), 8.38 (d, J = 8.1 Hz, 1H), 8.22 (dd, J = 20.3, 8.9 Hz, 4H), 8.05 (s, 1H), 7.68-7.58 (m, 2H), 7.52-7.40 (m, 1H), 7.34-7.19 (m, 3H), 4.42 (t, J = 7.0 Hz, 2H), 3.15 (t, J = 7.0 Hz, 2H). HPLC (max plot) 97.4%; Rt 2.65 min. UPLC/MS: (MS+) 476.2, (MS−) 474.3. |
| 177 | 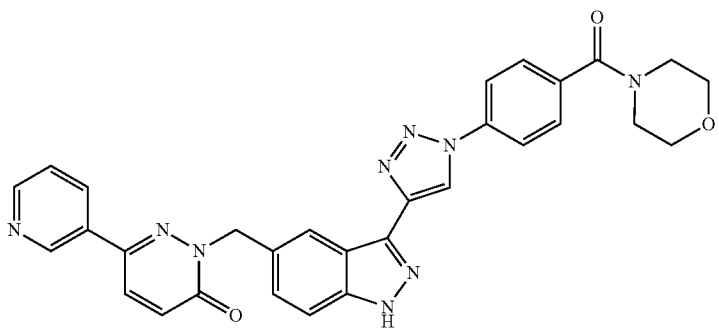 [SMILES: O=C(c1ccc(-n2cc(-c3n[nH]c4ccc(Cn5nc(-c6cccnc6)ccc5=O)cc34)nn2)cc1)N1CCOCC1] | white solid, 1H NMR (300 MHz, DMSO) δ 13.41 (s, 1H), 9.38 (s, 1H), 9.11 (d, J = 1.7 Hz, 1H), 8.68-8.58 (m, 1H), 8.48 (s, 1H), 8.36-8.27 (m, 1H), 8.18-8.04 (m, 3H), 7.69 (d, J = 8.6 Hz, 2H), 7.63-7.48 (m, 3H), 7.15 (d, J = 9.7 Hz, 1H), 5.52 (s, 2H), 3.68-3.61 (m, 8H). HPLC (max plot) 93.7%; Rt 2.32 min. UPLC/MS: (MS+) 560.3, (MS−) 558.3. |
| 178 | 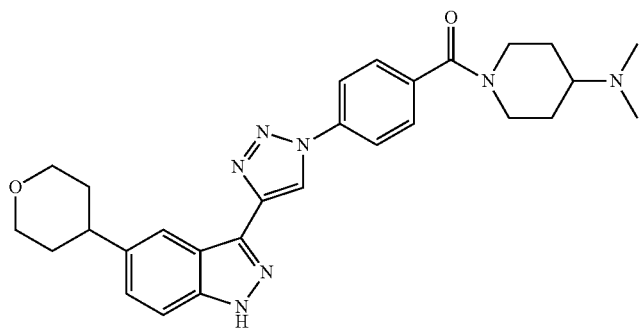 | white foam, 1H NMR (300 MHz, DMSO) δ 13.30 (brs, 1H), 9.37 (s, 1H), 8.20-8.07 (m, 3H), 7.66 (d, J = 8.6 Hz, 2H), 7.55 (d, J = 8.6 Hz, 1H), 7.45-7.33 (m, 1H), 4.57-4.37 (m, 1H), 4.06-3.94 (m, 2H), 3.88-3.29 (m, 1H), 3.29-2.65 (m, 6H), 2.47-2.34 (m, 1H), 2.22 (s, 6H), 1.97-1.62 (m, 5H), 1.52-1.27 (m, 2H). 1H NMR (DMSO) δ. 1H NMR (DMSO) δ. HPLC (max plot) 97.9%; Rt 2.54 min. UPLC/MS: (MS+) 500.2, (MS−) 498.4. |
| 179 | 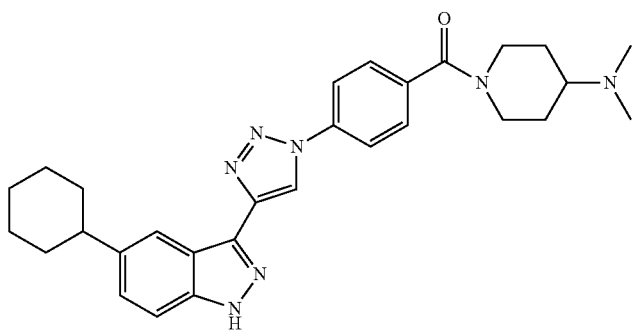 [SMILES: CN(C)C1CCN(C(=O)c2ccc(-n3cc(-c4n[nH]c5ccc(C6CCCCC6)cc45)nn3)cc2)CC1] | white foam, 1H NMR (300 MHz, DMSO) δ 13.26 (brs, 1H), 9.35 (s, 1H), 8.20-8.01 (m, 3H), 7.73-7.59 (m, 2H), 7.52 (d, J = 8.7 Hz, 1H), 7.34 (dd, J = 8.6, 1.4 Hz, 1H), 4.60-4.28 (m, 1H), 3.78-3.54 (m, 1H), 3.17-2.75 (m, 4H), 2.75-2.58 (m, 1H), 2.45-2.30 (m, 1H), 2.20 (s, 6H), 2.00-1.64 (m, 6H), 1.63-1.16 (m, 6H). 1H NMR (DMSO) δ. 1H NMR (DMSO) δ. HPLC (max plot) 98.8%; Rt 3.74 min. UPLC/MS: (MS+) 498.3, (MS−) 496.3. |
| 180 | 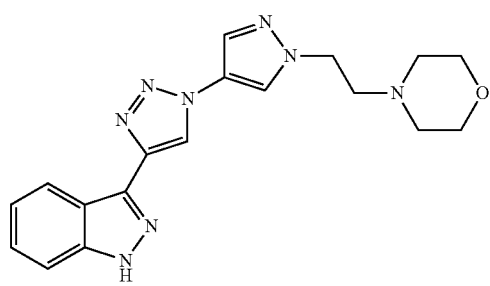 [SMILES: c1ccc2c(-c3cn(-c4cnn(CCN5CCOCC5)c4)nn3)n[nH]c2c1] | beige solid, 1H NMR (300 MHz, DMSO) δ 13.33 (brs, 1H), 9.08 (s, 1H), 8.53 (s, 1H), 8.33 (d, J = 8.1 Hz, 1H), 8.10 (s, 1H), 7.60 (d, J = 8.4 Hz, 1H), 7.44 (t, J = 7.2 Hz, 1H), 7.25 (t, J = 7.5 Hz, 1H), 4.33 (t, J = 6.4 Hz, 2H), 3.64-3.50 (m, 4H), 2.77 (t, J = 6.4 Hz, 2H), 2.48-2.36 (m, 4H). HPLC (max plot) 93.3%; Rt 2.16 min. UPLC/MS: (MS+) 365.1, (MS−) 363.2. |

TABLE 1-continued

181 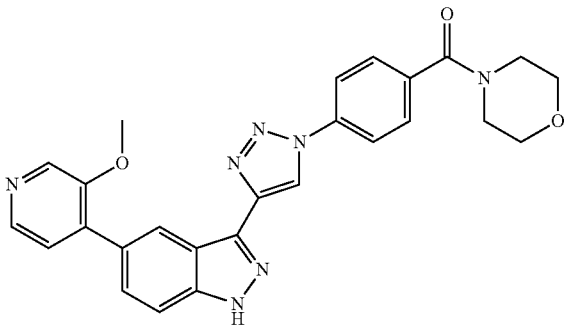 [SMILES: COc1cnccc1-c1ccc2[nH]nc(-c3cn(-c4ccc(C(=O)N5CCOCC5)cc4)nn3)c2c1]

purple solid, 1H NMR (DMSO) δ 13.51 (brs, 1H), 9.43 (s, 1H), 8.53 (s, 1H), 8.50 (s, 1H), 8.32 (d, J = 4.8 Hz, 1H), 8.15 (d, J = 8.6 Hz, 2H), 7.70-7.63 (m, 4H), 7.45 (d, J = 4.8 Hz, 1H), 3.92 (s, 3H), 3.63 (m, 6H), 3.41 (m, 2H). HPLC (max plot) 95.0%; Rt 2.60 min. UPLC/MS: (MS+) 482.1, (MS−) 480.1.

182 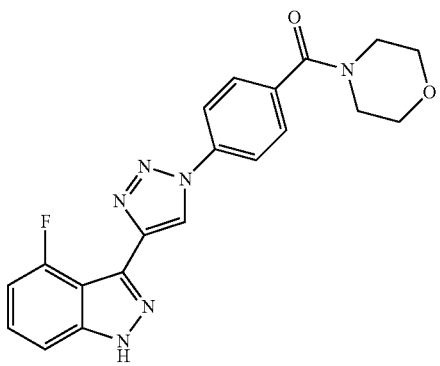

white amorphous solid, 1H NMR (DMSO) δ 13.75 (bs, 1H), 9.23 (s, 1H), 8.11 (d, J = 8.5 Hz, 2H), 7.68 (d, J = 8.5 Hz, 2H), 7.48-7.39 (m, 2H), 7.02-6.95 (m, 1H), 3.64 (m, 6H), 3.41 (m, 2H). HPLC (max plot) 100.0%; Rt 2.79 min. UPLC/MS: (MS+) 393.1.

183 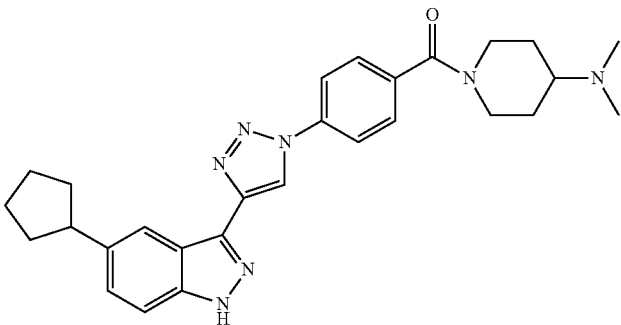 [SMILES: CN(C)C1CCN(C(=O)c2ccc(-n3cc(-c4n[nH]c5ccc(C6CCCC6)cc45)nn3)cc2)CC1]

yellowish electrostatic powder, 1H NMR (300 MHz, DMSO) δ 13.26 (brs, 1H), 9.35 (s, 1H), 8.21-8.08 (m, 3H), 7.70-7.61 (m, 2H), 7.53 (d, J = 8.6 Hz, 1H), 7.37 (dd, J = 8.7, 1.5 Hz, 1H), 3.74-3.55 (m, 2H), 3.26-2.98 (m, 1H), 2.97-2.75 (m, 2H), 2.47-2.31 (m, 1H), 2.21 (s, 6H), 2.16-2.01 (m, 2H), 1.96-1.53 (m, 8H), 1.49-1.27 (m, 2H). HPLC (max plot) 92.0%; Rt 3.89 min. UPLC/MS: (MS+) 484.3, (MS−) 482.3.

184 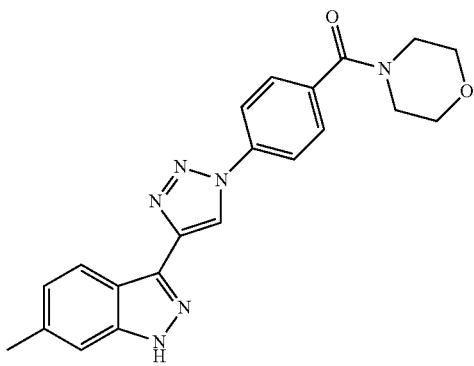 [SMILES: Cc1ccc2c(-c3cn(-c4ccc(C(=O)N5CCOCC5)cc4)nn3)n[nH]c2c1]

white amorphous solid, 1H NMR (DMSO) δ 13.21 (bs, 1H), 9.37 (s, 1H), 8.23 (d, J = 8.5 Hz, 1H), 8.15 (d, J = 8.5 Hz, 2H), 7.68 (d, J = 8.5 Hz, 2H), 7.38 (m, 1H), 7.09 (dd, J = 8.5 Hz, 1.0 Hz, 1H), 3.64 (m, 6H), 3.41 (m, 2H), 2.48 (s, 3H). HPLC (max plot) 97.9%; Rt % min. UPLC/MS: (MS+) 389.1, (MS−) 387.1.

TABLE 1-continued

| 185 | 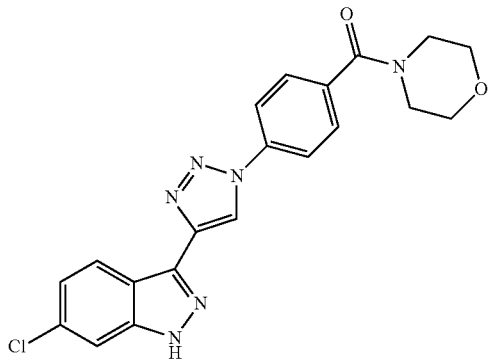 [SMILES: O=C(c1ccc(-n2cc(-c3n[nH]c4cc(Cl)ccc34)nn2)cc1)N1CCOCC1] | brown solid, 1H NMR (DMSO) δ 13.572 (bs, 1H), 9.43 (s, 1H), 8.37 (d, J = 8.7 Hz, 1H), 8.15 (d, J = 8.4 Hz, 2H), 7.70-7.67 (m, 3H), 7.29 (dd, J = 8.7 Hz, 7.5 Hz, 1H), 3.64 (m, 6H), 3.41 (m, 2H). HPLC (max plot) 96.5%; Rt 3.40 min. UPLC/MS: (MS+) 409.2, (MS−) 407.2. |
|---|---|---|
| 186 | 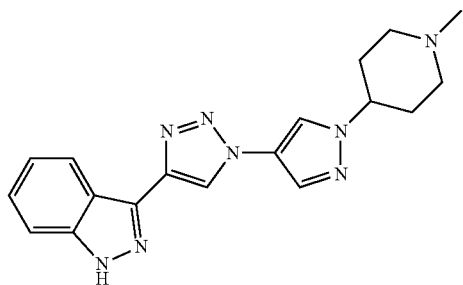 [SMILES: CN1CCC(n2cc(-n3cc(-c4n[nH]c5ccccc45)nn3)cn2)CC1] | white fluffy solid, 1H NMR (300 MHz, DMSO) δ 13.33 (brs, 1H), 9.05 (s, 1H), 8.59 (s, 1H), 8.33 (d, J = 8.1 Hz, 1H), 8.18 (s, 1H), 8.12 (s, 1H), 7.60 (d, J = 8.4 Hz, 1H), 7.44 (t, J = 7.2 Hz, 1H), 7.25 (t, J = 7.4 Hz, 1H), 4.33-4.15 (m, 1H), 2.91 (d, J = 11.2 Hz, 2H), 2.25 (s, 3H), 2.19-1.92 (m, 6H). HPLC (max plot) 99.5%; Rt 2.62 min. UPLC/MS: (MS+) 349.1, (MS−) 347.2. |
| 187 | 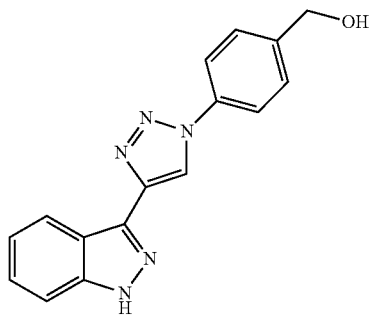 [SMILES: OCc1ccc(-n2cc(-c3n[nH]c4ccccc34)nn2)cc1] | white amorphous solid, 1H NMR (DMSO) δ 13.36 (bs, 1H), 9.30 (s, 1H), 8.36 (d, J = 8.2 Hz, 1H), 8.01 (d, J = 8.5 Hz, 2H), 7.61 (d, J = 8.2 Hz, 1H), 7.56 (d, J = 8.5 Hz, 2H), 7.47-7.41 (m, 1H), 7.28-7.23 (m, 1H), 5.38 (t, J = 5.6 Hz, 1H), 4.60 (d, J = 5.6 Hz, 2H). HPLC (max plot) 98.9%; Rt 2.78 min. UPLC/MS: (MS+) 292.0, (MS−) 290.1. |
| 188 | 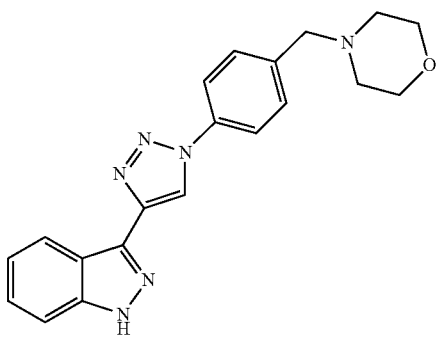 [SMILES: c1ccc2c(-c3cn(-c4ccc(CN5CCOCC5)cc4)nn3)n[nH]c2c1] | beige solid, 1H NMR (DMSO) δ 13.36 (bs, 1H), 9.307 (s, 1H), 8.36 (d, J = 8.1 Hz, 1H), 8.01 (d, J = 8.5 Hz, 2H), 7.61 (d, J = 8.4 Hz, 1H), 7.56 (d, J = 8.5 Hz, 2H), 7.47-7.41 (m, 1H), 7.28-7.23 (m, 1H), 3.60 (t, J = 4.5 Hz, 4H), 3.56 (s, 2H), 2.40 (t, J = 4.5 Hz, 4H). HPLC (max plot) 99.2%; Rt 2.30 min. UPLC/MS: (MS+) 361.1, (MS−) 359.2. |

TABLE 1-continued

| 189 | 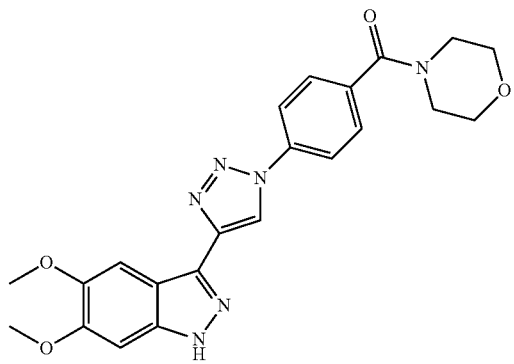 [SMILES: COc1cc2[nH]nc(-c3cn(-c4ccc(C(=O)N5CCOCC5)cc4)nn3)c2cc1OC] | white solid, 1H NMR (DMSO) δ 13.06 (bs, 1H), 9.31 (s, 1H), 8.14 (d, J = 8.6 Hz, 2H), 7.70-7.67 (m, 3H), 7.01 (s, 1H), 3.87 (m, 6H), 3.63 (m, 6H), 3.41 (m, 2H). HPLC (max plot) 99.6%; Rt 2.70 min. UPLC/MS: (MS+) 435.1, (MS−) 433.1. |
| --- | --- | --- |
| 190 | 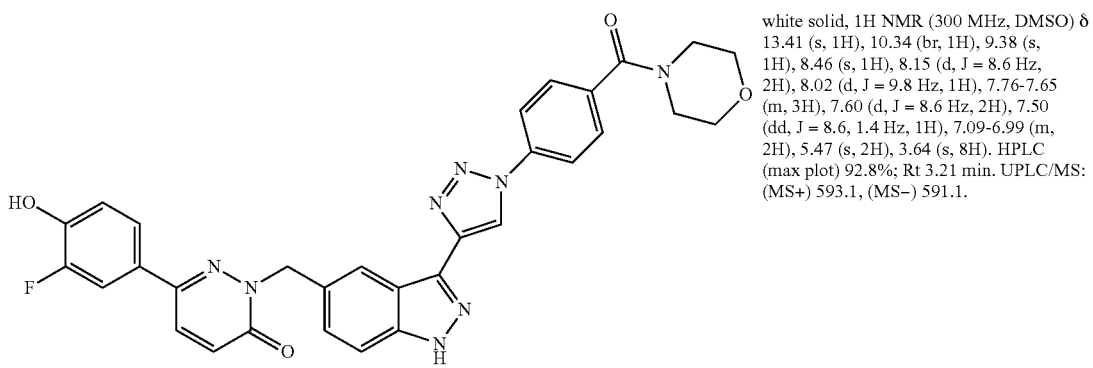 | white solid, 1H NMR (300 MHz, DMSO) δ 13.41 (s, 1H), 10.34 (br, 1H), 9.38 (s, 1H), 8.46 (s, 1H), 8.15 (d, J = 8.6 Hz, 2H), 8.02 (d, J = 9.8 Hz, 1H), 7.76-7.65 (m, 3H), 7.60 (d, J = 8.6 Hz, 2H), 7.50 (dd, J = 8.6, 1.4 Hz, 1H), 7.09-6.99 (m, 2H), 5.47 (s, 2H), 3.64 (s, 8H). HPLC (max plot) 92.8%; Rt 3.21 min. UPLC/MS: (MS+) 593.1, (MS−) 591.1. |
| 191 | 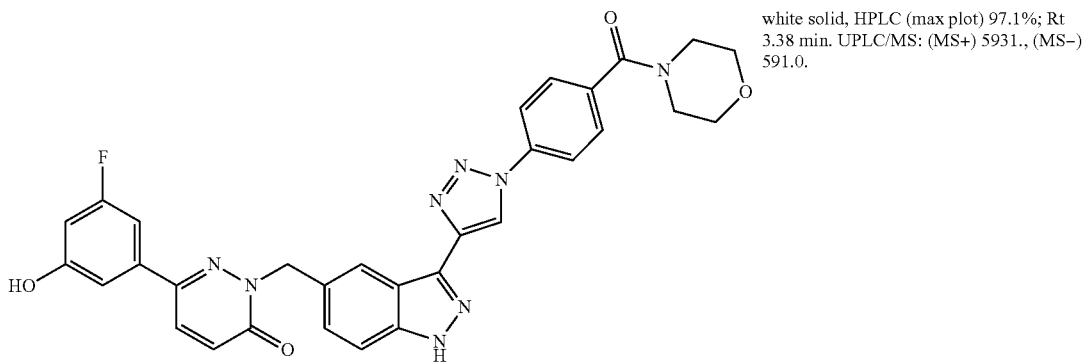 | white solid, HPLC (max plot) 97.1%; Rt 3.38 min. UPLC/MS: (MS+) 5931., (MS−) 591.0. |
| 192 | 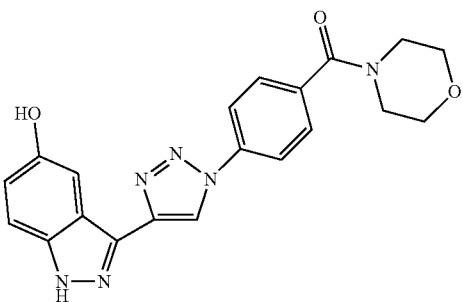 [SMILES: O=C(c1ccc(-n2cc(-c3n[nH]c4ccc(O)cc34)nn2)cc1)N1CCOCC1] | white solid, 1H NMR (DMSO) δ 1H NMR (300 MHz, DMSO) δ 13.12 (s, 1H), 9.31 (s, 2H), 8.15 (d, J = 8.5 Hz, 2H), 7.77-7.62 (m, 3H), 7.43 (d, J = 8.9 Hz, 1H), 6.99 (dd, J = 8.9, 2.2 Hz, 1H), 3.80-3.52 (m, 8H). HPLC (max plot) 96.3%; Rt 2.31 min. UPLC/MS: (MS+) 391.1, (MS−) 389.0 |

TABLE 1-continued

| 193 | 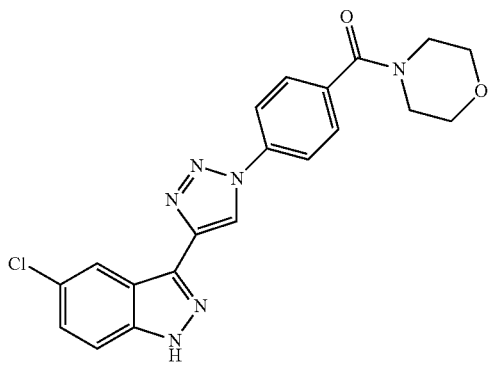 [SMILES: O=C(c1ccc(-n2cc(-c3n[nH]c4ccc(Cl)cc34)nn2)cc1)N1CCOCC1] | beige amorphous solid, 1H NMR (DMSO) δ 13.62 (bs, 1H), 9.45 (s, 1H), 8.39 (d, J = 2.0 Hz, 1H), 8.16 (d, J = 8.6 Hz, 2H), 7.70-7.66 (m, 3H), 7.46 (dd, J = 8.6 Hz, 2.0 Hz, 1H), 3.64 (m, 6H), 3.41 (m, 2H). HPLC (max plot) 99.1%; Rt 3.51 min. UPLC/MS: (MS+) 409.0, (MS−) 407.1. |
|---|---|---|
| 194 | 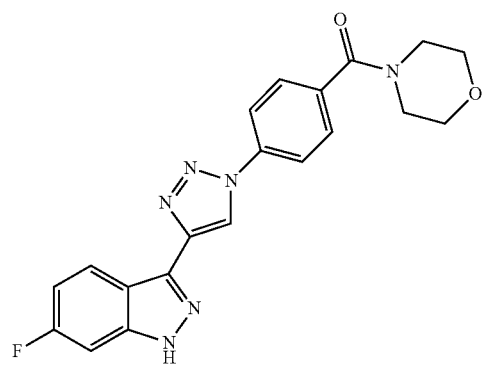 [SMILES: O=C(c1ccc(-n2cc(-c3n[nH]c4cc(F)ccc34)nn2)cc1)N1CCOCC1] | brown solid, 1H NMR (DMSO) δ 13.46 (bs, 1H), 9.42 (s, 1H), 8.38 (dd, J = 8.6 Hz, 5.4 Hz, 1H), 8.15 (d, J = 8.6 Hz, 2H), 7.69 (d, J = 8.6 Hz, 2H), 7.41 (dd, J = 9.3 Hz, 2.1 Hz, 1H), 7.16 (dt, J = 9.3 Hz, 2.1 Hz, 1H), 3.64 (m, 6H), 3.41 (m, 2H). HPLC (max plot) 98.7%; Rt 3.21 min. UPLC/MS: (MS+) 393.1, (MS−) 391.1. |
| 195 | 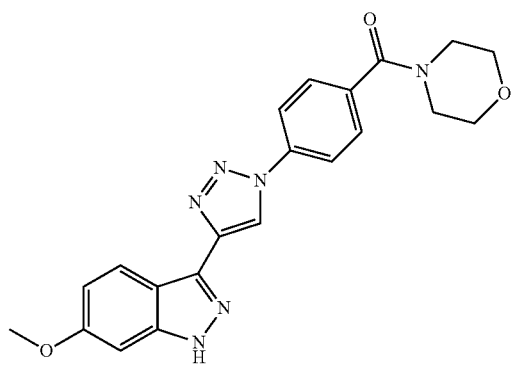 [SMILES: COc1ccc2c(-c3cn(-c4ccc(C(=O)N5CCOCC5)cc4)nn3)n[nH]c2c1] | brown solid, 1H NMR (DMSO) δ 13.14 (bs, 1H), 9.35 (s, 1H), 8.20 (d, J = 9.0 Hz, 1H), 8.15 (d, J = 8.5 Hz, 2H), 7.68 (d, J = 8.5 Hz, 2H), 6.98 (d, J = 2.0 Hz, 1H), 6.88 (dd, J = 9.0 Hz, 2.0 Hz, 1H), 3.85 (s, 3H), 3.64 (m, 6H), 3.41 (m, 2H). HPLC (max plot) 100.0%; Rt 3.05 min. UPLC/MS: (MS+) 405.1. |
| 196 | 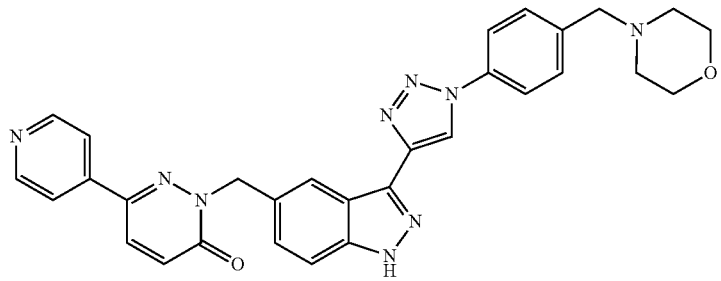 | white solid, 1H NMR (300 MHz, DMSO) δ 13.40 (s, 1H), 9.30 (s, 1H), 8.70 (dd, J = 4.6, 1.6 Hz, 2H), 8.50 (s, 1H), 8.16 (d, J = 9.8 Hz, 1H), 8.10-7.96 (m, 2H), 7.92 (dd, J = 4.6, 1.7 Hz, 2H), 7.64-7.56 (m, 3H), 7.52 (dd, J = 8.7, 1.4 Hz, 1H), 7.17 (d, J = 9.8 Hz, 1H), 5.53 (s, 2H), 3.73-3.46 (m, 6H), 2.46-2.32 (m, 4H). HPLC (max plot) 97.0%; Rt 1.88 min. UPLC/MS: (MS+) 546.1, (MS−) 544.1 |

TABLE 1-continued

| | | |
|---|---|---|
| 197 | 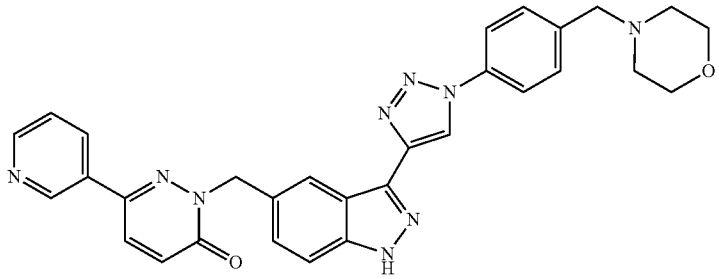 | white solid, 1H NMR (300 MHz, DMSO) δ 13.39 (s, 1H), 9.28 (s, 1H), 9.11 (d, J = 2.0 Hz, 1H), 8.64 (dd, J = 4.8, 1.5 Hz, 1H), 8.48 (s, 1H), 8.35-8.27 (m, 1H), 8.14 (d, J = 9.7 Hz, 1H), 8.00 (d, J = 8.5 Hz, 2H), 7.65-7.47 (m, 5H), 7.15 (d, J = 9.7 Hz, 1H), 5.52 (s, 2H), 3.64-3.54 (m, 6H), 2.45-2.35 (m, 4H). 1H NMR (DMSO) δ. HPLC (max plot) 96.7%; Rt 1.94 min. UPLC/MS: (MS+) 546.1, (MS−) 544.1 |
| 198 | 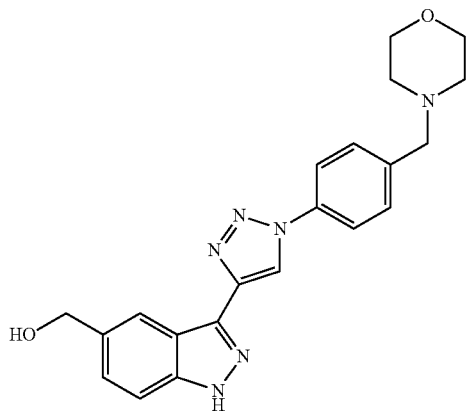 [SMILES: OCc1ccc2[nH]nc(-c3cn(-c4ccc(CN5CCOCC5)cc4)nn3)c2c1] | white solid, 1H NMR (300 MHz, DMSO) δ 13.29 (s, 1H), 9.28 (s, 1H), 8.30 (s, 1H), 8.02 (d, J = 8.5 Hz, 2H), 7.67-7.51 (m, 3H), 7.41 (d, J = 8.6 Hz, 1H), 5.25 (t, J = 5.7 Hz, 1H), 4.65 (d, J = 5.6 Hz, 2H), 3.70-3.51 (m, 6H), 2.45-2.29 (m, 4H). 1H NMR (DMSO) δ. HPLC (max plot) 94.3%; Rt 1.75 min. UPLC/MS: (MS+) 391.1, (MS−) 389.1 |
| 199 | 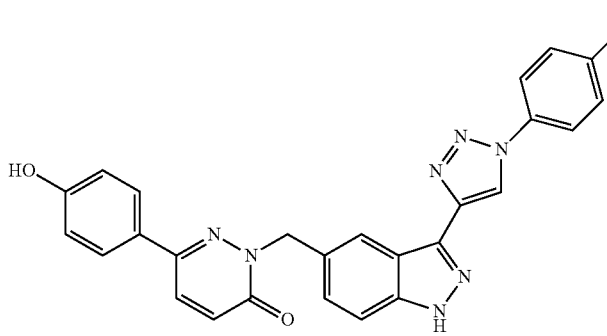 | white solid, 1H NMR (300 MHz, DMSO) δ 13.40 (s, 1H), 9.87 (s, 1H), 9.31 (s, 1H), 8.46 (s, 1H), 8.12-7.93 (m, 3H), 7.76 (d, J = 8.7 Hz, 2H), 7.59 (d, J = 8.6 Hz, 2H), 7.50 (d, J = 8.5 Hz, 1H), 7.04 (d, J = 9.7 Hz, 1H), 6.85 (d, J = 8.7 Hz, 2H), 5.46 (s, 2H), 3.80-3.45 (m, 6H), 2.46-2.26 (m, 4H). HPLC (max plot) 92.5%; Rt 2.68 min. UPLC/MS: (MS+) 561.1, (MS−) 559.1 |
| 200 | 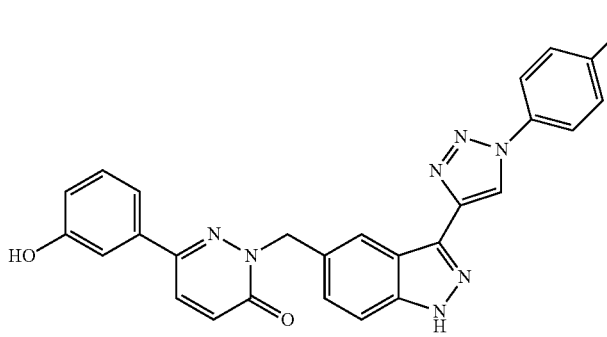 | white solid, 1H NMR (300 MHz, DMSO) δ 13.39 (s, 1H), 9.67 (s, 1H), 9.28 (s, 1H), 8.42 (s, 1H), 8.00 (d, J = 9.7 Hz, 2H), 7.63-7.45 (m, 4H), 7.36-7.23 (m, 3H), 7.08 (d, J = 9.8 Hz, 1H), 6.87-6.80 (m, 1H), 5.49 (s, 2H), 3.70-3.48 (m, 6H), 2.46-2.33 (m, 4H). HPLC (max plot) 93.0%; Rt 2.63 min. UPLC/MS: (MS+) 561.1, (MS−) 559.1 UPLC/MS: (MS+) 561.2, (MS−) 559.1 |

TABLE 1-continued

| | | |
|---|---|---|
| 201 | 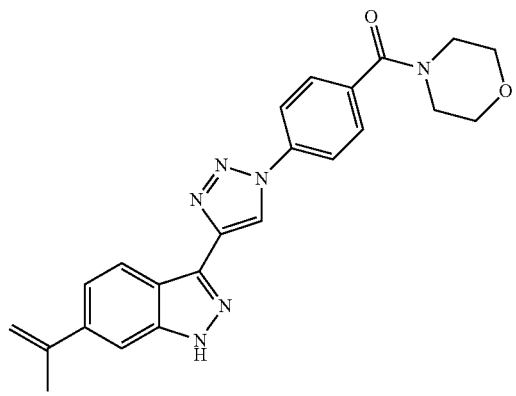 [SMILES: C=C(C)c1ccc2c(-c3cn(-c4ccc(C(=O)N5CCOCC5)cc4)nn3)n[nH]c2c1] | beige amorphous solid, 1H NMR (DMSO) δ 13.38 (brs, 1H), 9.39 (s, 1H), 8.30 (d, J = 8.7 Hz, 1H), 8.15 (d, J = 8.5 hz, 2H), 7.68 (d, J = 8.5 Hz, 2H), 7.60 (s, 1H), 7.50 (dd, J = 8.7 Hz, 1.3 Hz, 1H), 5.59 (m, 1H), 5.23 (m, 1H), 3.64 (m, 6H), 3.41 (m, 2H), 2.23 (s 3H). HPLC (max plot) 98.1%; Rt 4.12 min. UPLC/MS: (MS+) 415.1, (MS−) 413.1. |
| 202 | 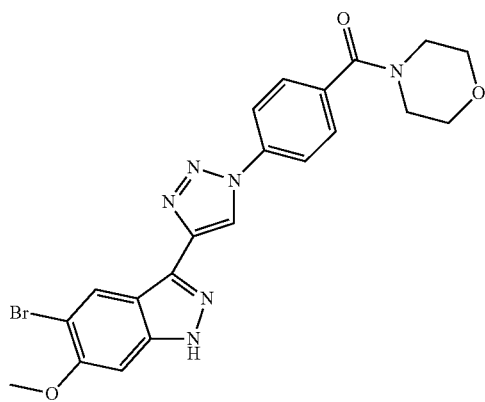 [SMILES: COc1cc2[nH]nc(-c3cn(-c4ccc(C(=O)N5CCOCC5)cc4)nn3)c2cc1Br] | beige powder, 1H NMR (DMSO) δ 13.37 (s, 1H), 9.42 (s, 1H), 8.54 (s, 1H), 8.15 (d, J = 8.6 Hz, 2H), 7.68 (d, J = 8.6 Hz, 2H), 7.15 (s, 1H), 3.96 (s, 3H), 3.75-3.57 (m, 6H), 3.49-3.35 (m, 2H). HPLC (max plot) 98.4%; Rt 3.45 min. UPLC/MS: (MS+) 485.0, (MS−) 483.0 |
| 203 | 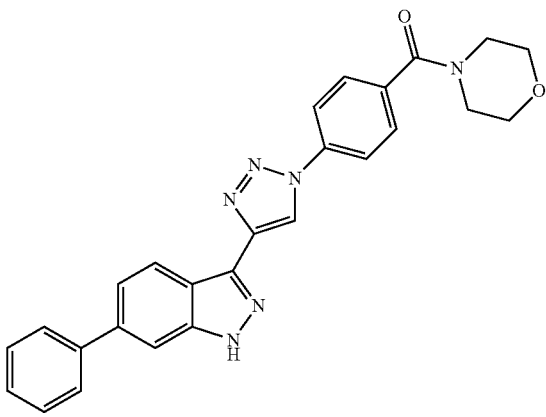 [SMILES: O=C(c1ccc(-n2cc(-c3n[nH]c4cc(-c5ccccc5)ccc34)nn2)cc1)N1CCOCC1] | beige solid, 1H NMR (DMSO) δ 13.48 (bs, 1H), 9.43 (s, 1H), 8.43 (d, J = 8.5 Hz, 1H), 8.17 (d, J = 8.5 Hz, 2H), 7.80-7.78 (m, 3H), 7.69 (d, J = 8.5 Hz, 2H), 7.60-7.57 (m, 1H), 7.55-7.50 (m, 2H), 7.44-7.41 (m, 1H), 3.65 (m, 6H), 3.42 (m, 2H). HPLC (max plot) 98.9%; Rt 3.96 min. UPLC/MS: (MS+) 451.1, (MS−) 449.4. |
| 204 | 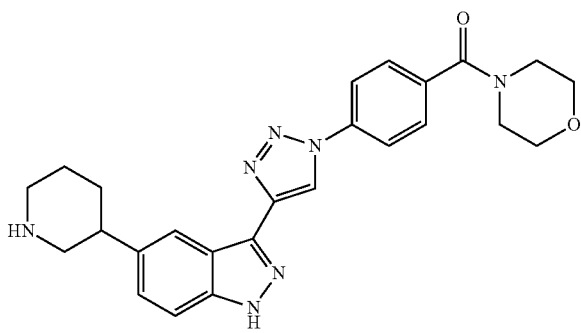 [SMILES: O=C(c1ccc(-n2cc(-c3n[nH]c4ccc(C5CCCNC5)cc34)nn2)cc1)N1CCOCC1] | brown powder, 1H NMR (300 MHz, DMSO) δ 13.42 (brs, 1H), 9.40 (s, 1H), 9.14-8.70 (m, 2H), 8.23 (s, 1H), 8.15 (d, J = 8.5 Hz, 2H), 7.75-7.65 (m, 2H), 7.61 (d, J = 8.6 Hz, 1H), 7.47-7.34 (m, 1H), 3.97-3.58 (m, 8H), 3.54-3.24 (m, 2H), 3.23-2.88 (m, 3H), 2.08-1.70 (m, 4H). HPLC (max plot) 65.3%; Rt 2.51 min. UPLC/MS: (MS+) 458.4, (MS−) 456.2. |

TABLE 1-continued

| 205 | 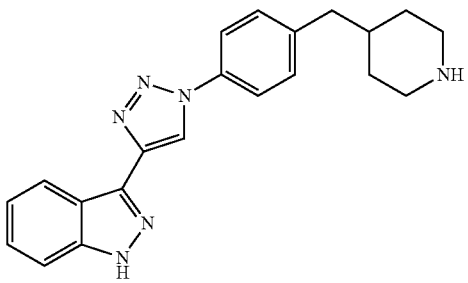 [SMILES: c1ccc2c(-c3cn(-c4ccc(CC5CCNCC5)cc4)nn3)n[nH]c2c1] | beige powder, 1H NMR (300 MHz, DMSO) δ 13.39 (brs, 1H), 9.29 (s, 1H), 8.96-8.71 (m, 1H), 8.67-8.43 (m, 1H), 8.36 (d, J = 8.2 Hz, 1H), 8.05-7.94 (m, 2H), 7.66-7.57 (m, 1H), 7.51-7.38 (m, 3H), 7.31-7.19 (m, 1H), 3.24 (d, 2H), 2.95-2.70 (m, 2H), 2.65 (d, J = 6.9 Hz, 2H), 2.00-1.64 (m, 3H), 1.51-1.23 (m, 2H). HPLC (max plot) 93.4%; Rt 3.21 min. UPLC/MS: (MS+) 359.1, (MS−) 357.2. |
| --- | --- | --- |
| 206 | 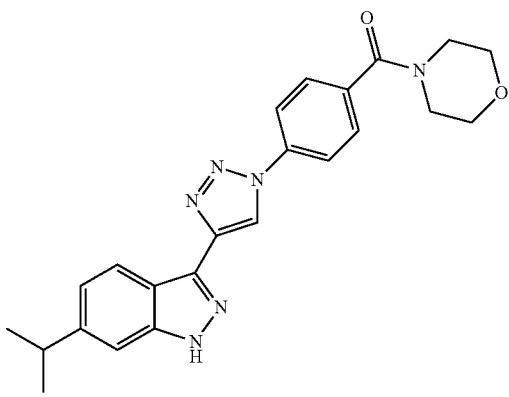 [SMILES: CC(C)c1ccc2c(-c3cn(-c4ccc(C(=O)N5CCOCC5)cc4)nn3)n[nH]c2c1] | white solid, 1H NMR (DMSO) δ 13.21 (brs, 1H), 9.36 (s, 1H), 8.26 (d, J = 8.4 Hz, 1H), 8.15 (d, J = 8.7 Hz, 2H), 7.68 (d, J = 8.7 Hz, 2H), 7.39 (m, 1H), 7.19 (dd, J = 8.6 Hz, 1.2 Hz, 1H), 3.64 (m, 6H), 3.41 (m, 2H), 3.07 (sext., J = 6.9 Hz, 1H), 1.30 (d, J = 6.9 Hz, 6H). HPLC (max plot) 98.8%; Rt 3.85 min. UPLC/MS: (MS+) 417.2, (MS−) 415.2 |
| 207 | 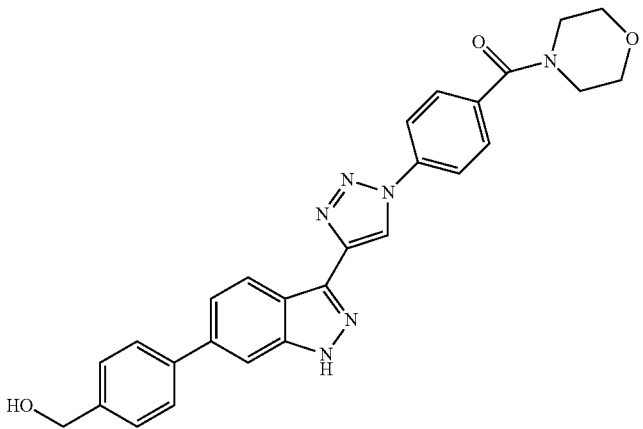 [SMILES: O=C(c1ccc(-n2cc(-c3n[nH]c4cc(-c5ccc(CO)cc5)ccc34)nn2)cc1)N1CCOCC1] | brown solid, 1H NMR (DMSO) δ 13.45 (brs, 1H), 9.43 (s, 1H), 8.42 (d, J = 8.6 Hz, 1H), 8.17 (d, J = 8.6 Hz, 2H), 7.79 (m, 1H), 7.74 (d, J = 8.2 Hz, 2H), 7.69 (d, J = 8.6 Hz, 2H), 7.58 (dd, J = 8.6 Hz, 1.3 HZ, 1H), 7.45 (d, J = 8.2 Hz, 2H), 5.26 (t, J = 5.8 Hz, 1H), 4.57 (d, J = 5.8 Hz, 2H), 3.64 (m, 6H), 3.43 (m, 2H). HPLC (max plot) 92.6%; Rt % 3.13 min. UPLC/MS: (MS+) 481.2, (MS−) 479.2. |
| 208 | 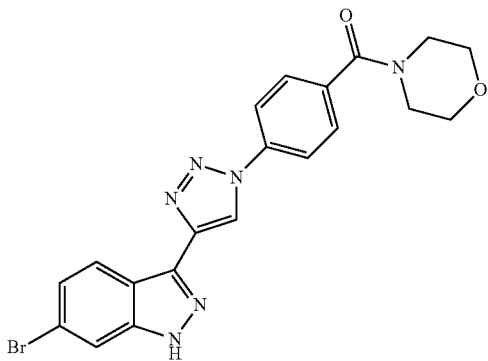 | brown solid, 1H NMR (DMSO) δ 13.52 (brs, 1H), 9.43 (s, 1H), 8.32 (d, J = 8.6 Hz, 1H), 8.15 (d, J = 8.6 Hz, 2H), 7.86 (d, J = 1.5 Hz, 1H), 7.68 (d, J = 8.6 Hz, 2H), 7.40 (dd, J = 8.6 Hz, 1.5 Hz, 1H), 3.64 (m, 6H), 3.41 (m, 2H). HPLC (max plot) 90.4%; Rt % 2.89 min. UPLC/MS: (MS+) 455.0, (MS−) 453.0. |

| | | |
|---|---|---|
| 209 | 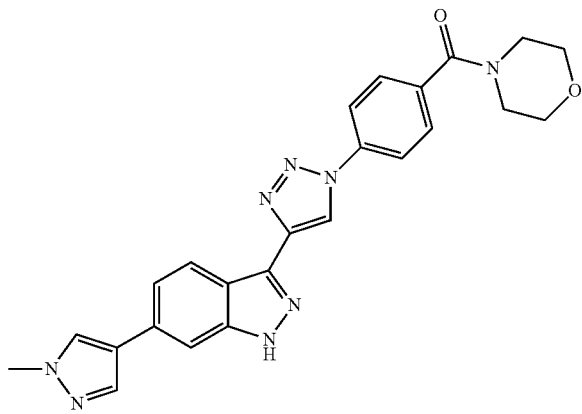 [SMILES: Cn1cc(-c2ccc3c(-c4cn(-c5ccc(C(=O)N6CCOCC6)cc5)nn4)n[nH]c3c2)cn1] | beige amorphous solid, 1H NMR (DMSO) δ 13.32 (bs, 1H), 9.39 (s, 1H), 8.31 (d, J = 8.5 Hz, 1H), 8.28(s, 1H), 8.16 (d, J = 8.7 Hz, 2H), 7.99 (s, 1H), 7.71-7.67 (m, 3H), 7.50 (dd, J = 8.5 Hz, 1.3 Hz, 1H), 3.90 (s, 3H), 3.64 (m, 6H), 3.43 (m, 2H). HPLC (max plot) 96.1%; Rt % 2.99 min. UPLC/MS: (MS+) 455.1, (MS−) 453.1. |
| 210 | 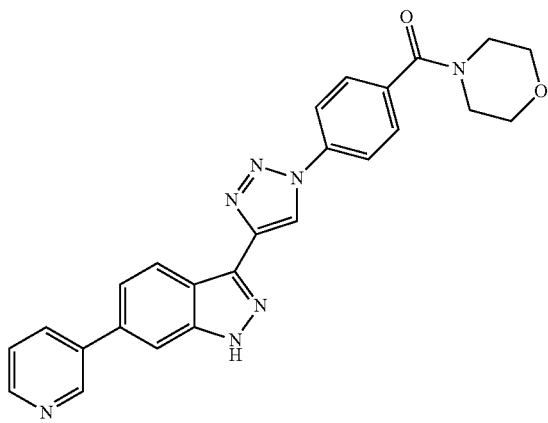 [SMILES: O=C(c1ccc(-n2cc(-c3n[nH]c4cc(-c5cccnc5)ccc34)nn2)cc1)N1CCOCC1] | white solid, 1H NMR (DMSO) δ 13.57 (bs, 1H), 9.44 (s, 1H), 9.02 (d, J = 2.5 Hz, 1H), 8.62 (dd, J = 4.7 Hz, 1.5 Hz, 1H), 8.48 (dd, J = 8.7 Hz, 0.9 HZ, 1H), 8.23-8.15 8 m, 3H), 7.90 (t, J = 0.9 Hz, 1H), 7.70 (d, J = 8.7 Hz, 2H), 7.63 (d, J = 8.7 Hz, 1.5 Hz, 1H), 7.56-7.52 (m, 1H), 3.64 (m, 6H), 3.46 (m, 2H). HPLC (max plot) 96.3%; Rt % 2.04 min. UPLC/MS: (MS+) 452.1, (MS−) 450.1. |
| 211 | 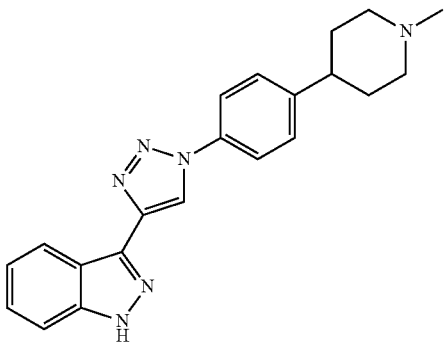 [SMILES: CN1CCC(c2ccc(-n3cc(-c4n[nH]c5ccccc45)nn3)cc2)CC1] | white electrostatic foam, 1H NMR (300 MHz, DMSO) δ 13.36 (brs, 1H), 9.27 (s, 1H), 8.44-8.31 (m, 1H), 8.03-7.92 (m, 2H), 7.66-7.57 (m, 1H), 7.56-7.39 (m, 3H), 7.31-7.20 (m, 1H), 2.99-2.84 (m, 2H), 2.68-2.53 (m, 1H), 2.23 (s, 3H), 2.08-1.96 (m, 2H), 1.86-1.62 (m, 4H). 1H NMR (DMSO) δ. HPLC (max plot) 96.4%; Rt % 3.05 min. UPLC/MS: (MS+) 359.1, (MS−) 357.2 |
| 212 | 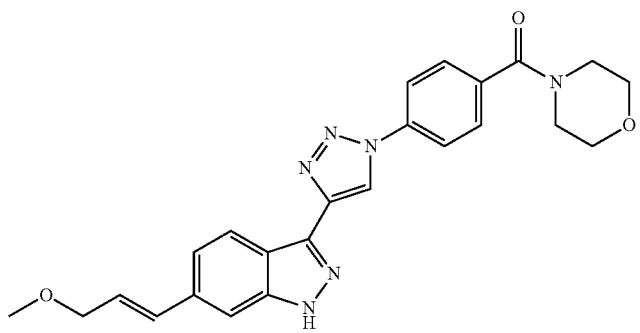 [SMILES: COC/C=C/c1ccc2c(-c3cn(-c4ccc(C(=O)N5CCOCC5)cc4)nn3)n[nH]c2c1] | yellow solid, 1H NMR (300 MHz, DMSO) δ 13.42 (s, 1H), 9.39 (s, 1H), 8.29 (d, J = 8.5 Hz, 1H), 8.15 (d, J = 8.6 Hz, 2H), 7.68 (d, J = 8.5 Hz, 2H), 7.57 (s, 1H), 7.47 (d, J = 8.6 Hz, 1H), 6.80 (d, J = 16.1 Hz, 1H), 6.49 (dt, J = 16.0, 5.7 Hz, 1H), 4.09 (d, J = 5.3 Hz, 2H), 3.82-3.40 (m, 8H), 3.32 (s, 3H). HPLC (max plot) 96.4%; Rt % 3.23 min. UPLC/MS: (MS+) 445.1, (MS−) 443.1 |

TABLE 1-continued

| | | |
|---|---|---|
| 213 | 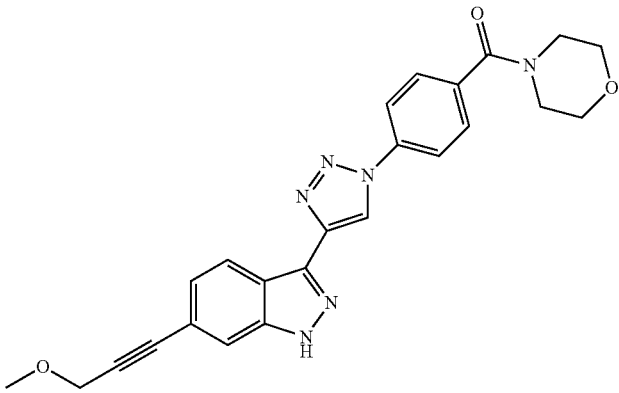 [SMILES: COCC#Cc1ccc2c(-c3cn(-c4ccc(C(=O)N5CCOCC5)cc4)nn3)n[nH]c2c1] | white solid, 1H NMR (DMSO) δ 13.56 (bs, 1H), 9.42 (s, 1H), 8.36 (dd, J = 8.4 Hz, 1.0 Hz, 1H), 8.15 (d, J = 8.6 Hz, 2H), 7.72 (t, J = 1.0 Hz, 1H), 7.68 (d, J = 8.6 Hz, 2H), 7.30 (dd, J = 8.4 Hz, 1.0 Hz, 1H), 4.32 (s, 2H), 3.63 (m, 6H), 3.40(m, 2H), 3.37 (s, 3H). HPLC (max plot) 97.5%; Rt % 3.33 min. UPLC/MS: (MS+) 443.1, (MS−) 441.1 |
| 214 | 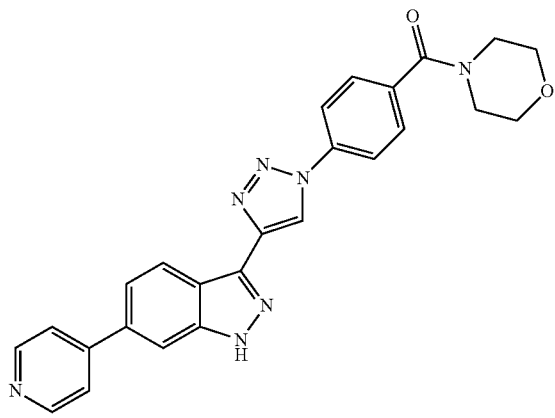 [SMILES: O=C(c1ccc(-n2cc(-c3n[nH]c4cc(-c5ccncc5)ccc34)nn2)cc1)N1CCOCC1] | beige solid, 1H NMR (300 MHz, DMSO-d6) : 13.65 (bs, 1H), 9.47 (s, 1H), 8.70 (d, J = 6.0 Hz, 2H), 8.50 (d, J = 8.6 Hz, 1H), 8.18 (d, J = 8.5 Hz, 2H), 8.00 (s, 1H), 7.86 (d, J = 6.0 Hz, 2H), 7.73-7.69 (m, 3H), 3.66 (m, 6H), 3.45 (m, 2H). HPLC (max plot) 88.2%; Rt % 2.18 min. UPLC/MS: (MS+) 452.1, (MS−) 450.1. |
| 215 | 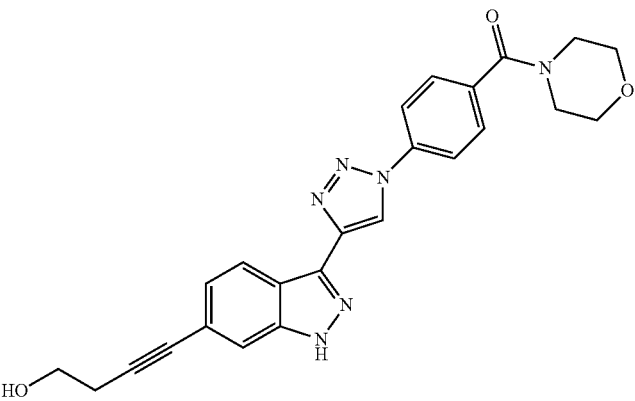 [SMILES: O=C(c1ccc(-n2cc(-c3n[nH]c4cc(C#CCCO)ccc34)nn2)cc1)N1CCOCC1] | white amorphous solid, 1H NMR (DMSO) δ 13.47 (bs, 1H), 9.41 (s, 1H), 8.31 (dd, J = 8.5 hz, 1.0 Hz, 1H), 8.14 (d, J = 8.6 Hz, 2H), 7.68 (d, J = 8.6 Hz, 2H), 7.63 (t, J = 1.0 Hz, 1H), 7.24 (dd, J = 8.5 hz, 1.0 Hz, 1H), 4.96 (t, J = 5.7 Hz, 1H), 3.68-3.59 (m, 8H), 3.40 (m, 2H), 2.60 (t, J = 6.8 Hz, 2H). HPLC (max plot) 97.8%; Rt % 2.87 min. UPLC/MS: (MS+) 443.1, (MS−) 441.2. |
| 216 | 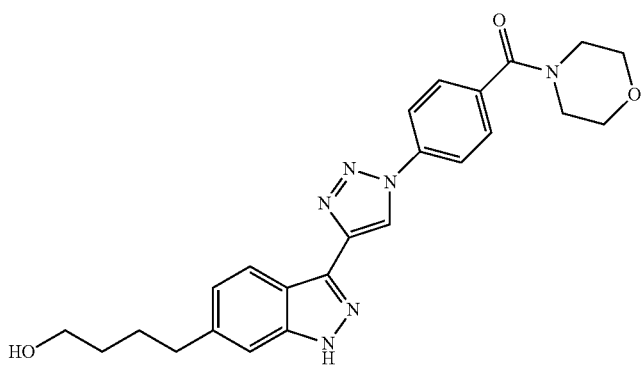 [SMILES: O=C(c1ccc(-n2cc(-c3n[nH]c4cc(CCCCO)ccc34)nn2)cc1)N1CCOCC1] | white solid, 1H NMR (DMSO) δ 13.22 (brs, 1H), 9.37 (s, 1H), 8.24 (d, J = 8.5 Hz, 1H), 8.15 (d, J = 8.5 Hz, 2H), 7.68 (d, J = 8.5 Hz, 2H), 7.37 (s, 1H), 7.12 (d, J = 8.5 Hz, 1H), 4.40 (t, J = 5.2 Hz, 1H), 3.64 (m, 6H), 3.46-3.36 (m, 4H), 2.75 (t, J = 7.5 Hz, 2H), 1.73-1.63 (m, 2H), 1.52-1.43 (m, 2H). HPLC (max plot) 94.6%; Rt % 3.28 min. UPLC/MS: (MS+) 447.2, (MS−) 445.2 |

TABLE 1-continued

| | | |
|---|---|---|
| 217 | 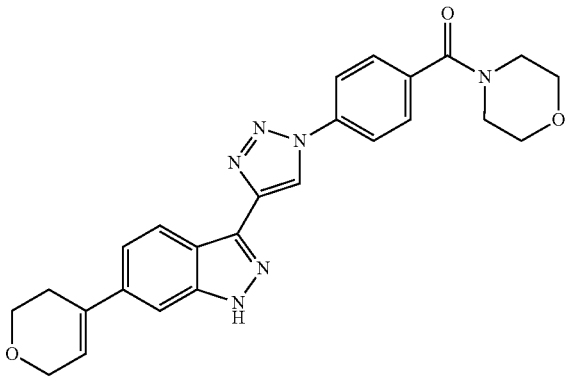 [SMILES: O=C(c1ccc(-n2cc(-c3n[nH]c4cc(C5=CCOCC5)ccc34)nn2)cc1)N1CCOCC1] | brown solid, 1H NMR (300 MHz, DMSO) δ 13.36 (s, 1H), 9.39 (s, 1H), 8.30 (d, J = 8.6 Hz, 1H), 8.15 (d, J = 8.5 Hz, 2H), 7.69 (d, J = 8.6 Hz, 2H), 7.53 (s, 1H), 7.46 (d, J = 9.9 Hz, 1H), 6.43 (s, 1H), 4.28 (d, J = 2.3 Hz, 2H), 3.88 (t, J = 5.4 Hz, 2H), 3.76-3.35 (m, 8H), 2.57 (s, 2H). HPLC (max plot) 96.5%; Rt % 3.19 min. UPLC/MS: (MS+) 457.1, (MS−) 455.2 |
| 218 | 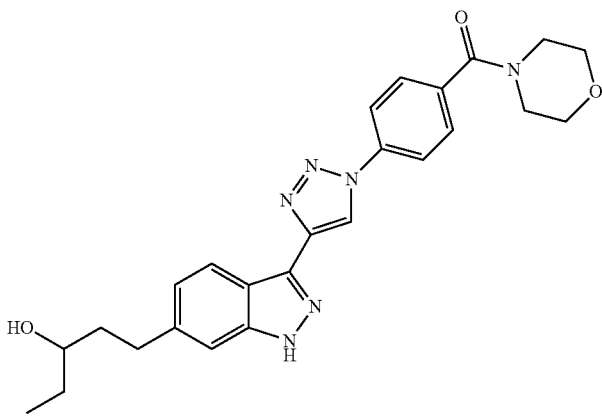 [SMILES: CCC(O)CCc1ccc2c(-c3cn(-c4ccc(C(=O)N5CCOCC5)cc4)nn3)n[nH]c2c1] | brown solid, 1H NMR (DMSO) δ 13.21 (brs, 1H), 9.37 (s, 1H), 8.24 (d, J = 8.4 Hz, 1H), 8.15 (d, J = 8.6 Hz, 2H), 7.67 (d, J = 8.6 Hz, 2H), 7.37 (m, 1H), 7.12 (dd, J = 8.4 Hz, 1.2 Hz, 1H), 4.46 (d, J = 5.4 Hz, 1H), 3.64 (m, 6H), 3.44-3.33 (m, 3H), 2.92-2.69 (m, 2H), 1.78-1.58 (m, 2H), 1.49-1.29 (m, 2H), 0.87 (t, J = 7.4 Hz, 3H). HPLC (max plot) 94.4%; Rt % 3.11 min. UPLC/MS: (MS+) 461.1, (MS−) 459.2 |
| 219 | 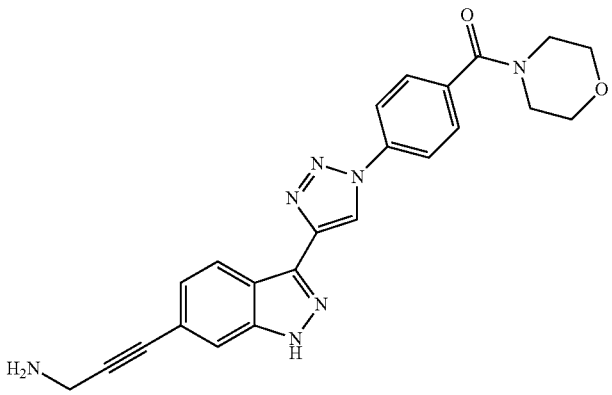 [SMILES: NCC#Cc1ccc2c(-c3cn(-c4ccc(C(=O)N5CCOCC5)cc4)nn3)n[nH]c2c1] | beige amorphous solid, 1H NMR (DMSO) δ 9.42 (s, 1H), 8.36 (d, J = 8.5 Hz, 1H), 8.15 (d, J = 8.6 Hz, 2H), 7.70-7.67 (m, 3H), 7.27 (dd, J = 8.5 Hz, 1.0 Hz, 1H), 3.75 (s, 2H), 3.64 (m, 6H), 3.40 (m, 2H). HPLC (max plot) 95.4%; Rt % 2.09 min. UPLC/MS: (MS+) 428.1, (MS−) 426.2 |
| 220 | 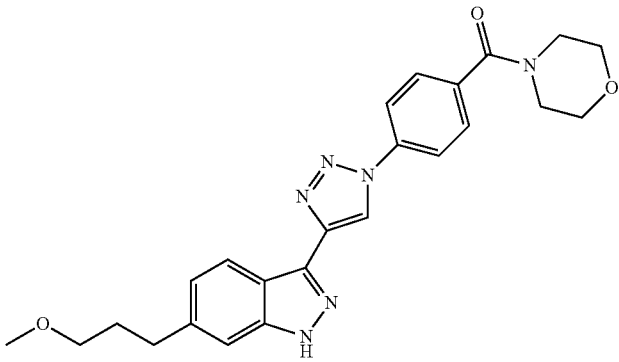 [SMILES: COCCCc1ccc2c(-c3cn(-c4ccc(C(=O)N5CCOCC5)cc4)nn3)n[nH]c2c1] | white solid, 1H NMR (DMSO) δ 1H NMR (300 MHz, DMSO) δ 13.24 (s, 1H), 9.37 (s, 1H), 8.25 (d, J = 8.5 Hz, 1H), 8.15 (d, J = 8.6 Hz, 2H), 7.68 (d, J = 8.6 Hz, 2H), 7.38 (s, 1H), 7.13 (d, J = 9.6 Hz, 1H), 3.63 (s, 8H), 3.39-3.35 (m, 2H), 3.25 (s, 3H), 2.83-2.74 (m, 2H), 1.95-1.82 (m, HPLC (max plot) 98.6%; Rt % 3.29 min. UPLC/MS: (MS+) 447.1, (MS−) 445.2. |

| | | |
|---|---|---|
| 221 | 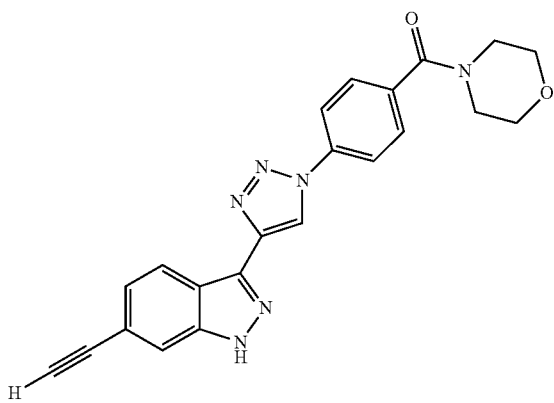 [SMILES: C#Cc1ccc2c(-c3cn(-c4ccc(C(=O)N5CCOCC5)cc4)nn3)n[nH]c2c1] | brown solid, 1H NMR (DMSO) δ 13.56 (brs, 1H), 9.42 (s, 1H), 8.35 (dd, J = 8.4 Hz, 1.0 Hz, 1H), 8.15 (d, J = 8.6 Hz, 2H), 7.75 (t, J = 1.0 Hz, 1H), 7.68 (d, J = 8.6 Hz, 2H), 7.31 (dd, J = 8.4 Hz, 1.0 Hz, 1H), 4.28 (s, 1H), 3.63 (m, 6H), 3.41 (m, 2H). HPLC (max plot) 92.7%; Rt % 3.28 min. UPLC/MS: (MS+) 399.1. |
| 222 | 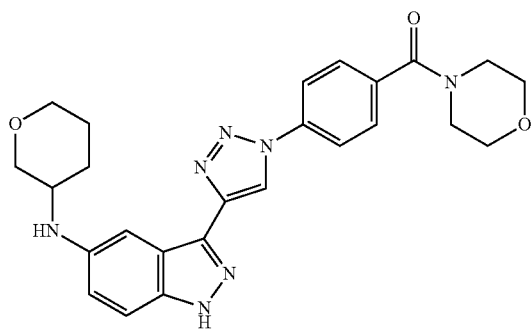 [SMILES: O=C(c1ccc(-n2cc(-c3n[nH]c4ccc(NC5CCCOC5)cc34)nn2)cc1)N1CCOCC1] | beige foam, 1H NMR (300 MHz, DMSO) δ 12.97 (brs, 1H), 9.26 (s, 1H), 8.20-8.08 (m, 2H), 7.73-7.63 (m, 2H), 7.41-7.30 (m, 2H), 6.95 (dd, J = 9.1, 1.9 Hz, 1H), 5.41 (d, J = 8.1 Hz, 1 4.06-3.90 (m, 1H), 3.90-3.71 (m, 2H), 3.71-3.39 (m, 8H), 3.21-3.05 (m, 1H), 2.06 (t, J = 10.5 Hz, 1H), 1.83-1.39 (m, 4H). HPLC (max plot) 89.4%; Rt % 2.45 min. UPLC/MS: (MS+) 474.1, (MS−) 472.2 |
| 223 | 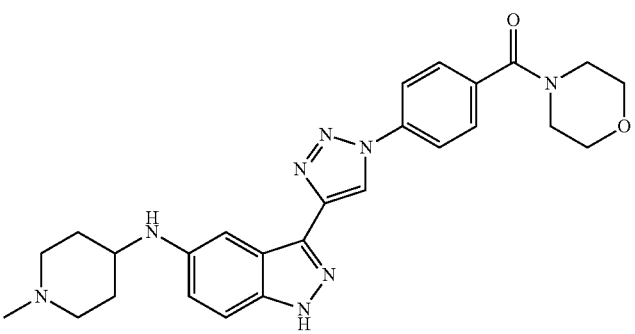 [SMILES: CN1CCC(Nc2ccc3[nH]nc(-c4cn(-c5ccc(C(=O)N6CCOCC6)cc5)nn4)c3c2)CC1] | brown amorphous solid, 1H NMR (300 MHz, DMSO) δ 12.94 (brs, 1H), 9.25 (s, 1H), 8.20-8.09 (m, 2H), 7.74-7.63 (m, 2H), 7.39-7.25 (m, 2H), 6.92 (dd, J = 8.9, 2.1 Hz, 1H), 5.34 (d, J = 7.9 Hz, 1H), 3.85-3.13 (m, 9H), 2.87-2.66 (m, 2H), 2.19 (s, 3H), 2.14-1.88 (m, 4H), 1.55-1.31 (m, 2H). HPLC (max plot) 92.3%; Rt % 2.02 min. UPLC/MS: (MS+) 487.1, (MS−) 485.3 |
| 224 | 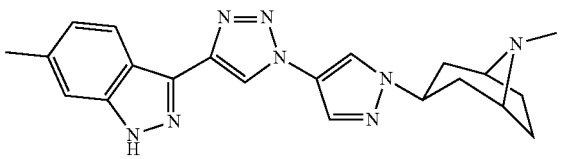 | yellow solid, 1H NMR (DMSO) δ 1H NMR (300 MHz, DMSO) δ 13.15 (s, 1H), 9.00 (s, 1H), 8.54 (s, 1H), 8.24-8.13 (m, 2H), 8.08 (s, 1H), 7.36 (s, 1H), 7.07 (dd, J = 8.5, 1.1 Hz, 1H), 4.67-4.52 (m, 1H), 3.29 (s, 2H), 2.47 (s, 3H), 2.31 (s, 3H), 2.21-2.09 (m, 2H), 2.09-1.97 (m, 2H), 1.94-1.83 (m, 2H), 1.78-1.67 (m, 2H). HPLC (max plot) 98.6%; Rt % 2.53 min. UPLC/MS: (MS+) 389.1, (MS−) 387.2. |
| 225 | 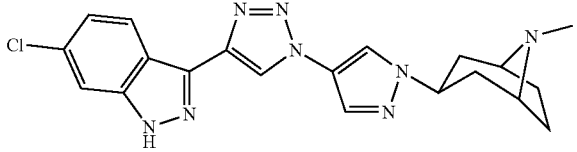 | white solid, 1H NMR (300 MHz, DMSO) δ 13.47 (s, 1H), 9.06 (s, 1H), 8.55 (s, 1H), 8.33 (d, J = 8.7 Hz, 1H), 8.20 (s, 1H), 8.08 (s, 1H), 7.69 (d, J = 1.3 Hz, 1H), 7.27 (dd, J = 8.7, 1.8 Hz, 1H), 4.66-4.49 (m, 1H), 3.27 (s, 2H), 2.29 (s, 3H), 2.20-2.07 (m, 2H), 2.07-1.96 (m, 2H), 1.93-1.81 (m, 2H), 1.77-1.66 (m, 2H). HPLC (max plot) 99.6%; Rt % 2.71 min. UPLC/MS: (MS+) 389.1, (MS−) 387.2. |

TABLE 1-continued

| 226 | 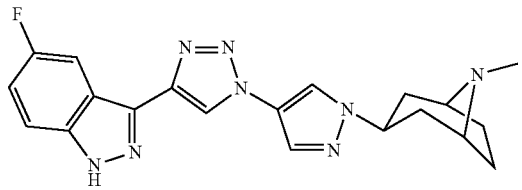 [SMILES: CN1C2CCC1CC(n1cc(-n3cc(-c4n[nH]c5ccc(F)cc45)nn3)cn1)C2] | yellow solid, 1H NMR (300 MHz, DMSO) δ 13.49 (brs, 1H), 9.06 (s, 1H), 8.55 (s, 1H), 8.23 (s, 1H), 8.09 (d, J = 0.5 Hz, 1H), 7.99 (dd, J = 9.2, 2.4 Hz, 1H), 7.65 (dd, J = 9.2, 4.1 Hz, 1H), 7.34 (dd, J = 9.2, 2.5 Hz, 1H), 4.71-4.52 (m, 1H), 3.35 (s, 2H), 2.34 (s, 3H), 2.25-2.11 (m, 2H), 2.10-1.98 (m, 2H), 1.97-1.85 (m, 2H), 1.81-1.68 (m, 2H). HPLC (max plot) 95.9%; Rt % 2.43 min. UPLC/MS: (MS+) 393.1, (MS−) 391.2. |
| --- | --- | --- |
| 227 | 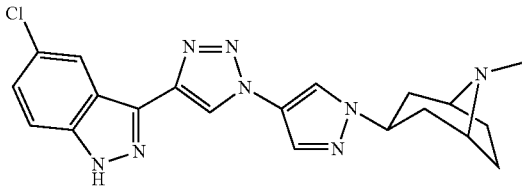 [SMILES: CN1C2CCC1CC(n1cc(-n3cc(-c4n[nH]c5ccc(Cl)cc45)nn3)cn1)C2] | white solid, 1H NMR (300 MHz, DMSO) δ 13.55 (s, 1H), 9.08 (s, 1H), 8.55 (s, 1H), 8.33 (d, J = 1.7 Hz, 1H), 8.19 (s, 1H), 8.09 (s, 1H), 7.65 (d, J = 8.9 Hz, 1H), 7.45 (dd, J = 8.9, 2.0 Hz, 1H), 4.67-4.53 (m, 1H), 3.29 (s, 2H), 2.30 (s, 3H), 2.21-2.09 (m, 2H), 2.08-1.98 (m, 2H), 1.94-1.83 (m, 2H), 1.78-1.67 (m, 2H). HPLC (max plot) 98.6%; Rt % 2.70 min. UPLC/MS: (MS+) 409.1, (MS−) 407.2. |
| 228 | 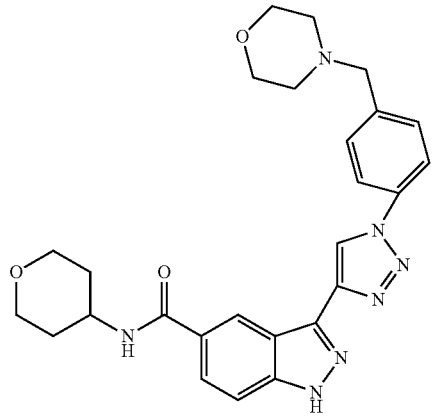 [SMILES: O=C(NC1CCOCC1)c1ccc2[nH]nc(-c3cn(-c4ccc(CN5CCOCC5)cc4)nn3)c2c1] | white solid, 1H NMR (300 MHz, DMSO) δ 13.57 (s, 1H), 9.35 (s, 1H), 8.86 (s, 1H), 8.47 (d, J = 7.6 Hz, 1H), 8.02 (d, J = 8.5 Hz, 2H), 7.93 (dd, J = 8.8, 1.5 Hz, 1H), 7.71-7.49 (m, 3H), 4.16-3.98 (m, 1H), 3.91 (brd, J = 9.3 Hz, 2H), 3.66-3.54 (m, 6H), 3.41 (brt, J = 10.9 Hz, 2H), 2.49-1 2.30 (m, 4H), 1.80 (brd, J = 12.4 Hz, 2H), 1.73-1.55 (m, 2H). HPLC (max plot) 98.0%; Rt % 2.08 min. UPLC/MS: (MS+) 488.2, (MS−) 486.2 |
| 229 | 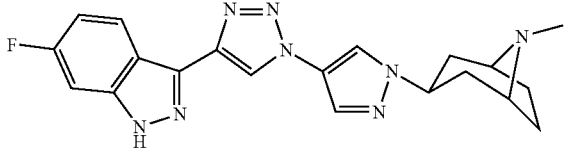 [SMILES: CN1C2CCC1CC(n1cc(-n3cc(-c4n[nH]c5cc(F)ccc45)nn3)cn1)C2] | white solid, 1H NMR (300 MHz, DMSO) δ 13.41 (s, 1H), 9.05 (s, 1H), 8.55 (s, 1H), 8.34 (dd, J = 8.9, 5.3 Hz, 1H), 8.08 (s, 1H), 7.39 (dd, J = 9.6, 2.1 Hz, 1H), 7.14 (td, J = 9.3, 2.2 Hz, 1H), 4.68-4.50 (m, 1H), 3.27 (s, 2H), 2.29 (s, 3H), 2.20-2.08 (m, 2H), 2.08-1.95 (m, 2H), 1.93-1.81 (m, 2H), 1.77-1.67 (m, 2H). HPLC (max plot) 99.7%; Rt % 2.46 min. UPLC/MS: (MS+) 393.2, (MS−) 391.2. |
| 230 | 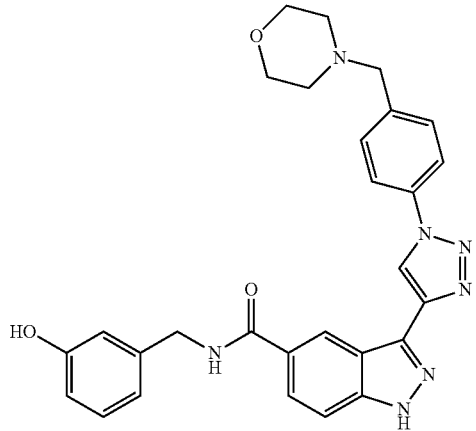 [SMILES: O=C(NCc1cccc(O)c1)c1ccc2[nH]nc(-c3cn(-c4ccc(CN5CCOCC5)cc4)nn3)c2c1] | white solid, 1H NMR (300 MHz, DMSO + D2O) δ 9.40 (s, 1H), 8.96-8.89 (m, 1H), 8.15 (d, J = 7.6 Hz, 2H), 7.99 (dd, J = 8.8, 1.6 Hz, 1H), 7.71 (dd, J = 20.8, 8.6 Hz, 3H), 7.12 (t, J = 8.0 Hz, 1H), 6.83-6.73 (m, 2H), 6.68-6.57 (m, 1H), 4.57-4.18 (m, 4H), 4.06-3.56 (m, 4H), 3.37-2.91 (m, 4H). HPLC (max plot) 98.3%; Rt % 2.29 min. UPLC/MS: (MS+) 510.2, (MS−) 508.1 |

| | | |
|---|---|---|
| 231 | 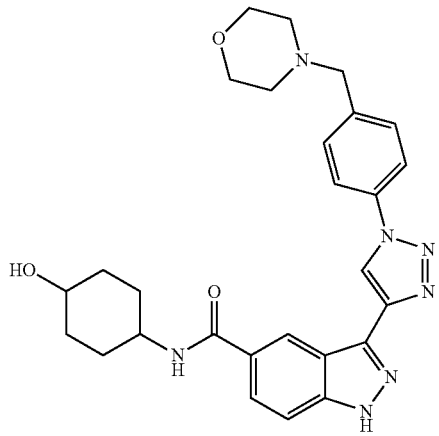 [SMILES: O=C(NC1CCC(O)CC1)c1ccc2[nH]nc(-c3cn(-c4ccc(CN5CCOCC5)cc4)nn3)c2c1] | yellow solid, 1H NMR (300 MHz, DMSO + D2O) δ 9.35 (s, 1H), 8.82 (s, 1H), 8.33 (d, J = 7.9 Hz, 1H), 8.18-7.98 (m, 3H), 7.91 (dd, J = 8.8, 1.5 Hz, 1H), 7.74-7.54 (m, 3H), 3.86-3.53 (m, 6H), 3.53-3.31 (m, 5H), 1.96-1.76 (m, 4H), 1.56-1.13 (m, 4H). HPLC (max plot) 98.0%; Rt % 1.93 min. UPLC/MS: (MS+) 502.2, (MS−) 500.1 |
| 232 | 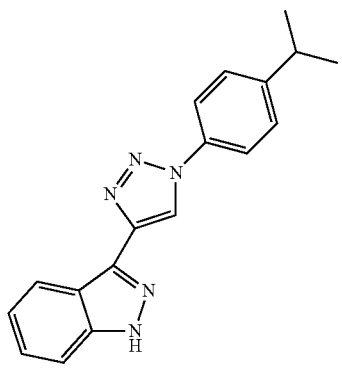 [SMILES: CC(C)c1ccc(-n2cc(-c3n[nH]c4ccccc34)nn2)cc1] | grey solid, 1H NMR (DMSO) δ 13.36 (s, 1H), 9.27 (s, 1H), 8.38-8.35 (m, 1H), 7.99-7.94 (m, 2H), 7.62-7.59 (m, 1H), 7.52-7.49 (m, 2H), 7.47-7.41 (m, 1H), 7.28-7.23 (m, 1H), 3.06-2.96 (quint, J = 6.9 Hz, 1H), 1.28-1.25 (d, J = 6.9 Hz, 6H). HPLC (max plot) 99.1%; Rt % 4.35 min. UPLC/MS: (MS+) 304.3, (MS−) 302.3. |
| 233 | 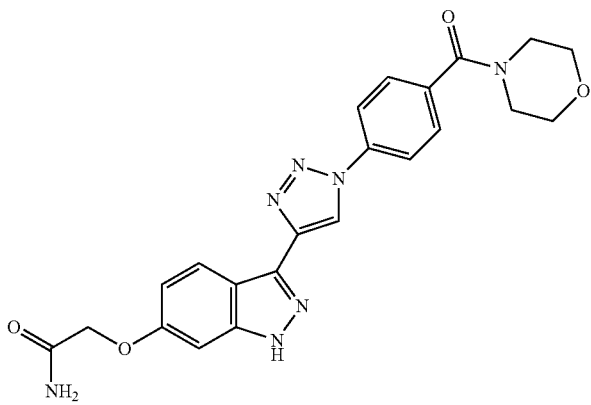 [SMILES: NC(=O)COc1ccc2c(-c3cn(-c4ccc(C(=O)N5CCOCC5)cc4)nn3)n[nH]c2c1] | white solid, 1H NMR (300 MHz, DMSO) δ 13.18 (s, 1H), 9.37 (s, 1H), 8.29-8.07 (m, 3H), 7.75-7.58 (m, 3H), 7.47 (brs, 1H), 7.04-6.89 (m, 2H), 4.54 (s, 2H), 3.78-3.22 (m, 8H). HPLC (max plot) 95.2%; Rt % 2.36 min. UPLC/MS: (MS+) 448.3, (MS−) 446.3. |
| 234 | 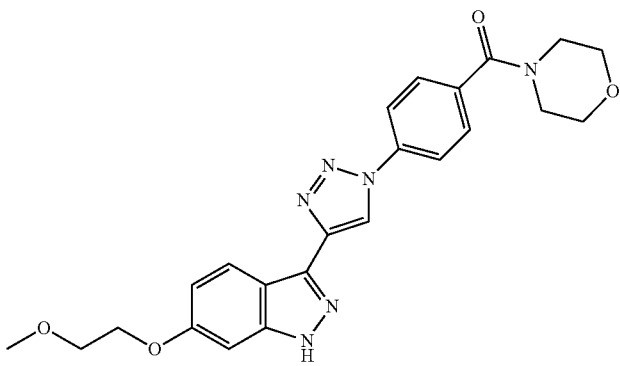 [SMILES: COCCOc1ccc2c(-c3cn(-c4ccc(C(=O)N5CCOCC5)cc4)nn3)n[nH]c2c1] | white solid, 1H NMR (300 MHz, DMSO) δ 13.15 (s, 1H), 9.36 (s, 1H), 8.28-8.06 (m, 3H), 7.68 (d, J = 8.5 Hz, 2H), 6.99 (brs, 1H), 6.90 (dd, J = 8.9, 1.9 Hz, 1H), 4.31-4.09 (m, 2H), 3.79-3.52 (m, 8H), 3.51-3.23 (m, 5H). 1H NMR (DMSO) δ. HPLC (max plot) 94.1%; Rt % 2.93 min. UPLC/MS: (MS+) 449.4, (MS−) 447.4. |

TABLE 1-continued
| 235 | 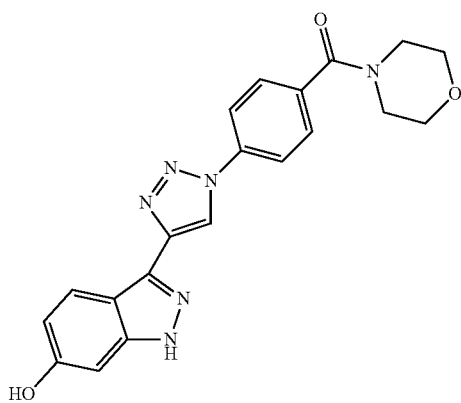 [SMILES: O=C(c1ccc(-n2cc(-c3n[nH]c4cc(O)ccc34)nn2)cc1)N1CCOCC1] | brown solid, 1H NMR (DMSO) δ 12.88 (s, 1H), 9.72 (s, 1H), 9.32 (s, 1H), 8.15-8.11 (m, 3H), 7.69-7.66 (d, 2H), 6.82-6.76 (m, 2H), 3.73-3.37 (m, 8H). HPLC (max plot) 93.0%; Rt % 2.40 min. UPLC/MS: (MS+) 391.3, (MS−) 389.4. |
| --- | --- | --- |
| 236 | 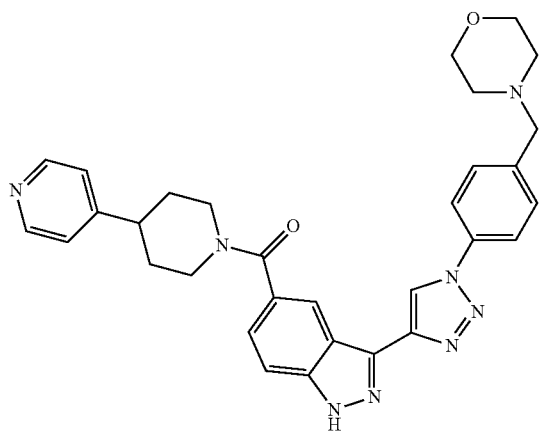 [SMILES: O=C(c1ccc2[nH]nc(-c3cn(-c4ccc(CN5CCOCC5)cc4)nn3)c2c1)N1CCC(c2ccncc2)CC1] | yellow solid, 1H NMR (300 MHz, DMSO + D2O) δ 9.34 (s, 1H), 8.53-8.40 (m, 3H), 8.14 (s, 1H), 8.01 (d, J = 8.5 Hz, 2H), 7.94 (s, 1H), 7.68 (d, J = 8.6 Hz, 1H), 7.61-7.49 (m, 3H), 7.34 (d, J = 6.1 Hz, 2H), 3.66-3.54 (m, 5H), 3.50-3.29 (m, 1H), 2.98-2.80 (m, 2H), 2.45-2.36 (m, 4H), 2.04-1.51 (m, 6H). HPLC (max plot) 98.7%; Rt % 1.70 min. UPLC/MS: (MS+) 549.4, (MS−) 547.5 |
| 237 | 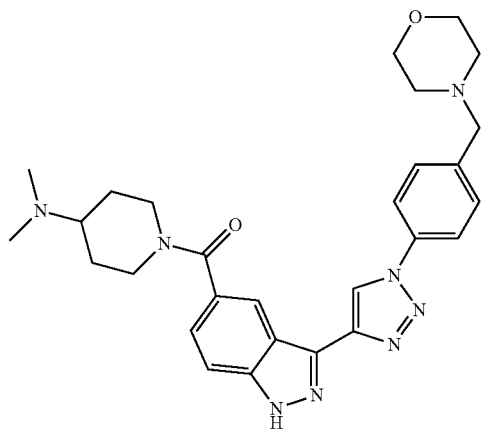 [SMILES: CN(C)C1CCN(C(=O)c2ccc3[nH]nc(-c4cn(-c5ccc(CN6CCOCC6)cc5)nn4)c3c2)CC1] | yellow solid, 1H NMR (300 MHz, DMSO) δ 9.36 (s, 1H), 8.45 (s, 1H), 8.19-8.00 (m, 2H), 7.94 (s, 1H), 7.80-7.57 (m, 2H), 7.57-7.42 (m, 1H), 4.86-4.25 (m, 2H), 3.87-3.55 (m, 4H), 3.53-3.19 (m, 2H), 3.17-2.91 (m, 3H), 2.89 (s, 3H), 2.73 (s, 3H), 2.18-1.85 (m, 4H), 1.62 (s, 4H). HPLC (max plot) 93.9%; Rt % 1.44 min. UPLC/MS: (MS+) 515.2, (MS−) 513.1 |

TABLE 1-continued

| 238 | 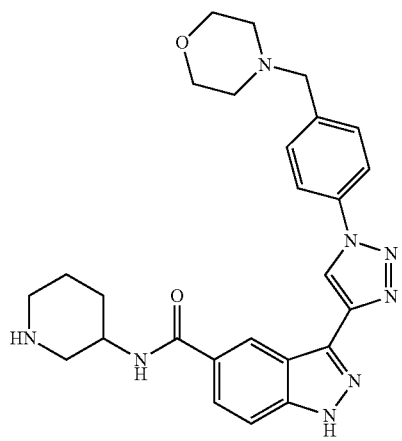 [SMILES: O=C(NC1CCCNC1)c1ccc2[nH]nc(-c3cn(-c4ccc(CN5CCOCC5)cc4)nn3)c2c1] | yellow solid, 1H NMR (300 MHz, DMSO) δ 13.67 (s, 1H), 10.96 (brs, 1H), 9.59 (brs, 1H), 8.92 (brs, 2H), 8.71 (d, J = 7.8, 1H), 8.21 (d, J = 7.1, 2H), 7.95 (dd, J = 1.4, 8.8, 1H), 7.82 (d, J = 7.7, 2H), 7.66 (d, J = 8.6, 1H), 4.45 (m, 2H), 4.25 (m, 1H), 3.96 (m, 2H), 3.72 (m, 2H), 3.60 (brs, 1H), 3.12-3.35 (m, 6H), 2.88 (m, 2H), 1.94 (, 2H), 1.70 (m, 2H). HPLC (max plot) 97.3%; Rt % 1.61 min. UPLC/MS: (MS+) 487.1. |
| 239 | 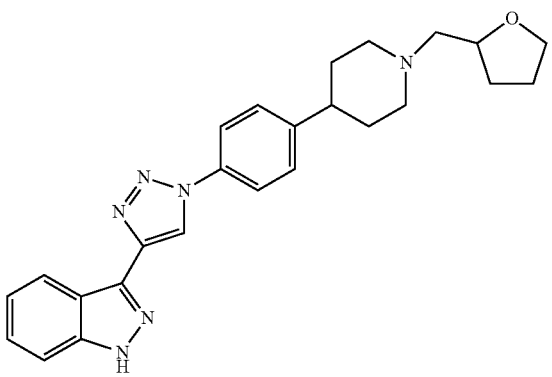 [SMILES: c1ccc2c(-c3cn(-c4ccc(C5CCN(CC6CCCO6)CC5)cc4)nn3)n[nH]c2c1] | amorphous white foam, 1H NMR (300 MHz, DMSO) δ 13.36 (brs, 1H), 9.29-9.25 (m, 1H), 8.41-8.29 (m, 1H), 8.04-7.91 (m, 2H), 7.65-7.58 (m, 1H), 7.56-7.48 (m, 2H), 7.48-7.38 (m, 1H), 7.31-7.18 (m, 1H), 4.05-3.88 (m, 1H), 3.81-3.69 (m, 1H), 3.66-3.54 (m, 1H), 3.17-3.07 (m, 1H), 3.05-2.94 (m, 1H), 2.63-2.53 (m, 1H), 2.44-2.37 (m, 1H), 2.21-2.01 (m, 2H), 1.97-1.64 (m, 7H), 1.58-1.40 (m, 1H), 1.30-1.19 (m, 1H). HPLC (max plot) 75.0%; Rt % 2.91 min. UPLC/MS: (MS+) 429.4, (MS−) 427.5 |
| 240 | 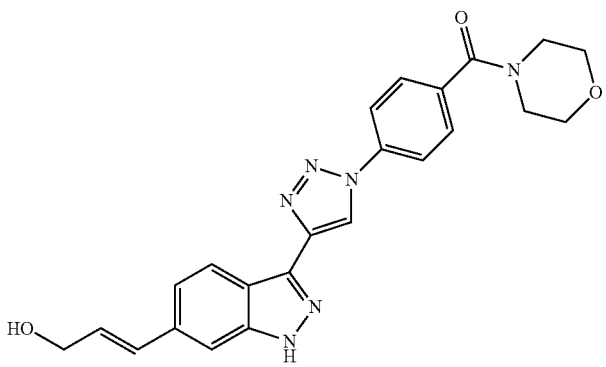 [SMILES: O=C(c1ccc(-n2cc(-c3n[nH]c4cc(/C=C/CO)ccc34)nn2)cc1)N1CCOCC1] | white solid, 1H NMR (DMSO) δ 13.34 (brs, 1H), 9.39 (s, 1H), 8.28 (d, J = 8.5 Hz, 1H), 8.15 (d, J = 8.7 Hz, 2H), 7.68 (d, J = 8.7 Hz, 2H), 7.53 (s, 1H), 7.46-7.42 (m, 1H), 6.74 (d, J = 15.9 Hz, 1H), 6.52 (dt, J = 15.9 Hz, 5.0 Hz, 1H), 4.93 (t, J = 5.5 Hz, 1H), 4.19-4.16 (m, 2H), 3.64 (m, 6H), 3.40 (m, 2H). HPLC (max plot) 99.2%; Rt % 2.68 min. UPLC/MS: (MS+) 431.4, (MS−) 429.4. |
| 241 | 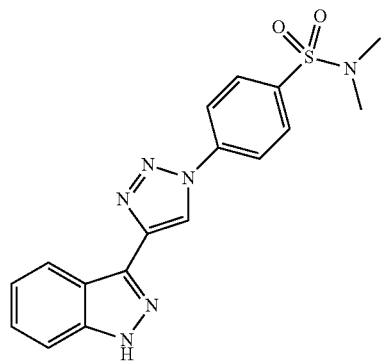 [SMILES: CN(C)S(=O)(=O)c1ccc(-n2cc(-c3n[nH]c4ccccc34)nn2)cc1] | white solid, 1H NMR (DMSO) δ 13.43 (bs, 1H), 9.51 (s, 1H), 8.40-8.35 (m, 3H), 8.01 (d, J = 8.8 Hz, 2H), 7.62 (dt, J = 8.4 Hz, 1.0 Hz, 1H), 7.48-42 (m, 1H), 7.30-7.24 (m, 1H), 2.69 (s, 6H). HPLC (max plot) 99.1%; Rt % 3.55 min. UPLC/MS: (MS+) 369.3, (MS−) 367.3 |

TABLE 1-continued

| 242 | 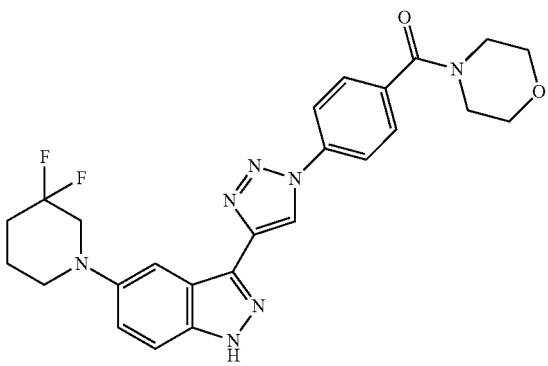 [SMILES: O=C(c1ccc(-n2cc(-c3n[nH]c4ccc(N5CCCC(F)(F)C5)cc34)nn2)cc1)N1CCOCC1] | beige residue, 1H NMR (300 MHz, CDCl3) δ 8.58 (s, 1H), 8.08-7.88 (m, 3H), 7.66 (d, J = 8.2 Hz, 2H), 7.48 (d, J = 8.7 Hz, 1H), 7.38-7.29 (m, 1H), 4.04-3.33 (m, 10H), 3.33-3.18 (m, 2H), 2.25-1.78 (m, 6H). HPLC (max plot) 84.2%; Rt % 3.47 min. UPLC/MS: (MS+) 494.4, (MS−) 492.4 |
| --- | --- | --- |
| 243 | 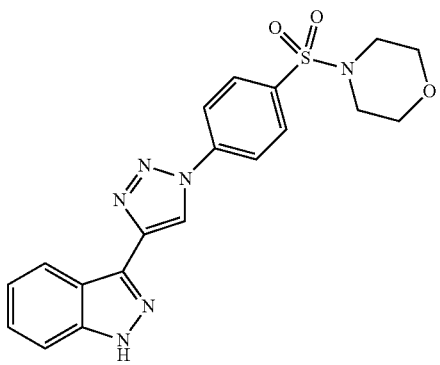 [SMILES: O=S(=O)(c1ccc(-n2cc(-c3n[nH]c4ccccc34)nn2)cc1)N1CCOCC1] | white solid, 1H NMR (DMSO) δ 13.43 (brs, 1H), 9.52 (s, 1H), 8.42-8.35 (m, 3H), 8.00 d, J = 8.8 Hz, 2H), 7.63 (dt, J = 8.5 Hz, 1.0 Hz, 1H), 7.48-7.43 (m, 1H), 7.30-7.25 (m, 1H), 3.68-3.65 (m, 4H), 2.97-2.94 (m, 4H). HPLC (max plot) 97.7%; Rt % 3.71 min. UPLC/MS: (MS+) 411.3, (MS−) 409.3 |
| 244 | 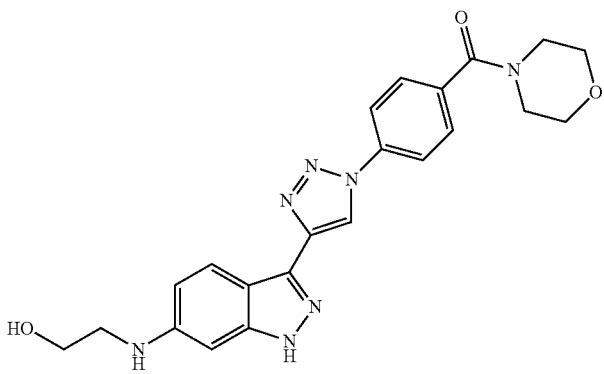 [SMILES: O=C(c1ccc(-n2cc(-c3n[nH]c4cc(NCCO)ccc34)nn2)cc1)N1CCOCC1] | beige solid, 1H NMR (DMSO) δ 12.64 (brs, 1H), 9.27 (s, 1H), 8.13 (dt, J = 8.7 Hz, 2H), 7.98 (d, J = 8.7 Hz, 1H), 7.66 (d, J = 8.7 Hz, 2H), 6.69 (dd, J = 8.7 Hz, 1.8 Hz, 1H), 6.41 (d, J = 1.8 Hz, 1H), 5.90 (t, J = 5.5 Hz, 1H), 4.76 (t, J = 5.5 Hz, 1H), 3.65-3.59 (m, 8H), 3.41 (m, 2H), 3.18-3.13 (m, 2H). HPLC (max plot) 99.5%; Rt % 1.86 min. UPLC/MS: (MS+) 434.4, (MS−) 432.4 |
| 245 | 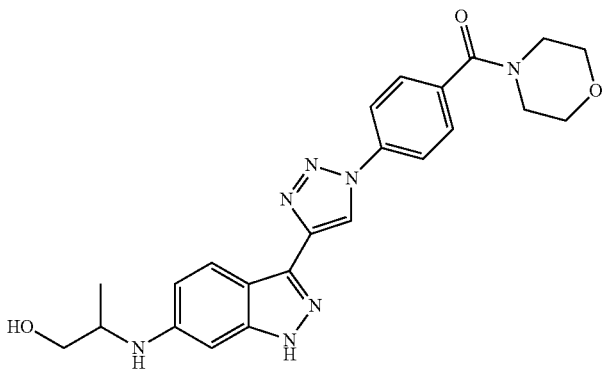 [SMILES: CC(CO)Nc1ccc2c(-c3cn(-c4ccc(C(=O)N5CCOCC5)cc4)nn3)n[nH]c2c1] | beige solid, 1H NMR (DMSO) δ 12.62 (brs, 1H), 9.27 (s, 1H), 8.13 (dt, J = 8.5 Hz, 2H), 7.96 (d, J = 8.9 Hz, 1H), 7.67 (d, J = 8.5 Hz, 2H), 6.67 (dd, J = 8.9 Hz, 1.6 Hz, 1H), 6.43 (d, J = 1.6 Hz, 1H), 5.69 (d, J = 7.6 Hz, 1H), 4.77 (bs, 1H), 3.63-3.38 (m, 10H), 3.18-3.13 (m, 1H), 1.17 (d, J = 6.2 Hz, 3H). HPLC (max plot) 99.7%; Rt % 2.01 min. UPLC/MS: (MS+) 448.4, (MS−) 446.4 |

TABLE 1-continued

| | | |
|---|---|---|
| 246 | 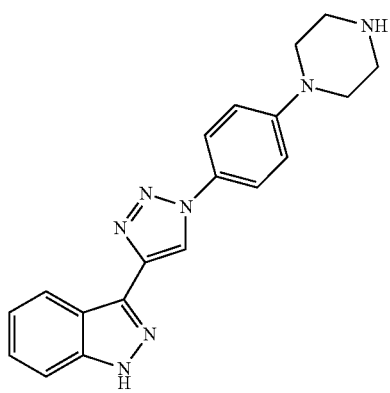 [SMILES: c1ccc2c(-c3cn(-c4ccc(N5CCNCC5)cc4)nn3)n[nH]c2c1] | beige solid, 1H NMR (DMSO) δ 13.36 (brs, 1H), 9.21 (s, 1H), 9.17 (brs, 2H), 8.35 (dt, J = 8.0 Hz, 1.0 Hz, 1H), 7.92 (d, J = 9.0 Hz, 2H), 7.60 (dt, J = 8.4 Hz, 1.0 Hz, 1H), 7.46-7.41 (m, 1H), 7.17-7.20 (m, 3H), 3.51-3.48 (m, 4H), 3.25 (m, 4H). HPLC (max plot) 99.4%; Rt % 2.35 min. UPLC/MS: (MS+) 346.3, (MS−) 344.4 |
| 247 | 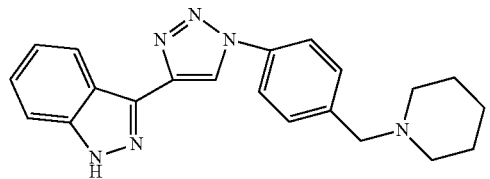 [SMILES: c1ccc2c(-c3cn(-c4ccc(CN5CCCCC5)cc4)nn3)n[nH]c2c1] | beige powder, 1H NMR (300 MHz, DMSO) δ 13.36 (s, 1H), 9.30 (s, 1H), 8.37 (d, J = 8.2 Hz, 1H), 8.00 (d, J = 8.5 Hz, 2H), 7.61 (d, J = 8.4 Hz, 1H), 7.54 (d, J = 8.5 Hz, 2H), 7.49-7.39 (m, 1H), 7.32-7.20 (m, 1H), 3.52 (s, 2H), 2.45-2.25 (m, 4H), 1.60-1.31 (m, 6H). HPLC (max plot) 97.9%; Rt % 2.71 min. UPLC/MS: (MS+) 359.4, (MS−) 357.5. |
| 248 | 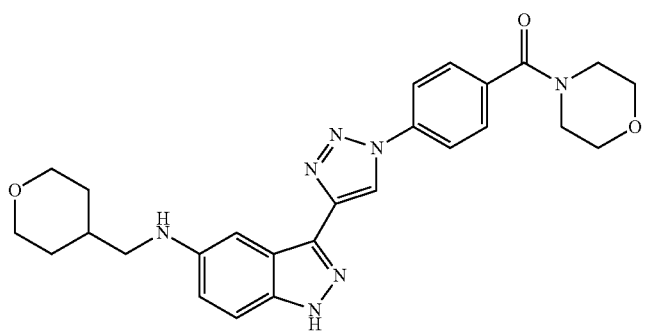 [SMILES: O=C(c1ccc(-n2cc(-c3n[nH]c4ccc(NCC5CCOCC5)cc34)nn2)cc1)N1CCOCC1] | brown solid, 1H NMR (DMSO) δ 12.93 (brs, 1H), 9.25 (s, 1H), 8.13 (d, J = 8.6 Hz, 2H), 7.687 (d, J = 8.6 Hz, 2H), 7.34 (d, J = 9.0 Hz, 1H), 7.24 (m, 1H), 6.94 (dd, J = 9.0 Hz, 2.0 Hz, 1H), 5.55 (t, J = 5.5 Hz, 1H), 3.91-3.86 (m, 2H), 3.64 (m, 6H), 3.43 (m, 2H), 3.34-3.27 (m, 2H), 2.97 (t, J = 6.0 Hz, 2H), 1.90-1.84 (m, 1H), 1.78-1.74 (m, 2H), 1.36-1.24 (m, 2H). HPLC (max plot) 94.8%; Rt % 2.02 min. UPLC/MS: (MS+) 488.3, (MS−) 486.3 |
| 249 | 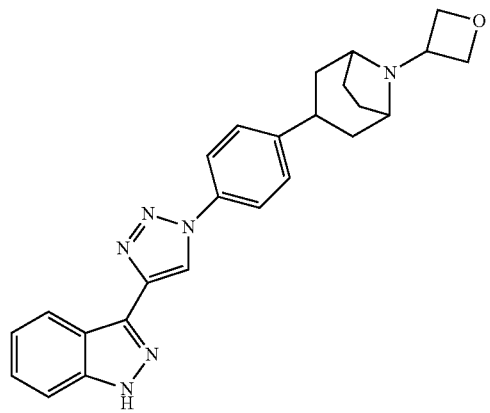 [SMILES: c1ccc2c(-c3cn(-c4ccc(C5CC6CCC(C5)N6C5COC5)cc4)nn3)n[nH]c2c1] | white powder, 13.34 (s, 1H), 9.26 (s, 1H), 8.34 (d, J = 8.3 Hz, 1H), 7.92 (d, J = 8.3 Hz, 2H), 7.58 (m, 3H), 7.42 (t, J = 7.4 Hz, 1H), 7.23 (t, J = 7.5 Hz, 1H), 4.55 (t, J = 6.2 Hz, 2H), 4.34 (t, J = 5.6 Hz, 2H), 3.57 (m, 1H), 3.17 (m, 3H), 2.34 (m, 2H), 1.79 (m, 2H), 1.56 (m, 2H), 1.45 (m, 2H). HPLC (max plot) 96.8%; Rt % 2.77 min. UPLC/MS: (MS+) 427.5, (MS−) 425.6. |

TABLE 1-continued

| 250 | 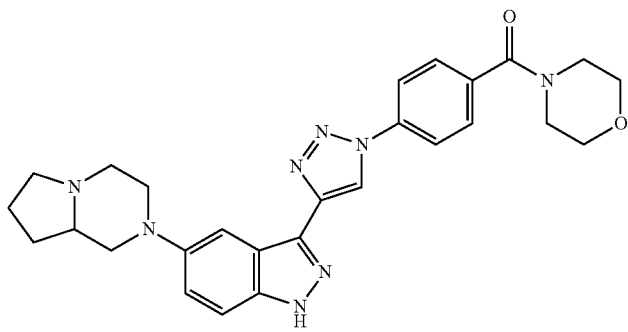 [SMILES: O=C(c1ccc(-n2cc(-c3n[nH]c4ccc(N5CCN6CCCC6C5)cc34)nn2)cc1)N1CCOCC1] | beige amorphous solid, 1H NMR (MeOH) δ 9.01(s, 1H), 8.12 (d, J = 8.6 Hz, 2H), 7.90 (d, J = 2.0 Hz, 1H), 7.73 (d, J = 8.6 Hz, 2H), 7.56 (d, J = 9.0 Hz, 1H), 7.38 (dd, J = 9.0 Hz, 2.0 Hz, 1H), 3.88-3.63 (m, 8H), 3.63-3.50 (m, 4H), 3.37 (m, 1H), 3.27-3.18 (m, 2H), 3.12-3.04 (m, 2H), 2.30-2.11 (m, 3H), 2.00-1.90 (m, 1H). HPLC (max plot) 97.0%; Rt % 2.17 min. UPLC/MS: (MS+) 499.5, (MS−) 497.6 |
| --- | --- | --- |
| 251 | 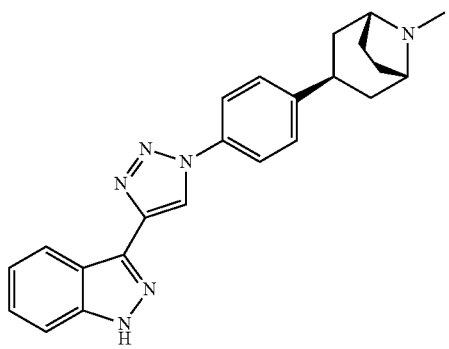 [SMILES: CN1[C@@H]2CC[C@H]1C[C@@H](c1ccc(-n3cc(-c4n[nH]c5ccccc45)nn3)cc1)C2] | white solid, 1H NMR (DMSO) δ 13.39 (brs, 1H), 9.32 (s, 1H), 8.37 (dt, J = 8.5 Hz, 1.0 Hz, 1H), 8.00 (d, J = 8.7 Hz, 2H), 7.72 (d, J = 8.7 Hz, 2H), 7.61 (dt, J = 8.5 Hz, 1.0 Hz, 1H), 7.47-7.41 (m, 1H), 7.28-7.23 (m, 1H), 3.64 (m, 2H), 3.23 (m, 1H), 2.50-2.45 (m, 2H), 2.24-2.20 (m, 2H), 2.07-2.01 (m, 2H), 1.59-1.52 (m, 2H) + 3H missing under peaks of water or DMSO. HPLC (max plot) 99.6%; Rt % 2.70 min. UPLC/MS: (MS+) 385.4, (MS−) 383.5. |
| 252 | 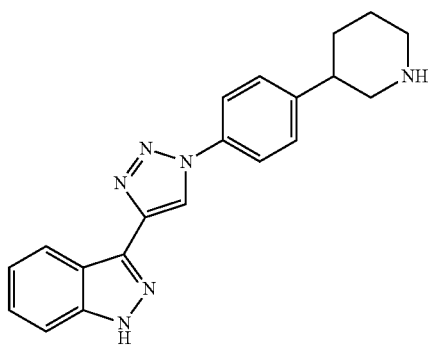 [SMILES: c1ccc2c(-c3cn(-c4ccc(C5CCCNC5)cc4)nn3)n[nH]c2c1] | brown powder, 1H NMR (300 MHz, DMSO) δ 13.41 (brs, 1H), 9.32 (s, 1H), 9.20 (brs, J = 11.2 Hz, 1H), 8.97 (brs, 1H), 8.42-8.31 (m, 1H), 8.13-7.99 (m, 2H), 7.67-7.51 (m, 3H), 7.51-7.38 (m, 1H), 7.32-7.19 (m, 1H), 3.44-3.25 (m, 2H), 3.23-3.03 (m, 2H), 3.03-2.80 (m, 1H), 2.04-1.65 (m, 4H). 1H NMR (DMSO) δ. HPLC (max plot) 98.0%; Rt % 2.72 min. CHN analysis: [C20H20N6 - 2.0 HCl - 1.5 H20] calculated: C 54.06%, H 5.67%, N 18.91%; Found: C 53.70%, H 5.70%, N 18.50%. UPLC/MS: (MS+) 345.4, (MS−) 343.5. |
| 253 | 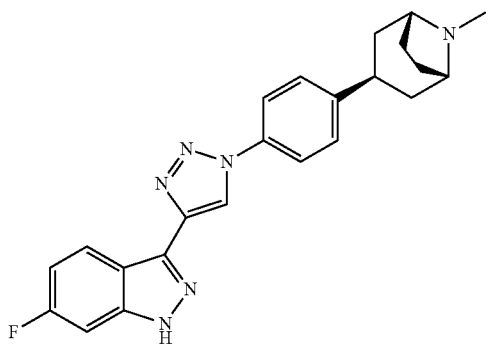 [SMILES: CN1[C@@H]2CC[C@H]1C[C@@H](c1ccc(-n3cc(-c4n[nH]c5cc(F)ccc45)nn3)cc1)C2] | white amorphous solid, 1H NMR (DMSO) δ 13.45 (brs, 1H), 9.313 (s, 1H), 8.37 (dd, J = 9.0 Hz, 5.3 Hz, 1H), 7.96 (d, J = 8.6 Hz, 2H), 7.63 (d, J = 8.6 Hz, 2H), 7.40 (dd, J = 9.6 Hz, 2.0 Hz, 1H), 7.15 (ddd, J = 18.4 Hz, 9.0 Hz, 2.0 Hz, 1H), 3.40 (m, 2H), 3.14 (quint, J = 7.0 Hz, 1H), 2.45-2.36 (m, 2H), 2.32 (s, 3H), 2.09-1.99 (m, 2H), 1.91-1.84 (m, 2H), 1.52-1.46 (m, 2H). HPLC (max plot) 100.0%; Rt % 2.91 min. UPLC/MS: (MS+) 403.5, (MS−) 401.5 |

| | | |
|---|---|---|
| 254 | 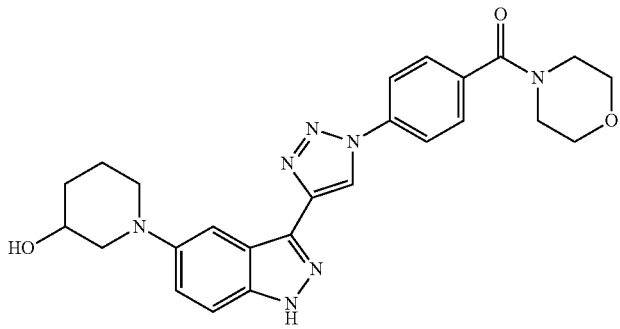 [SMILES: O=C(c1ccc(-n2cc(-c3n[nH]c4ccc(N5CCCC(O)C5)cc34)nn2)cc1)N1CCOCC1] | beige amorphous solid, 1H NMR (DMSO) δ 13.13 (brs, 1H), 9.31(s, 1H), 8.14 (d, J = 8.6 Hz, 2H), 7.70-7.64 (m, 3H), 7.47 (d, J = 9.0 Hz, 1H), 7.25 (dd, J = 9.0 Hz, 1.0 Hz, 1H), 4.85 (d, J = 4.6 Hz, 1H), 3.69-3.55 (m, 8H), 3.46-3.39 (m, 3H), 2.64 (dt, J = 11.4 Hz, 3.0 Hz, 1H), 1.95-1.80 (m, 2H), 1.69-1.56 (m, 1H), 1.32-1.20 (m, 1H) + 1H missing under the peak of DMSO. HPLC (max plot) 96.7%; Rt % 1.87 min. UPLC/MS: (MS+) 474.5, (MS−) 472.6 |
| 255 | 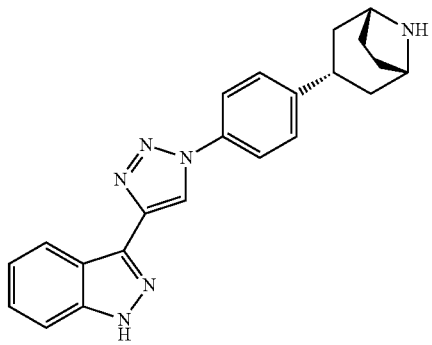 [SMILES: c1ccc2c(-c3cn(-c4ccc([C@@H]5C[C@H]6CC[C@@H](C5)N6)cc4)nn3)n[nH]c2c1] | beige powder, 1H NMR (300 MHz, DMSO) δ 13.39 (brs, 1H), 9.33 (s, 1H), 8.89 (brs, 2H), 8.36 (d, J = 8.2 Hz, 1H), 8.10-7.97 (m, 2H), 7.80-7.65 (m, 2H), 7.65-7.54 (m, 1H), 7.51-7.39 (m, 1H), 7.32-7.20 (m, 1H), 4.11-3.91 (m, 2H), 3.30-3.15 (m, 1H), 2.49-2.37 (m, 2H), 2.35-2.18 (m, 2H), 1.98-1.81 (m, 2H), 1.77-1.59 (m, 2H). HPLC (max plot) 95.2%; Rt % 2.61 min. CHN analysis: [C22H22N6- HCl-2.0 H20] Corrected: C 59.66%, H 6.14%, N 18.97%; Found: C 59.27%, H 5.46%, N 18.44%. UPLC/MS: (MS+) 371.4, (MS−) 369.5 |
| 256 | 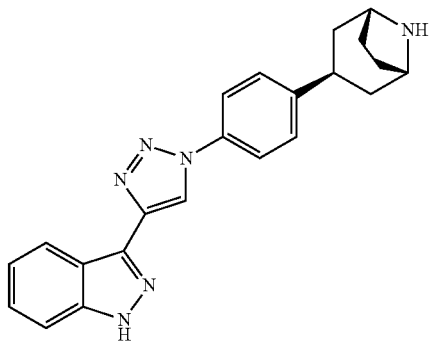 [SMILES: c1ccc2c(-c3cn(-c4ccc([C@H]5C[C@H]6CC[C@@H](C5)N6)cc4)nn3)n[nH]c2c1] | beige powder, 1H NMR (300 MHz, DMSO) δ 13.39 (brs, 1H), 9.29 (s, 1H), 9.21-9.07 (m, 1H), 9.00-8.86 (m, 1H), 8.36 (d, J = 8.2 Hz, 1H), 8.08-7.98 (m, 2H), 7.66-7.52 (m, 3H), 7.50-7.38 (m, 1H), 7.32-7.20 (m, 1H), 4.16-3.98 (m, 2H), 3.31-3.13 (m, 1H), 2.24-1.98 (m, 6H), 1.93-1.79 (m, 2H). HPLC (max plot) 96.6%; Rt % 2.69 min. CHN analysis: [C22H22N6- HCl-1.6 H20] Corrected: C60.64%, H 6.06%, N 19.29%; Found: C60.65%, H 5.37%, N 18.85%. UPLC/MS: (MS+) 371.5, (MS−) 369.5 |
| 257 | 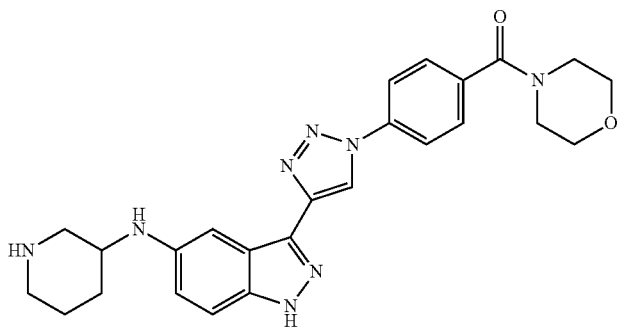 [SMILES: O=C(c1ccc(-n2cc(-c3n[nH]c4ccc(NC5CCCNC5)cc34)nn2)cc1)N1CCOCC1] | white foam, 1H NMR (300 MHz, DMSO) δ 13.05 (brs, 1H), 9.30 (s, 1H), 8.78 (brs, 1H), 8.20-8.10 (m, 2H), 7.72-7.63 (m, 2H), 7.45-7.35 (m, 2H), 6.94 (dd, J = 9.1, 1.8 Hz, 1H), 5.69-5.59 (m, 1H), 3.90-3.47 (m, 8H), 3.28-3.17 (m, 1H), 2.79 (d, J = 52.6 Hz, 3H), 2.13-1.39 (m, 5H). HPLC (max plot) 98.2%; Rt % 1.92 min. UPLC/MS: (MS+) 473.5, (MS−) 471.6 |

TABLE 1-continued

| 258 | 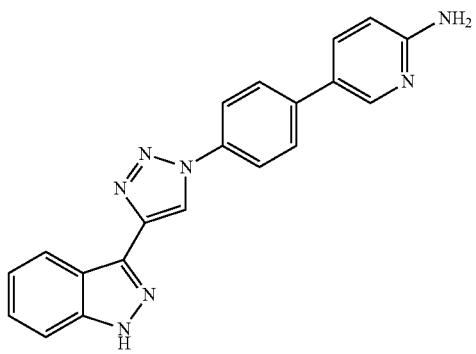 [SMILES: Nc1ccc(-c2ccc(-n3cc(-c4n[nH]c5ccccc45)nn3)cc2)cn1] | brown solid, 1H NMR (300 MHz, DMSO) δ 13.37 (brs, 1H), 9.35 (s, 1H), 8.43-8.33 (m, 2H), 8.14-8.05 (m, 2H), 7.89-7.77 (m, 3H), 7.62 (dt, J = 8.4 Hz, 1H), 7.51-7.39 (m, 1H), 7.32-7.21 (m, 1H), 6.56 (dd, J = 8.7 Hz, 1H), 6.19 (brs, 2H). HPLC (max plot) 99.3%; Rt % 2.76 min. UPLC/MS: (MS+) 354.3, (MS−) 352.4. |
| --- | --- | --- |
| 259 | 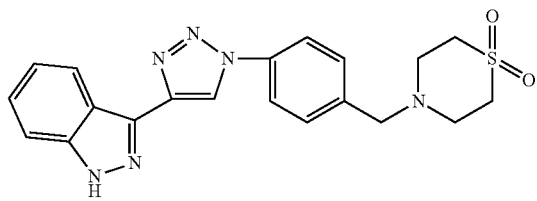 [SMILES: O=S1(=O)CCN(Cc2ccc(-n3cc(-c4n[nH]c5ccccc45)nn3)cc2)CC1] | beige solid, 1H NMR (300 MHz, DMSO) δ 13.36 (s, 1H), 9.32 (s, 1H), 8.37 (d, J = 8.1 Hz, 1H), 8.04 (d, J = 8.5 Hz, 2H), 7.66-7.54 (m, 3H), 7.51-7.39 (m, 1H), 7.26 (t, J = 7.3 Hz, 1H), 3.79 (s, 2H), 3.21-3.06 (m, 4H), 3.04-2.85 (m, 4H). HPLC (max plot) 99.6%; Rt % 1.69 min. UPLC/MS: (MS+) 409.2, (MS−) 407.1. |
| 260 | 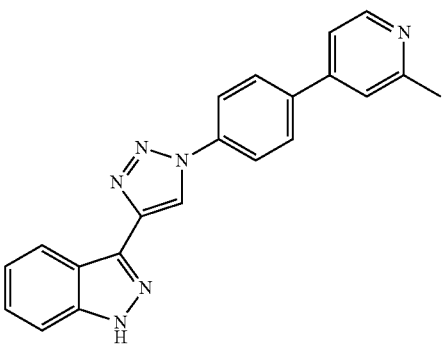 [SMILES: Cc1cc(-c2ccc(-n3cc(-c4n[nH]c5ccccc45)nn3)cc2)ccn1] | brown powder, 1H NMR (300 MHz, DMSO) δ 9.36 (s, 1H), 8.60 (d, J = 2.5 Hz, 1H), 8.42-8.33 (m, 1H), 8.18-8.08 (m, 2H), 8.01 (dd, J = 8.9, 2.6 Hz, 1H), 7.97-7.86 (m, 2H), 7.64 (d, J = 8.3 Hz, 1H), 7.50-7.38 (m, 1H), 7.31-7.19 (m, 1H), 6.97 (d, J = 9.0 Hz, 1H), 3.79-3.68 (m, 4H), 3.56-3.50 (m, 4H), 2.50 (dt, J = 3.6, 1.8 Hz, 3H). 1H NMR (DMSO) δ. HPLC (max plot) 98.5%; Rt % 2.84 min. UPLC/MS: (MS+) 353.4, (MS−) 351.4 |
| 261 | 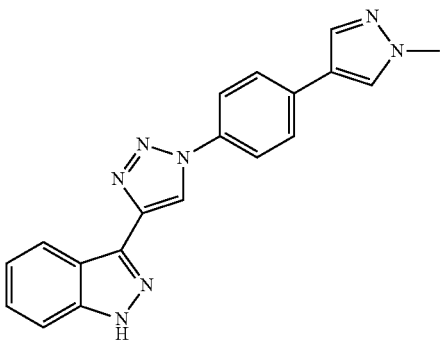 [SMILES: Cn1cc(-c2ccc(-n3cc(-c4n[nH]c5ccccc45)nn3)cc2)cn1] | brown powder, 1H NMR (300 MHz, DMSO) δ 13.37 (brs, 1H), 9.33 (s, 1H), 8.42-8.33 (m, 1H), 8.29 (s, 1H), 8.10-7.97 (m, 3H), 7.88-7.78 (m, 2H), 7.67-7.57 (m, 1H), 7.51-7.39 (m, 1H), 7.32-7.20 (m, 1H), 3.90 (s, 3H). HPLC (max plot) 99.7%; Rt % 3.48 min. UPLC/MS: (MS+) 342.4, (MS−) 340.4 |

TABLE 1-continued

| 262 | 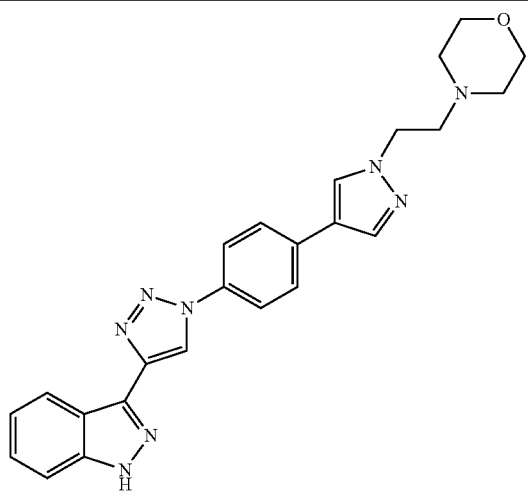 | brown powder, 1H NMR (DMSO) δ 1H NMR (300 MHz, DMSO) δ 13.36 (brs, 1H), 9.33 (s, 1H), 8.42-8.31 (m, 2H), 8.11-7.98 (m, 3H), 7.89-7.78 (m, 2H), 7.67-7.57 (m, 1H), 7.51-7.39 (m, 1H), 7.32-7.21 (m, 1H), 4.27 (t, J = 6.6 Hz, 2H), 3.63-3.50 (m, 4H), 2.76 (t, J = 6.6 Hz, 2H), 2.48-2.34 (m, 4H). HPLC (max plot) 99.8%; Rt % 2.79 min. UPLC/MS: (MS+) 441.5, (MS−) 439.5 |
|---|---|---|
| 263 | 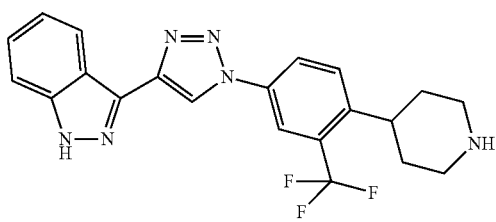 [SMILES: FC(F)(F)c1cc(-n2cc(-c3n[nH]c4ccccc34)nn2)ccc1C1CCNCC1] | beige solid, 13.39 (s, 1H), 9.47 (s, 1H), 8.37-8.33 (m, 3H), 7.91-7.88 (m, 1H), 7.63-7.60 (m, 1H), 7.47-7.42 (m, 1H), 7.29-7.24 (m, 1H), 3.10-2.97 (m, 3H), 2.63-2.54 (m, 2H), 1.78-1.62 (m, 4H). HPLC (max plot) 96.8%; Rt % 3.17 min. UPLC/MS: (MS+) 413.4, (MS−) 411.5. |
| 264 | 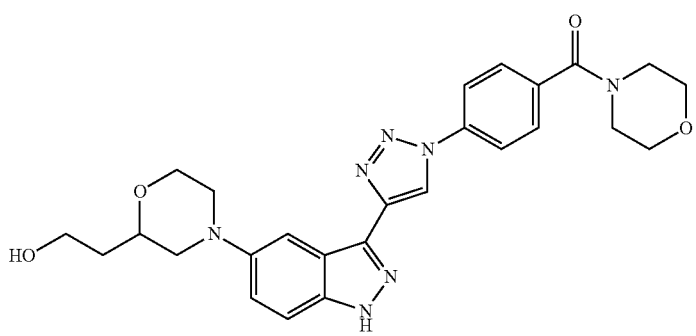 [SMILES: O=C(c1ccc(-n2cc(-c3n[nH]c4ccc(N5CCOC(CCO)C5)cc34)nn2)cc1)N1CCOCC1] | white solid, 1H NMR (DMSO) δ 13.17 (bs, 1H), 9.33 (s, 1H), 8.142 (d, J = 8.7 Hz, 2H), 7.70-7.67 (m, 3H), 7.50 (d, J = 9.0 Hz, 1H), 7.31 (dd, J = 9.0 Hz, 2.0 Hz, 1H), 4.51 (t, J = 5.1 Hz, 1H), 3.98-3.48 (m, 1H), 3.76-3.48 (m, 13H), 2.77-2.68 (m, 1H), 2.48-2.42 (m, 2H), 1.66 (q, J = 6.5 Hz, 2H). HPLC (max plot) 98.8%; Rt % 1.78 min. UPLC/MS: (MS+) 504.5, (MS−) 502.6. |
| 265 | 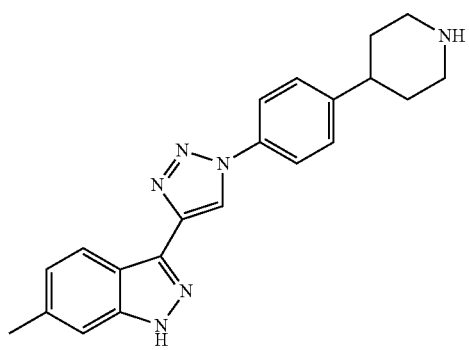 [SMILES: Cc1ccc2c(-c3cn(-c4ccc(C5CCNCC5)cc4)nn3)n[nH]c2c1] | beige-brown powder, 1H NMR (300 MHz, DMSO) δ 13.21 (brs, 1H), 9.26 (s, 1H), 9.00-8.62 (m, 2H), 8.22 (d, J = 8.4 Hz, 1H), 8.08-7.97 (m, 2H), 7.53-7.45 (m, 2H), 7.41-7.35 (m, 1H), 7.13-7.05 (m, 1H), 3.50-3.40 (m, 1H), 3.15-2.86 (m, 4H), 2.48 (s, 3H), 1.93 (dt, J = 22.5, 10.8 Hz, 4H). HPLC (max plot) 96.4%; Rt % 2.87 min. m.p. = 303° C. CHN analysis: [C21H22N6- HCl-2.0 H20] Corrected: C 58.53%, H 6.32%, N 19.50%; Found: C 59.65%, H 6.12%, N 18.48%. UPLC/MS: (MS+) 359.4, (MS−) 357.5. |

| | | |
|---|---|---|
| 266 | 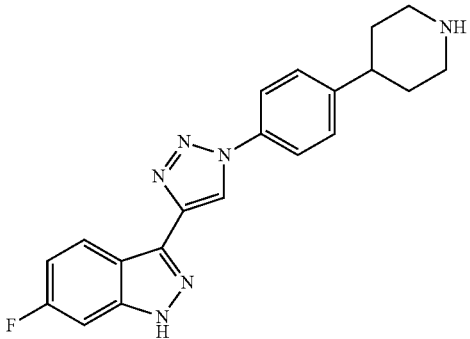 [SMILES: Fc1ccc2c(-c3cn(-c4ccc(C5CCNCC5)cc4)nn3)n[nH]c2c1] | beige powder, 1H NMR (300 MHz, DMSO) δ 13.47 (brs, 1H), 9.31 (s, 1H), 9.02-8.63 (m, 2H), 8.38 (dd, J = 8.9, 5.4 Hz, 1H), 8.10-7.95 (m, 2H), 7.56-7.45 (m, 2H), 7.41 (dd, J = 9.6, 2.1 Hz, 1H), 7.15 (td, J = 9.3, 2.1 Hz, 1H), 3.54-3.16 (m, 2H), 3.18-2.87 (m, 3H), 2.11-1.77 (m, 4H). HPLC (max plot) 99.1%; Rt % 2.79 min. CHN analysis: [C20H19N6F-HCl-2.0 H20] Corrected: C 55.24%, H 5.56%, N 19.32%; Found: C 55.79%, H 5.48%, N 18.33%. UPLC/MS: (MS+) 363.5, (MS−) 361.5. |
| 267 | 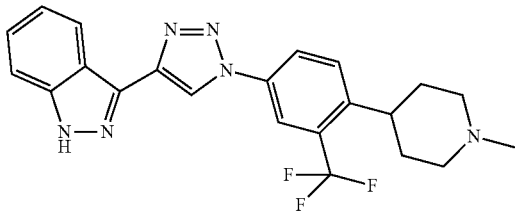 [SMILES: CN1CCC(c2ccc(-n3cc(-c4n[nH]c5ccccc45)nn3)cc2C(F)(F)F)CC1] | off-white powder, 1H NMR (300 MHz, DMSO) δ 13.39 (s, 1H), 9.48 (s, 1H), 8.37-8.32 (m, 3H), 7.94-7.91 (m, 1H), 7.63-7.60 (m, 1H), 7.47-7.42 (m, 1H), 7.29-7.24 (m, 1H), 2.94-2.79 (m, 3H), 2.22 (s, 3H), 2.01-1.82 (m, 4H), 1.71-1.67 (m, 2H). HPLC (max plot) 100.0%; Rt % 3.22 min. UPLC/MS: (MS+) 427.5, (MS−) 425.5 |
| 268 | 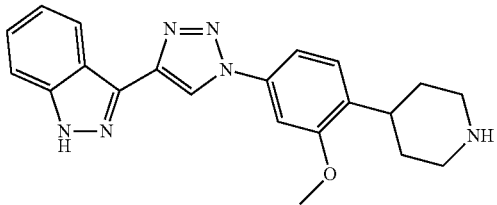 [SMILES: COc1cc(-n2cc(-c3n[nH]c4ccccc34)nn2)ccc1C1CCNCC1] | yellow powder, 1H NMR (DMSO) δ 13.36 (s, 1H), 9.34 (s, 1H), 8.38-8.35 (m, 1H), 7.62-7.58 (m, 3H), 7.47-7.38 (m, 2H), 7.28-7.23 (m, 1H), 3.94 (s, 3H), 3.05-2.98 (m, 3H), 2.64 (m, 2H), 1.69-1.46 (m, 4H). HPLC (max plot) 97.1%; Rt % 2.85 min. UPLC/MS: (MS+) 375.4, (MS−) 373.5 |
| 269 | 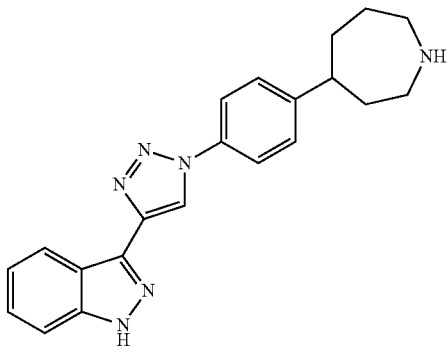 [SMILES: c1ccc2c(-c3cn(-c4ccc(C5CCCNCC5)cc4)nn3)n[nH]c2c1] | beige solid, 1H NMR (300 MHz, DMSO-d6) : 13.39 (brs, 1H), 9.28 (s, 1H), 8.96 (brs, 2H), 8.36 (d, J = 8.1 Hz, 1H), 7.99 (d, J = 8.6 Hz, 2H), 7.61 (d, J = 8.4 Hz, 1H), 7.50 (d, J = 8.6 Hz, 2H), 7.46-7.41 (m, 1H), 7.28-7.23 (m, 1H), 3.27-3.06 (m, 4H), 2.94 (m, 1H), 2.16-2.72 (m, 6H). HPLC (max plot) 97.0%; Rt % 2.75 min. UPLC/MS: (MS+) 359.4, (MS−) 357.4 |
| 270 | 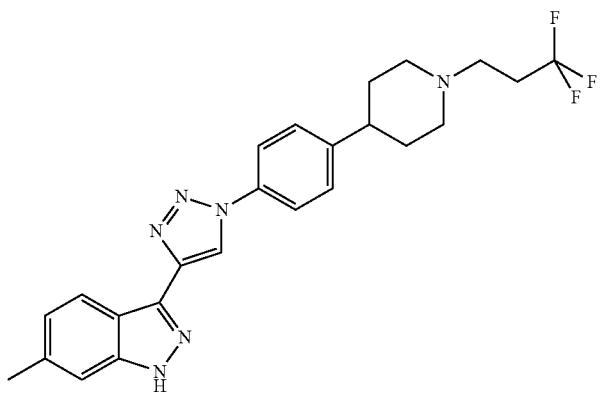 [SMILES: Cc1ccc2c(-c3cn(-c4ccc(C5CCN(CCC(F)(F)F)CC5)cc4)nn3)n[nH]c2c1] | white foam, 1H NMR (300 MHz, DMSO) δ 13.18 (brs, 1H), 9.24 (s, 1H), 8.22 (d, J = 8.3 Hz, 1H), 8.03-7.88 (m, 2H), 7.60-7.42 (m, 2H), 7.37 (s, 1H), 7.15-7.03 (m, 1H), 3.08-2.96 (m, 2H), 2.70-2.52 (m, 5H), 2.48 (s, 3H), 2.17-2.00 (m, 2H), 1.91-1.56 (m, 4H). HPLC (max plot) 95.3%; Rt % 3.29 min. UPLC/MS: (MS+) 455.5, (MS−) 453.5 |

TABLE 1-continued

| | | |
|---|---|---|
| 271 | 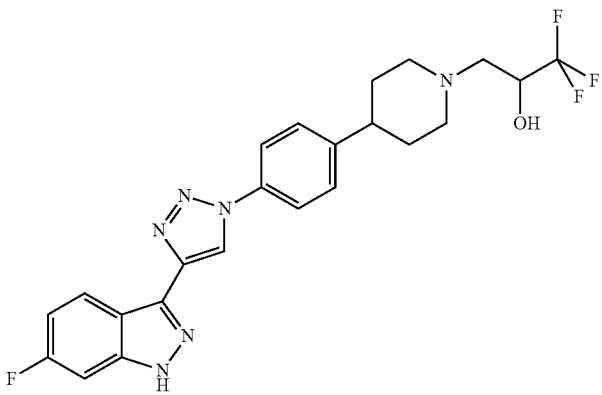 [SMILES: OC(CN1CCC(c2ccc(-n3cc(-c4n[nH]c5cc(F)ccc45)nn3)cc2)CC1)C(F)(F)F] | amorphous white foam, 1H NMR (300 MHz, DMSO) δ 13.44 (brs, 1H), 9.29 (s, 1H), 8.38 (dd, J = 9.0, 5.3 Hz, 1H), 8.03-7.90 (m, 2H), 7.58-7.45 (m, 2H), 7.40 (dd, J = 9.6, 2.1 Hz, 1H), 7.15 (td, J = 9.3, 2.2 Hz, 1H), 4.26-4.07 (m, 1H), 3.14-2.97 (m, 2H), 2.70-2.52 (m, 3H), 2.31-2.04 (m, 2H), 1.87-1.56 (m, 4H). HPLC (max plot) 97.0%; Rt % 3.11 min. UPLC/MS: (MS+) 475.4, (MS−) 473.5 |
| 272 | 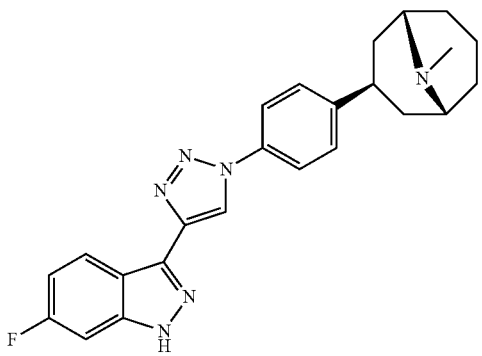 [SMILES: CN1[C@@H]2CCC[C@H]1C[C@H](c1ccc(-n3cc(-c4n[nH]c5cc(F)ccc45)nn3)cc1)C2] | amorphous beige foam, 1H NMR (300 MHz, DMSO) δ 13.46 (brs, 1H), 9.31 (s, 1H), 8.38 (dd, J = 8.9, 5.3 Hz, 1H), 8.03-7.90 (m, 2H), 7.66-7.52 (m, 2H), 7.41 (dd, J = 9.6, 2.0 Hz, 1H), 7.15 (td, J = 9.3, 2.2 Hz, 1H), 3.31-3.15 (m, 1H), 3.15-3.02 (m, 2H), 2.53 (s, 3H), 2.34-1.89 (m, 5H), 1.71-1.42 (m, 3H), 1.14-0.89 (m, 2H). HPLC (max plot) 96.7%; Rt % 3.08 min. UPLC/MS: (MS+) 417.5, (MS−) 415.5 |
| 273 | 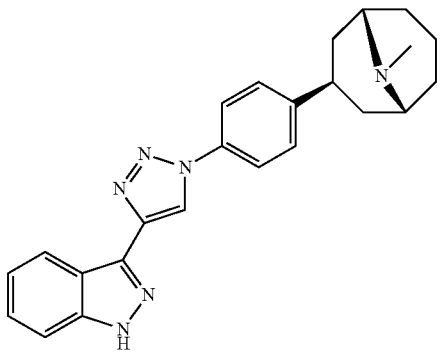 [SMILES: CN1[C@@H]2CCC[C@H]1C[C@H](c1ccc(-n3cc(-c4n[nH]c5ccccc45)nn3)cc1)C2] | white amorphous foam, 1H NMR (300 MHz, DMSO) δ 13.39 (brs, 1H), 9.28 (s, 1H), 8.41-8.33 (m, 1H), 8.02-7.92 (m, 2H), 7.66-7.55 (m, 3H), 7.49-7.40 (m, 1H), 7.31-7.21 (m, 1H), 3.33-3.18 (m, 1H), 3.18-3.06 (m, 2H), 2.54 (s, 3H), 2.35-1.88 (m, 5H), 1.71-1.42 (m, 3H), 1.13-0.96 (m, 2H). HPLC (max plot) 97.9%; Rt % 2.88 min. UPLC/MS: (MS+) 399.5, (MS−) 397.6 |
| 274 | 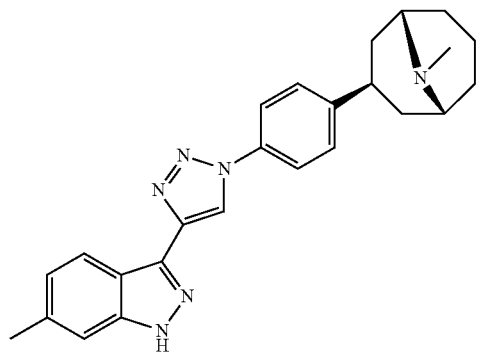 [SMILES: Cc1ccc2c(-c3cn(-c4ccc([C@@H]5C[C@H]6CCC[C@@H](C5)N6C)cc4)nn3)n[nH]c2c1] | amorphous beige foam, 1H NMR (300 MHz, DMSO) δ 13.19 (brs, 1H), 9.25 (s, 1H), 8.23 (d, J = 8.5 Hz, 1H), 8.04-7.90 (m, 2H), 7.66-7.50 (m, 2H), 7.43-7.31 (m, 1H), 7.09 (dd, J = 8.5, 1.1 Hz, 1H), 3.30-3.13 (m, 1H), 3.06 (d, J = 11.0 Hz, 2H), 2.50 (s, 3H), 2.48 (s, 3H), 2.33-1.89 (m, 5H), 1.68-1.42 (m, 3H), 1.00 (d, J = 12.7 Hz, 2H). HPLC (max plot) 98.3%; Rt % 3.21 min. UPLC/MS: (MS+) 413.5, (MS−) 411.5 |

| | | |
|---|---|---|
| 275 | 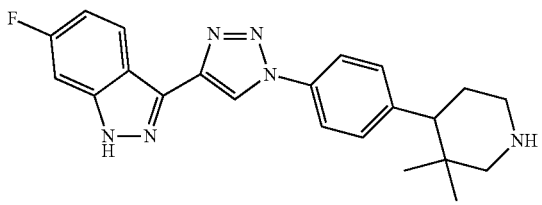 [SMILES: CC1(C)CNCCC1c1ccc(-n2cc(-c3n[nH]c4cc(F)ccc34)nn2)cc1] | white solid, 1H NMR (DMSO) δ 13.47 (s, 1H), 9.31 (s, 1H), 8.40-8.34 (m, 2H), 7.98-7.95 (d, J = 8.5 Hz, 2H), 7.42-7.39 (m, 3H), 7.18-7.11 (m, 1H), 3.18-3.15 (m, 1H), 2.78-2.54 (m, 4H), 2.19-2.07 (m, 1H), 1.52-1.47 (m, 1H), 0.88 (s, 3H), 0.75 (s, 3H). HPLC (max plot) 97.9%; Rt % 3.03 min. UPLC/MS: (MS+) 391.5, (MS−) 389.5. |
| 276 | 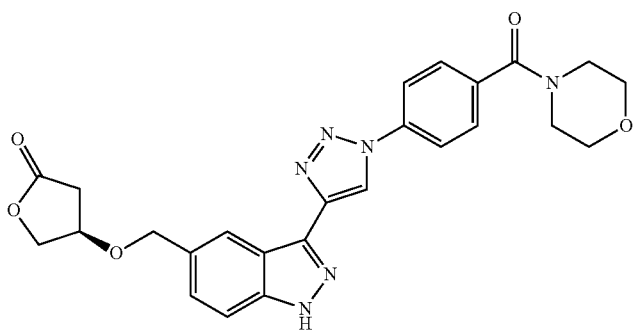 [SMILES: O=C1C[C@@H](OCc2ccc3[nH]nc(-c4cn(-c5ccc(C(=O)N6CCOCC6)cc5)nn4)c3c2)CO1] | white solid, 1H NMR (300 MHz, DMSO) δ 13.41 (s, 1H), 9.38 (s, 1H), 8.33 (s, 1H), 8.15 (d, J = 8.6 Hz, 2H), 7.69 (d, J = 8.6 Hz, 2H), 7.61 (d, J = 8.6 Hz, 1H), 7.43 (dd, J = 8.6, 1.4 Hz, 1H), 4.69 (s, 2H), 4.48-4.34 (m, 3H), 3.79-3.44 (m, 8H), 2.88 (dd, J = 17.8, 5.6 Hz, 1H), 2.55 (d, J = 17.8 Hz, 1H). HPLC (max plot) 97.1%; Rt % 2.56 min. UPLC/MS: (MS+) 489.5, (MS−) 487.5 |
| 277 | 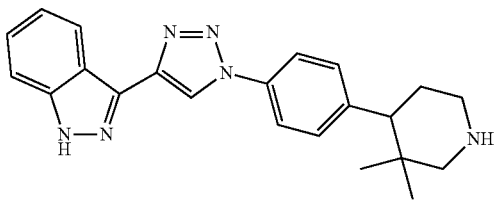 [SMILES: CC1(C)CNCCC1c1ccc(-n2cc(-c3n[nH]c4ccccc34)nn2)cc1] | white solid, 1H NMR (DMSO) δ 13.38 (s, 1H), 9.29 (s, 1H), 8.37-8.35 (d, J = 8.1 Hz, 1H), 8.32 (s, 1H), 7.99-7.96 (d, J = 8.6 Hz, 2H), 7.63-7.60 (d, J = 8.4 Hz, 1H), 7.47-7.39 (m, 3H), 7.28-7.23 (m, 1H), 3.20-3.16 (m, 1H), 2.81-2.57 (m, 4H), 2.20-2.07 (m, 1H), 1.54-1.50 (m, 1H), 0.89 (s, 3H), 0.76 (s, 3H). HPLC (max plot) 98.9%; Rt % 2.84 min. UPLC/MS: (MS+) 373.3, (MS−) 371.3 |
| 278 | 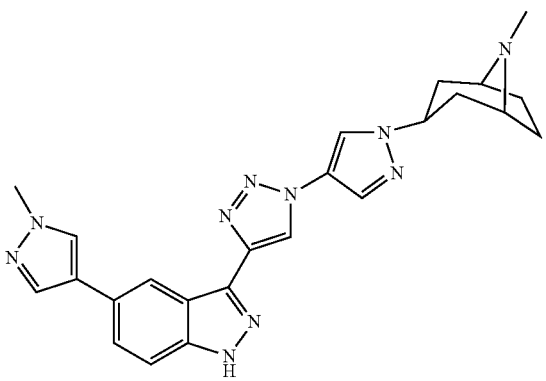 [SMILES: CN1C2CCC1CC(n1cc(-n3cc(-c4n[nH]c5ccc(-c6cnn(C)c6)cc45)nn3)cn1)C2] | yellow powder, 1H NMR (300 MHz, DMSO) δ 13.31 (s, 1H), 9.05 (s, 1H), 8.55 (s, 1H), 8.38 (s, 1H), 8.19 (s, 1H), 8.09 (s, 1H), 7.90 (s, 1H), 7.66 (d, J = 8.3 Hz, 1H), 7.59 (d, J = 8.3 Hz, 1H), 4.67-4.50 (m, 1H), 3.89 (s, 3H), 3.50-3.10 (m, 2H), 2.27 (s, 3H), 2.21-2.06 (m, 2H), 2.06-1.93 (m, 2H), 1.93-1.78 (m, 2H), 1.77-1.62 (m, 2H). HPLC (max plot) 92.3%; Rt ? |
| 279 | 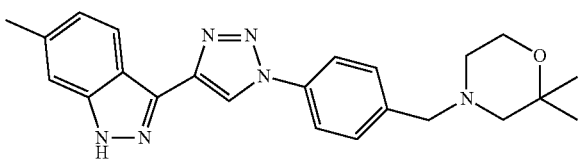 | brown powder, 1H NMR (DMSO) δ 13.18 (s, 1H), 9.27 (s, 1H), 8.24-8.21 (d, J = 8.3 Hz, 1H), 8.02-8.00 (d, J = 8.3 Hz, 2H), 7.58-7.55 (d, J = 8.2 Hz, 2H), 7.37 (s, 1H), 7.10-7.07 (d, J = 8.2 Hz, 1H), 3.65-3.62 (m, 2H), 3.53 (s, 2H), 2.48 (s, 3H), 2.37-2.34 (m, 2H), 2.17 (s, 2H), 1.17 (s, 6H). HPLC (max plot) 98.6%; Rt % 2.93 min. UPLC/MS: (MS+) 403.4, (MS−) 401.3 |

TABLE 1-continued

| 280 | 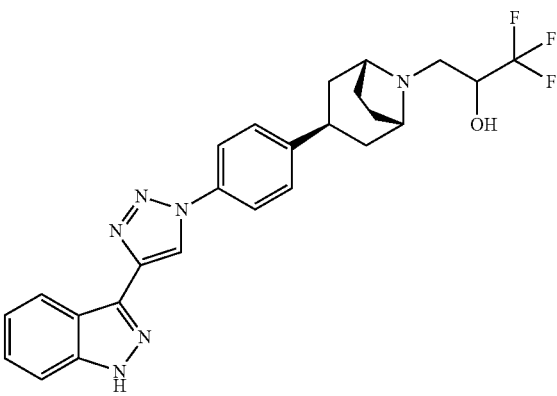 [SMILES: OC(CN1[C@@H]2CC[C@H]1C[C@@H](c1ccc(-n3cc(-c4n[nH]c5ccccc45)nn3)cc1)C2)C(F)(F)F] | brown solid, 1H NMR (DMSO) δ 13.35 (brs, 1H), 9.28 (s, 1H), 8.35 (d, J = 8.1 Hz, 1H), 8.01 (m, 2H), 7.62-7.54 (m, 3H), 7.46-7.42 (m, 1H), 7.27-7.23 (m, 1H), 4.05 (m, 1H), 3.42 (m, 2H), 3.13 (m, 1H), 2.91 (m, 1H), 2.38 (m, 3H), 1.92 (m, 1H), 1.61-1.46 (m, 4H), 1.08 (m, 1H). HPLC (max plot) 95.6%; Rt % 3.10 min. UPLC/MS: (MS+) 483.5, (MS−) 481.5 |
| --- | --- | --- |
| 281 | 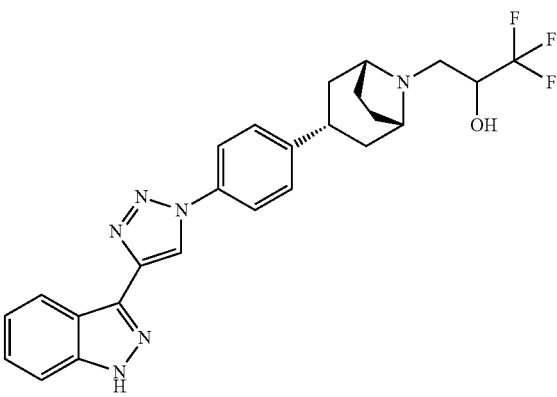 [SMILES: OC(CN1[C@@H]2CC[C@H]1C[C@H](c1ccc(-n3cc(-c4n[nH]c5ccccc45)nn3)cc1)C2)C(F)(F)F] | brown solid, 1H NMR (300 MHz, DMS0-d6) d 13.35 (brs, 1H), 9.28 (s, 1H), 8.35 (d, J = 8.1 Hz, 1H), 8.01 (m, 2H), 7.62-7.54 (m, 3H), 7.47-7.42 (m, 1H), 7.28-7.23 (m, 1H), 4.14 (m, 1H), 2.73 (m, 1H), 2.27-1.75 (m, 10H), 1.23 (m, 1H), 1.17-1.07 (m, 2H). HPLC (max plot) 97.7%; Rt % 3.10 min. UPLC/MS: (MS+) 483.5, (MS−) 481.5 |
| 282 | 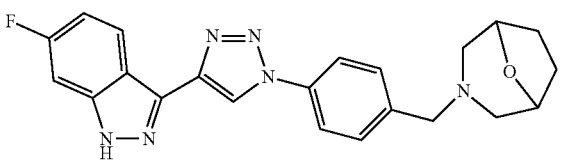 [SMILES: Fc1ccc2c(-c3cn(-c4ccc(CN5CC6CCC(C5)O6)cc4)nn3)n[nH]c2c1] | beige powder, 1H NMR (DMSO) δ 13.43 (s, 1H), 9.31 (s, 1H), 8.40-8.35 (quad, J = 5.3 Hz, 1H), 8.02-7.99 (d, J = 8.4 Hz, 2H), 7.56-7.54 (d, J = 8.5 Hz, 2H), 7.42-7.38 (m, 1H), 7.18-7.11 (m, 1H), 4.23-4.22 (m, 2H), 3.53 (s, 2H), 2.56 (s, 1H), 2.52-2.51 (m, 1H), 2.26-2.23 (m, 2H), 1.94-1.88 (m, 2H), 1.76-1.72 (m, 2H). HPLC (max plot) 97.3%; Rt % 2.80 min. UPLC/MS: (MS+) 405.3, (MS−) 403.2 |
| 283 | 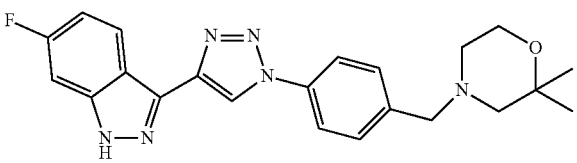 [SMILES: CC1(C)CN(Cc2ccc(-n3cc(-c4n[nH]c5cc(F)ccc45)nn3)cc2)CCO1] | brown powder, 1H NMR (DMSO) δ 13.43 (s, 1H), 9.32 (s, 1H), 8.40-8.36 (quad, J = 5.3 Hz, 1H), 8.03-8.00 (d, J = 8.5 Hz, 2H), 7.58-7.55 (d, J = 8.5 Hz, 2H), 7.42-7.38 (m, 1H), 7.18-7.11 (m, 1H), 3.66-3.62 (m, 2H), 3.53 (s, 2H), 2.37-2.36 (m, 2H), 2.18 (s, 2H), 1.17 (s, 6H). HPLC (max plot) 97.9%; Rt % 2.87 min. UPLC/MS: (MS+) 407.3, (MS−) 405.3 |
| 284 | 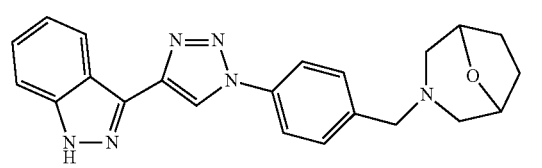 [SMILES: c1ccc2c(-c3cn(-c4ccc(CN5CC6CCC(C5)O6)cc4)nn3)n[nH]c2c1] | beige powder, 1H NMR (DMSO) δ 13.35 (s, 1H), 9.29 (s, 1H), 8.38-8.35 (d, J = 8.1 Hz, 1H), 8.02-8.00 (d, J = 8.5 Hz, 2H), 7.62-7.60 (d, J = 8.5 Hz, 1H), 7.57-7.54 (d, J = 8.5 Hz, 2H), 7.46-7.42 (m, 1H), 7.28-7.23 (m, 1H), 4.23-4.21 (m, 2H), 3.57 (s, 1H), 3.53 (s, 2H), 2.56 (s, 1H), 2.26-2.23 (m, 2H), 1.92-1.90 (m, 2H), 1.76-1.73 (m, 2H). HPLC (max plot) 95.6%; Rt % 2.49 min. UPLC/MS: (MS+) 387.3, (MS−) 385.2 |

| | | |
|---|---|---|
| 285 | 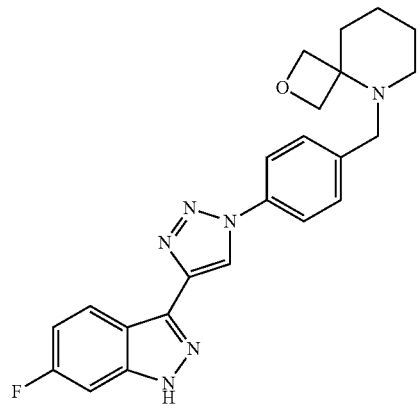 [SMILES: Fc1ccc2c(-c3cn(-c4ccc(CN5CCCCC56COC6)cc4)nn3)n[nH]c2c1] | amorphous beige foam, 1H NMR (300 MHz, DMSO) δ 13.46 (brs, 1H), 9.31 (s, 1H), 8.38 (dd, J = 8.9, 5.3 Hz, 1H), 8.05-7.95 (m, 2H), 7.68-7.56 (m, 2H), 7.41 (dd, J = 9.6, 2.1 Hz, 1H), 7.15 (td, J = 9.3, 2.2 Hz, 1H), 4.66 (d, J = 6.4 Hz, 2H), 4.29 (d, J = 6.4 Hz, 2H), 3.87 (s, 2H), 2.46-2.30 (m, 2H), 1.97-1.80 (m, 2H), 1.60-1.29 (m, 4H). HPLC (max plot) 99.5%; Rt % 2.68 min. UPLC/MS: (MS+) 419.5, (MS−) 417.5 |
| 286 | 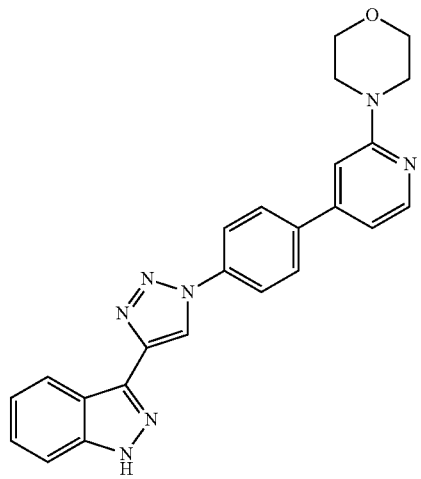 [SMILES: c1ccc2c(-c3cn(-c4ccc(-c5ccnc(N6CCOCC6)c5)cc4)nn3)n[nH]c2c1] | brown powder, 1H NMR (300 MHz, DMSO) δ 13.39 (brs, 1H), 9.44 (s, 1H), 8.38 (d, J = 8.1 Hz, 1H), 8.29-8.15 (m, 3H), 8.15-8.01 (m, 2H), 7.68-7.58 (m, 1H), 7.52-7.39 (m, 1H), 7.33-7.23 (m, 1H), 7.19 (s, 1H), 7.15-7.06 (m, 1H), 3.81-3.67 (m, 4H), 3.61-3.52 (m, 4H). HPLC (max plot) 99.2%; Rt % 2.96 min. UPLC/MS: (MS+) 120.0, (MS−) 422.3 |
| 287 | 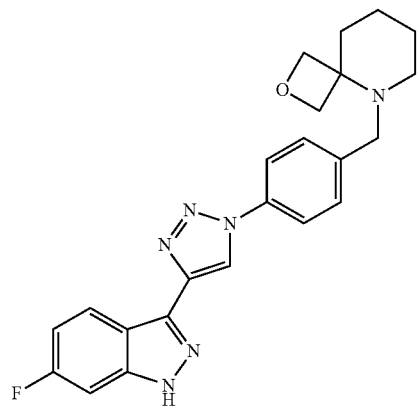 [SMILES: Fc1ccc2c(-c3cn(-c4ccc(CN5CCCCC56COC6)cc4)nn3)n[nH]c2c1] | amorphous beige foam, 1H NMR (300 MHz, DMSO) δ 13.18 (brs, 1H), 9.25 (s, 1H), 8.22 (d, J = 8.3 Hz, 1H), 8.04-7.94 (m, 2H), 7.66-7.54 (m, 2H), 7.37 (s, 1H), 7.09 (dd, J = 8.4, 1.0 Hz, 1H), 4.66 (d, J = 6.4 Hz, 2H), 4.28 (d, J = 6.4 Hz, 2H), 3.86 (s, 2H), 2.47 (s, 3H), 2.42-2.32 (m, 2H), 1.93-1.80 (m, 2H), 1.59-(m, 4H). HPLC (max plot) 98.2%; Rt % 2.76 min. UPLC/MS: (MS+) 415.5, (MS−) 413.5 |

TABLE 1-continued

| 288 | 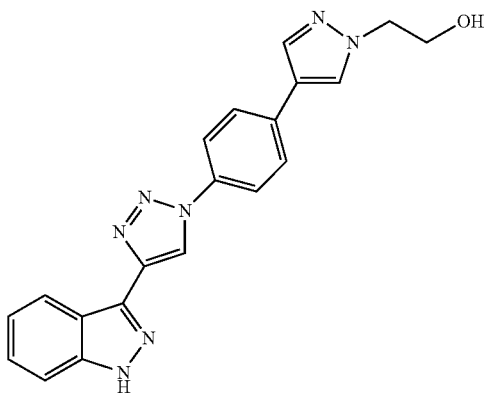 [SMILES: OCCn1cc(-c2ccc(-n3cc(-c4n[nH]c5ccccc45)nn3)cc2)cn1] | brown solid, 1H NMR (300 MHz, DMSO) δ 13.36 (brs, 1H), 9.33 (s, 1H), 8.42-8.34 (m, 1H), 8.30 (s, 1H), 8.09-7.99 (m, 3H), 7.89-7.79 (m, 2H), 7.65-7.57 (m, 1H), 7.49-7.40 (m, 1H), 7.31-7.21 (m, 1H), 4.97 (t, J = 5.3 Hz, 1H), 4.18 (t, J = 5.6 Hz, 2H), 3.79 (q, J = 5.5 Hz, 2H). HPLC (max plot) 99.0%; Rt % 3.08 min. UPLC/MS: (MS+) 126.2, (MS−) 370.5 |
| --- | --- | --- |
| 289 | 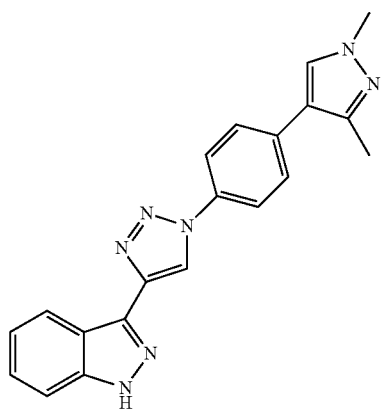 [SMILES: Cc1nn(C)cc1-c1ccc(-n2cc(-c3n[nH]c4ccccc34)nn2)cc1] | brown solid, 1H NMR (300 MHz, DMSO) δ 13.38 (brs, 1H), 9.32 (s, 1H), 8.42-8.33 (m, 1H), 8.12-8.01 (m, 3H), 7.73-7.57 (m, 3H), 7.50-7.39 (m, 1H), 7.33-7.21 (m, 1H), 3.82 (s, 3H), 2.37 (s, 3H). HPLC (max plot) 98.8%; Rt % 3.52 min. UPLC/MS: (MS+) 356.4, (MS−) 354.5 |
| 290 | 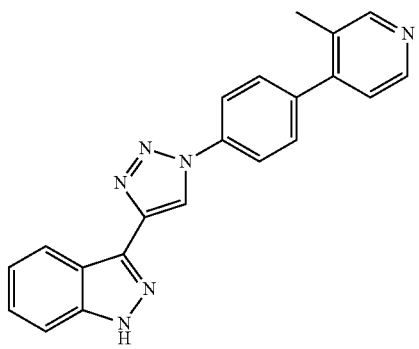 [SMILES: Cc1cnccc1-c1ccc(-n2cc(-c3n[nH]c4ccccc34)nn2)cc1] | brown powder, 1H NMR (300 MHz, DMSO) δ 9.42 (s, 1H), 8.57 (s, 1H), 8.51 (d, J = 4.9 Hz, 1H), 8.38 (d, J = 8.1 Hz, 1H), 8.27-8.14 (m, 2H), 7.79-7.67 (m, 2H), 7.64 (d, J = 8.4 Hz, 1H), 7.50-7.39 (m, 1H), 7.35 (d, J = 5.0 Hz, 1H), 7.31-7.19 (m, 1H), 2.33 (s, 3H). HPLC (max plot) 98.2%; Rt % 2.69 min. UPLC/MS: (MS+) 353.4, (MS−) 351.4 |
| 291 | 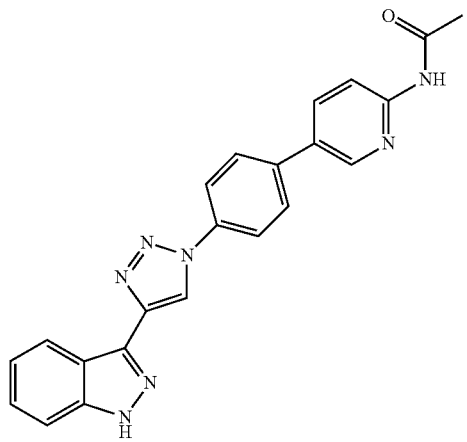 [SMILES: CC(=O)Nc1ccc(-c2ccc(-n3cc(-c4n[nH]c5ccccc45)nn3)cc2)cn1] | brown powder, 1H NMR (300 MHz, DMSO) δ 13.39 (brs, 1H), 10.67 (s, 1H), 9.41 (s, 1H), 8.82-8.73 (m, 1H), 8.38 (d, J = 8.1 Hz, 1H), 8.28-8.11 (m, 4H), 8.09-7.92 (m, 2H), 7.62 (d, J = 8.4 Hz, 1H), 7.53-7.38 (m, 1H), 7.35-7.20 (m, 1H), 2.14 (s, 3H). HPLC (max plot) 98.2%; Rt % 2.92 min. UPLC/MS: (MS+) 396.5, (MS−) 394.5 |

TABLE 1-continued

| 292 | 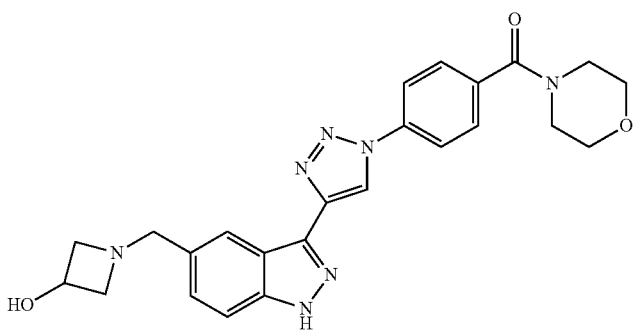 [SMILES: O=C(c1ccc(-n2cc(-c3n[nH]c4ccc(CN5CC(O)C5)cc34)nn2)cc1)N1CCOCC1] | white solid, 1H NMR (300 MHz, DMSO) δ 13.49 (s, 1H), 9.41 (s, 1H), 8.44 (s, 1H), 8.15 (d, J = 8.6 Hz, 2H), 7.69 (d, J = 8.6 Hz, 2H), 7.64 (d, J = 8.7 Hz, 1H), 7.48 (d, J = 8.7 Hz, 1H), 5.88 (br, 1H), 4.48-4.34 (m, 1H), 4.32-4.15 (m, 2H), 4.04-3.84 (m, 2H), 3.77-3.15 (m, 10H). HPLC (max plot) 91.6%; Rt % 1.73 min. UPLC/MS: (MS+) 460.4, (MS−) 458.3 |
|---|---|---|
| 293 | 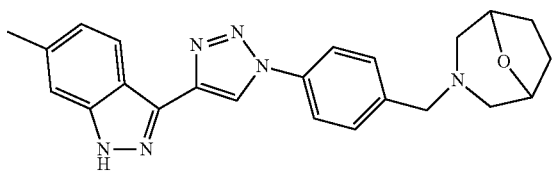 [SMILES: Cc1ccc2c(-c3cn(-c4ccc(CN5CC6CCC(C5)O6)cc4)nn3)n[nH]c2c1] | brown solid, 1H NMR (300 MHz, DMSO) δ 13.18 (bs, 1H), 9.26 (s, 1H), 8.22 (d, J = 8.3 Hz, 1H), 8.00 (d, J = 8.6 Hz, 2H), 7.55 (d, J = 8.6 Hz, 2H), 7.37 (s, 1H), 7.08 (dd, J = 8.5 Hz, 1.0 Hz, 1H), 4.24-4.20 (m, 2H), 3.53 (s, 2H), 2.54 (d, J = 11.0 Hz, 2H), 2.47 (s, 3H), 2.24 (dd, J = 11.0 Hz, 1.8 Hz, 2H), 1.94-1.88 (m, 2H), 1.77-1.72 (m, 2H). HPLC (max plot) 94.9%; Rt % 2.78 min. UPLC/MS: (MS+) 401.3, (MS−) 399.3 |
| 294 | 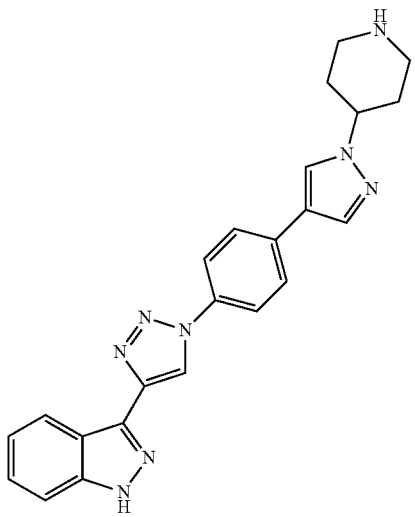 [SMILES: c1ccc2c(-c3cn(-c4ccc(-c5cnn(C6CCNCC6)c5)cc4)nn3)n[nH]c2c1] | beige powder, 1H NMR (300 MHz, DMSO) δ 13.40 (brs, 1H), 9.35 (s, 1H), 9.08 (brs, 1H), 8.85 (brs, 1H), 8.45-8.33 (m, 2H), 8.13-8.02 (m, 3H), 7.88 (d, J = 8.7 Hz, 2H), 7.67-7.57 (m, 1H), 7.51-7.39 (m, 1H), 7.33-7.20 (m, 1H), 4.61-4.44 (m, 1H), 3.51-3.32 (m, 2H), 3.23-2.99 (m, 2H), 2.36-2.06 (m, 4H). HPLC (max plot) 96.6%; Rt % 2.79 min. UPLC/MS: (MS+) 411.4, (MS−) 409.6 |
| 295 | 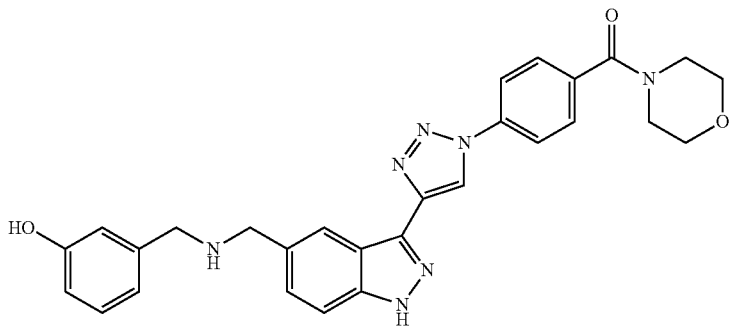 [SMILES: O=C(c1ccc(-n2cc(-c3n[nH]c4ccc(CNCc5cccc(O)c5)cc34)nn2)cc1)N1CCOCC1] | white solid, 1H NMR (300 MHz, DMSO) δ 13.33 (s, 1H), 9.36 (s, 1H), 8.34-8.23 (m, 2H), 8.15 (d, J = 8.7 Hz, 2H), 7.69 (d, J = 8.7 Hz, 2H), 7.56 (d, J = 8.6 Hz, 1H), 7.47 (dd, J = 8.6, 1.4 Hz, 1H), 7.10 (t, J = 7.7 Hz, 1H), 6.85-6.72 (m, 2H), 6.67-6.56 (m, 1H), 3.85 (s, 2H), 3.76-3.11 (m, 10H), 2.54 (s, 1H). HPLC (max plot) 96.6%; Rt % 2.26 min. UPLC/MS: (MS+) 510.5, (MS−) 508.6 |

TABLE 1-continued

| 296 | 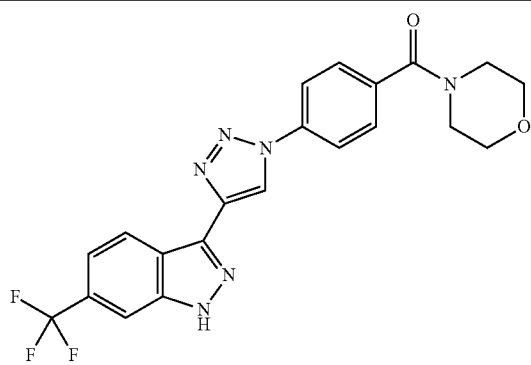 | beige powder, 1H NMR (300 MHz, DMSO) δ 13.88 (brs, 1H), 9.48 (s, 1H), 8.64-8.56 (m, 1H), 8.21-8.12 (m, 2H), 8.02 (s, 1H), 7.74-7.65 (m, 2H), 7.57 (d, J = 8.5 Hz, 1H), 3.90-3.40 (m, 8H). HPLC (max plot) 97.8%; Rt % 3.85 min. UPLC/MS: (MS+) 443.4, (MS−) 441.5 |
| --- | --- | --- |
| 297 | 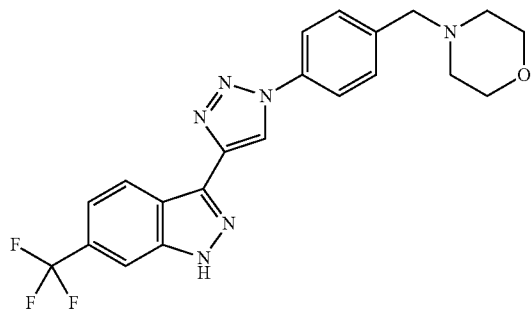 [SMILES: FC(F)(F)c1ccc2c(-c3cn(-c4ccc(CN5CCOCC5)cc4)nn3)n[nH]c2c1] | beige powder, 1H NMR (300 MHz, DMSO) δ 13.85 (brs, 1H), 9.38 (s, 1H), 8.62-8.56 (m, 1H), 8.08-7.97 (m, 3H), 7.61-7.52 (m, 3H), 3.65-3.58 (m, 4H), 3.57 (s, 2H), 2.45-2.37 (m, 4H). HPLC (max plot) 92.2%; Rt % 3.19 min. UPLC/MS: (MS+) 429.4, (MS−) 427.5 |
| 298 | 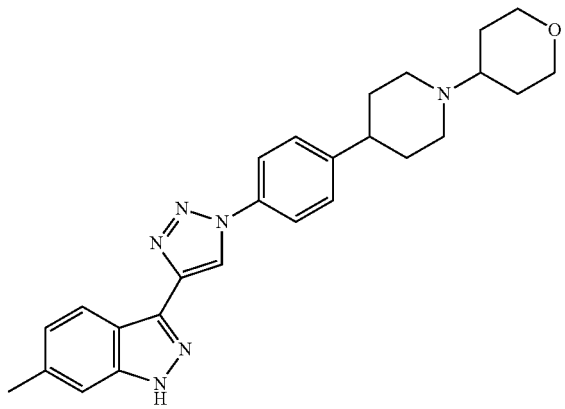 [SMILES: Cc1ccc2c(-c3cn(-c4ccc(C5CCN(C6CCOCC6)CC5)cc4)nn3)n[nH]c2c1] | beige amorphous foam, 1H NMR (300 MHz, DMSO) δ 13.17 (brs, 1H), 9.24 (s, 1H), 8.22 (d, J = 8.2 Hz, 1H), 8.00-7.91 (m, 2H), 7.56-7.46 (m, 2H), 7.40-7.34 (m, 1H), 7.13-7.04 (m, 1H), 3.97-3.86 (m, 2H), 3.35-3.15 (m, 1H), 3.15-3.00 (m, 3H), 2.73-2.54 (m, 2H), 2.48 (s, 3H), 2.42-2.25 (m, 2H), 1.91-1.62 (m, 6H), 1.57-1.40 (m, 2H). HPLC (max plot) 97.4%; Rt % 2.97 min. UPLC/MS: (MS+) 443.5, (MS−) 441.6 |
| 299 | 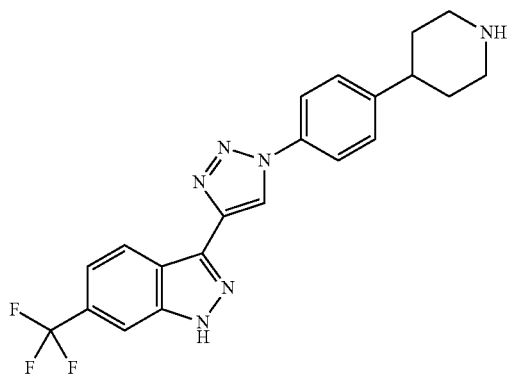 [SMILES: FC(F)(F)c1ccc2c(-c3cn(-c4ccc(C5CCNCC5)cc4)nn3)n[nH]c2c1] | white amorphous foam, 1H NMR (300 MHz, DMSO) δ 13.91 (brs, 1H), 9.36 (s, 1H), 8.77 (brs, 1H), 8.64-8.51 (m, 1H), 8.10-7.97 (m, 3H), 7.62-7.44 (m, 3H), 3.69-3.17 (m, 1H), 3.14-2.86 (m, 4H), 2.10-1.79 (m, 4H). 1H NMR (DMSO) δ. 1H NMR (DMSO) δ. HPLC (max plot) 97.2%; Rt % 3.34 min. HPLC (max plot) 97.4% Rt % 3.36 min. UPLC/MS: (MS+) 413.5, (MS−) 411.5 |

Example 300

In Vitro Assays

IRAK1 Enzymatic Assays:

IRAK1 is a human purified recombinant enzyme (His-TEV-IRAK1 (194-712))

In this assay, IRAK-1 hydrolyses ATP and autophosphorylates.

ATP-Consumption Format:

Measurement of IRAK-1 inhibition is done in 384 well format based on luminescence assay (PKLight® ATP Detection Reagent Lonza: based in Basel CH LT07-501). This PKLight® assay is based on bioluminescent measurement of the remaining ATP in the wells after kinase activity and luciferase activity that generates light from ATP and luciferin.

His-TEV-IRAK-1 (30 ng/well), ATP (1.5 µM) and compounds in DMSO (range of concentrations from 20 µM to 1 nM) or controls (2% DMSO) are incubated for 2 hours at 30° C. in assay buffer: Hepes pH7.0 50 mM, Fatty acid-free BSA 0.1%, Dithiothreitol DTT 2 mM, MgCl$_2$ 10 mM, EGTA 0.5 mM, Triton-X-100 0.01%.

Kinase reaction is stopped by adding PKLight® ATP Detection Reagent mix according to supplier instructions. Luminescence signal is then measured after 1 hour incubation time with a luminometer (BMG Pherastar reader or equivalent).

Flashplate Format:

Measurement of IRAK-1 inhibition is performed in streptavidin coated 384 well FlashPlate (PerkinElmer #SMP410A).

His-TEV-IRAK-1 (15 ng/well), ATP (1 µM, [$^{33}$P]ATP 0.25 µCi/well) and compounds in DMSO (range of concentrations from 20 µM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Triton-X-100 0.01%. Kinase reaction is stopped by addition of EDTA. Supernatant is discarded, plates are washed three times with 150 mM NaCl and radioactivity is then measured in a Microbeta Trilux reader.

IRAK4 Enzymatic Assay:

IRAK4 is a human purified recombinant enzyme (His-TEV-IRAK1 (194-712)

IRAK4 hydrolyses ATP, autophosphorylates and phosphorylates a Serine/Threonine generic peptidic substrate (STK: 61ST1BLC from CisBio International based in Bagnols/Cèze FR).

ATP-Consumption Format:

Measurement of IRAK-4 inhibition is done in 384 well format based on luminescence assay (PKLight® ATP Detection Reagent Lonza: based in Basel CH LT07-501). This PKLight® assay is based upon bioluminescent measurement of the remaining ATP in the wells after kinase activity and luciferase activity that generates light from ATP and luciferin.

His-TEV-IRAK4 (8 ng/well), ATP (2 µM), STK1-biotin peptide (300 nM) and compounds in DMSO (range of concentrations from 20 µM to 1 nM) or controls (2% DMSO) are incubated for 2 hours at 300 in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM.

Kinase reaction is stopped by adding PKLight® ATP Detection Reagent mix according to supplier instructions. Luminescence signal is then measured after 1 hour incubation time with a luminometer (BMG Pherastar reader or equivalent).

Flashplate Format:

Measurement of IRAK-4 inhibition is performed in streptavidin coated 384 well FlashPlate (PerkinElmer #SMP410A). His-TEV-IRAK4 (20 ng/well), ATP (2 µM, [$^{33}$P]ATP 0.25 µCi/well), STK1-biotin peptide (300 nM) and compounds in DMSO (range of concentrations from 20 µM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM.

Kinase reaction is stopped by addition of EDTA. Supernatant is discarded, plates are washed three times with 150 mM NaCl and radioactivity is then measured in a Microbeta Trilux reader.

IRAK IL8 Secretion Functional Assay:

THP1 cells are human monocytes derived from acute monocytic leukemia. IL1β receptor expressed on the surface membrane of THP1 cells induced IL8 release. IRAKs are kinase signaling downstream of TLRs and TNF, IL-18, IL-33 and IL-1 receptors.

In cells, IRAK4 is upstream of IRAK1.

The Human IL8 Kit, provided by CysBio International based in Bagnols/Cèze FR, allows for the quantitative determination of IL-8 in cell-culture supernatants.

Anti-cytokine IL8 antibodies are respectively labeled with europium Cryptate and XL665. Upon their binding to IL-8 molecules, the two antibodies come into close proximity, allowing FRET (Fluorescence Resonance Energy Transfer) to occur. This FRET increases proportionally to IL-8 concentrations and be converted in IL8 pg amounts.

THP-1 cells are seeded on Day 1 in 384 well plate with RPMI 1640 at a density of 30 000 cells/well. Compounds 4×/2% DMSO (range of concentrations from 20 µM to 1 nM) and IL1β 4× at 100 ng/ml final are added to cells overnight at 37° C., 5% CO2. Measurement of IL-8 secretion is done by mixing on Day2 10 µl of supernatant with 10 µl of a mix solution of europium Cryptate and XL665 (v:v) as described by supplier.

HTRF (homogeneous time resolved fluorescence) signal is measured after 3 hours incubation time at 30° C. with a BMG Pherastar reader or equivalent.

Results are summarized in table 2 below:

| Ex | compounds | IC50, Phosphorylation IRAK1/4 human | IC50, Secretion THP-1/IL-β induced IL8 release |
|---|---|---|---|
| 1 | 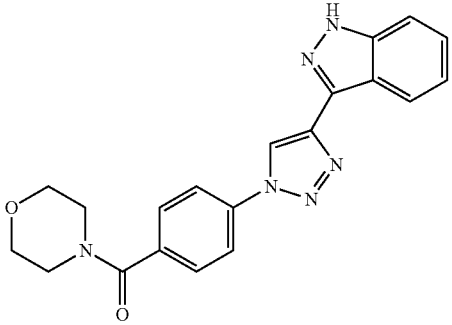 [SMILES: O=C(c1ccc(-n2cc(-c3n[nH]c4ccccc34)nn2)cc1)N1CCOCC1] |  |  |
| 2 | 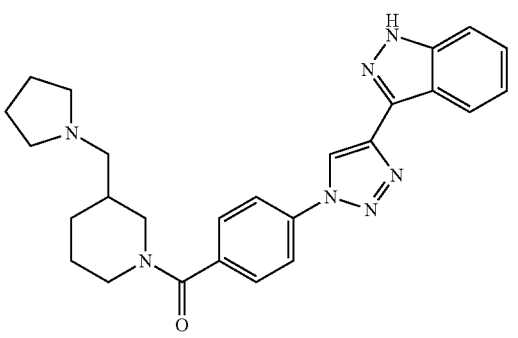 | * | * |
| 3 | 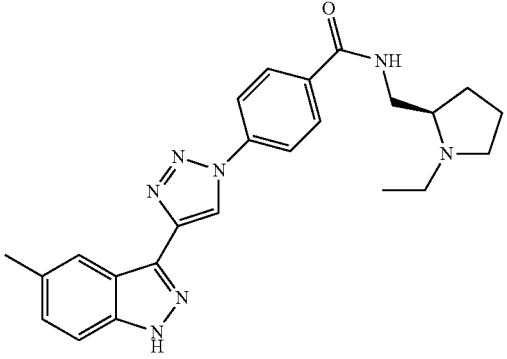 |  |  |
| 4 | 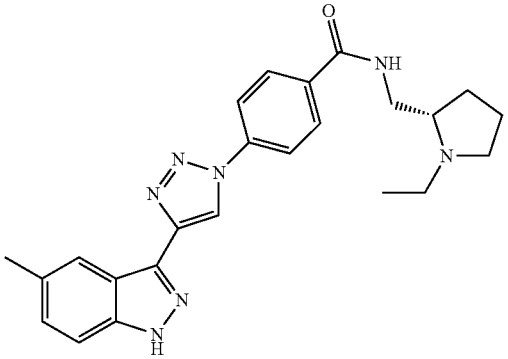 [SMILES: CCN1CCC[C@H]1CNC(=O)c1ccc(-n2cc(-c3n[nH]c4ccc(C)cc34)nn2)cc1] |  |  |

-continued
| | | | |
|---|---|---|---|
| 5 | 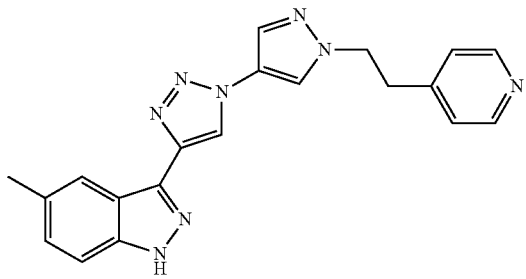 [SMILES: Cc1ccc2[nH]nc(-c3cn(-c4cnn(CCc5ccncc5)c4)nn3)c2c1] |  |  |
| 6 | 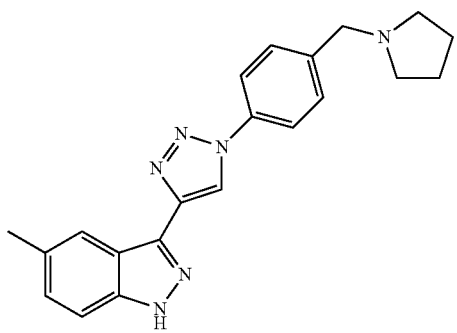 [SMILES: Cc1ccc2[nH]nc(-c3cn(-c4ccc(CN5CCCC5)cc4)nn3)c2c1] |  |  |
| 7 | 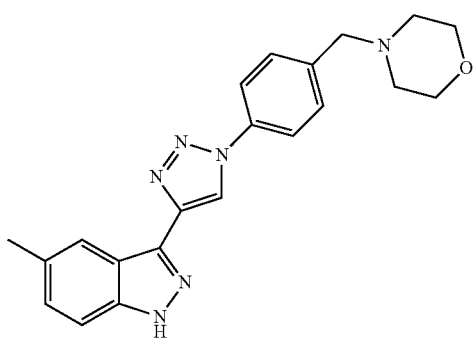 [SMILES: Cc1ccc2[nH]nc(-c3cn(-c4ccc(CN5CCOCC5)cc4)nn3)c2c1] |  |  |
| 8 | 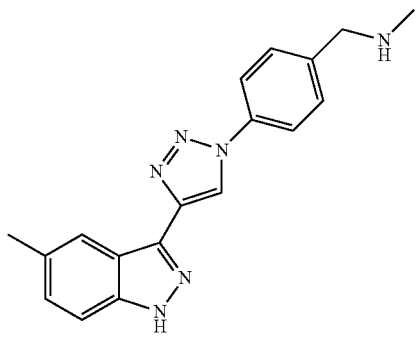 |  |  |
| 9 | 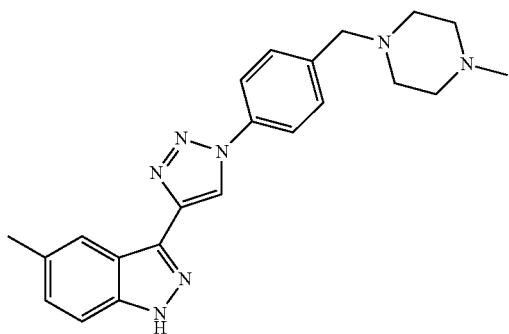 | * | ** |

-continued
| | | | |
|---|---|---|---|
| 10 | 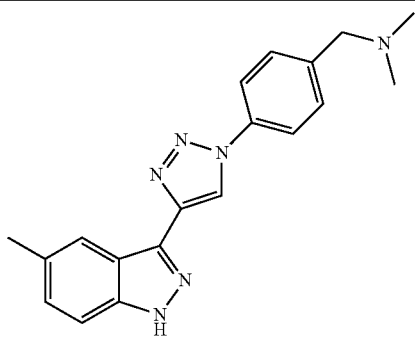 |  |  |
| 11 | 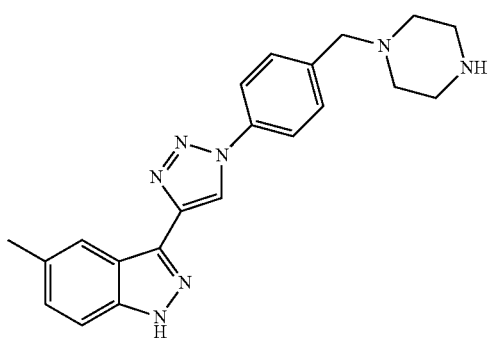 [SMILES: Cc1ccc2[nH]nc(-c3cn(-c4ccc(CN5CCNCC5)cc4)nn3)c2c1] |  |  |
| 12 | 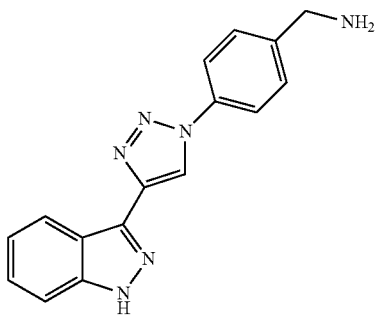 [SMILES: NCc1ccc(-n2cc(-c3n[nH]c4ccccc34)nn2)cc1] | * | nd |
| 13 | 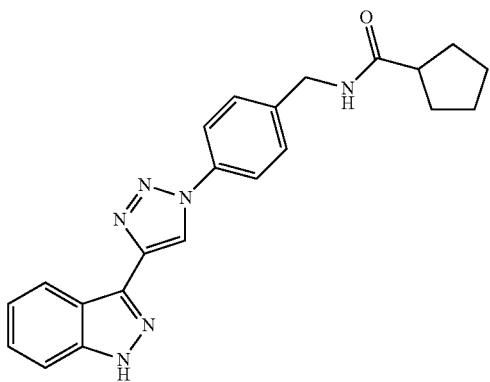 [SMILES: O=C(NCc1ccc(-n2cc(-c3n[nH]c4ccccc34)nn2)cc1)C1CCCC1] | * | nd |

| | | | |
|---|---|---|---|
| 15 | 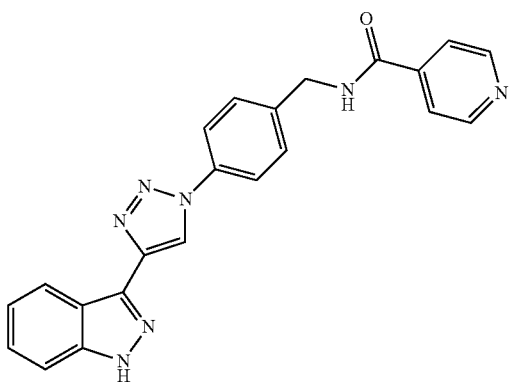 [SMILES: O=C(NCc1ccc(-n2cc(-c3n[nH]c4ccccc34)nn2)cc1)c1ccncc1] | * | ** |
| 16 | 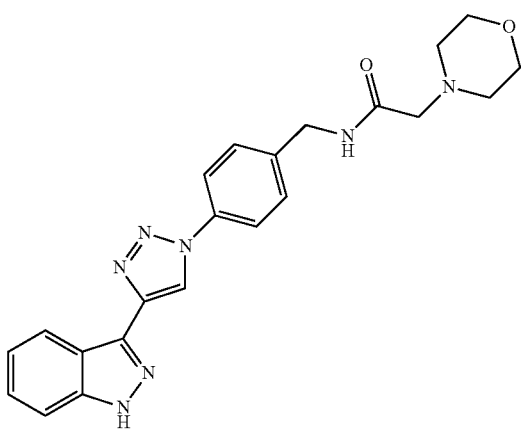 [SMILES: O=C(CN1CCOCC1)NCc1ccc(-n2cc(-c3n[nH]c4ccccc34)nn2)cc1] | * | nd |
| 17 | 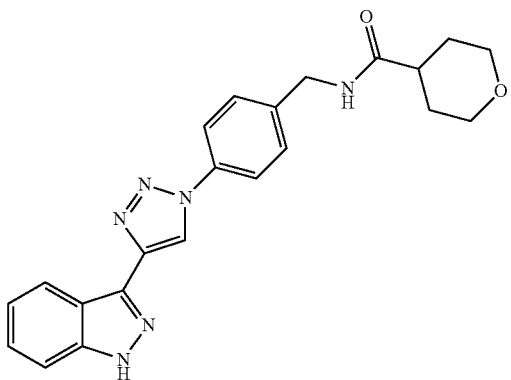 [SMILES: O=C(NCc1ccc(-n2cc(-c3n[nH]c4ccccc34)nn2)cc1)C1CCOCC1] | * | nd |
| 18 | 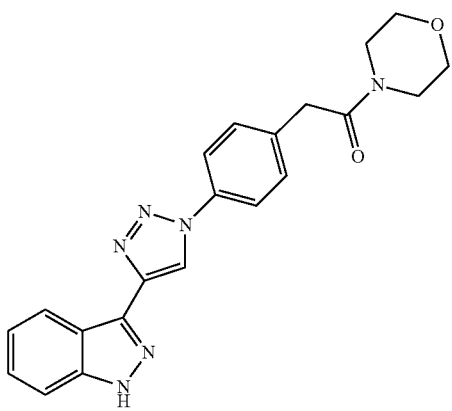 [SMILES: O=C(Cc1ccc(-n2cc(-c3n[nH]c4ccccc34)nn2)cc1)N1CCOCC1] | ** | nd |

-continued
| | | | |
|---|---|---|---|
| 19 | 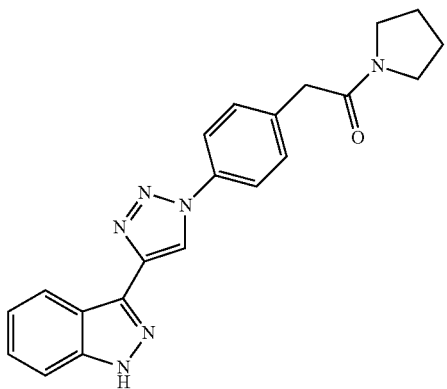 [SMILES: O=C(Cc1ccc(-n2cc(-c3n[nH]c4ccccc34)nn2)cc1)N1CCCC1] |  |  |
| 20 | 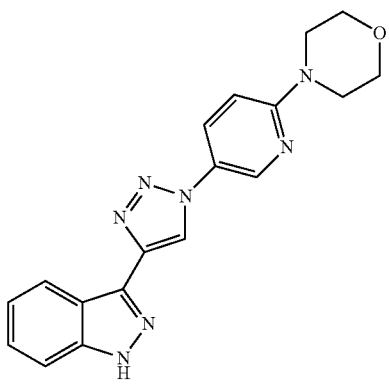 [SMILES: c1ccc2c(-c3cn(-c4ccc(N5CCOCC5)nc4)nn3)n[nH]c2c1] | * | nd |
| 22 | 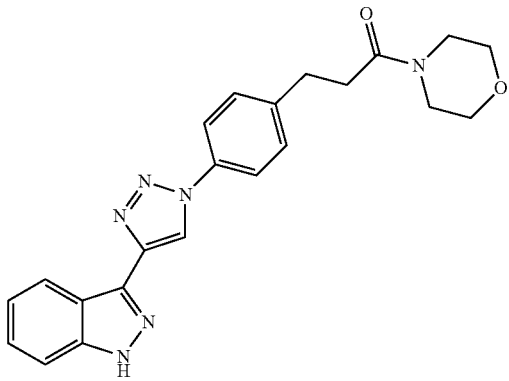 [SMILES: O=C(CCc1ccc(-n2cc(-c3n[nH]c4ccccc34)nn2)cc1)N1CCOCC1] | * | ** |
| 23 | 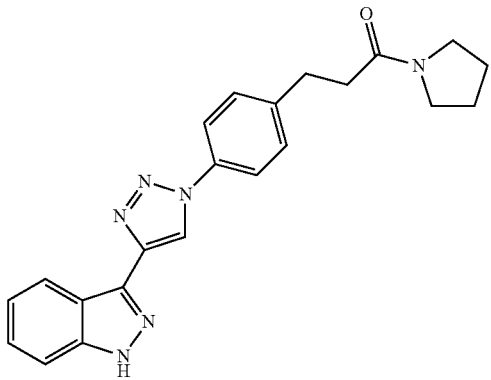 [SMILES: O=C(CCc1ccc(-n2cc(-c3n[nH]c4ccccc34)nn2)cc1)N1CCCC1] | * | ** |

| | | 403 | 404 | |
|---|---|---|---|---|
| | | -continued | | |
| 24 | 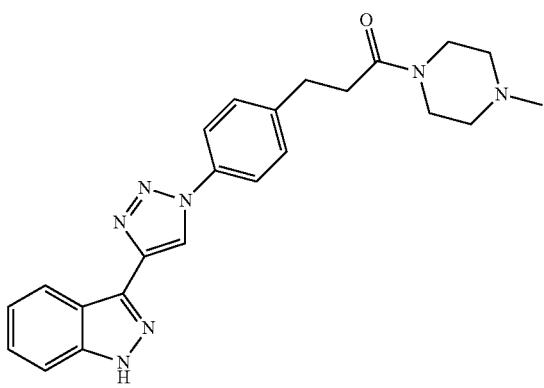 [SMILES: CN1CCN(C(=O)CCc2ccc(-n3cc(-c4n[nH]c5ccccc45)nn3)cc2)CC1] | | * | nd |
| 25 | 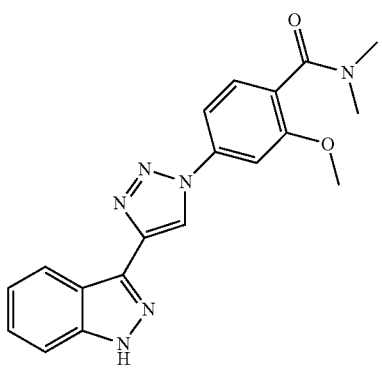 [SMILES: COc1cc(-n2cc(-c3n[nH]c4ccccc34)nn2)ccc1C(=O)N(C)C] | |  |  |
| 26 | 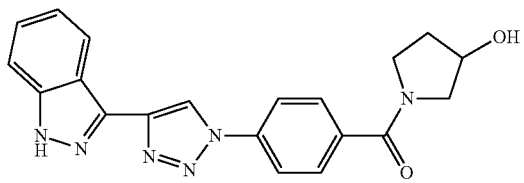 [SMILES: O=C(c1ccc(-n2cc(-c3n[nH]c4ccccc34)nn2)cc1)N1CCC(O)C1] | |  |  |
| 27 | 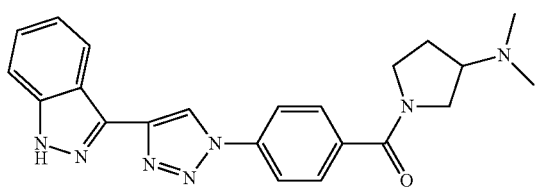 [SMILES: CN(C)C1CCN(C(=O)c2ccc(-n3cc(-c4n[nH]c5ccccc45)nn3)cc2)C1] | |  |  |
| 28 | 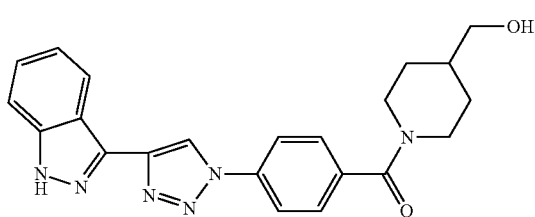 [SMILES: O=C(c1ccc(-n2cc(-c3n[nH]c4ccccc34)nn2)cc1)N1CCC(CO)CC1] | |  |  |
| 29 | 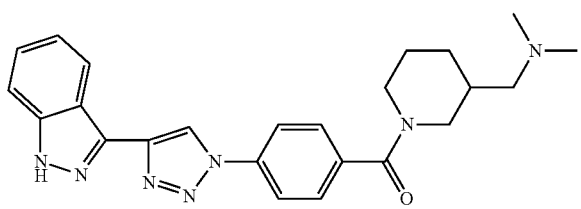 [SMILES: CN(C)CC1CCCN(C(=O)c2ccc(-n3cc(-c4n[nH]c5ccccc45)nn3)cc2)C1] | |  |  |

| | | 405 | 406 |
|---|---|---|---|
| 30 | 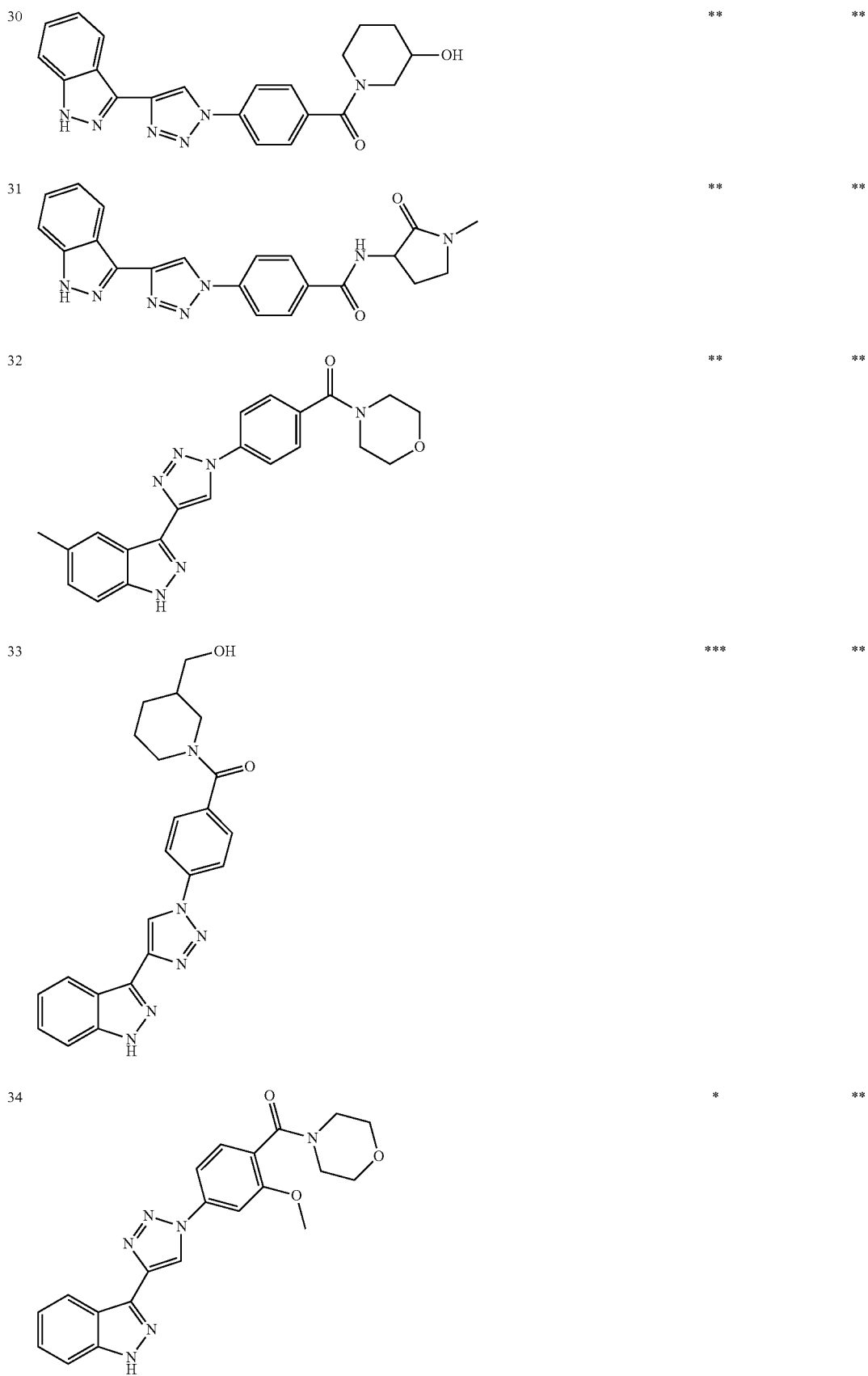 |  |  |
| 31 | |  |  |
| 32 | | ** | ** |
| 33 | | *** | ** |
| 34 | | * | ** |

-continued
| | | | |
|---|---|---|---|
| 35 | 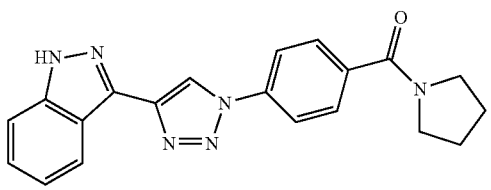 [SMILES: O=C(c1ccc(-n2cc(-c3n[nH]c4ccccc34)nn2)cc1)N1CCCC1] | * |  |
| 36 | 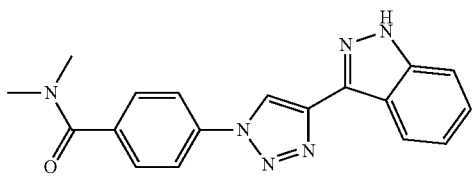 [SMILES: CN(C)C(=O)c1ccc(-n2cc(-c3n[nH]c4ccccc34)nn2)cc1] |  |  |
| 37 | 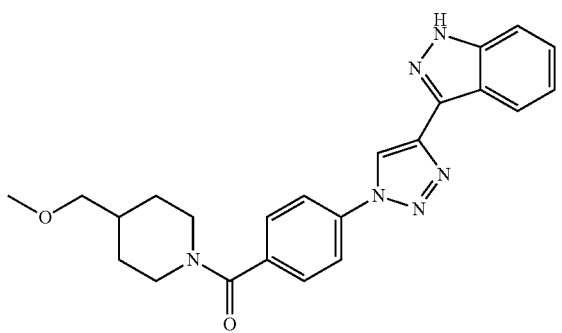 [SMILES: COCC1CCN(C(=O)c2ccc(-n3cc(-c4n[nH]c5ccccc45)nn3)cc2)CC1] |  |  |
| 38 | 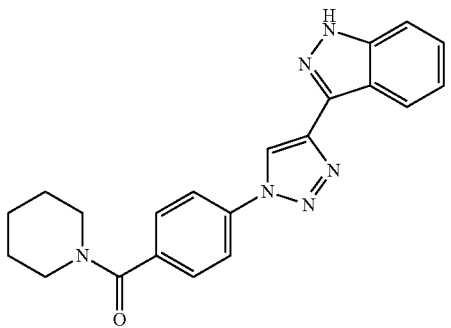 [SMILES: O=C(c1ccc(-n2cc(-c3n[nH]c4ccccc34)nn2)cc1)N1CCCCC1] | * | ** |
| 39 | 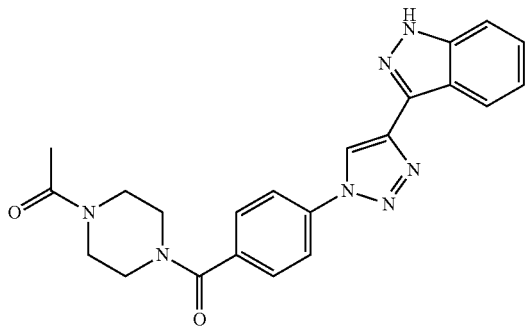 [SMILES: CC(=O)N1CCN(C(=O)c2ccc(-n3cc(-c4n[nH]c5ccccc45)nn3)cc2)CC1] |  |  |

| | | | |
|---|---|---|---|
| 40 | 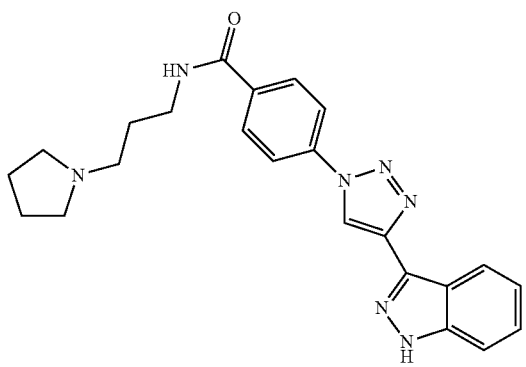 [SMILES: O=C(NCCCN1CCCC1)c1ccc(-n2cc(-c3n[nH]c4ccccc34)nn2)cc1] |  |  |
| 41 | 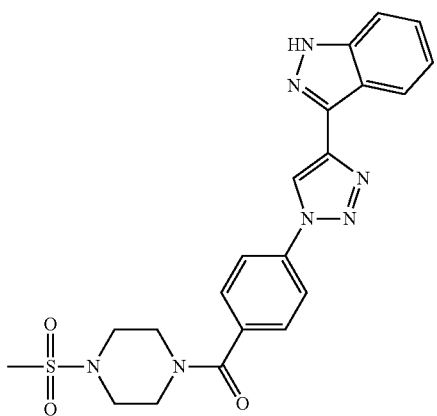 [SMILES: CS(=O)(=O)N1CCN(C(=O)c2ccc(-n3cc(-c4n[nH]c5ccccc45)nn3)cc2)CC1] | ** | nd |
| 42 | 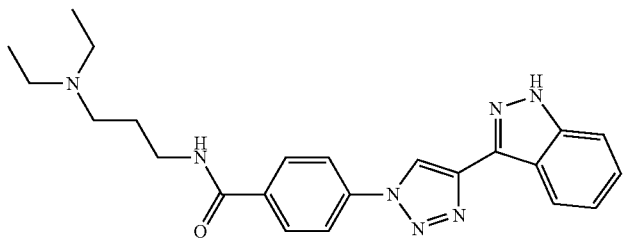 [SMILES: CCN(CC)CCCNC(=O)c1ccc(-n2cc(-c3n[nH]c4ccccc34)nn2)cc1] |  |  |
| 43 | 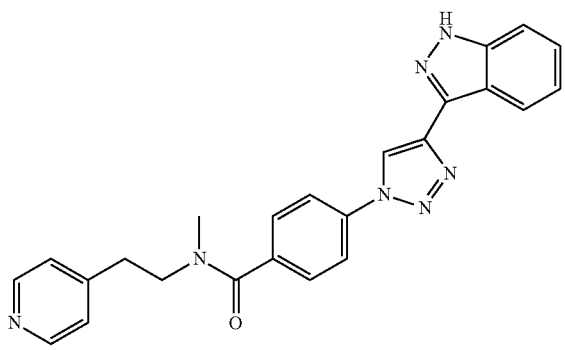 [SMILES: CN(CCc1ccncc1)C(=O)c1ccc(-n2cc(-c3n[nH]c4ccccc34)nn2)cc1] |  |  |

| | 411 | 412 | |
|---|---|---|---|
| 44 | 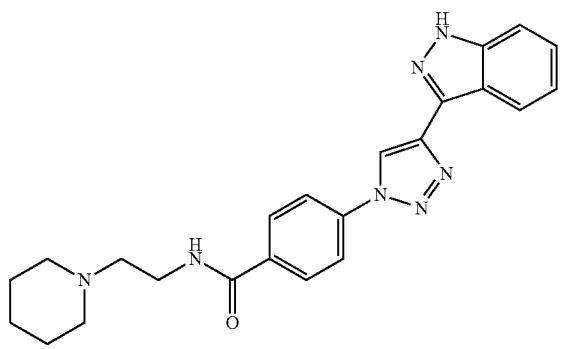 [SMILES: O=C(NCCN1CCCCC1)c1ccc(-n2cc(-c3n[nH]c4ccccc34)nn2)cc1] |  |  |
| 45 | 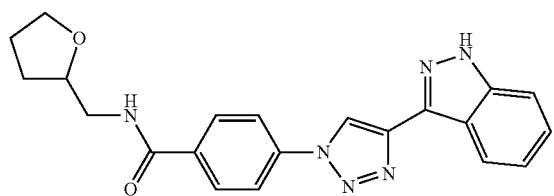 [SMILES: O=C(NCC1CCCO1)c1ccc(-n2cc(-c3n[nH]c4ccccc34)nn2)cc1] | ** | nd |
| 46 | 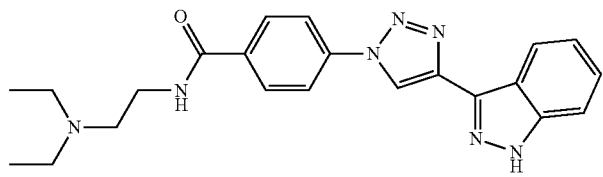 [SMILES: CCN(CC)CCNC(=O)c1ccc(-n2cc(-c3n[nH]c4ccccc34)nn2)cc1] | ** | nd |
| 47 | 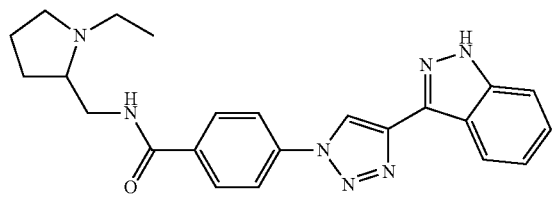 [SMILES: CCN1CCCC1CNC(=O)c1ccc(-n2cc(-c3n[nH]c4ccccc34)nn2)cc1] | ** | nd |
| 48 | 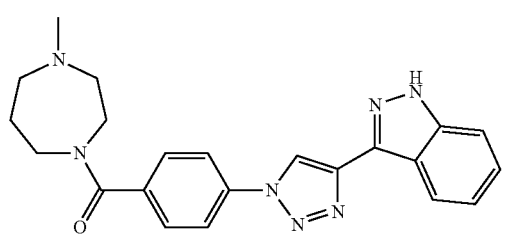 [SMILES: CN1CCCN(C(=O)c2ccc(-n3cc(-c4n[nH]c5ccccc45)nn3)cc2)CC1] |  |  |
| 49 | 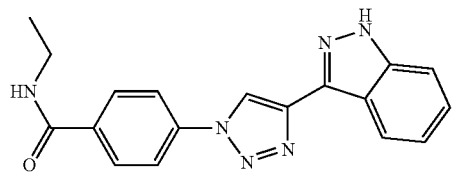 [SMILES: CCNC(=O)c1ccc(-n2cc(-c3n[nH]c4ccccc34)nn2)cc1] |  |  |
| 50 | 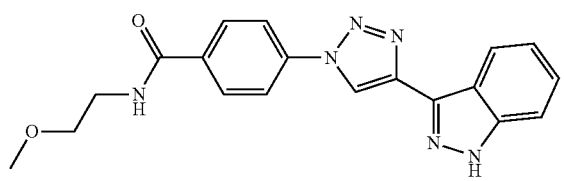 [SMILES: COCCNC(=O)c1ccc(-n2cc(-c3n[nH]c4ccccc34)nn2)cc1] |  |  |

-continued
| | 413 | 414 | |
|---|---|---|---|
| 51 | 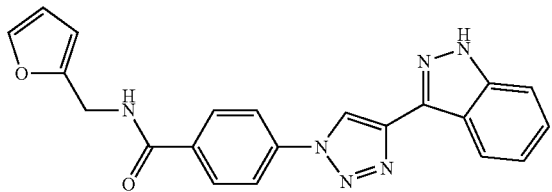 [SMILES: O=C(NCc1ccco1)c1ccc(-n2cc(-c3n[nH]c4ccccc34)nn2)cc1] | ** | * |
| 52 | 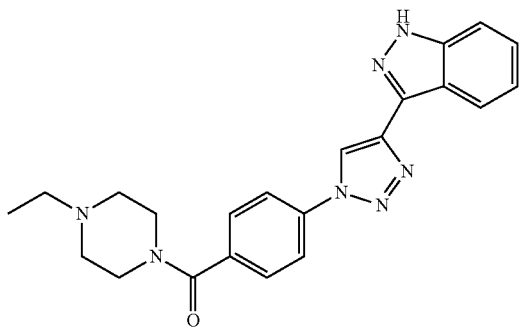 [SMILES: CCN1CCN(C(=O)c2ccc(-n3cc(-c4n[nH]c5ccccc45)nn3)cc2)CC1] |  |  |
| 53 | 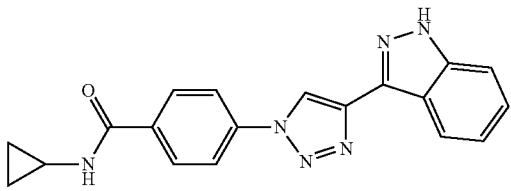 [SMILES: O=C(NC1CC1)c1ccc(-n2cc(-c3n[nH]c4ccccc34)nn2)cc1] |  |  |
| 54 | 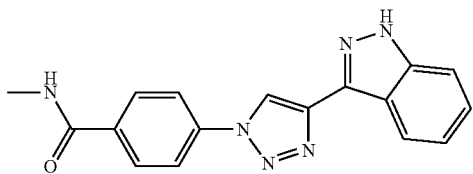 [SMILES: CNC(=O)c1ccc(-n2cc(-c3n[nH]c4ccccc34)nn2)cc1] |  |  |
| 55 | 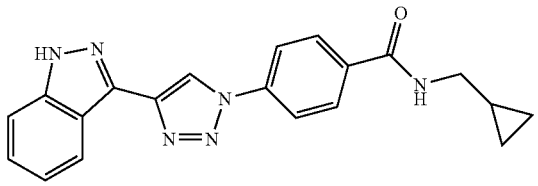 [SMILES: O=C(NCC1CC1)c1ccc(-n2cc(-c3n[nH]c4ccccc34)nn2)cc1] |  |  |
| 56 | 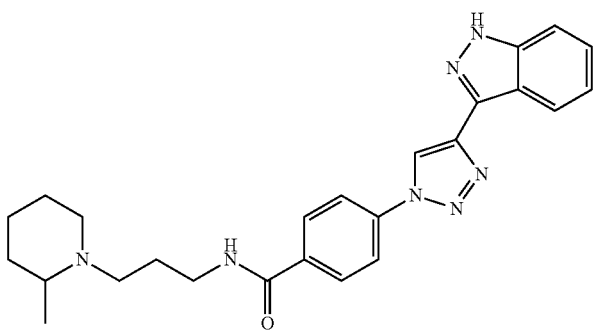 [SMILES: CC1CCCCN1CCCNC(=O)c1ccc(-n2cc(-c3n[nH]c4ccccc34)nn2)cc1] | ** | nd |

| | | | |
|---|---|---|---|
| 57 | 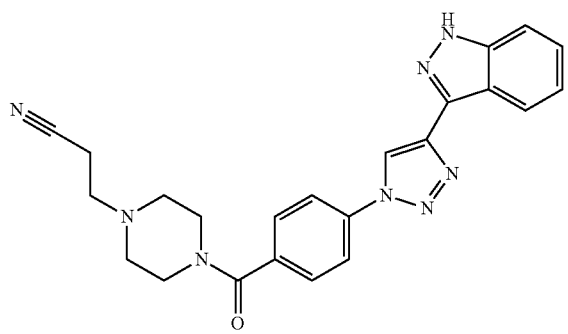 [SMILES: N#CCCN1CCN(C(=O)c2ccc(-n3cc(-c4n[nH]c5ccccc45)nn3)cc2)CC1] | ** | nd |
| 58 | 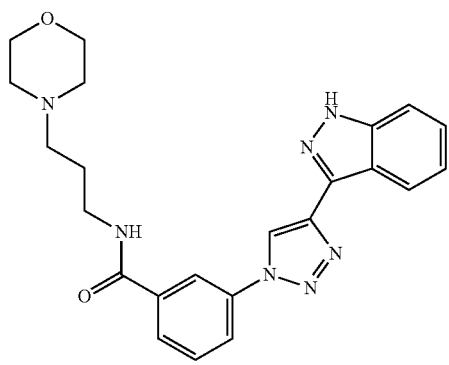 [SMILES: O=C(NCCCN1CCOCC1)c1cccc(-n2cc(-c3n[nH]c4ccccc34)nn2)c1] | ** | nd |
| 59 | 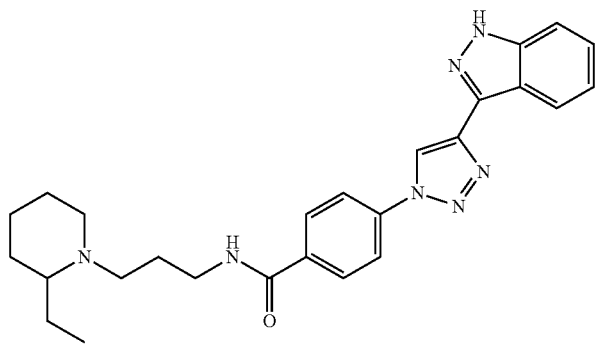 [SMILES: CCC1CCCCN1CCCNC(=O)c1ccc(-n2cc(-c3n[nH]c4ccccc34)nn2)cc1] | ** | nd |
| 60 | 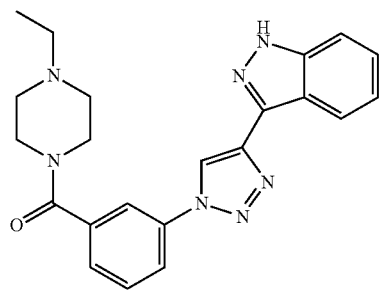 [SMILES: CCN1CCN(C(=O)c2cccc(-n3cc(-c4n[nH]c5ccccc45)nn3)c2)CC1] | * | * |

| | | | |
|---|---|---|---|
| 61 | 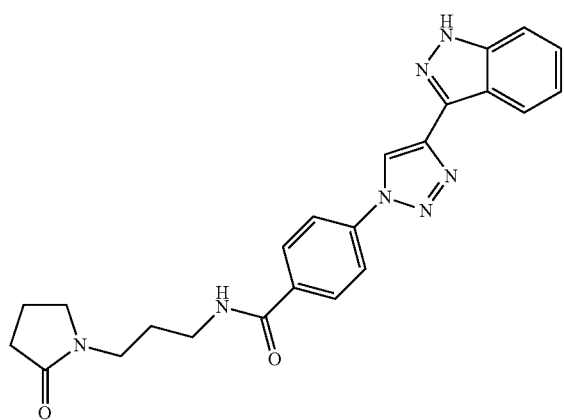 [SMILES: O=C(NCCCN1CCCC1=O)c1ccc(-n2cc(-c3n[nH]c4ccccc34)nn2)cc1] | * | nd |
| 62 | 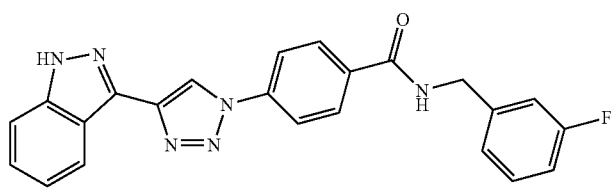 [SMILES: O=C(NCc1cccc(F)c1)c1ccc(-n2cc(-c3n[nH]c4ccccc34)nn2)cc1] | * | nd |
| 63 | 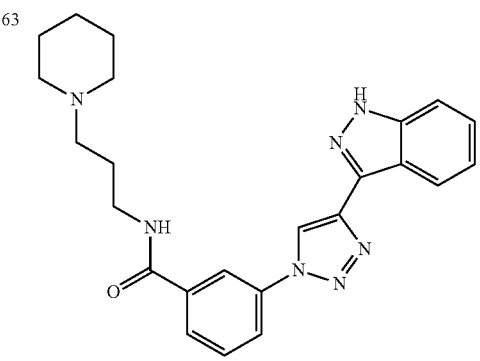 | * | nd |
| 64 | 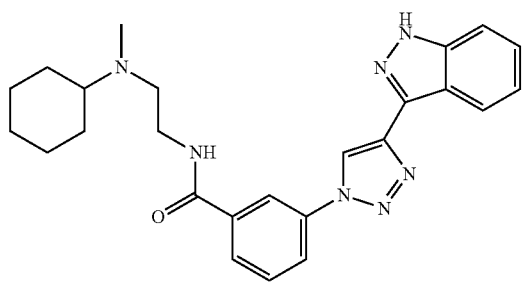 [SMILES: CN(CCNC(=O)c1cccc(-n2cc(-c3n[nH]c4ccccc34)nn2)c1)C1CCCCC1] | * | nd |
| 65 | 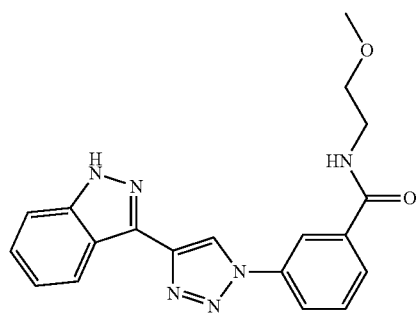 [SMILES: COCCNC(=O)c1cccc(-n2cc(-c3n[nH]c4ccccc34)nn2)c1] | * | nd |

-continued

| | | |
|---|---|---|
| 66 (structure) | * | nd |
| 67 (structure) | * | nd |
| 68 (structure) | * | nd |
| 69 (structure) | * | nd |
| 70 (structure) | ** | nd |

| | 421 | 422 | |
|---|---|---|---|
| 71 | 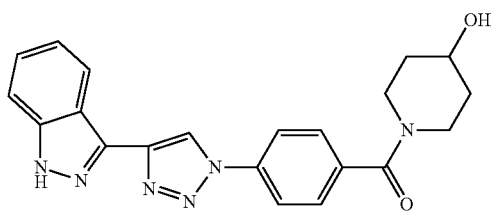 [SMILES: O=C(c1ccc(-n2cc(-c3n[nH]c4ccccc34)nn2)cc1)N1CCC(O)CC1] |  |  |
| 72 | 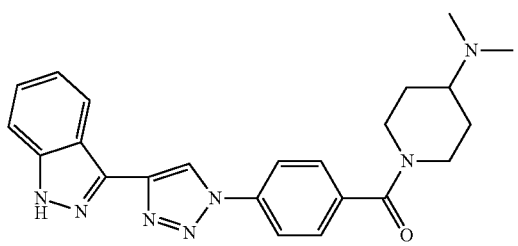 [SMILES: CN(C)C1CCN(C(=O)c2ccc(-n3cc(-c4n[nH]c5ccccc45)nn3)cc2)CC1] |  | * |
| 73 | 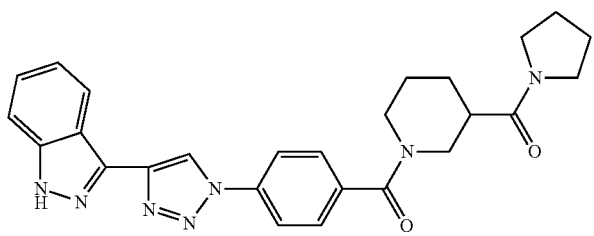 [SMILES: O=C(c1ccc(-n2cc(-c3n[nH]c4ccccc34)nn2)cc1)N1CCCC(C(=O)N2CCCC2)C1] |  | * |
| 74 | 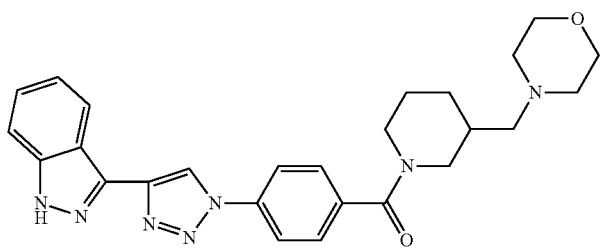 [SMILES: O=C(c1ccc(-n2cc(-c3n[nH]c4ccccc34)nn2)cc1)N1CCCC(CN2CCOCC2)C1] |  |  |
| 75 | 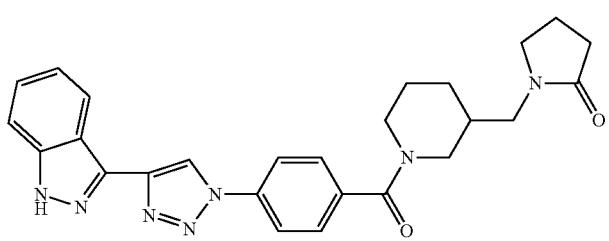 [SMILES: O=C1CCCN1CC1CCCN(C(=O)c2ccc(-n3cc(-c4n[nH]c5ccccc45)nn3)cc2)C1] |  |  |
| 76 | 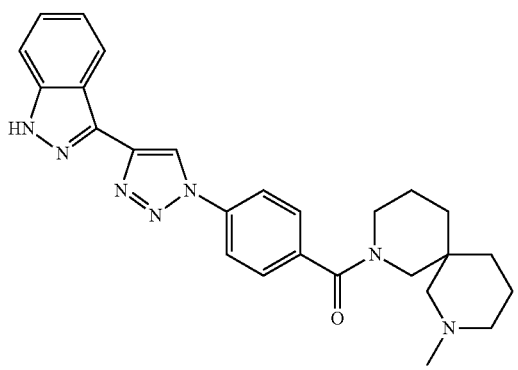 [SMILES: CN1CCCC2(CCCN(C(=O)c3ccc(-n4cc(-c5n[nH]c6ccccc56)nn4)cc3)C2)C1] | * | * |

-continued
| | | | |
|---|---|---|---|
| 77 | 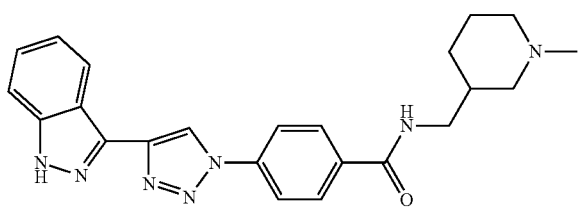 [SMILES: CN1CCCC(CNC(=O)c2ccc(-n3cc(-c4n[nH]c5ccccc45)nn3)cc2)C1] |  |  |
| 78 | 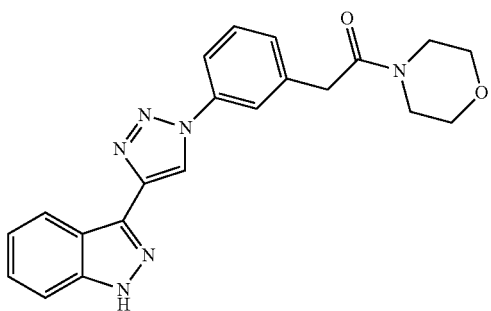 [SMILES: O=C(Cc1cccc(-n2cc(-c3n[nH]c4ccccc34)nn2)c1)N1CCOCC1] | * | nd |
| 79 | 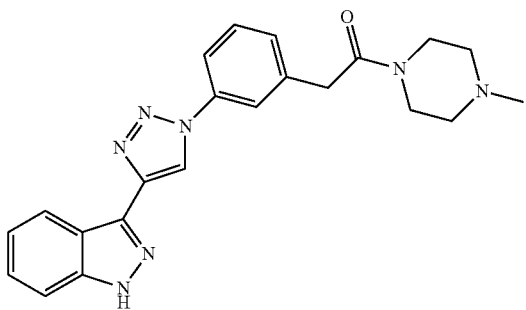 [SMILES: CN1CCN(C(=O)Cc2cccc(-n3cc(-c4n[nH]c5ccccc45)nn3)c2)CC1] | * | * |
| 80 | 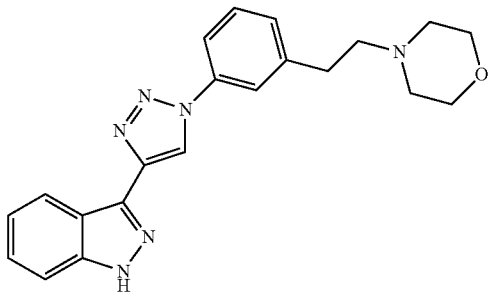 [SMILES: c1cc(CCN2CCOCC2)cc(-n2cc(-c3n[nH]c4ccccc34)nn2)c1] | * | * |
| 81 | 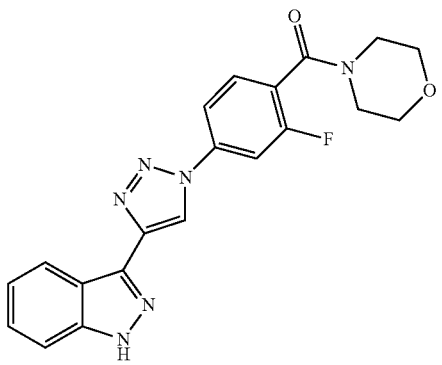 [SMILES: O=C(c1ccc(-n2cc(-c3n[nH]c4ccccc34)nn2)cc1F)N1CCOCC1] |  |  |

-continued
| | | | |
|---|---|---|---|
| 82 | 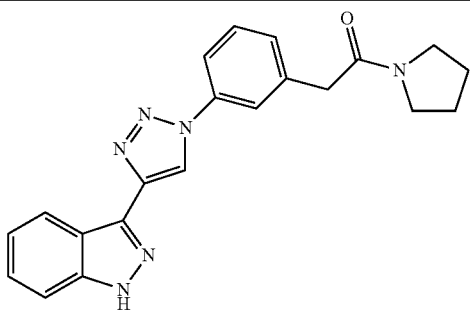 | * | * |
| 83 | 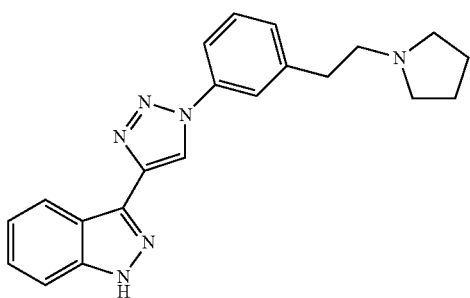 [SMILES: c1cc(CCN2CCCC2)cc(-n2cc(-c3n[nH]c4ccccc34)nn2)c1] | * | ** |
| 84 | 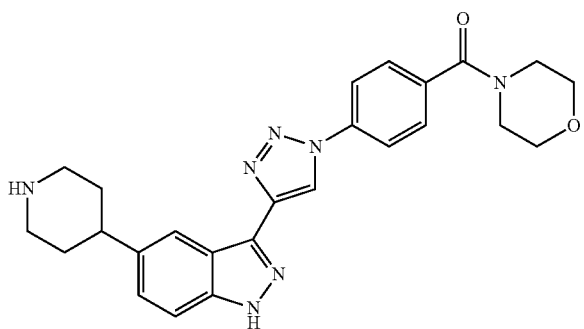 [SMILES: O=C(c1ccc(-n2cc(-c3n[nH]c4ccc(C5CCNCC5)cc34)nn2)cc1)N1CCOCC1] | *** | * |
| 86 | 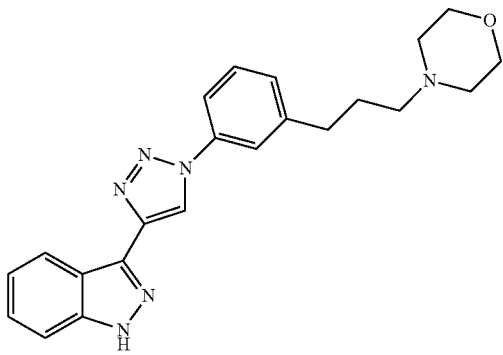 [SMILES: c1cc(CCCN2CCOCC2)cc(-n2cc(-c3n[nH]c4ccccc34)nn2)c1] | * | * |
| 87 | 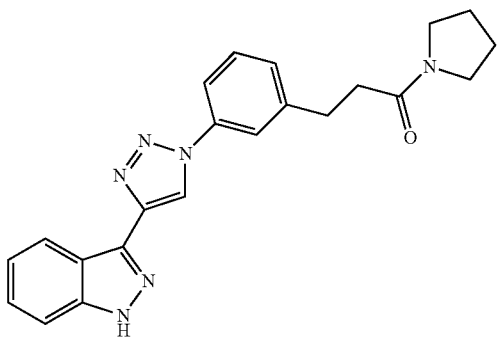 [SMILES: O=C(CCc1cccc(-n2cc(-c3n[nH]c4ccccc34)nn2)c1)N1CCCC1] | * | nd |

| | | | |
|---|---|---|---|
| 88 | 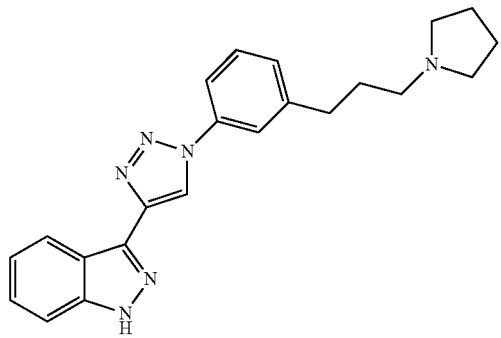 [SMILES: c1cc(CCCN2CCCC2)cc(-n2cc(-c3n[nH]c4ccccc34)nn2)c1] | * | ** |
| 89 | 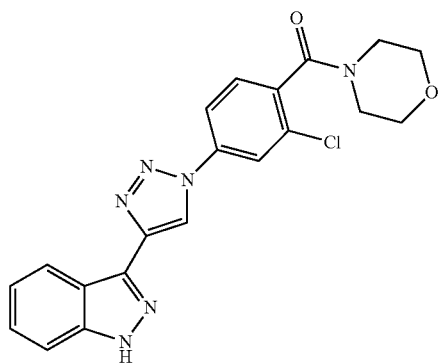 [SMILES: O=C(c1ccc(-n2cc(-c3n[nH]c4ccccc34)nn2)cc1Cl)N1CCOCC1] | ** | * |
| 90 | 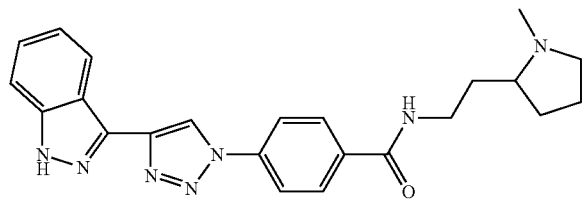 [SMILES: CN1CCCC1CCNC(=O)c1ccc(-n2cc(-c3n[nH]c4ccccc34)nn2)cc1] | ** | nd |
| 91 | 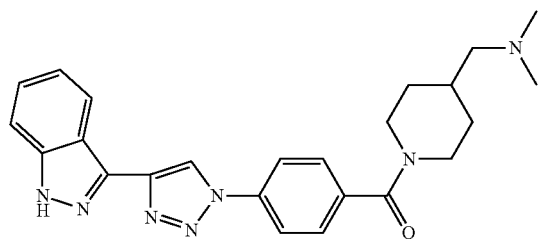 [SMILES: CN(C)CC1CCN(C(=O)c2ccc(-n3cc(-c4n[nH]c5ccccc45)nn3)cc2)CC1] |  |  |
| 92 | 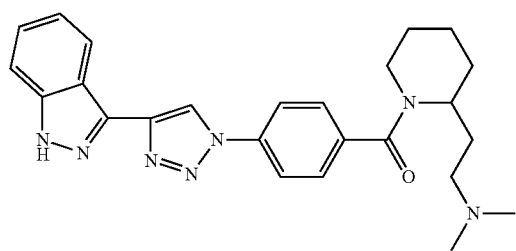 [SMILES: CN(C)CCC1CCCCN1C(=O)c1ccc(-n2cc(-c3n[nH]c4ccccc34)nn2)cc1] |  |  |

| | | | |
|---|---|---|---|
| 93 | 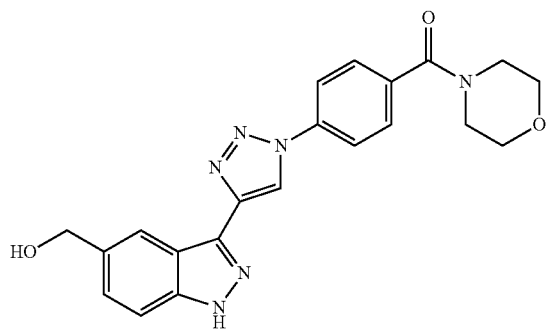 [SMILES: O=C(c1ccc(-n2cc(-c3n[nH]c4ccc(CO)cc34)nn2)cc1)N1CCOCC1] | ** | * |
| 94 | 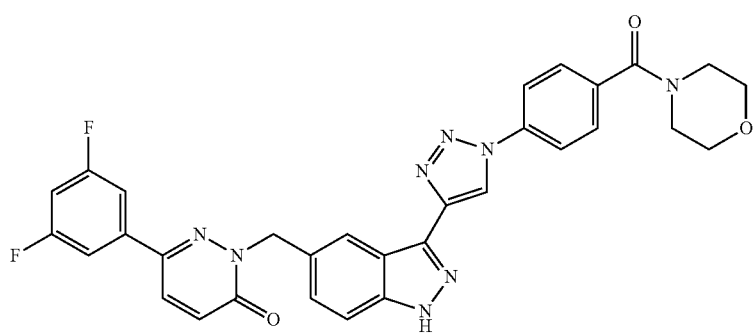 [SMILES: O=C(c1ccc(-n2cc(-c3n[nH]c4ccc(Cn5nc(-c6cc(F)cc(F)c6)ccc5=O)cc34)nn2)cc1)N1CCOCC1] | * |  |
| 95 | 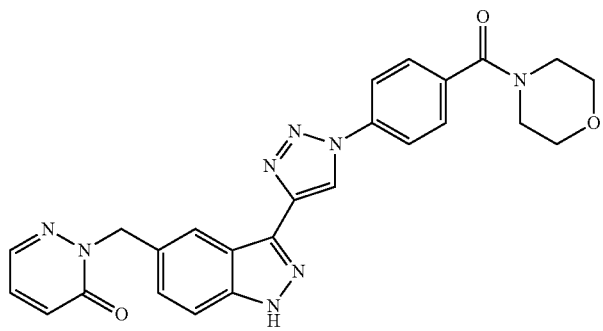 [SMILES: O=C(c1ccc(-n2cc(-c3n[nH]c4ccc(Cn5ncccc5=O)cc34)nn2)cc1)N1CCOCC1] | ** | * |
| 96 | 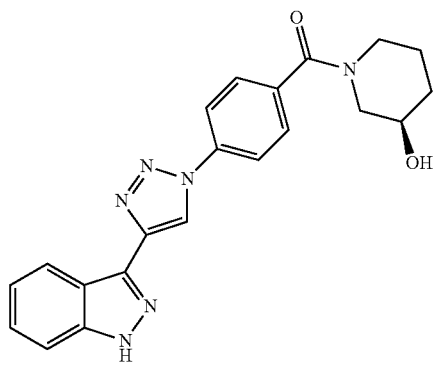 [SMILES: O=C(c1ccc(-n2cc(-c3n[nH]c4ccccc34)nn2)cc1)N1CCC[C@@H](O)C1] |  |  |

-continued
| | | | |
|---|---|---|---|
| 97 | 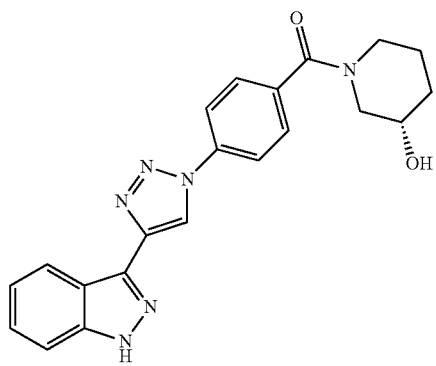 [SMILES: O=C(c1ccc(-n2cc(-c3n[nH]c4ccccc34)nn2)cc1)N1CCC[C@H](O)C1] |  |  |
| 98 | 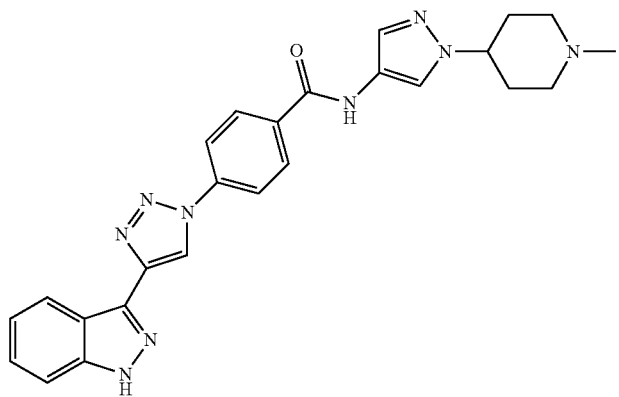 [SMILES: CN1CCC(n2cc(NC(=O)c3ccc(-n4cc(-c5n[nH]c6ccccc56)nn4)cc3)cn2)CC1] | * |  |
| 99 | 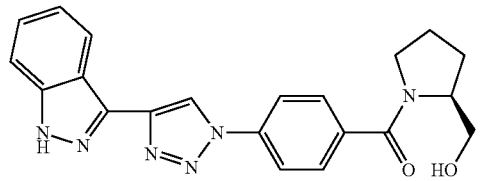 [SMILES: O=C(c1ccc(-n2cc(-c3n[nH]c4ccccc34)nn2)cc1)N1CCC[C@H]1CO] |  |  |
| 100 | 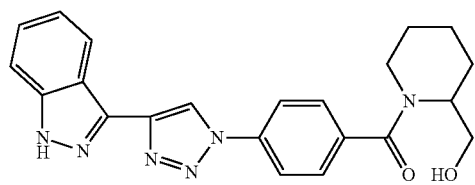 [SMILES: O=C(c1ccc(-n2cc(-c3n[nH]c4ccccc34)nn2)cc1)N1CCCCC1CO] |  |  |
| 101 | 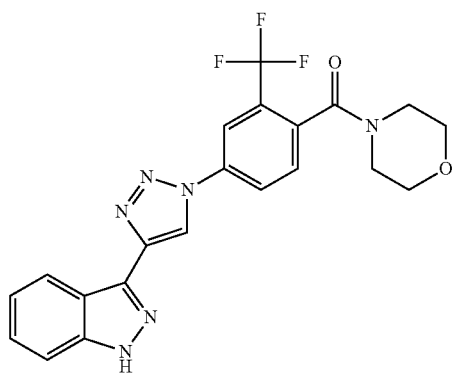 [SMILES: O=C(c1ccc(-n2cc(-c3n[nH]c4ccccc34)nn2)cc1C(F)(F)F)N1CCOCC1] | ** | * |

| | | | |
|---|---|---|---|
| 102 | 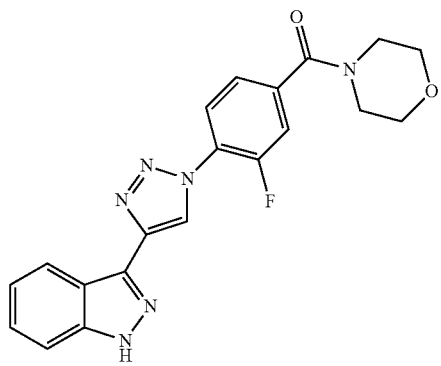 [SMILES: O=C(c1ccc(-n2cc(-c3n[nH]c4ccccc34)nn2)c(F)c1)N1CCOCC1] | * | nd |
| 103 | 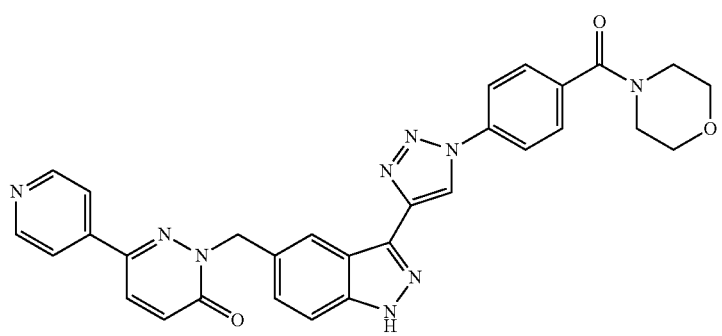 [SMILES: O=C(c1ccc(-n2cc(-c3n[nH]c4ccc(Cn5nc(-c6ccncc6)ccc5=O)cc34)nn2)cc1)N1CCOCC1] | * |  |
| 104 | 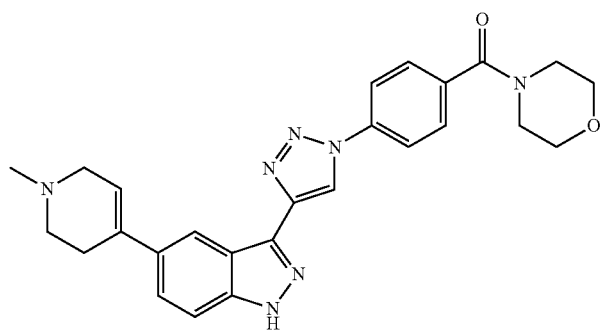 | * |  |
| 105 | 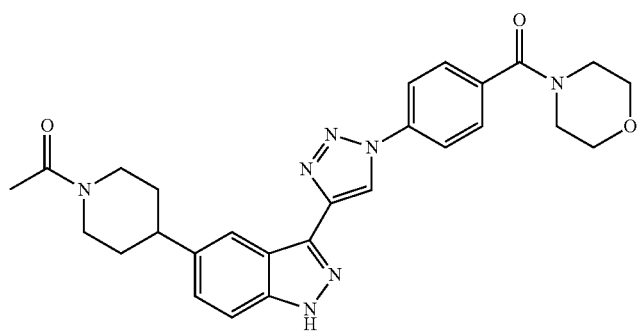 [SMILES: CC(=O)N1CCC(c2ccc3[nH]nc(-c4cn(-c5ccc(C(=O)N6CCOCC6)cc5)nn4)c3c2)CC1] | ** | * |

-continued

| | | | |
|---|---|---|---|
| 106 | | ** | * |
| 107 | | ** | nd |
| 108 | | *** | ** |
| 109 | | ** | ** |
| 110 | | ** | * |

| | | | |
|---|---|---|---|
| 111 | 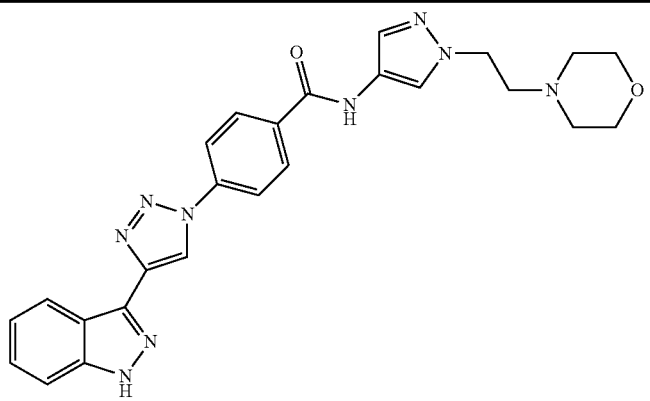 |  |  |
| 112 | 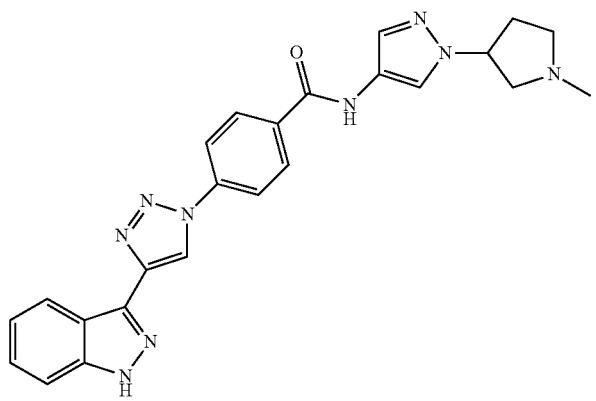 [SMILES: CN1CCC(n2cc(NC(=O)c3ccc(-n4cc(-c5n[nH]c6ccccc56)nn4)cc3)cn2)C1] | * |  |
| 113 | 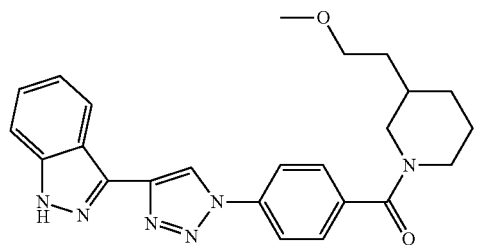 [SMILES: COCCC1CCCN(C(=O)c2ccc(-n3cc(-c4n[nH]c5ccccc45)nn3)cc2)C1] |  |  |
| 114 | 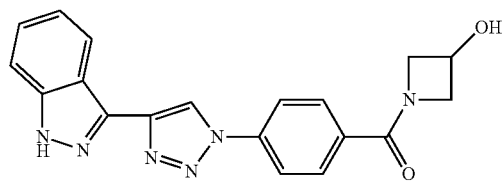 [SMILES: O=C(c1ccc(-n2cc(-c3n[nH]c4ccccc34)nn2)cc1)N1CC(O)C1] |  |  |
| 115 | 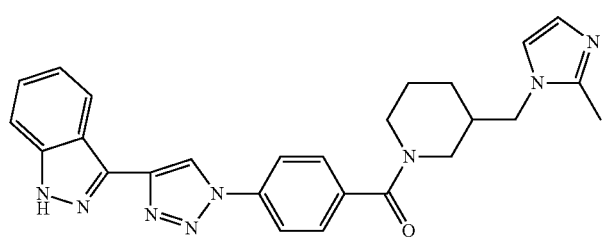 [SMILES: Cc1nccn1CC1CCCN(C(=O)c2ccc(-n3cc(-c4n[nH]c5ccccc45)nn3)cc2)C1] |  |  |

| | | | |
|---|---|---|---|
| 116 | 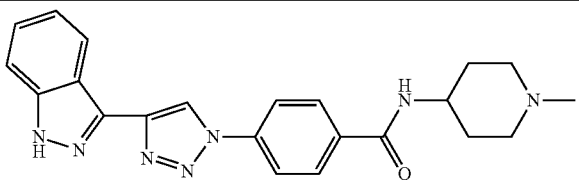 | * | nd |
| 117 | 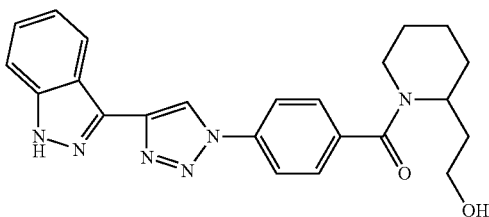 [SMILES: O=C(c1ccc(-n2cc(-c3n[nH]c4ccccc34)nn2)cc1)N1CCCCC1CCO] |  |  |
| 118 | 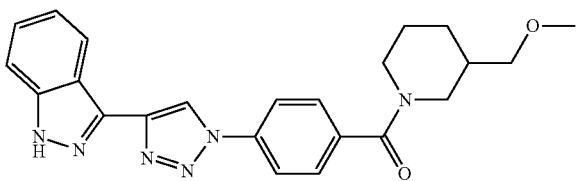 [SMILES: COCC1CCCN(C(=O)c2ccc(-n3cc(-c4n[nH]c5ccccc45)nn3)cc2)C1] |  |  |
| 119 | 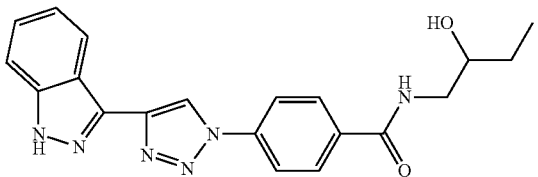 [SMILES: CCC(O)CNC(=O)c1ccc(-n2cc(-c3n[nH]c4ccccc34)nn2)cc1] | ** | nd |
| 120 | 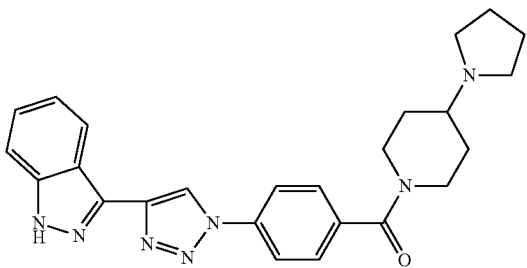 [SMILES: O=C(c1ccc(-n2cc(-c3n[nH]c4ccccc34)nn2)cc1)N1CCC(N2CCCC2)CC1] |  |  |
| 121 | 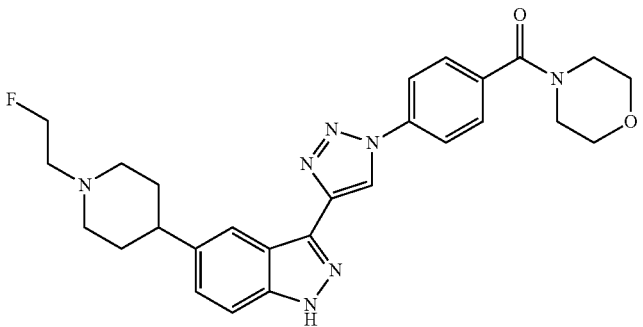 [SMILES: O=C(c1ccc(-n2cc(-c3n[nH]c4ccc(C5CCN(CCF)CC5)cc34)nn2)cc1)N1CCOCC1] | * |  |

-continued
| | | | |
|---|---|---|---|
| 122 | 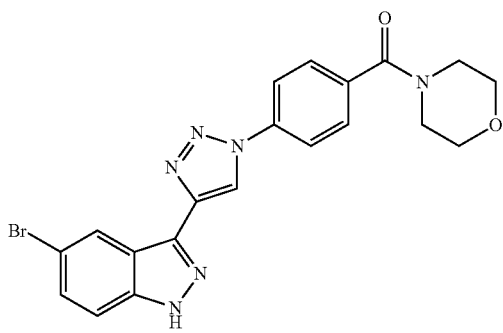 [SMILES: O=C(c1ccc(-n2cc(-c3n[nH]c4ccc(Br)cc34)nn2)cc1)N1CCOCC1] | ** | nd |
| 123 | 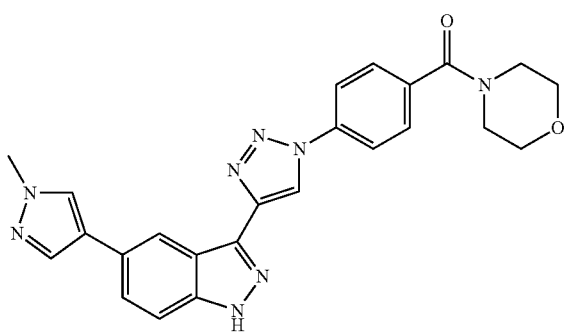 [SMILES: Cn1cc(-c2ccc3[nH]nc(-c4cn(-c5ccc(C(=O)N6CCOCC6)cc5)nn4)c3c2)cn1] | * | * |
| 124 | 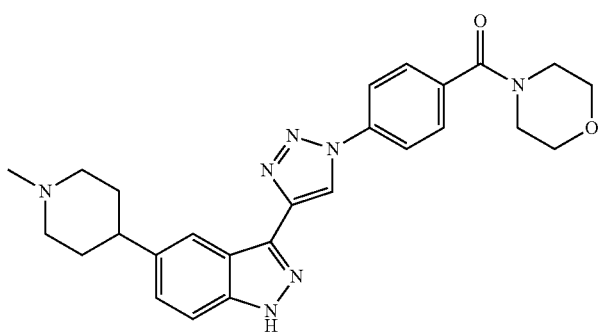 [SMILES: CN1CCC(c2ccc3[nH]nc(-c4cn(-c5ccc(C(=O)N6CCOCC6)cc5)nn4)c3c2)CC1] | * |  |
| 125 | 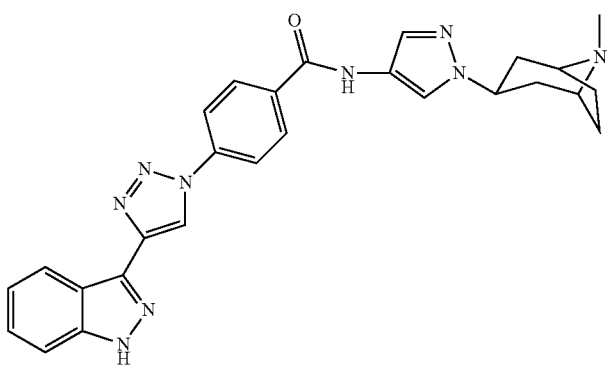 [SMILES: CN1C2CCC1CC(n1cc(NC(=O)c3ccc(-n4cc(-c5n[nH]c6ccccc56)nn4)cc3)cn1)C2] | * |  |
| 126 | 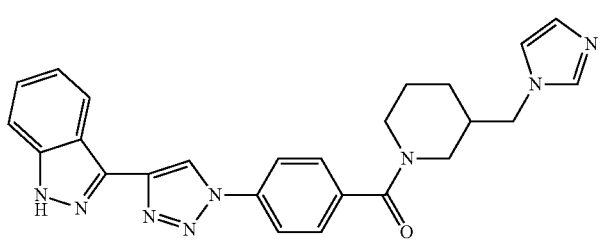 [SMILES: O=C(c1ccc(-n2cc(-c3n[nH]c4ccccc34)nn2)cc1)N1CCCC(Cn2ccnc2)C1] | * |  |

-continued
| Ex | Compounds | | IC50, phosphorylation IRAK 1/4 human |
|---|---|---|---|
| 127 | 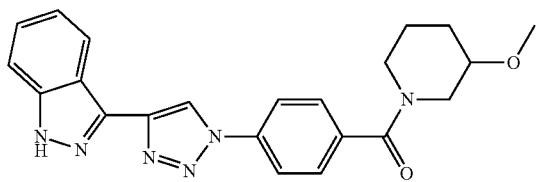 [SMILES: COC1CCCN(C(=O)c2ccc(-n3cc(-c4n[nH]c5ccccc45)nn3)cc2)C1] | * |  |
| 128 | 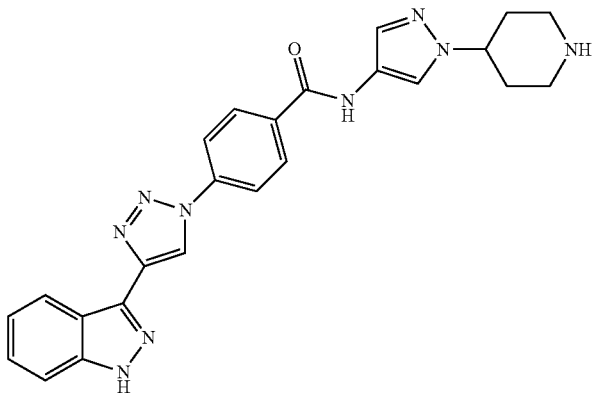 [SMILES: O=C(Nc1cnn(C2CCNCC2)c1)c1ccc(-n2cc(-c3n[nH]c4ccccc34)nn2)cc1] | ** | * |
| 129 | 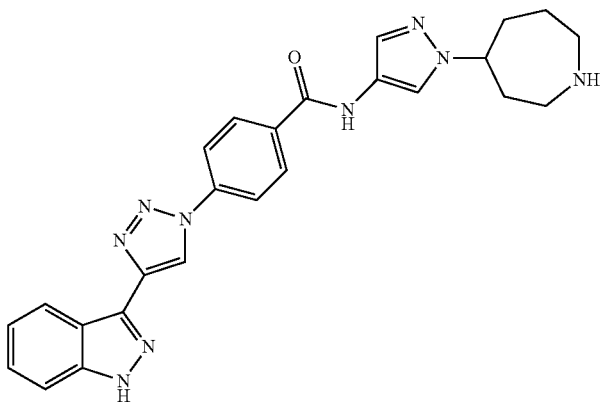 [SMILES: O=C(Nc1cnn(C2CCCNCC2)c1)c1ccc(-n2cc(-c3n[nH]c4ccccc34)nn2)cc1] | ** | * |
| Ex | Compounds | IC50, phosphorylation IRAK 1/4 human |
|---|---|---|
| 131 | | ** |
| 132 | 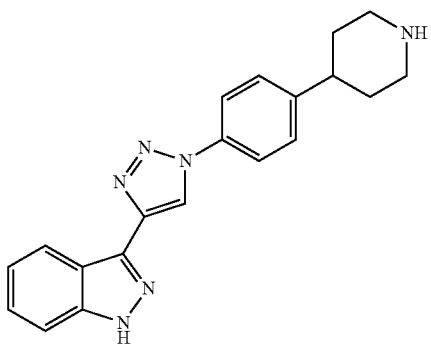 [SMILES: c1ccc2c(-c3cn(-c4ccc(C5CCNCC5)cc4)nn3)n[nH]c2c1] | ** |

| | | |
|---|---|---|
| 133 | 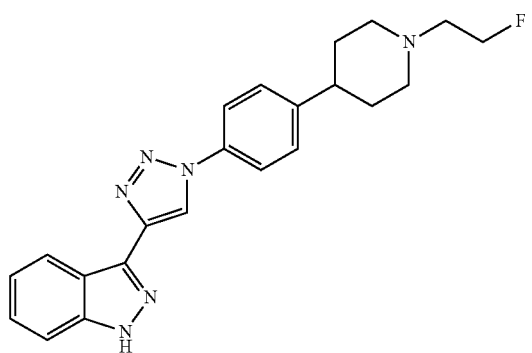 [SMILES: FCCN1CCC(c2ccc(-n3cc(-c4n[nH]c5ccccc45)nn3)cc2)CC1] | ** |
| 134 | 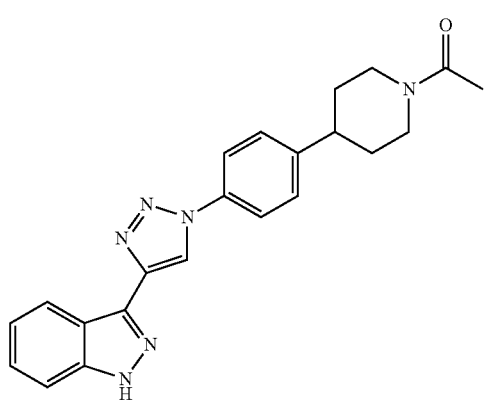 [SMILES: CC(=O)N1CCC(c2ccc(-n3cc(-c4n[nH]c5ccccc45)nn3)cc2)CC1] | ** |
| 135 | 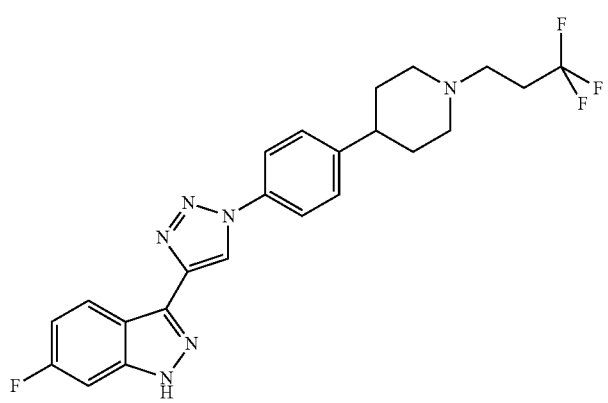 [SMILES: Fc1ccc2c(-c3cn(-c4ccc(C5CCN(CCC(F)(F)F)CC5)cc4)nn3)n[nH]c2c1] | ** |
| 136 | 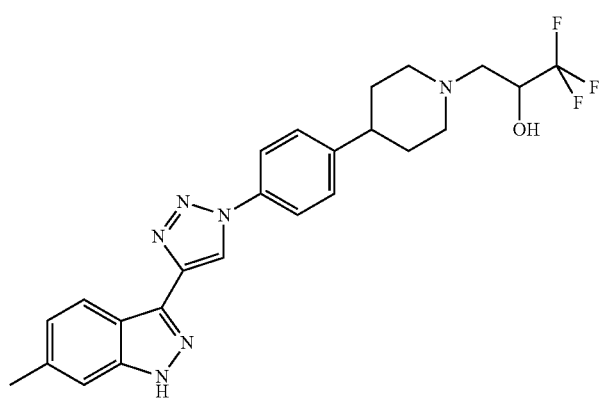 [SMILES: Cc1ccc2c(-c3cn(-c4ccc(C5CCN(CC(O)C(F)(F)F)CC5)cc4)nn3)n[nH]c2c1] | *** |

-continued
| | | |
|---|---|---|
| 137 | 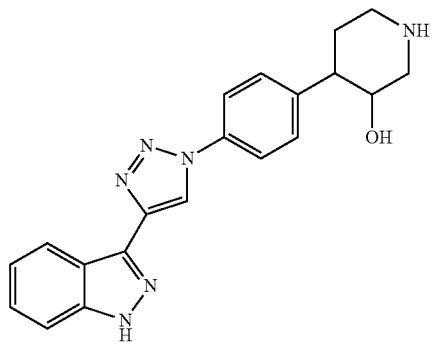 [SMILES: OC1CNCCC1c1ccc(-n2cc(-c3n[nH]c4ccccc34)nn2)cc1] | ** |
| 138 | 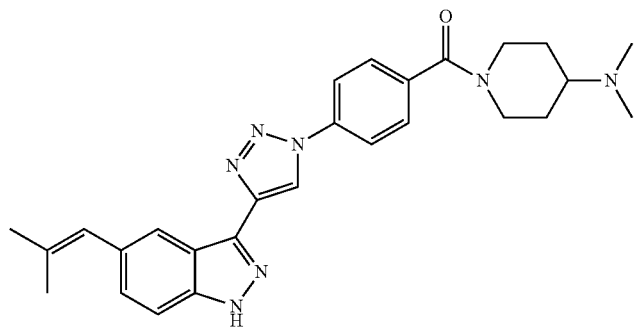 [SMILES: CC(C)=Cc1ccc2[nH]nc(-c3cn(-c4ccc(C(=O)N5CCC(N(C)C)CC5)cc4)nn3)c2c1] | ** |
| 139 | 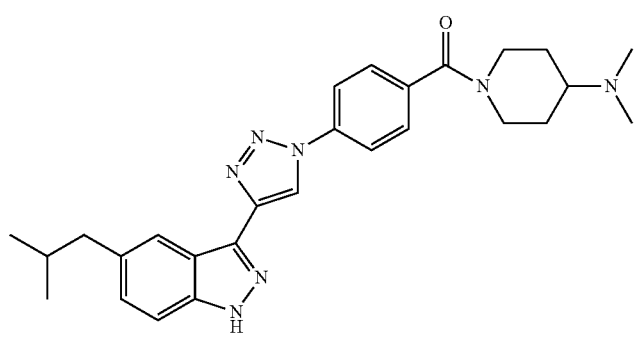 | ** |
| 140 | 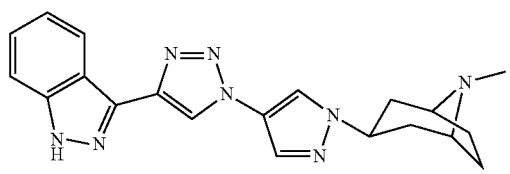 [SMILES: CN1C2CCC1CC(n1cc(-n3cc(-c4n[nH]c5ccccc45)nn3)cn1)C2] | *** |
| 141 | 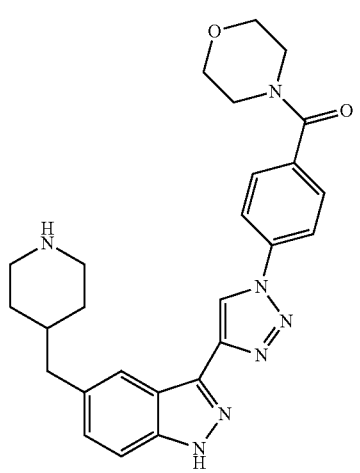 [SMILES: O=C(c1ccc(-n2cc(-c3n[nH]c4ccc(CC5CCNCC5)cc34)nn2)cc1)N1CCOCC1] | *** |

| | | |
|---|---|---|
| 142 | 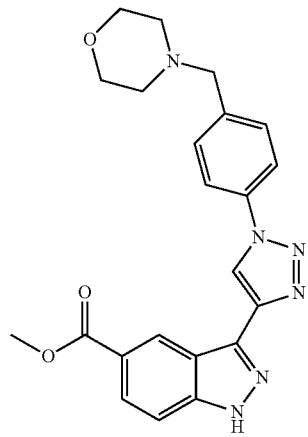 [SMILES: COC(=O)c1ccc2[nH]nc(-c3cn(-c4ccc(CN5CCOCC5)cc4)nn3)c2c1] | ** |
| 143 | 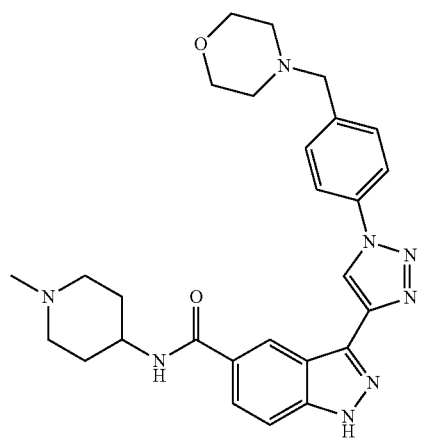 [SMILES: CN1CCC(NC(=O)c2ccc3[nH]nc(-c4cn(-c5ccc(CN6CCOCC6)cc5)nn4)c3c2)CC1] | ** |
| 144 | 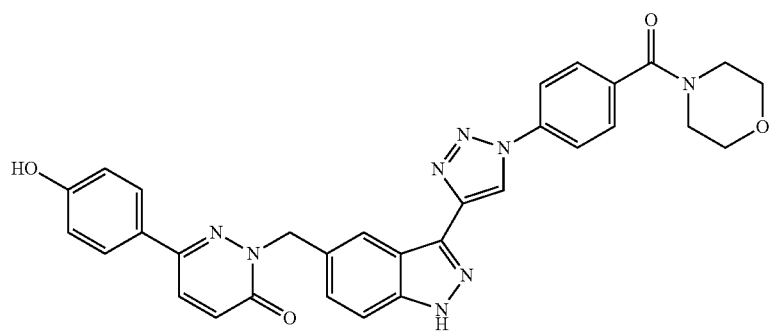 [SMILES: O=C(c1ccc(-n2cc(-c3n[nH]c4ccc(Cn5nc(-c6ccc(O)cc6)ccc5=O)cc34)nn2)cc1)N1CCOCC1] | *** |
| 145 | 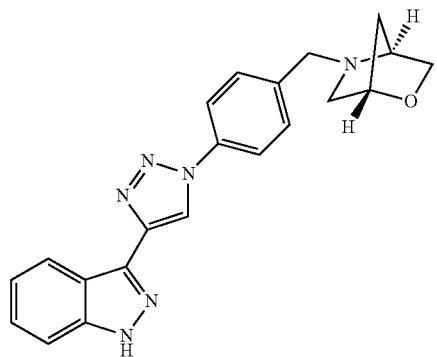 [SMILES: c1ccc2c(-c3cn(-c4ccc(CN5C[C@@H]6C[C@H]5CO6)cc4)nn3)n[nH]c2c1] | ** |

-continued
| | | |
|---|---|---|
| 146 | 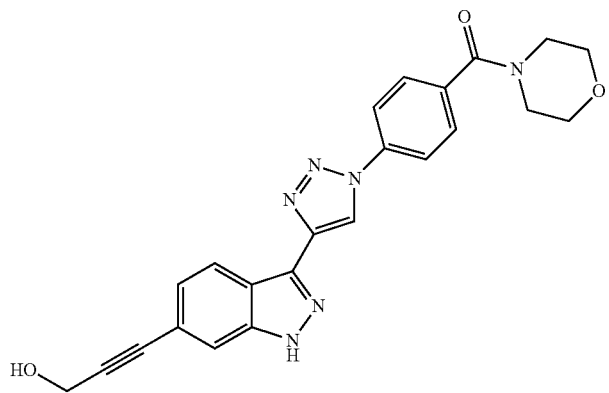 [SMILES: O=C(c1ccc(-n2cc(-c3n[nH]c4cc(C#CCO)ccc34)nn2)cc1)N1CCOCC1] | ** |
| 147 | 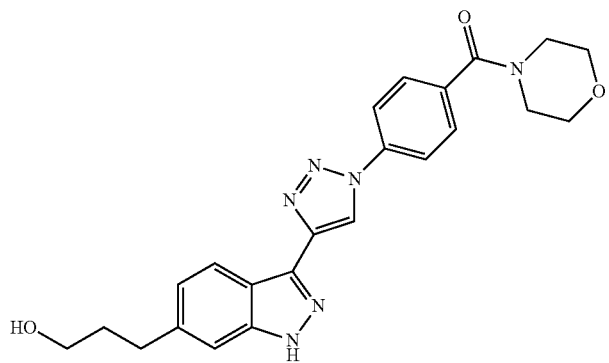 [SMILES: O=C(c1ccc(-n2cc(-c3n[nH]c4cc(CCCO)ccc34)nn2)cc1)N1CCOCC1] | ** |
| 148 | 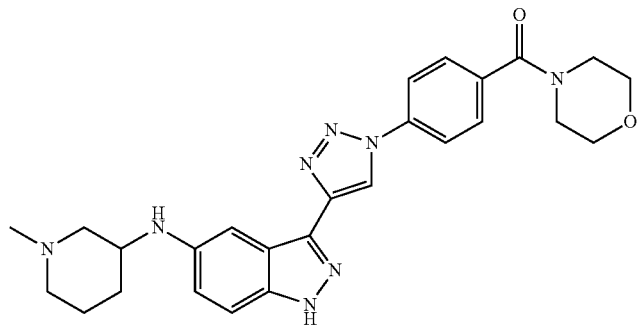 [SMILES: CN1CCCC(Nc2ccc3[nH]nc(-c4cn(-c5ccc(C(=O)N6CCOCC6)cc5)nn4)c3c2)C1] | *** |
| 149 | 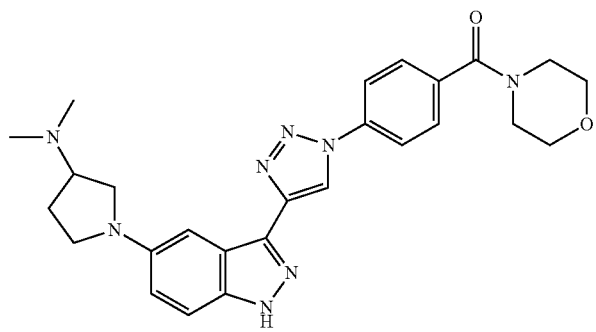 [SMILES: CN(C)C1CCN(c2ccc3[nH]nc(-c4cn(-c5ccc(C(=O)N6CCOCC6)cc5)nn4)c3c2)C1] | *** |

| | |
|---|---|
| 150 | ** 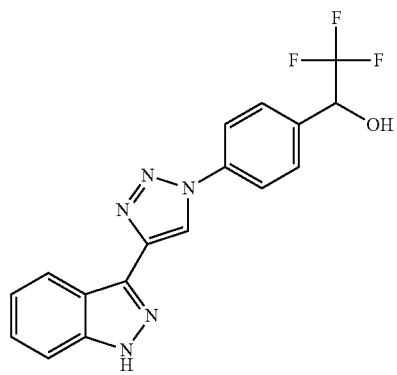 [SMILES: OC(c1ccc(-n2cc(-c3n[nH]c4ccccc34)nn2)cc1)C(F)(F)F] |
| 151 | *** 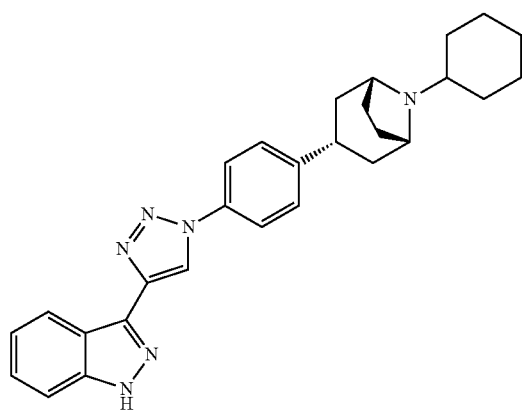 [SMILES: c1ccc2c(-c3cn(-c4ccc([C@@H]5C[C@H]6CC[C@@H](C5)N6C5CCCCC5)cc4)nn3)n[nH]c2c1] |
| 152 | ** 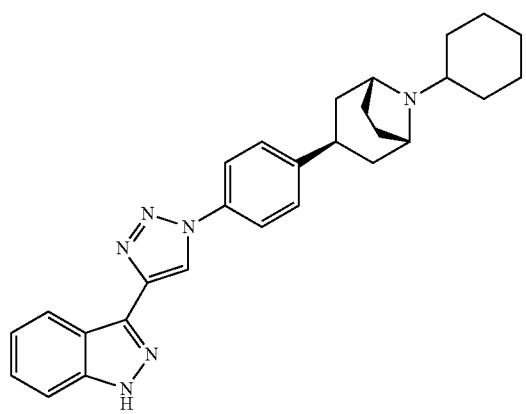 [SMILES: c1ccc2c(-c3cn(-c4ccc([C@H]5C[C@H]6CC[C@@H](C5)N6C5CCCCC5)cc4)nn3)n[nH]c2c1] |
| 153 | ** 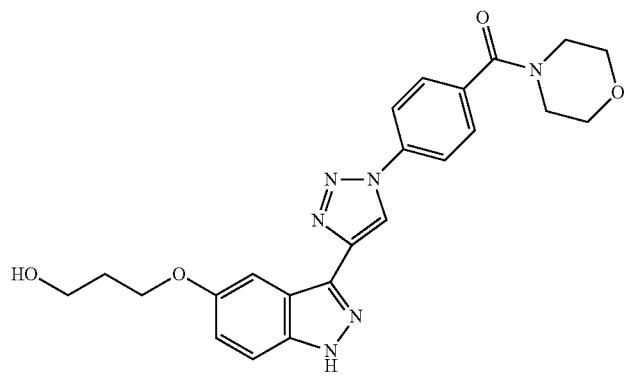 [SMILES: O=C(c1ccc(-n2cc(-c3n[nH]c4ccc(OCCCO)cc34)nn2)cc1)N1CCOCC1] |

| | |
|---|---|
| 154 | ** |
| 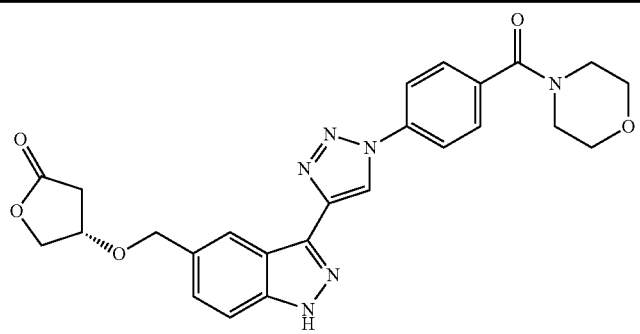 | |
| 155 | ** |
| 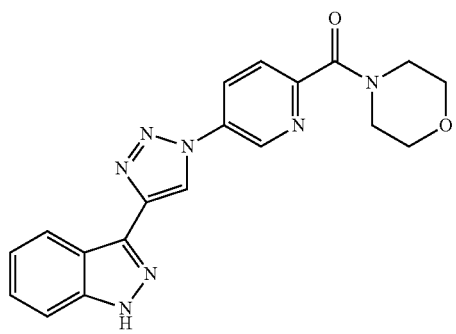 [SMILES: O=C(c1ccc(-n2cc(-c3n[nH]c4ccccc34)nn2)cn1)N1CCOCC1] | |
| 156 | ** |
| 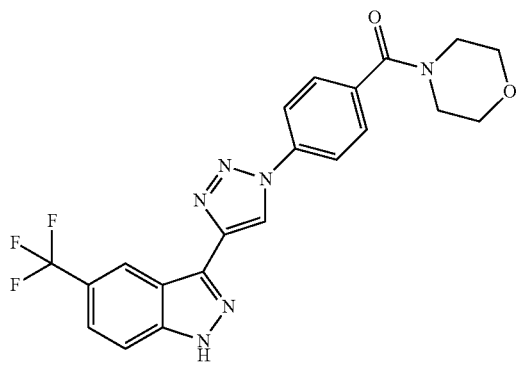 [SMILES: O=C(c1ccc(-n2cc(-c3n[nH]c4ccc(C(F)(F)F)cc34)nn2)cc1)N1CCOCC1] | |
| 157 | ** |
| 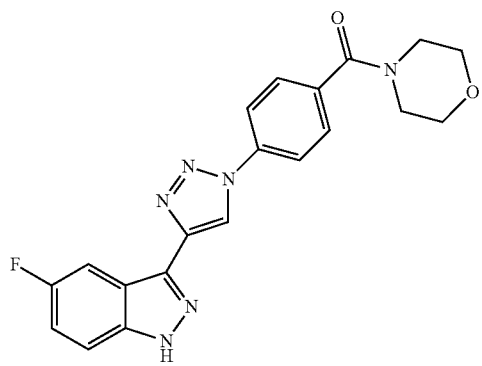 [SMILES: O=C(c1ccc(-n2cc(-c3n[nH]c4ccc(F)cc34)nn2)cc1)N1CCOCC1] | |

-continued
| | | |
|---|---|---|
| 158 | 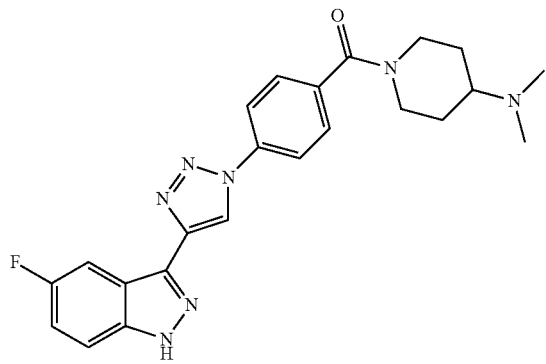 [SMILES: CN(C)C1CCN(C(=O)c2ccc(-n3cc(-c4n[nH]c5ccc(F)cc45)nn3)cc2)CC1] | ** |
| 159 | 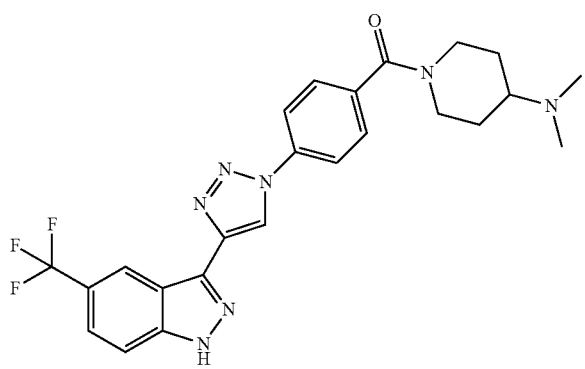 [SMILES: CN(C)C1CCN(C(=O)c2ccc(-n3cc(-c4n[nH]c5ccc(C(F)(F)F)cc45)nn3)cc2)CC1] | ** |
| 160 | 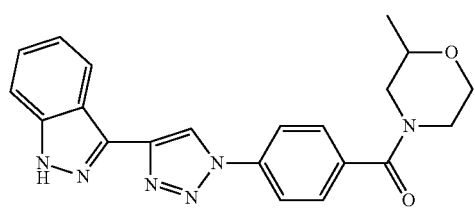 [SMILES: CC1CN(C(=O)c2ccc(-n3cc(-c4n[nH]c5ccccc45)nn3)cc2)CCO1] | ** |
| 161 | 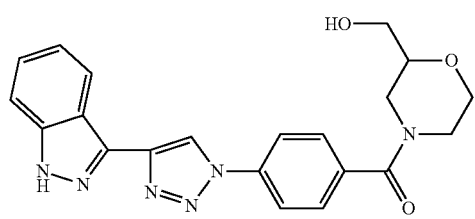 [SMILES: O=C(c1ccc(-n2cc(-c3n[nH]c4ccccc34)nn2)cc1)N1CCOC(CO)C1] | ** |
| 162 | 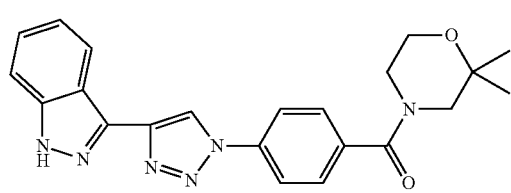 [SMILES: CC1(C)CN(C(=O)c2ccc(-n3cc(-c4n[nH]c5ccccc45)nn3)cc2)CCO1] | ** |
| 163 | 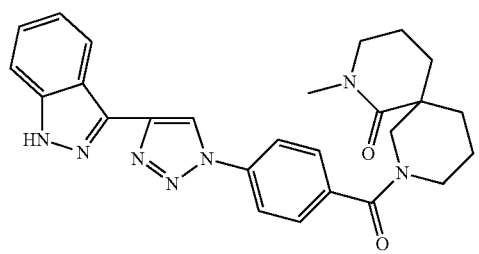 [SMILES: CN1CCCC2(CCCN(C(=O)c3ccc(-n4cc(-c5n[nH]c6ccccc56)nn4)cc3)C2)C1=O] | ** |

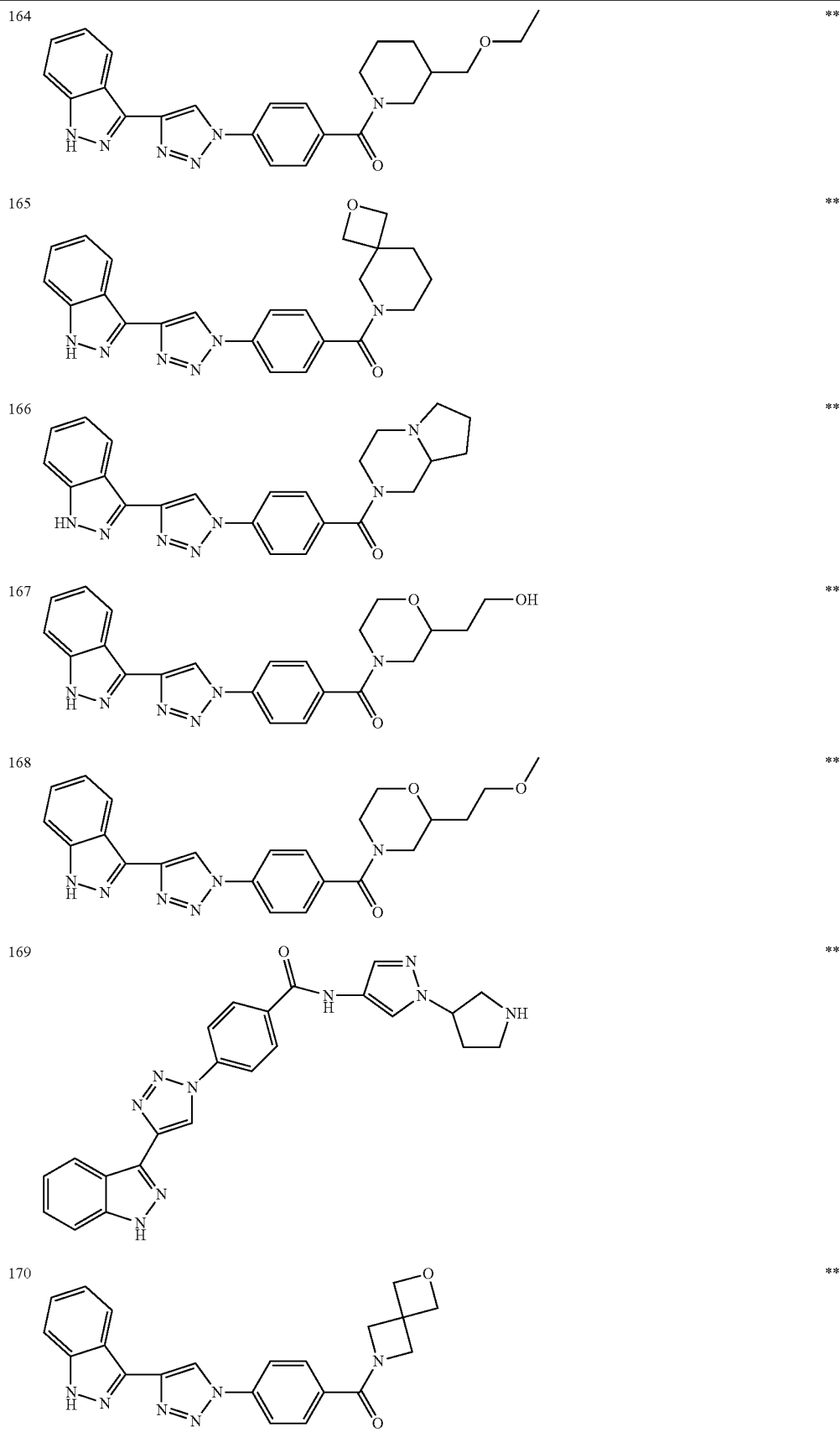

| | | |
|---|---|---|
| 171 | 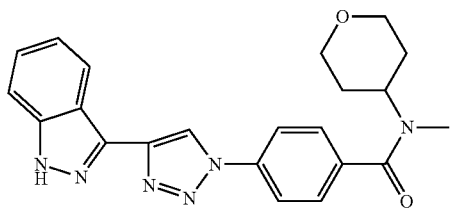 [SMILES: CN(C(=O)c1ccc(-n2cc(-c3n[nH]c4ccccc34)nn2)cc1)C1CCOCC1] | ** |
| 172 | 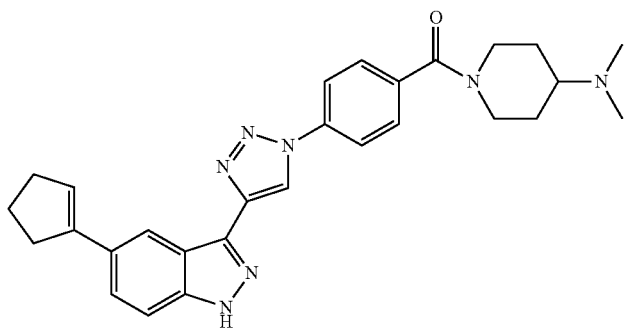 | ** |
| 173 | 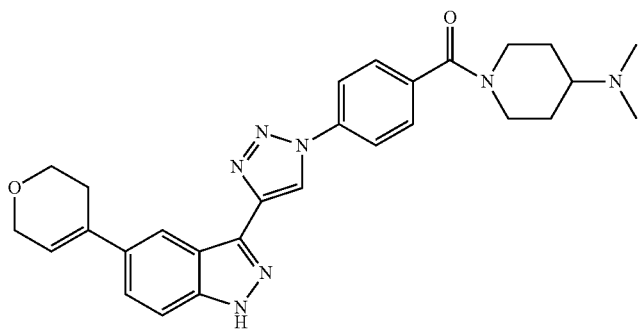 [SMILES: CN(C)C1CCN(C(=O)c2ccc(-n3cc(-c4n[nH]c5ccc(C6=CCOCC6)cc45)nn3)cc2)CC1] | ** |
| 174 | 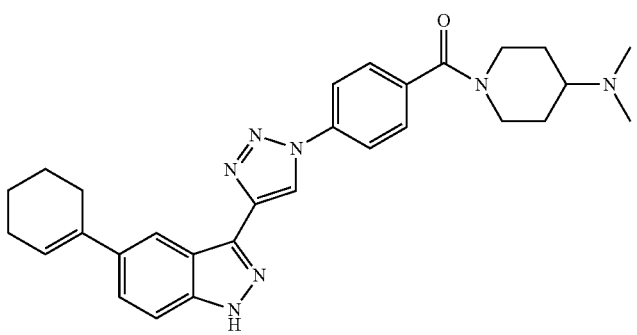 [SMILES: CN(C)C1CCN(C(=O)c2ccc(-n3cc(-c4n[nH]c5ccc(C6=CCCCC6)cc45)nn3)cc2)CC1] | ** |
| 175 | 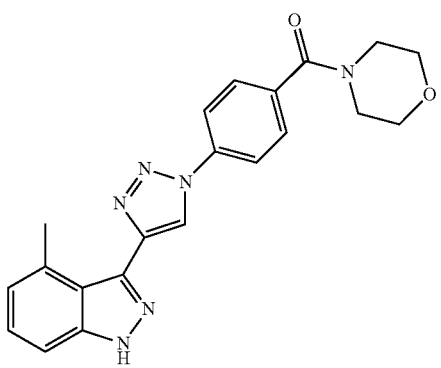 [SMILES: Cc1cccc2[nH]nc(-c3cn(-c4ccc(C(=O)N5CCOCC5)cc4)nn3)c12] | * |

| | | |
|---|---|---|
| 176 | 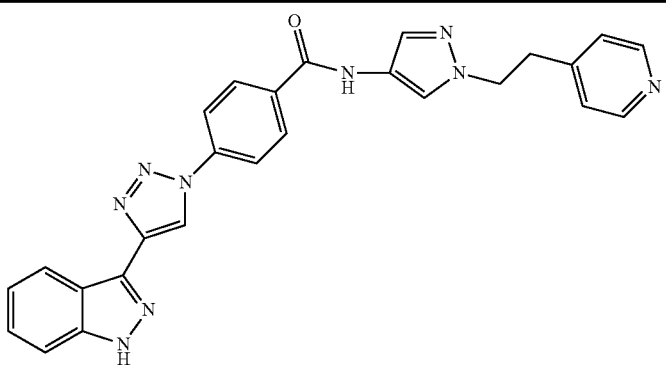 | ** |
| 177 | 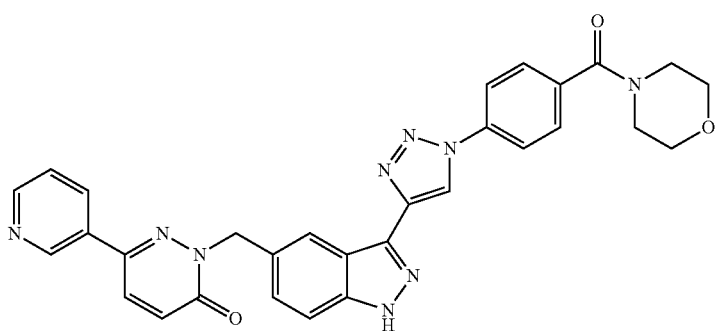 [SMILES: O=C(c1ccc(-n2cc(-c3n[nH]c4ccc(Cn5nc(-c6cccnc6)ccc5=O)cc34)nn2)cc1)N1CCOCC1] | *** |
| 178 | 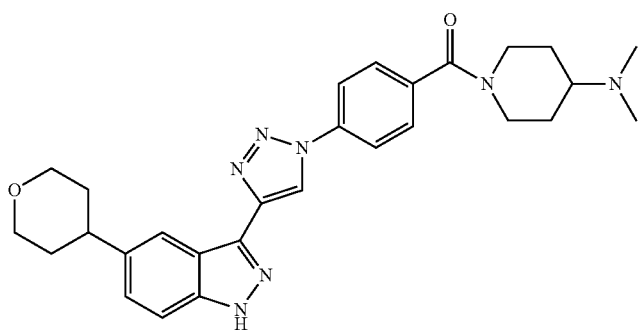 [SMILES: CN(C)C1CCN(C(=O)c2ccc(-n3cc(-c4n[nH]c5ccc(C6CCOCC6)cc45)nn3)cc2)CC1] | ** |
| 179 | 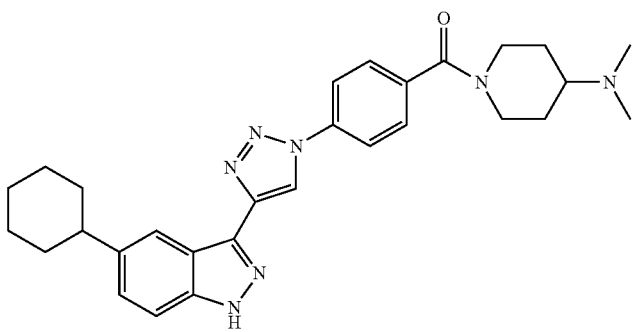 [SMILES: CN(C)C1CCN(C(=O)c2ccc(-n3cc(-c4n[nH]c5ccc(C6CCCCC6)cc45)nn3)cc2)CC1] | ** |
| 180 | 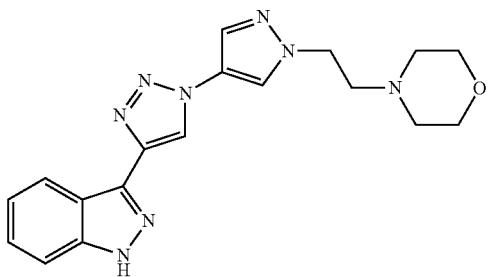 [SMILES: c1ccc2c(-c3cn(-c4cnn(CCN5CCOCC5)c4)nn3)n[nH]c2c1] | ** |

| | |
|---|---|
| 181 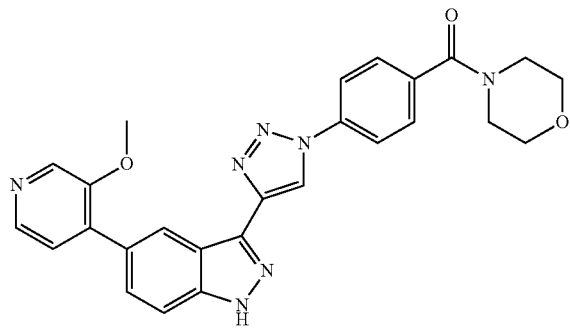 [SMILES: COc1cnccc1-c1ccc2[nH]nc(-c3cn(-c4ccc(C(=O)N5CCOCC5)cc4)nn3)c2c1] | ** |
| 182 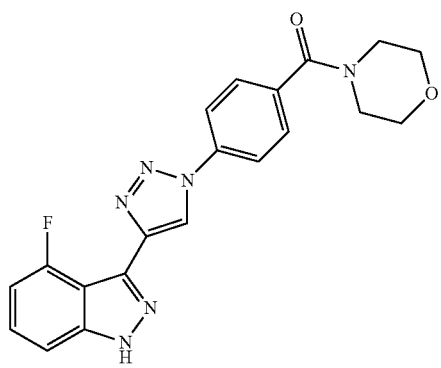 | * |
| 183 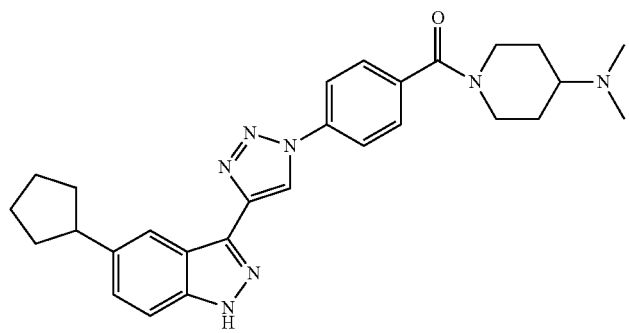 | ** |
| 184 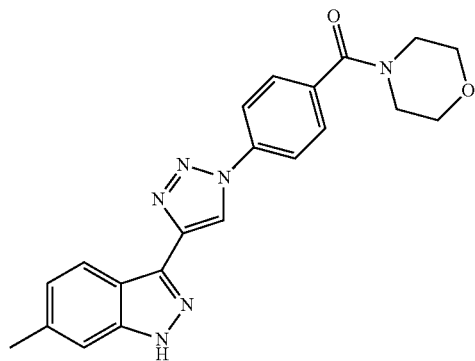 [SMILES: Cc1ccc2c(-c3cn(-c4ccc(C(=O)N5CCOCC5)cc4)nn3)n[nH]c2c1] | *** |

| | | |
|---|---|---|
| 185 | 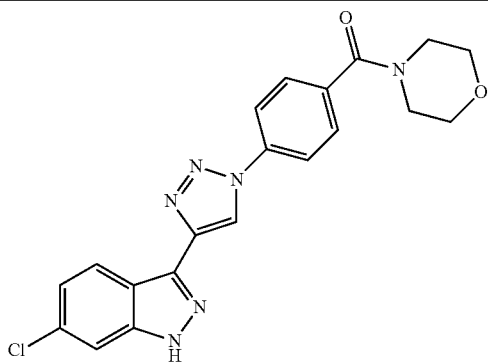 | ** |
| 186 | 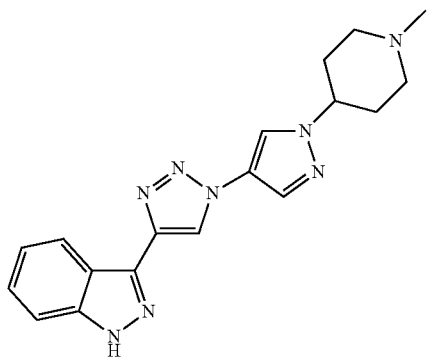 [SMILES: CN1CCC(n2cc(-n3cc(-c4n[nH]c5ccccc45)nn3)cn2)CC1] | *** |
| 187 | 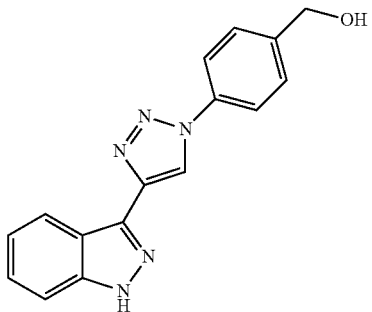 [SMILES: OCc1ccc(-n2cc(-c3n[nH]c4ccccc34)nn2)cc1] | ** |
| 188 | 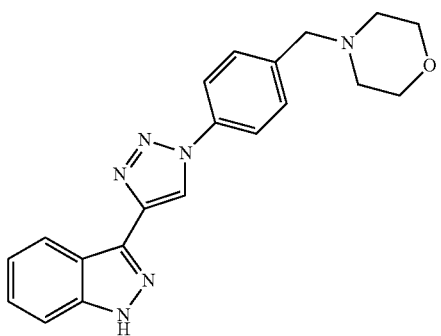 [SMILES: c1ccc2c(-c3cn(-c4ccc(CN5CCOCC5)cc4)nn3)n[nH]c2c1] | ** |

189 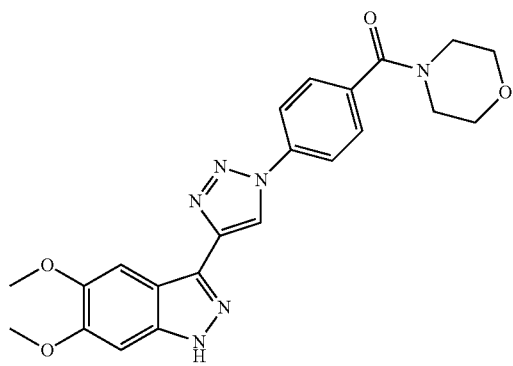 [SMILES: COc1cc2[nH]nc(-c3cn(-c4ccc(C(=O)N5CCOCC5)cc4)nn3)c2cc1OC] **
190 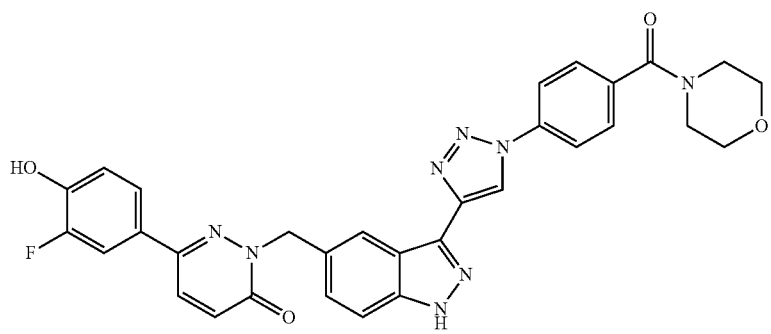 [SMILES: O=C(c1ccc(-n2cc(-c3n[nH]c4ccc(Cn5nc(-c6ccc(O)c(F)c6)ccc5=O)cc34)nn2)cc1)N1CCOCC1] ***
191 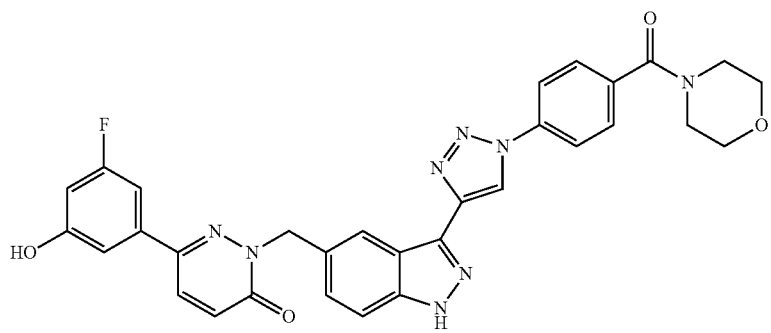 [SMILES: O=C(c1ccc(-n2cc(-c3n[nH]c4ccc(Cn5nc(-c6cc(O)cc(F)c6)ccc5=O)cc34)nn2)cc1)N1CCOCC1] **
192 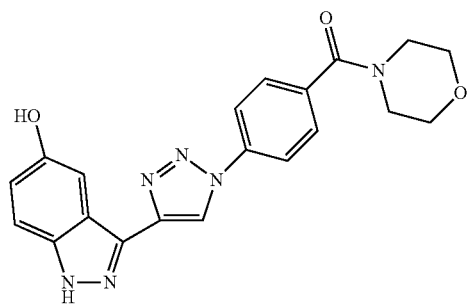 [SMILES: O=C(c1ccc(-n2cc(-c3n[nH]c4ccc(O)cc34)nn2)cc1)N1CCOCC1] ***

| | | |
|---|---|---|
| 193 | 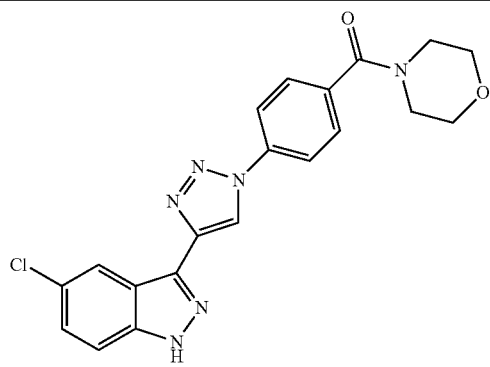 | ** |
| 194 | 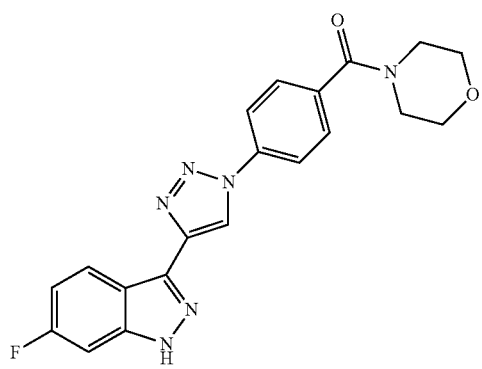 [SMILES: O=C(c1ccc(-n2cc(-c3n[nH]c4cc(F)ccc34)nn2)cc1)N1CCOCC1] | ** |
| 195 | 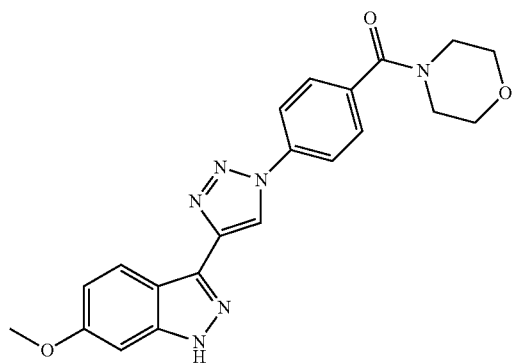 [SMILES: COc1ccc2c(-c3cn(-c4ccc(C(=O)N5CCOCC5)cc4)nn3)n[nH]c2c1] | ** |
| 196 | 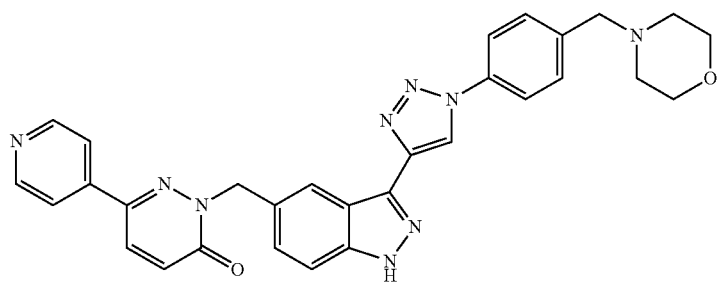 | *** |

| | | |
|---|---|---|
| 197 | 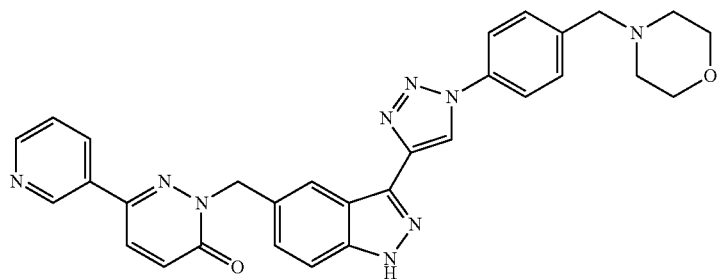 | *** |
| 198 | 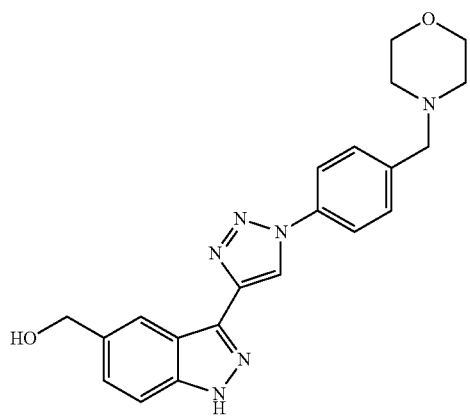 [SMILES: OCc1ccc2[nH]nc(-c3cn(-c4ccc(CN5CCOCC5)cc4)nn3)c2c1] | ** |
| 199 | 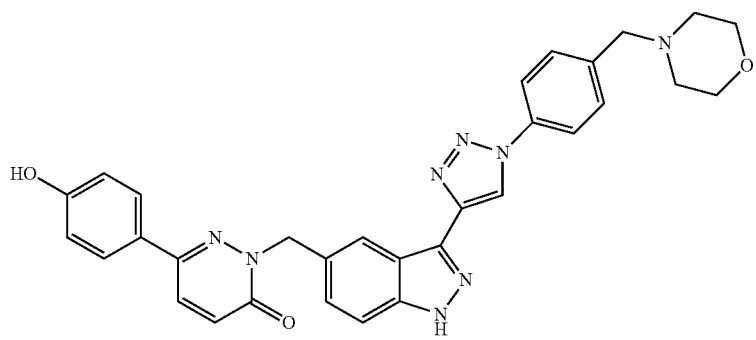 [SMILES: O=c1ccc(-c2ccc(O)cc2)nn1Cc1ccc2[nH]nc(-c3cn(-c4ccc(CN5CCOCC5)cc4)nn3)c2c1] | ** |
| 200 | 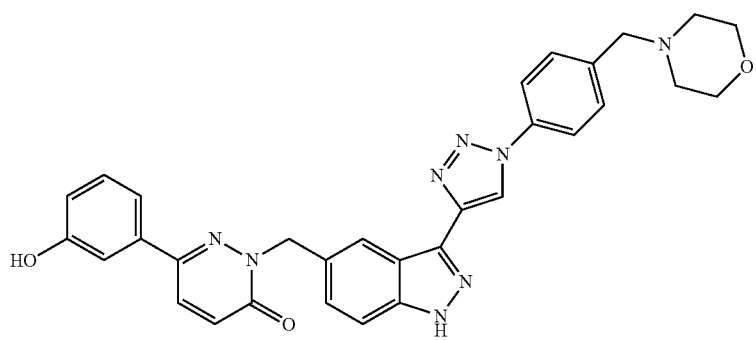 [SMILES: O=c1ccc(-c2cccc(O)c2)nn1Cc1ccc2[nH]nc(-c3cn(-c4ccc(CN5CCOCC5)cc4)nn3)c2c1] | *** |

| 201 | 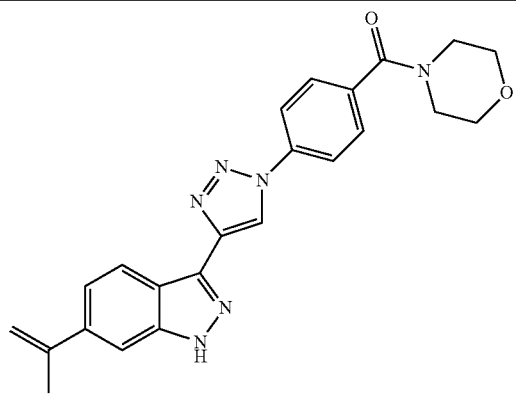 | ** |
| 202 | 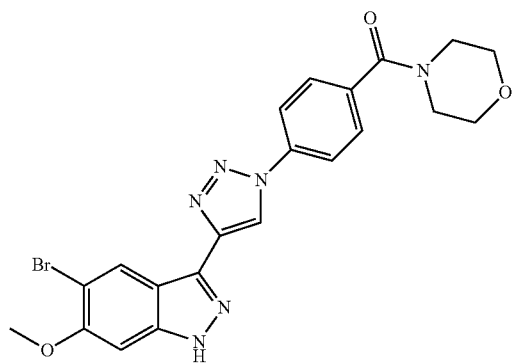 [SMILES: COc1cc2[nH]nc(-c3cn(-c4ccc(C(=O)N5CCOCC5)cc4)nn3)c2cc1Br] | * |
| 203 | 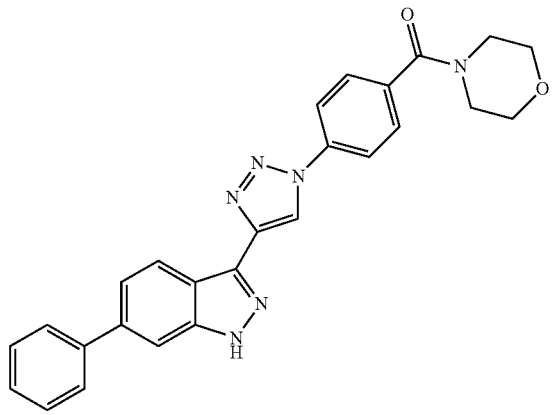 [SMILES: O=C(c1ccc(-n2cc(-c3n[nH]c4cc(-c5ccccc5)ccc34)nn2)cc1)N1CCOCC1] | * |
| 204 | 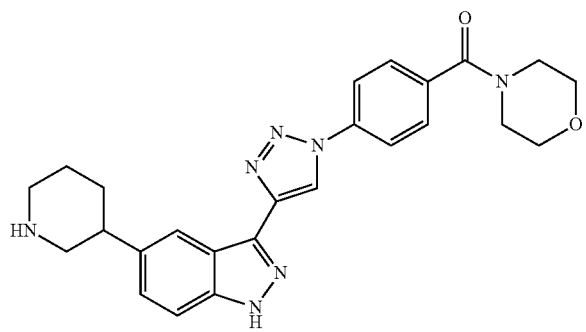 [SMILES: O=C(c1ccc(-n2cc(-c3n[nH]c4ccc(C5CCCNC5)cc34)nn2)cc1)N1CCOCC1] | *** |

| | | |
|---|---|---|
| 205 | 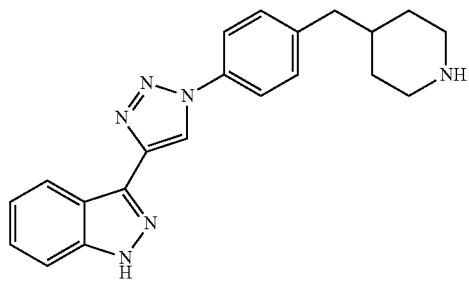 [SMILES: c1ccc2c(-c3cn(-c4ccc(CC5CCNCC5)cc4)nn3)n[nH]c2c1] | ** |
| 206 | 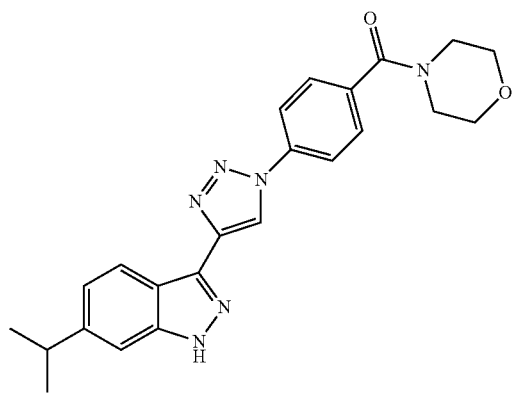 [SMILES: CC(C)c1ccc2c(-c3cn(-c4ccc(C(=O)N5CCOCC5)cc4)nn3)n[nH]c2c1] | ** |
| 207 | 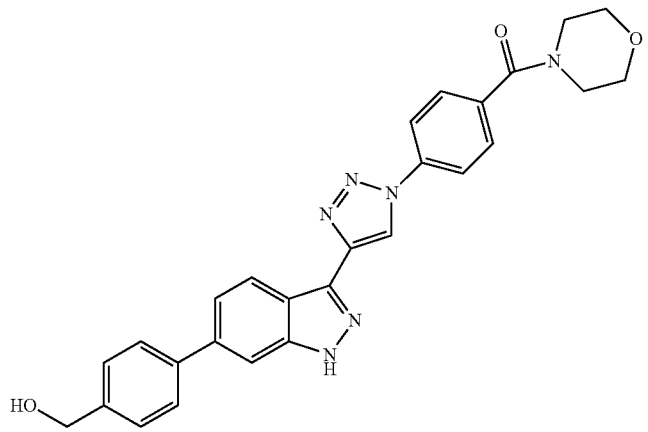 [SMILES: O=C(c1ccc(-n2cc(-c3n[nH]c4cc(-c5ccc(CO)cc5)ccc34)nn2)cc1)N1CCOCC1] | * |
| 208 | 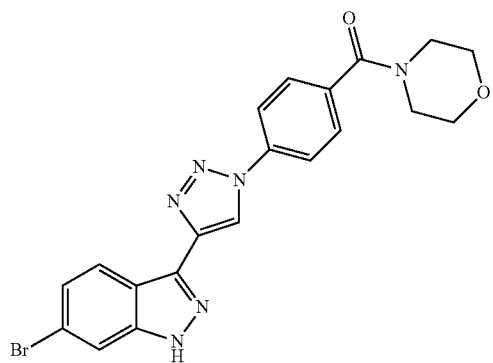 | ** |

| | | |
|---|---|---|
| 209 | 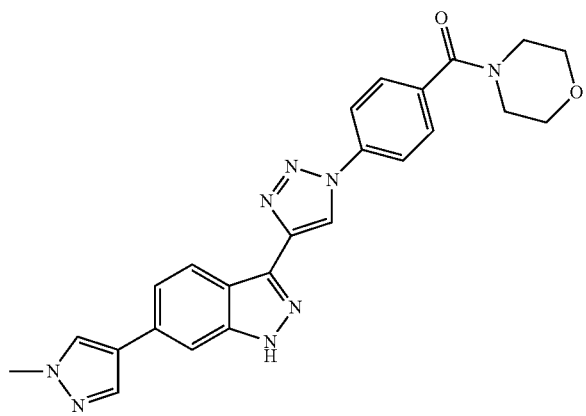 [SMILES: Cn1cc(-c2ccc3c(-c4cn(-c5ccc(C(=O)N6CCOCC6)cc5)nn4)n[nH]c3c2)cn1] | * |
| 210 | 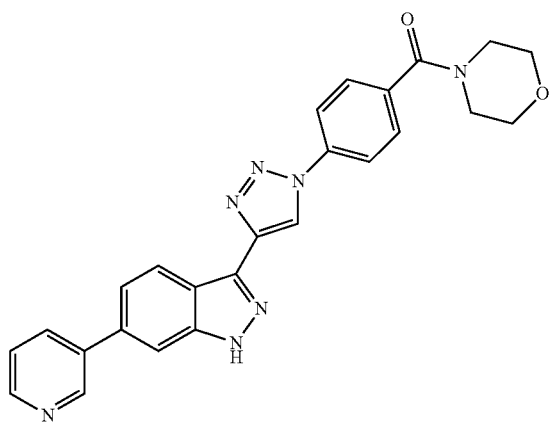 [SMILES: O=C(c1ccc(-n2cc(-c3n[nH]c4cc(-c5cccnc5)ccc34)nn2)cc1)N1CCOCC1] | ** |
| 211 | 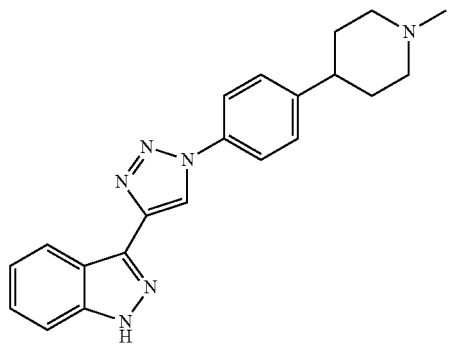 [SMILES: CN1CCC(c2ccc(-n3cc(-c4n[nH]c5ccccc45)nn3)cc2)CC1] | ** |
| 212 | 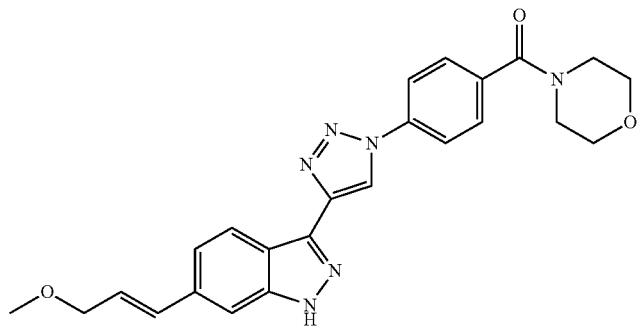 [SMILES: COC/C=C/c1ccc2c(-c3cn(-c4ccc(C(=O)N5CCOCC5)cc4)nn3)n[nH]c2c1] | ** |

| | | |
|---|---|---|
| 213 | 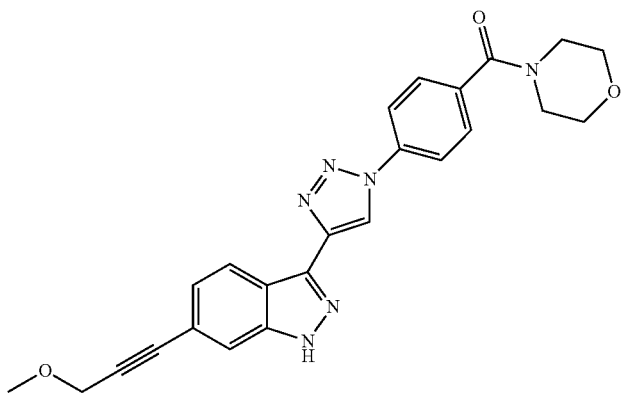 [SMILES: COCC#Cc1ccc2c(-c3cn(-c4ccc(C(=O)N5CCOCC5)cc4)nn3)n[nH]c2c1] | * |
| 214 | 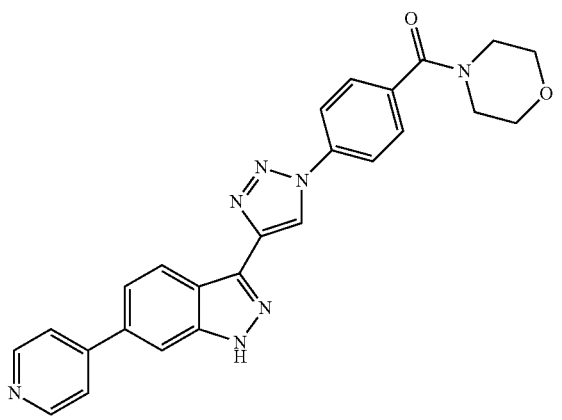 [SMILES: O=C(c1ccc(-n2cc(-c3n[nH]c4cc(-c5ccncc5)ccc34)nn2)cc1)N1CCOCC1] | ** |
| 215 | 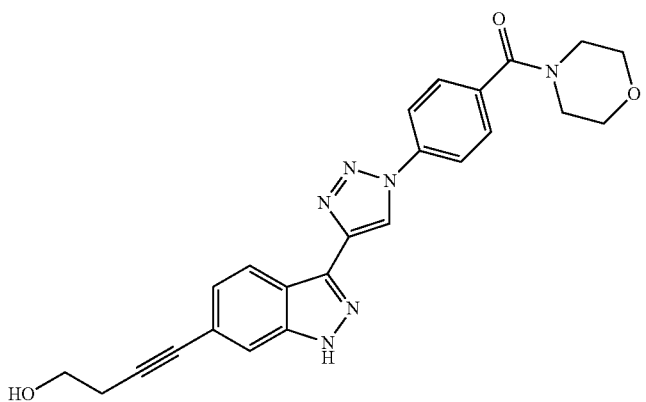 [SMILES: O=C(c1ccc(-n2cc(-c3n[nH]c4cc(C#CCCO)ccc34)nn2)cc1)N1CCOCC1] | * |
| 216 | 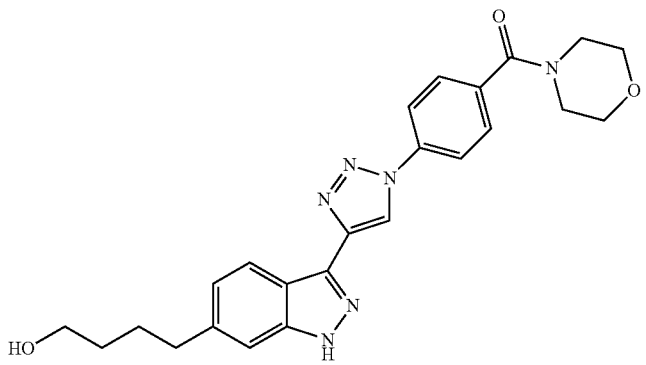 [SMILES: O=C(c1ccc(-n2cc(-c3n[nH]c4cc(CCCCO)ccc34)nn2)cc1)N1CCOCC1] | ** |

| | | |
|---|---|---|
| 217 | 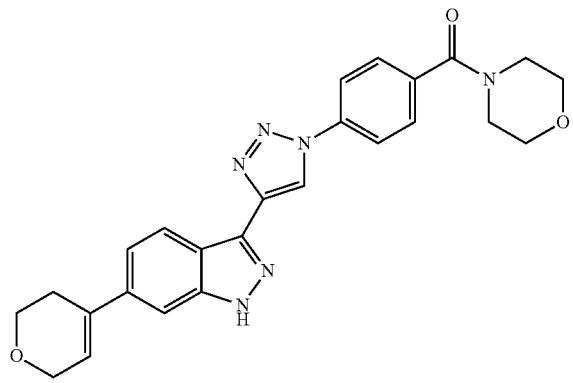 [SMILES: O=C(c1ccc(-n2cc(-c3n[nH]c4cc(C5=CCOCC5)ccc34)nn2)cc1)N1CCOCC1] | ** |
| 218 | 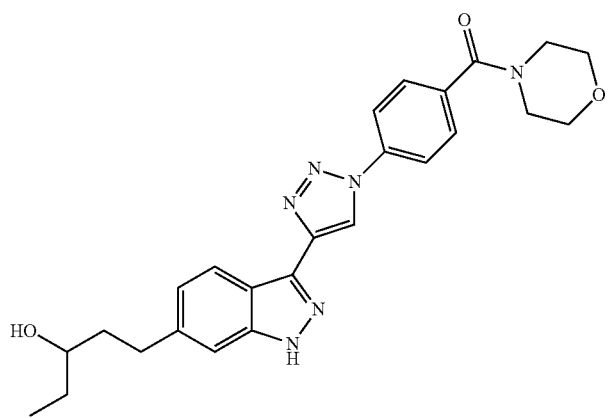 [SMILES: CCC(O)CCc1ccc2c(-c3cn(-c4ccc(C(=O)N5CCOCC5)cc4)nn3)n[nH]c2c1] | * |
| 219 | 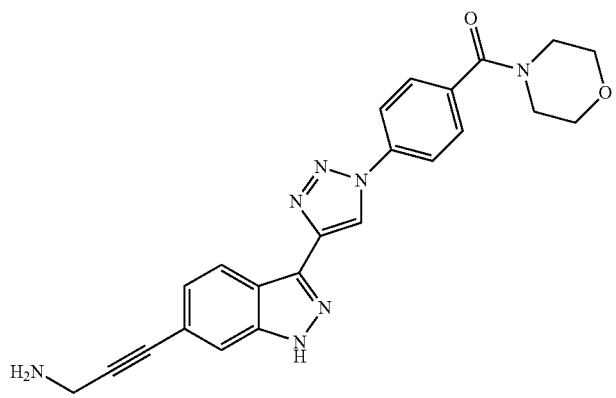 [SMILES: NCC#Cc1ccc2c(-c3cn(-c4ccc(C(=O)N5CCOCC5)cc4)nn3)n[nH]c2c1] | * |
| 220 | 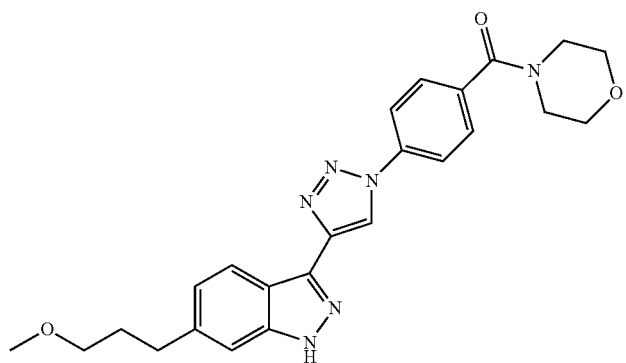 [SMILES: COCCCc1ccc2c(-c3cn(-c4ccc(C(=O)N5CCOCC5)cc4)nn3)n[nH]c2c1] | ** |

| | | |
|---|---|---|
| 221 | 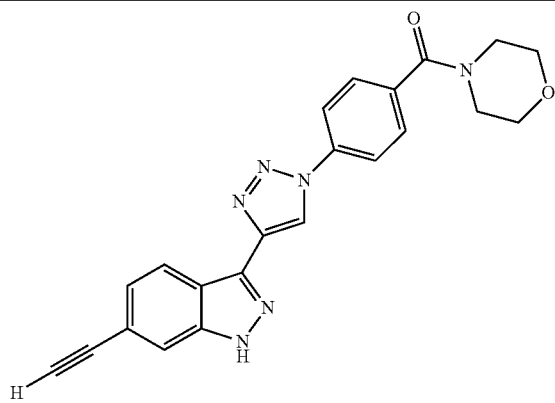 | ** |
| 222 | 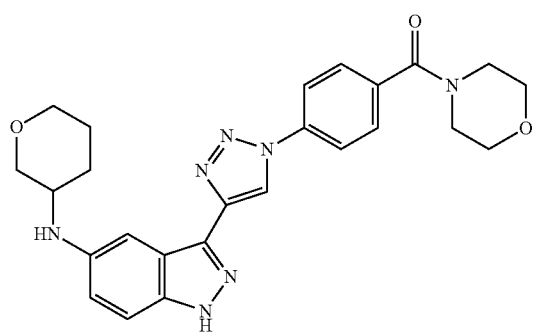 [SMILES: O=C(c1ccc(-n2cc(-c3n[nH]c4ccc(NC5CCCOC5)cc34)nn2)cc1)N1CCOCC1] | ** |
| 223 | 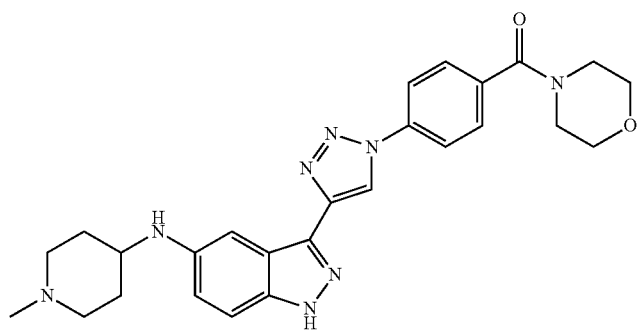 [SMILES: CN1CCC(Nc2ccc3[nH]nc(-c4cn(-c5ccc(C(=O)N6CCOCC6)cc5)nn4)c3c2)CC1] | *** |
| 224 | 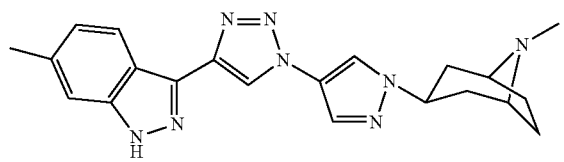 | *** |
| 225 | 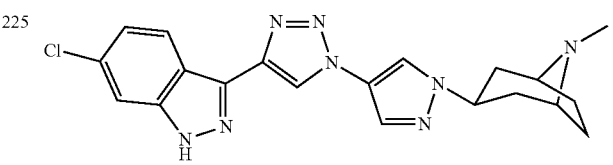 | *** |
| 226 | 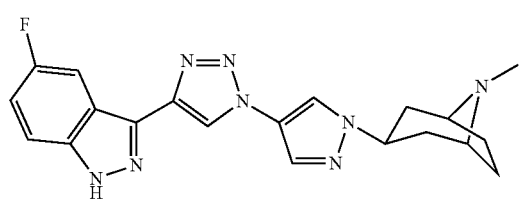 [SMILES: CN1C2CCC1CC(n1cc(-n3cc(-c4n[nH]c5ccc(F)cc45)nn3)cn1)C2] | ** |

-continued
| 227 | 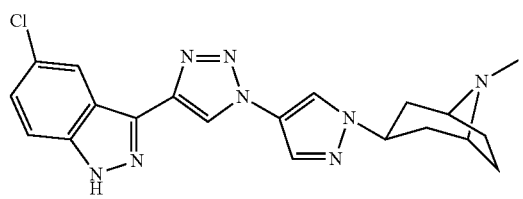 | ** |
| 228 | 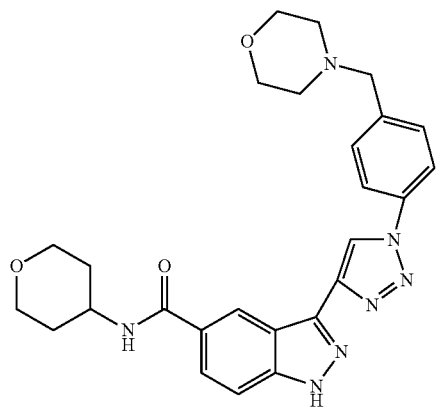 [SMILES: O=C(NC1CCOCC1)c1ccc2[nH]nc(-c3cn(-c4ccc(CN5CCOCC5)cc4)nn3)c2c1] | ** |
| 229 | 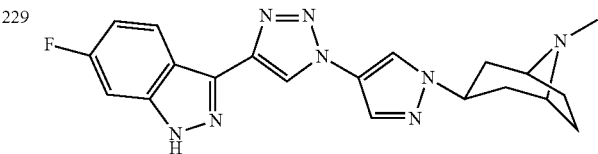 | *** |
| 230 | 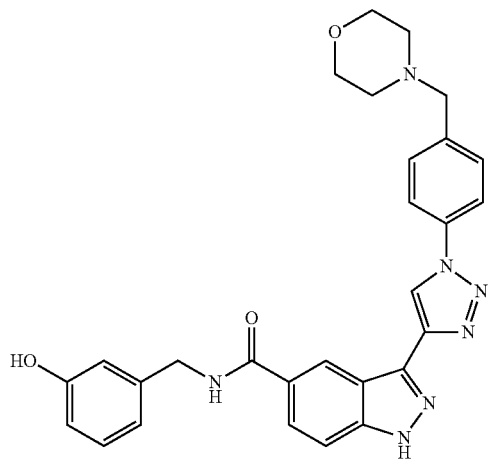 [SMILES: O=C(NCc1cccc(O)c1)c1ccc2[nH]nc(-c3cn(-c4ccc(CN5CCOCC5)cc4)nn3)c2c1] | *** |

| | | |
|---|---|---|
| 231 | 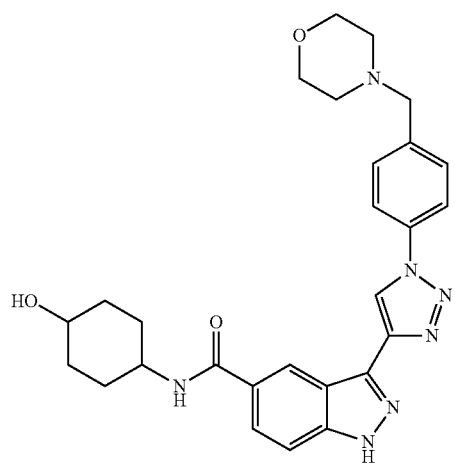 [SMILES: O=C(NC1CCC(O)CC1)c1ccc2[nH]nc(-c3cn(-c4ccc(CN5CCOCC5)cc4)nn3)c2c1] | ** |
| 232 | 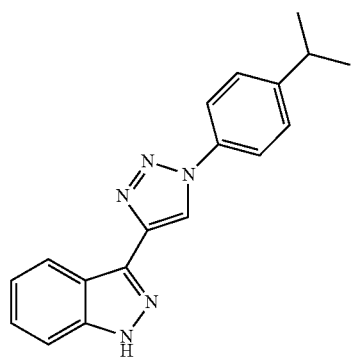 [SMILES: CC(C)c1ccc(-n2cc(-c3n[nH]c4ccccc34)nn2)cc1] | * |
| 233 | 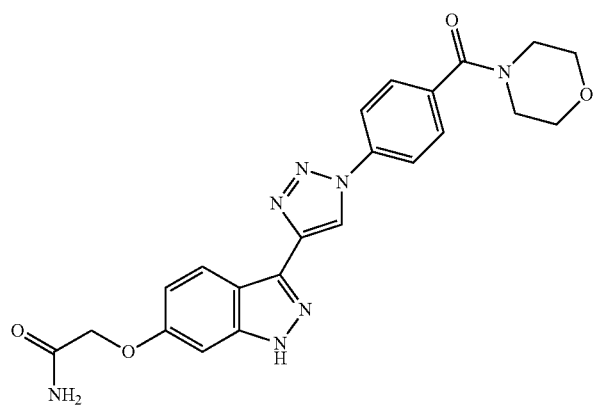 [SMILES: NC(=O)COc1ccc2c(-c3cn(-c4ccc(C(=O)N5CCOCC5)cc4)nn3)n[nH]c2c1] | ** |
| 234 | 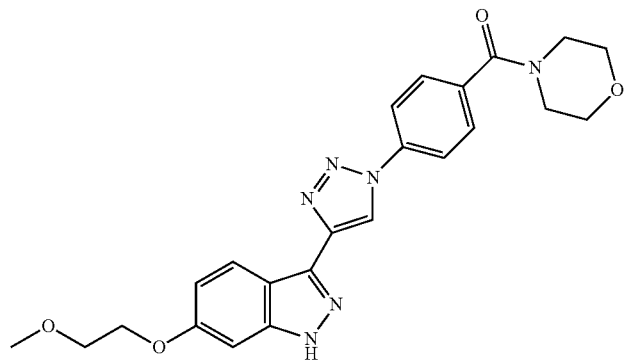 [SMILES: COCCOc1ccc2c(-c3cn(-c4ccc(C(=O)N5CCOCC5)cc4)nn3)n[nH]c2c1] | * |

| | | |
|---|---|---|
| 235 | 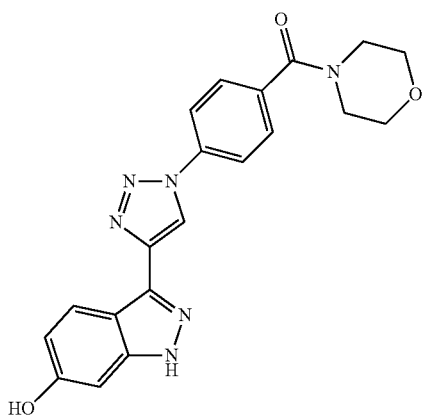 [SMILES: O=C(c1ccc(-n2cc(-c3n[nH]c4cc(O)ccc34)nn2)cc1)N1CCOCC1] | ** |
| 236 | 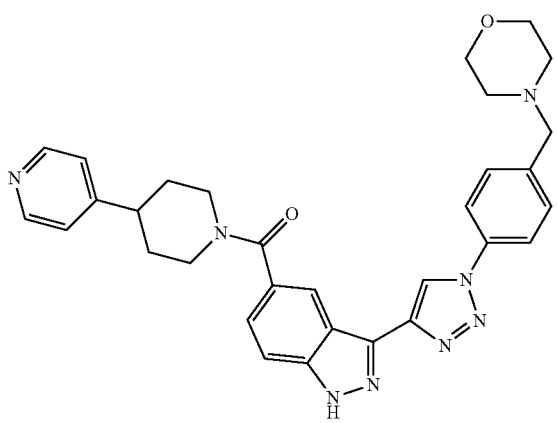 [SMILES: O=C(c1ccc2[nH]nc(-c3cn(-c4ccc(CN5CCOCC5)cc4)nn3)c2c1)N1CCC(c2ccncc2)CC1] | ** |
| 237 | 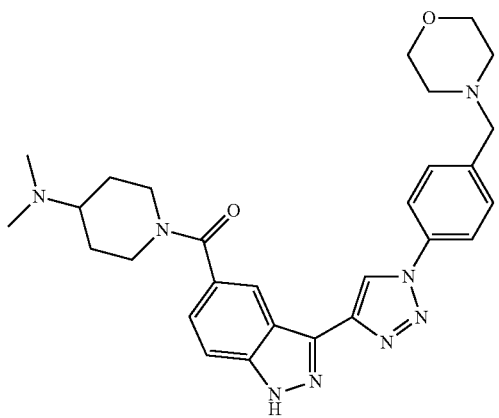 [SMILES: CN(C)C1CCN(C(=O)c2ccc3[nH]nc(-c4cn(-c5ccc(CN6CCOCC6)cc5)nn4)c3c2)CC1] | ** |

| | | |
|---|---|---|
| 238 | 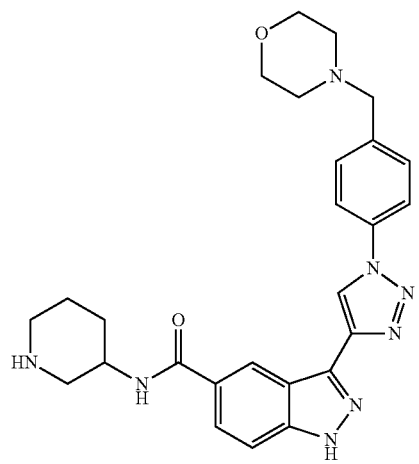 [SMILES: O=C(NC1CCCNC1)c1ccc2[nH]nc(-c3cn(-c4ccc(CN5CCOCC5)cc4)nn3)c2c1] | *** |
| 239 | 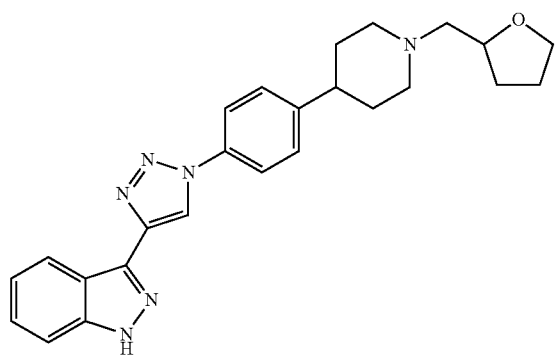 [SMILES: c1ccc2c(-c3cn(-c4ccc(C5CCN(CC6CCCO6)CC5)cc4)nn3)n[nH]c2c1] | ** |
| 240 | 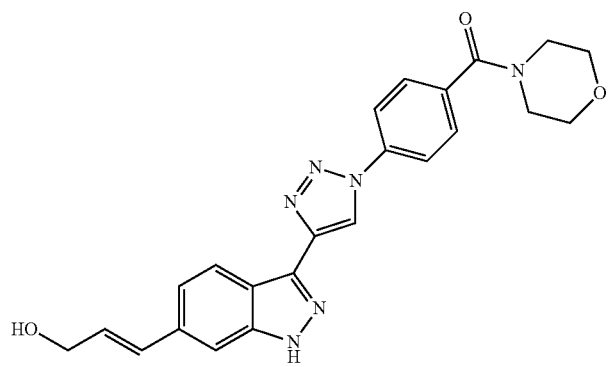 [SMILES: O=C(c1ccc(-n2cc(-c3n[nH]c4cc(/C=C/CO)ccc34)nn2)cc1)N1CCOCC1] | *** |
| 241 | 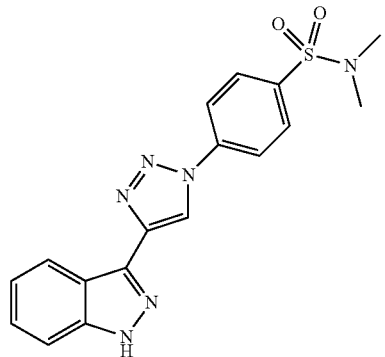 [SMILES: CN(C)S(=O)(=O)c1ccc(-n2cc(-c3n[nH]c4ccccc34)nn2)cc1] | ** |

| | | |
|---|---|---|
| 242 | 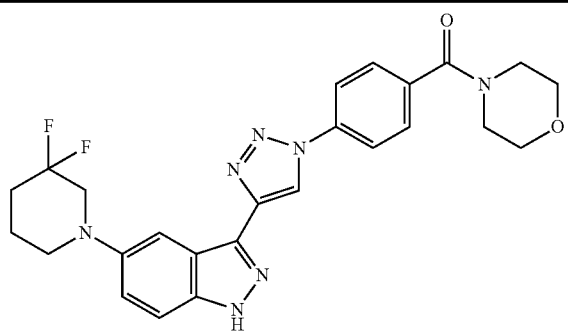 | ** |
| 243 | 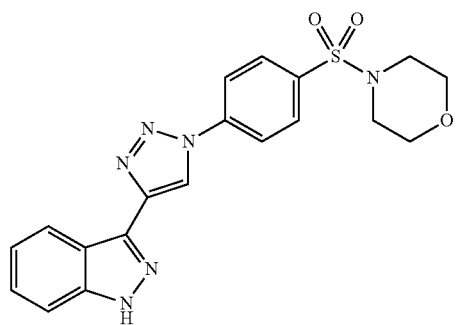 [SMILES: O=S(=O)(c1ccc(-n2cc(-c3n[nH]c4ccccc34)nn2)cc1)N1CCOCC1] | ** |
| 244 | 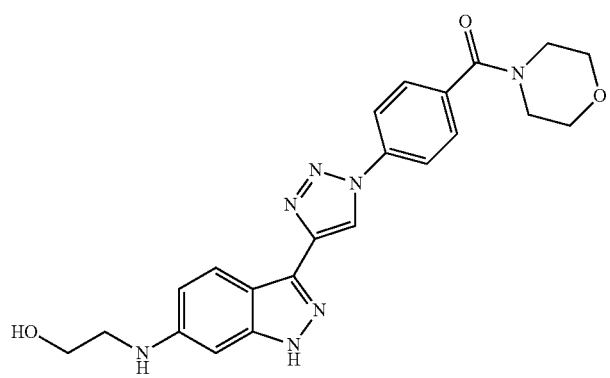 [SMILES: O=C(c1ccc(-n2cc(-c3n[nH]c4cc(NCCO)ccc34)nn2)cc1)N1CCOCC1] | ** |
| 245 | 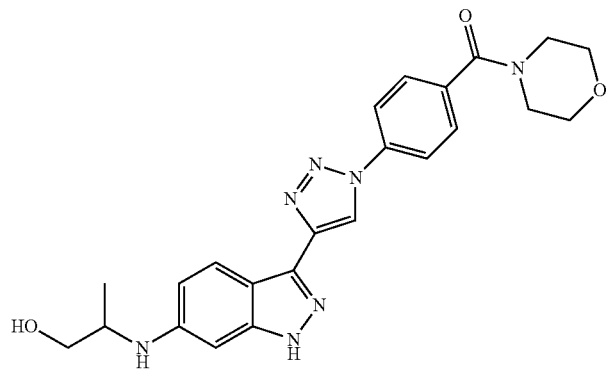 [SMILES: CC(CO)Nc1ccc2c(-c3cn(-c4ccc(C(=O)N5CCOCC5)cc4)nn3)n[nH]c2c1] | ** |

| | |
|---|---|
| 246 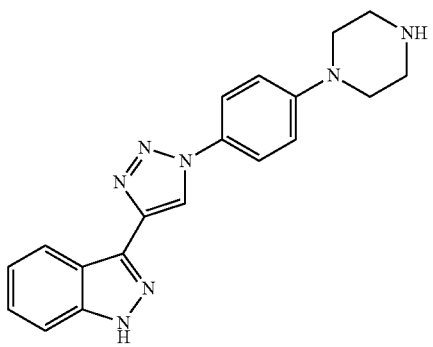 [SMILES: c1ccc2c(-c3cn(-c4ccc(N5CCNCC5)cc4)nn3)n[nH]c2c1] | ** |
| 247 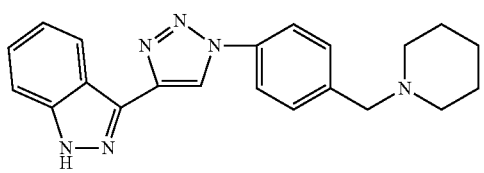 [SMILES: c1ccc2c(-c3cn(-c4ccc(CN5CCCCC5)cc4)nn3)n[nH]c2c1] | ** |
| 248 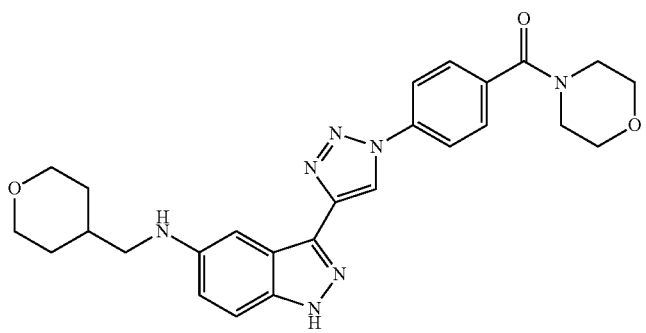 [SMILES: O=C(c1ccc(-n2cc(-c3n[nH]c4ccc(NCC5CCOCC5)cc34)nn2)cc1)N1CCOCC1] | ** |
| 249 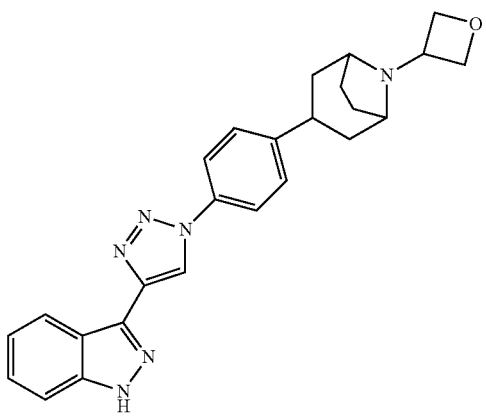 [SMILES: c1ccc2c(-c3cn(-c4ccc(C5CC6CCC(C5)N6C5COC5)cc4)nn3)n[nH]c2c1] | ** |
| 250 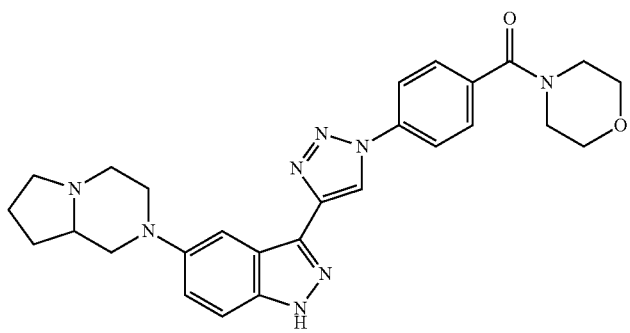 [SMILES: O=C(c1ccc(-n2cc(-c3n[nH]c4ccc(N5CCN6CCCC6C5)cc34)nn2)cc1)N1CCOCC1] | ** |

| | | |
|---|---|---|
| 251 | 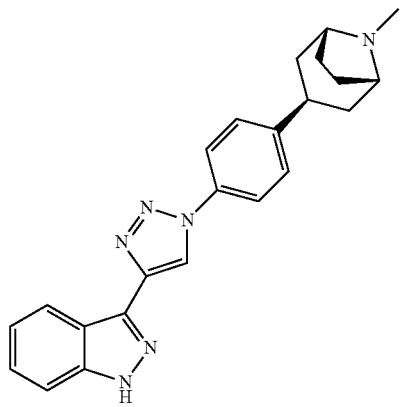 [SMILES: CN1[C@@H]2CC[C@H]1C[C@@H](c1ccc(-n3cc(-c4n[nH]c5ccccc45)nn3)cc1)C2] | ** |
| 252 | 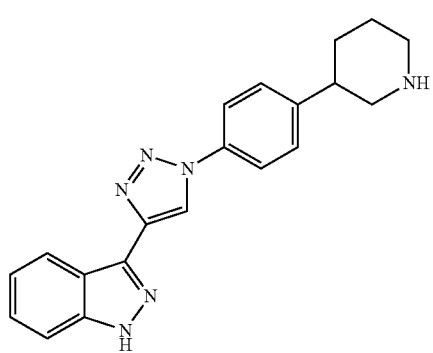 [SMILES: c1ccc2c(-c3cn(-c4ccc(C5CCCNC5)cc4)nn3)n[nH]c2c1] | *** |
| 253 | 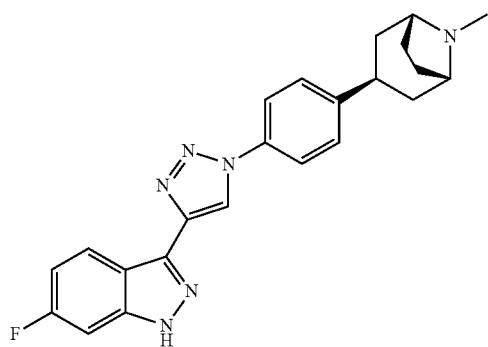 [SMILES: CN1[C@@H]2CC[C@H]1C[C@@H](c1ccc(-n3cc(-c4n[nH]c5cc(F)ccc45)nn3)cc1)C2] | *** |
| 254 | 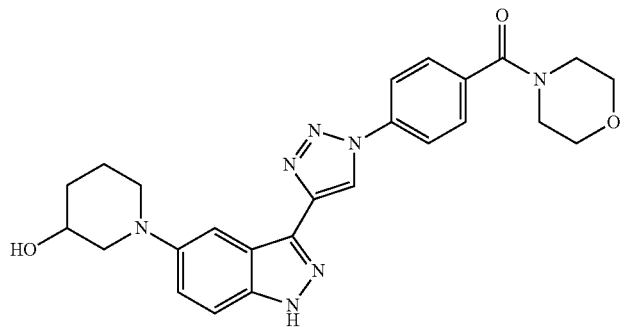 [SMILES: O=C(c1ccc(-n2cc(-c3n[nH]c4ccc(N5CCCC(O)C5)cc34)nn2)cc1)N1CCOCC1] | ** |

| | | |
|---|---|---|
| 255 | 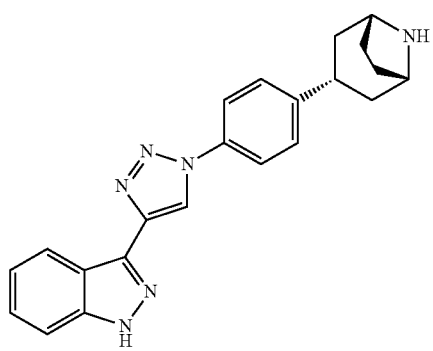 [SMILES: c1ccc2c(-c3cn(-c4ccc([C@@H]5C[C@H]6CC[C@@H](C5)N6)cc4)nn3)n[nH]c2c1] | *** |
| 256 | 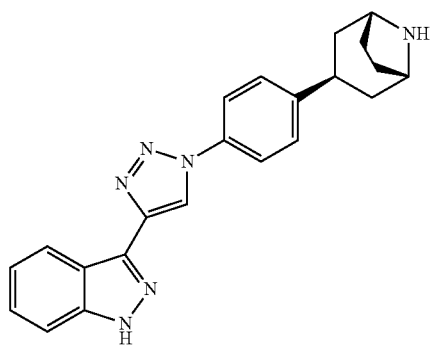 [SMILES: c1ccc2c(-c3cn(-c4ccc([C@H]5C[C@H]6CC[C@@H](C5)N6)cc4)nn3)n[nH]c2c1] | *** |
| 257 | 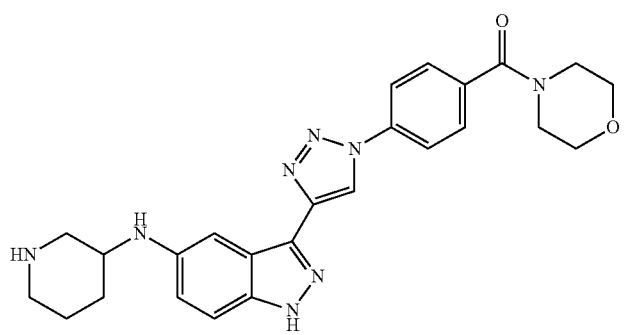 [SMILES: O=C(c1ccc(-n2cc(-c3n[nH]c4ccc(NC5CCCNC5)cc34)nn2)cc1)N1CCOCC1] | *** |
| 258 | 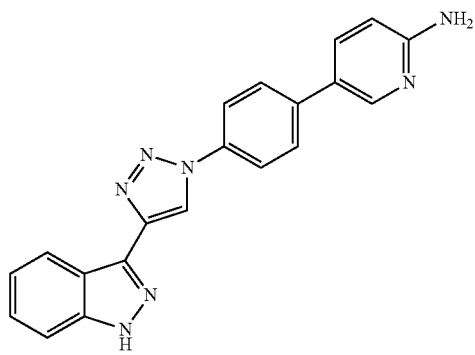 [SMILES: Nc1ccc(-c2ccc(-n3cc(-c4n[nH]c5ccccc45)nn3)cc2)cn1] | ** |
| 259 | 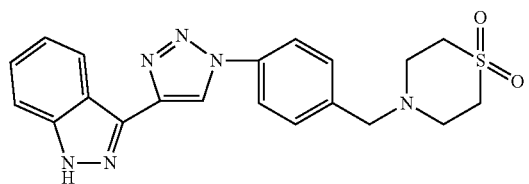 [SMILES: O=S1(=O)CCN(Cc2ccc(-n3cc(-c4n[nH]c5ccccc45)nn3)cc2)CC1] | ** |

| | | |
|---|---|---|
| 260 | 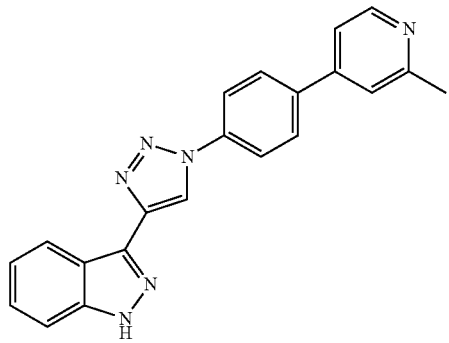 [SMILES: Cc1cc(-c2ccc(-n3cc(-c4n[nH]c5ccccc45)nn3)cc2)ccn1] | ** |
| 261 | 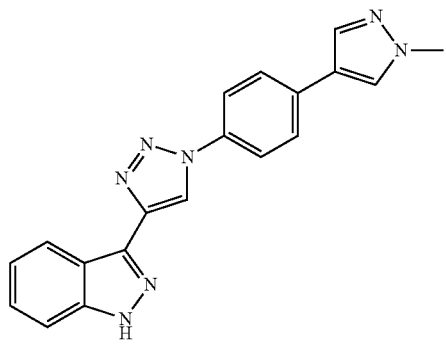 [SMILES: Cn1cc(-c2ccc(-n3cc(-c4n[nH]c5ccccc45)nn3)cc2)cn1] | ** |
| 262 | 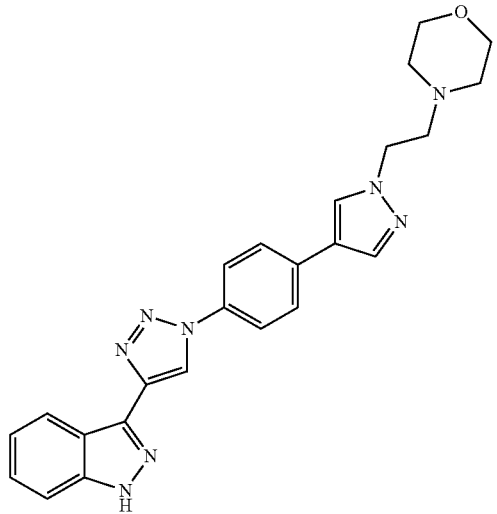 [SMILES: c1ccc2c(-c3cn(-c4ccc(-c5cnn(CCN6CCOCC6)c5)cc4)nn3)n[nH]c2c1] | ** |
| 263 | 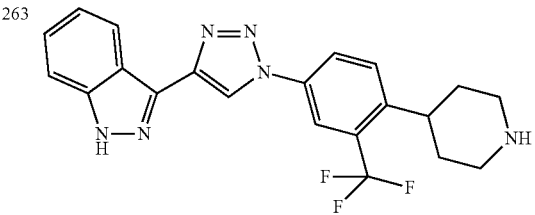 | ** |

| | | |
|---|---|---|
| 264 | 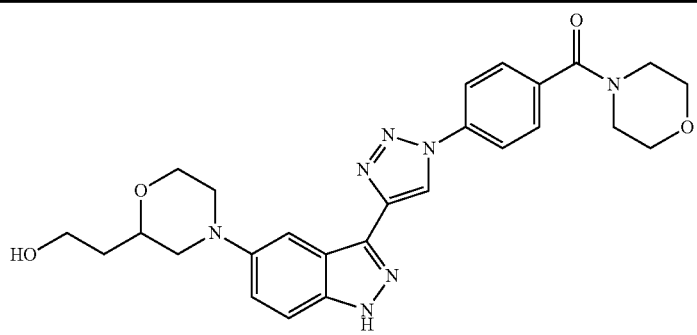 | ** |
| 265 | 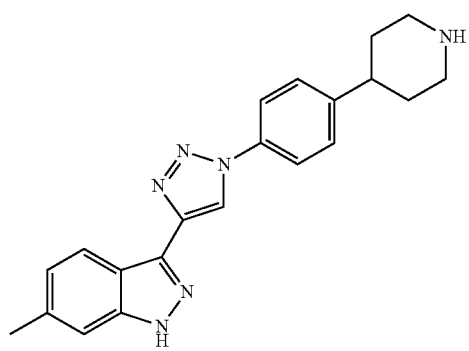 [SMILES: Cc1ccc2c(-c3cn(-c4ccc(C5CCNCC5)cc4)nn3)n[nH]c2c1] | *** |
| 266 | 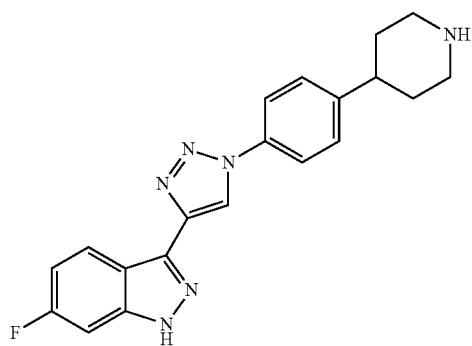 [SMILES: Fc1ccc2c(-c3cn(-c4ccc(C5CCNCC5)cc4)nn3)n[nH]c2c1] | *** |
| 267 | 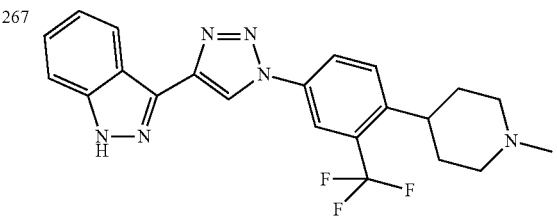 | ** |
| 268 | 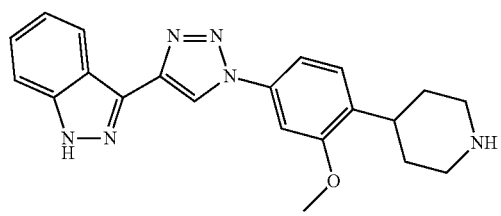 [SMILES: COc1cc(-n2cc(-c3n[nH]c4ccccc34)nn2)ccc1C1CCNCC1] | *** |

-continued
| | | |
|---|---|---|
| 269 | 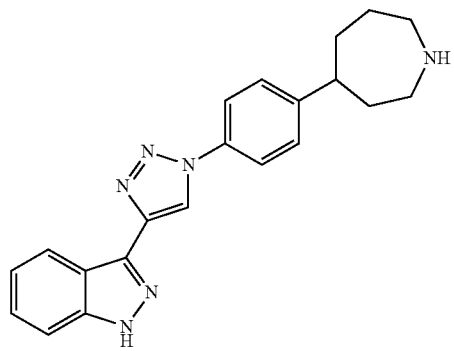 [SMILES: c1ccc2c(-c3cn(-c4ccc(C5CCCNCC5)cc4)nn3)n[nH]c2c1] | *** |
| 270 | 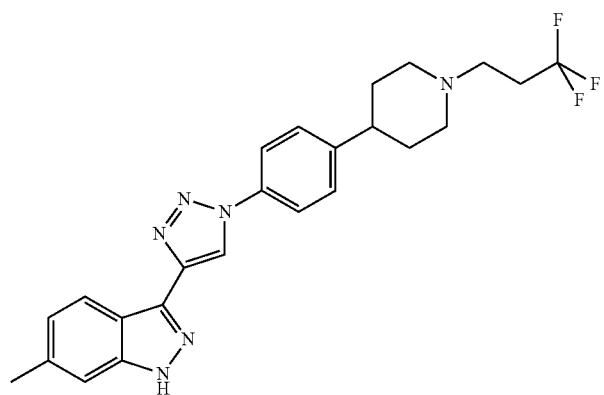 [SMILES: Cc1ccc2c(-c3cn(-c4ccc(C5CCN(CCC(F)(F)F)CC5)cc4)nn3)n[nH]c2c1] | * |
| 271 | 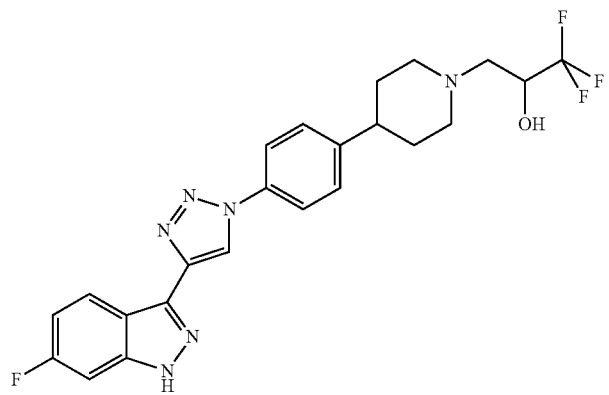 [SMILES: OC(CN1CCC(c2ccc(-n3cc(-c4n[nH]c5cc(F)ccc45)nn3)cc2)CC1)C(F)(F)F] | ** |
| 272 | 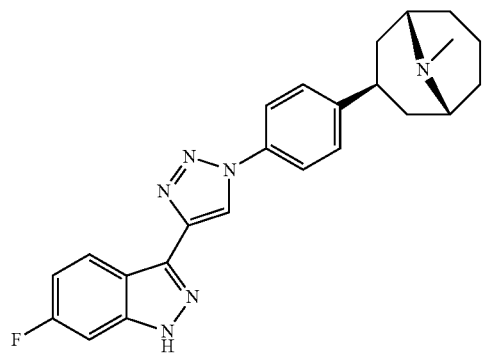 [SMILES: CN1[C@@H]2CCC[C@H]1C[C@H](c1ccc(-n3cc(-c4n[nH]c5cc(F)ccc45)nn3)cc1)C2] | *** |

-continued
| | | |
|---|---|---|
| 273 | 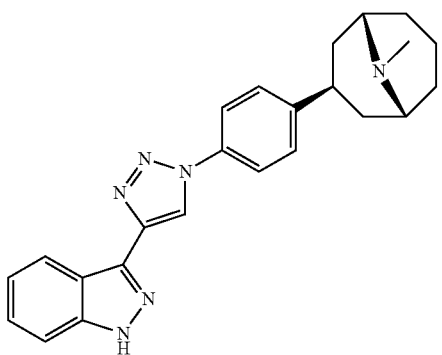 [SMILES: CN1[C@@H]2CCC[C@H]1C[C@H](c1ccc(-n3cc(-c4n[nH]c5ccccc45)nn3)cc1)C2] | *** |
| 274 | 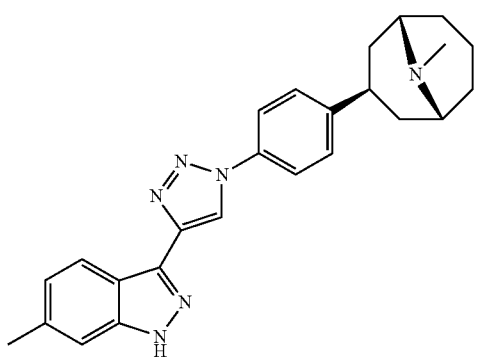 [SMILES: Cc1ccc2c(-c3cn(-c4ccc([C@@H]5C[C@H]6CCC[C@@H](C5)N6C)cc4)nn3)n[nH]c2c1] | *** |
| 275 | 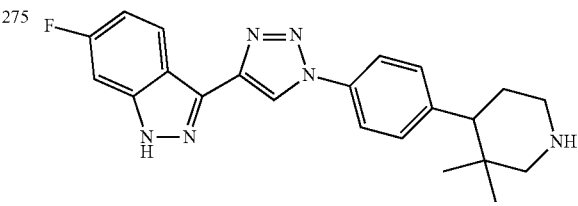 | *** |
| 276 | 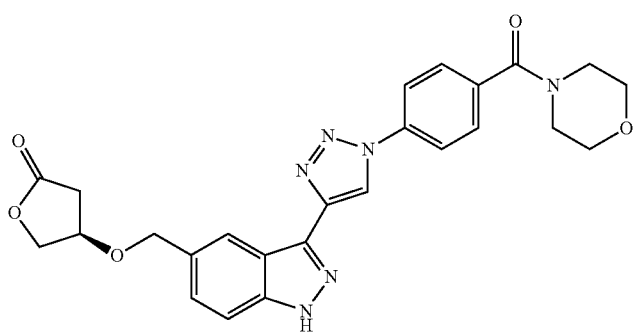 | ** |
| 277 | 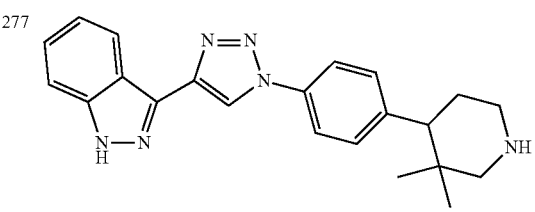 [SMILES: CC1(C)CNCCC1c1ccc(-n2cc(-c3n[nH]c4cc(F)ccc34)nn2)cc1] | *** |

| | | |
|---|---|---|
| 278 | 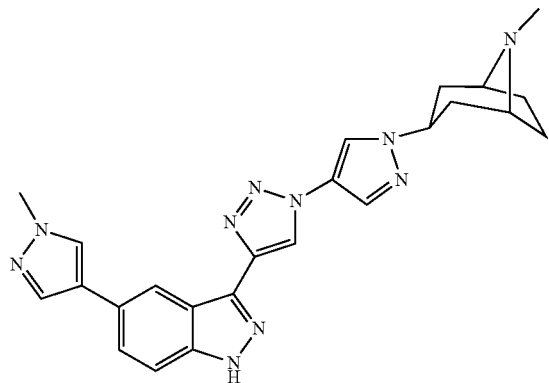 [SMILES: CN1C2CCC1CC(n1cc(-n3cc(-c4n[nH]c5ccc(-c6cnn(C)c6)cc45)nn3)cn1)C2] | *** |
| 279 | 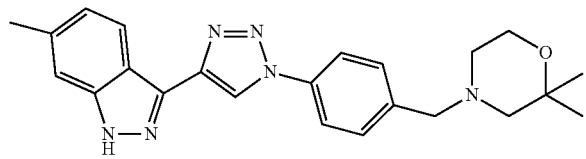 | ** |
| 280 | 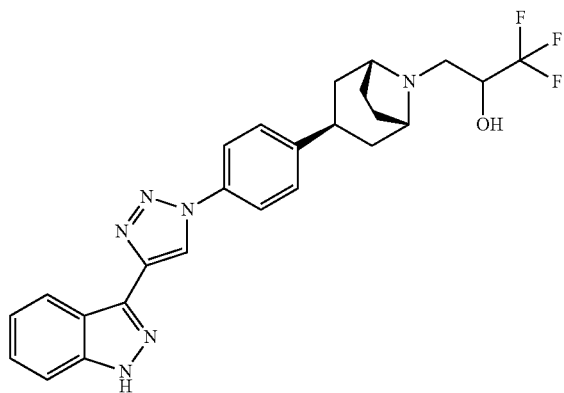 [SMILES: OC(CN1[C@@H]2CC[C@H]1C[C@@H](c1ccc(-n3cc(-c4n[nH]c5ccccc45)nn3)cc1)C2)C(F)(F)F] | ** |
| 281 | 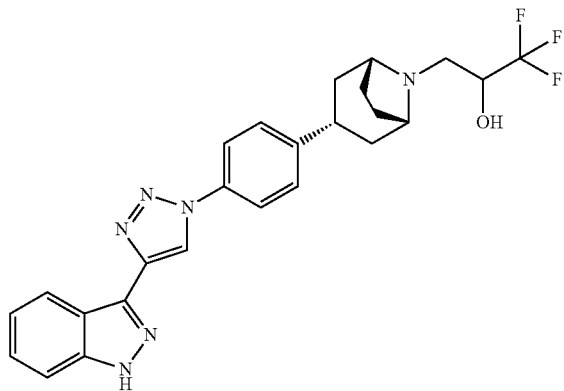 [SMILES: OC(CN1[C@@H]2CC[C@H]1C[C@H](c1ccc(-n3cc(-c4n[nH]c5ccccc45)nn3)cc1)C2)C(F)(F)F] | ** |
| 282 | 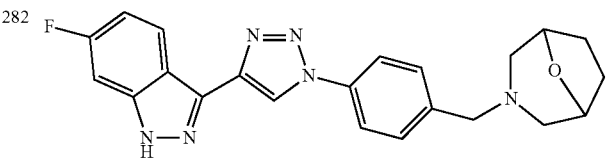 | * |

-continued

| | | |
|---|---|---|
| 283 | [structure: 6-fluoro-1H-indazol-3-yl triazole phenyl CH2-N-(2,2-dimethylmorpholine)] | * |
| 284 | [structure: 1H-indazol-3-yl triazole phenyl CH2-N-(8-oxa-3-azabicyclo[3.2.1]octane)] | * |
| 285 | [structure: 6-fluoro-1H-indazol-3-yl triazole phenyl CH2-N-(2-oxa-5-azaspiro[3.5]nonane)] | ** |
| 286 | [structure: 1H-indazol-3-yl triazole phenyl (2-morpholinopyridin-4-yl)] | ** |
| 287 | [structure: 6-methyl-1H-indazol-3-yl triazole phenyl CH2-N-(2-oxa-5-azaspiro[3.5]nonane)] | ** |

-continued
| | | |
|---|---|---|
| 288 | 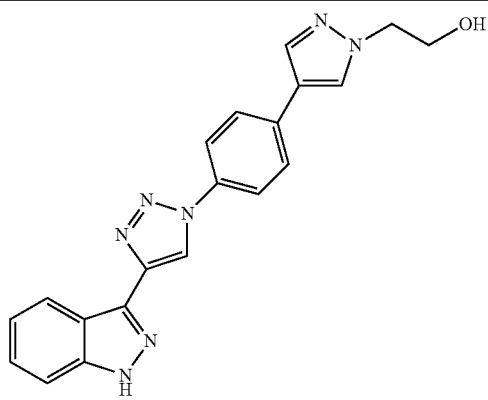 | ** |
| 289 | 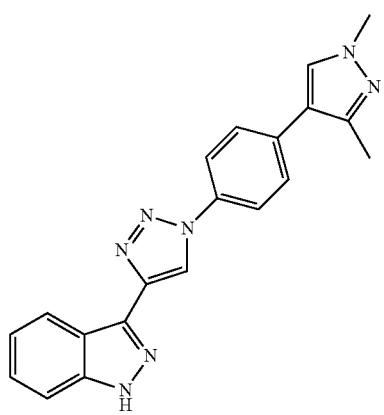 [SMILES: Cc1nn(C)cc1-c1ccc(-n2cc(-c3n[nH]c4ccccc34)nn2)cc1] | ** |
| 290 | 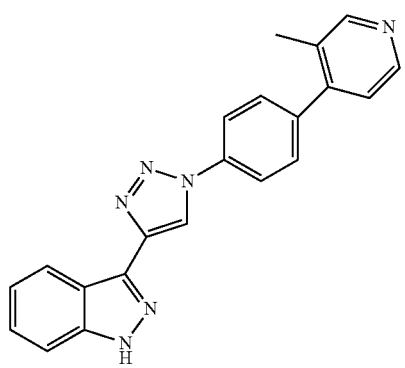 [SMILES: Cc1cnccc1-c1ccc(-n2cc(-c3n[nH]c4ccccc34)nn2)cc1] | ** |
| 291 | 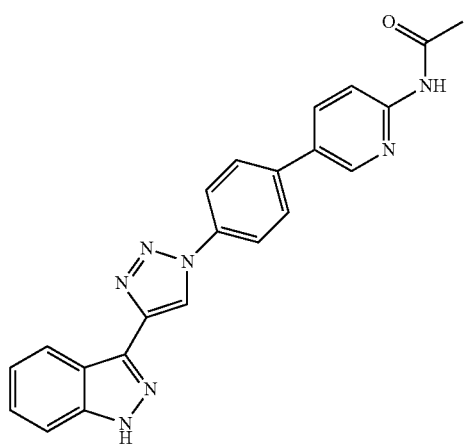 [SMILES: CC(=O)Nc1ccc(-c2ccc(-n3cc(-c4n[nH]c5ccccc45)nn3)cc2)cn1] | ** |

292 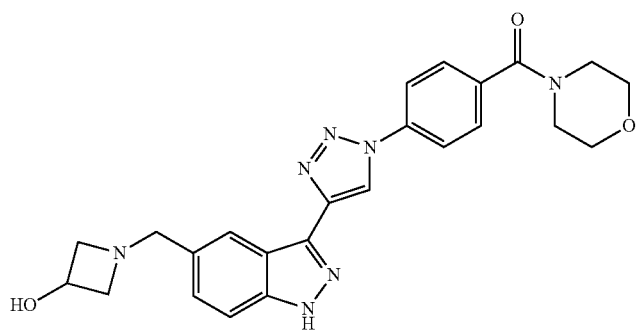 [SMILES: O=C(c1ccc(-n2cc(-c3n[nH]c4ccc(CN5CC(O)C5)cc34)nn2)cc1)N1CCOCC1] **
293 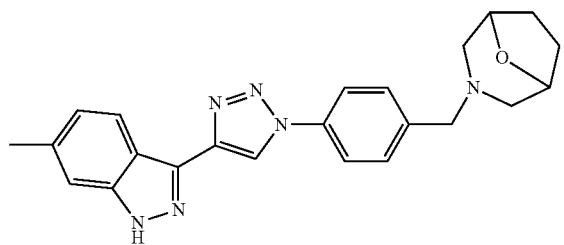 [SMILES: Cc1ccc2c(-c3cn(-c4ccc(CN5CC6CCC(C5)O6)cc4)nn3)n[nH]c2c1] **
294 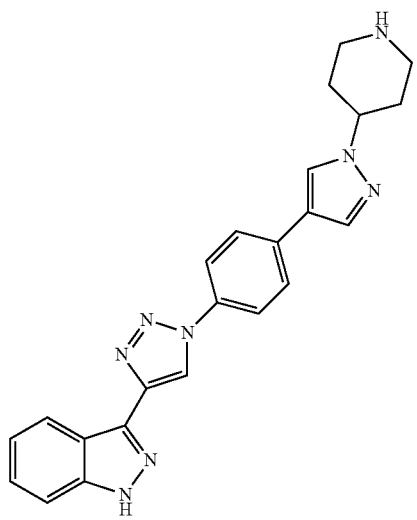 [SMILES: c1ccc2c(-c3cn(-c4ccc(-c5cnn(C6CCNCC6)c5)cc4)nn3)n[nH]c2c1] **
295 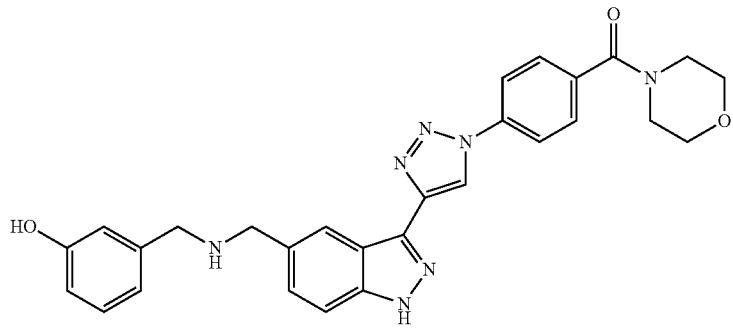 [SMILES: O=C(c1ccc(-n2cc(-c3n[nH]c4ccc(CNCc5cccc(O)c5)cc34)nn2)cc1)N1CCOCC1] **

| | | |
|---|---|---|
| 296 | 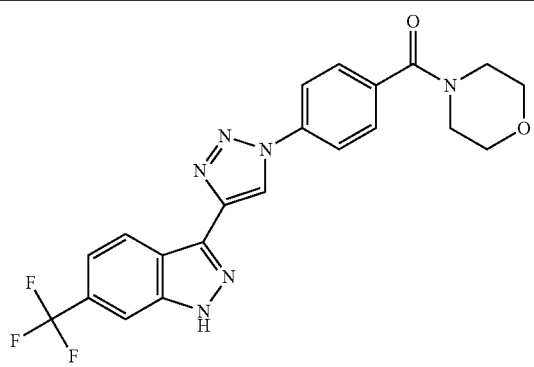 | ** |
| 297 | 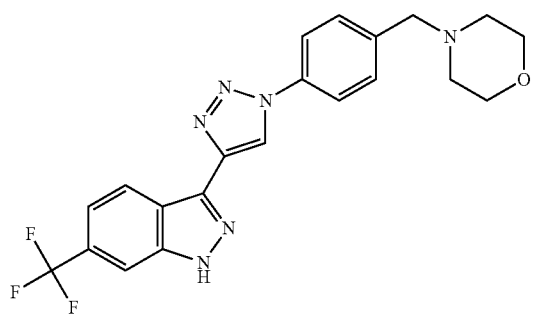 [SMILES: FC(F)(F)c1ccc2c(-c3cn(-c4ccc(CN5CCOCC5)cc4)nn3)n[nH]c2c1] | * |
| 298 | 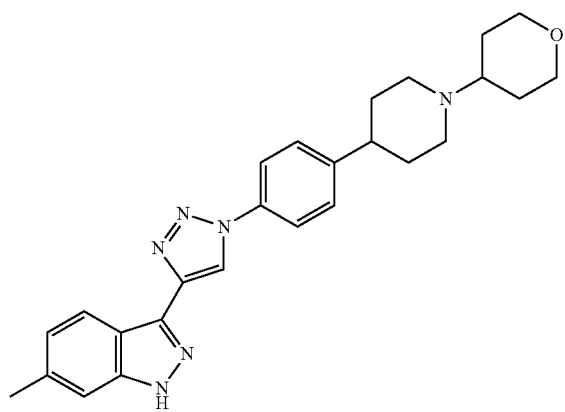 [SMILES: Cc1ccc2c(-c3cn(-c4ccc(C5CCN(C6CCOCC6)CC5)cc4)nn3)n[nH]c2c1] | ** |
| 299 | 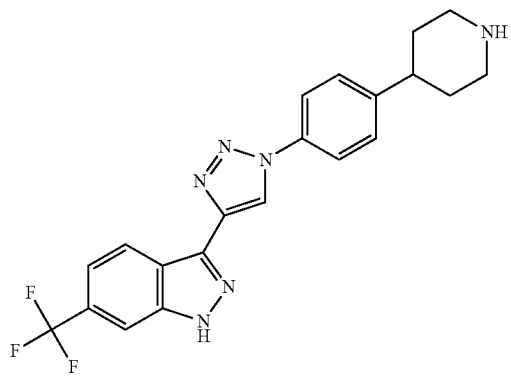 [SMILES: FC(F)(F)c1ccc2c(-c3cn(-c4ccc(C5CCNCC5)cc4)nn3)n[nH]c2c1] | ** |
*: 1 μM < IC$_{50}$ < 5 μM
**: 0.1 μM < IC$_{50}$ < 1 μM
***: IC$_{50}$ < 0.1 μM
n.d: not determined

Example 301

IRAK IL-6 Secretion Functional Assay in Human PBMC

Human PBMCs from healthy volunteers were purified from buffy coats of heparinized whole blood by density centrifugation on Ficoll-Hypaque. Isolated PBMCs were washed twice in PBS, counted, and seeded at a density of $7 \times 10^4$ cells/well in 180 l of complete RPMI 1640 medium containing 10% heat-inactivated FBS. PBMC were preincubated for 1 h with serial dilutions of test article dissolved in DMSO (final DMSO concentration 0.33%) at 37° C. in a 5% CO2 incubator. PBMC were then stimulated with 10 ng/ml of IL1-(final volume 200 l) and incubation was continued for 18-20 h. The supernatants were collected and IL-6 was quantified using the Duo-set ELISA kit (R&D Systems) following manufacturer's instructions Results are summarized in table 3 below:

TABLE 3

| Ex | Structure | IL-6 secretion |
|---|---|---|
| 1 | 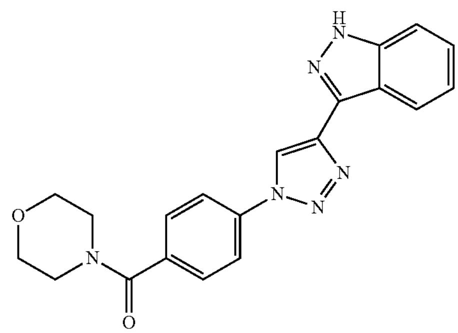 [SMILES: O=C(c1ccc(-n2cc(-c3n[nH]c4ccccc34)nn2)cc1)N1CCOCC1] | * |
| 2 | 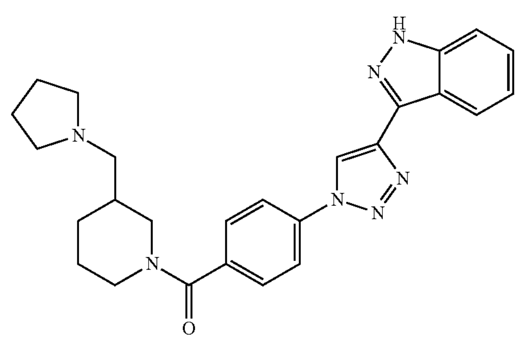 [SMILES: O=C(c1ccc(-n2cc(-c3n[nH]c4ccccc34)nn2)cc1)N1CCCC(CN2CCCC2)C1] | * |
| 7 | 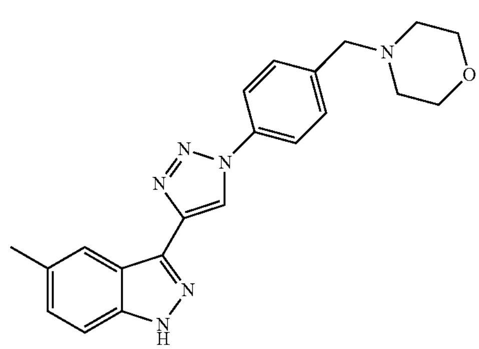 [SMILES: Cc1ccc2[nH]nc(-c3cn(-c4ccc(CN5CCOCC5)cc4)nn3)c2c1] | * |

TABLE 3-continued
| Ex | Structure | IL-6 secretion |
|---|---|---|
| 30 | 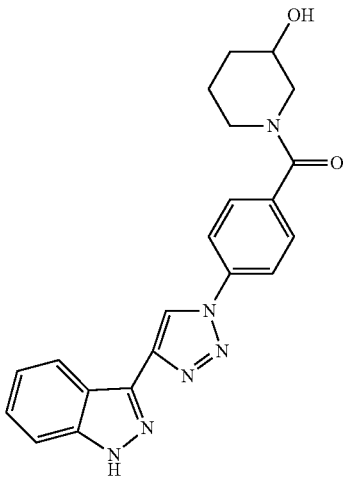 [SMILES: O=C(c1ccc(-n2cc(-c3n[nH]c4ccccc34)nn2)cc1)N1CCCC(O)C1] | * |
| 33 | 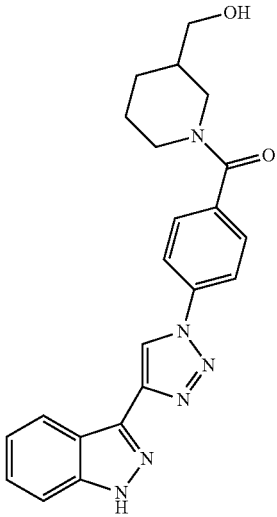 [SMILES: O=C(c1ccc(-n2cc(-c3n[nH]c4ccccc34)nn2)cc1)N1CCCC(CO)C1] | ** |
| 124 | 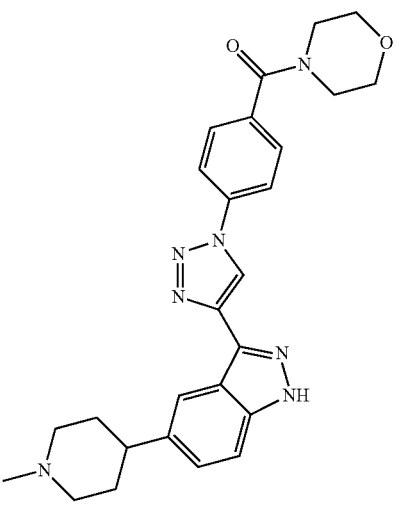 [SMILES: CN1CCC(c2ccc3[nH]nc(-c4cn(-c5ccc(C(=O)N6CCOCC6)cc5)nn4)c3c2)CC1] | ** |

TABLE 3-continued
| Ex | Structure | IL-6 secretion |
|---|---|---|
| 125 | 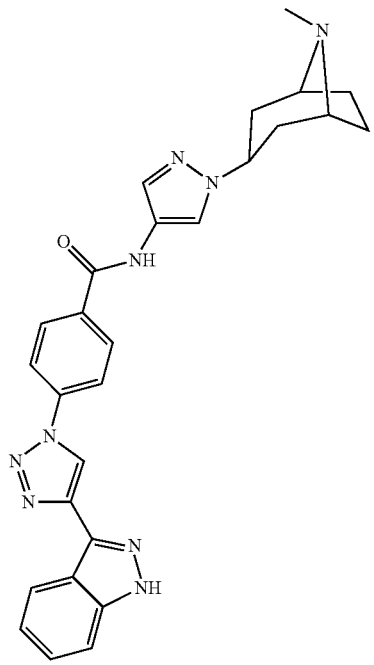 [SMILES: CN1C2CCC1CC(n1cc(NC(=O)c3ccc(-n4cc(-c5n[nH]c6ccccc56)nn4)cc3)cn1)C2] | * |
| 132 | 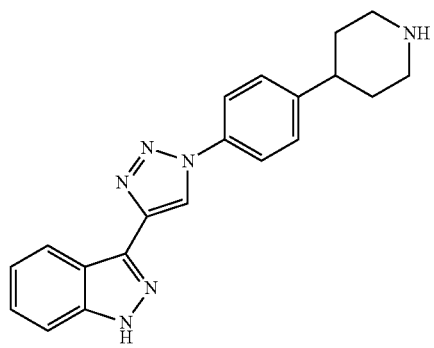 | * |
| 136 | 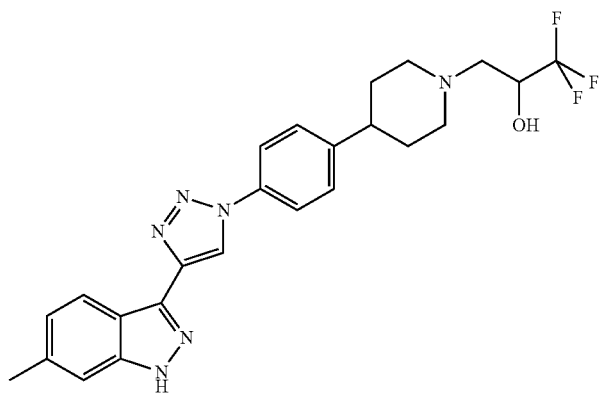 [SMILES: Cc1ccc2c(-c3cn(-c4ccc(C5CCN(CC(O)C(F)(F)F)CC5)cc4)nn3)n[nH]c2c1] | * |

TABLE 3-continued

| Ex | Structure | IL-6 secretion |
|---|---|---|
| 145 | 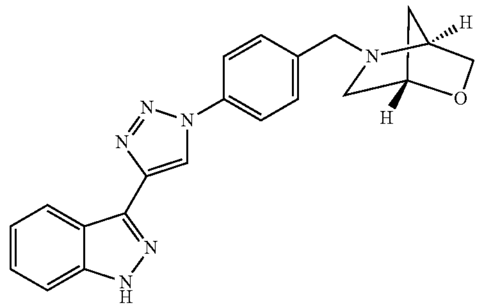 [SMILES: c1ccc2c(-c3cn(-c4ccc(CN5C[C@@H]6C[C@H]5CO6)cc4)nn3)n[nH]c2c1] | * |
| 158 | 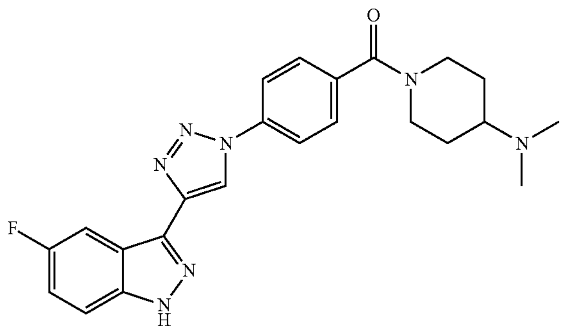 [SMILES: CN(C)C1CCN(C(=O)c2ccc(-n3cc(-c4n[nH]c5ccc(F)cc45)nn3)cc2)CC1] | ** |
| 188 | 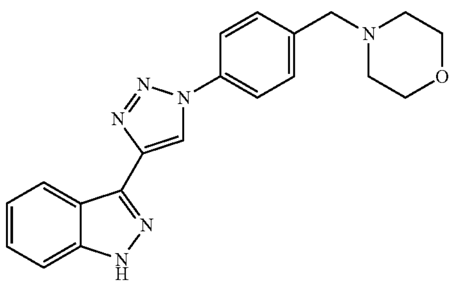 [SMILES: c1ccc2c(-c3cn(-c4ccc(CN5CCOCC5)cc4)nn3)n[nH]c2c1] | * |
| 197 | 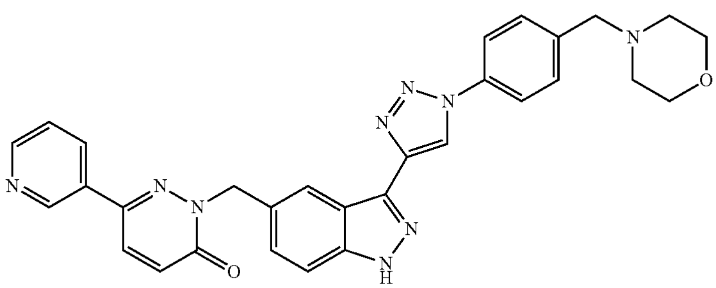 | ** |
| 204 | 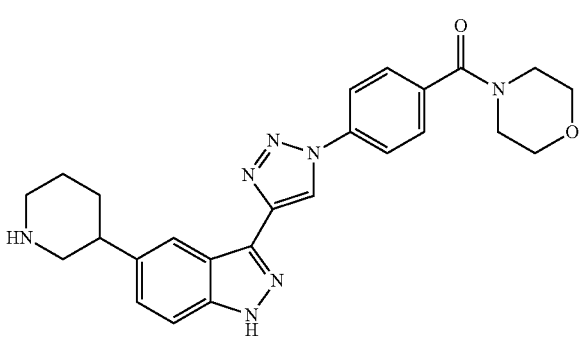 [SMILES: O=C(c1ccc(-n2cc(-c3n[nH]c4ccc(C5CCCNC5)cc34)nn2)cc1)N1CCOCC1] | * |

TABLE 3-continued
| Ex | Structure | IL-6 secretion |
|---|---|---|
| 210 | 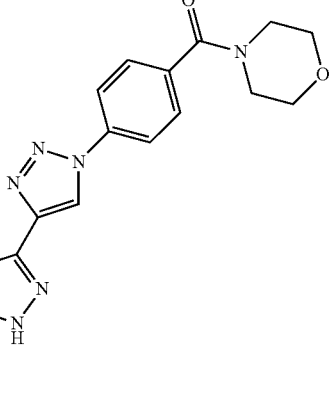 | * |
| 224 | 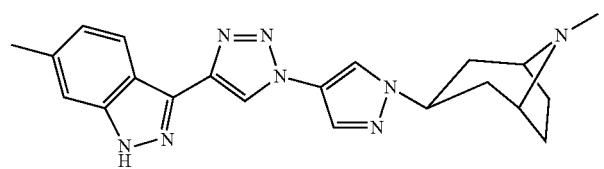 | * |
| 238 | 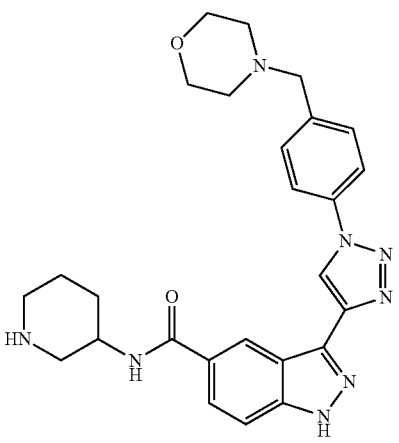 [SMILES: O=C(NC1CCCNC1)c1ccc2[nH]nc(-c3cn(-c4ccc(CN5CCOCC5)cc4)nn3)c2c1] | ** |
| 251 | 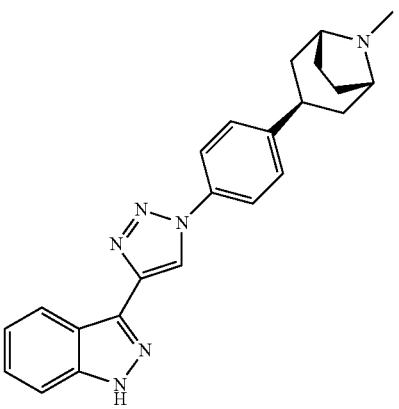 [SMILES: CN1[C@@H]2CC[C@H]1C[C@@H](c1ccc(-n3cc(-c4n[nH]c5ccccc45)nn3)cc1)C2] | * |

TABLE 3-continued

| Ex | Structure | IL-6 secretion |
|---|---|---|
| 298 | 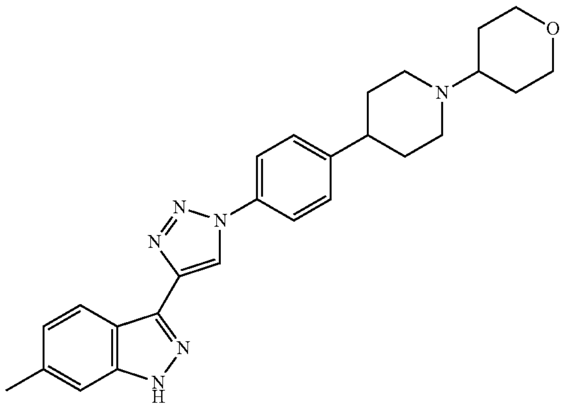 [SMILES: Cc1ccc2c(-c3cn(-c4ccc(C5CCN(C6CCOCC6)CC5)cc4)nn3)n[nH]c2c1] | * |

*: 200 nM < IC$_{50}$ < 2 μM
**: IC$_{50}$ < 200 nM

Example 302

LPS-Induced Cytokine Release in Mice

Female C57B6 mice (8-10 weeks 4-6 mice/group) were dosed p.o. with vehicle (40% Kleptose in water), reference compound dexamethasone (1 mg/kg) or three different doses of compound 1 (10, 30 and 60 mg/kg at 10 mL/kg). 30 minutes after compound administrations mice were injected i.p. with LPS (0111:B4, 1 mg/kg). 2 hours after LPS injection mice were sacrificed. Serum was collected; cytokine levels (TNF-α and IL-6) were detected by ELISA or OBA. Compound 1 inhibits dose dependently LPS-induced TNFα and IL-6 release in mice as showed in table 4 below.

TABLE 4 inhibition of LPS-induced TNFα and IL-6 release in mice

| dose (po) | TNFα | IL-6 |
|---|---|---|
| dexamethasone 1 mpk | 97% INH | 83% INH |
| cpd 1 10 mpk | 36% INH | 9% INH |
| cpd 1 30 mpk | 43% INH | 25% INH |
| cpd 1 60 mpk | 61% INH | 66% INH |

Example 303

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of Formula (I)

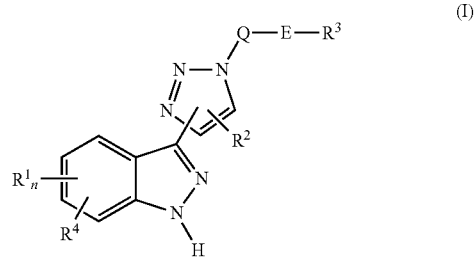

(I)

wherein
Q denotes Ar or Het;
E denotes —(CH$_2$)$_m$CO—, —(CH$_2$)$_m$SO$_2$, —(CH$_2$)$_q$—, —(CH$_2$)$_m$NHCO—, or a single bond;
R$^1$ denotes H, OH, NH—C$_1$-C$_6$-alkyl, OC$_1$-C$_6$-alkyl, C$_1$-C$_6$-alkyl, C$_2$-C$_6$-alkenyl, C$_2$-C$_6$-alkynyl, Cyc, Hal, Het$^1$, O-Het$^1$, CO-Het$^1$, NH-Het$^1$, CO—Ar$^1$, O—Ar$^1$, Ar$^1$, NH—Ar$^1$, —(CH$_2$)$_q$Het$^1$, —CONH—(CH$_2$)$_q$Het$^1$, —CONH-Het¹, —(CH₂)$_q$O-Het¹, —(CH₂)$_q$O—Ar¹, —(CH₂)$_q$Ar¹, —CONH—(CH₂)$_q$Ar¹, —CONH—Ar¹, —CONHC₃-C₆-cycloalkyl, —(CH₂)$_q$Hal, —(CH₂)$_q$Cyc, CF₃, —(CH₂)$_s$NH—(CH₂)$_q$-Het¹, or —(CH₂)$_s$NH—(CH₂)$_q$—Ar¹, wherein NH—C₁-C₆-alkyl, OC₁-C₆-alkyl, C₁-C₆-alkyl, C₂-C₆-alkenyl, C₂-C₆-alkynyl, C₃-C₆-cycloalkyl may be substituted by 1 to 3 groups independently selected from OC₁-C₃-alkyl, OH, CONH₂, and NH₂;

R² denotes H, C₁-C₆-alkyl, C₂-C₆-alkenyl, C₂-C₆-alkynyl, Hal, or CF₃;

R³ denotes Het¹, Ar¹, NR$^a$R$^b$, COOH, —(CH₂)$_q$Het¹, —(CH₂)$_q$Ar¹, —(CH₂)$_q$NR$^a$R$^b$, —(CH₂)$_q$COOH, or C₁-C₆-alkyl wherein 1 to 3 hydrogen atoms may each be independently replaced by OH or CF₃;

R⁴ denotes H, C₁-C₆-alkyl, C₂-C₆-alkenyl, or Hal;

R$^a$ denotes H, linear, branched or cyclic C₁-C₆-alkyl;

R$^b$ denotes H, Het$^b$, Ar$^b$, —CO-Het$^b$, —CO—Ar$^b$, a C₃-C₈-cycloalkyl or a linear or branched alkyl having 1 to 6 carbon atoms, wherein 1 to 3 hydrogen atoms may each be replaced by Het$^b$, Ar$^b$, NH₂, N(C₁-C₆-alkyl)₂, NH(C₁-C₆-alkyl), N(C₁-C₆-alkyl)(C₃-C₈-cycloalkyl), NH(C₃-C₈-cycloalkyl), O(C₁-C₆-alkyl), CN, OH, CF₃, or Hal;

n is 0, 1, 2, 3 or 4;

m is 0, 1, 2, 3 or 4;

q is 1, 2, or 3;

s is 0, 1, 2 or 3;

Hal denotes Cl, Br, I, F;

Ar denotes a divalent monocyclic or fused bicyclic arylene group having 6 to 14 carbon atoms, which may be further substituted with 1 to 4 substituents selected from Hal, C₁-C₆-alkyl, —(CH₂)$_m$OC₁-C₆-alkyl, CN, OH, NO₂, CF₃, —(CH₂)$_m$COOH, and —(CH₂)$_m$COOC₁-C₆-alkyl;

Het denotes a divalent monocyclic or fused bicyclic unsaturated, saturated or aromatic heterocyclic group having 1 to 5 heteroatoms independently selected from N, O, S and/or a group —C=O, which may be further substituted with 1 to 4 substituent selected from Hal, C₁-C₆-alkyl, —(CH₂)$_m$OC₁-C₆-alkyl, CN, OH, NO₂, CF₃, —(CH₂)$_m$COOH, and —(CH₂)$_m$COOC₁-C₆-alkyl;

Ar¹ denotes a monocyclic or bicyclic, aromatic carbocyclic ring having 6 to 14 carbon atoms, which is unsubstituted or monosubstituted, disubstituted or trisubstituted by Hal, —CF₃, —OCF₃, —NO₂, —CN, perfluoroalkyl, Hal, —CF₃, —OCF₃, —NO₂, —CN, perfluoroalkyl, linear or branched C₁-C₆-alkyl, cycloalkyl, —OH, —OC₁-C₆-alkyl, —COC₁-C₆-alkyl, —NH₂, —COH, —COOH, —CONH₂, a group R$^b$, —SO₂NR$^a$R$^b$ or SO₂(C₁-C₆alkyl);

Het¹ denotes a monocyclic or bicyclic saturated, unsaturated or aromatic heterocyclic ring having 1 to 4 heteroatom independently selected from N, O, S and/or a CO group, which is unsubstituted or monosubstituted, disubstituted or trisubstituted by Hal, —CF₃, —OCF₃, —NO₂, —CN, perfluoroalkyl, linear or branched C₁-C₆-alkyl, C₃-C₈-cycloalkyl, —OH, —OC₁-C₆-alkyl, —NH₂, —N(C₁-C₆-alkyl)₂, —COH, —COOH, —CONH₂, —COC₁-C₆-alkyl, —NHCO(C₃-C₆cycloalkyl), a group R$^b$, —SO₂NR$^a$R$^b$ or SO₂(C₁-C₆alkyl), wherein the bicyclic heterocyclic ring can be fused, bridged or spiro;

Het$^b$ denotes a monocyclic or bicyclic saturated, unsaturated or aromatic heterocyclic ring having 1 to 4 heteroatom independently selected from N, O, S and/or a CO group, which is unsubstituted or monosubstituted, disubstituted or trisubstituted by Hal, —CF₃, —OCF₃, —NO₂, —CN, perfluoroalkyl, —OH, —OC₁-C₆-alkyl, —NH₂, —COH, —COOH, —CONH₂, or by a linear or branched C₁-C₆-alkyl wherein 1 to 3 hydrogen atoms may each be replaced by NH₂, N(C₁-C₆-alkyl)₂, NH(C₁-C₆-alkyl), N(C₁-C₆-alkyl)(C₃-C₈-cycloalkyl), NH(C₃-C₈-cycloalkyl), O(C₁-C₆-alkyl), CN, OH, CF₃, Hal, C₃-C₈-cycloalkyl, or by a 4 to 8-membered heterocyclic ring containing a heteroatom selected from O, S and N, wherein the bicyclic heterocyclic ring can be fused or spiro;

Ar$^b$ denotes a monocyclic or bicyclic, aromatic carbocyclic ring having 6 to 14 carbon atoms, which is unsubstituted or monosubstituted, disubstituted or trisubstituted by Hal, —CF₃, —OCF₃, —NO₂, —CN, perfluoroalkyl, Hal, —CF₃, —OCF₃, —NO₂, —CN, perfluoroalkyl, —OH, —OC₁-C₆-alkyl, —NH₂, —COH, —COOH, —CONH₂, or by a linear or branched C₁-C₆-alkyl wherein 1 to 3 hydrogen atoms may each be replaced by NH₂, N(C₁-C₆-alkyl)₂, NH(C₁-C₆-alkyl), N(C₁-C₆-alkyl)(C₃-C₈-cycloalkyl), NH(C₃-C₈-cycloalkyl), O(C₁-C₆-alkyl), CN, OH, CF₃, Hal, C₃-C₈-cycloalkyl, or by a 4 to 8-membered heterocyclic ring containing an heteroatom selected from O, S and N; and Cyc denotes a saturated or unsaturated carbocyclic ring having 3 to 8 carbon atoms, wherein 1 to 5 H atoms are replaced by Hal, —CF₃, —OCF₃, —NO₂, —CN, perfluoroalkyl, Hal, —CF₃, —OCF₃, —NO₂, —CN, perfluoroalkyl, linear or branched C₁-C₆-alkyl, cycloalkyl, —OH, —OC₁-C₆-alkyl, —COC₁-C₆-alkyl, —NH₂, —COH, —COOH, —CONH₂, a group R$^b$ such as —CH₂O(C₁-C₆-alkyl), —SO₂NR$^a$R$^b$ or SO₂(C₁-C₆alkyl);

or a pharmaceutically acceptable solvate, tautomer, salt, hydrate, or stereoisomer-thereof, including mixtures thereof in all ratios.

2. A compound according to claim 1, wherein the group Q-E-R³ denotes one of the following groups:

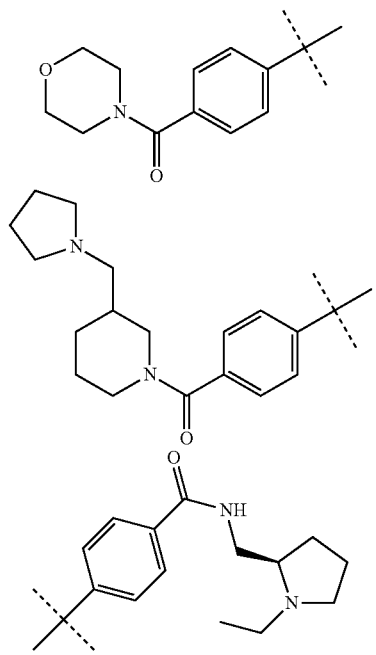

535
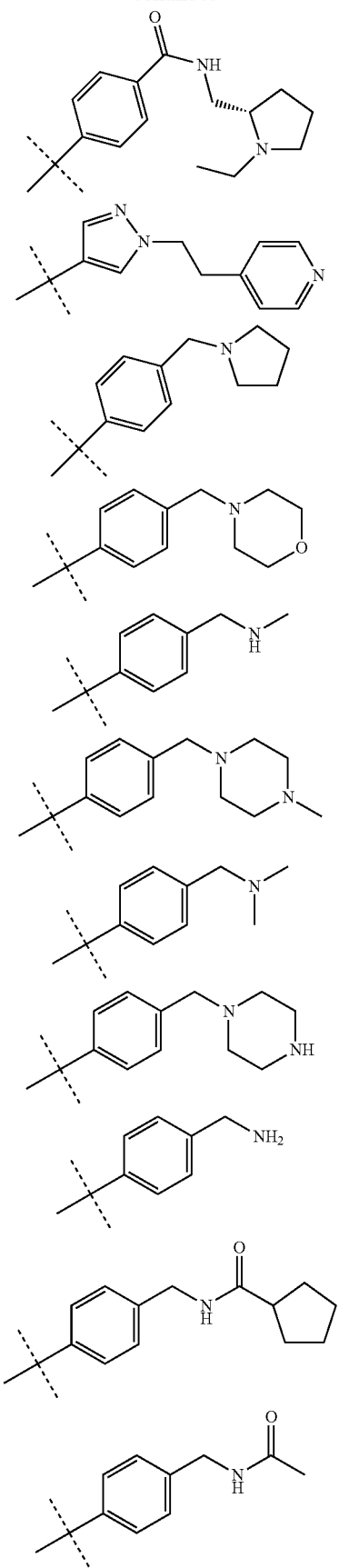
536
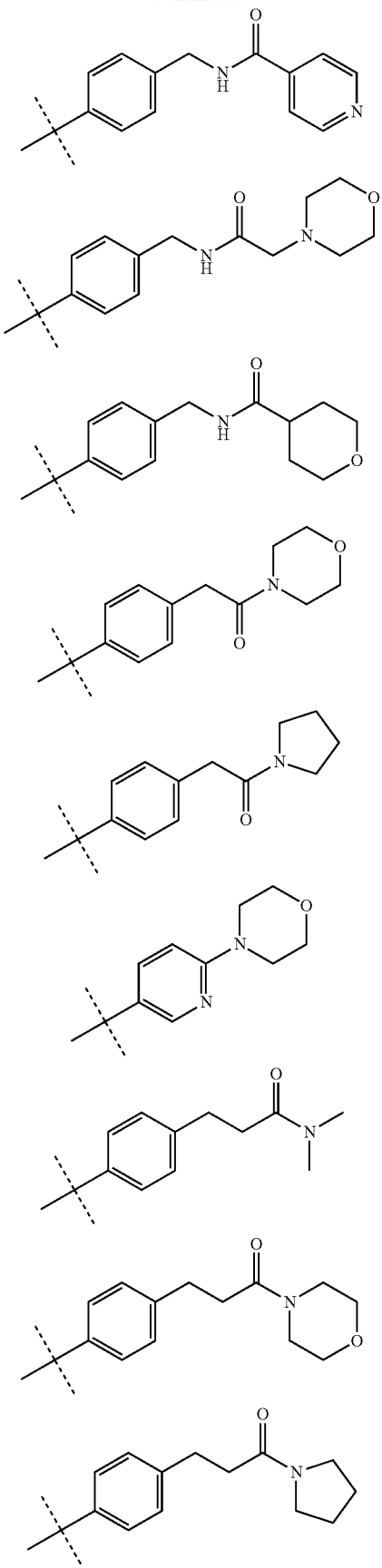

537
-continued
538
-continued
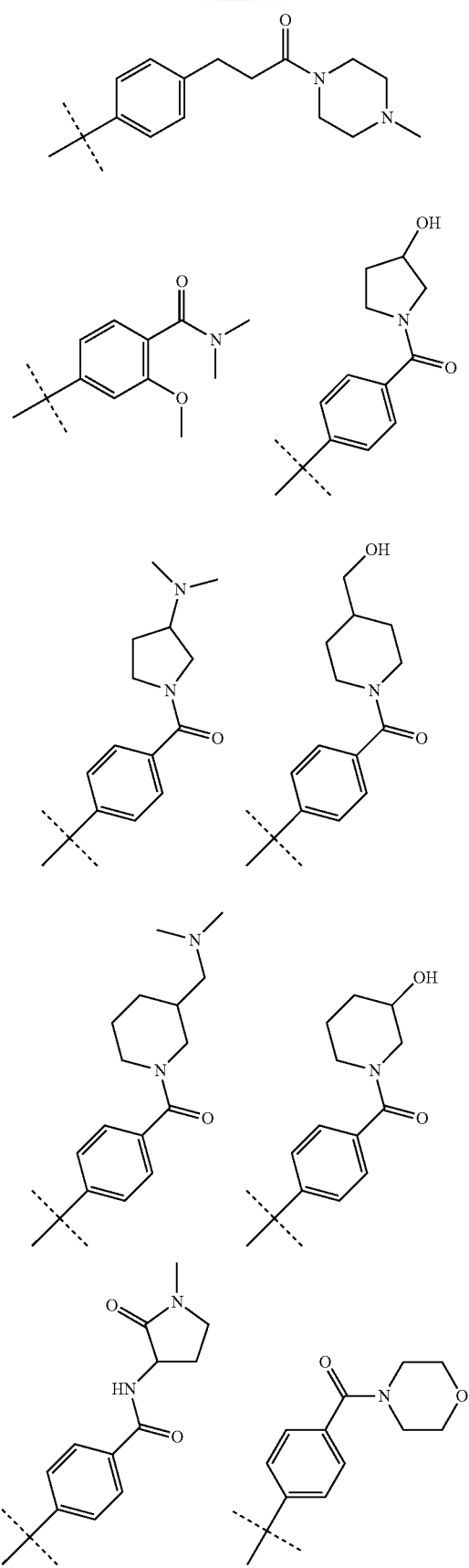
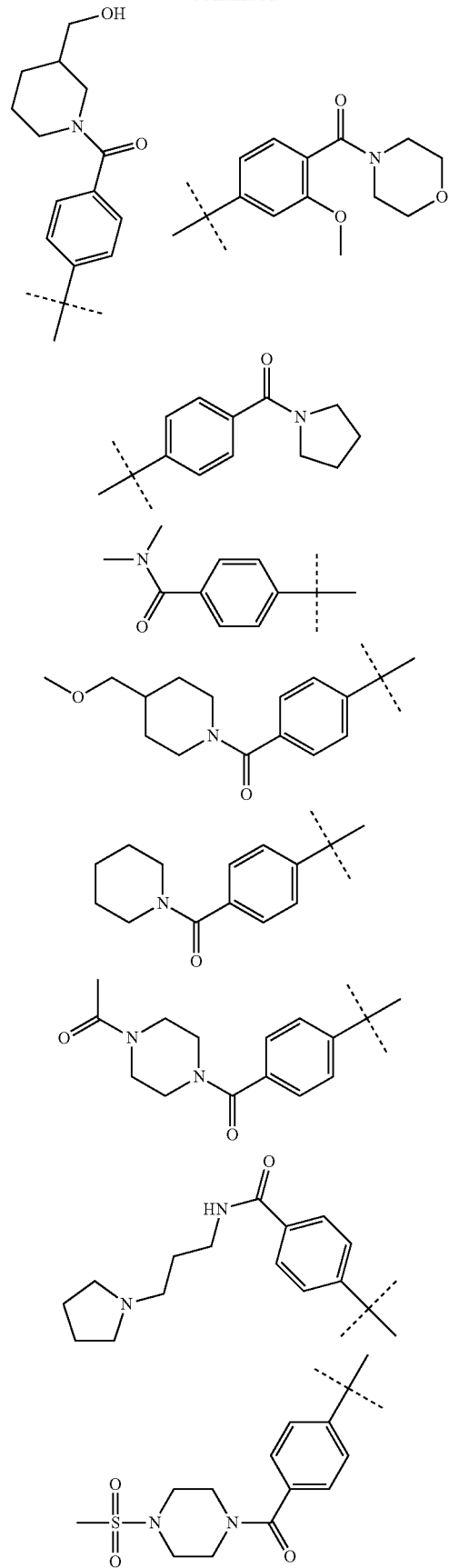

539
-continued
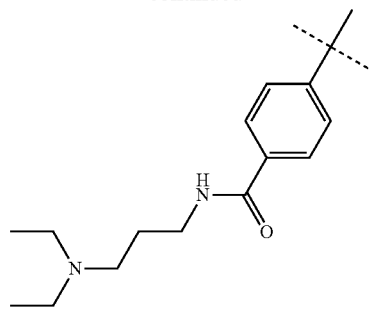
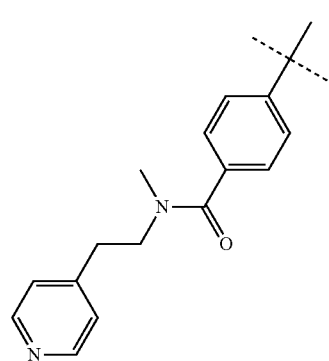
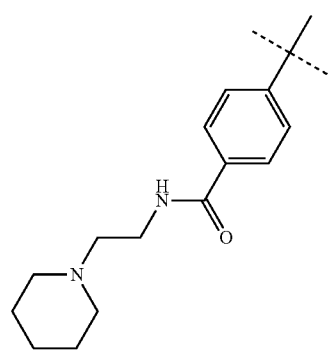
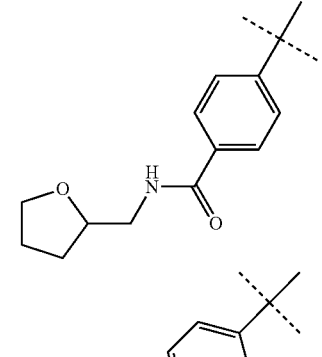
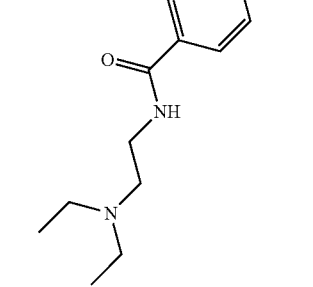
540
-continued
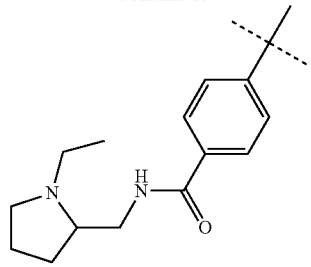
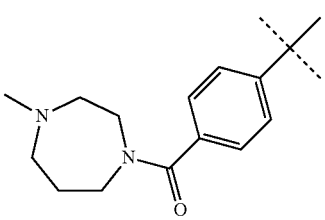
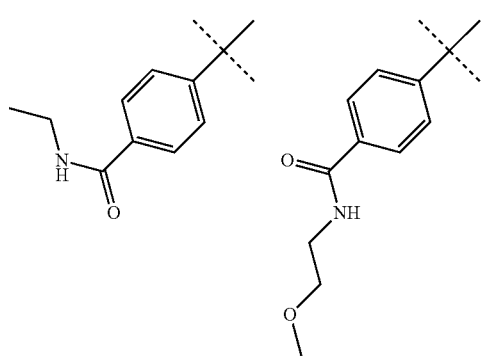
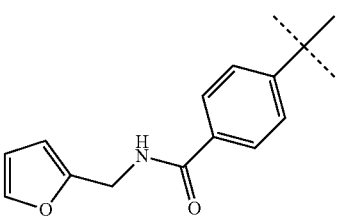
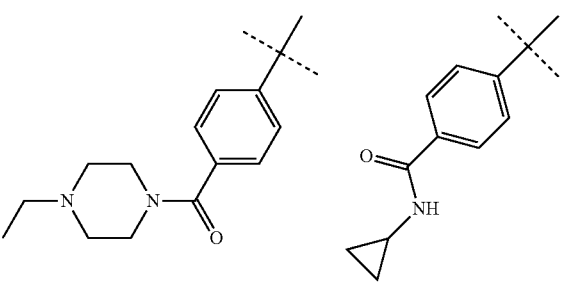
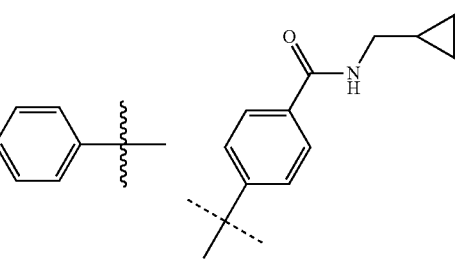

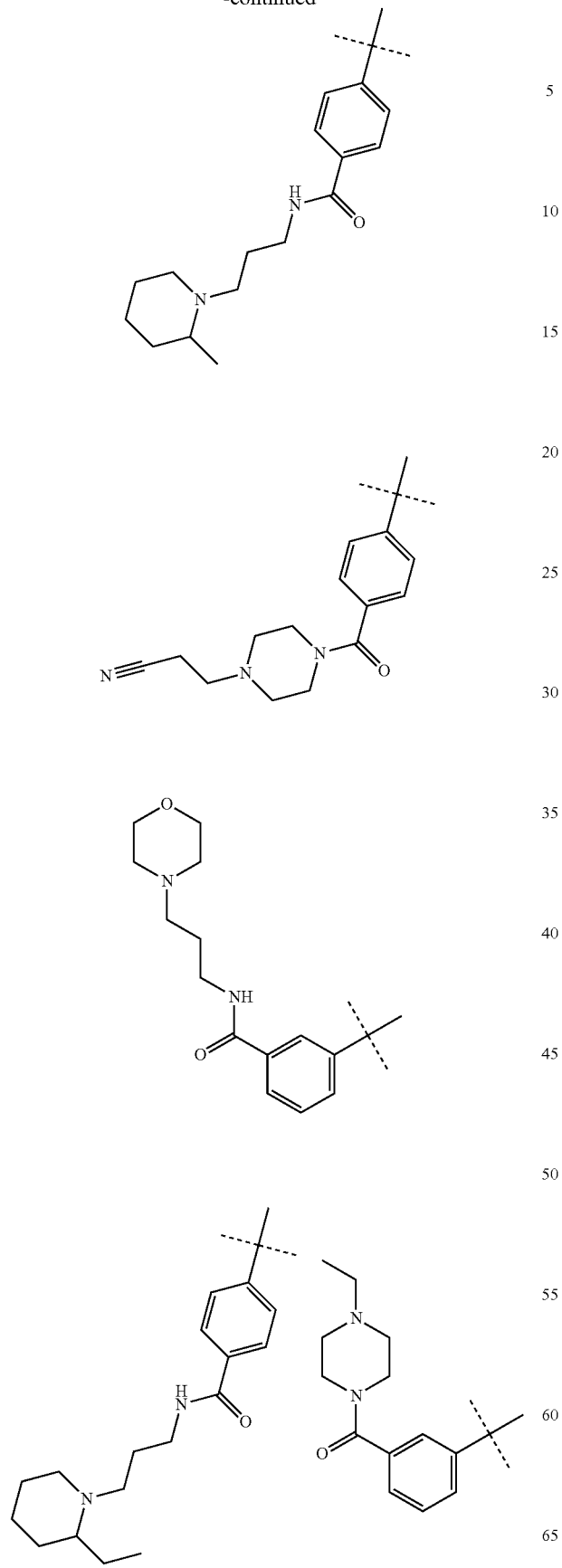

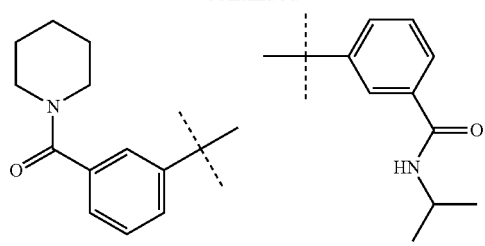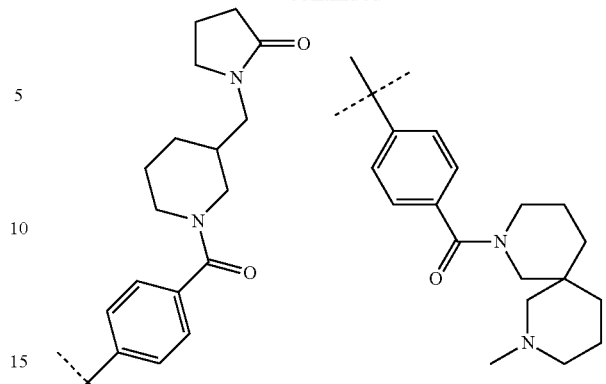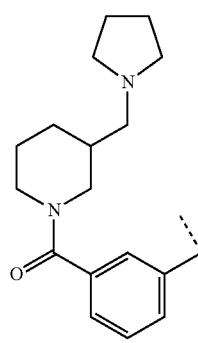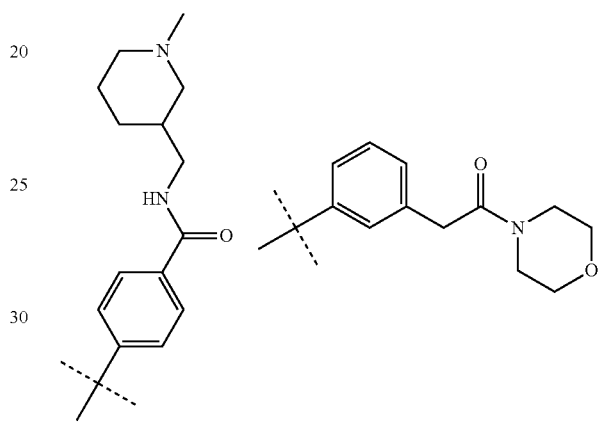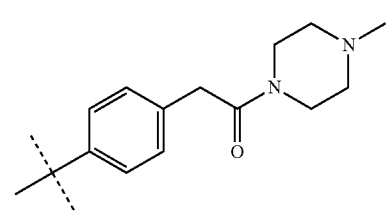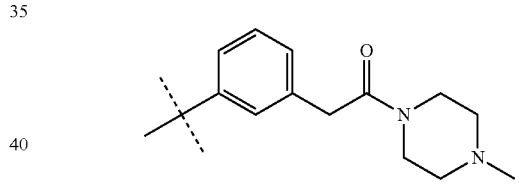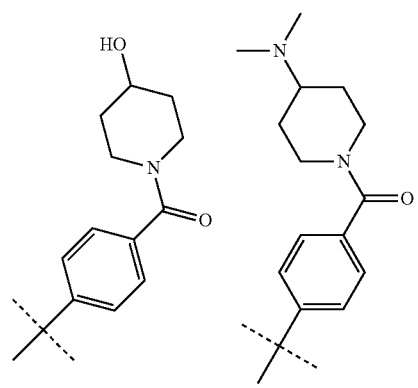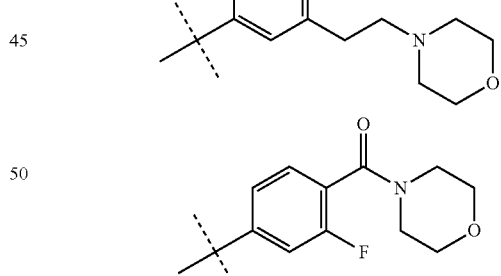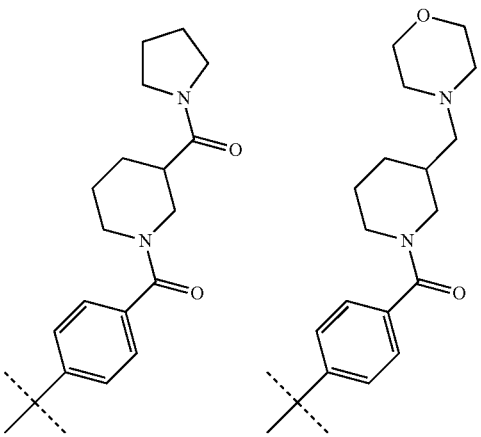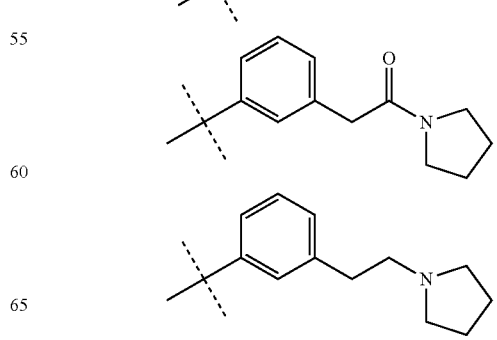

545
-continued
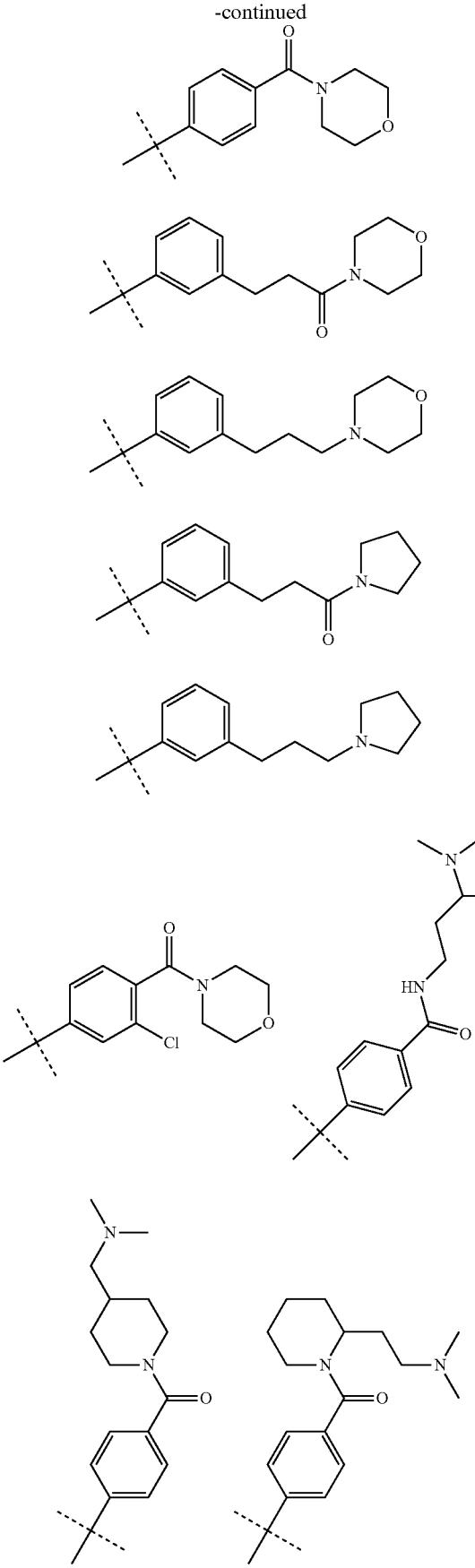
546
-continued
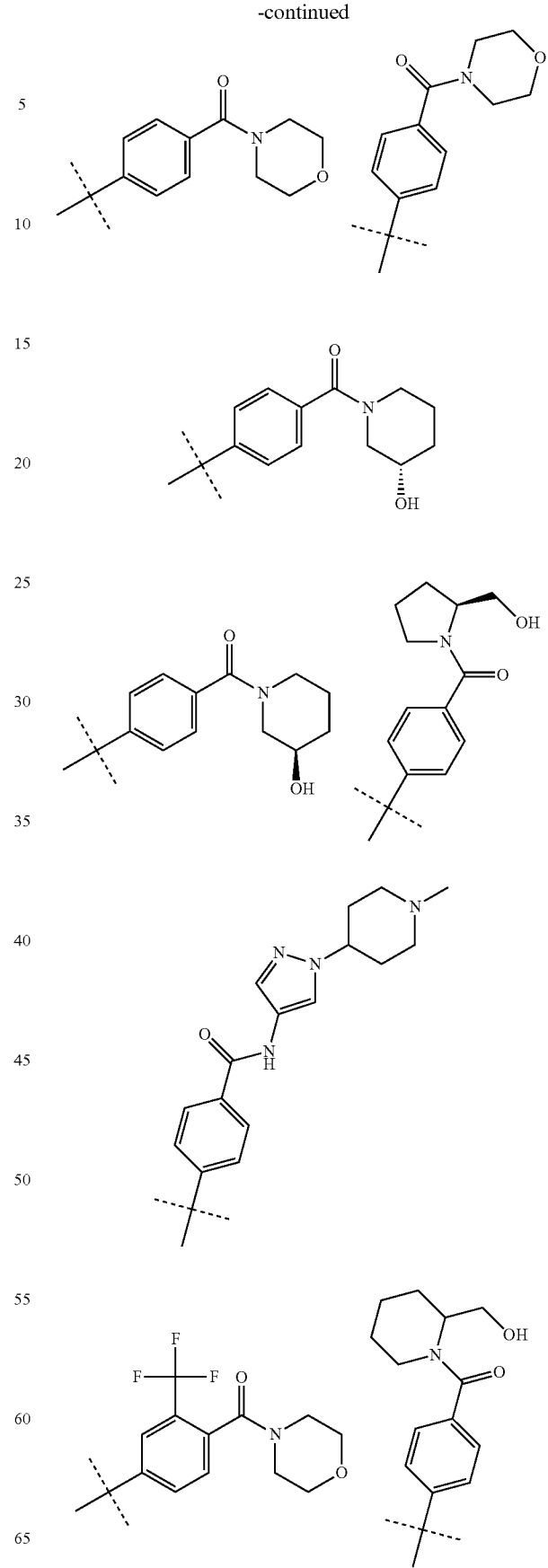

547
-continued
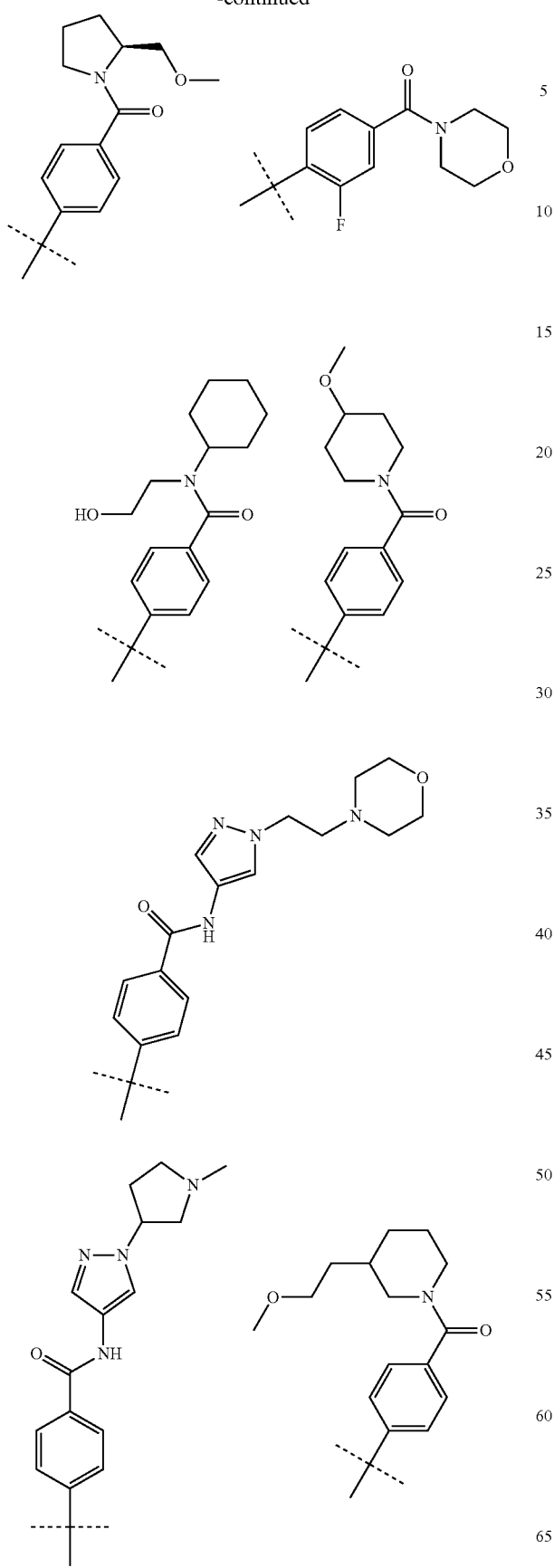
548
-continued
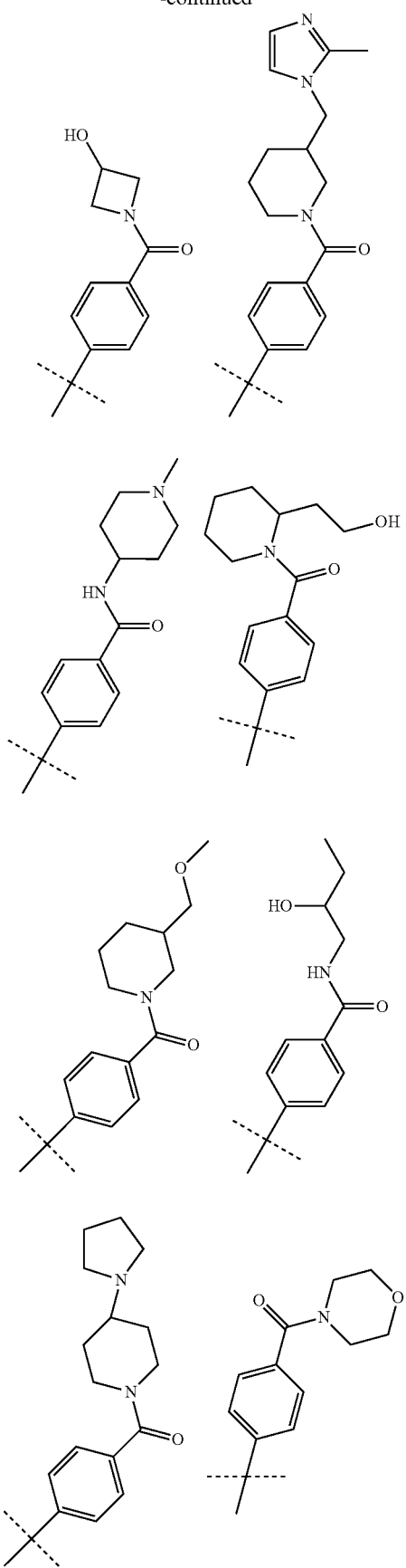

549
-continued
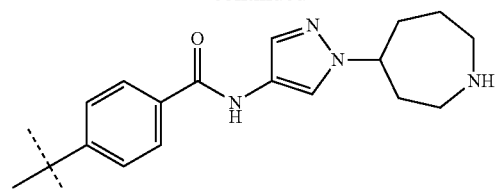
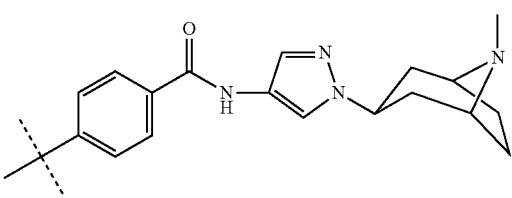
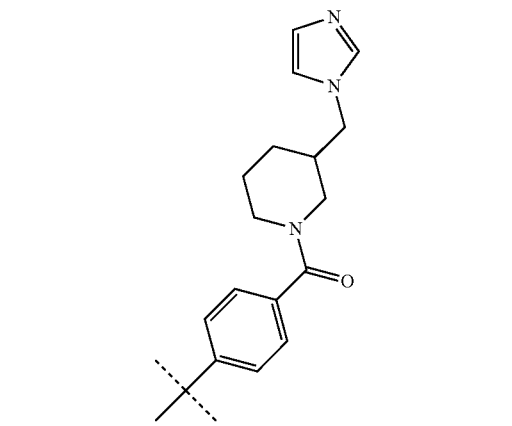
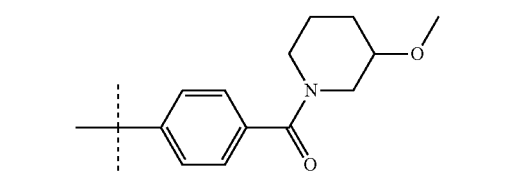
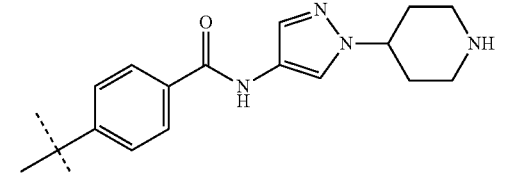
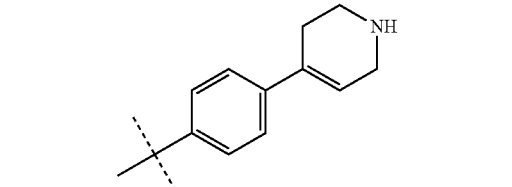
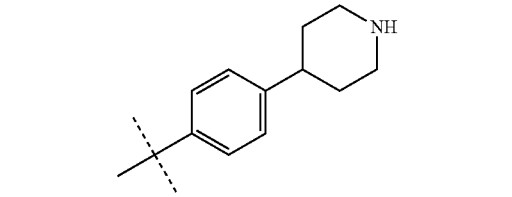
550
-continued
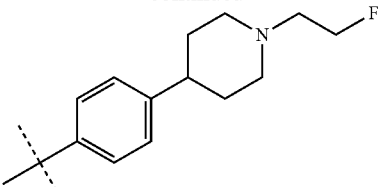
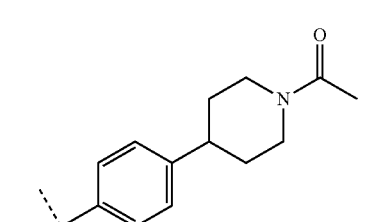
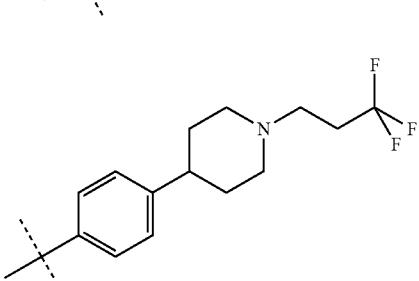
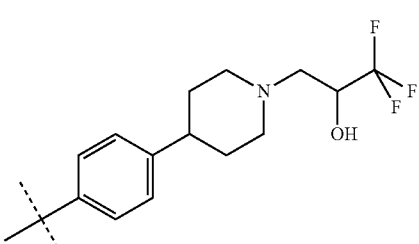
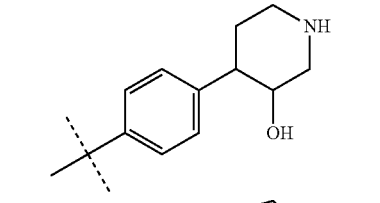
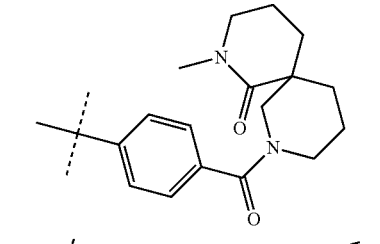
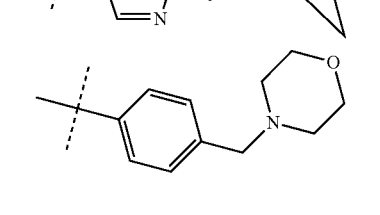

| 551 -continued | 552 -continued |
|---|---|
| 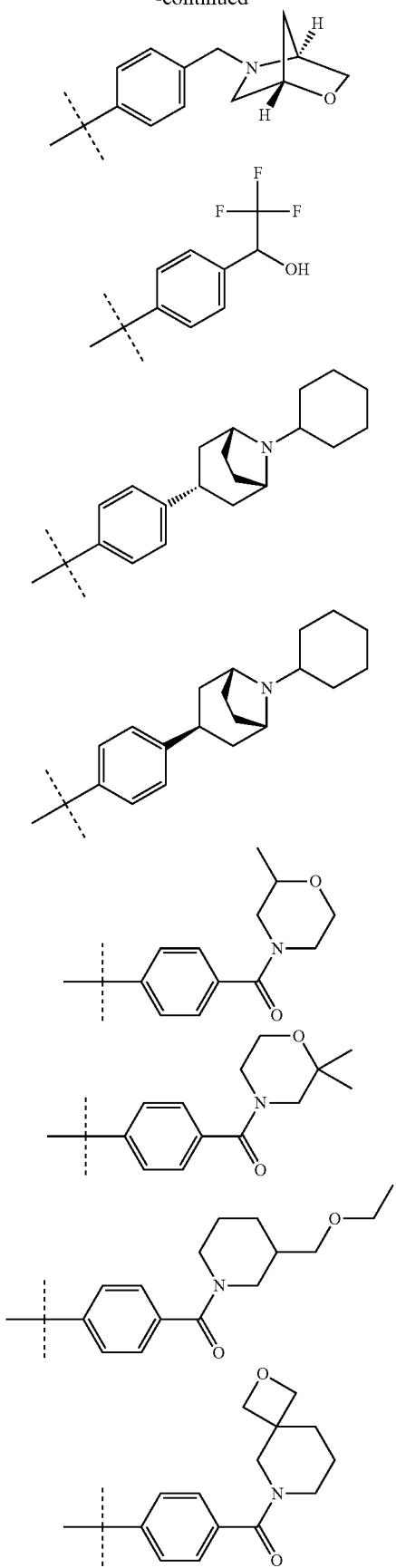 | 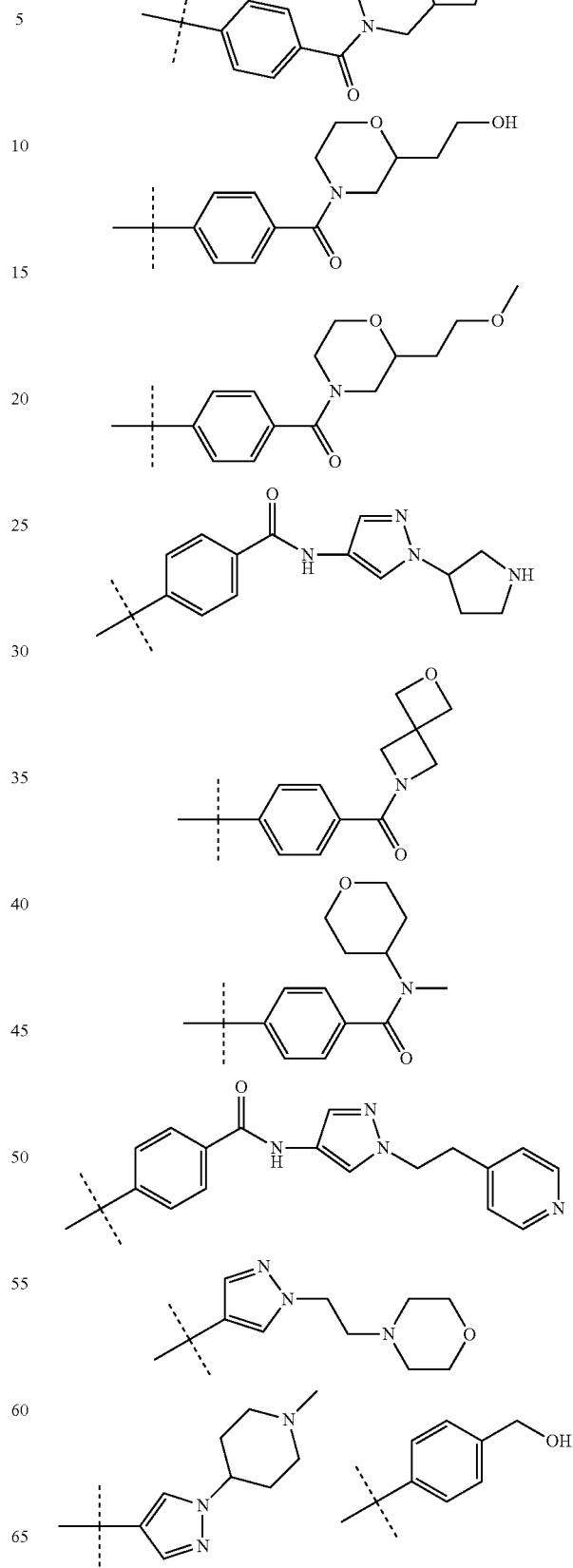 |

553
-continued
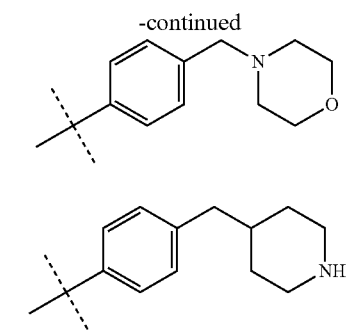
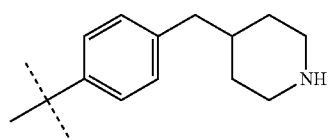
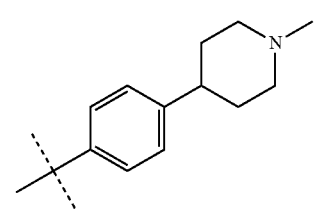
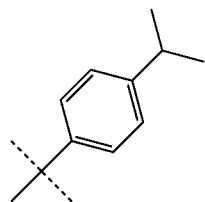
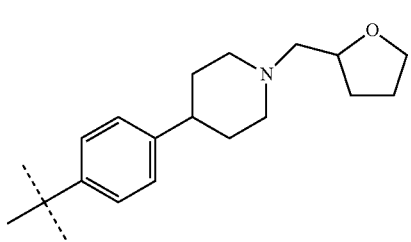
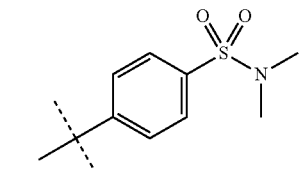
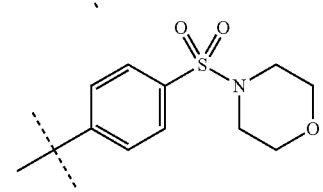
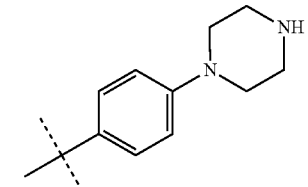
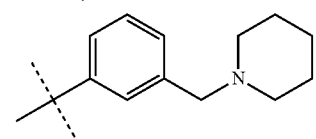
554
-continued
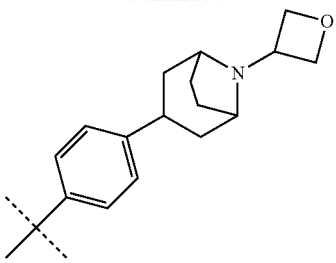
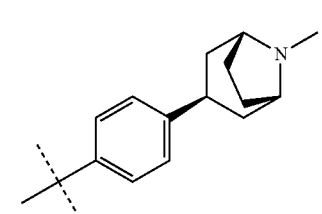
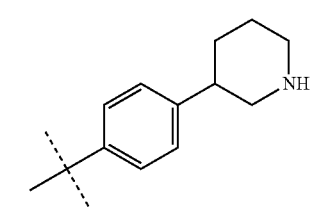
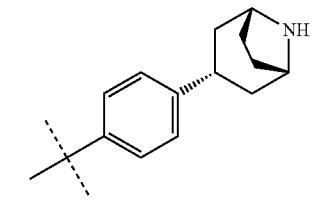
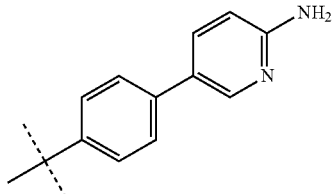
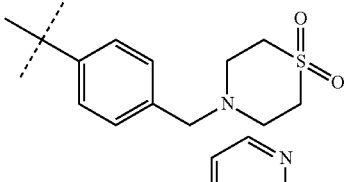
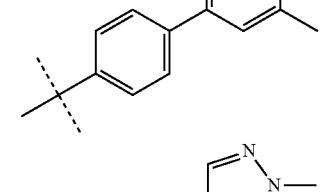
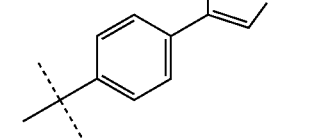

555
-continued
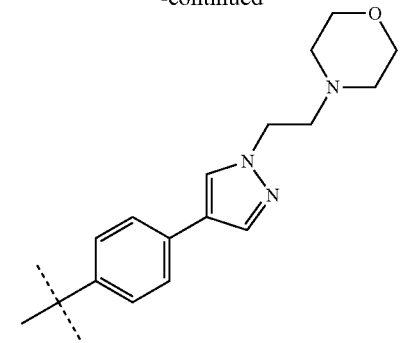
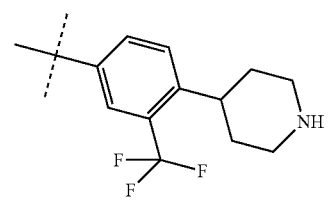
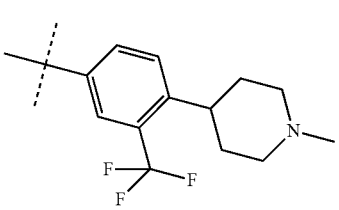
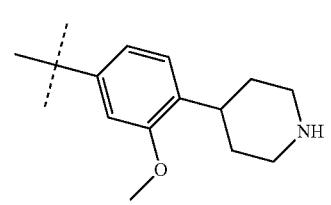
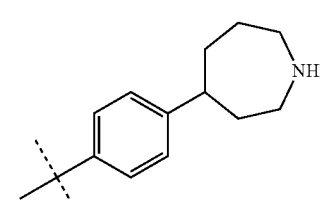
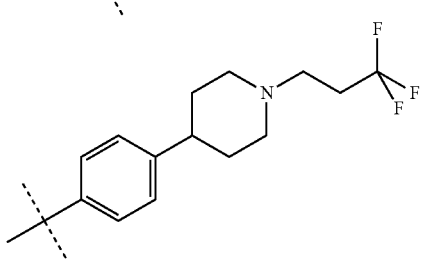
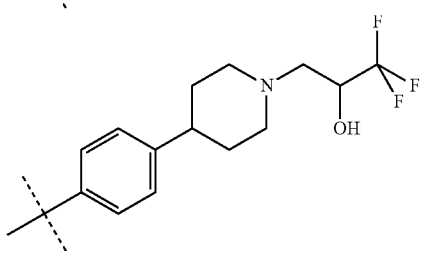
556
-continued
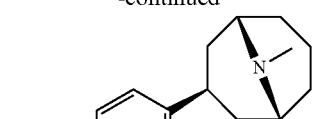
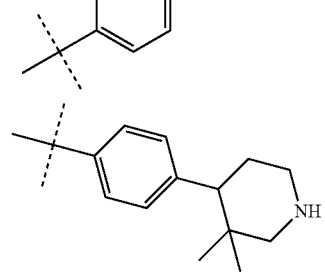
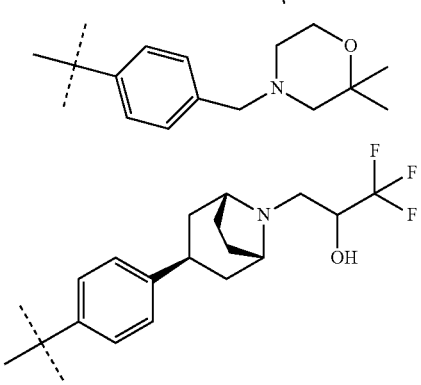
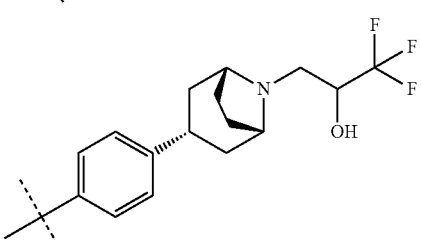
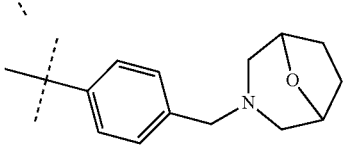
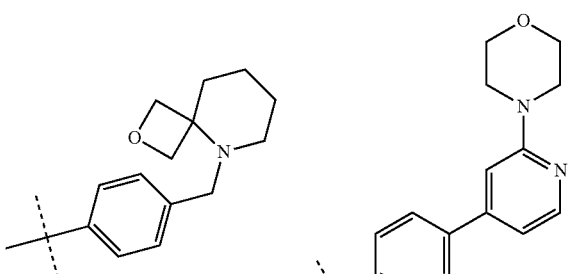
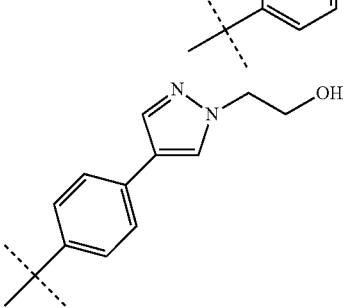

-continued
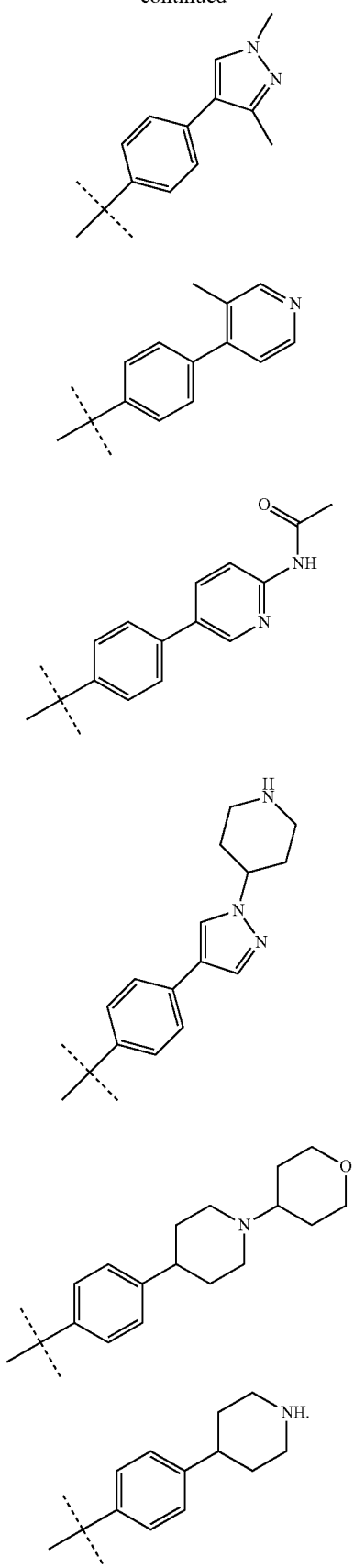
3. A compound according to claim 1, wherein $R^1$ denotes H, Hal, Methyl, trifluoromethyl, methoxy, hydroxy or one of the following groups:
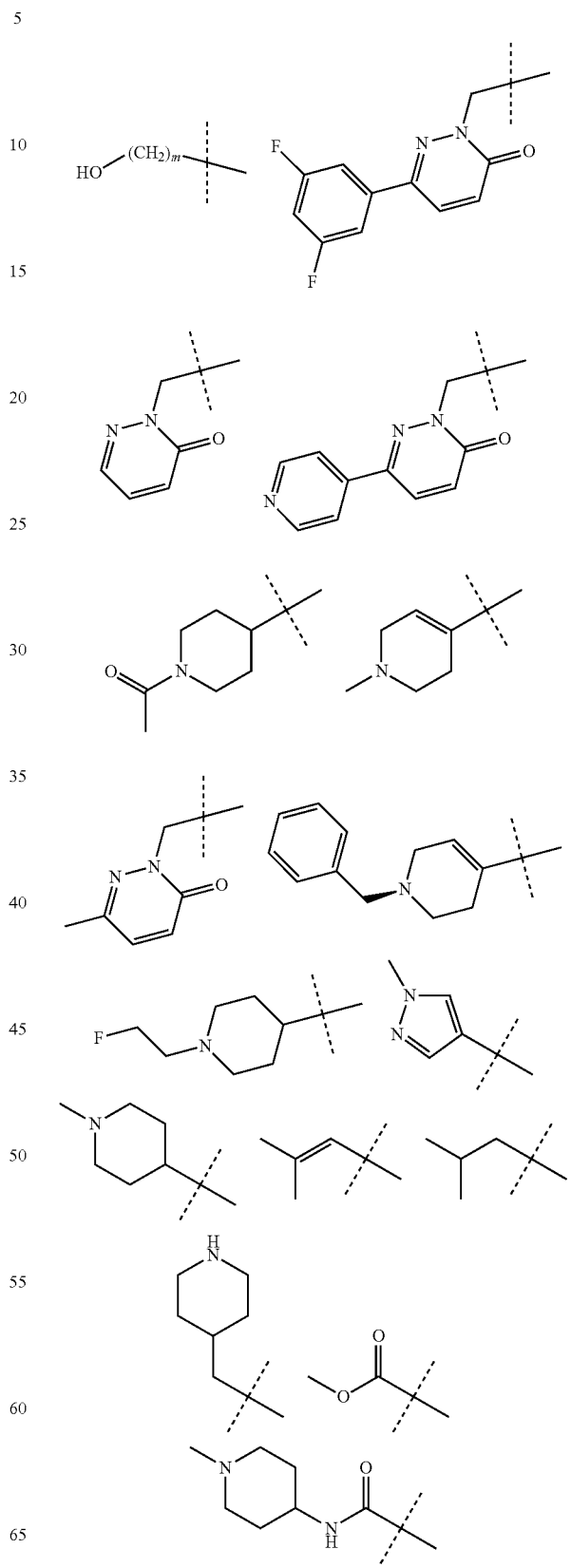

559
-continued
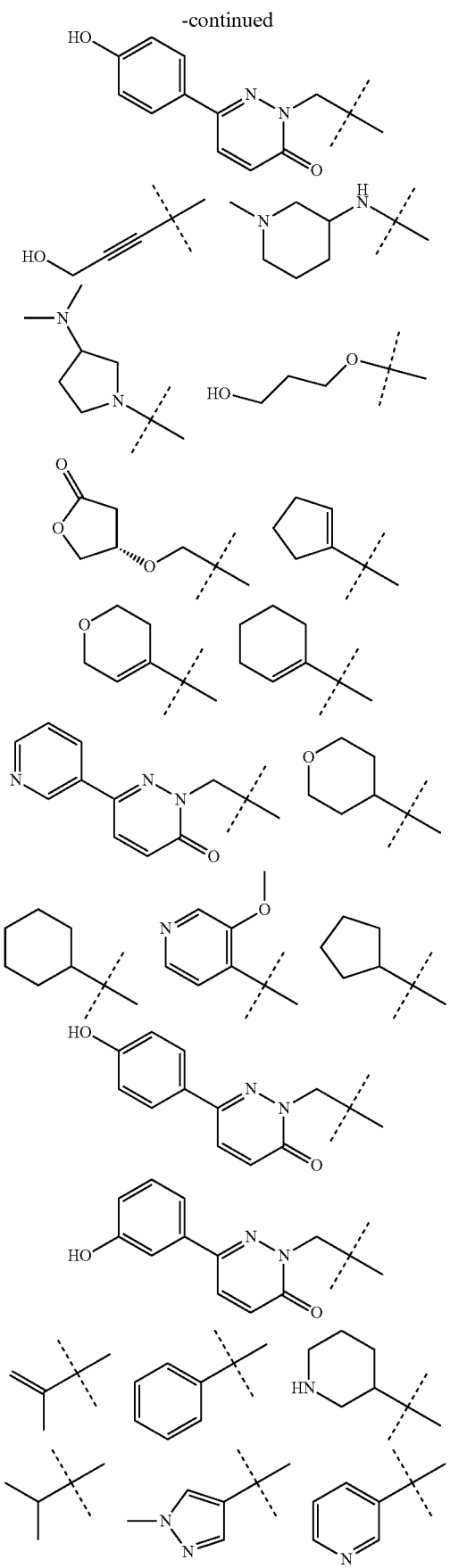
560
-continued
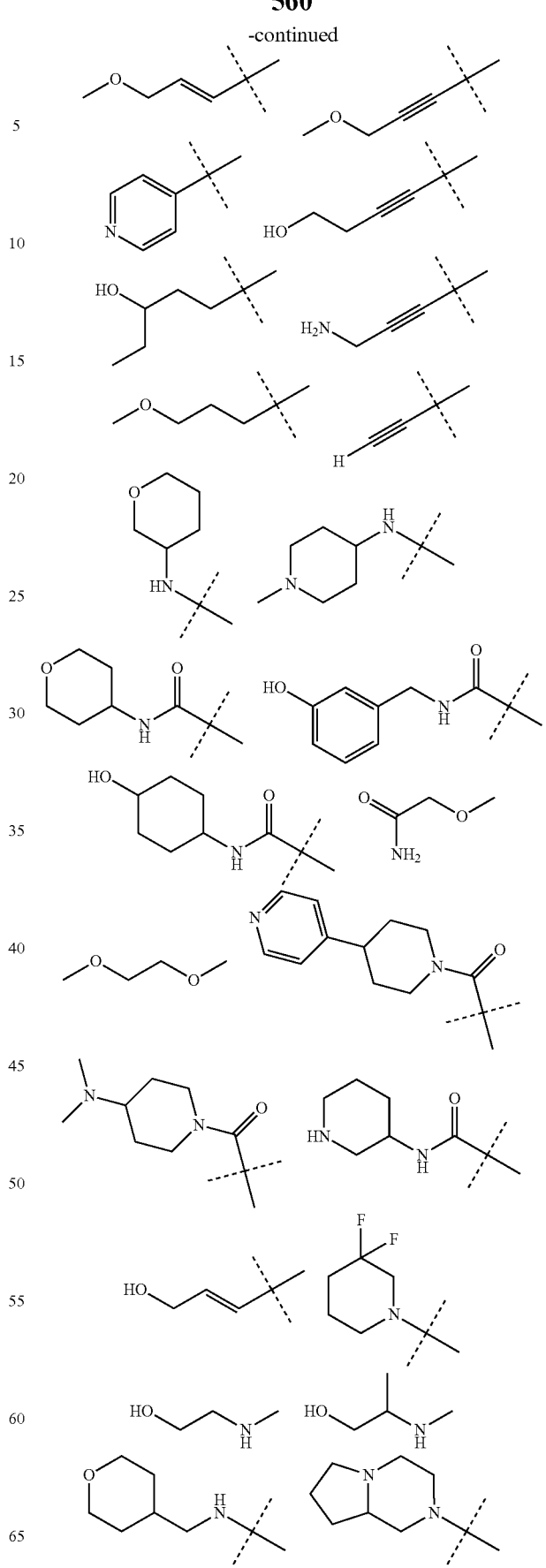

-continued
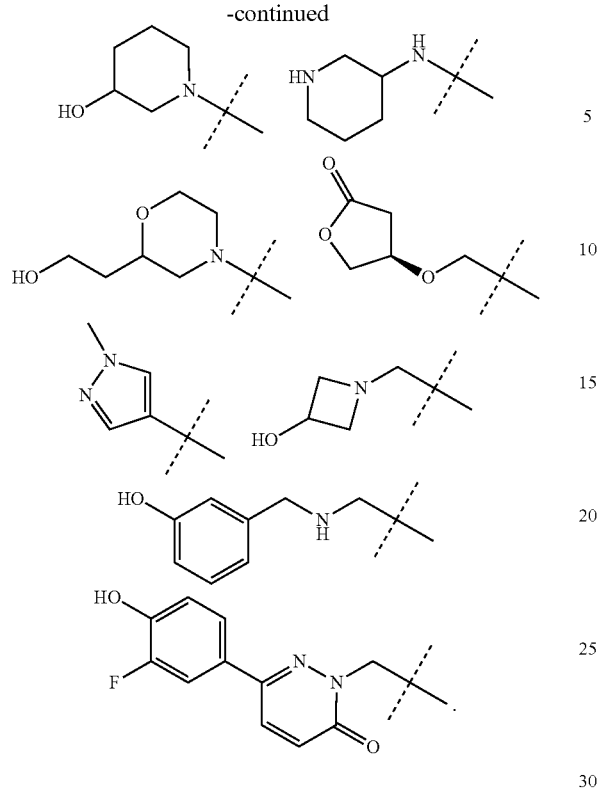
4. A compound according to claim 1, wherein the compound is selected from the following group:

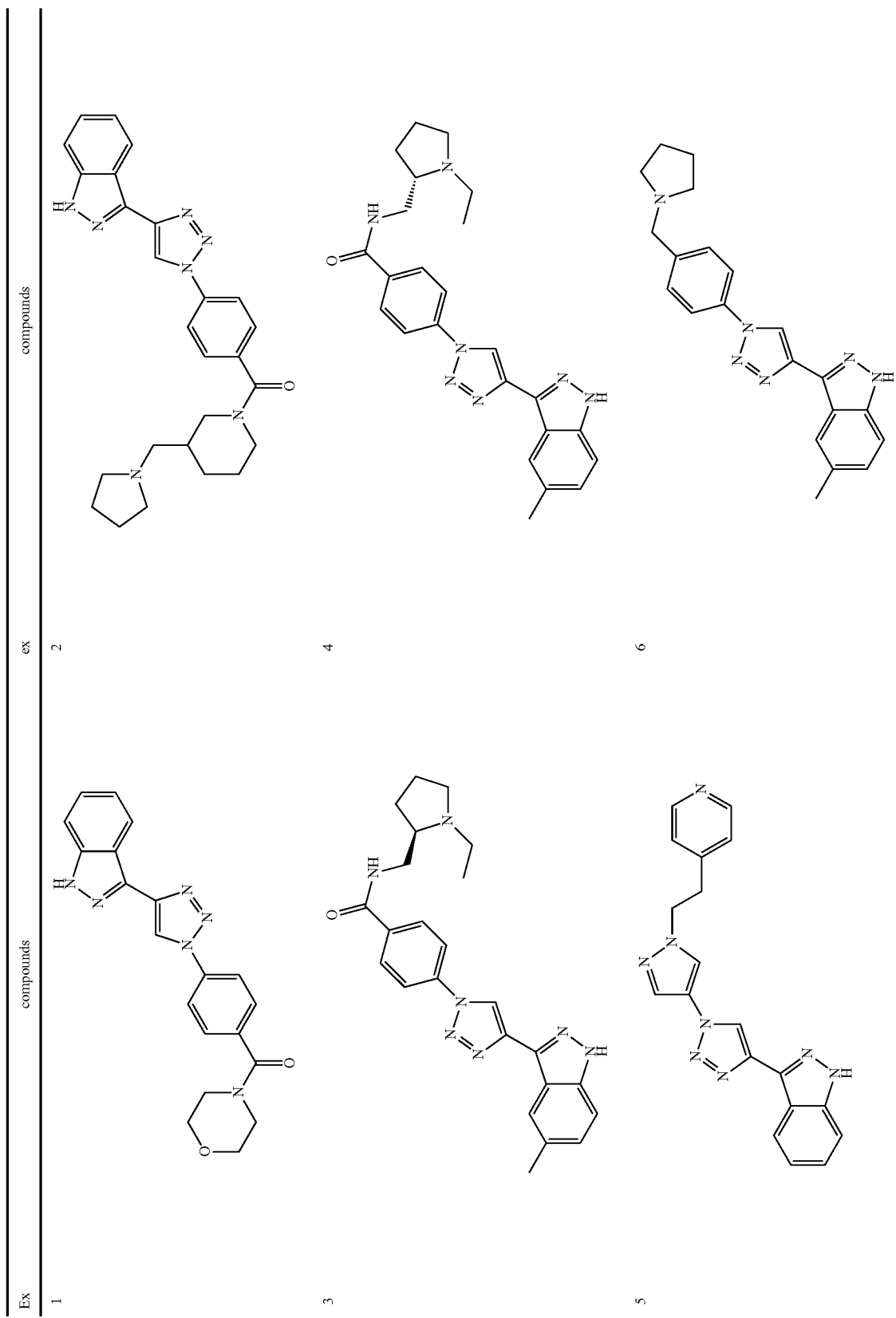

-continued

| Ex | compounds | ex | compounds |
|---|---|---|---|
| 7 | (morpholine-CH2-C6H4-triazole-5-methyl-1H-indazole) | 8 | (CH3NH-CH2-C6H4-triazole-5-methyl-1H-indazole) |
| 9 | (4-methylpiperazine-CH2-C6H4-triazole-5-methyl-1H-indazole) | 10 | ((CH3)2N-CH2-C6H4-triazole-5-methyl-1H-indazole) |
| 11 | (piperazine-CH2-C6H4-triazole-5-methyl-1H-indazole) | 12 | (H2N-CH2-C6H4-triazole-1H-indazole) |

-continued

| Ex | ex compounds |
|---|---|
| 13 | (cyclopentanecarboxamide derivative) |
| 14 | (acetamide derivative) |
| 15 | (isonicotinamide derivative) |
| 16 | (morpholinoacetamide derivative) |

-continued

| Ex | compounds | ex | compounds |
|---|---|---|---|
| 17 | | 18 | |
| 19 | | 20 | |
| 21 | | 22 | |

| Ex | compounds | ex | compounds |
|---|---|---|---|
| 23 | 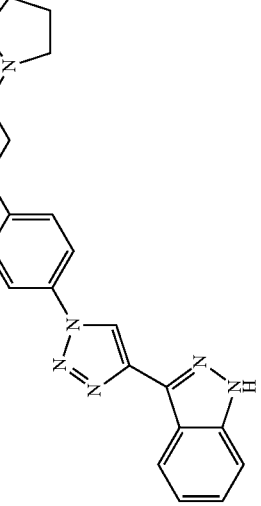 | 24 | 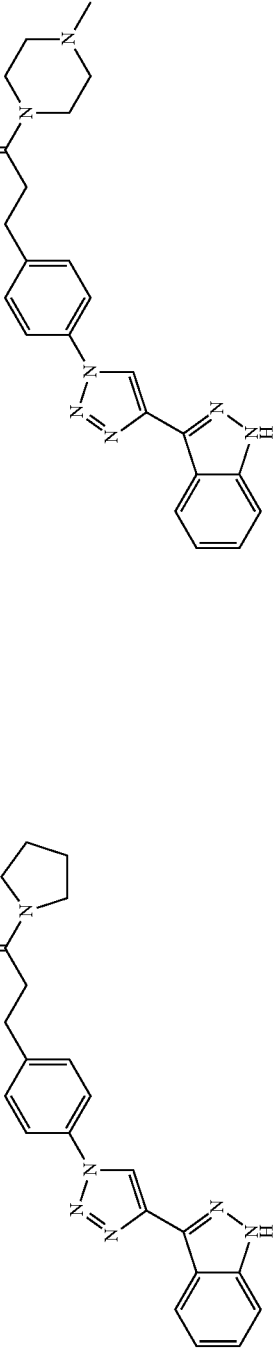 |
| 25 | 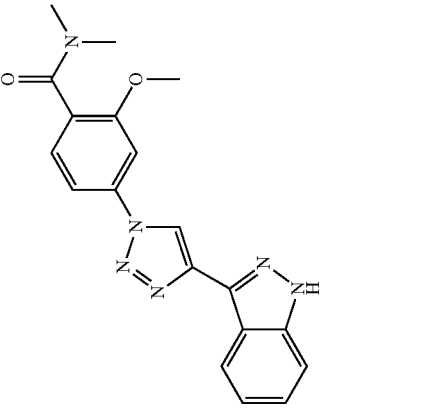 | 26 | 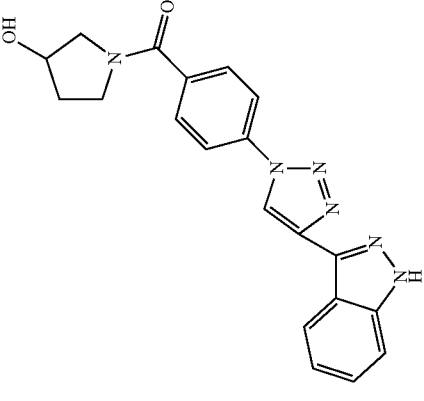 |

-continued

| Ex | compounds | ex | compounds |
|---|---|---|---|
| 27 | (structure) | 28 | (structure) |
| 29 | (structure) | 30 | (structure) |

| Ex | compounds | ex | compounds |
|---|---|---|---|
| 31 | 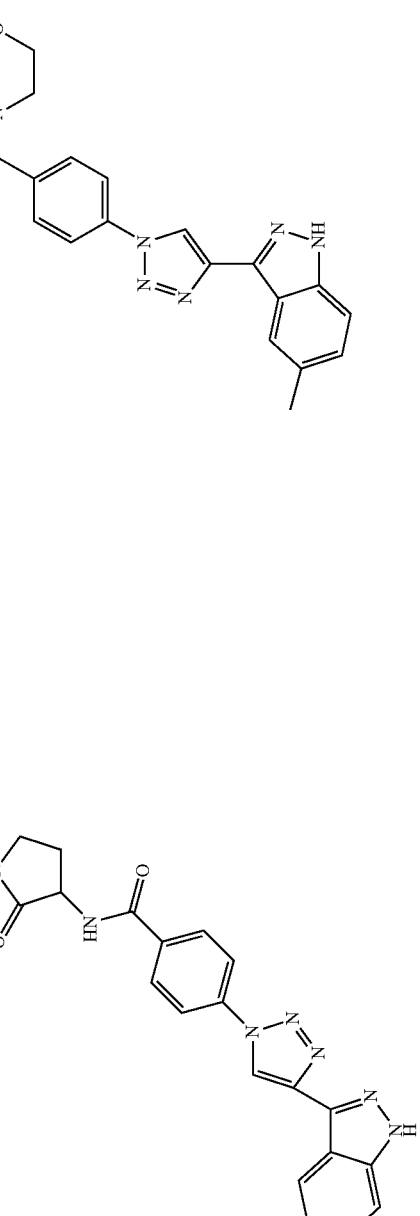 | 32 | 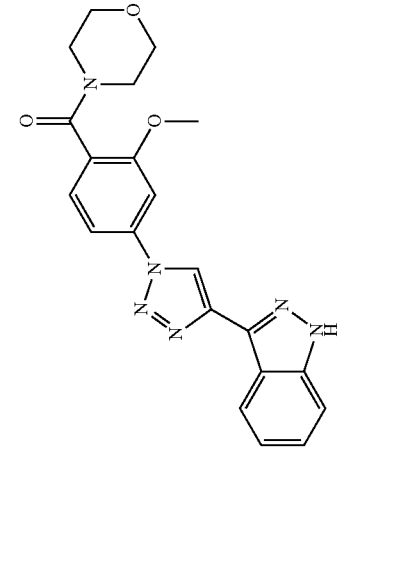 |
| 33 | 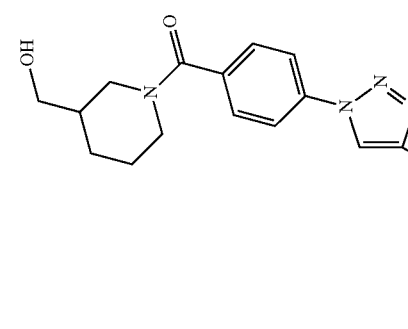 | 34 | 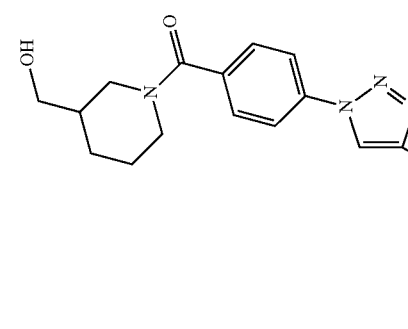 |

-continued

| Ex | compounds | ex | compounds |
|---|---|---|---|
| 35 | | 36 | |
| 37 | | 38 | |
| 39 | | 40 | |

-continued

| Ex | ex compounds | ex | compounds |
|---|---|---|---|
| 41 | | 42 | |
| 43 | | 44 | |

| Ex | compounds | ex | compounds |
|---|---|---|---|
| 45 | (structure) | 46 | (structure) |
| 47 | (structure) | 48 | (structure) |

-continued
| Ex | compounds | ex | compounds |
|---|---|---|---|
| 49 | 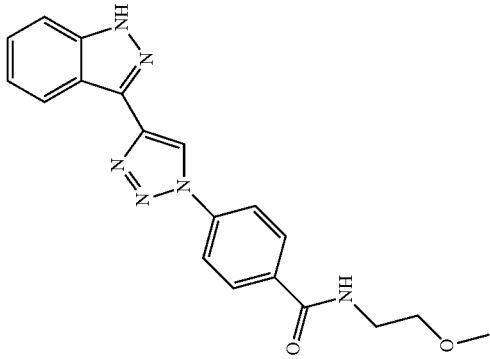 | 50 | 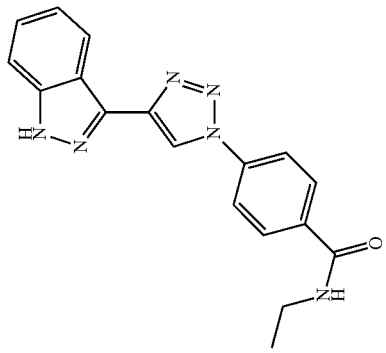 |
| 51 | 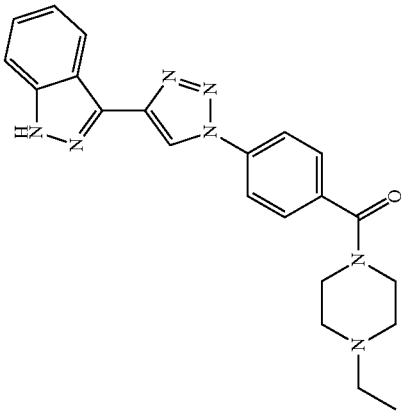 | 52 | 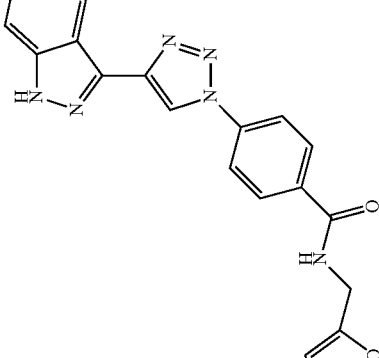 |

| Ex | compounds | ex | compounds |
|---|---|---|---|
| 53 | | 54 | |
| 55 | | 56 | |

-continued

| Ex | compounds |
|---|---|
| 57 | |
| 58 | |
| 59 | |
| 60 | |

-continued

| Ex | compounds | ex | compounds |
|---|---|---|---|
| 61 | | 62 | |
| 63 | | 64 | |

| Ex | compounds | ex | compounds |
|---|---|---|---|
| 65 | (structure) | 66 | (structure) |
| 67 | (structure) | 68 | (structure) |
| 69 | (structure) | 70 | (structure) |

| Ex | ex compounds | compounds |
|---|---|---|
| 71 | 72 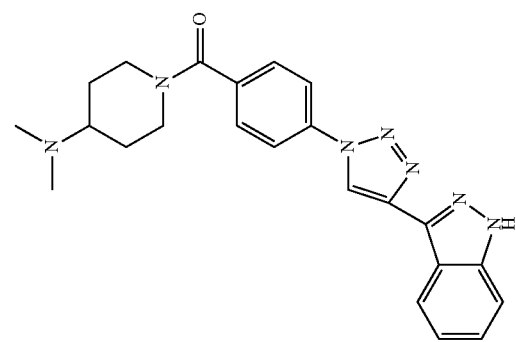 | 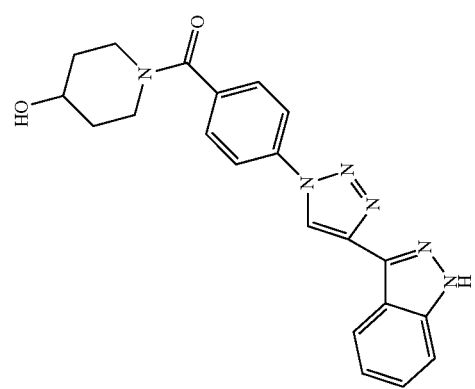 |

-continued
| Ex | compounds | ex | compounds |
|---|---|---|---|
| 73 | 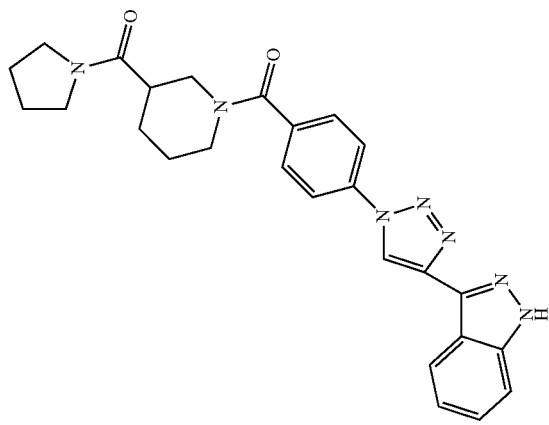 | 74 | |

| Ex | compounds | ex | compounds |
|---|---|---|---|
| 75 | 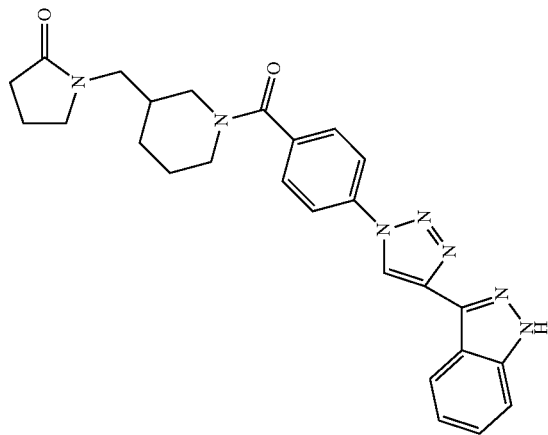 | 76 | 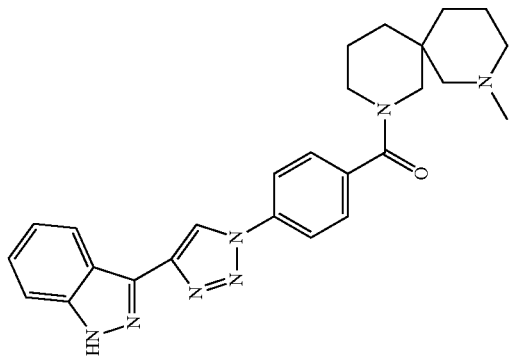 |

-continued

| Ex | compounds | ex | compounds |
|---|---|---|---|
| 77 | | 78 | |
| 79 | | 80 | |

-continued

| Ex | compounds | Ex | compounds |
|---|---|---|---|
| 81 | | 82 | |
| 83 | | 84 | |

| Ex | ex | compounds | ex | compounds |
|---|---|---|---|---|
| 85 | 86 | 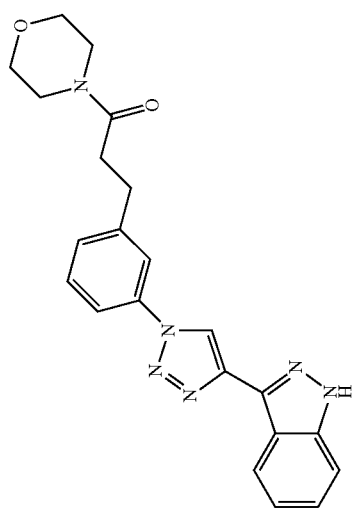 | 88 | 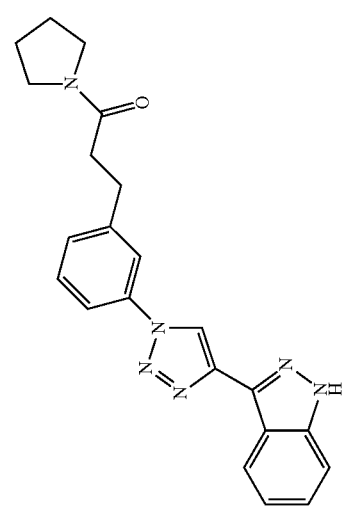 |
| 87 | | 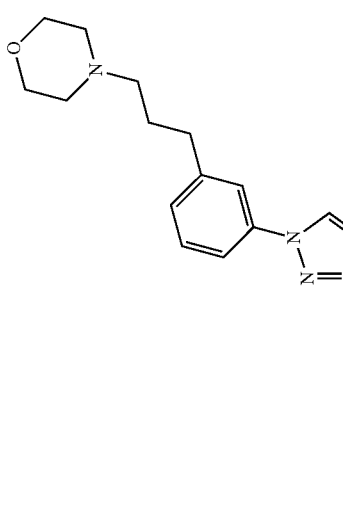 | | 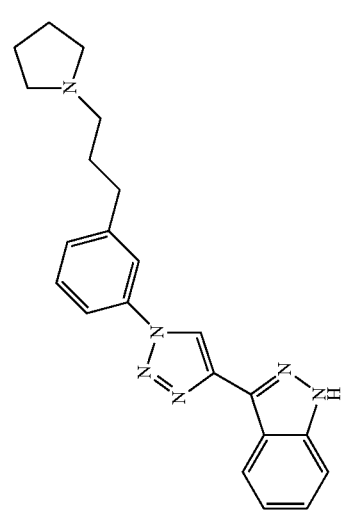 |

| Ex | ex compounds | Ex | compounds |
|---|---|---|---|
| 89 | 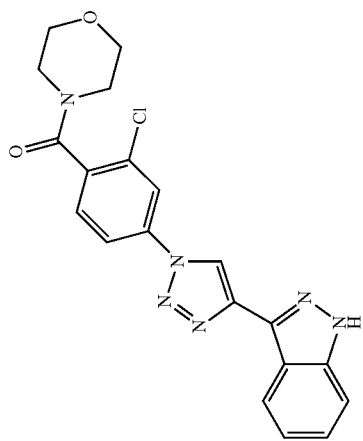 | 90 | 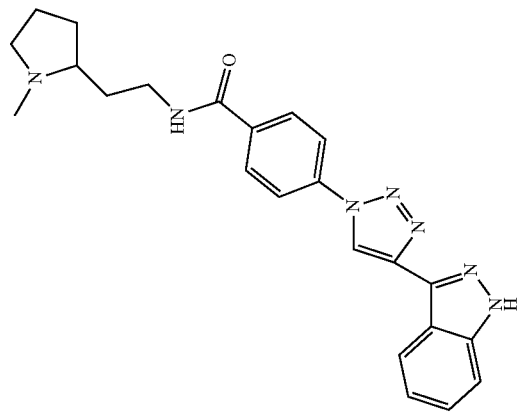 |

| Ex | ex | compounds | compounds |
|---|---|---|---|
| 91 | 92 | 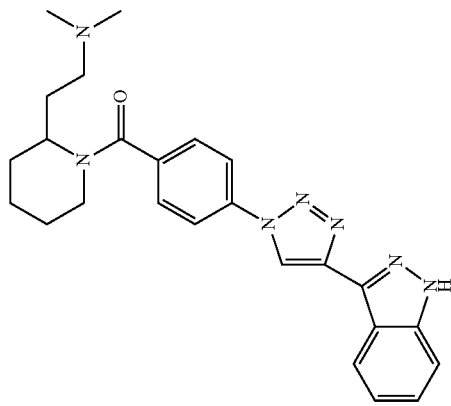 | 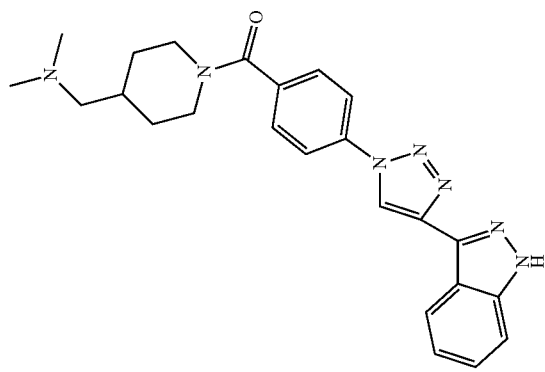 |

| Ex | ex | compounds |
|---|---|---|
| 94 | | 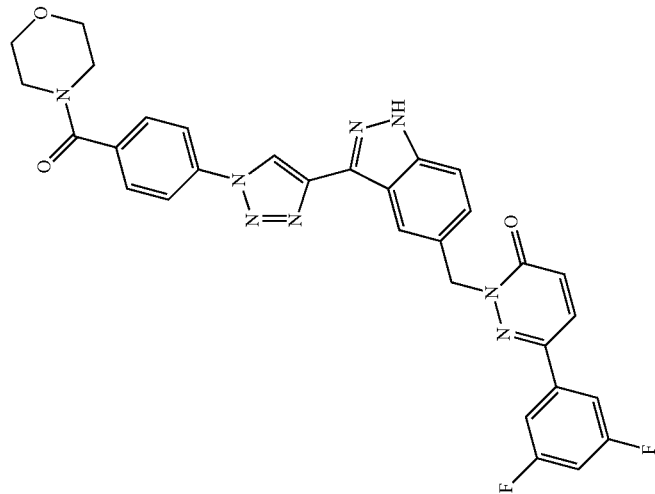 |
| 93 | | 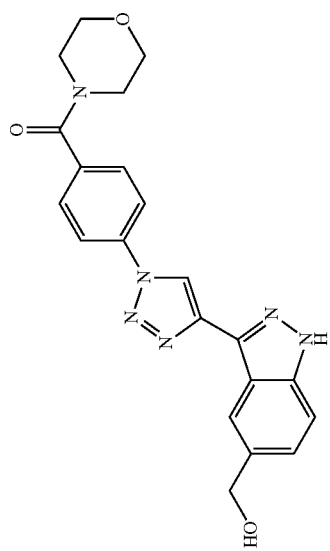 |

-continued

| Ex | compounds |
|---|---|
| 95 | (morpholine-carbonyl-phenyl-triazole-indazole-CH2-pyridazinone structure) |
| 96 | ((3-hydroxypiperidine-carbonyl-phenyl-triazole-indazole structure) |

| Ex | ex | compounds | compounds |
|---|---|---|---|
| 97 | 98 | 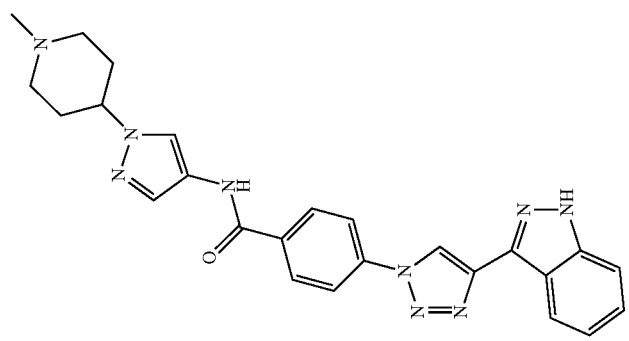 | 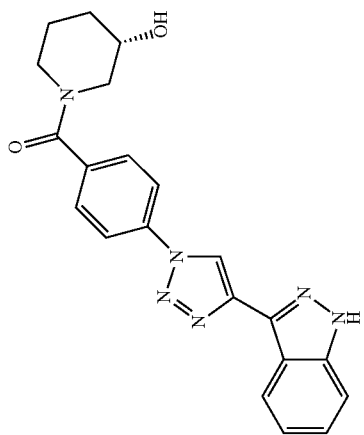 |

-continued
| Ex | compounds | ex | compounds |
|---|---|---|---|
| 99 | 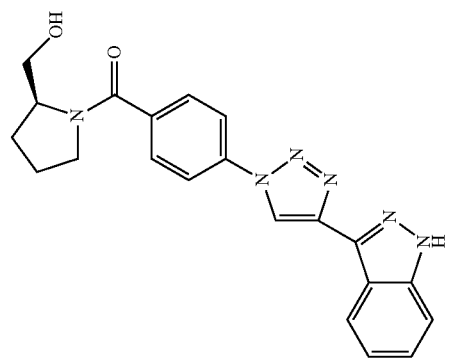 | 100 | 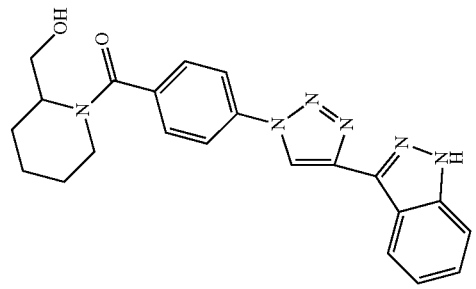 |
| 101 | 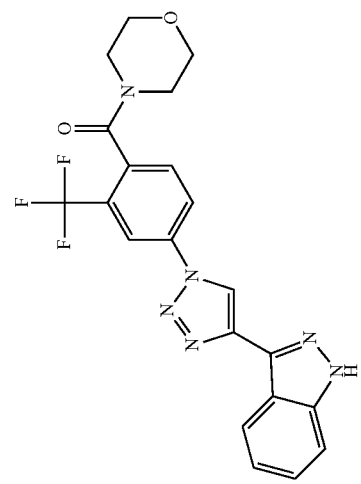 | 102 | 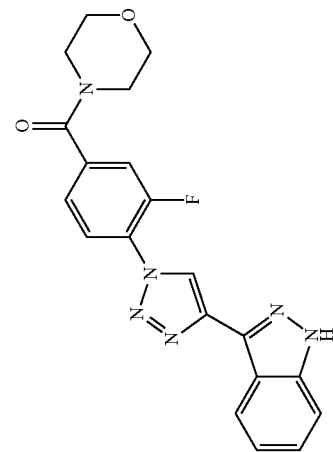 |

| Ex | ex | compounds | compounds |
|---|---|---|---|
| 103 | | 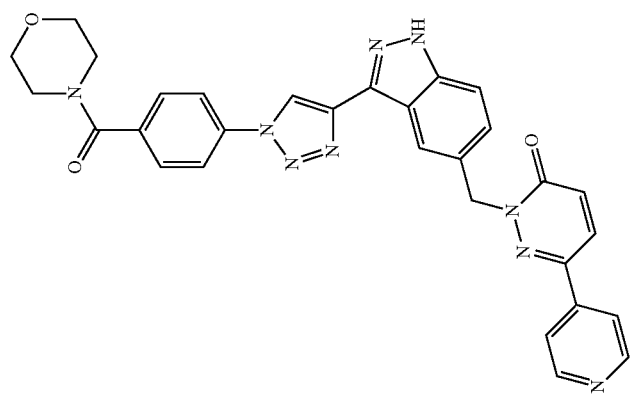 | |
| | 104 | | 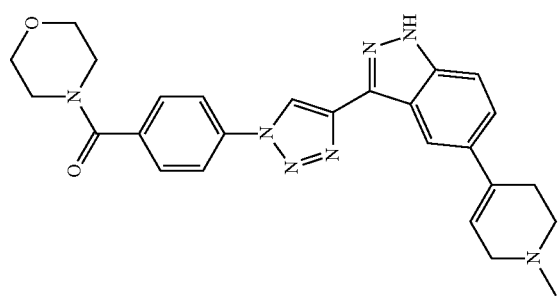 |

| Ex | ex | compounds |
|---|---|---|
| | | -continued |
| 105 | 106 | 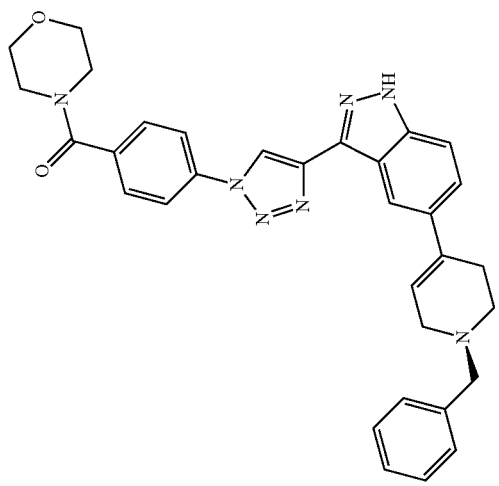 |
| | | 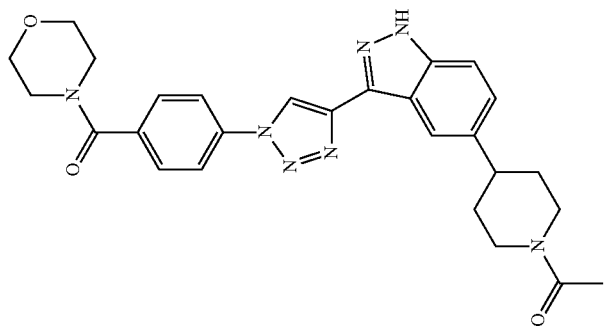 |

| Ex | compounds | ex | compounds |
|---|---|---|---|
| 107 | (structure) | 108 | (structure) |
| 109 | (structure) | 110 | (structure) |

| Ex | ex | compounds |
|---|---|---|
| 111 | 112 | |

-continued

-continued
| Ex | ex | compounds |
|---|---|---|
| 113 | | 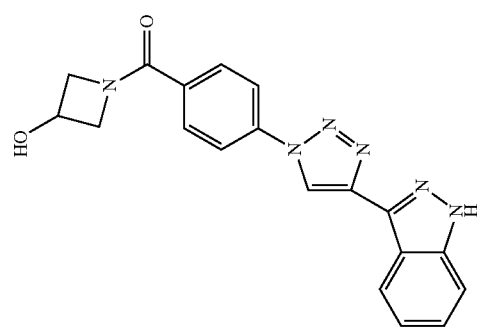 |
| 114 | | 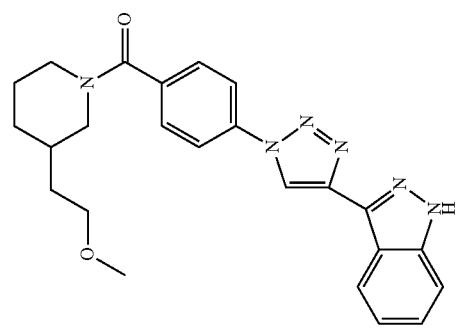 |

| Ex | compounds | ex | compounds |
|---|---|---|---|
| 115 | 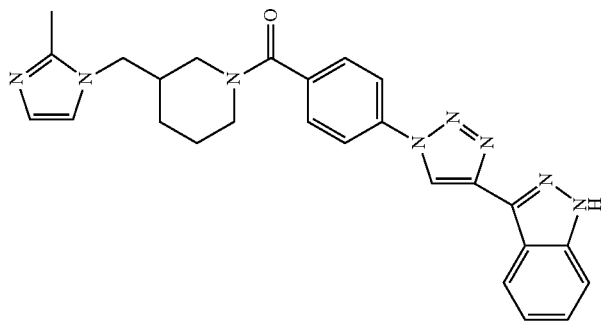 | 116 | 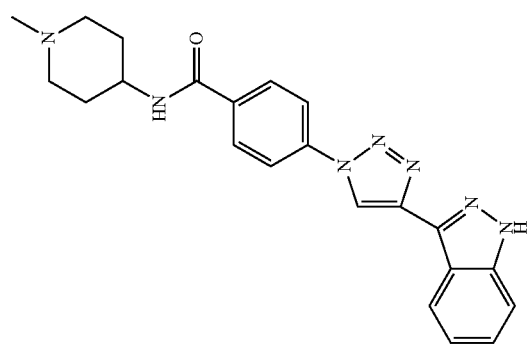 |

| Ex | compounds | Ex | compounds |
|---|---|---|---|
| 117 | 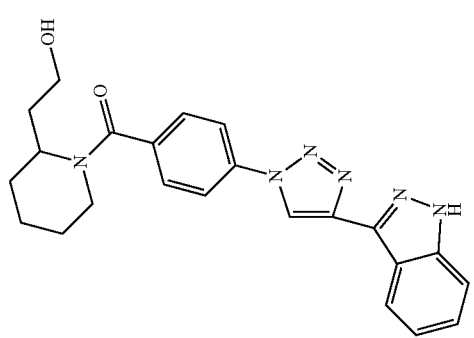 | 118 | 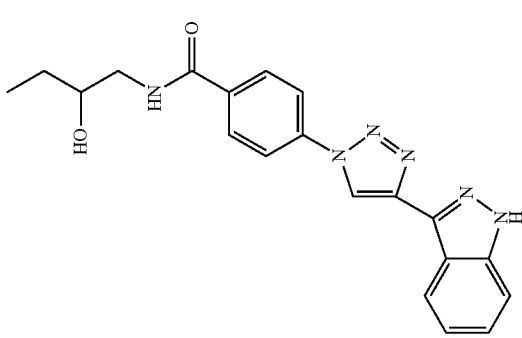 |
| 119 | 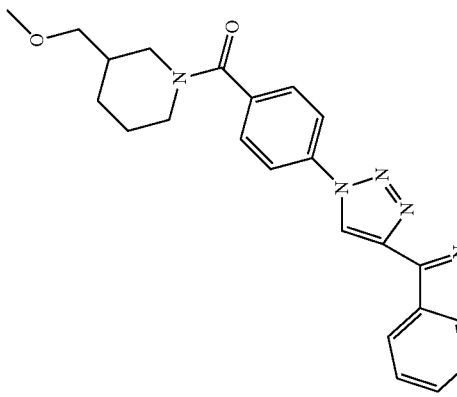 | 120 | 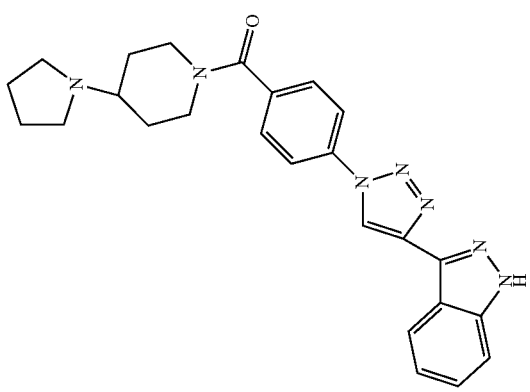 |

| Ex | compounds |
|---|---|
| 121 | (structure) |
| 122 | (structure) |
| 123 | (structure) |
| 124 | (structure) |

| Ex | ex | compounds |
|---|---|---|
| 125 | 126 | 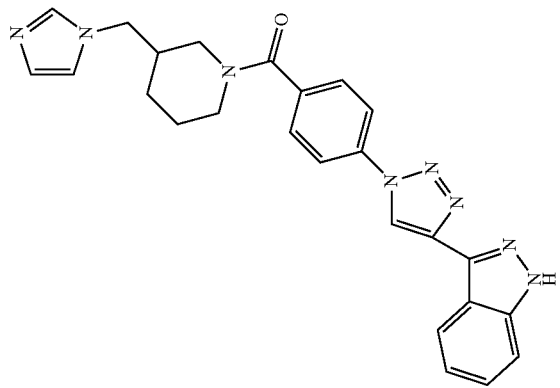 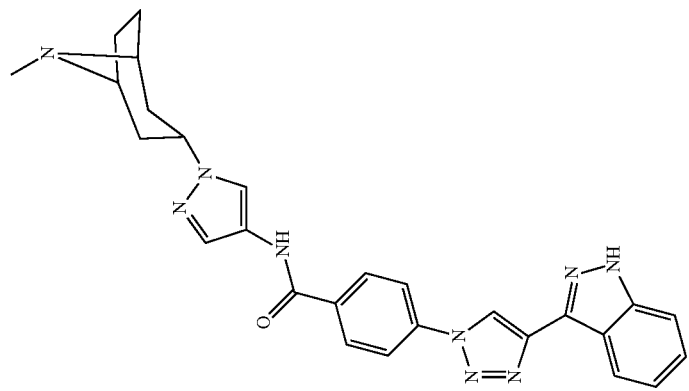 |

| Ex | compounds | Ex | compounds |
|---|---|---|---|
| 127 | (structure) | 128 | (structure) |
| 129 | (structure) | 130 | (structure) |

| Ex | compounds | ex | compounds |
|---|---|---|---|
| 131 | (4-(1,2,3,6-tetrahydropyridin-4-yl)phenyl-triazole-indazole structure) | 132 | (4-(piperidin-4-yl)phenyl-triazole-indazole structure) |
| 133 | (1-(2-fluoroethyl)piperidin-4-yl)phenyl-triazole-indazole structure) | 134 | (1-acetylpiperidin-4-yl)phenyl-triazole-indazole structure) |

-continued

| Ex | compounds | ex | compounds |
|---|---|---|---|
| 135 | | 136 | |
| 137 | | 138 | |

-continued

| Ex | compounds | ex | compounds |
|---|---|---|---|
| 139 | | 140 | |
| 141 | | 142 | |

-continued
| Ex | compounds | ex | compounds |
|---|---|---|---|
| 143 | 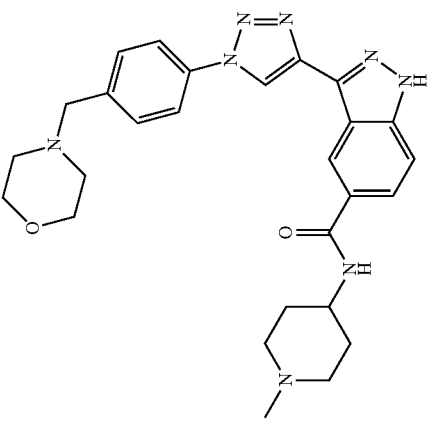 | 144 | 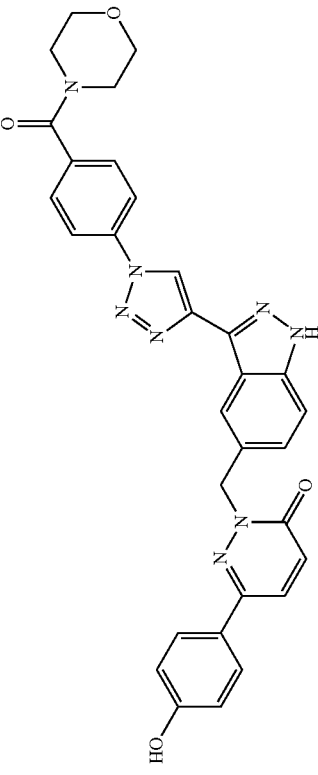 |
| 145 | 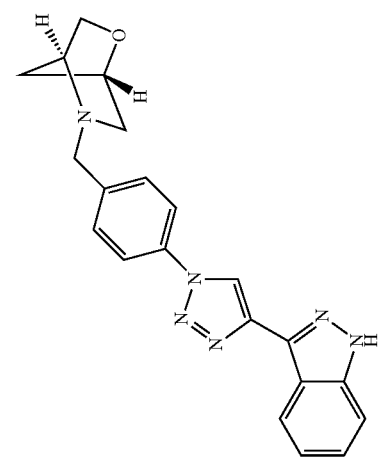 | 146 | 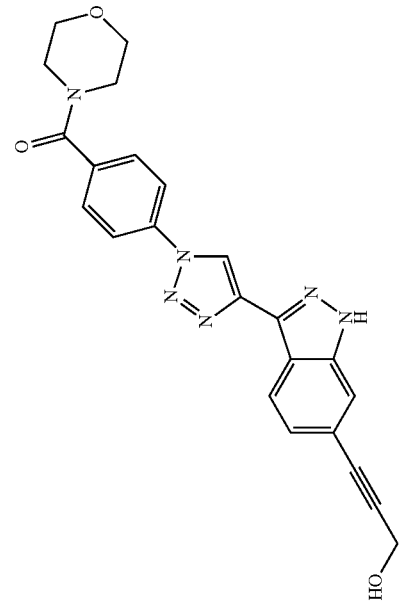 |

-continued

| Ex | compounds | Ex | compounds |
|---|---|---|---|
| 147 | | 148 | |
| 149 | | 150 | |

| Ex | compounds | ex | compounds |
|---|---|---|---|
| 151 | | 152 | |
| 153 | | 154 | |

-continued

| Ex | compounds | Ex | compounds |
|---|---|---|---|
| 155 | | 156 | |
| 157 | | 158 | |

| Ex | compounds | ex | compounds |
|---|---|---|---|
| 159 | 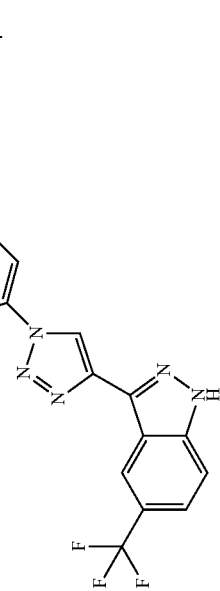 | 160 | 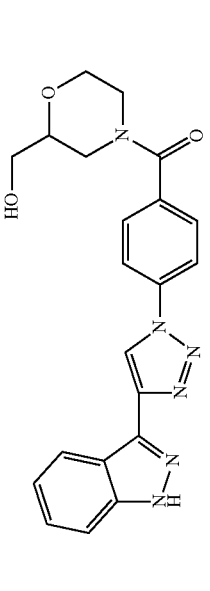 |
| 161 | 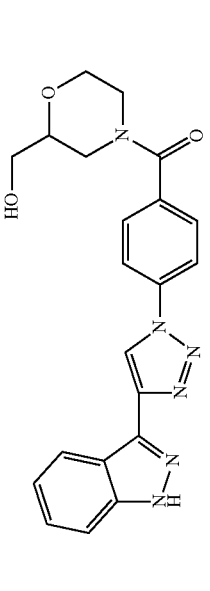 | 162 | 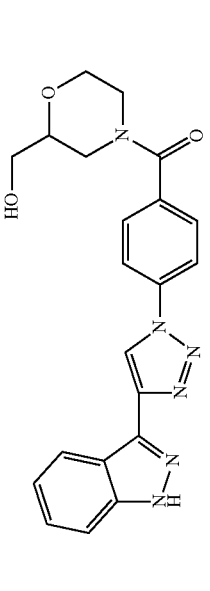 |
| 163 | 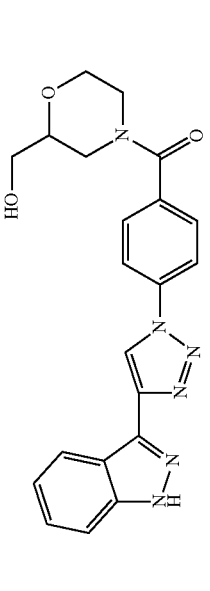 | 164 | 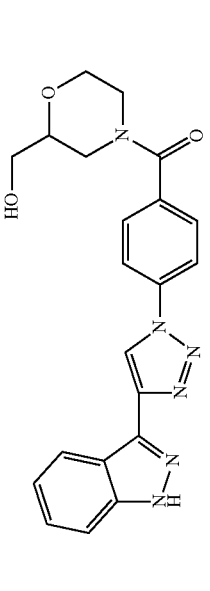 |

-continued

| Ex | compounds | ex | compounds |
|---|---|---|---|
| 165 | | 166 | |
| 167 | | 168 | |
| 169 | | 170 | |

| Ex | compounds | ex | compounds |
|---|---|---|---|
| 171 | | 172 | |
| 173 | | 174 | |
| 175 | | 176 | |

| Ex | compounds | ex | compounds |
|---|---|---|---|
| 177 | | 178 | |
| 179 | | 180 | |
| 181 | | 182 | |

-continued
| Ex | compounds | ex | compounds |
|---|---|---|---|
| 183 | 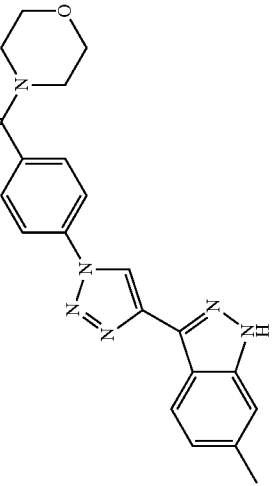 | 184 | 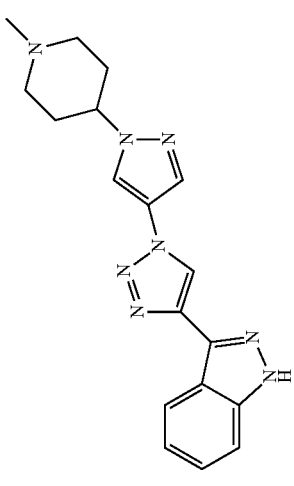 |
| 185 | 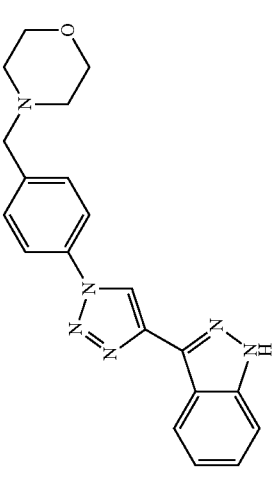 | 186 | 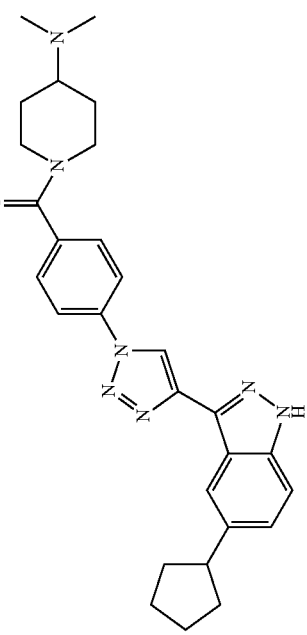 |
| 187 | 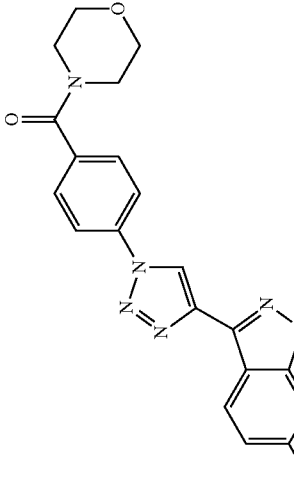 | 188 | 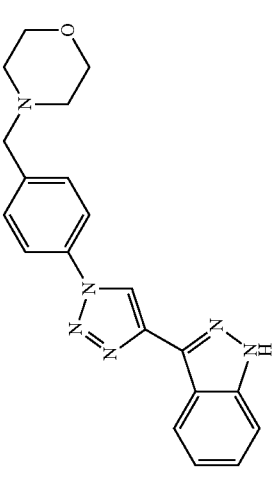 |

-continued
| Ex | compounds | ex | compounds |
|---|---|---|---|
| 189 | 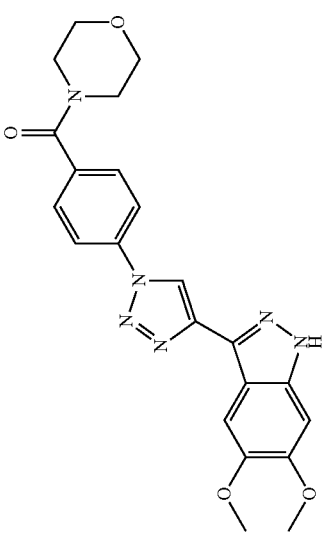 | 190 | 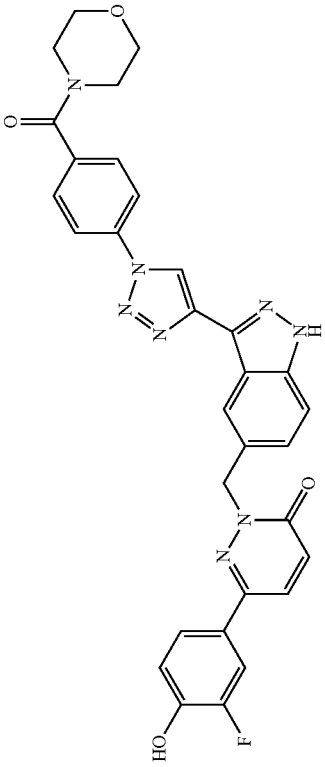 |
| 191 | 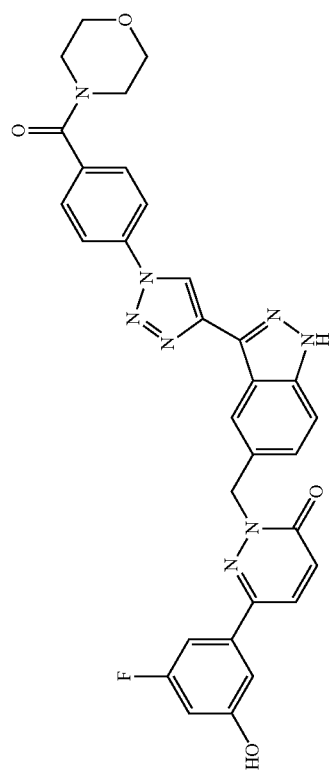 | 192 | 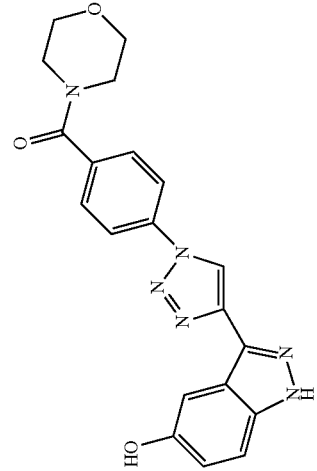 |
| 193 | 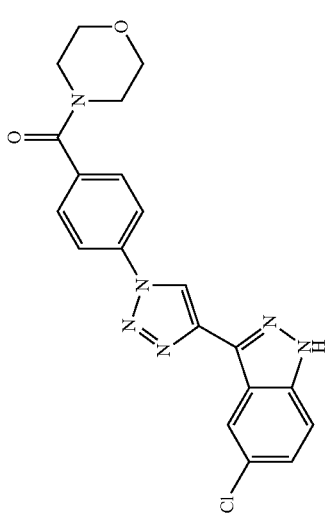 | 194 | 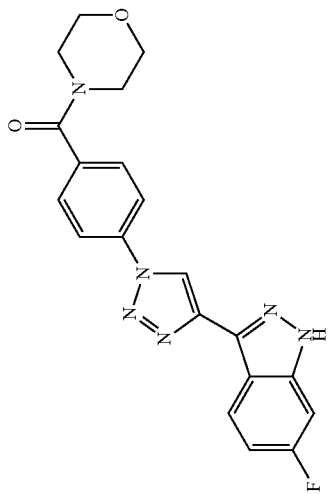 |

-continued
| Ex | compounds | ex | compounds |
|---|---|---|---|
| 195 | 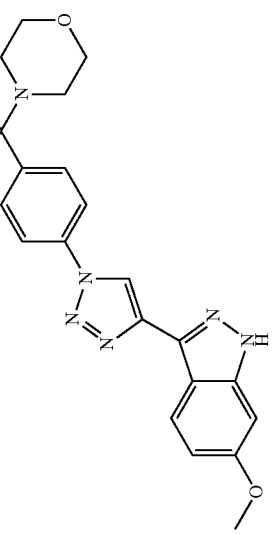 | 196 | 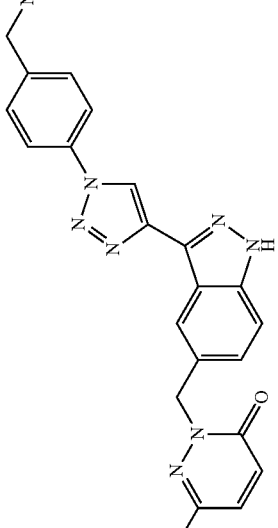 |
| 197 | 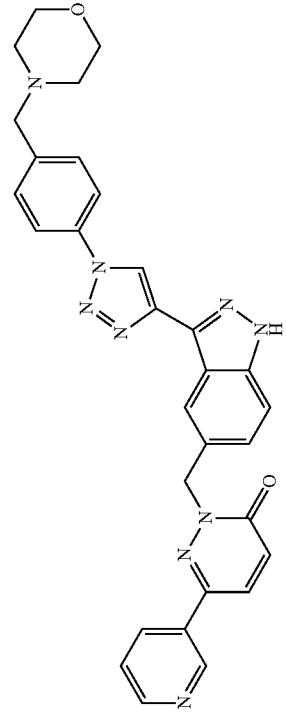 | 198 | 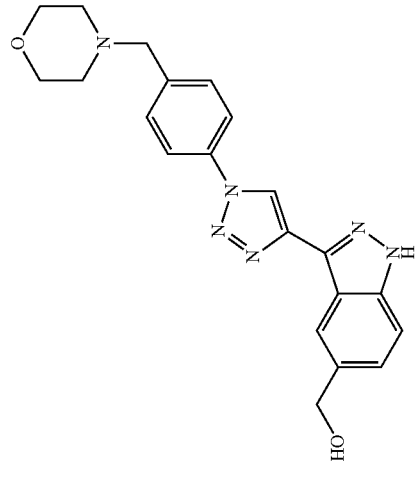 |
| 199 | 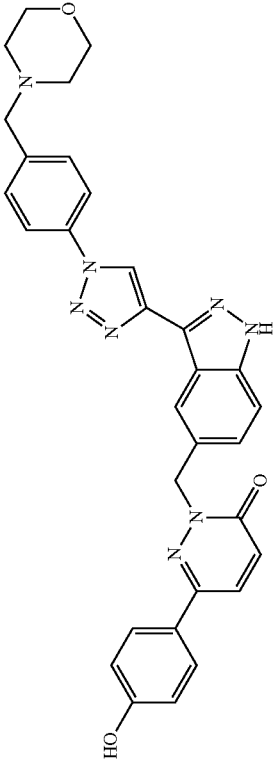 | 200 | 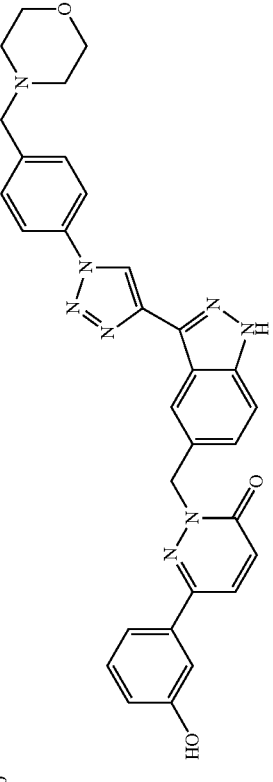 |

| Ex | compounds | ex | compounds |
|---|---|---|---|
| 201 | | 202 | |
| 203 | | 204 | |

-continued

| Ex | compounds | ex | compounds |
|---|---|---|---|
| 205 | | 206 | |
| 207 | | 208 | |

| Ex | compounds | ex | compounds |
|---|---|---|---|
| 209 | | 210 | |
| 211 | | 212 | |

| Ex | compounds | ex | compounds |
|---|---|---|---|
| 213 | 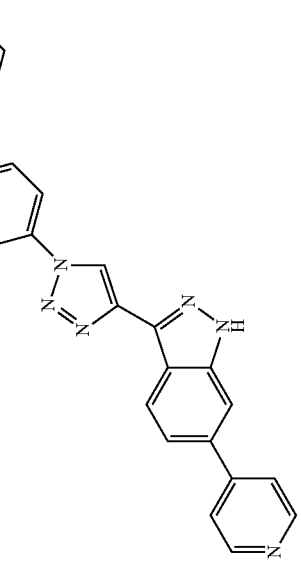 | 214 | 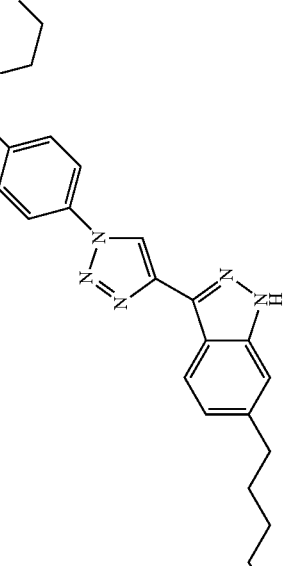 |
| 215 | 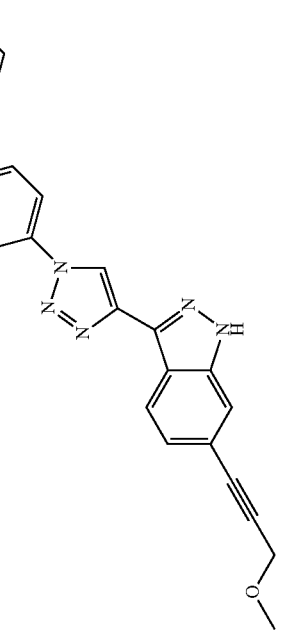 | 216 | |

| Ex | compounds | Ex | compounds |
|---|---|---|---|
| 217 | | 218 | |
| 219 | | 220 | |

-continued

| Ex | compounds | ex | compounds |
|---|---|---|---|
| 221 | (structure) | 222 | (structure) |
| 223 | (structure) | 224 | (structure) |
| 225 | (structure) | 226 | (structure) |

-continued

| Ex | compounds | ex | compounds |
|---|---|---|---|
| 227 | | 228 | |
| 229 | | 230 | |

| Ex | compounds | ex | compounds |
|---|---|---|---|
| 231 | 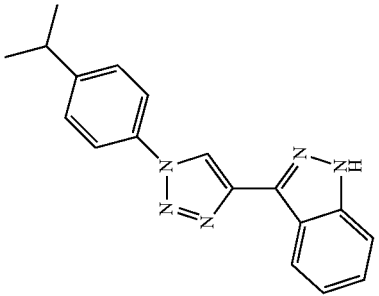 | 232 | 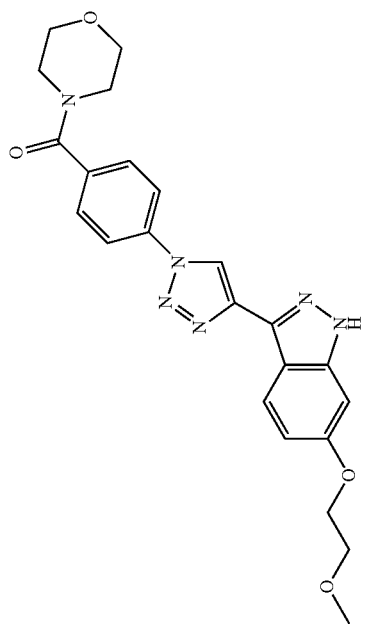 |
| 233 | 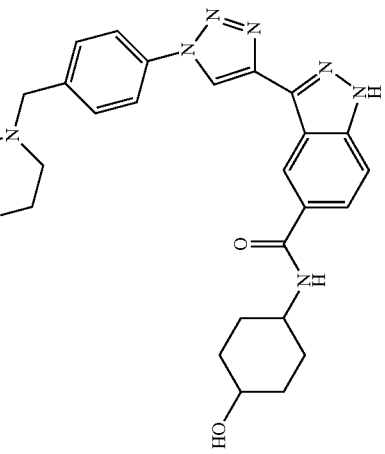 | 234 | 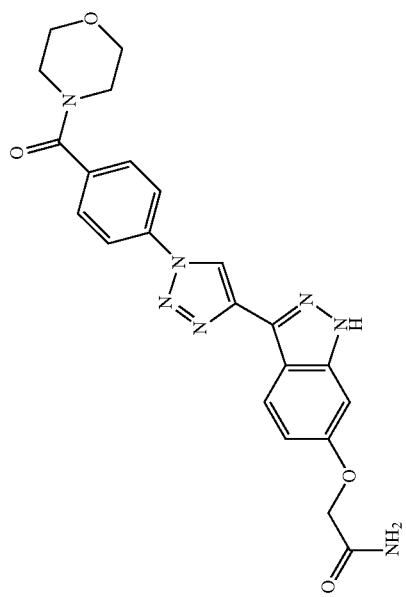 |

-continued

| Ex | ex compounds | Ex | ex compounds |
|---|---|---|---|
| 235 | | 236 | |
| 237 | | 238 | |

| Ex | compounds | ex | compounds |
|---|---|---|---|
| 239 | | 240 | |
| 241 | | 242 | |

-continued

| Ex | compounds | ex | compounds |
|---|---|---|---|
| 243 | (structure) | 244 | (structure) |
| 245 | (structure) | 246 | (structure) |

-continued

| Ex | compounds | ex | compounds |
|---|---|---|---|
| 247 | | 248 | |
| 249 | | 250 | |

-continued

| Ex | compounds | ex | compounds |
|---|---|---|---|
| 251 | | 252 | |
| 253 | | 254 | |

| Ex | compounds | ex | compounds |
|---|---|---|---|
| 255 | | 256 | |
| 257 | | 258 | |

| Ex | compounds | ex | compounds |
|---|---|---|---|
| 259 | | 260 | |
| 261 | | 262 | |

-continued
| Ex | compounds | ex | compounds |
|---|---|---|---|
| 263 | 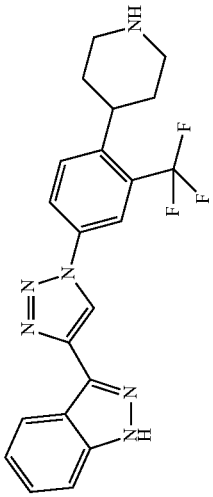 | 264 | 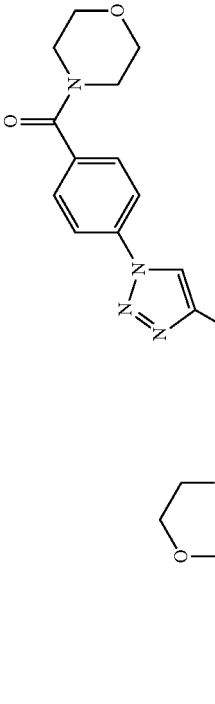 |
| 265 | 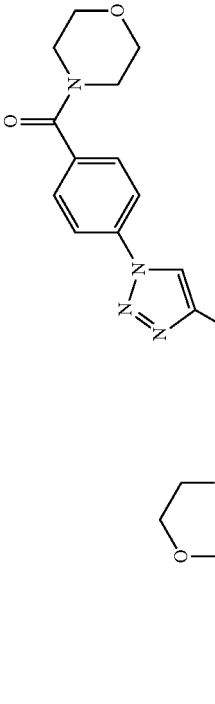 | 266 | 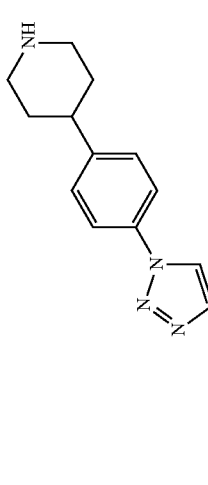 |
| 267 | 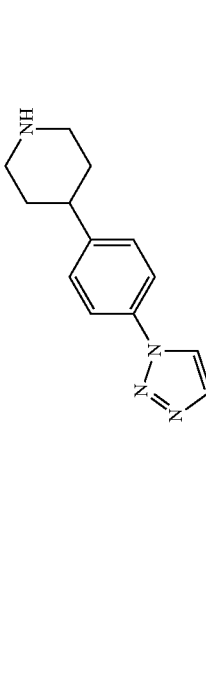 | 268 | 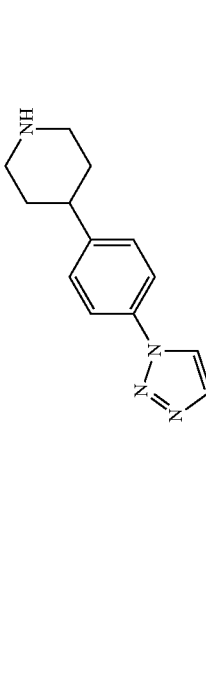 |

-continued

| Ex | compounds | ex | compounds |
|---|---|---|---|
| 269 | | 270 | |
| 271 | | 272 | |

-continued
| Ex | compounds | ex | compounds |
|---|---|---|---|
| 273 | | 274 | |
| 275 | | 276 | |
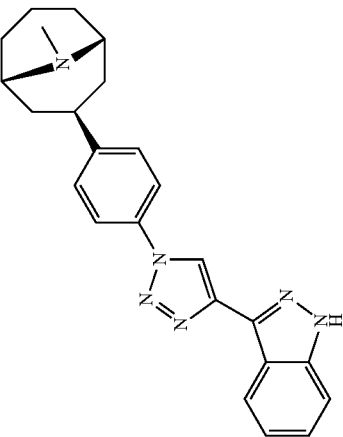

| Ex | compounds | ex | compounds |
|---|---|---|---|
| 277 | | 278 | |
| 279 | | 280 | |

-continued

| Ex | compounds | ex | compounds |
|---|---|---|---|
| 281 | | 282 | |
| 283 | | 284 | |
| 285 | | 286 | |

-continued

| Ex | compounds | ex | compounds |
|---|---|---|---|
| 287 | | 288 | |
| 289 | | 290 | |

| Ex | compounds | ex | compounds |
|---|---|---|---|
| 291 | | 292 | |
| 293 | | 294 | |

-continued

| Ex | compounds | ex | compounds |
|---|---|---|---|
| 295 | | 296 | |
| 297 | | 298 | |

| Ex | compounds | ex | compounds |
|---|---|---|---|
| 299 | ![structure] | | |

5. A method for treating a patient suffering from human melanoma or colon cancer comprising administering to said patient an effective amount of a compound of Formula (I):

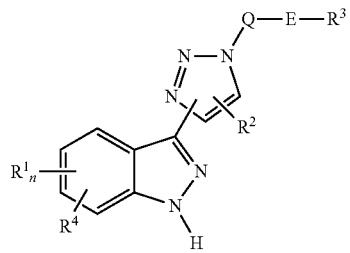

wherein
Q denotes Ar or Het,
E denotes $—(CH_2)_mCO—$, $—(CH_2)_mSO_2—$, $—(CH_2)_q—$, $—(CH_2)_mNHCO—$, or a single bond;
$R^1$ denotes H, OH, $NH—C_1-C_6$-alkyl, $OC_1-C_6$-alkyl, $C_1-C_6$-alkyl, $C_2-C_6$-alkenyl, $C_2-C_6$-alkynyl, Cyc, Hal, $Het^1$, $O-Het^1$, $CO-Het^1$, $NH-Het^1$, $CO—Ar^1$, $O—Ar^1$, $Ar^1$, $NH—Ar^1$, $—(CH_2)_qHet^1$, $—CONH—(CH_2)_qHet^1$, $—CONH-Het^1$, $—(CH_2)_qO-Het^1$, $—(CH_2)_q—Ar^1$, $—(CH_2)_qAr^1$, $—CONH—(CH_2)_qAr^1$, $—CONH—Ar^1$, $—CONHC_3-C_6$-cycloalkyl, $—(CH_2)_qHal$, $—(CH_2)_q$ Cyc, $CF_3$, $—(CH_2)_qNH—(CH_2)_q-Het^1$, or $—(CH_2)_q NH—(CH_2)_q—Ar^1$, wherein $NH—C_1-C_6$-alkyl, $OC_1-C_6$-alkyl, $C_1-C_6$-alkyl, $C_2-C_6$-alkenyl, $C_2-C_6$-alkynyl, $C_3-C_6$-cycloalkyl may be further substituted by 1 to 3 groups independently selected from $OC_1-C_3$-alkyl, OH, $CONH_2$, and $NH_2$;
$R^2$ denotes H, $C_1-C_6$-alkyl, $C_2-C_6$-alkenyl, $C_2-C_6$-alkynyl, Hal, or $CF_3$;
$R^3$ denotes $Het^1$, $Ar^1$, $NR^aR^b$, COOH, $—(CH_2)_qHet^1$, $—(CH_2)_qAr^1$, $—(CH_2)_qNR^aR^b$, $—(CH_2)_qCOOH$, or $C_1-C_6$-alkyl wherein 1 to 3 hydrogen atoms may each be independently replaced by OH or $CF_3$;
$R^4$ denotes H, $C_1-C_6$-alkyl, $C_2-C_6$-alkenyl, or Hal;
$R^a$ denotes H, linear, branched or cyclic $C_1-C_6$-alkyl,
$R^b$ denotes H, $Het^b$, $Ar^b$, $—CO-Het^b$, $—CO—Ar^b$, a $C_3-C_8$-cycloalkyl or a linear or branched alkyl having 1 to 6 carbon atoms, wherein 1 to 3 hydrogen atoms may each be replaced by $Het^b$, $Ar^b$, $NH_2$, $N(C_1-C_6$-alkyl$)_2$, $NH(C_1-C_6$-alkyl$)$, $N(C_1-C_6$-alkyl$)(C_3-C_8$-cycloalkyl$)$, $NH(C_3-C_8$-cycloalkyl$)$, $O(C_1-C_6$-alkyl$)$, CN, OH, $CF_3$, or Hal;
n is 0, 1, 2, 3 or 4;
m is 0, 1, 2, 3 or 4;
q is 1, 2, or 3;
s is 0, 1, 2 or 3;
Hal denotes Cl, Br, I, F;
Ar denotes a divalent monocyclic or fused bicyclic arylene group having 6 to 14 carbon atoms, which may be further substituted with 1 to 4 substituents selected from Hal, $C_1-C_6$-alkyl, $—(CH_2)_mOC_1-C_6$-alkyl, CN, OH, $NO_2$, $CF_3$, $—(CH_2)_mCOOH$, and $—(CH_2)_mCOOC_1-C_6$-alkyl;
Het denotes a divalent monocyclic or fused bicyclic unsaturated, saturated or aromatic heterocyclic group having 1 to 5 heteroatoms independently selected from N, O, S and/or a group $—C=O$, which may be further substituted with 1 to 4 substituent selected from Hal, $C_1-C_6$-alkyl, $—(CH_2)_mOC_1-C_6$-alkyl, CN, OH, $NO_2$, $CF_3$, $—(CH_2)_mCOOH$, and $—(CH_2)_mCOOC_1-C_6$-alkyl;
$Ar^1$ denotes a monocyclic or bicyclic, aromatic carbocyclic ring having 6 to 14 carbon atoms, which is unsubstituted or monosubstituted, disubstituted or trisubstituted by Hal, $—CF_3$, $—OCF_3$, $—NO_2$, $—CN$, perfluoroalkyl, Hal, $—CF_3$, $—OCF_3$, $—NO_2$, $—CN$, perfluoroalkyl, linear or branched $C_1-C_6$-alkyl, cycloalkyl, $—OH$, $—OC_1-C_6$-alkyl, $—COC_1-C_6$-alkyl, $—NH_2$, $—COH$, $—COOH$, $—CONH_2$, a group $R^b$, $—SO_2NR^aR^b$ or $SO_2$($C_1-C_6$alkyl);
$Het^1$ denotes a monocyclic or bicyclic saturated, unsaturated or aromatic heterocyclic ring having 1 to 4 heteroatom independently selected from N, O, S and/or a CO group, which is unsubstituted or monosubstituted, disubstituted or trisubstituted by Hal, $—CF_3$, $—OCF_3$, $—NO_2$, $—CN$, perfluoroalkyl, linear or branched $C_1-C_6$-alkyl, $C_3-C_8$-cycloalkyl, $—OH$, $—OC_1-C_6$-alkyl, $—NH_2$, $—N(C_1-C_6$-alkyl$)_2$, $—COH$, $—COOH$, $—CONH_2$, $—COC_1-C_6$-alkyl, $—NHCO(C_3-C_6$cycloalkyl$)$, a group $R^b$, $—SO_2NR^aR^b$ or $SO_2(C_1-C_6$alkyl$)$, wherein the bicyclic heterocyclic ring can be fused, bridged, or spiro:
$Het^b$ denotes a monocyclic or bicyclic (fused or spiro) saturated, unsaturated or aromatic heterocyclic ring having 1 to 4 heteroatom independently selected from N, O, S and/or a CO group, which is unsubstituted or monosubstituted, disubstituted or trisubstituted by Hal, $—CF_3$, $—OCF_3$, $—NO_2$, $—CN$, perfluoroalkyl, $—OH$, $—OC_1-C_6$-alkyl, $—NH_2$, $—COH$, $—COOH$, $—CONH_2$, or by a linear or branched $C_1-C_6$-alkyl wherein 1 to 3 hydrogen atoms may each be replaced by $NH_2$, $N(C_1-C_6$-alkyl$)_2$, $NH(C_1-C_6$-alkyl$)$, $N(C_1-C_6$-alkyl$)(C_3-C_8$-cycloalkyl$)$, $NH(C_3-C_8$-cycloalkyl$)$, $O(C_1-C_6$-alkyl$)$, CN, OH, $CF_3$, Hal, $C_3-C_8$-cycloalkyl, or by a 4 to 8-membered heterocyclic ring containing a heteroatom selected from O, S and N, wherein the bicyclic heterocyclic ring can be fused or spiro;
$Ar^b$ denotes a monocyclic or bicyclic, aromatic carbocyclic ring having 6 to 14 carbon atoms, which is unsubstituted or monosubstituted, disubstituted or trisubstituted by Hal, $—CF_3$, $—OCF_3$, $—NO_2$, $—CN$, perfluoroalkyl, Hal, $—CF_3$, $—OCF_3$, $—NO_2$, $—CN$, perfluoroalkyl, $—OH$, $—OC_1-C_6$-alkyl, $—NH_2$, $—COH$, $—COOH$, $—CONH_2$, or by a linear or branched $C_1-C_6$-alkyl wherein 1 to 3 hydrogen atoms may each be replaced by $NH_2$, $N(C_1-C_6$-alkyl$)_2$, $NH(C_1-C_6$-alkyl$)$, $N(C_1-C_6$-alkyl$)(C_3-C_8$-cycloalkyl$)$, $NH(C_3-C_8$-cycloalkyl$)$, $O(C_1-C_6$-alkyl$)$, CN, OH, $CF_3$, Hal, $C_3-C_8$-cycloalkyl, or by a 4 to 8-membered heterocyclic ring containing an heteroatom selected from O, S and N; and
Cyc denotes a saturated or unsaturated carbocyclic ring having 3 to 8 carbon atoms, wherein 1 to 5 H atoms are replaced by Hal, $—CF_3$, $—OCF_3$, $—NO_2$, $—CN$, perfluoroalkyl, Hal, $—CF_3$, $—OCF_3$, $—NO_2$, $—CN$, perfluoroalkyl, linear or branched $C_1-C_6$-alkyl, cycloalkyl, $—OH$, $—OC_1-C_6$-alkyl, $—COC_1-C_6$-alkyl, $—NH_2$, $—COH$, $—COOH$, $—CONH_2$, a group $R^b$ such as $—CH_2O(C_1-C_6$-alkyl$)$, $—SO_2NR^aR^b$ or $SO_2(C_1-C_6$alkyl$)$;
or a pharmaceutically acceptable solvate, tautomer, salt, hydrate or stereoisomer thereof, including mixtures thereof in all ratios.

6. A method according to claim 5, wherein said patient is suffering from human melanoma.

7. A method according to claim 5, wherein said patient is suffering from colon cancer.

8. A kit consisting of separate packs of:
(a) an effective amount of a compound according to claim 1, and
(b) an effective amount of at least one immunomodulating agent.

9. A pharmaceutical composition comprising at least one compound according to claim 1.

10. A pharmaceutical composition according to claim 9, wherein said composition further comprises a suitable carrier.

11. A pharmaceutical composition according to claim 9, wherein said composition further comprises at least one immunomodulating agent.

12. A process for the production of a compound according to claim 1, said process comprising:
reacting a compound of Formula II

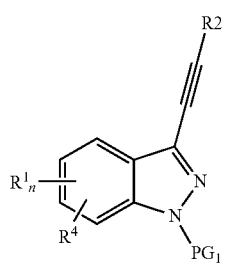

(II)

wherein $R^1$, $R^2$, $R^4$ and n are as defined in claim 1, and $PG_1$ denotes H or a nitrogen protecting group,
with a compound of Formula (III)

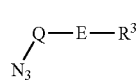

(III)

wherein Q, E and $R^3$ are as defined in claim 1.

13. A compound according to claim 1, wherein said compound is of sub-Formula (Ia) or sub-Formula (Ib)

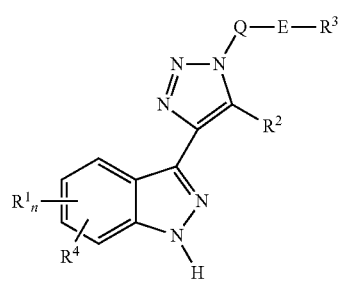

(Ia)

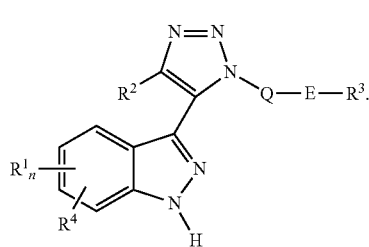

(Ib)

14. A compound according to claim 1, wherein
Q denotes Ar,
E denotes —$(CH_2)_m$CO—,
$R^1$ denotes H, $C_1$-$C_6$-alkyl, $C_2$-$C_6$-alkenyl, $C_2$-$C_6$-alkynyl, Cyc, Hal, $Het^1$, O-$Het^1$, O—$Ar^1$, $Ar^1$, —$(CH_2)_q Het^1$, —$(CH_2)_q$O-$Het^1$, —$(CH_2)_q$O—$Ar^1$, —$(CH_2)_q Ar^1$, —$(CH_2)_q$Hal, —$(CH_2)_q$Cyc, $CF_3$,
$R^2$ denotes H, $C_1$-$C_6$-alkyl, $C_2$-$C_6$-alkenyl, $C_2$-$C_6$-alkynyl, Hal, $CF_3$,
$R^3$ denotes $Het^1$ or $NR^a R^b$, and
$R^4$ denotes H.

15. A compound according to claim 13, wherein
Q denotes Ar,
E denotes —$(CH_2)_m$CO—,
$R^1$ denotes H, $C_1$-$C_6$-alkyl, $C_2$-$C_6$-alkenyl, $C_2$-$C_6$-alkynyl, Cyc, Hal, $Het^1$, O-$Het^1$, O—$Ar^1$, $Ar^1$, —$(CH_2)_q Het^1$, —$(CH_2)_q$O-$Het^1$, —$(CH_2)_q$O—$Ar^1$, —$(CH_2)_q Ar^1$, —$(CH_2)_q$Hal, —$(CH_2)_q$Cyc, $CF_3$,
$R^2$ denotes H, $C_1$-$C_6$-alkyl, $C_2$-$C_6$-alkenyl, $C_2$-$C_6$-alkynyl, Hal, $CF_3$,
$R^3$ denotes $Het^1$ or $NR^a R^b$, and
$R^4$ denotes H.

16. A compound according to claim 1, wherein
Q denotes Ar,
E denotes —$(CH_2)_m$CO—,
$R^1$, $R^2$ are both H,
$R^3$ denotes $Het^1$ or $NR^a R^b$, and
$R^4$ denotes H.

17. A compound according to claim 13, wherein
Q denotes Ar,
E denotes —$(CH_2)_m$CO—,
$R^1$, $R^2$ are both H,
$R^3$ denotes $Het^1$ or $NR^a R^b$, and
$R^4$ denotes H.

18. A compound according to claim 1, wherein said compound is of sub-Formulae (Ic), (Id) or (Ie):

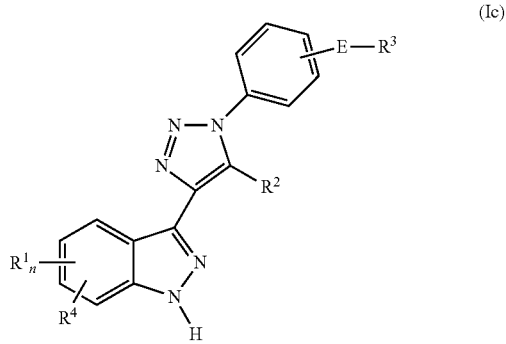

(Ic)

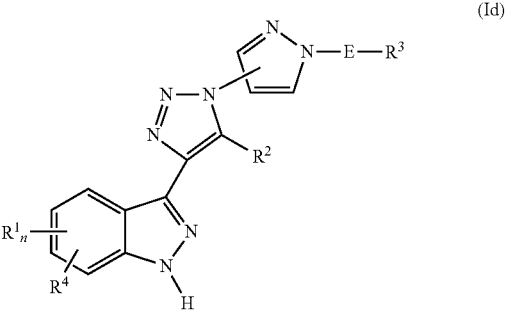

(Id)

-continued

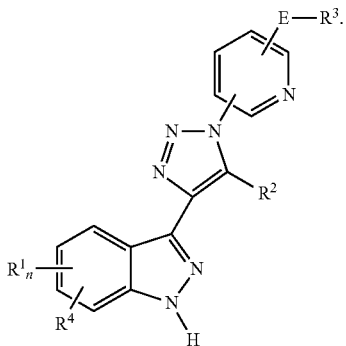
(Ie)

19. A compound according to claim 1, wherein said compound is of sub-Formula (If):

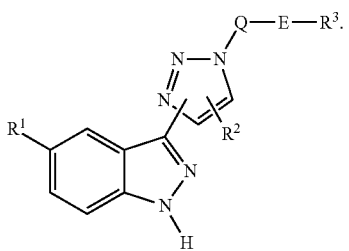
(If)

20. A compound according to claim 1, wherein E denotes —(CH$_2$)$_m$CO— or —(CH$_2$)$_m$NHCO—.

21. A compound according to claim 20, wherein m is 0, 1 or 2.

22. A compound according to claim 1, wherein E denotes —(CH$_2$)$_q$— or a single bond.

23. A compound according to claim 22, wherein q is 1.

24. A compound according to claim 19, wherein
Q is Ar,
E is —CO—, —(CH$_2$)— or a bond,
R$^3$ is Het$^1$, and
R$^1$ is H, F, —CH$_3$, Het$^1$, —(CH$_2$)$_q$-Het$^1$, —NH-Het$^1$, —CONH—(CH$_2$)$_q$Het$^1$, —CONH-Het$^1$, —CONH—Ar$^1$, or a C$_2$-C$_6$-alkenyl which may be substituted by 1 to 3 groups independently selected from OC$_1$-C$_3$-alkyl, OH, CONH$_2$, and NH$_2$.

25. A compound according to claim 1, wherein
Het$^1$ denotes a monocyclic or bicyclic, fused or spiro, saturated, unsaturated or aromatic 5-12-membered heterocyclic ring having 1 to 3 heteroatoms independently selected from N and a CO group, which is unsubstituted or monosubstituted, or disubstituted by C$_3$-C$_8$-cycloalkyl, —OH, —OC$_1$-C$_6$-alkyl, —NH$_2$, —N(C$_1$-C$_6$-alkyl)$_2$, —COHet$^b$, Het$^b$, Ar$^b$ or a linear or branched alkyl having 1 to 6 carbon atoms wherein 1 to 3 hydrogen atoms may each be independently replaced by Het$^b$, Ar$^b$, OH, CF$_3$,
Het$^b$ denotes a saturated or aromatic 5- or 6-membered ring having 1 nitrogen atom, optionally substituted with 1 to 3 substituent selected from C$_1$-C$_6$-alkyl, OH, or Hal, and
Ar$^b$ denotes a phenyl ring optionally substituted by 1 to 3 substituents selected from Hal and OH.

26. A compound according to claim 1, wherein Q is phenylene wherein 1 H atom may be replaced by C$_1$-C$_6$-alkyl, O—C$_1$-C$_6$-alkyl or CF$_3$.

27. A compound according to claim 1, wherein Q is a divalent monocyclic unsaturated or aromatic 5- or 6-membered heterocyclic group having 1 or 2 nitrogen atoms.

28. A compound according to claim 1, wherein only one of R$^a$ and R$^b$ denotes H.

* * * * *